United States Patent
Jang et al.

(10) Patent No.: US 11,271,167 B2
(45) Date of Patent: Mar. 8, 2022

(54) ORGANIC LIGHT-EMITTING DEVICE

(71) Applicant: LG CHEM, LTD., Seoul (KR)

(72) Inventors: Boonjae Jang, Daejeon (KR); Dong Hoon Lee, Daejeon (KR); Jungoh Huh, Daejeon (KR); Minyoung Kang, Daejeon (KR); Dong Uk Heo, Daejeon (KR); Miyeon Han, Daejeon (KR); Wooyung Jung, Daejeon (KR); Min Woo Jung, Daejeon (KR)

(73) Assignee: LG CHEM, LTD., Seoul (KR)

( * ) Notice: Subject to any disclaimer, the term of this patent is extended or adjusted under 35 U.S.C. 154(b) by 548 days.

(21) Appl. No.: 15/128,381

(22) PCT Filed: Apr. 1, 2015

(86) PCT No.: PCT/KR2015/003256
§ 371 (c)(1),
(2) Date: Sep. 22, 2016

(87) PCT Pub. No.: WO2015/152634
PCT Pub. Date: Oct. 8, 2015

(65) Prior Publication Data
US 2018/0175302 A1    Jun. 21, 2018

(30) Foreign Application Priority Data

Apr. 4, 2014  (KR) .................. 10-2014-0040818
Jan. 23, 2015  (KR) .................. 10-2015-0011540
Jan. 23, 2015  (KR) .................. 10-2015-0011570

(51) Int. Cl.
*H01L 51/54*   (2006.01)
*H01L 51/00*   (2006.01)
(Continued)

(52) U.S. Cl.
CPC ........ *H01L 51/0067* (2013.01); *C07D 209/82* (2013.01); *C07D 215/30* (2013.01);
(Continued)

(58) Field of Classification Search
CPC .. C07D 235/02; C07D 235/14; C07D 235/20; C07D 401/10; C07D 401/14;
(Continued)

(56) References Cited

U.S. PATENT DOCUMENTS 6,821,643 B1   11/2004   Hu et al.
8,679,647 B2    3/2014   Pflumm et al.
(Continued)

FOREIGN PATENT DOCUMENTS

CN   1702065 A   11/2005
CN   1867646 A   11/2006
(Continued)

OTHER PUBLICATIONS

Reghu, Renji R., et al., "Glass forming donor-substituted s-triazines: Photophysical and electrochemical properties," Dyes and Pigments, 2013, 97, pp. 412-422.
(Continued)

*Primary Examiner* — Andrew K Bohaty
(74) *Attorney, Agent, or Firm* — Dentons US LLP

(57) ABSTRACT

Disclosed is an organic light emitting diode including a cathode, an anode, a light emitting layer provided between the cathode and the anode, a first electron transporting layer including a heterocyclic compound represented by Formula 1 and provided between the cathode and the light emitting layer, and a second electron transporting layer including a host material including one or two or more of compounds represented by Formulae 3 to 5 and one or two or more n-type dopants selected from alkali metals and alkaline earth metals and provided between the cathode and the first electron transporting layer:

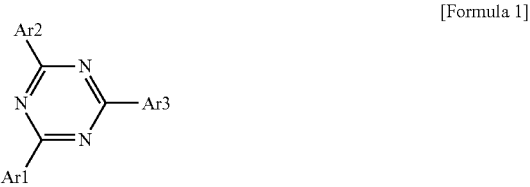

[Formula 1]

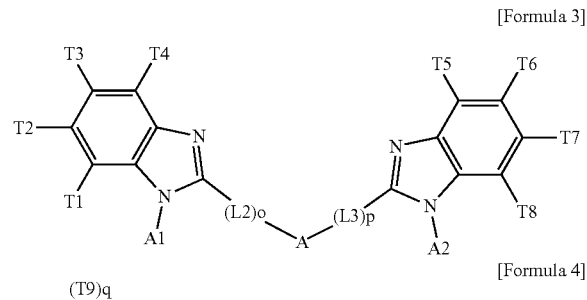

[Formula 3]

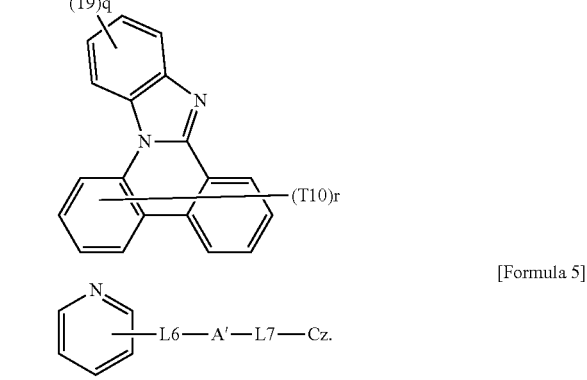

[Formula 4]

[Formula 5]

12 Claims, 6 Drawing Sheets

(51) Int. Cl.

| | |
|---|---|
| C07D 401/14 | (2006.01) |
| C07D 403/14 | (2006.01) |
| C07D 251/12 | (2006.01) |
| C07D 209/82 | (2006.01) |
| C07D 215/30 | (2006.01) |
| C07D 219/06 | (2006.01) |
| C07D 221/10 | (2006.01) |
| C07D 235/14 | (2006.01) |
| C07D 471/04 | (2006.01) |
| C07D 263/57 | (2006.01) |
| C07D 277/42 | (2006.01) |
| C07D 277/66 | (2006.01) |
| C07D 235/02 | (2006.01) |
| C07D 235/20 | (2006.01) |
| C07D 251/24 | (2006.01) |
| C07D 401/10 | (2006.01) |
| C07D 405/14 | (2006.01) |
| C07D 409/14 | (2006.01) |
| C07F 9/6561 | (2006.01) |
| H01L 51/50 | (2006.01) |
| H01L 51/52 | (2006.01) |

(52) U.S. Cl.
CPC ......... *C07D 219/06* (2013.01); *C07D 221/10* (2013.01); *C07D 235/02* (2013.01); *C07D 235/14* (2013.01); *C07D 235/20* (2013.01); *C07D 251/12* (2013.01); *C07D 251/24* (2013.01); *C07D 263/57* (2013.01); *C07D 277/42* (2013.01); *C07D 277/66* (2013.01); *C07D 401/10* (2013.01); *C07D 401/14* (2013.01); *C07D 403/14* (2013.01); *C07D 405/14* (2013.01); *C07D 409/14* (2013.01); *C07D 471/04* (2013.01); *C07F 9/6561* (2013.01); *H01L 51/0052* (2013.01); *H01L 51/0054* (2013.01); *H01L 51/0055* (2013.01); *H01L 51/0056* (2013.01); *H01L 51/0058* (2013.01); *H01L 51/0072* (2013.01); *H01L 51/0077* (2013.01); *H01L 51/508* (2013.01); *H01L 51/5016* (2013.01); *H01L 51/5076* (2013.01); *H01L 51/5278* (2013.01); *H01L 2251/552* (2013.01)

(58) Field of Classification Search
CPC .. C07D 403/10; C07D 403/14; C07D 405/14; C07D 409/14; C07D 471/04; C07D 209/82; C07D 215/30; C07D 219/06; C07D 221/10; C07D 251/12; C07D 251/24; C07D 263/57; C07D 277/42; C07D 277/66; C07F 9/6561; H01L 51/0032; H01L 51/005; H01L 51/0052; H01L 51/0054; H01L 51/0055; H01L 51/0056; H01L 51/0058; H01L 51/0072; H01L 51/0077; H01L 51/50; H01L 51/5012; H01L 51/5016; H01L 51/5076; H01L 51/508; H01L 51/5278; H01L 51/552; H01L 51/5052; H01L 51/5092; H01L 51/5096

See application file for complete search history.

(56) References Cited

U.S. PATENT DOCUMENTS

| | | | |
|---|---|---|---|
| 9,502,669 B2 | 11/2016 | Huh et al. | |
| 9,960,363 B2 | 5/2018 | Eum et al. | |
| 10,032,990 B2 | 7/2018 | Lee et al. | |
| 2003/0165715 A1* | 9/2003 | Yoon et al. | C07D 235/08 428/690 |
| 2003/0170490 A1 | 9/2003 | Hu et al. | |
| 2006/0135766 A1 | 6/2006 | Hayoz et al. | |
| 2007/0190355 A1 | 8/2007 | Ikeda et al. | |
| 2009/0162612 A1 | 6/2009 | Hatwar et al. | |
| 2010/0039026 A1 | 2/2010 | Yang et al. | |
| 2011/0037062 A1 | 2/2011 | Fukumatsu et al. | |
| 2011/0095282 A1 | 4/2011 | Pflumm et al. | |
| 2011/0121274 A1 | 5/2011 | Parham et al. | |
| 2011/0215308 A1 | 9/2011 | Im et al. | |
| 2011/0284831 A1 | 11/2011 | Kaiser et al. | |
| 2012/0126217 A1 | 5/2012 | Yoshida et al. | |
| 2012/0214993 A1 | 8/2012 | Aihara et al. | |
| 2012/0286249 A1 | 11/2012 | Lee et al. | |
| 2013/0248830 A1 | 9/2013 | Welsh et al. | |
| 2014/0014927 A1 | 1/2014 | Kim et al. | |
| 2014/0061629 A1 | 3/2014 | Murase et al. | |
| 2014/0110694 A1 | 4/2014 | Shin et al. | |
| 2014/0367654 A1 | 12/2014 | Kim et al. | |
| 2015/0069351 A1 | 3/2015 | Kambe et al. | |
| 2015/0123089 A1 | 5/2015 | Lee et al. | |
| 2015/0144897 A1 | 5/2015 | Kang et al. | |
| 2015/0236273 A1 | 8/2015 | Jang et al. | |
| 2015/0243897 A1 | 8/2015 | Montenegro et al. | |
| 2015/0303380 A1 | 10/2015 | Kambe et al. | |
| 2015/0349270 A1 | 12/2015 | Lee et al. | |
| 2016/0072073 A1 | 3/2016 | Lee et al. | |
| 2016/0093808 A1 | 3/2016 | Adamovich et al. | |
| 2016/0218298 A1 | 7/2016 | Lee et al. | |
| 2016/0248020 A1 | 8/2016 | Ondari et al. | |
| 2017/0005273 A1 | 1/2017 | Hwang et al. | |
| 2017/0104163 A1 | 4/2017 | Lee et al. | |
| 2018/0053900 A1 | 2/2018 | Eum et al. | |

FOREIGN PATENT DOCUMENTS

| | | |
|---|---|---|
| CN | 1934213 A | 3/2007 |
| CN | 101656301 A | 2/2010 |
| CN | 101960637 A | 1/2011 |
| CN | 102077379 A | 5/2011 |
| CN | 102077384 A | 5/2011 |
| CN | 102201432 A | 9/2011 |
| CN | 102292841 A | 12/2011 |
| CN | 102471320 A | 5/2012 |
| CN | 105392789 A | 3/2016 |
| CN | 106471093 A | 3/2017 |
| EP | 2 463 351 A2 | 6/2012 |
| EP | 2749560 A1 | 7/2014 |
| EP | 2752902 A1 | 7/2014 |
| JP | 2012-513668 A | 6/2012 |
| KR | 10-2000-0051826 A | 8/2000 |
| KR | 10-2010-0073954 A | 7/2010 |
| KR | 10-2011-0085174 A | 7/2011 |
| KR | 10-2011-0111093 A | 10/2011 |
| KR | 10-2011-0113469 A | 10/2011 |
| KR | 10-2012-0138673 A | 12/2012 |
| KR | 10-2013-0115160 A | 10/2013 |
| KR | 10-2013-0116041 A | 10/2013 |
| KR | 10-2014-0008126 A | 1/2014 |
| KR | 10-2014-0009919 A | 1/2014 |
| KR | 10-2015-0002072 A | 1/2015 |
| TW | 201522317 A | 6/2015 |
| WO | 2004/077885 A2 | 9/2004 |
| WO | 2007/029798 A1 | 3/2007 |
| WO | 2009/072587 A1 | 6/2009 |
| WO | 2010/072300 A1 | 7/2010 |
| WO | 2010/102706 A1 | 9/2010 |
| WO | 2010/126270 A1 | 11/2010 |
| WO | 2011/021520 A1 | 2/2011 |
| WO | 2012/150826 A1 | 11/2012 |
| WO | 2012/173369 A2 | 12/2012 |
| WO | 2013077352 A1 | 5/2013 |
| WO | 2013/085243 A1 | 6/2013 |
| WO | 2013/145666 A1 | 10/2013 |
| WO | 2013/145667 A1 | 10/2013 |
| WO | 2013/154378 A1 | 10/2013 |
| WO | 2013/180503 A1 | 12/2013 |
| WO | 2014/023388 A1 | 2/2014 |

(56) References Cited

FOREIGN PATENT DOCUMENTS

| WO | 2014185694 A1 | 11/2014 |
| WO | 2014200148 A1 | 12/2014 |
| WO | 2015005559 A1 | 1/2015 |
| WO | 2016/024728 A1 | 2/2016 |
| WO | 2016/105141 A2 | 6/2016 |

OTHER PUBLICATIONS

Hongliang Zhong et al., "New Conjugated Triazine Based Molecular Materials for Application in Optoelectronic Devices: Design, Synthesis, and Properties", The Journal of Physical Chemistry, C 2011,115, pp. 2423-2427.
Ren, et al.: "Star-Shaped Donor-pi-Acceptor Conjugated Oligomers with 1,3,5-Triazine Cores: Convergent Synthesis and Multifunctional Properties", J. Phys. Chem. B, vol. 114, No. 32, 2010, p. 10374-10383.
U.S. Appl. No. 16/171,737, filed Oct. 26, 2018.
U.S. Appl. No. 16/171,805, filed Oct. 26, 2018.

* cited by examiner

[Figure 1]
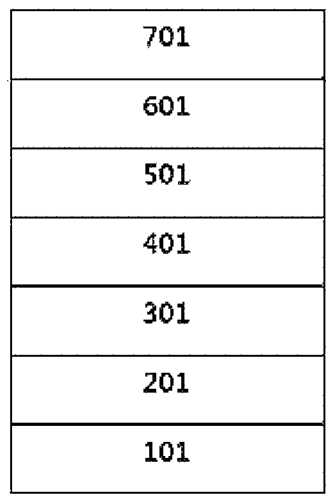
[Figure 2]
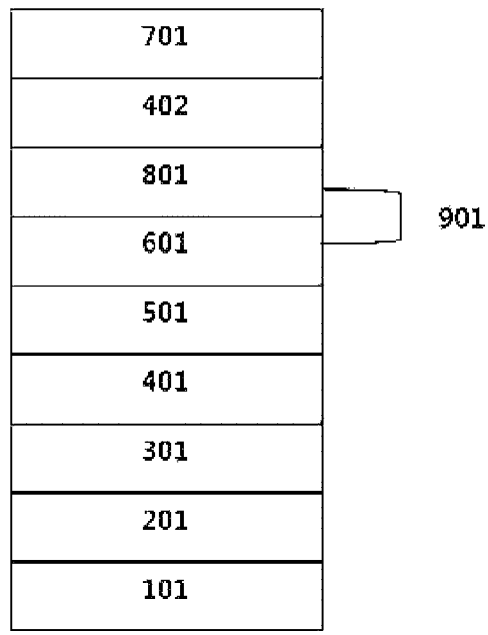

[Figure 3]
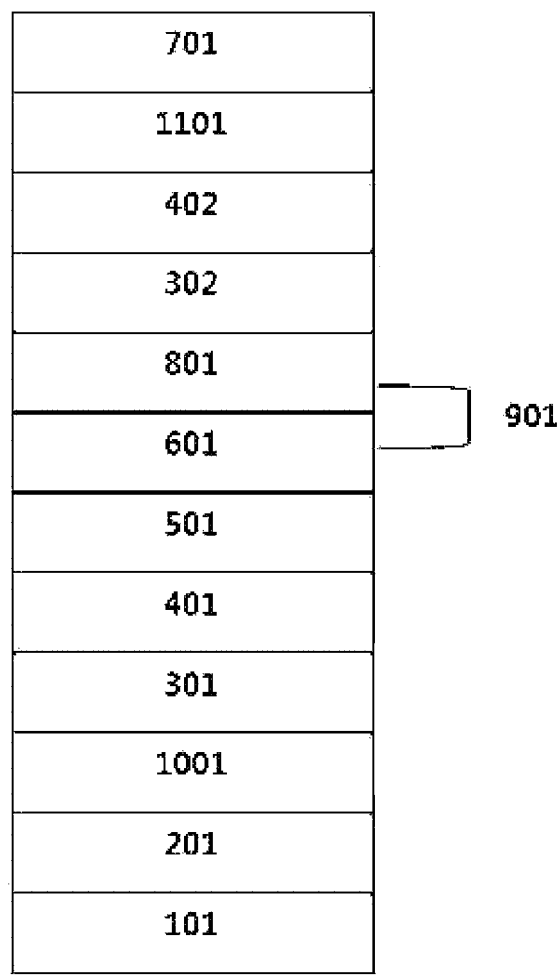

[Figure 4]
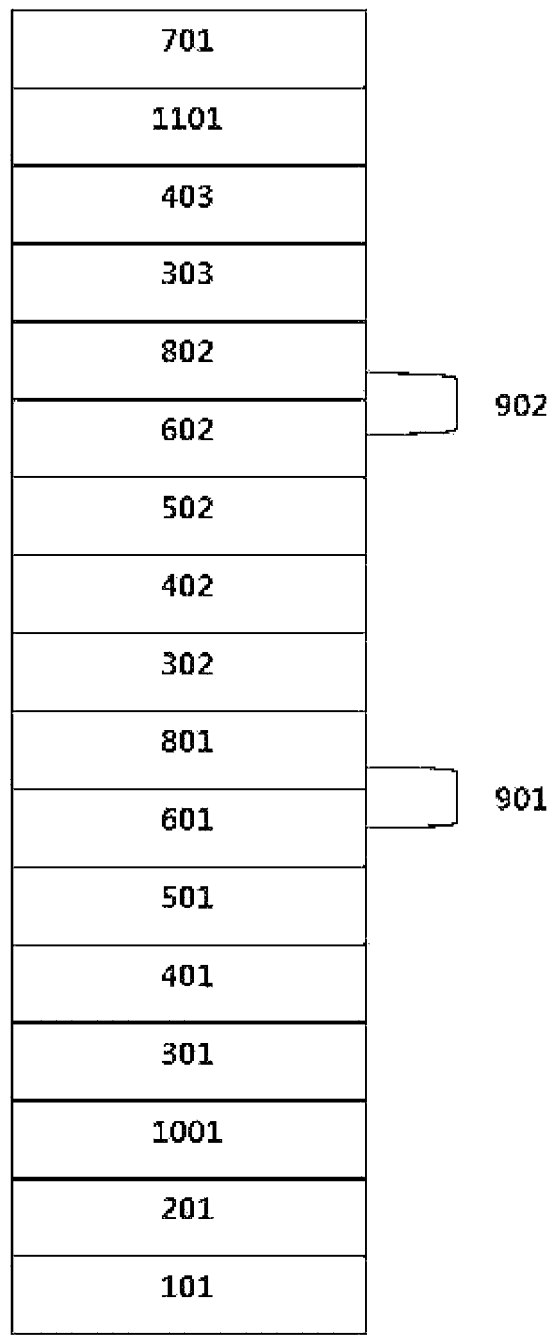

[Figure 5]
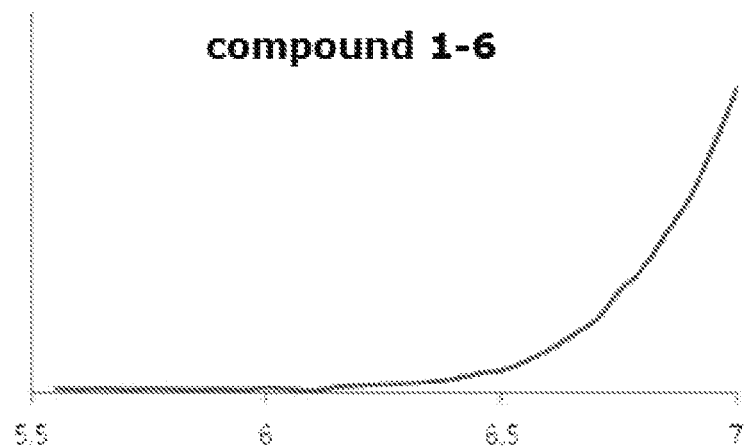
[Figure 6]
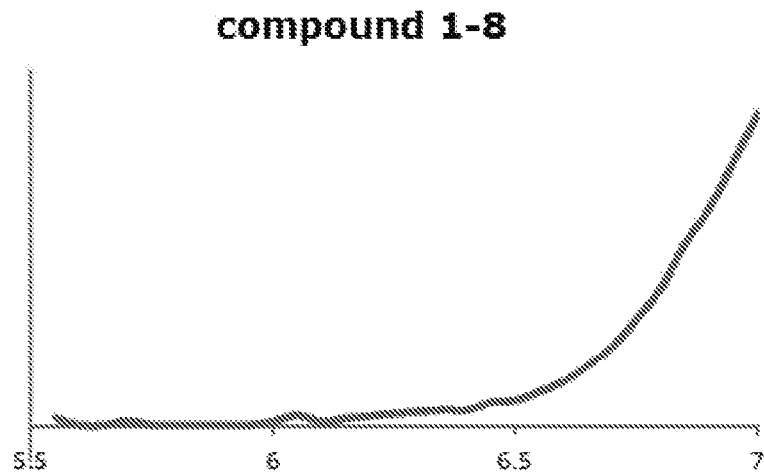

[Figure 7]
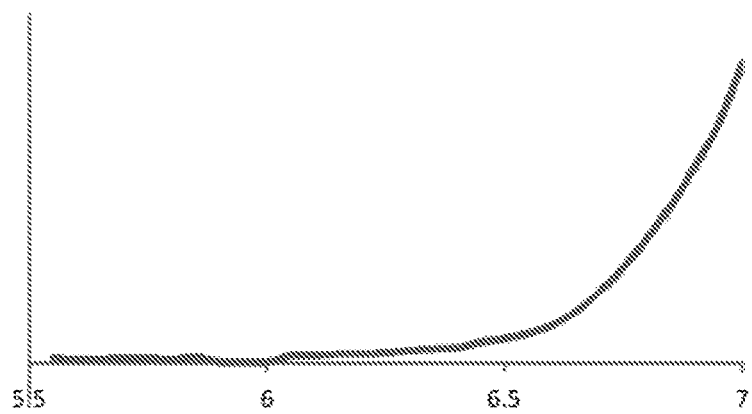
[Figure 8]
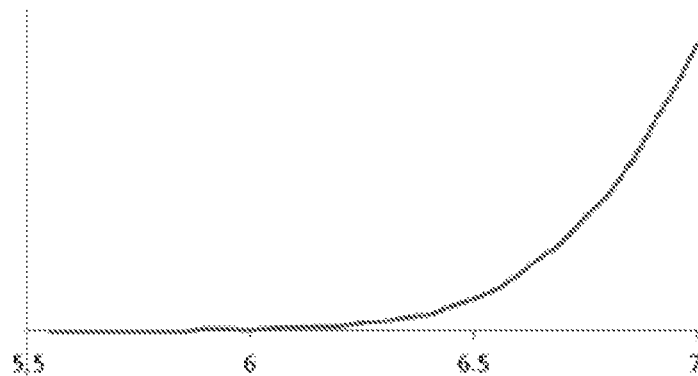

[Figure 9]
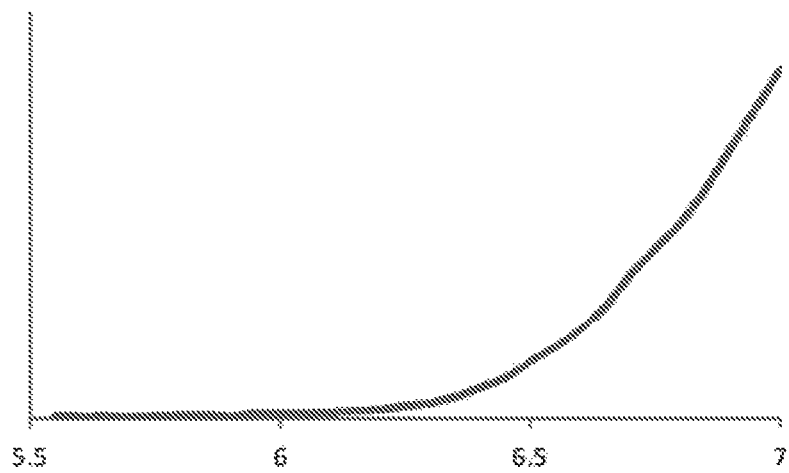

ORGANIC LIGHT-EMITTING DEVICE

This application is a National Stage Application of International Application No. PCT/KR2015/003256, filed Apr. 1, 2015, and claims the benefit of Korean Patent Application No. 10-2015-0011570, filed Jan. 23, 2015, Korean Patent Application No. 10-2015-0011540, filed Jan. 23, 2015, and Korean Patent Application No. 10-2014-0040818, filed Apr. 4, 2014, the contents of which are incorporated herein by reference in their entirety for all purposes as if fully set forth below.

TECHNICAL FIELD

The present specification claims priority from Korean Patent Application No. 10-2014-0040818, filed on Apr. 4, 2014, Korean Patent Application No. 10-2015-0011540, filed on Jan. 23, 2015, and Korean Patent Application No. 10-2015-0011570, filed on Jan. 23, 2015, the contents of which are incorporated herein by reference in their entireties.

The present specification relates to an organic light emitting diode.

BACKGROUND ART

An organic light emission phenomenon is one of the examples of converting current into visible rays through an internal process of a specific organic molecule. The principle of the organic light emission phenomenon is as follows.

When an organic material layer is disposed between an anode and a cathode, if voltage is applied between the two electrodes, electrons and holes are injected from the cathode and the anode, respectively, into the organic material layer. The electrons and the holes which are injected into the organic material layer are recombined to form an exciton, and the exciton falls down again to the ground state to emit light. An organic light emitting diode using this principle may be composed of a cathode, an anode, and an organic material layer disposed therebetween, for example, an organic material layer including a hole injection layer, a hole transporting layer, a light emitting layer, and an electron transporting layer.

The materials used in the organic light emitting diode are mostly pure organic materials or complex compounds in which organic materials and metals form a complex, and may be classified into a hole injection material, a hole transporting material, a light emitting material, an electron transporting material, an electron injection material, and the like according to the use thereof. Here, an organic material having a p-type property, that is, an organic material, which is easily oxidized and electrochemically stable when the material is oxidized, is usually used as the hole injection material or the hole transporting material. Meanwhile, an organic material having an n-type property, that is, an organic material, which is easily reduced and electrochemically stable when the material is reduced, is usually used as the electron injection material or the electron transporting material. As the light emitting layer material, a material having both p-type and n-type properties, that is, a material, which is stable during both the oxidation and reduction states, is preferred, and when an exciton is formed, a material having high light emitting efficiency for converting the exciton into light is preferred.

There is a need for developing an organic light emitting diode having high efficiency in the art.

CITATION LIST

Patent Document

Official Gazette of Korean Patent Application Laid-Open No. 2000-0051826

DETAILED DESCRIPTION OF THE INVENTION

Technical Problem

An object of the present specification is to provide an organic light emitting diode having high light emitting efficiency and/or low driving voltage.

Technical Solution

The present specification provides an organic light emitting diode including: a cathode; an anode; a light emitting layer provided between the cathode and the anode; a first electron transporting layer including a heterocyclic compound represented by the following Formula 1 and provided between the cathode and the light emitting layer; and a second electron transporting layer provided between the cathode and the first electron transporting layer, in which the second electron transporting layer includes a host material including one or two or more of compounds represented by the following Formulae 3 to 5 and one or two or more n-type dopants selected from alkali metals and alkaline earth metals.

[Formula 1]

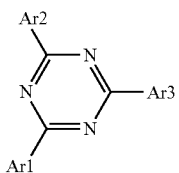

in Formula 1,
Ar1 to Ar3 are different from each other,
Ar1 and Ar2 are each independently a substituted or unsubstituted aryl group; or a substituted or unsubstituted heterocyclic group,
Ar3 is represented by the following Formula 2,

[Formula 2]

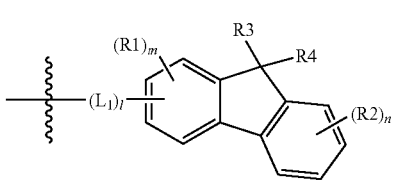

in Formula 2,
R1 to R4 are the same as or different from each other, and each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted heterocyclic group, or combine with an adjacent group to form a substituted or unsubstituted hydrocarbon ring or a substituted or unsubstituted hetero ring, or the substituents in the same carbon combine with each other to form a substituted or unsubstituted spiro bond, L1 is a direct bond; a substituted or unsubstituted arylene group; or a substituted or unsubstituted divalent heterocyclic group, l is an integer of 1 to 5, m is an integer of 1 to 3, n is an integer of 1 to 4, and when l, m, and n are each an integer of 2 or more, two or more structures in the parenthesis are the same as or different from each other, T1 to T8, T12, and T13 are the same as or different from each other, and each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted heterocyclic group, or combine with an adjacent group to form a substituted or unsubstituted hydrocarbon ring or a substituted or unsubstituted hetero ring,

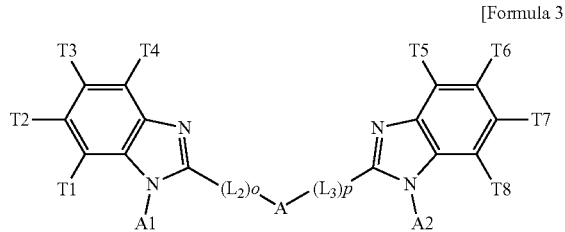

[Formula 3]

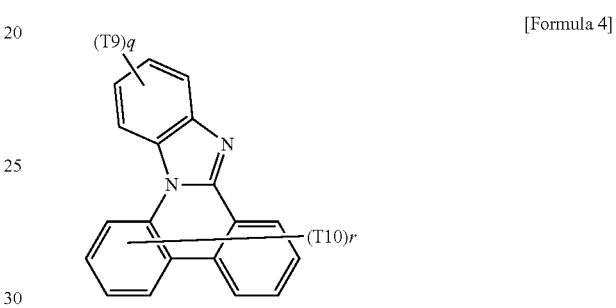

[Formula 4]

in Formula 3,

A1 and A2 are the same as or different from each other, and each independently a substituted or unsubstituted alkyl group; a substituted or unsubstituted cycloalkyl group; a substituted or unsubstituted aryl group; or a substituted or unsubstituted heterocyclic group, L2 and L3 are the same as or different from each other, and each independently a direct bond; a substituted or unsubstituted arylene group; or a substituted or unsubstituted divalent heterocyclic group, A is any one of the following substituted or unsubstituted structures,

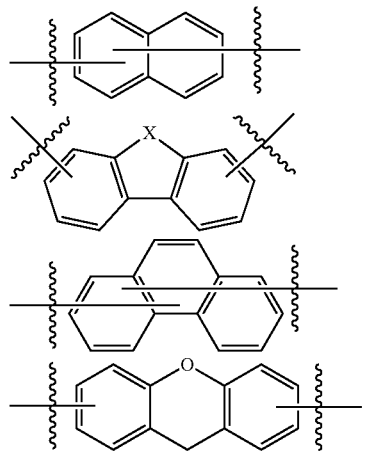

X is O; S; or CT12T13, o and p are an integer of 1 to 3, and when o and p are an integer of 2 or more, two or more structures in the parenthesis are the same as or different from each other, in Formula 4, q is an integer of 1 to 4, r is an integer of 1 to 8, and when q and r are an integer of 2 or more, two or more structures in the parenthesis are the same as or different from each other, T9 and T10 are the same as or different from each other, and each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted heterocyclic group, or combine with an adjacent group to form a substituted or unsubstituted hydrocarbon ring or a substituted or unsubstituted hetero ring, at least one of T9 and T10 has the following structure,

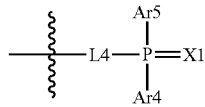

L4 is a direct bond; a substituted or unsubstituted arylene group; or a substituted or unsubstituted divalent heterocyclic group, X1 is O; S; or Se, Ar4 and Ar5 are the same as or different from each other, and each independently a substituted or unsubstituted aryl group; or a substituted or unsubstituted heterocyclic group,

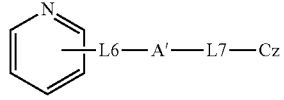

[Formula 5]

in Formula 5,

L6 and L7 are the same as or different from each other, and each independently a direct bond; a substituted or unsubstituted arylene group; or a substituted or unsubstituted divalent heterocyclic group, A' is a substituted or unsubstituted pyrenylene group, and Cz is a substituted or unsubstituted carbazole group.

Advantageous Effects

The organic light emitting diode according to an exemplary embodiment of the present specification provides low driving voltage and/or high light emitting efficiency.

DESCRIPTION OF DRAWINGS

FIG. 1 is a view illustrating an organic light emitting diode according to an exemplary embodiment of the present specification.

FIG. 2 is a view illustrating an organic light emitting diode according to an exemplary embodiment of the present specification.

FIG. 3 is a view illustrating an organic light emitting diode according to an exemplary embodiment of the present specification.

FIG. 4 is a view illustrating an organic light emitting diode according to an exemplary embodiment of the present specification.

FIG. 5 is a view illustrating a result of measurement data of the HOMO(AC3) levels of Compound 1-6.

FIG. 6 is a view illustrating a result of measurement data of the HOMO(AC3) levels of Compound 1-8.

FIG. 7 is a view illustrating a result of measurement data of the HOMO(AC3) levels of Compound 1-30.

FIG. 8 is a view illustrating a result of measurement data of the HOMO(AC3) levels of Compound 1-138.

FIG. 9 is a view illustrating a result of measurement data of the HOMO(AC3) levels of Compound 2-5.

EXPLANATION OF REFERENCE NUMERALS AND SYMBOLS

101: Substrate
201: Anode
301, 302, 303: Hole transporting layer
401, 402, 403: Light emitting layer
501, 502: First electron transporting layer
601, 602: Second electron transporting layer
701: Cathode
801, 802: P-type organic material layer
901, 902: Charge generating layer
1001: Hole injection layer
1101: Electron transporting layer

BEST MODE

Hereinafter, the present specification will be described in more detail.

When one member is disposed "on" another member in the present specification, this includes not only a case where the one member is in contact with the another member, but also a case where still another member is present between the two members.

When one part "includes" one constituent element in the present specification, unless otherwise specifically described, this does not mean that another constituent element is excluded, but means that another constituent element may be further included.

The present specification provides an organic light emitting diode including: a cathode; an anode; a light emitting layer provided between the cathode and the anode; a first electron transporting layer including the heterocyclic compound represented by Formula 1 and provided between the cathode and the light emitting layer; and a second electron transporting layer including one or more host materials of compounds represented by Formulae 3 to 5 and one or more dopants of alkali metals and alkaline earth metals and provided between the cathode and the first electron transporting layer.

In an exemplary embodiment of the present specification, an organic material layer including the heterocyclic compound represented by Formula 1 is the first electron transporting layer and provided more adjacent to the light emitting layer than the second electron transporting layer.

In an exemplary embodiment of the present specification, the second electron transporting layer is provided more adjacent to the cathode than the first electron transporting layer.

The "adjacent" in the present specification means being relatively closely disposed. In this case, the present specification may include a case of being in physical contact with each other, and may also include a case where an additional organic material layer is provided between the adjacent organic material layers.

In an exemplary embodiment of the present specification, the organic light emitting diode emits blue fluorescent light.

In an exemplary embodiment of the present specification, the organic light emitting diode emits white light.

In an exemplary embodiment of the present specification, the HOMO energy level of the heterocyclic compound represented by Formula 1 is 6 eV or more. In an exemplary embodiment of the present specification, the HOMO energy level of the heterocyclic compound represented by Formula 1 is 6.0 eV or more and 7.0 eV or less. According to an exemplary embodiment of the present specification, in the case of having a deep HOMO energy level as in the compound represented by Formula 1, holes may be effectively blocked from a light emitting layer, and thus, high light emitting efficiency may be provided, and the stability of the diode may be improved, and thus, a diode having a long service life may be provided.

In an exemplary embodiment of the present specification, the light emitting layer includes a host and a dopant, and the difference between the HOMO energy level of the host and the HOMO energy level of the heterocyclic compound represented by Formula 1 is 0.2 eV or more. As described above, when the difference in HOMO energy level between the host material of the light emitting layer and the heterocyclic compound represented by Formula 1 is 0.2 eV or more, holes may be further effectively blocked from the light emitting layer, and thus, it is possible to provide an organic light emitting diode having high light emitting efficiency and a long service life.

In an exemplary embodiment of the present specification, an organic material layer including the heterocyclic compound represented by Formula 1 is provided to be adjacent to the light emitting layer. In this case, holes may be effectively blocked by having a deeper HOMO energy level than that of the host compound of the light emitting layer.

In the case of an organic light emitting diode which emits blue fluorescent light as in an exemplary embodiment of the present specification, an anthracene derivative is usually used as a host material, and in this case, the host material has a HOMO energy level of less than 6 eV. Accordingly, when an organic material layer including the heterocyclic compound represented by Formula 1 is provided between the cathode and the light emitting layer, it is possible to simultaneously play a role of blocking a hole along with the transfer of an electron.

In the present specification, the energy level means the size of energy. Accordingly, even when the energy level is expressed in the negative (−) direction from the vacuum level, it is interpreted that the energy level means an absolute value of the corresponding energy value. For example, the HOMO energy level means the distance from the vacuum level to the highest occupied molecular orbital.

In an exemplary embodiment of the present specification, the HOMO level may be measured by using an atmospheric pressure photoelectron spectrometer AC3 (manufactured by RIKEN KEIKI Co., Ltd.). Specifically, the HOMO level may be measured by irradiating light on a material, and measuring the amount of electron produced due to separation of a charge at that time.

In an exemplary embodiment of the present specification, the triplet energy of the heterocyclic compound represented by Formula 1 is 2.2 eV or more.

According to an exemplary embodiment of the present specification, in the case of including the heterocyclic compound represented by Formula 1, which has the triplet energy in various ranges, it is possible to expect a diode having high efficiency and/or a long service life by effectively blocking the triplet exciton of the light emitting layer in the organic light emitting diode.

In an exemplary embodiment of the present specification, the light emitting layer includes a host and a dopant, and the triplet energy of the heterocyclic compound represented by Formula 1 is larger than that of the host.

In an exemplary embodiment of the present specification, the triplet energy ($E_T$) may be measured by using the low temperature photoluminescence method. The triplet energy may be obtained by measuring the $\lambda_{edge}$ value and using the following conversion formula.

$$E_T(eV) = 1239.85/(\lambda_{edge})$$

When a phosphorescence spectrum is expressed by taking the phosphorescence intensity in the longitudinal axis and the wavelength in the lateral axis, "$\lambda_{edge}$" in the conversion formula means a wavelength value of a cross-section of a tangent line and the lateral axis by drawing the tangent line with respect to an increase at the short wavelength side of the phosphorescence spectrum, and the unit thereof is nm.

In another exemplary embodiment of the present specification, the triplet energy ($E_T$) may also be obtained by the quantum chemical calculation. The quantum chemical calculation may be performed by using a quantum chemical calculation program Gaussian 03 manufactured by U.S. Gaussian Corporation. In the calculation, the density functional theory (DFT) is used, and a calculated value of the triplet energy may be obtained by the time-dependent-density functional theory (TD-DFT) with respect to a structure optimized using B3LYP as a functional and 6-31G* as a basis function.

In another exemplary embodiment of the present specification, the phosphorescence spectrum is not observed in a specific organic compound in some cases, and in the organic compound, it is possible to assume and use the triplet energy ($E_T$) obtained by using the quantum chemical calculation as shown above.

In an exemplary embodiment of the present specification, the dipole moment of the heterocyclic compound represented by Formula 1 is 2 debye or less. More preferably, the dipole moment of the heterocyclic compound represented by Formula 1 is 1 debye or less.

In an exemplary embodiment of the present specification, the dipole moment of a host material included in the second electron transporting layer is 1 debye or more.

The dipole moment in the present specification is a physical quantity which indicates the degree of polarity, and may be calculated by the following Equation 1.

$$p(r) = \int_V \rho(r_0)(r_0 - r) d^3 r_0 \qquad \text{[Equation 1]}$$

$\rho(r_0)$: molecular density $V$: volume $r$: the point of observation $d^3 r_0$: an elementary volume The value of the dipole moment may be obtained by calculating the molecular density in Equation 1. For example, the molecular density may be obtained by using a method called Hirshfeld Charge Analysis to obtain a charge and a dipole for each atom and performing the calculation according to the following equations, and the dipole moment may be obtained by substituting the Equation 1 with the calculation result.

Weight Function $$W_\alpha = \rho_\alpha(r - R_\alpha) \left[ \sum_\beta \rho_\beta(r - R_\beta) \right]^{-1}$$

$\rho_\alpha(r - R_\alpha)$: spherically averaged ground-state amomic density $\sum_\beta \rho_\beta(r - R_\beta)$: promolecule density Deformation Density $$\rho_d(r) = \rho(r) - \sum_\alpha \rho_\alpha(r - R_\alpha)$$

$\rho(r)$: molecular density $\rho_\alpha(r - R_\alpha)$: density of the free atom $\alpha$ located at coordinates $R_\alpha$ Atomic Charge $$q(\alpha) = -\int \rho_d(r) W_\alpha(r) d^3 r$$

$W_\alpha(r)$: weight function

The organic light emitting diode having the aforementioned dipole moment value range may provide low driving voltage and high light emitting efficiency because the capability of injecting and transporting electrons introduced from the cathode is improved. Further, the arrangement of the molecules in the organic light emitting diode is excellent, thereby providing a dense and compact film. Accordingly, an organic light emitting diode including the electron transporting material is excellent in stability, and thus, may provide an organic light emitting diode having a long service life.

In an exemplary embodiment of the present specification, the electron mobility of the heterocyclic compound represented by Formula 1 is $10^{-6}$ cm$^2$/Vs or more.

In another exemplary embodiment, the electron mobility of the heterocyclic compound represented by Formula 1 is $10^{-6}$ cm$^2$/Vs or more under an electric field condition of 0.1 to 0.5 MV/cm. In still another exemplary embodiment, the electron mobility of the heterocyclic compound represented by Formula 1 is $10^{-6}$ cm$^2$/Vs or more under an electric field condition of 0.1 MV/cm. In this case, the number of excitons produced in the light emitting layer is increased, and thus, a high efficiency may be expected.

In the present specification, the electron mobility may be measured by a method used in the art. Specifically, a time of flight (TOF) or a method of measuring a space charge limited current (SCLC) may be used, and the method is not limited thereto.

Specifically, in an exemplary embodiment of the present specification, bathophenanthroline and lithium (2%) were heated under vacuum on an ITO substrate and deposited to have a thickness of 20 nm, and then the compound was deposited to have a thickness of 200 nm. Bathophenanthroline and lithium (2%) were heated under vacuum on the layer and deposited to have a film having a thickness of 20 nm, and then aluminum was deposited to have a thickness of 100 nm or more, thereby preparing a sample. The electron mobility in the space charge limited current (SCLC) region may be calculated by measuring the currently density (mA/cm$^2$) for the voltage of the sample.

In an exemplary embodiment of the present specification, the first electron transporting layer further includes an n-type dopant represented by the following Formula 10.

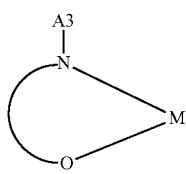

[Formula 10]

A3 is hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted heterocyclic group, the curved line represents a bond required for forming a 5-membered or 6-membered ring having M, and two or three atoms, and the atom is unsubstituted or substituted with a substituent which is the same as the definition of one or two or more A's, and M is an alkali metal or an alkaline earth metal.

In an exemplary embodiment of the present specification, the n-type dopant represented by Formula 10 is represented by the following Formula 10-1 or 10-2.

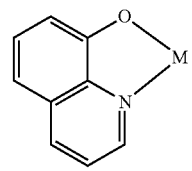

[Formula 10-1]

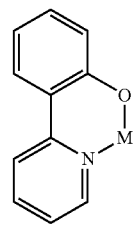

[Formula 10-2]

In Formulae 10-1 and 10-2,

M is the same as that defined in Formula 10, and

Formulae 10-1 and 10-2 are each independently unsubstituted or substituted with one or two or more substituents selected from the group consisting of hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; and a substituted or unsubstituted heterocyclic group, or adjacent substituents combine with each other to form a substituted or unsubstituted hydrocarbon ring or a substituted or unsubstituted hetero ring.

In an exemplary embodiment of the present specification, the n-type dopant represented by Formula 10 may be any one of the following structures.

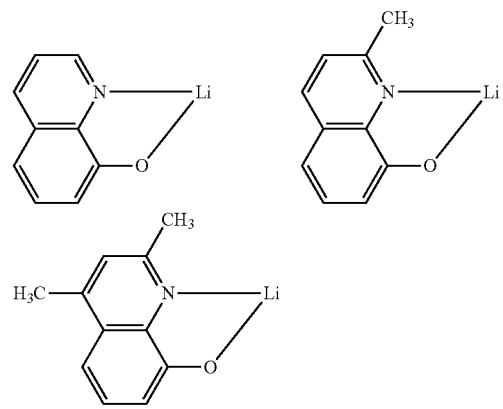

-continued
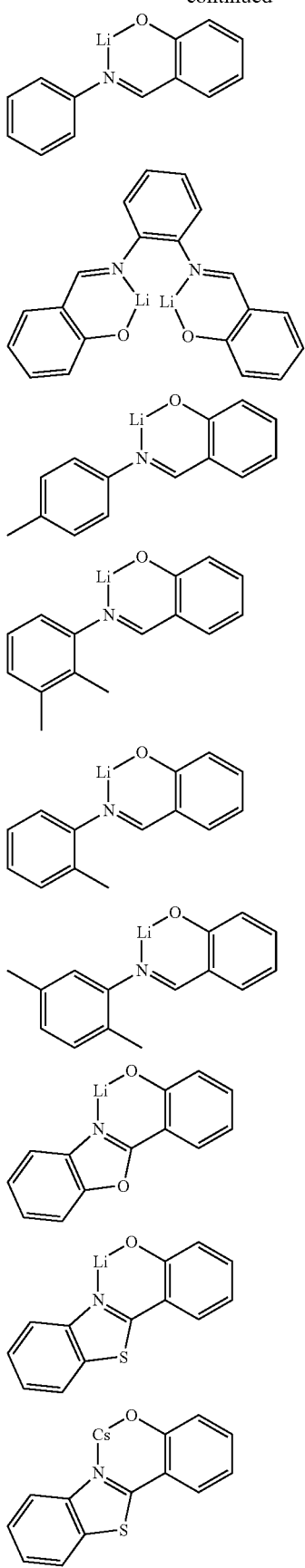
-continued
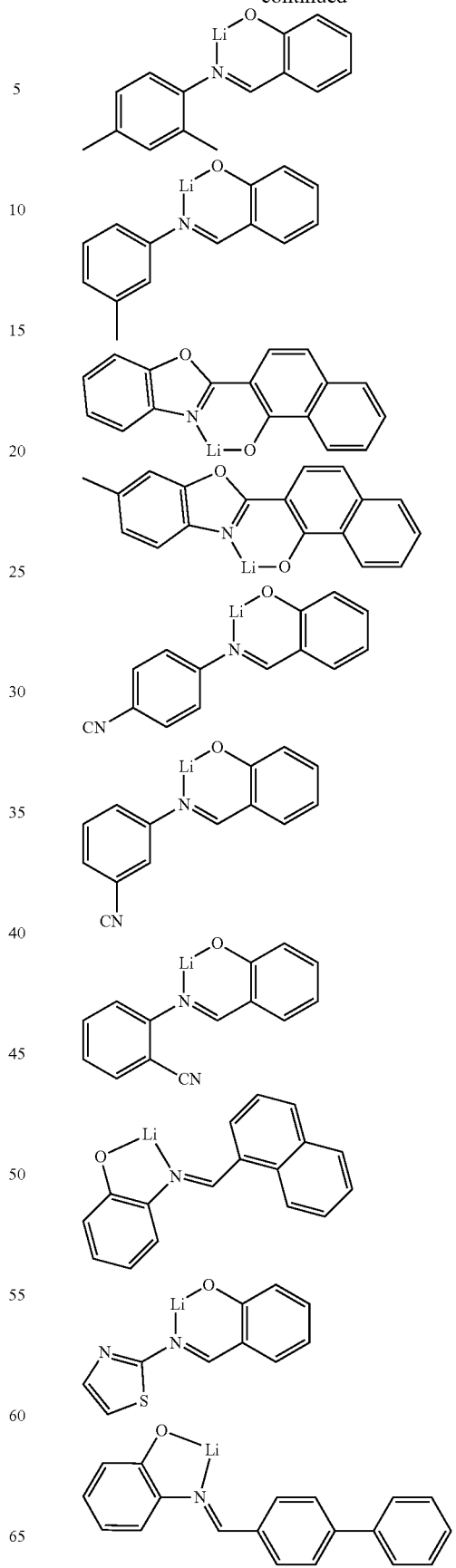

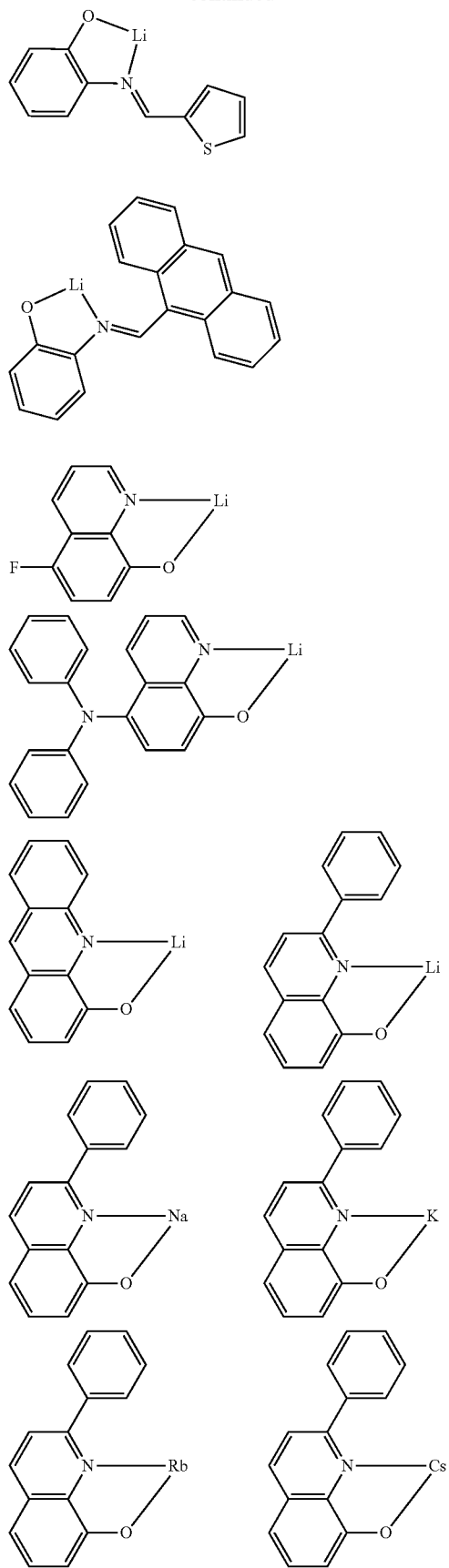
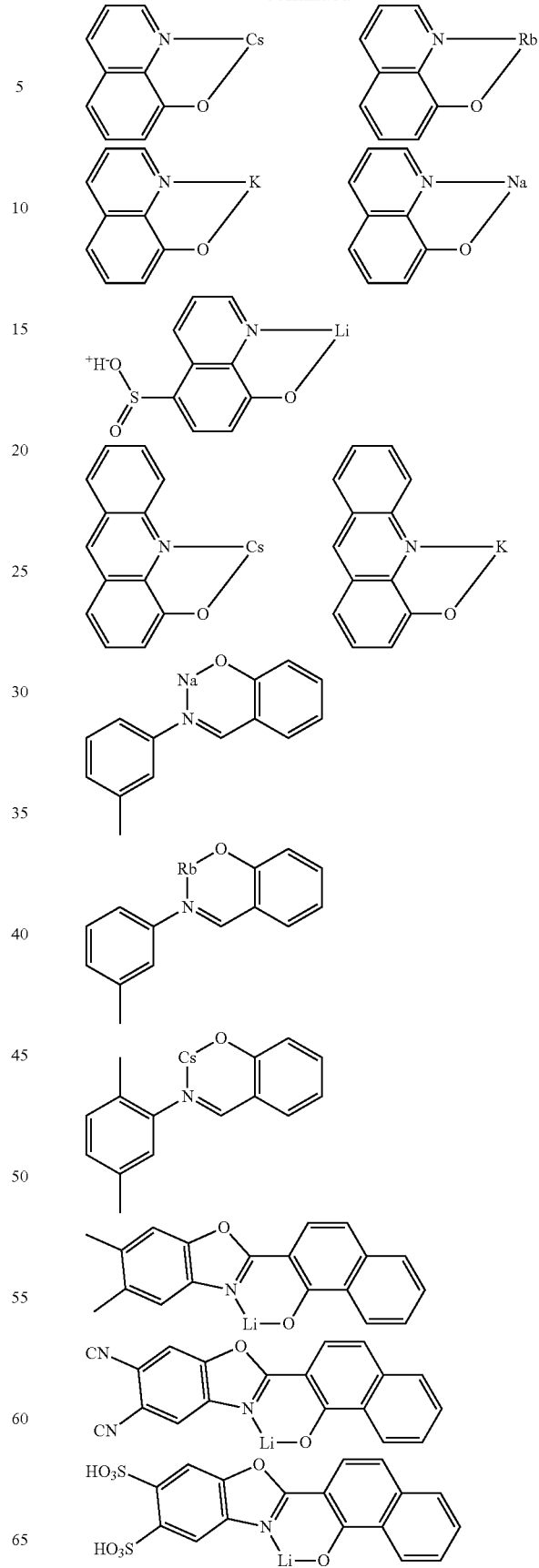

-continued

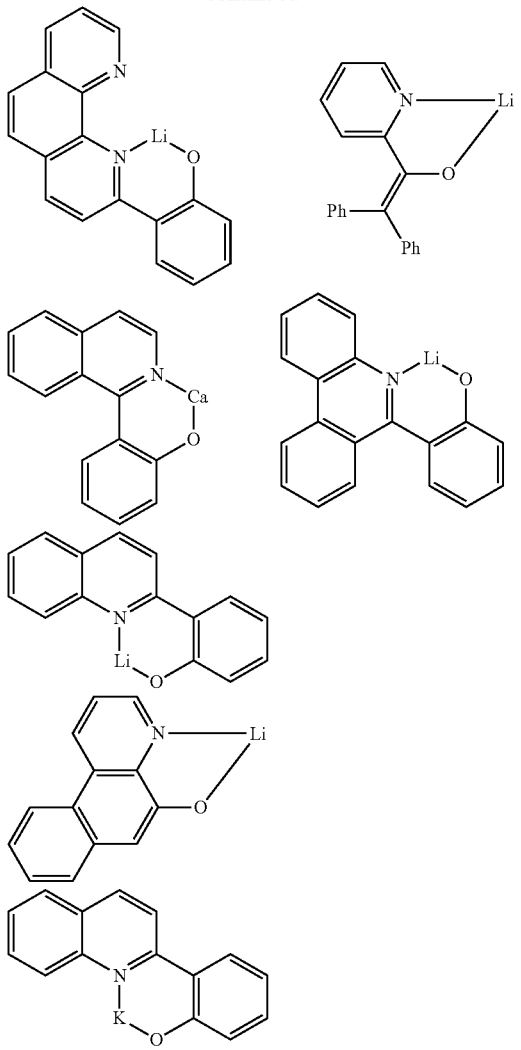

The structure may be unsubstituted or substituted with one or two or more substituents selected from the group consisting of hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; and a substituted or unsubstituted heterocyclic group.

In an exemplary embodiment of the present specification, when the organic alkali metal compound or the organic alkaline earth metal compound represented by Formula 10 is used as the n-type dopant, the compound may serve to prevent the diffusion of the metal dopant used in the second electron transporting layer, may secure stability to the holes from the light emitting layer, and thus, may improve the service life of the organic light emitting diode. In addition, for the electron mobility of the first electron transporting layer, the balance of holes and electrons in the light emitting layer may be maximized by controlling the ratio of the organic alkali metal compound or the organic alkaline earth metal compound, thereby increasing the light emitting efficiency. Accordingly, it is more preferred to include the organic alkali metal compound or the organic alkaline earth metal compound as the n-type dopant in the first electron transporting layer in view of the service life of the diode.

In the present specification, as the n-type dopant used in the first electron transporting layer, Liq is more preferred.

In an exemplary embodiment of the present specification, the n-type dopant of the organic alkali metal compound or the organic alkaline earth metal compound, which is represented by Formula 10, is present in an amount of 10 wt % to 90 wt % based on the total weight of the first electron transporting layer. Preferably, the n-type dopant of the organic alkali metal compound or the organic alkaline earth metal compound, which is represented by Formula 10, is present in an amount of 20 wt % to 80 wt % based on the total weight of the first electron transporting layer.

The first electron transporting layer may include the heterocyclic compound represented by Formula 1 and the n-type dopant represented by Formula 10 at a weight ratio of 1:9 to 9:1. Preferably, the first electron transporting layer may include the heterocyclic compound of Formula 1 and the n-dopant of Formula 10 at a weight ratio of 2:8 to 8:2, and more preferably at a weight ratio of 3:7 to 7:3.

In an exemplary embodiment of the present specification, the second electron transporting layer includes one or two or more n-type dopants selected from alkali metals and alkaline earth metals.

According to an exemplary embodiment of the present specification, the compound represented by Formula 1 and the n-type dopant may be stacked on an organic light emitting diode at a weight ratio of 9:1 to 1:9.

Specifically, the second electron transporting layer may further include one or two or more n-type dopants selected from the group consisting of alkali metals of Li, Na, K, Rb, Cs or Fr and alkaline earth metals of Be, Mg, Ca, Sr, Ba or Ra.

In an exemplary embodiment of the present specification, the n-type dopant of the second electron transporting layer is Li.

In another exemplary embodiment, the n-type dopant of the second electron transporting layer is Ca.

According to an exemplary embodiment of the present specification, the n-type dopant of the alkali metal or the alkaline earth metal may be included in an amount in a range of 0.1 wt % to 20 wt % based on the total weight of the second electron transporting layer.

According to an exemplary embodiment of the present specification, the first electron transporting layer includes the compound represented by Formula 1 as the host and Liq as the n-type dopant, and the second electron transporting layer includes the one or more compounds selected from Formulae 3 to 5 as the host and the alkali metal and/or the alkaline earth metal as the n-type dopant.

In this case, electrons are smoothly injected into the electrode, and thus, it is possible to implement an organic light emitting diode having low driving voltage. Furthermore, when the second electron transporting layer, which is the n-type organic material layer, and the p-type organic material layer form an NP junction, electrons are smoothly produced from the p-type organic material layer to the second electron transporting layer, and thus, it is possible to implement an organic light emitting diode having an effective tandem structure.

Specifically, the first electron transporting layer of the compound represented by Formula 1 is provided to be adjacent to the light emitting layer, and thus, it is possible to prevent the triplet excitons from migrating out of the light emitting layer, and the second electron transporting layer is provided to be adjacent to the cathode, and thus it is possible to increase the density of the triplet excitons. Accordingly, the organic light emitting diode according to an exemplary embodiment of the present specification induces an effect of transporting and injecting the electrons and the focusing of the triplet excitons, thereby providing low driving voltage and high efficiency.

In an exemplary embodiment of the present specification, the first electron transporting layer is provided to be adjacent to the light emitting layer. In another exemplary embodiment, the second electron transporting layer is provided to be adjacent to the cathode.

In this case, the transfer of electrons and the focusing of the triplet excitons may be efficiently achieved.

In the present specification, the n-dopant means a material which allows a host material to have n-semiconductor characteristics. The n-semiconductor characteristics means characteristics that electrons are injected or transported at the lowest unoccupied molecular orbit (LUMO) energy level, that is, characteristics of a material having a large electron conductivity.

The organic light emitting diode according to an exemplary embodiment of the present specification includes a first electron transporting layer which includes the heterocyclic compound represented by Formula 1 as the host between the light emitting layer and the cathode, and Liq having the structure as the n-type dopant.

In an exemplary embodiment of the present specification, the organic light emitting diode may further include a hole blocking layer between the aforementioned first electron transporting layer and the light emitting layer.

Examples of the substituents will be described below, but the present specification is not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a nitrile group; a nitro group; an imide group; an amide group; a hydroxy group; a substituted or unsubstituted alkyl group; a substituted or unsubstituted cycloalkyl group; a substituted or unsubstituted alkoxy group; a substituted or unsubstituted alkenyl group; a substituted or unsubstituted amine group; a substituted or unsubstituted aryl group; and a substituted or unsubstituted heterocyclic group or being substituted with a substituent to which two or more substituents are linked among the substituents exemplified above, or having no substituent. For example, "the substituent to which two or more substituents are linked" may be a biphenyl group. That is, the biphenyl group may also be an aryl group, and may be interpreted as a substituent to which two phenyl groups are linked.

In an exemplary embodiment of the present specification, the "substituted or unsubstituted" may be interpreted as being unsubstituted or substituted with one or more substituents selected from the group consisting of deuterium; a halogen group; a nitrile group; a hydroxy group; a carbonyl group; an ester group; an alkoxy group; an aryloxy group; an alkylthioxy group; an arylthioxy group; an alkylsulfoxy group; an arylsulfoxy group; a silyl group; an alkyl group; a cycloalkyl group; an alkenyl group; an aryl group; an aralkyl group; an aralkenyl group; and an alkylaryl group.

According to an exemplary embodiment of the present specification, it is more preferred that the expression "substituted or unsubstituted" is unsubstituted or substituted with one or more substituents selected from the group consisting of deuterium; an alkyl group; and an aryl group.

In an exemplary embodiment of the present specification, the hydrogen atom of the heterocyclic compound represented by Formula 1 may be deuterium. That is, the heterocyclic compound represented by Formula 1 according to an exemplary embodiment of the present specification may include one or more deuteriums. The meaning of including deuterium also includes the case where the substituent of the heterocyclic compound itself may also be deuterium, and the case where the substituent of the heterocyclic compound is substituted with deuterium. In the present specification, the halogen group may be fluorine, chlorine, bromine or iodine.

In the present specification, the alkyl group may be straight-chained or branched, and the number of carbon atoms thereof is not particularly limited, but is preferably 1 to 40. According to an exemplary embodiment, the number of carbon atoms of the alkyl group is 1 to 20. According to another exemplary embodiment, the number of carbon atoms of the alkyl group is 1 to 10. According to still another exemplary embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the cycloalkyl group is not particularly limited, but has preferably 3 to 60 carbon atoms, and according to an exemplary embodiment, the number of carbon atoms of the cycloalkyl group is 3 to 30. According to another exemplary embodiment, the number of carbon atoms of the cycloalkyl group is 3 to 20. According to still another exemplary embodiment, the number of carbon atoms of the cycloalkyl group is 3 to 6. Specifically, examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight-chained, branched, or cyclic. The number of carbon atoms of the alkoxy group is not particularly limited, but is preferably 1 to 20. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the alkenyl group may be straight-chained or branched, and the number of carbon atoms thereof is not particularly limited, but is preferably 2 to 40. According to an exemplary embodiment, the number of carbon atoms of the alkenyl group is 2 to 20. According to another exemplary embodiment, the number of carbon atoms of the alkenyl group is 2 to 10. According to still another exemplary embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, specific examples of the boron group include a trimethylboron group, a triethylboron group, a t-butyldimethylboron group, a triphenylboron group, a phenylboron group, and the like, but are not limited thereto.

In the present specification, the aryl group is not particularly limited, but has preferably 6 to 60 carbon atoms, and may be a monocyclic aryl group or a polycyclic aryl group. According to an exemplary embodiment, the number of carbon atoms of the aryl group is 6 to 30. According to an exemplary embodiment, the number of carbon atoms of the aryl group is 6 to 20. When the aryl group is a monocyclic aryl group, the aryl group may be a phenyl group, a biphenyl group, a terphenyl group, a quarterphenyl group, and the like, but is not limited thereto. When the aryl group is a polycyclic aryl group, the aryl group may be a naphthyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and two substituents may combine with each other to form a spiro structure.

When the fluorenyl group is substituted, the fluorenyl group may be

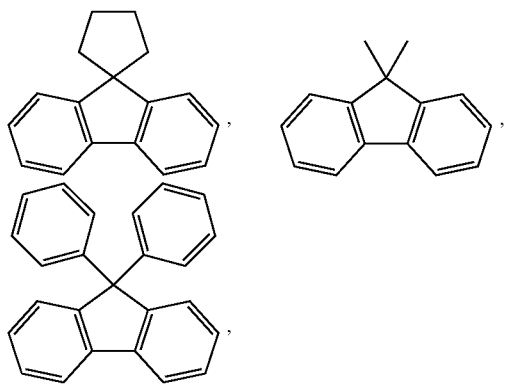

and the like, but is not limited thereto.

In the present specification, the heterocyclic group is a heterocyclic group including one or more of O, N, S, Si, and Se as a hetero element, and the number of carbon atoms thereof is not particularly limited, but is preferably 2 to 60. Examples of the heterocyclic group include a thiophene group, a furan group, a pyrrole group, an imidazole group, a triazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

The heterocyclic group may be monocyclic or polycyclic, and may be an aromatic ring, an aliphatic ring, or a condensed ring of the aromatic ring and the aliphatic ring.

In the present specification, the description on the above-described aryl group may be applied to an aryl group of an aryloxy group, an arylthioxy group, and an arylsulfoxy group.

In the present specification, the description on the above-described alkyl group may be applied to an alkyl group of an alkylthioxy group and an alkylsulfoxy group.

In the present specification, the description on the above-described aryl group may be applied to an arylene group except for a divalent arylene group.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, an alkylene, which is unsubstituted or substituted with two adjacent hydrocarbons or hetero rings, or an alkenylene, which is unsubstituted or substituted with a hydrocarbon or a hetero ring, may combine with each other to form a ring. In the present specification, the ring formed by combining the adjacent groups with each other may be monocyclic or polycyclic, may be any of an aliphatic ring, an aromatic ring, or a condensed ring of the aliphatic ring and the aromatic ring, and may form a hydrocarbon ring or hetero ring.

In the present specification, the meaning of combining with an adjacent group to form a ring means of combining with an adjacent group to form a substituted or unsubstituted aliphatic hydrocarbon ring; a substituted or unsubstituted aromatic hydrocarbon ring; a substituted or unsubstituted aliphatic hetero ring; a substituted or unsubstituted aromatic hetero ring; and a condensed ring thereof.

The hydrocarbon ring may be selected from the example of the cycloalkyl group or the aryl group, except for the hydrocarbon ring which is not monovalent. The hetero ring may be any of an aromatic ring, an aliphatic ring, or a condensed ring of the aromatic ring and the aliphatic ring, and may be selected from the example of the heterocyclic group, except for the hetero ring which is not monovalent.

In the present specification, the "spiro bond" may mean a structure in which substituents in the same carbon combine with each other, and two ring compounds are linked to each other through one atom.

In an exemplary embodiment of the present specification, the heterocyclic compound represented by Formula 1 may be represented by the following Formula 1-A.

[Formula 1-A]

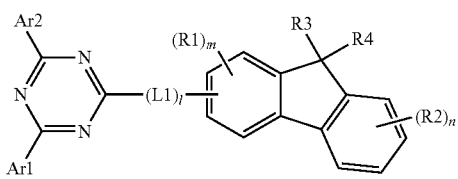

In Formula 1-A, the definition of Ar1, Ar2, L1, R1 to R4, l, m, and n is the same as defined in Formula 1.

One of the important characteristics of an organic material used in the organic light emitting diode is that an amorphous deposition film needs to be formed. An organic material having high crystallinity has a disadvantage in that a film is non-uniformly deposited during the deposition, and thus, the driving voltage is largely increased when a diode is driven, and the service life of the diode is decreased, and thus the diode quickly deteriorates. In order to alleviate the disadvantage, an amorphous film needs to be formed.

Thus, the present inventors have confirmed that an asymmetric material in a triazine derivative structure does not exhibit crystallinity. In an exemplary embodiment of the present specification, for the heterocyclic compound represented by Formula 1, Ar1 to Ar3, which are a substituent of triazine, are different from each other. In this case, the heterocyclic compound may provide a diode which is capable of forming an amorphous deposition film because the substituents of triazine are asymmetric, and has a low driving voltage and long service life.

In an exemplary embodiment of the present specification, for the heterocyclic compound represented by Formula 1, Ar1 to Ar3, which are a substituent of triazine, are different from each other.

According to an exemplary embodiment of the present specification, Formula 1 may be represented by any one of the following Formulae 1-A-1 to 1-A-4.

[Formula 1-A-1]

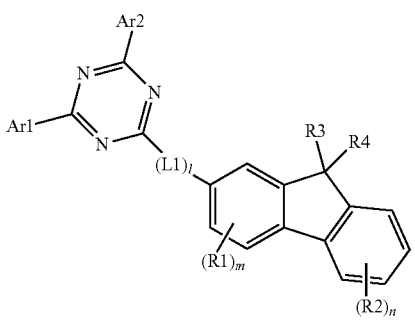

[Formula 1-A-2]

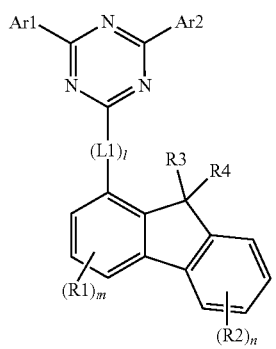

[Formula 1-A-3]

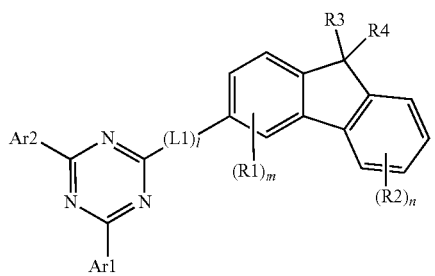

[Formula 1-A-4]

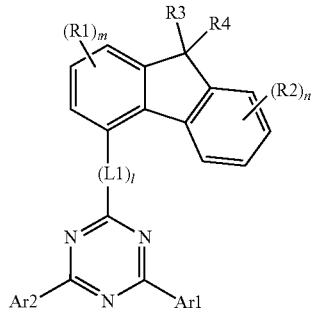

In Formulae 1-A-1 to 1-A-4, the definition of Ar1, Ar2, L1, R1 to R4, l, m, and n is the same as defined in Formula 1.

In an exemplary embodiment of the present specification, the heterocyclic compound represented by Formula 1 may be represented by Formula 1-A-1.

In another exemplary embodiment, the heterocyclic compound represented by Formula 1 is represented by Formula 1-A-2.

In still another exemplary embodiment, the heterocyclic compound represented by Formula 1 is represented by Formula 1-A-3.

In yet another exemplary embodiment, the heterocyclic compound represented by Formula 1 is represented by Formula 1-A-4.

The heterocyclic compound serving as an electron transporting layer in the present specification is preferably the compound represented by Formula 1-A-1 in terms of light emitting efficiency and service life.

In an exemplary embodiment of the present specification, the heterocyclic compound represented by Formula 1 is represented by the following Formula 1-B.

[Formula 1-B]

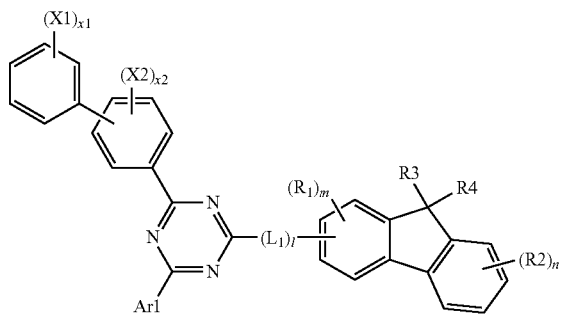

The definition of R1 to R4, Ar1, L1, l, m, and n is the same as defined in Formula 1.

x1 is an integer of 1 to 5, and x2 is an integer of 1 to 4, and when x1 and x2 are an integer of 2 or more, two or more structures in the parenthesis are the same as or different from each other, and X1 and X2 are the same as or different from each other, and each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted heterocyclic group, or two or more adjacent groups combine with each other to form a substituted or unsubstituted hydrocarbon ring; or a substituted or unsubstituted hetero ring.

In an exemplary embodiment of the present specification, the heterocyclic compound represented by Formula 1 is represented by the following Formula 1-B-1.

[Formula 1-B-1]

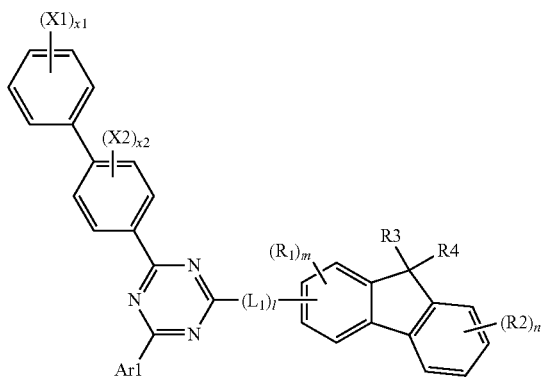

In Formula 1-B-1,

R1 to R4, Ar1, L1, l, m, n, x1, x2, X1, and X2 are the same as those defined in Formula 1-B.

In an exemplary embodiment of the present specification, X1 is hydrogen.

In another exemplary embodiment, X2 is hydrogen.

When Ar1 or Ar2 includes a biphenyl group as in an exemplary embodiment of the present specification, there is an excellent effect in terms of service life of the diode. According to an exemplary embodiment of the present specification, Ar1 and Ar2 are different from each other, and each independently a substituted or unsubstituted aryl group.

According to an exemplary embodiment of the present specification, Ar1 and Ar2 are different from each other, and each independently an aryl group of substituted or unsubstituted 1-membered to 4-membered ring.

According to an exemplary embodiment of the present specification, Ar1 and Ar2 are different from each other, and each independently an aryl group, which is unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group, an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group.

According to an exemplary embodiment of the present specification, Ar1 and Ar2 are different from each other, and each independently an aryl group, which is unsubstituted or substituted with one or more substituents selected from the group consisting of deuterium, an alkyl group, and an aryl group.

According to an exemplary embodiment of the present specification, Ar1 and Ar2 are different from each other, and each independently a substituted or unsubstituted aryl group, and at least one of Ar1 and Ar2 is an aryl group, which is unsubstituted or substituted with deuterium.

According to an exemplary embodiment of the present specification, Ar1 and Ar2 are different from each other, and each independently an aryl group, which is unsubstituted or substituted with deuterium.

According to an exemplary embodiment of the present specification, Ar1 and Ar2 are different from each other, and each independently a substituted or unsubstituted phenyl group; a substituted or unsubstituted naphthyl group; a substituted or unsubstituted biphenyl group; a substituted or unsubstituted terphenyl group; a substituted or unsubstituted quarterphenyl group; a substituted or unsubstituted phenanthryl group; a substituted or unsubstituted chrysenyl group; a substituted or unsubstituted fluorenyl group; or a substituted or unsubstituted heteroaryl group.

According to an exemplary embodiment of the present specification, Ar1 and Ar2 are different from each other, and each independently a phenyl group; a naphthyl group; a biphenyl group; a terphenyl group; a quarterphenyl group; a phenanthryl group; a chrysenyl group; a fluorenyl group; or a heteroaryl group.

According to an exemplary embodiment of the present specification, Ar1 and Ar2 are different from each other, and each independently a substituted or unsubstituted phenyl group; a substituted or unsubstituted naphthyl group; a substituted or unsubstituted biphenyl group; a substituted or unsubstituted terphenyl group; a substituted or unsubstituted quarterphenyl group; a substituted or unsubstituted phenanthryl group; a substituted or unsubstituted chrysenyl group; or a substituted or unsubstituted heteroaryl group.

In an exemplary embodiment of the present specification, Ar1 and Ar2 are different from each other, and each independently a phenyl group, which is unsubstituted or substituted with an aryl group; a biphenyl group, which is unsubstituted or substituted with an aryl group; a terphenyl group, which is unsubstituted or substituted with an aryl group; a quarterphenyl group, which is unsubstituted or substituted with an aryl group; a naphthyl group, which is unsubstituted or substituted with an aryl group; or a phenanthryl group, which is unsubstituted or substituted with an aryl group.

According to an exemplary embodiment of the present specification, Ar1 and Ar2 are different from each other, and each independently a phenyl group; a naphthyl group; a biphenyl group; a terphenyl group; a quarterphenyl group; a phenanthryl group; a chrysenyl group; or a heteroaryl group.

According to an exemplary embodiment of the present specification, Ar1 is a substituted or unsubstituted phenyl group; a substituted or unsubstituted biphenyl group; a substituted or unsubstituted naphthyl group; or a substituted or unsubstituted phenanthryl group.

According to an exemplary embodiment of the present specification, Ar1 is a phenyl group; a biphenyl group; a naphthyl group; or a phenanthryl group.

According to an exemplary embodiment of the present specification, Ar1 is a substituted or unsubstituted phenyl group.

According to an exemplary embodiment of the present specification, Ar1 is a substituted or unsubstituted biphenyl group.

According to an exemplary embodiment of the present specification, Ar1 is a substituted or unsubstituted naphthyl group.

According to an exemplary embodiment of the present specification, Ar1 is a substituted or unsubstituted phenanthryl group.

According to an exemplary embodiment of the present specification, when Ar1 is a substituted or unsubstituted phenyl group, Ar2 is a substituted or unsubstituted biphenyl group; a substituted or unsubstituted terphenyl group; a substituted or unsubstituted quarterphenyl group; a substituted or unsubstituted naphthyl group; a substituted or unsubstituted phenanthryl group; or a substituted phenyl group.

According to an exemplary embodiment of the present specification, when Ar1 is a phenyl group, Ar2 is a biphenyl group; a terphenyl group; a terphenyl group substituted with a phenyl group; a quarterphenyl group; a naphthyl group; a phenanthryl group; or a phenyl group substituted with a naphthyl group.

According to an exemplary embodiment of the present specification, when Ar1 is a substituted or unsubstituted biphenyl group, Ar2 is a substituted or unsubstituted terphenyl group; a substituted or unsubstituted biphenyl group; a substituted phenyl group; a substituted or unsubstituted naphthyl group; or a substituted or unsubstituted phenanthryl group.

According to an exemplary embodiment of the present specification, when Ar1 is a biphenyl group, Ar2 is a terphenyl group; a biphenyl group; a phenyl group substituted with a naphthyl group; a phenyl group substituted with a phenanthryl group; a biphenyl group substituted with a naphthyl group; a naphthyl group; a naphthyl group substituted with a phenyl group; or a phenanthryl group.

According to an exemplary embodiment of the present specification, when Ar1 is a substituted or unsubstituted naphthyl group, Ar2 is a substituted or unsubstituted biphenyl group; a substituted phenyl group; a substituted or unsubstituted terphenyl group; a substituted or unsubstituted phenanthryl group; or a substituted or unsubstituted quarterphenyl group.

According to an exemplary embodiment of the present specification, when Ar1 is a naphthyl group, Ar2 is a biphenyl group; a phenyl group substituted with a naphthyl group; a phenyl group substituted with a phenanthryl group; a terphenyl group; a biphenyl group substituted with a naphthyl group; a phenanthryl group substituted with a phenyl group; a phenanthryl group; a quarterphenyl group; or a terphenyl group substituted with a phenyl group.

According to an exemplary embodiment of the present specification, when Ar1 is a substituted or unsubstituted phenanthryl group, Ar2 is a substituted or unsubstituted biphenyl group; a substituted phenyl group; a substituted or unsubstituted terphenyl group; or a substituted or unsubstituted quarterphenyl group.

According to an exemplary embodiment of the present specification, when Ar1 is a phenanthryl group, Ar2 is a biphenyl group; a phenyl group substituted with a phenanthryl group; a phenyl group substituted with a naphthyl group; a terphenyl group; a quarterphenyl group; or a terphenyl group substituted with a phenyl group.

According to an exemplary embodiment of the present specification, Ar2 is a substituted or unsubstituted phenyl group; a substituted or unsubstituted biphenyl group; a substituted or unsubstituted terphenyl group; a substituted or unsubstituted quarterphenyl group; a substituted or unsubstituted naphthyl group; or a substituted or unsubstituted phenanthryl group.

According to an exemplary embodiment of the present specification, Ar2 is a phenyl group; a biphenyl group; a terphenyl group; a quarterphenyl group; a naphthyl group; or a phenanthryl group.

According to an exemplary embodiment of the present specification, at least one of Ar1 and Ar2 is a substituted or unsubstituted biphenyl group.

According to an exemplary embodiment of the present specification, Ar1 is a phenyl group, which is unsubstituted or substituted with an aryl group; a biphenyl group, which is unsubstituted or substituted with an aryl group; a naphthyl group, which is unsubstituted or substituted with an aryl group; or a phenanthryl group, which is unsubstituted or substituted with an aryl group, and Ar2 is a phenyl group, which is unsubstituted or substituted with an aryl group; a biphenyl group, which is unsubstituted or substituted with an aryl group; a terphenyl group, which is unsubstituted or substituted with an aryl group; a quarterphenyl group, which is unsubstituted or substituted with an aryl group; a naphthyl group, which is unsubstituted or substituted with an aryl group; or a phenanthryl group, which is unsubstituted or substituted with an aryl group.

According to an exemplary embodiment of the present specification, Ar1 is a phenyl group, and Ar2 is a biphenyl group.

According to an exemplary embodiment of the present specification, Ar1 and Ar2 are different from each other, and each independently a phenyl group; a biphenyl group; a terphenyl group; a naphthyl group; a phenanthryl group; or a phenyl group substituted with a naphthyl group.

According to an exemplary embodiment of the present specification, R1 is hydrogen; a substituted or unsubstituted alkyl group; or a substituted or unsubstituted aryl group.

According to an exemplary embodiment of the present specification, R1 is hydrogen; a substituted or unsubstituted alkyl group having 1 to 30 carbon atoms; or a substituted or unsubstituted aryl group having 6 to 40 carbon atoms.

According to an exemplary embodiment of the present specification, R1 is hydrogen; a substituted or unsubstituted alkyl group having 1 to 6 carbon atoms; or a substituted or unsubstituted aryl group having 6 to 20 carbon atoms, or two or more adjacent R1's combine with each other to form a substituted or unsubstituted hydrocarbon ring or a substituted or unsubstituted hetero ring.

According to an exemplary embodiment of the present specification, R1 is hydrogen; deuterium; an alkyl group having 1 to 6 carbon atoms; or an aryl group having 6 to 20 carbon atoms, or two or more adjacent R1's combine with each other to form a substituted or unsubstituted hydrocarbon ring or a substituted or unsubstituted hetero ring.

According to an exemplary embodiment of the present specification, R1 is hydrogen; deuterium; or an alkyl group. According to an exemplary embodiment of the present specification, R1 is hydrogen.

In an exemplary embodiment of the present specification, two or more R1's combine with each other to form a substituted or unsubstituted hydrocarbon ring.

In another exemplary embodiment, the two or more adjacent R1's combine with each other to form a substituted or unsubstituted benzene ring.

In an exemplary embodiment of the present specification, the two or more adjacent R1's combine with each other to form a benzene ring.

According to an exemplary embodiment of the present specification, R2 is hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; a substituted or unsubstituted monocyclic or bicyclic heterocyclic group including one or more of O and S atoms; a substituted or unsubstituted pyrrole group; a substituted or unsubstituted imidazole group; a substituted or unsubstituted triazole group; a substituted or unsubstituted pyridyl group; a substituted or unsubstituted bipyridyl group; a substituted or unsubstituted pyrimidyl group; a substituted or unsubstituted triazole group; a substituted or unsubstituted acridyl group; a substituted or unsubstituted pyridazine group; a substituted or unsubstituted pyrazinyl group; a substituted or unsubstituted quinolinyl group; a substituted or unsubstituted quinazoline group; a substituted or unsubstituted quinoxalinyl group; a substituted or unsubstituted phthalazinyl group; a substituted or unsubstituted pyridopyrimidinyl group; a substituted or unsubstituted pyridopyrazinyl group; a substituted or unsubstituted pyrazinopyrazinyl group; a substituted or unsubstituted isoquinoline group; a substituted or unsubstituted indole group; a substituted or unsubstituted benzimidazole group; or a substituted or unsubstituted phenanthroline group, or two or more adjacent R2's combine with each other to form a substituted or unsubstituted hydrocarbon ring or a substituted or unsubstituted hetero ring.

According to an exemplary embodiment of the present specification, R2 is hydrogen; a substituted or unsubstituted alkyl group; a substituted or unsubstituted aryl group; or a substituted or unsubstituted heterocyclic group, or two or more adjacent R2's combine with each other to form a substituted or unsubstituted hydrocarbon ring.

According to an exemplary embodiment of the present specification, R2 is hydrogen; deuterium; a substituted or unsubstituted alkyl group having 1 to 20 carbon atoms; a substituted or unsubstituted aryl group having 6 to 20 carbon atoms; or a substituted or unsubstituted heterocyclic group having 2 to 20 carbon atoms, or two or more adjacent R2's combine with each other to form a substituted or unsubstituted hydrocarbon ring.

According to an exemplary embodiment of the present specification, R2 is hydrogen; deuterium; or a substituted or unsubstituted aryl group having 6 to 40 carbon atoms.

According to an exemplary embodiment of the present specification, R2 is hydrogen; deuterium; or a substituted or unsubstituted aryl group having 6 to 20 carbon atoms.

According to an exemplary embodiment of the present specification, R2 is hydrogen; or an aryl group having 6 to 20 carbon atoms.

According to an exemplary embodiment of the present specification, R2 is hydrogen; or a substituted or unsubstituted phenyl group.

According to an exemplary embodiment of the present specification, R2 is hydrogen; deuterium; or a phenyl group. According to an exemplary embodiment of the present specification, R2 is hydrogen; or deuterium.

According to an exemplary embodiment of the present specification, R2 is hydrogen.

In an exemplary embodiment of the present specification, R2 is a substituted or unsubstituted phenyl group.

In another exemplary embodiment, R2 is a phenyl group.

In an exemplary embodiment of the present specification, the two or more R2's combine with each other to form a substituted or unsubstituted hydrocarbon ring.

In another exemplary embodiment, the two or more adjacent R2's combine with each other to form a substituted or unsubstituted benzene ring.

In an exemplary embodiment of the present specification, the two or more adjacent R2's combine with each other to form a benzene ring.

In another exemplary embodiment, R1 is hydrogen; or adjacent groups combine with each other to form a benzene ring.

In still another exemplary embodiment, R2 is hydrogen.

According to an exemplary embodiment of the present specification, R3 and R4 are the same as or different from each other, and each independently hydrogen; deuterium; a halogen group; a substituted or unsubstituted, straight-chained alkyl group having 1 to 40 carbon atoms; a substituted or unsubstituted, straight-chained alkoxy group having 1 to 40 carbon atoms; a substituted or unsubstituted, straight-chained thioalkyl group having 1 to 40 carbon atoms; a substituted or unsubstituted, branched mono or poly cycloalkyl group having 3 to 40 carbon atoms; a substituted or unsubstituted, branched alkenyl group having 3 to 40 carbon atoms; a substituted or unsubstituted, branched alkoxy group having 3 to 40 carbon atoms; a substituted or unsubstituted, branched thioalkoxy group having 3 to 40 carbon atoms; a 6 to 40-membered substituted or unsubstituted aryl group; a 5 to 40-membered substituted or unsubstituted heterocyclic group; a 5 to 40-membered substituted or unsubstituted aryloxy group; or a 5 to 40-membered substituted or unsubstituted heteroaryloxy group, or combine with each other to form a substituted or unsubstituted hydrocarbon ring, or the substituents in the same carbon combine with each other to form a substituted or unsubstituted spiro bond.

According to an exemplary embodiment of the present specification, R3 and R4 are the same as or different from each other, and each independently a substituted or unsubstituted alkyl group; a substituted or unsubstituted aryl group; or a substituted or unsubstituted heterocyclic group, or combine with each other to form a substituted or unsubstituted hydrocarbon ring, or the substituents in the same carbon combine with each other to form a substituted or unsubstituted spiro bond.

According to an exemplary embodiment of the present specification, R3 and R4 are the same as or different from each other, and each independently a substituted or unsubstituted alkyl group; or a substituted or unsubstituted aryl group.

According to an exemplary embodiment of the present specification, R3 and R4 are the same as or different from each other, and each independently a substituted or unsubstituted alkyl group; a substituted or unsubstituted aryl group having 6 to 20 carbon atoms; or a substituted or unsubstituted heterocyclic group.

According to an exemplary embodiment of the present specification, R3 and R4 are the same as or different from each other, and each independently an alkyl group; an aryl group having 6 to 20 carbon atoms; or a heterocyclic group.

According to an exemplary embodiment of the present specification, R3 and R4 are the same as or different from each other, and each independently an alkyl group; a substituted or unsubstituted phenyl group; a substituted or unsubstituted biphenyl group; or a substituted or unsubstituted naphthyl group, or R3 and R4 combine with each other to form a 5-membered aliphatic ring.

According to an exemplary embodiment of the present specification, R3 and R4 are the same as or different from each other, and each independently a methyl group; a substituted or unsubstituted phenyl group; a substituted or unsubstituted biphenyl group; or a substituted or unsubstituted naphthyl group, or R3 and R4 combine with each other to form a 5-membered aliphatic ring.

According to an exemplary embodiment of the present specification, R3 and R4 are the same as or different from each other, and each independently a methyl group; an unsubstituted phenyl group; a phenyl group substituted with a methyl group; a biphenyl group; or a naphthyl group, or R3 and R4 combine with each other to form a 5-membered aliphatic ring.

In another exemplary embodiment, R3 and R4 are the same as or different from each other, and each independently a methyl group; a phenyl group; or a phenyl group substituted with a methyl group.

In an exemplary embodiment of the present specification, R1 to R4 are the same as or different from each other, and each independently hydrogen; a substituted or unsubstituted alkyl group; or a substituted or unsubstituted aryl group, or two or more adjacent substituents combine with each other to form a substituted or unsubstituted hydrocarbon ring, or the substituents in the same carbon combine with each other to form a spiro bond.

In an exemplary embodiment of the present specification, R1 to R4 are the same as or different from each other, and each independently hydrogen; a substituted or unsubstituted alkyl group; or a substituted or unsubstituted aryl group, or two or more adjacent substituents combine with each other to form a substituted or unsubstituted hydrocarbon ring, or the substituents in the same carbon combine with each other to form a substituted or unsubstituted spiro bond.

In an exemplary embodiment of the present specification, L1 is a direct bond; or a substituted or unsubstituted arylene group.

In another exemplary embodiment, L1 is a direct bond; or an arylene group having 6 to 20 carbon atoms.

According to an exemplary embodiment of the present specification, L1 may be a direct bond; or any one selected from the following structures.

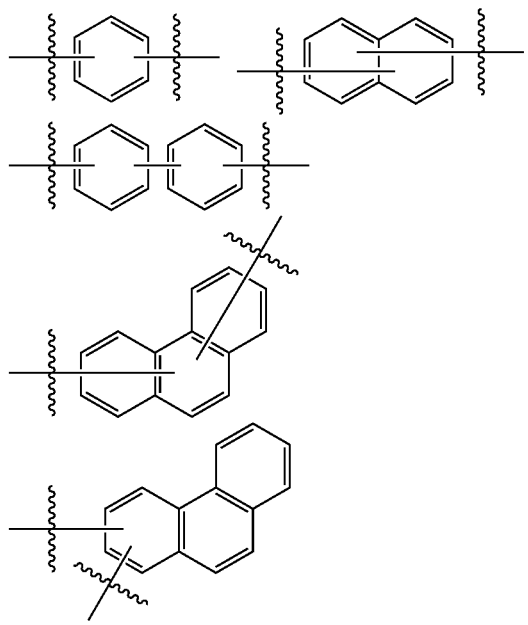

The structures may be unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group, an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an amine group; an arylphosphine group; or a heterocyclic group.

In an exemplary embodiment of the present specification, L1 is a direct bond; a substituted or unsubstituted phenylene group; a substituted or unsubstituted biphenylylene group; a substituted or unsubstituted naphthalene group; or a substituted or unsubstituted phenanthrenylene group.

In an exemplary embodiment of the present specification, (L1)₁ is a direct bond; a substituted or unsubstituted phenylene group; a substituted or unsubstituted biphenylylene group; a substituted or unsubstituted naphthalene group; or a substituted or unsubstituted phenanthrenylene group.

In an exemplary embodiment of the present specification, L1 is a direct bond.

In another exemplary embodiment, L1 is a substituted or unsubstituted phenylene group.

In still another exemplary embodiment, L1 is a phenylene group.

In an exemplary embodiment of the present specification, L1 is a substituted or unsubstituted biphenylylene group.

In one exemplary embodiment, L1 is a biphenylylene group.

In an exemplary embodiment of the present specification, L1 is a substituted or unsubstituted naphthalene group.

In an exemplary embodiment of the present specification, L1 is a naphthalene group.

In an exemplary embodiment of the present specification, L1 is a substituted or unsubstituted phenanthrenylene group.

In another exemplary embodiment, L1 is a phenanthrenylene group.

In an exemplary embodiment of the present specification, L1 is a direct bond; a phenylene group; or a naphthalene group.

In one exemplary embodiment of the present specification, L1 is unsubstituted or substituted with one or more deuteriums.

In an exemplary embodiment of the present specification, Formula 2 may be selected from any one of the following structures.

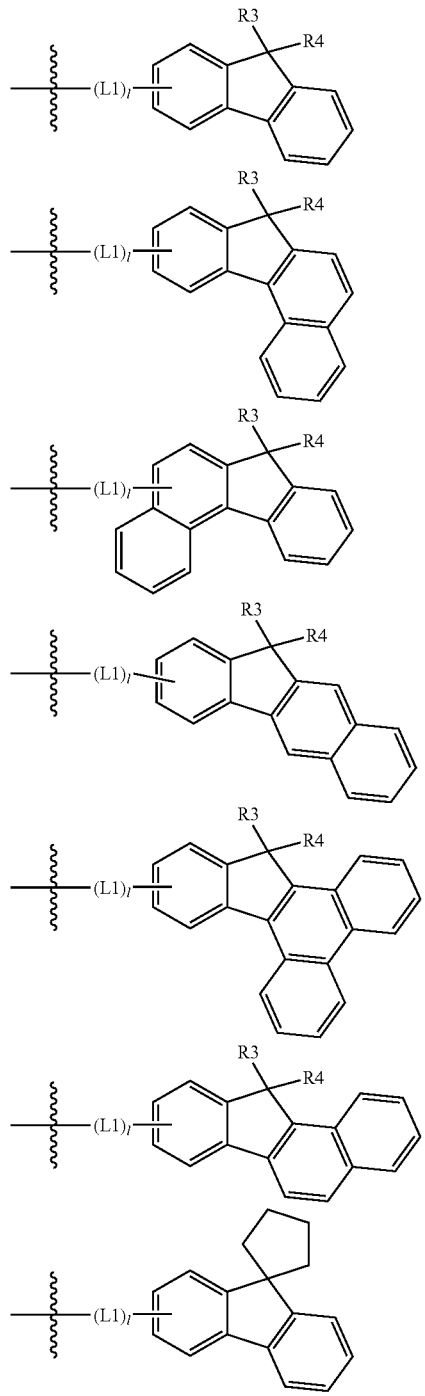

In the structures, R3, R4, L1, and l are the same as those described above, and the structures may be unsubstituted or substituted with one or more substituents selected from the group consisting of deuterium; a halogen group; a nitrile group; a nitro group; an imide group; an amide group; a hydroxy group; a substituted or unsubstituted alkyl group; a substituted or unsubstituted cycloalkyl group; a substituted or unsubstituted alkoxy group; a substituted or unsubstituted alkenyl group; a substituted or unsubstituted amine group; a substituted or unsubstituted aryl group; and a substituted or unsubstituted heterocyclic group.

In an exemplary embodiment of the present specification, Ar3 may be selected from the following structures.

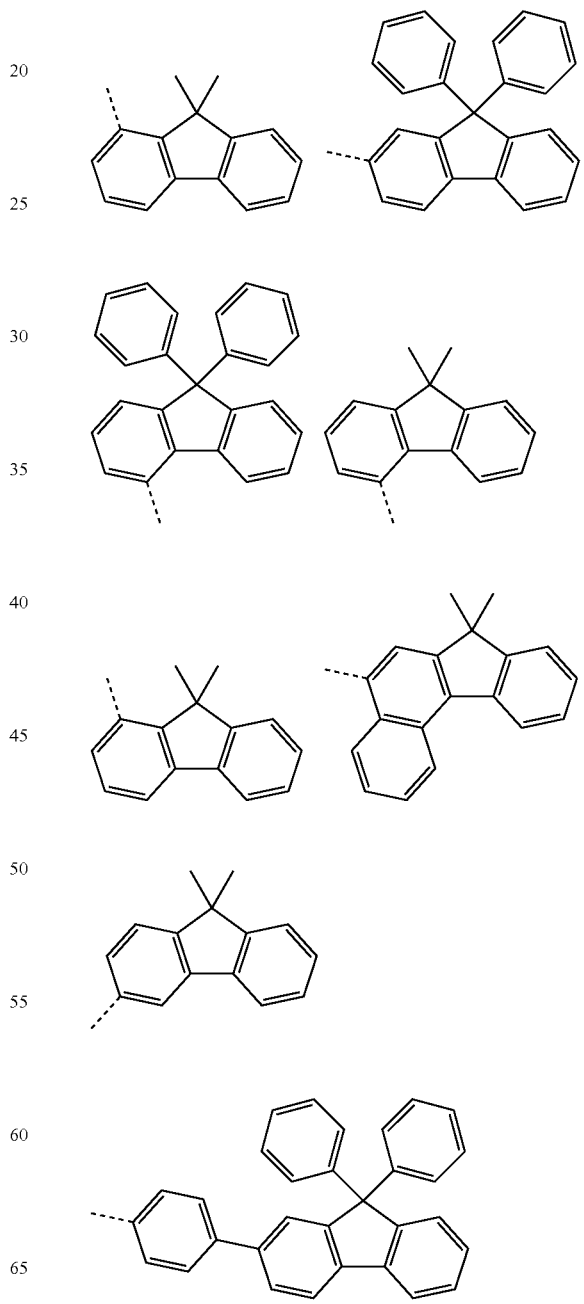

-continued
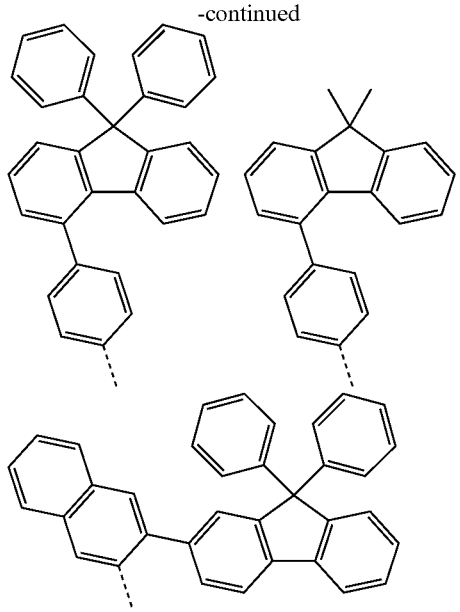
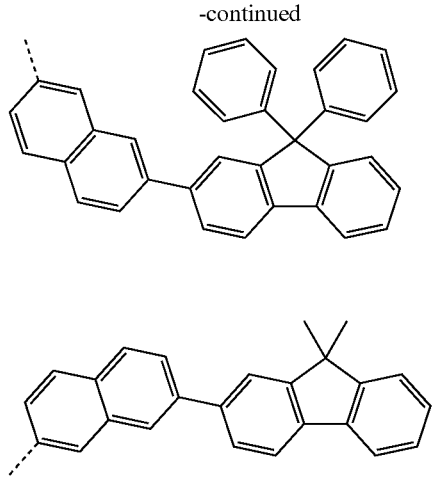
In an exemplary embodiment of the present specification, the heterocyclic compound represented by Formula 1 is represented by any one of the following Formulae 1-1 to 1-627 and 2-1 to 2-363.
| Formula | ---Ar1 | ---Ar2 | ---Ar3 |
|---|---|---|---|
| 1-1 | 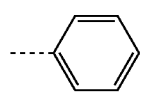 | 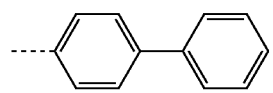 | 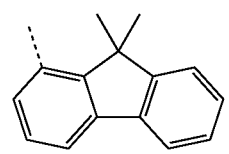 |
| 1-2 | 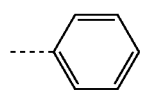 | 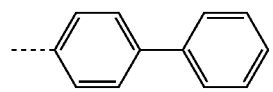 | 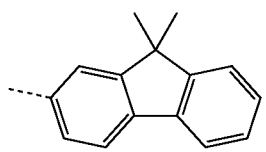 |
| 1-3 | 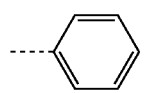 | 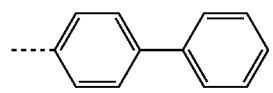 | 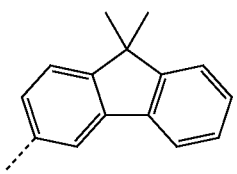 |
| 1-4 | 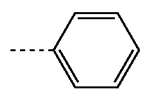 | 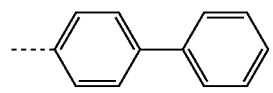 | 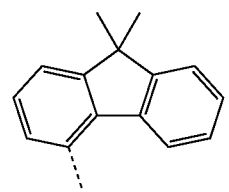 |
| 1-5 | 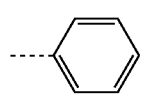 | 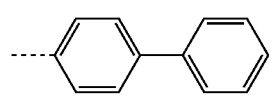 | 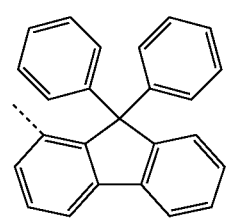 |

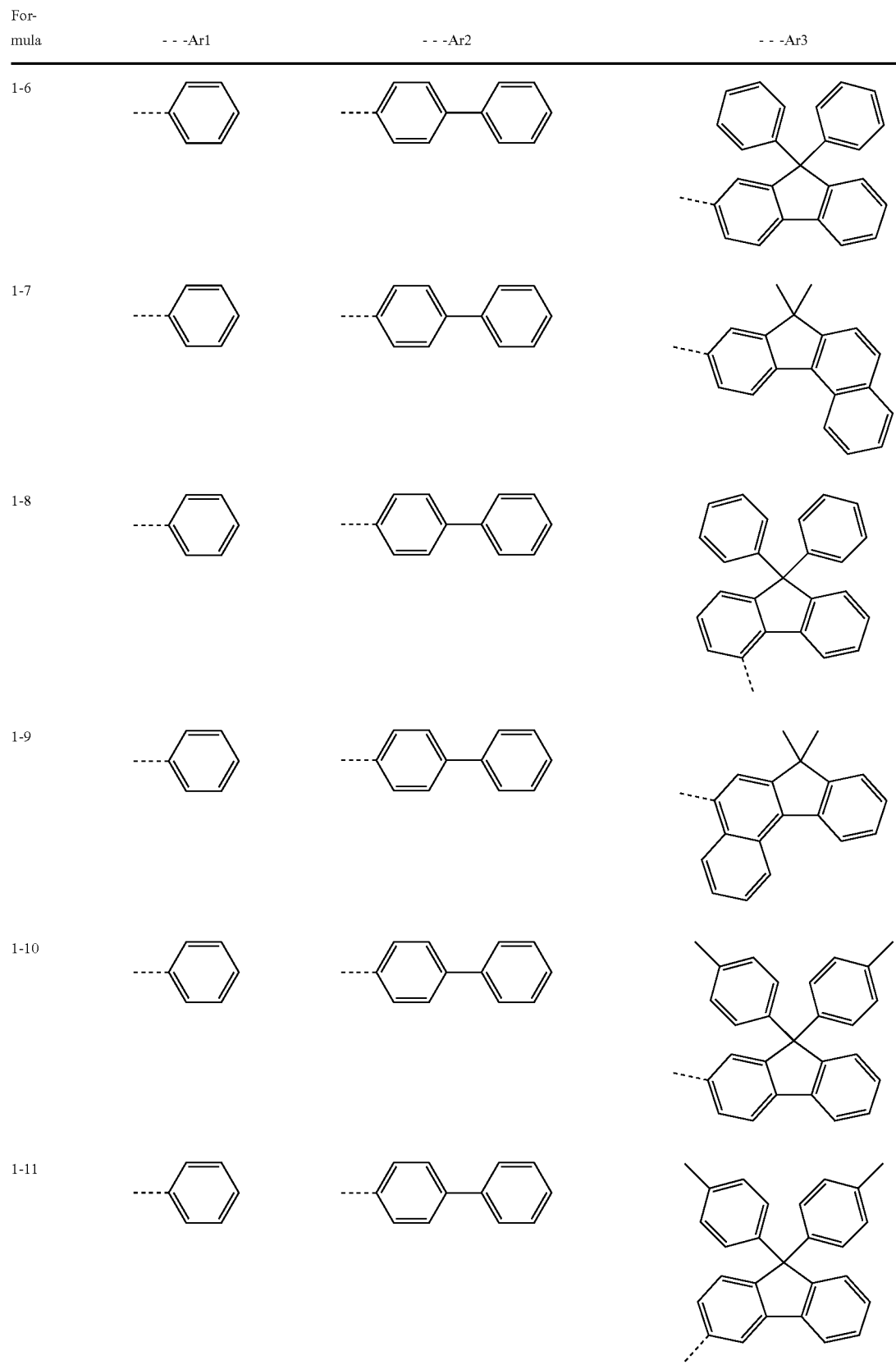

-continued

| Formula | - - -Ar1 | - - -Ar2 | - - -Ar3 |
|---|---|---|---|
| 1-12 | | | |
| 1-13 | | | |
| 1-14 | | | |
| 1-15 | | | |
| 1-16 | | | |
| 1-17 | | | |
| 1-18 | | | |

-continued
| Formula | ---Ar1 | ---Ar2 | ---Ar3 |
|---|---|---|---|
| 1-19 | 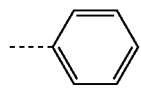 | 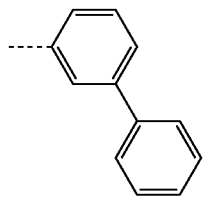 | 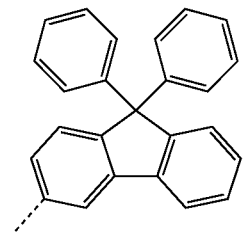 |
| 1-20 | 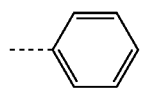 | 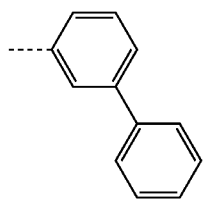 | 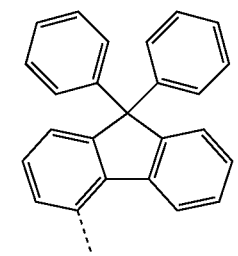 |
| 1-21 | 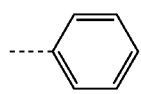 | 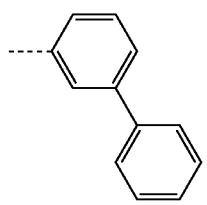 | 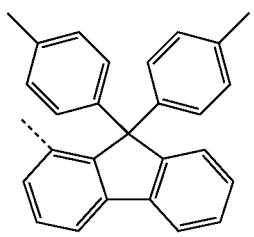 |
| 1-22 | 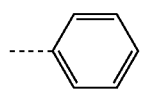 | 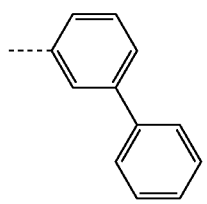 | 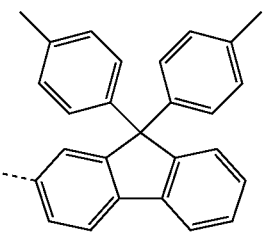 |
| 1-23 | 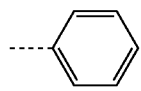 | 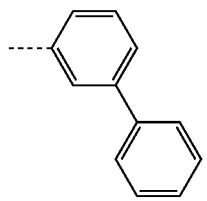 | 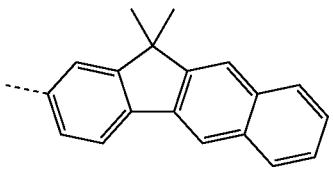 |
| 1-24 | 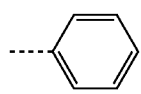 | 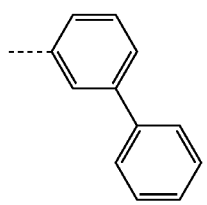 | 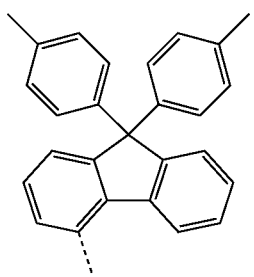 |

-continued

| Formula | - - -Ar1 | - - -Ar2 | - - -Ar3 |
|---|---|---|---|
| 1-25 | phenyl | 2-biphenyl | 9,9-dimethylfluoren-1-yl |
| 1-26 | phenyl | 2-biphenyl | 7-phenyl-9,9-dimethylfluoren-2-yl |
| 1-27 | phenyl | 2-biphenyl | 9-methyl-9-phenylfluoren-3-yl |
| 1-28 | phenyl | 2-biphenyl | 9,9-dimethylfluoren-4-yl |
| 1-29 | phenyl | 2-biphenyl | 9,9-diphenylfluoren-1-yl |
| 1-30 | phenyl | 2-biphenyl | 9,9-diphenylfluoren-2-yl |
| 1-31 | phenyl | 2-biphenyl | dimethyl-benzofluorenyl |

-continued
| Formula | - - -Ar1 | - - -Ar2 | - - -Ar3 |
|---|---|---|---|
| 1-32 | 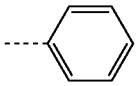 | 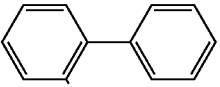 | 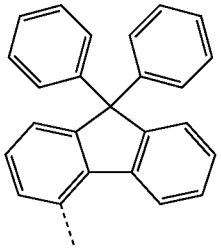 |
| 1-33 | 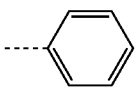 | 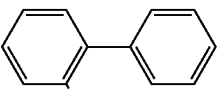 | 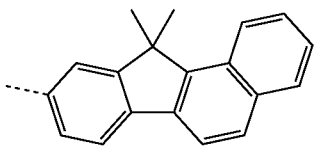 |
| 1-34 | 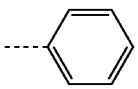 | 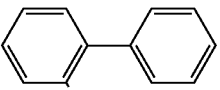 | 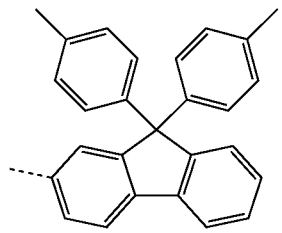 |
| 1-35 | 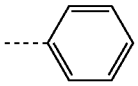 | 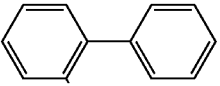 | 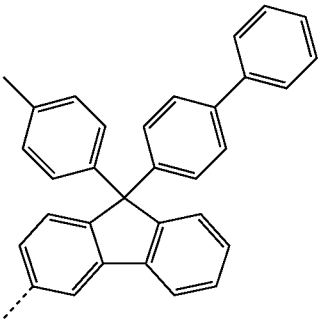 |
| 1-36 | 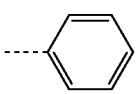 | 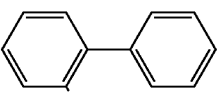 | 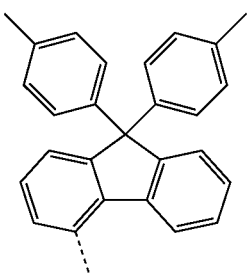 |
| 1-37 | 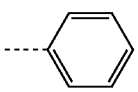 | 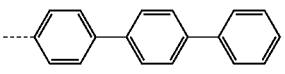 | 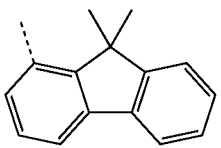 |
| 1-38 | 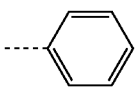 | 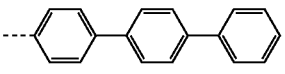 | 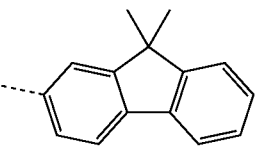 |

-continued

| Formula | ----Ar1 | ----Ar2 | ----Ar3 |
|---|---|---|---|
| 1-39 | phenyl | terphenyl | 9,9-dimethylfluorene |
| 1-40 | phenyl | terphenyl | 9,9-dimethylfluorene |
| 1-41 | phenyl | terphenyl | 9,9-diphenylfluorene |
| 1-42 | phenyl | terphenyl | 9,9-diphenyl-tert-butylfluorene |
| 1-43 | phenyl | terphenyl | 9,9-diphenylfluorene |
| 1-44 | phenyl | terphenyl | 9,9-diphenylfluorene |
| 1-45 | phenyl | terphenyl | methylbenzofluorene |

-continued
| Formula | - - -Ar1 | - - -Ar2 | - - -Ar3 |
|---|---|---|---|
| 1-46 | 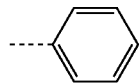 | 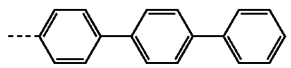 | 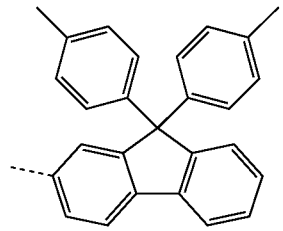 |
| 1-47 | 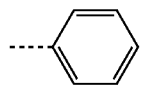 | 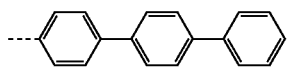 | 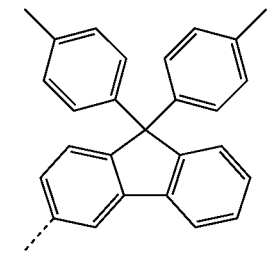 |
| 1-48 | 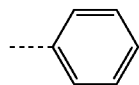 | 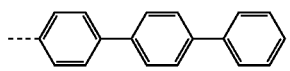 | 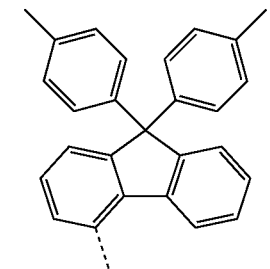 |
| 1-49 | 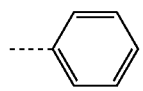 | 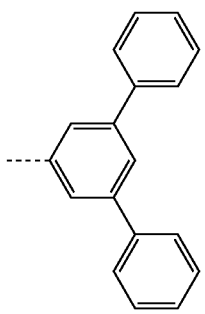 | 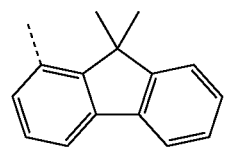 |
| 1-50 | 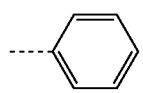 | 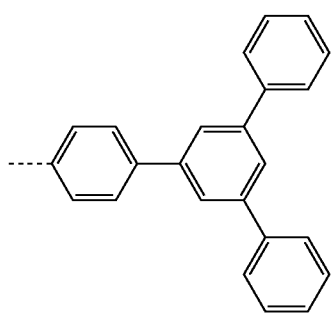 | 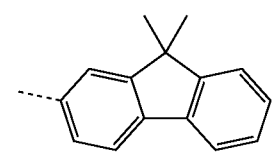 |

-continued
| Formula | - - -Ar1 | - - -Ar2 | - - -Ar3 |
|---|---|---|---|
| 1-51 | 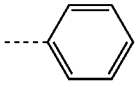 | 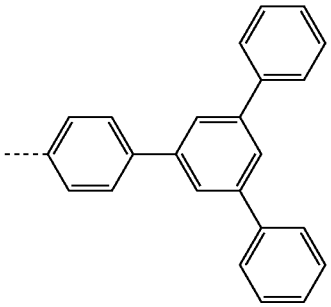 | 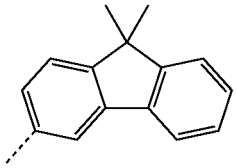 |
| 1-52 | 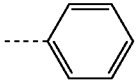 | 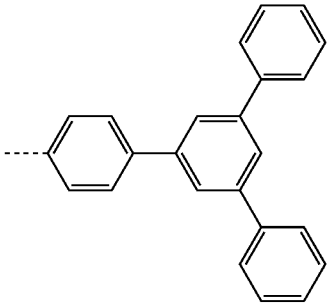 | 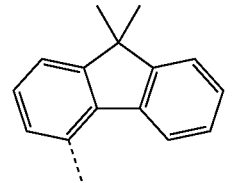 |
| 1-53 | 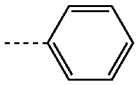 | 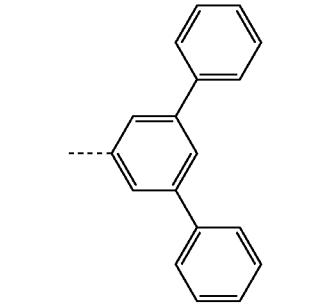 | 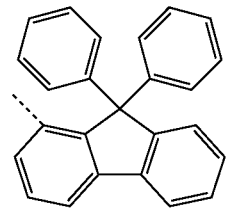 |
| 1-54 | 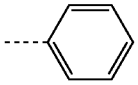 | 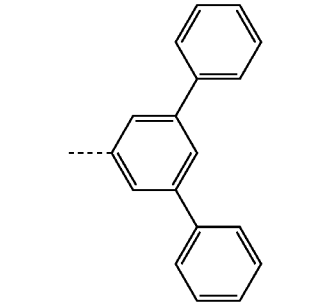 | 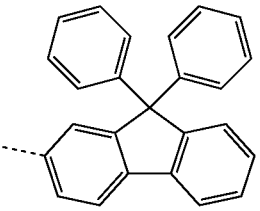 |
| 1-55 | 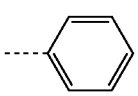 | 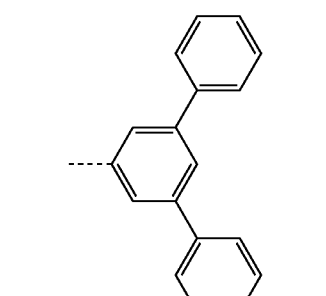 | 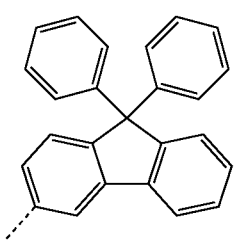 |

-continued

| Formula | - - -Ar1 | - - -Ar2 | - - -Ar3 |
|---|---|---|---|
| 1-56 | phenyl | 1,3,5-triphenylbenzene (attached at 5-position) | 9,9-diphenylfluorene (attached at 4-position) |
| 1-57 | phenyl | 1,3,5-triphenylbenzene (attached at 5-position) | 11,11-dimethyl-11H-benzo[b]fluorene |
| 1-58 | phenyl | 1,3,5-triphenylbenzene (attached at 5-position) | 9,9-di(p-tolyl)fluorene (attached at 2-position) |
| 1-59 | phenyl | 1,3,5-triphenylbenzene (attached at 5-position) | 9,9-di(p-tolyl)fluorene (attached at 3-position) |
| 1-60 | phenyl | 1,3,5-triphenylbenzene (attached at 5-position) | 9,9-di(p-tolyl)fluorene (attached at 4-position) |

-continued

| Formula | ---Ar1 | ---Ar2 | ---Ar3 |
|---|---|---|---|
| 1-61 | | | |
| 1-62 | | | |
| 1-63 | | | |
| 1-64 | | | |
| 1-65 | | | |
| 1-66 | | | |
| 1-67 | | | |

-continued

| Formula | ---Ar1 | ---Ar2 | ---Ar3 |
|---|---|---|---|
| 1-68 | phenyl | m-terphenyl | 9,9-diphenylfluoren-4-yl |
| 1-69 | phenyl | m-terphenyl | 9,9-dimethyl-benzo[a]fluorenyl |
| 1-70 | phenyl | m-terphenyl | 9,9-di(p-tolyl)fluoren-2-yl |
| 1-71 | phenyl | m-terphenyl | 9,9-di(p-tolyl)fluoren-3-yl |
| 1-72 | phenyl | m-terphenyl | 9,9-di(p-tolyl)fluoren-4-yl |
| 1-73 | phenyl | 2-naphthyl | 9,9-dimethylfluoren-1-yl |
| 1-74 | phenyl | 2-naphthyl | 9,9-dimethyl-7-phenylfluoren-2-yl |

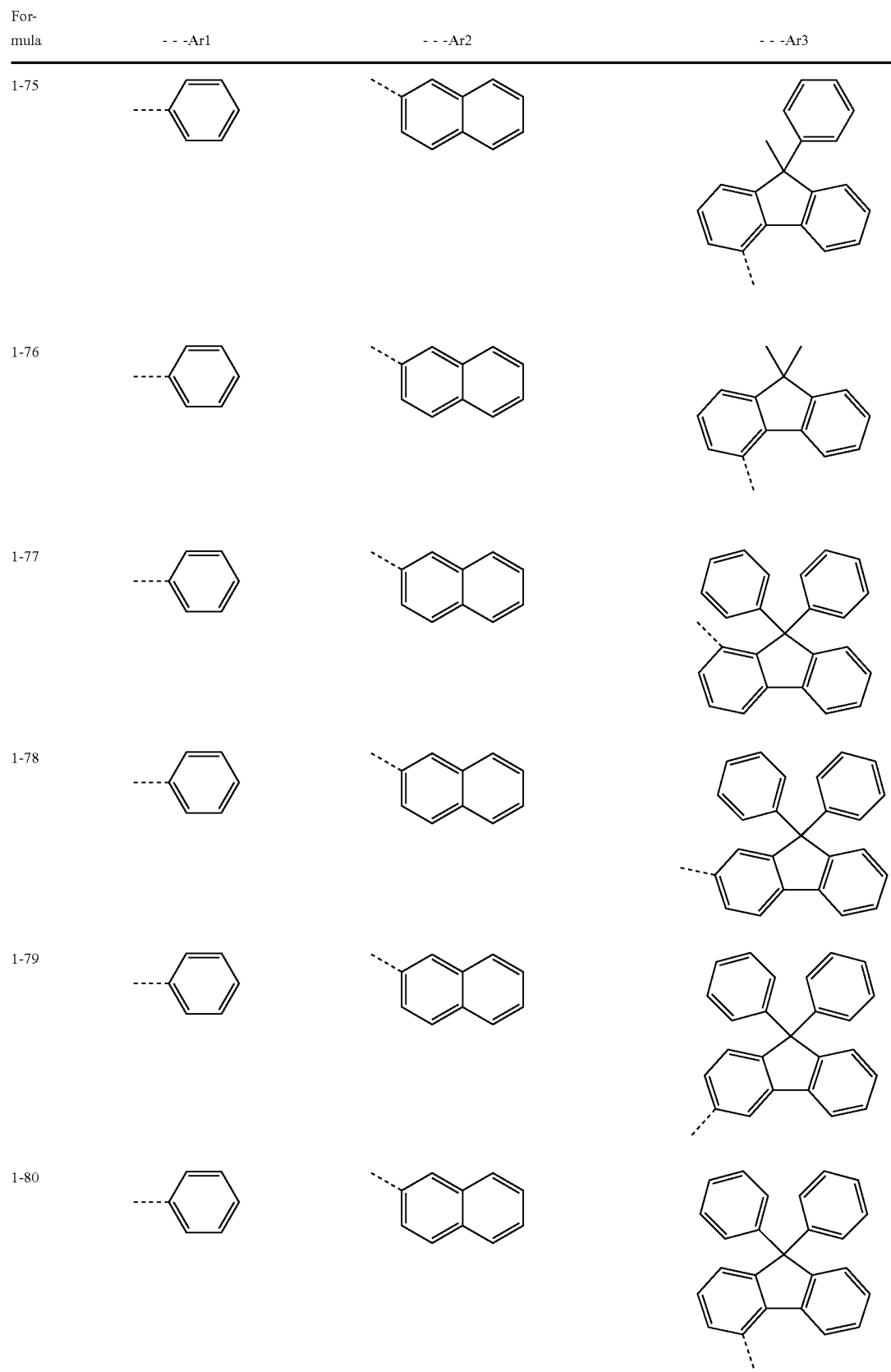

| Formula | ---Ar1 | ---Ar2 | ---Ar3 |
|---|---|---|---|
| 1-81 | 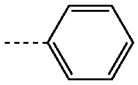 | 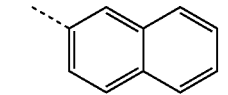 | 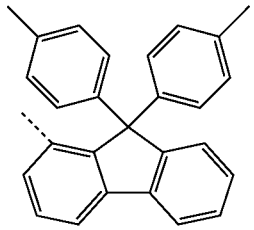 |
| 1-82 | 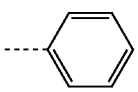 | 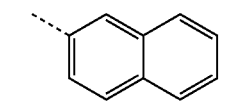 | 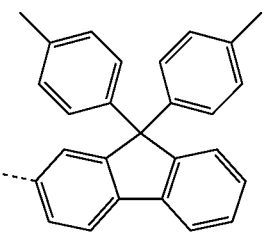 |
| 1-83 | 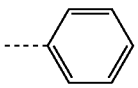 | 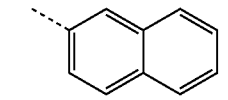 | 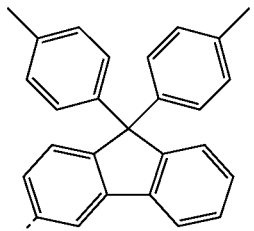 |
| 1-84 | 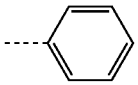 | 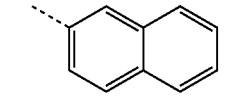 | 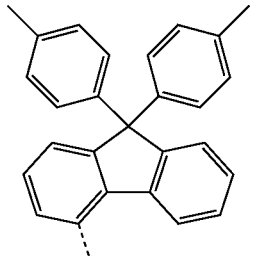 |
| 1-85 | 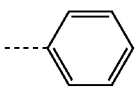 | 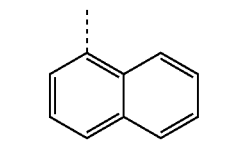 | 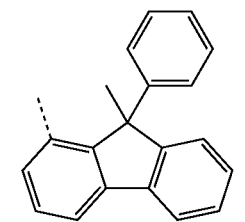 |
| 1-86 | 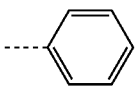 | 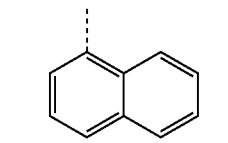 | 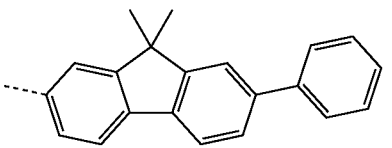 |
| 1-87 | 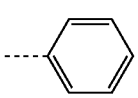 | 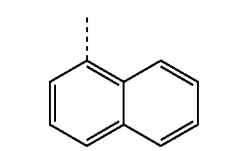 | 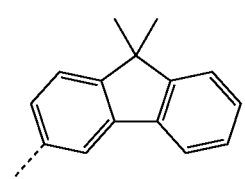 |

-continued
| Formula | ---Ar1 | ---Ar2 | ---Ar3 |
|---|---|---|---|
| 1-88 | 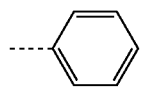 | 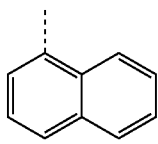 | 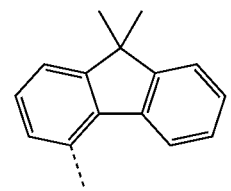 |
| 1-89 | 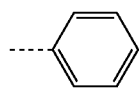 | 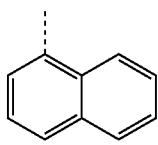 | 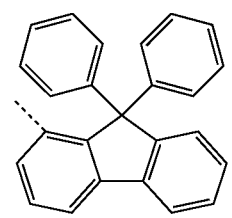 |
| 1-90 | 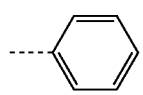 | 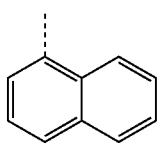 | 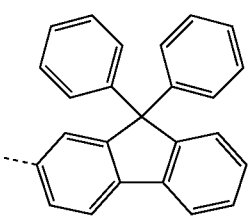 |
| 1-91 | 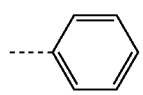 | 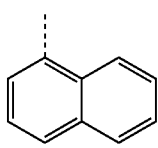 | 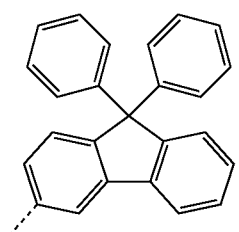 |
| 1-92 | 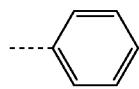 | 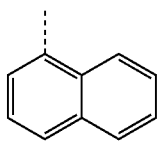 | 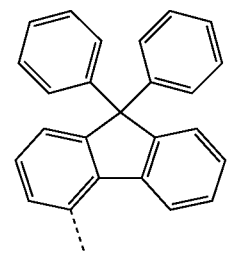 |
| 1-93 | 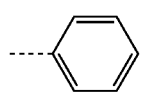 | 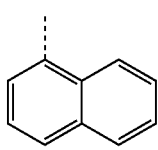 | 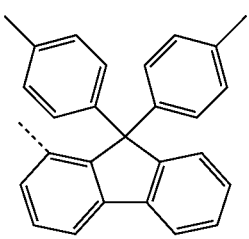 |

-continued

| Formula | ---Ar1 | ---Ar2 | ---Ar3 |
|---|---|---|---|
| 1-94 | phenyl | 1-naphthyl | 9,9-bis(p-tolyl)fluoren-2-yl |
| 1-95 | phenyl | 1-naphthyl | 9-phenyl-9-(2-naphthyl)fluoren-3-yl |
| 1-96 | phenyl | 1-naphthyl | 9,9-bis(p-tolyl)fluoren-4-yl |
| 1-97 | phenyl | 9-phenanthryl | 9,9-dimethylfluoren-1-yl |
| 1-98 | phenyl | 9-phenanthryl | 9,9-dimethylfluoren-2-yl |
| 1-99 | phenyl | 9-phenanthryl | 9,9-dimethyl-7-phenylfluoren-2-yl |
| 1-100 | phenyl | 9-phenanthryl | 9,9-dimethylfluoren-4-yl |

-continued

-continued
| Formula | - - -Ar1 | - - -Ar2 | - - -Ar3 |
|---|---|---|---|
| 1-107 | 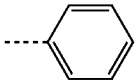 | 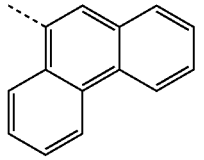 | 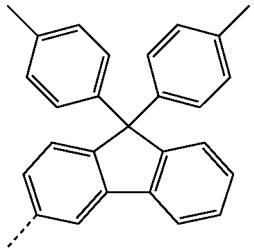 |
| 1-108 | 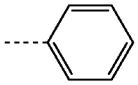 | 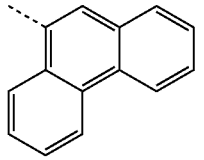 | 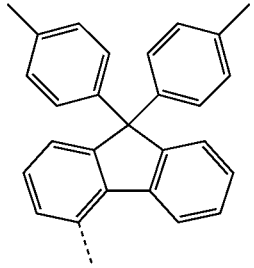 |
| 1-109 | 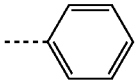 | 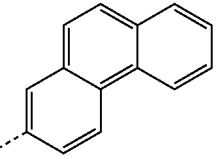 | 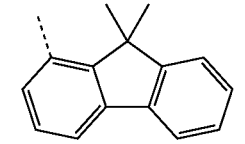 |
| 1-110 | 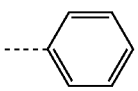 | 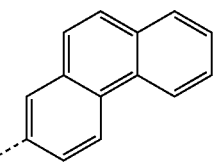 | 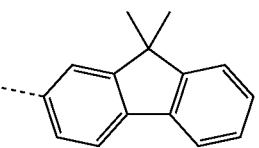 |
| 1-111 | 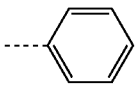 | 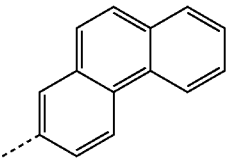 | 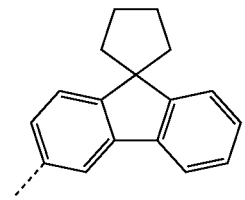 |
| 1-112 | 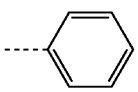 | 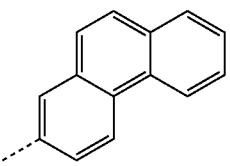 | 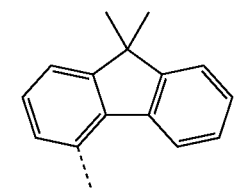 |
| 1-113 | 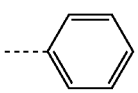 | 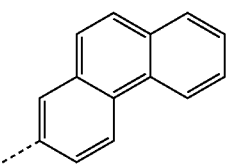 | 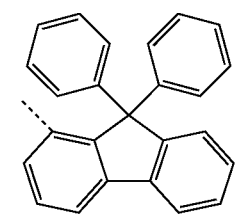 |

-continued
| Formula | ---Ar1 | ---Ar2 | ---Ar3 |
|---|---|---|---|
| 1-114 | 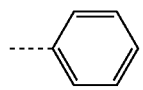 | 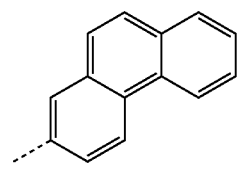 | 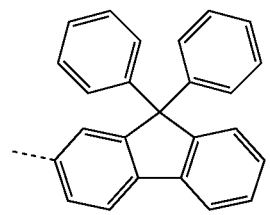 |
| 1-115 | 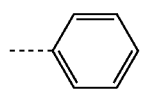 | 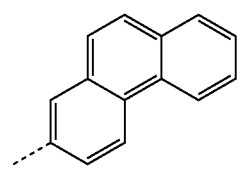 | 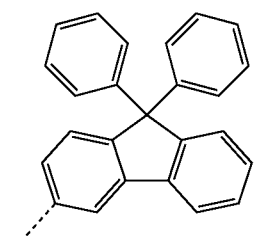 |
| 1-116 | 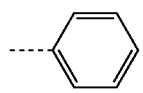 | 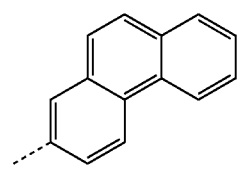 | 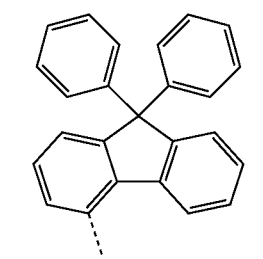 |
| 1-117 | 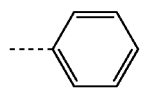 | 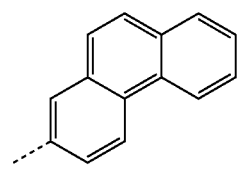 | 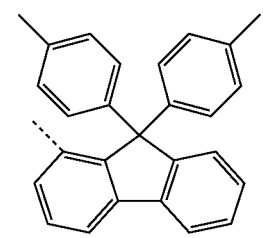 |
| 1-118 | 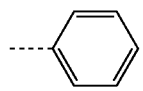 | 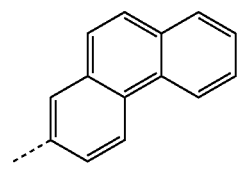 | 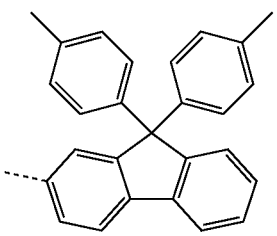 |
| 1-119 | 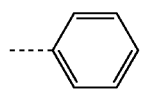 | 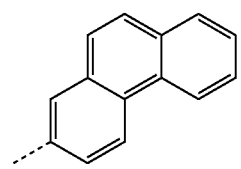 | 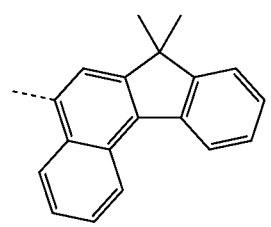 |

-continued

| Formula | - - -Ar1 | - - -Ar2 | - - -Ar3 |
|---|---|---|---|
| 1-120 | phenyl | phenanthrenyl | 9,9-di(p-tolyl)fluorenyl |
| 1-121 | phenyl | phenanthrenyl | 9,9-dimethylfluorenyl |
| 1-122 | phenyl | phenanthrenyl | 9,9-dimethyl-7-phenylfluorenyl |
| 1-123 | phenyl | phenanthrenyl | 9,9-dimethylfluorenyl |
| 1-124 | phenyl | phenanthrenyl | 9,9-dimethylfluorenyl |
| 1-125 | phenyl | phenanthrenyl | 9,9-diphenylfluorenyl |
| 1-126 | phenyl | phenanthrenyl | 9,9-diphenylfluorenyl |

US 11,271,167 B2
-continued
| Formula | ---Ar1 | ---Ar2 | ---Ar3 |
|---|---|---|---|
| 1-127 | 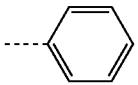 | 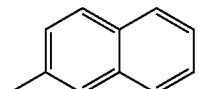 | 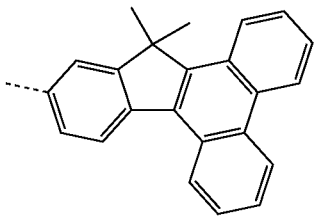 |
| 1-128 | 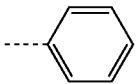 | 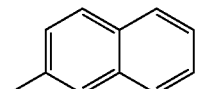 | 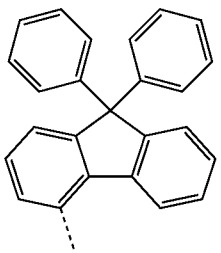 |
| 1-129 | 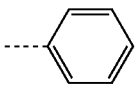 | 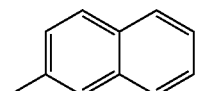 | 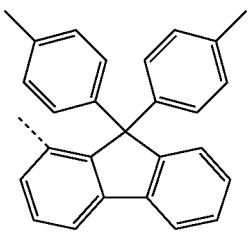 |
| 1-130 | 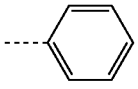 | 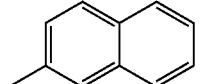 | 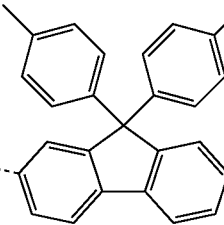 |
| 1-131 | 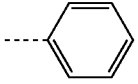 | 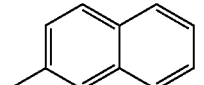 | 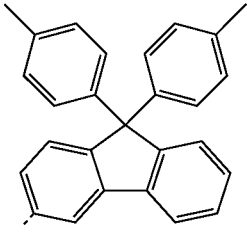 |
| 1-132 | 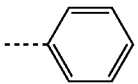 | 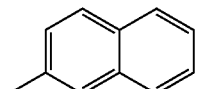 | 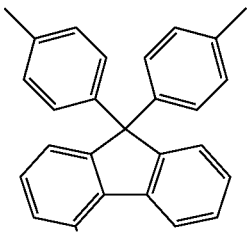 |

-continued
| Formula | ---Ar1 | ---Ar2 | ---Ar3 |
|---|---|---|---|
| 1-133 | 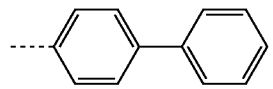 | 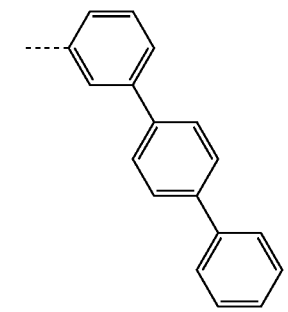 | 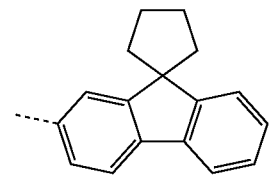 |
| 1-134 | 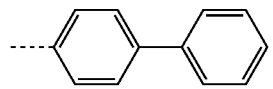 | 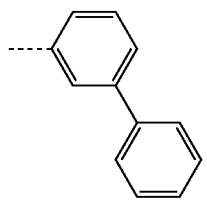 | 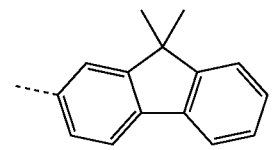 |
| 1-135 | 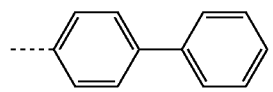 | 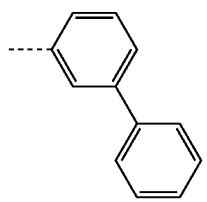 | 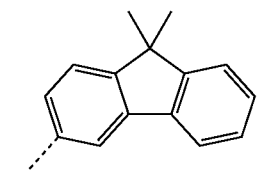 |
| 1-136 | 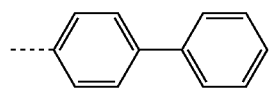 | 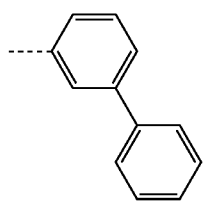 | 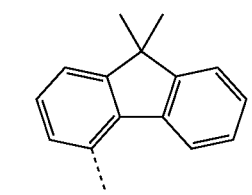 |
| 1-137 | 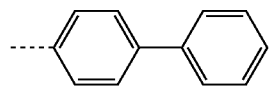 | 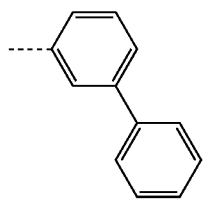 | 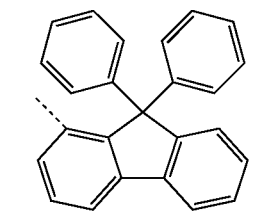 |
| 1-138 | 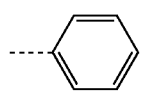 | 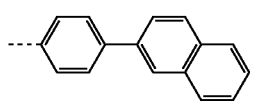 | 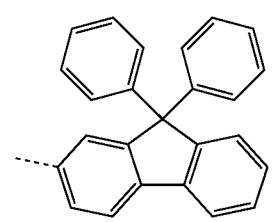 |

-continued

| Formula | ---Ar1 | ---Ar2 | ---Ar3 |
|---|---|---|---|
| 1-139 | biphenyl | biphenyl (meta) | 9,9-diphenylfluorene |
| 1-140 | biphenyl | biphenyl (meta) | 9,9-diphenylfluorene |
| 1-141 | biphenyl | biphenyl (meta) | 9,9-di(p-tolyl)fluorene |
| 1-142 | biphenyl | biphenyl (meta) | 9,9-di(p-tolyl)fluorene |
| 1-143 | biphenyl | 1-naphthylphenyl | 9,9-diphenylfluorene |
| 1-144 | biphenyl | biphenyl (meta) | 9,9-di(p-tolyl)fluorene |

-continued
| Formula | - - -Ar1 | - - -Ar2 | - - -Ar3 |
|---|---|---|---|
| 1-145 | 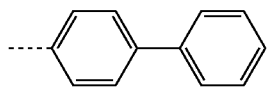 | 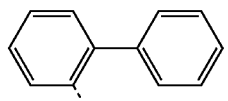 | 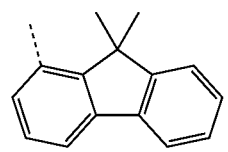 |
| 1-146 | 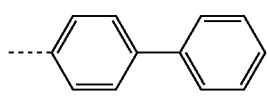 | 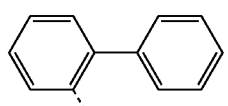 | 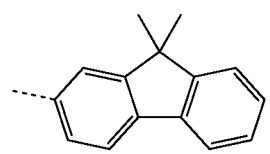 |
| 1-147 | 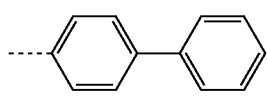 | 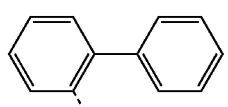 | 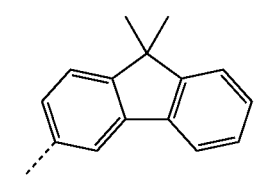 |
| 1-148 | 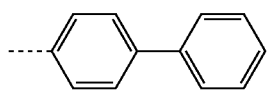 | 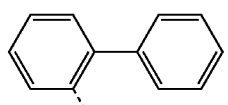 | 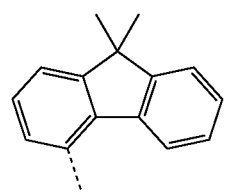 |
| 1-149 | 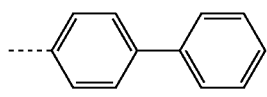 | 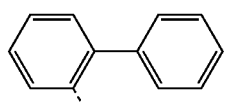 | 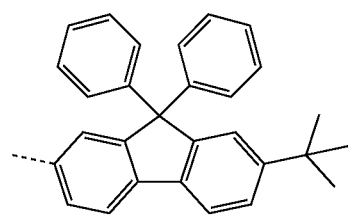 |
| 1-150 | 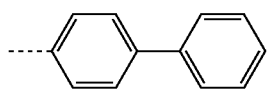 | 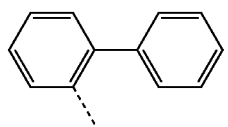 | 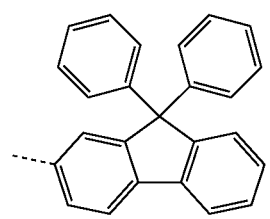 |
| 1-151 | 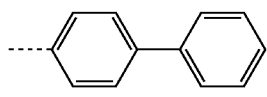 | 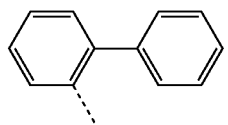 | 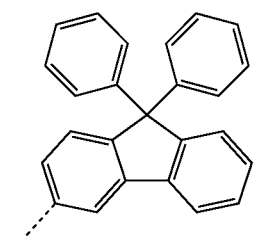 |

-continued

| Formula | ---Ar1 | ---Ar2 | ---Ar3 |
|---|---|---|---|
| 1-152 | | | |
| 1-153 | | | |
| 1-154 | | | |
| 1-155 | | | |
| 1-156 | | | |
| 1-157 | | | |
| 1-158 | | | |

-continued

| Formula | ---Ar1 | ---Ar2 | ---Ar3 |
|---|---|---|---|
| 1-159 | biphenyl | p-terphenyl | 9,9-dimethylfluorene (3-yl) |
| 1-160 | biphenyl | p-terphenyl | 9,9-dimethylfluorene (4-yl) |
| 1-161 | biphenyl | phenyl-naphthalene | 9,9-diphenylfluorene |
| 1-162 | biphenyl | p-terphenyl | 9,9-diphenylfluorene (2-yl) |
| 1-163 | biphenyl | p-terphenyl | 9,9-diphenylfluorene (3-yl) |
| 1-164 | biphenyl | p-terphenyl | 9,9-diphenylfluorene (4-yl) |
| 1-165 | biphenyl | phenyl-naphthalene | 9,9-bis(4-methylphenyl)fluorene |

-continued
| Formula | ---Ar1 | ---Ar2 | ---Ar3 |
|---|---|---|---|
| 1-166 | 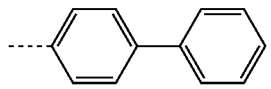 | 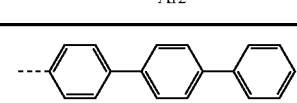 | 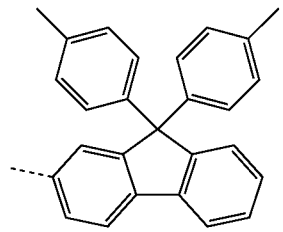 |
| 1-167 | 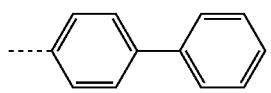 | 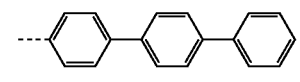 | 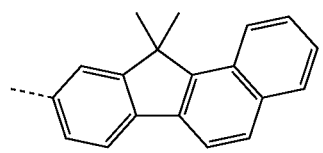 |
| 1-168 | 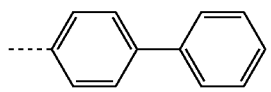 | 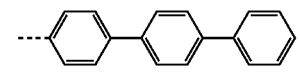 | 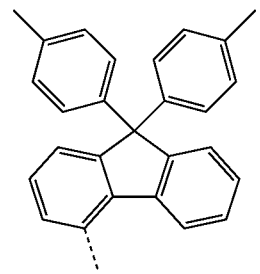 |
| 1-169 | 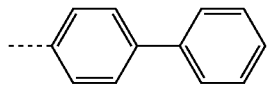 | 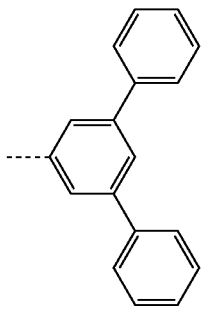 | 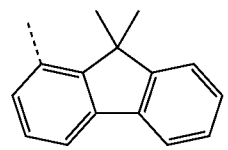 |
| 1-170 | 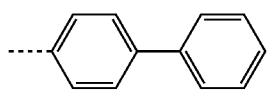 | 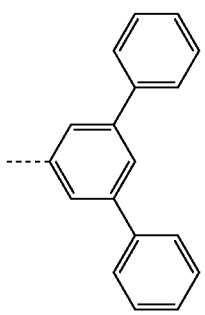 | 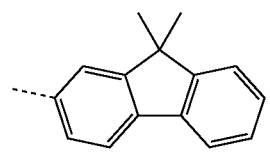 |

-continued

| Formula | ---Ar1 | ---Ar2 | ---Ar3 |
|---|---|---|---|
| 1-171 | | | |
| 1-172 | | | |
| 1-173 | | | |
| 1-174 | | | |
| 1-175 | | | |

-continued

| Formula | - - -Ar1 | - - -Ar2 | - - -Ar3 |
|---|---|---|---|
| 1-176 | | | |
| 1-177 | | | |
| 1-178 | | | |
| 1-179 | | | |
| 1-180 | | | |

-continued

| Formula | - - -Ar1 | - - -Ar2 | - - -Ar3 |
|---------|----------|----------|----------|
| 1-181 | biphenyl | m-terphenyl | 9,9-dimethylfluoren-1-yl |
| 1-182 | biphenyl | m-terphenyl | 9,9-dimethylfluoren-2-yl |
| 1-183 | biphenyl | m-terphenyl | 9,9-dimethylfluoren-3-yl |
| 1-184 | biphenyl | m-terphenyl | 9,9-dimethylfluoren-4-yl |
| 1-185 | biphenyl | m-terphenyl | 9,9-diphenylfluoren-1-yl |
| 1-186 | biphenyl | m-terphenyl | 9,9-diphenylfluoren-2-yl |
| 1-187 | biphenyl | m-terphenyl | 9,9-diphenylfluoren-3-yl |

-continued

| Formula | - - -Ar1 | - - -Ar2 | - - -Ar3 |
|---|---|---|---|
| 1-188 | | | |
| 1-189 | | | |
| 1-190 | | | |
| 1-191 | | | |
| 1-192 | | | |
| 1-193 | | | |

-continued

| Formula | - - -Ar1 | - - -Ar2 | - - -Ar3 |
|---|---|---|---|
| 1-194 | biphenyl | naphthyl | 9,9-dimethylfluorenyl |
| 1-195 | biphenyl | binaphthyl | 9,9-dimethylfluorenyl |
| 1-196 | biphenyl | naphthyl | 9,9-dimethylfluorenyl |
| 1-197 | biphenyl | naphthyl | 9,9-diphenylfluorenyl |
| 1-198 | biphenyl | naphthyl | 9,9-diphenylfluorenyl |
| 1-199 | biphenyl | phenylnaphthyl | 9,9-diphenylfluorenyl |
| 1-200 | biphenyl | phenylnaphthyl | 9,9-diphenylfluorenyl |

-continued
| Formula | - - -Ar1 | - - -Ar2 | - - -Ar3 |
|---|---|---|---|
| 1-201 | 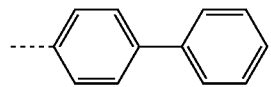 | 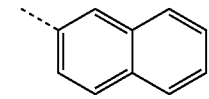 | 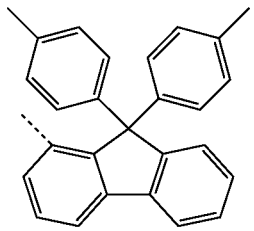 |
| 1-202 | 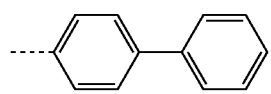 | 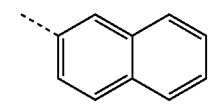 | 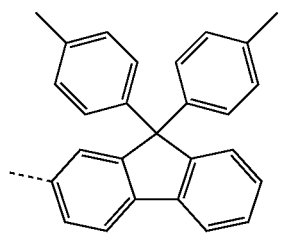 |
| 1-203 | 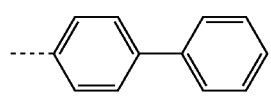 | 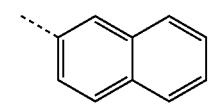 | 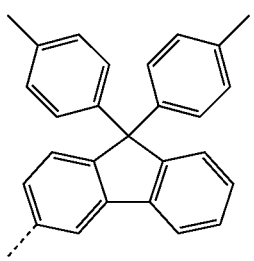 |
| 1-204 | 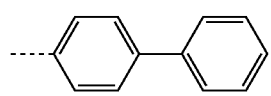 | 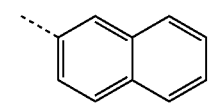 | 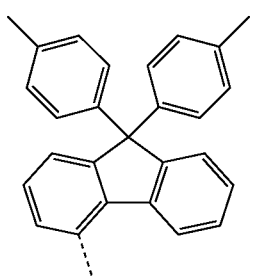 |
| 1-205 | 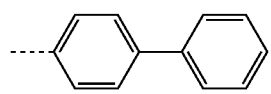 | 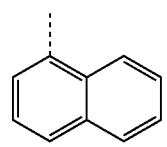 | 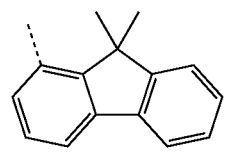 |
| 1-206 | 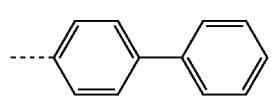 | 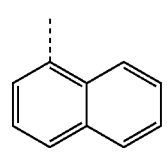 | 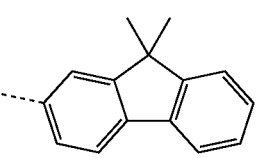 |

-continued
| Formula | - - -Ar1 | - - -Ar2 | - - -Ar3 |
|---|---|---|---|
| 1-207 | 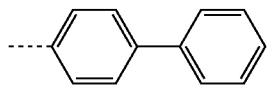 | 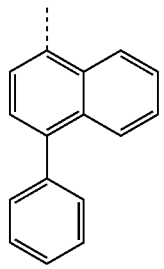 | 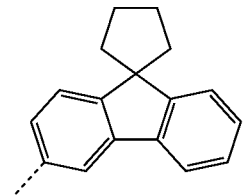 |
| 1-208 | 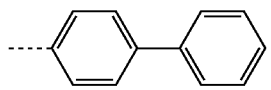 | 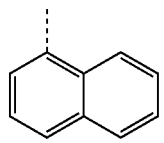 | 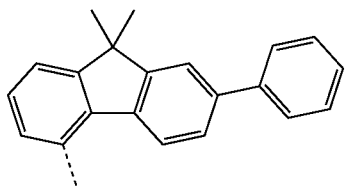 |
| 1-209 | 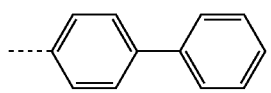 | 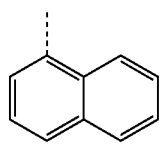 | 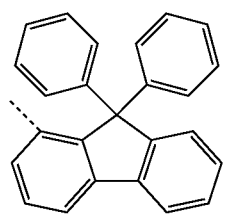 |
| 1-210 | 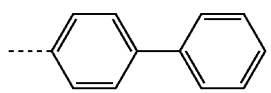 | 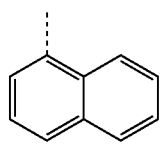 | 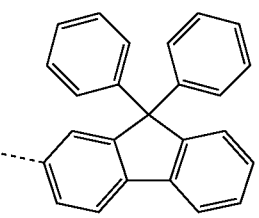 |
| 1-211 | 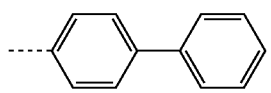 | 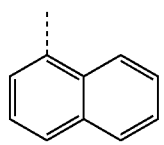 | 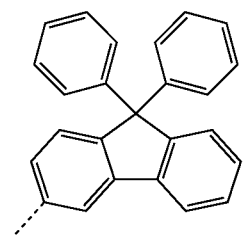 |
| 1-212 | 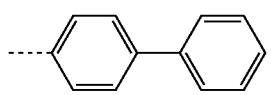 | 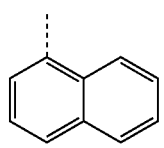 | 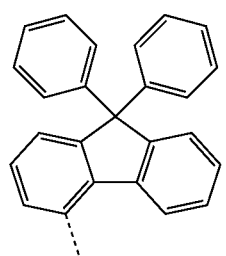 |

-continued

| Formula | ----Ar1 | ----Ar2 | ----Ar3 |
|---|---|---|---|
| 1-213 | biphenyl | 4-phenyl-1-naphthyl | 9,9-bis(p-tolyl)fluoren-1-yl |
| 1-214 | biphenyl | 1-naphthyl | 9,9-bis(p-tolyl)fluoren-2-yl |
| 1-215 | biphenyl | 1-naphthyl | 9,9-bis(p-tolyl)fluoren-3-yl |
| 1-216 | biphenyl | 1-naphthyl | 9,9-bis(p-tolyl)fluoren-4-yl |
| 1-217 | biphenyl | 9-phenanthryl | 9,9-dimethylfluoren-1-yl |
| 1-218 | biphenyl | 9-phenanthryl | 9,9-dimethylfluoren-2-yl |
| 1-219 | biphenyl | 9-phenanthryl | 9,9-dimethylfluoren-3-yl |

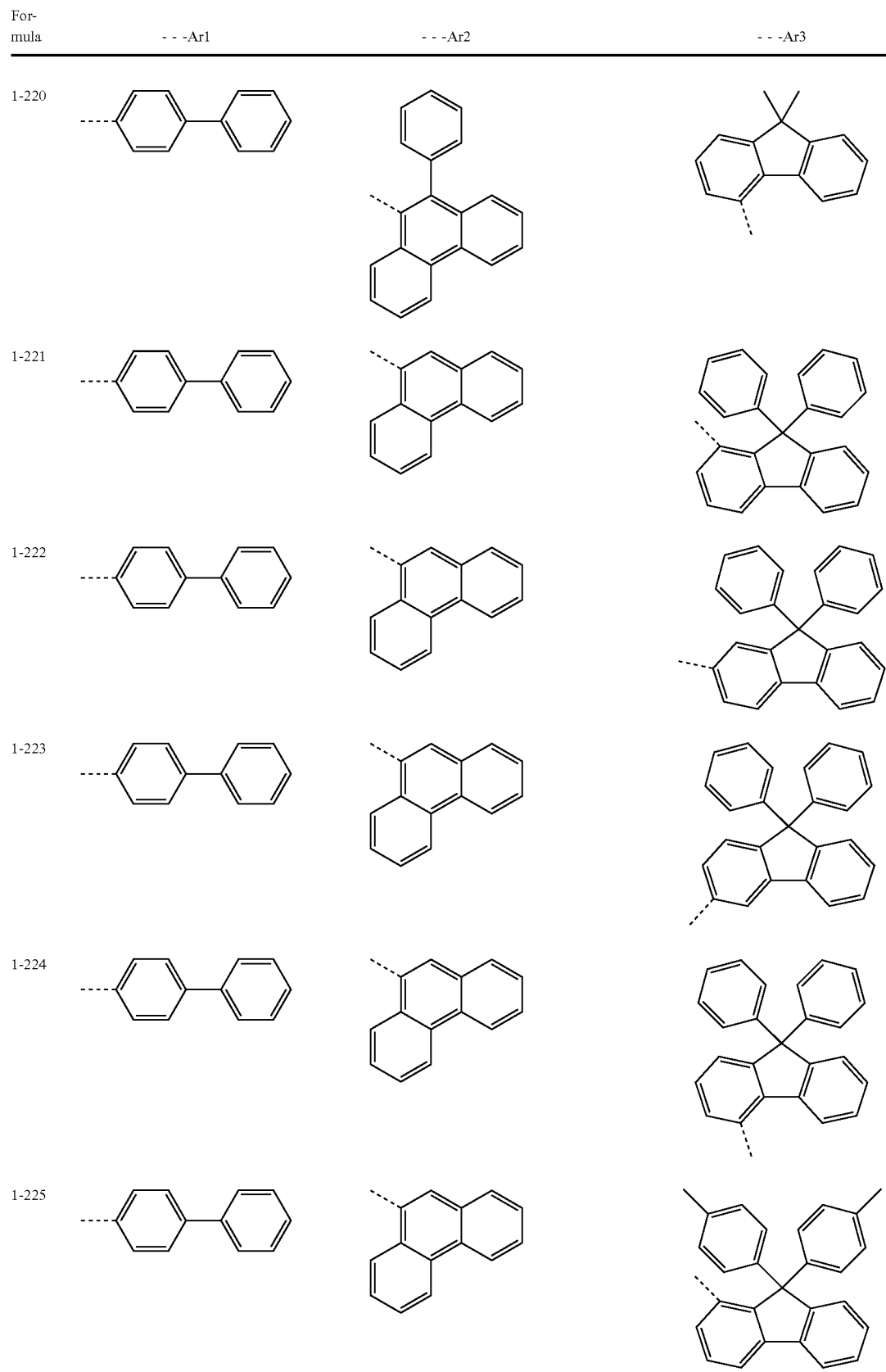

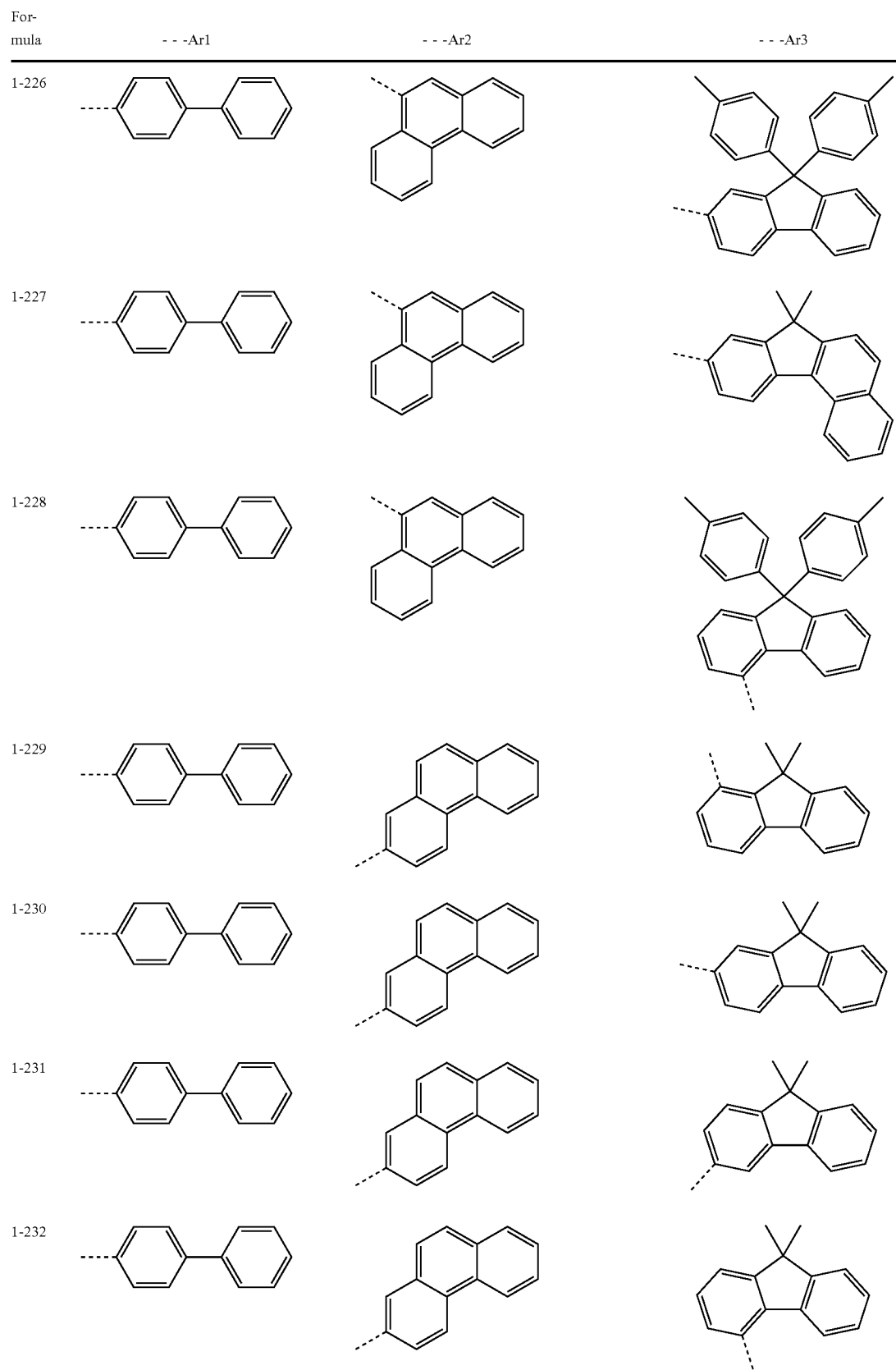

-continued
| Formula | ---Ar1 | ---Ar2 | ---Ar3 |
|---|---|---|---|
| 1-233 | 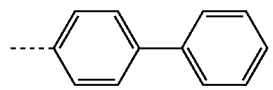 | 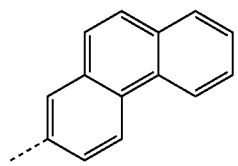 | 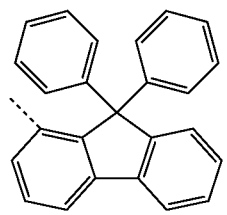 |
| 1-234 | 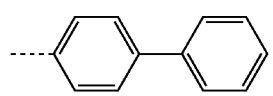 | 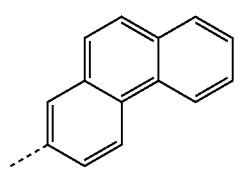 | 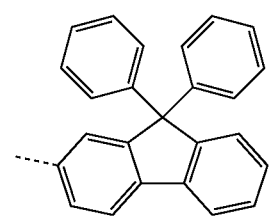 |
| 1-235 | 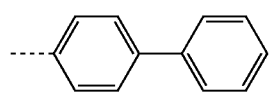 | 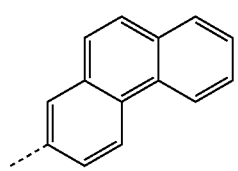 | 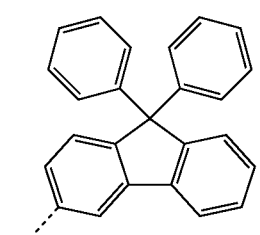 |
| 1-236 | 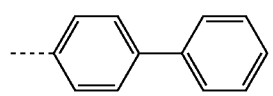 | 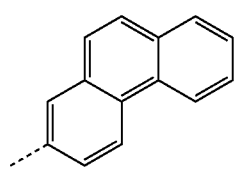 | 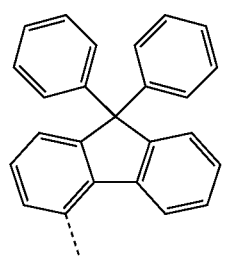 |
| 1-237 | 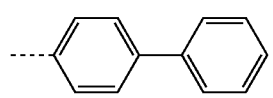 | 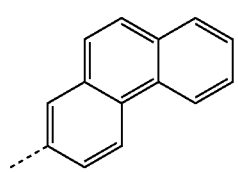 | 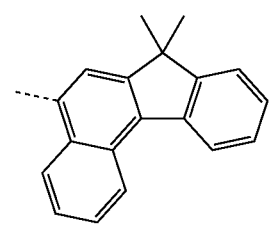 |
| 1-238 | 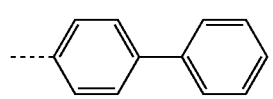 | 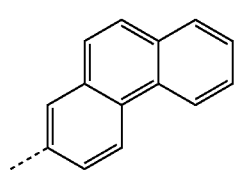 | 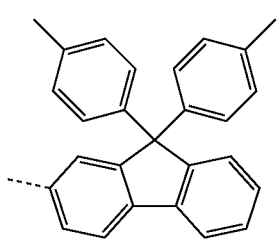 |

-continued
| Formula | ---Ar1 | ---Ar2 | ---Ar3 |
|---|---|---|---|
| 1-239 | 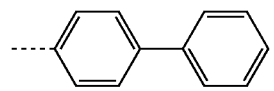 | 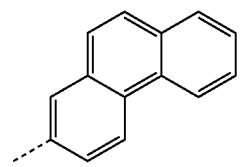 | 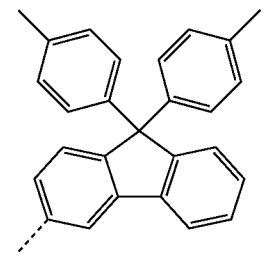 |
| 1-240 | 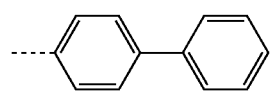 | 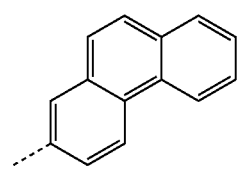 | 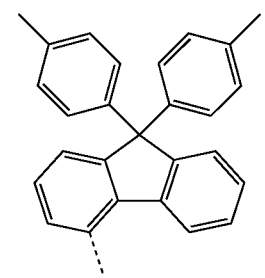 |
| 1-241 | 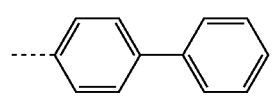 | 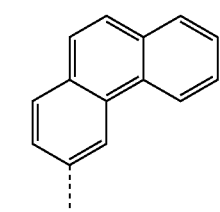 | 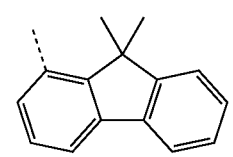 |
| 1-242 | 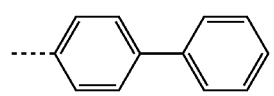 | 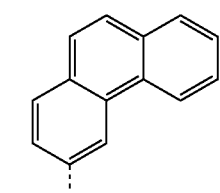 | 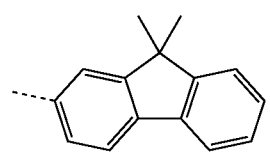 |
| 1-243 | 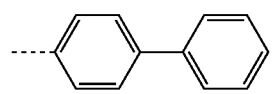 | 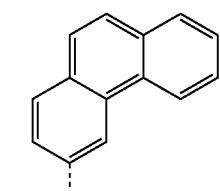 | 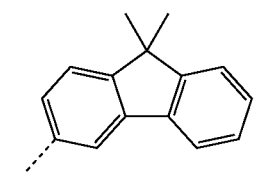 |
| 1-244 | 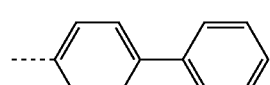 | 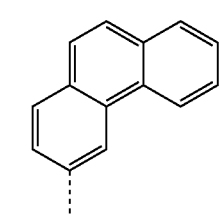 | 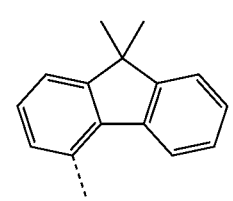 |

| Formula | ---Ar1 | ---Ar2 | ---Ar3 |
|---|---|---|---|
| 1-245 | 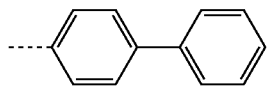 | 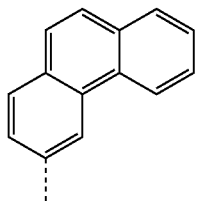 | 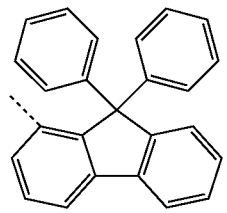 |
| 1-246 | 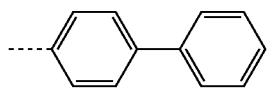 | 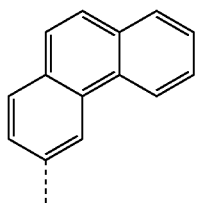 | 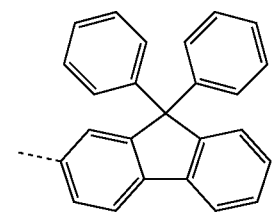 |
| 1-247 | 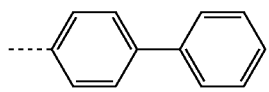 | 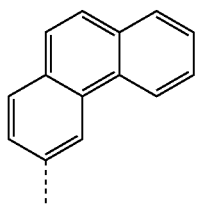 | 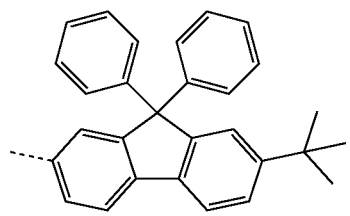 |
| 1-248 | 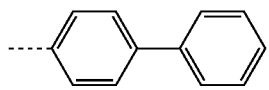 | 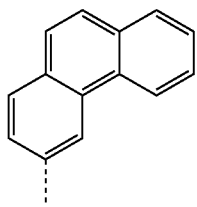 | 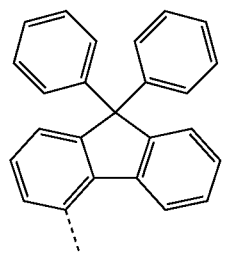 |
| 1-249 | 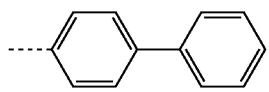 | 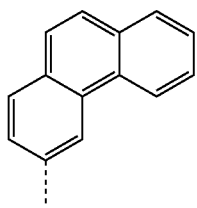 | 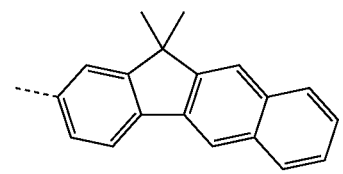 |
| 1-250 | 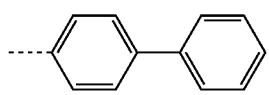 | 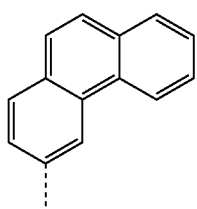 | 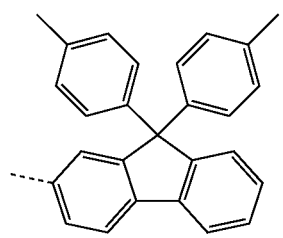 |

-continued

| Formula | ---Ar1 | ---Ar2 | ---Ar3 |
|---|---|---|---|
| 1-251 | biphenyl | phenanthrene | 9,9-di(p-tolyl)fluorene |
| 1-252 | biphenyl | phenanthrene | 9,9-di(p-tolyl)fluorene |
| 1-253 | naphthalene | biphenyl | 9,9-dimethylfluorene |
| 1-254 | naphthalene | biphenyl | 9,9-dimethylfluorene |
| 1-255 | naphthalene | biphenyl | 9,9-dimethylfluorene |
| 1-256 | naphthalene | biphenyl | 9,9-dimethylfluorene |
| 1-257 | naphthalene | phenyl-naphthalene | dimethyl-dibenzo[g,p]chrysene/fluorene derivative |

-continued
| Formula | ---Ar1 | ---Ar2 | ---Ar3 |
|---|---|---|---|
| 1-258 | 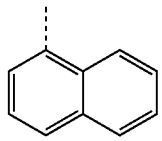 | 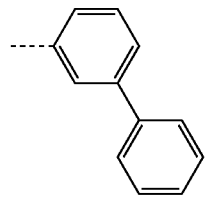 | 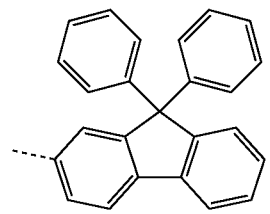 |
| 1-259 | 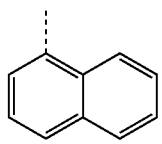 | 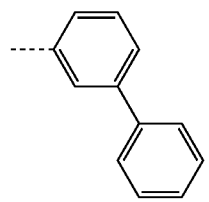 | 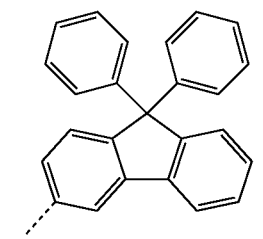 |
| 1-260 | 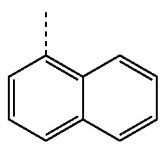 | 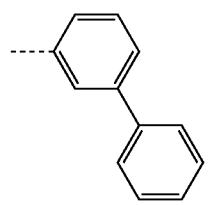 | 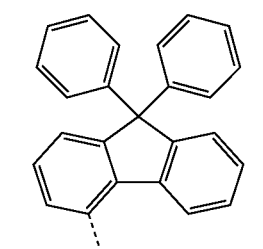 |
| 1-261 | 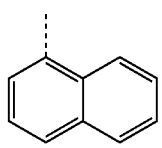 | 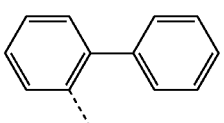 | 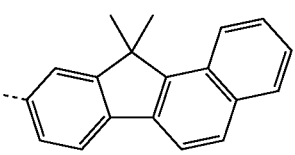 |
| 1-262 | 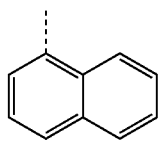 | 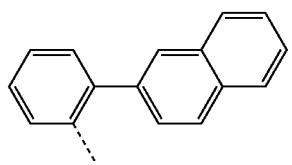 | 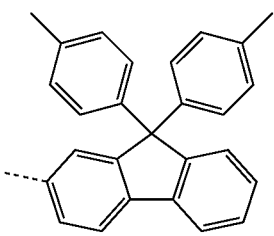 |
| 1-263 | 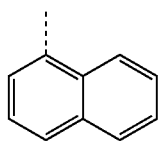 | 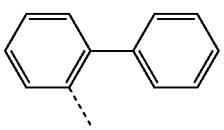 | 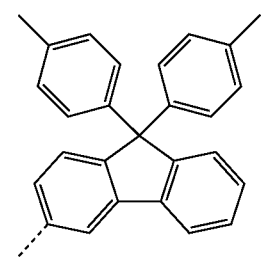 |

| For-mula | - - -Ar1 | - - -Ar2 | - - -Ar3 |
|---|---|---|---|
| 1-264 | 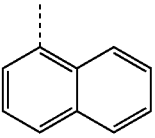 | 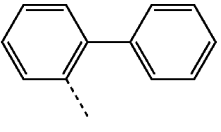 | 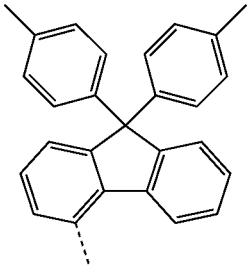 |
| 1-265 | 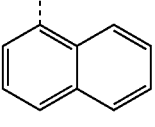 | 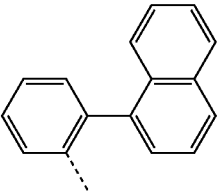 | 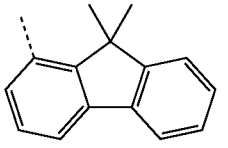 |
| 1-266 | 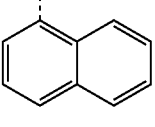 | 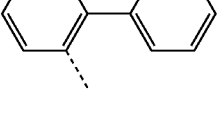 | 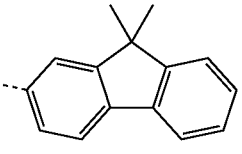 |
| 1-267 | 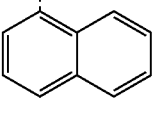 | 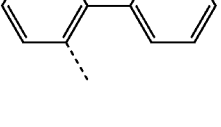 | 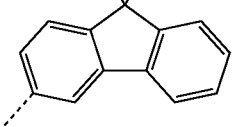 |
| 1-268 | 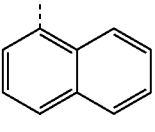 | 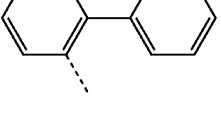 | 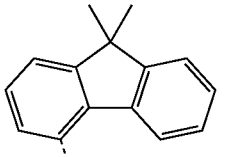 |
| 1-269 | 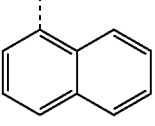 | 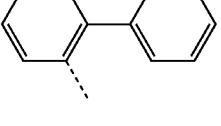 | 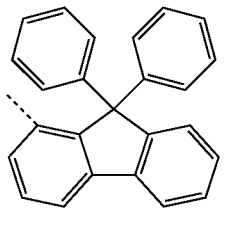 |
| 1-270 | 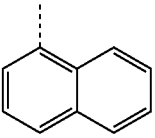 | 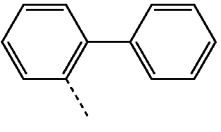 | 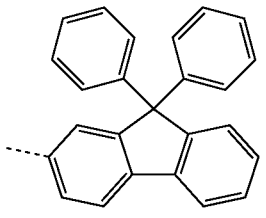 |

-continued
| Formula | ---Ar1 | ---Ar2 | ---Ar3 |
|---|---|---|---|
| 1-271 | | | |
| 1-272 | | | |
| 1-273 | | | |
| 1-274 | | | |
| 1-275 | | | |
| 1-276 | | | |
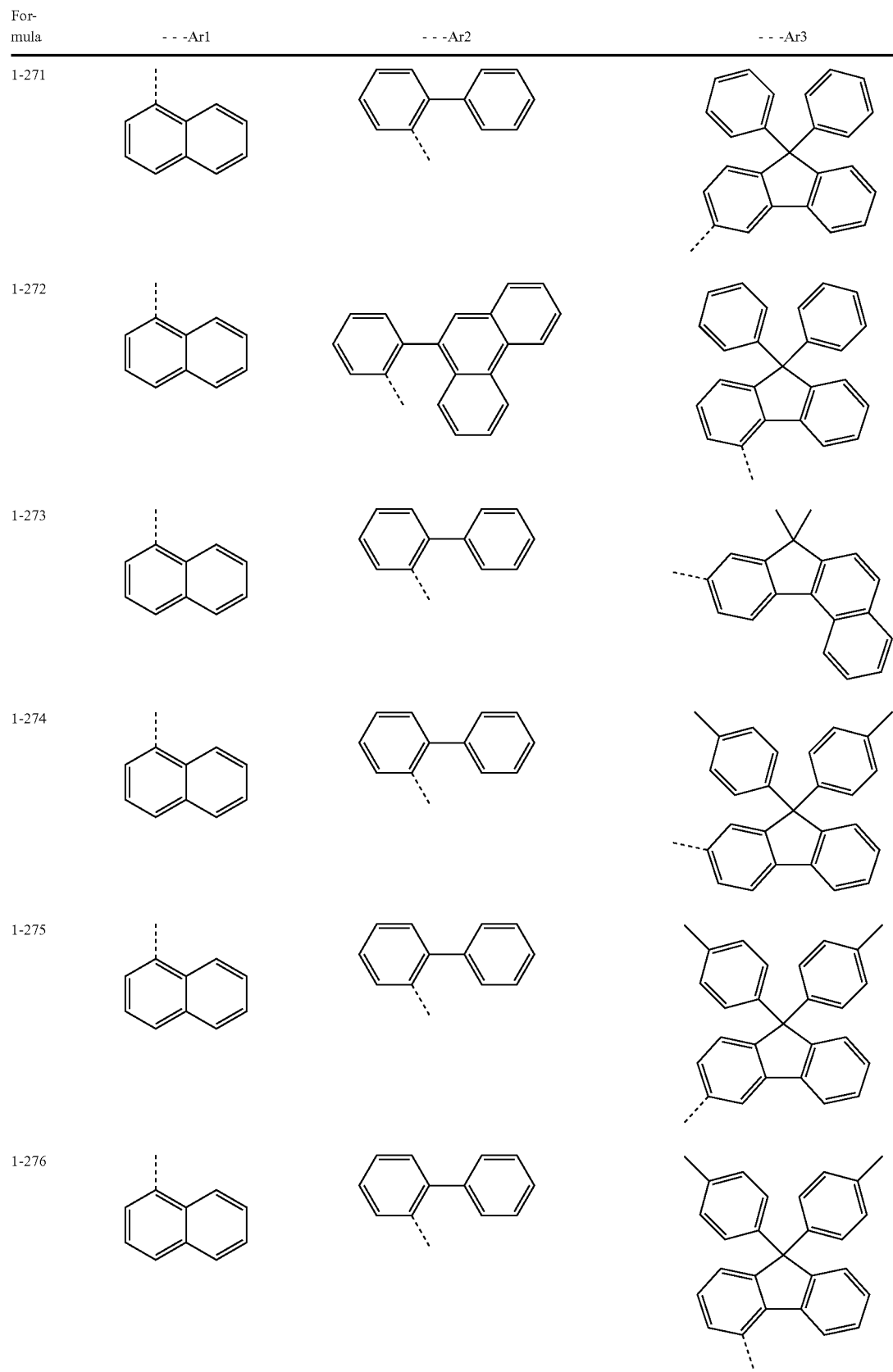

-continued
| Formula | - - -Ar1 | - - -Ar2 | - - -Ar3 |
|---|---|---|---|
| 1-277 | 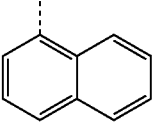 | 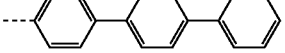 | 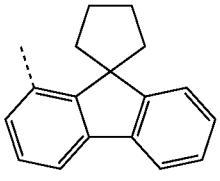 |
| 1-278 | 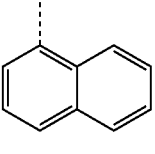 | 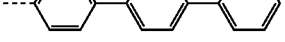 | 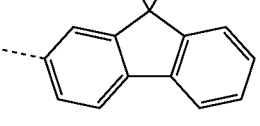 |
| 1-279 | 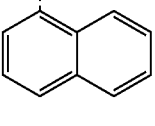 | 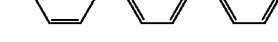 | 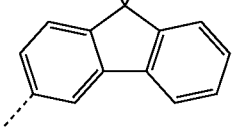 |
| 1-280 | 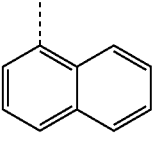 | 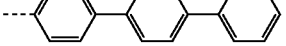 | 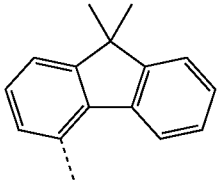 |
| 1-281 | 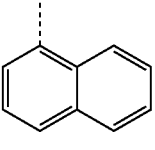 | 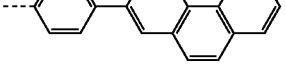 | 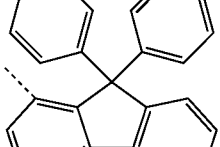 |
| 1-282 | 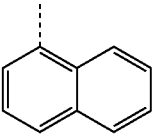 | 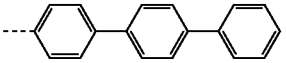 |  |
| 1-283 | 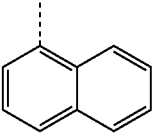 | 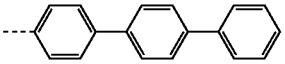 |  |

-continued
| Formula | - - -Ar1 | - - -Ar2 | - - -Ar3 |
|---|---|---|---|
| 1-284 | 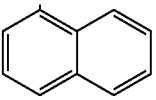 | 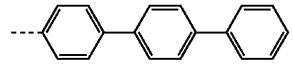 | 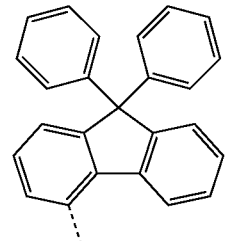 |
| 1-285 | 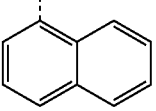 | 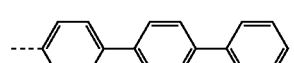 | 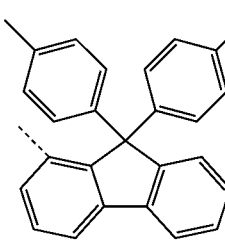 |
| 1-286 | 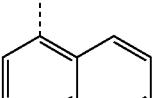 | 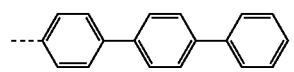 | 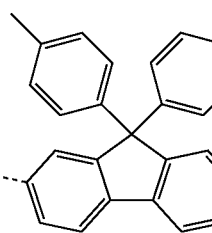 |
| 1-287 | 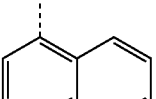 | 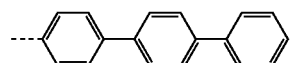 | 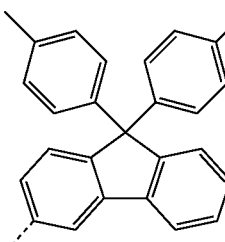 |
| 1-288 | 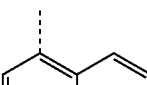 | 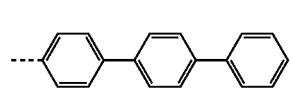 | 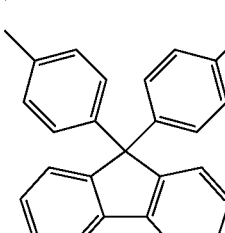 |
| 1-289 | 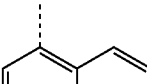 | 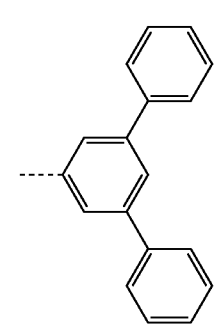 | 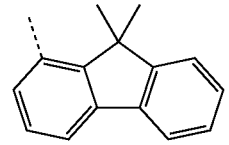 |

-continued
| Formula | - - -Ar1 | - - -Ar2 | - - -Ar3 |
|---|---|---|---|
| 1-290 | 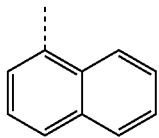 | 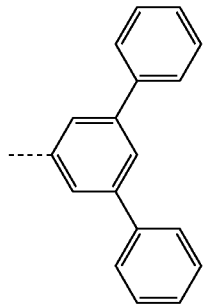 | 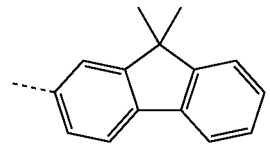 |
| 1-291 | 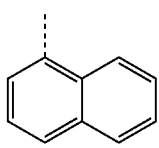 | 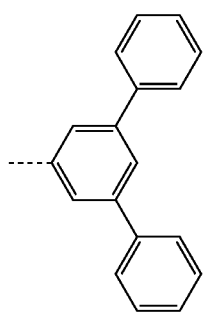 | 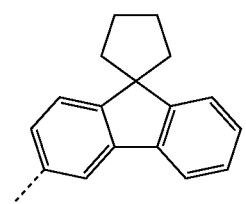 |
| 1-292 | 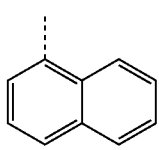 | 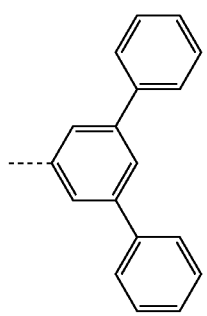 | 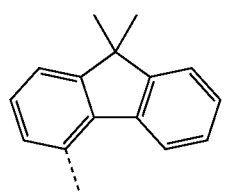 |
| 1-293 | 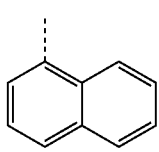 | 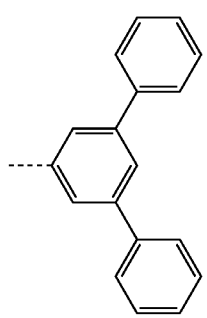 | 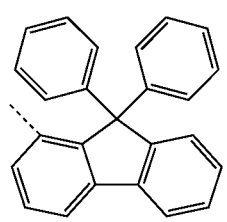 |
| 1-294 | 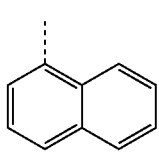 | 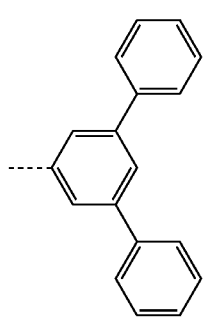 | 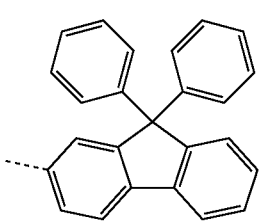 |

-continued
| Formula | - - -Ar1 | - - -Ar2 | - - -Ar3 |
|---|---|---|---|
| 1-295 | 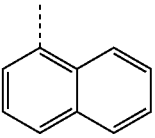 | 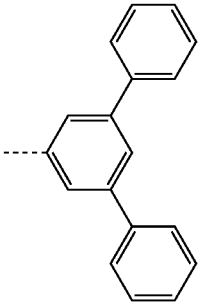 | 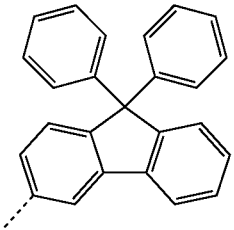 |
| 1-296 | 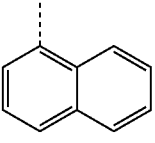 | 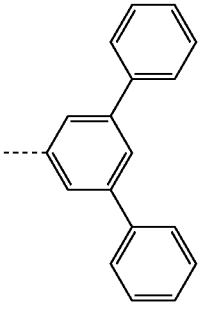 | 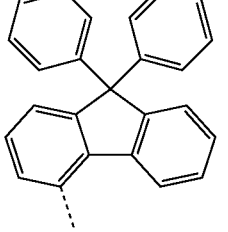 |
| 1-297 | 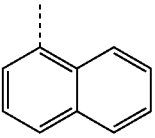 | 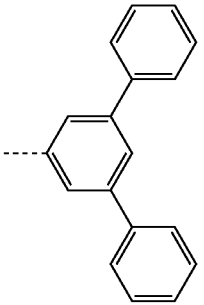 | 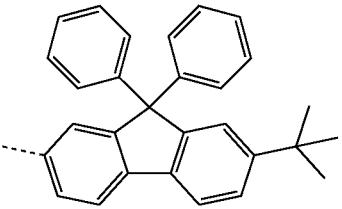 |
| 1-298 | 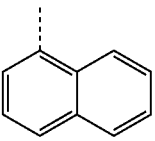 | 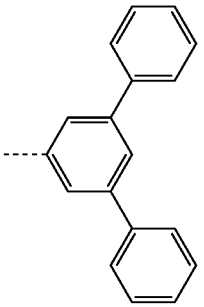 | 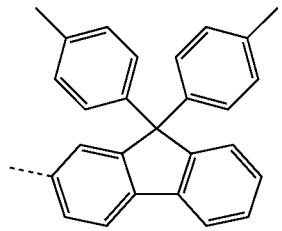 |
| 1-299 | 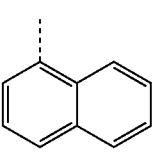 | 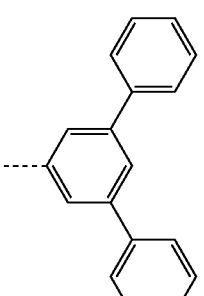 | 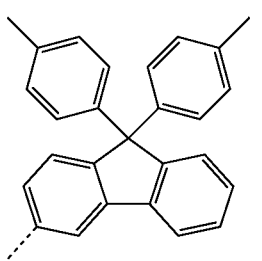 |

-continued
| Formula | ---Ar1 | ---Ar2 | ---Ar3 |
|---|---|---|---|
| 1-300 | 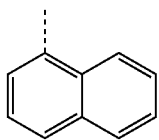 | 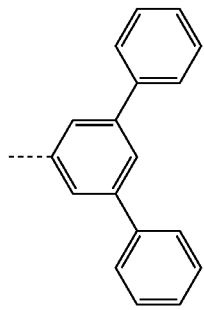 | 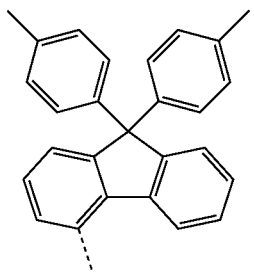 |
| 1-301 | 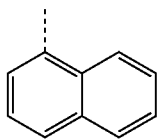 | 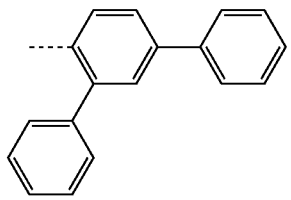 | 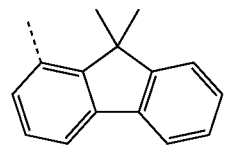 |
| 1-302 | 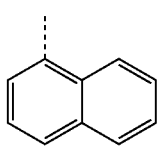 | 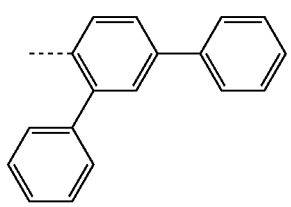 | 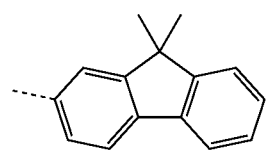 |
| 1-303 | 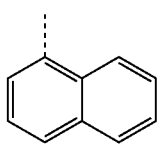 | 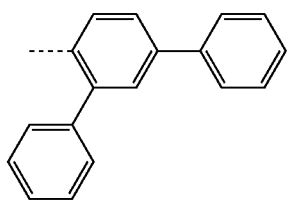 | 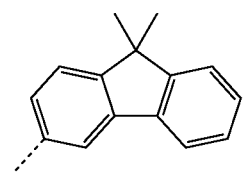 |
| 1-304 | 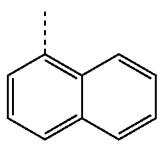 | 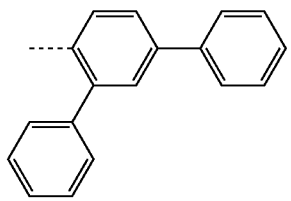 | 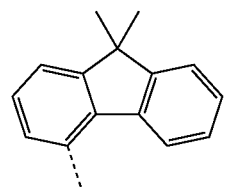 |
| 1-305 | 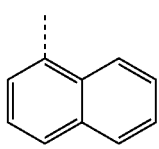 | 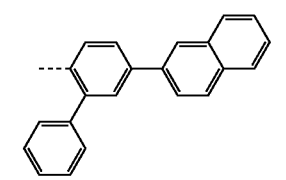 | 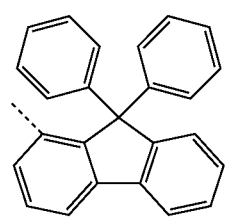 |

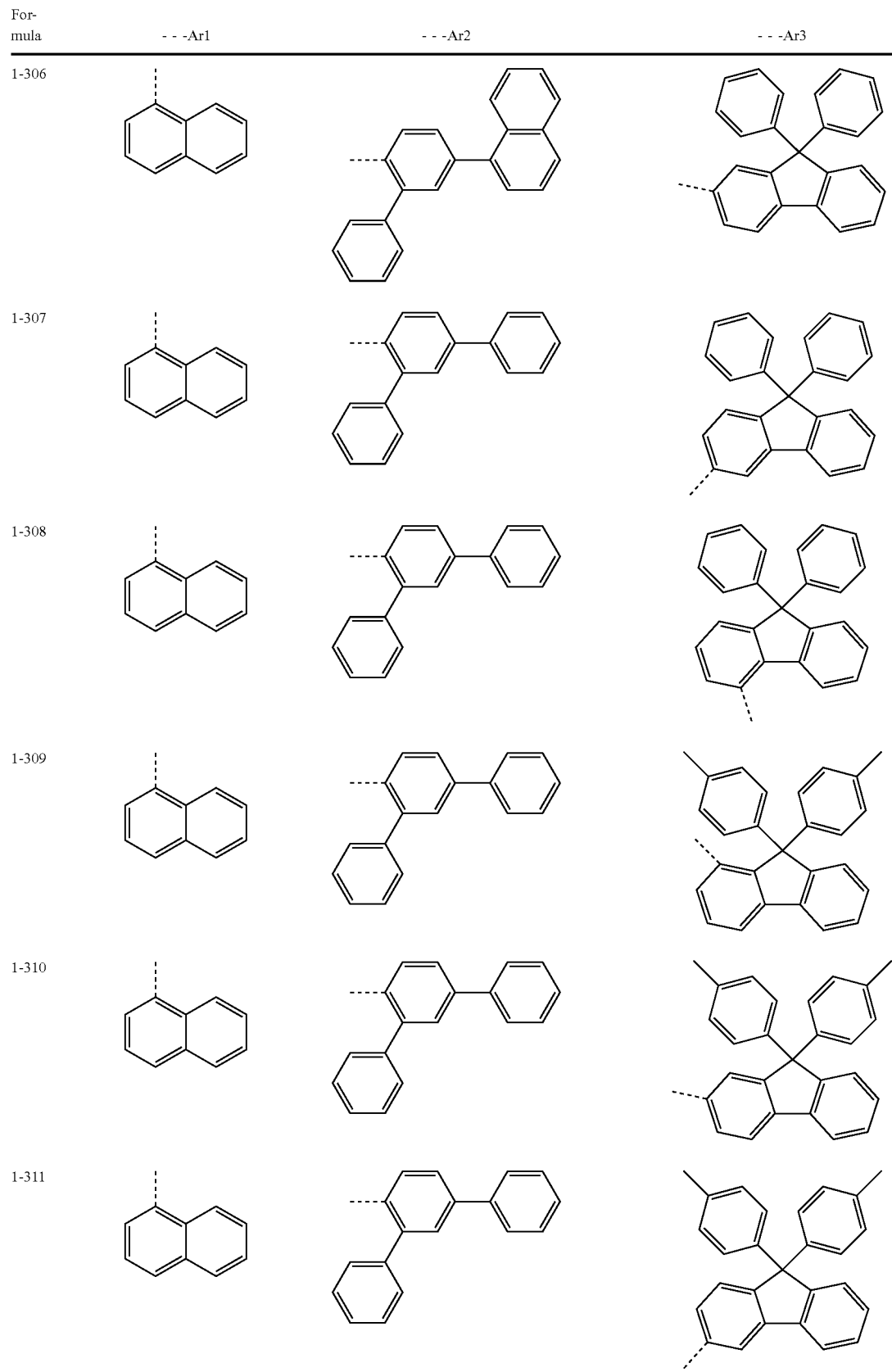

-continued
| Formula | - - -Ar1 | - - -Ar2 | - - -Ar3 |
|---|---|---|---|
| 1-312 | 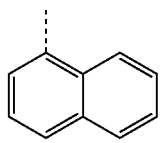 | 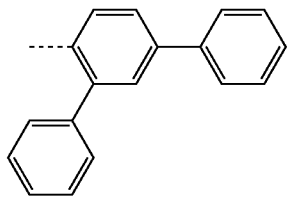 | 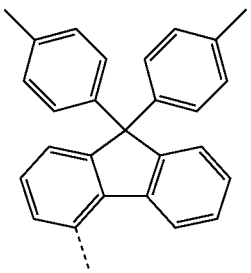 |
| 1-313 | 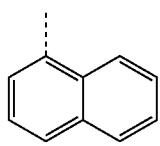 | 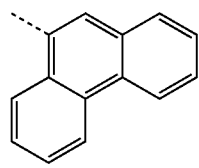 | 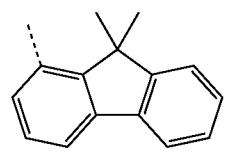 |
| 1-314 | 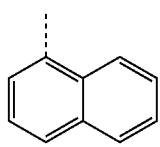 | 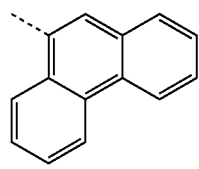 | 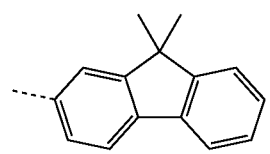 |
| 1-315 | 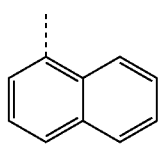 | 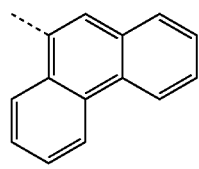 | 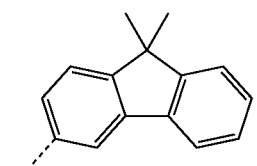 |
| 1-316 | 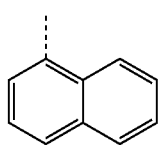 | 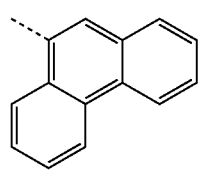 | 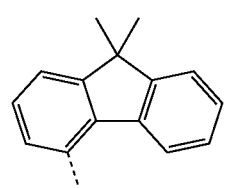 |
| 1-317 | 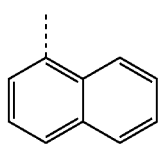 | 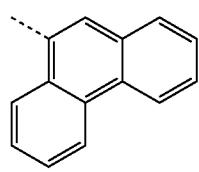 | 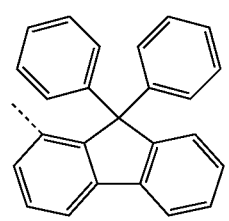 |
| 1-318 | 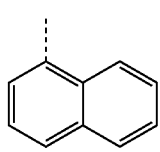 | 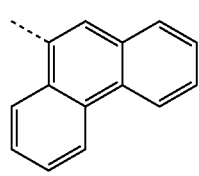 | 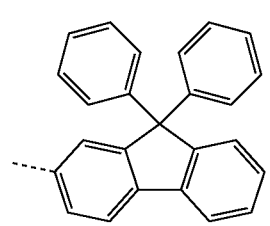 |

-continued
| Formula | ---Ar1 | ---Ar2 | ---Ar3 |
|---|---|---|---|
| 1-319 | 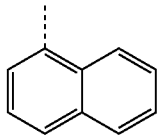 | 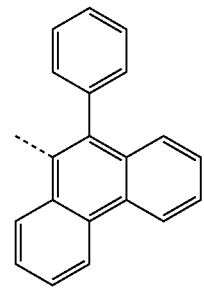 | 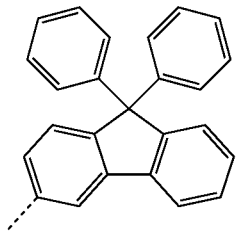 |
| 1-320 | 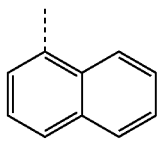 | 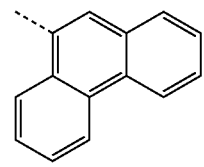 | 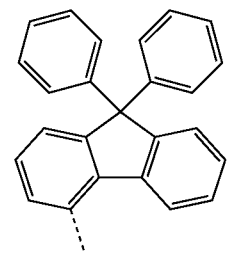 |
| 1-321 | 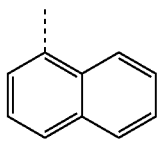 | 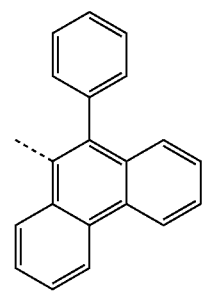 | 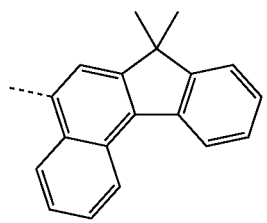 |
| 1-322 | 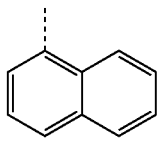 | 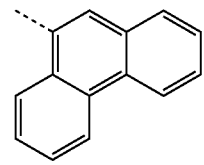 | 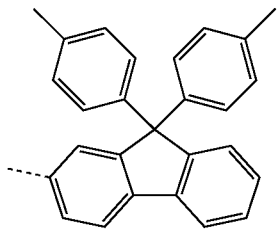 |
| 1-323 | 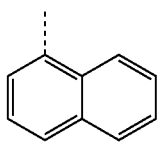 | 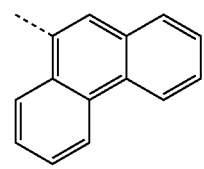 | 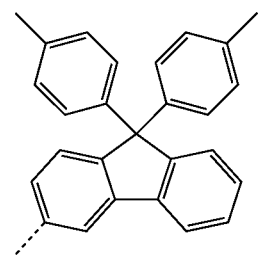 |

-continued
| Formula | - - -Ar1 | - - -Ar2 | - - -Ar3 |
|---|---|---|---|
| 1-324 | 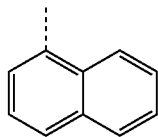 | 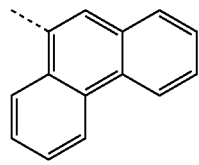 | 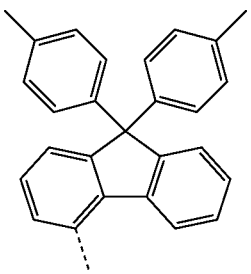 |
| 1-325 | 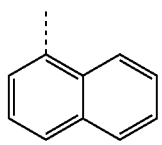 | 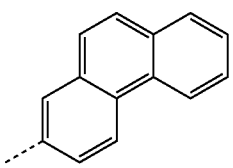 | 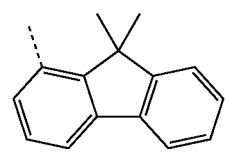 |
| 1-326 | 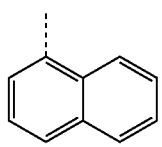 | 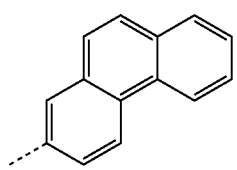 | 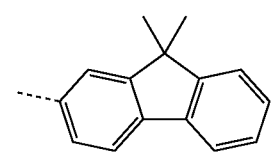 |
| 1-327 | 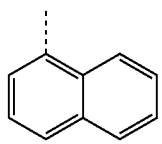 | 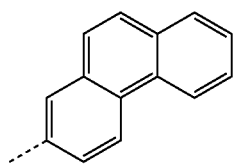 | 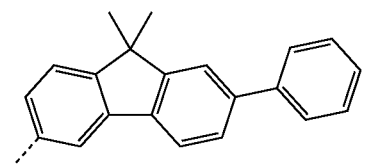 |
| 1-328 | 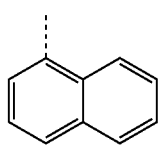 | 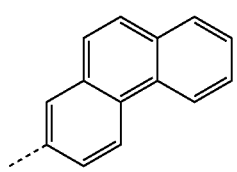 | 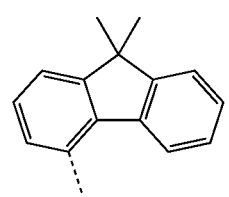 |
| 1-329 | 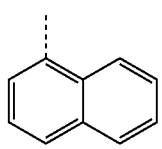 | 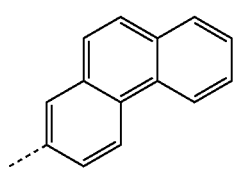 | 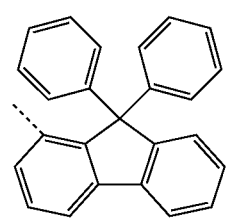 |
| 1-330 | 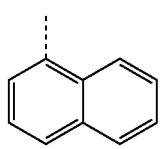 | 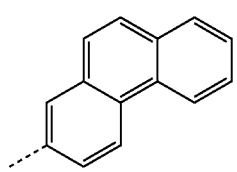 | 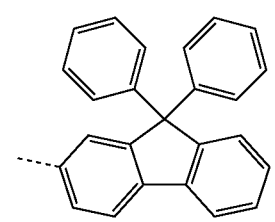 |

-continued
| Formula | - - -Ar1 | - - -Ar2 | - - -Ar3 |
|---|---|---|---|
| 1-331 | 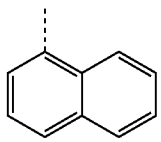 | 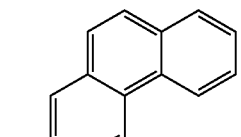 | 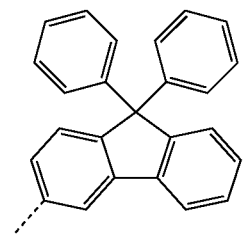 |
| 1-332 | 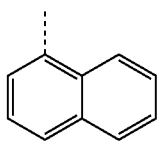 | 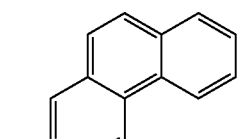 | 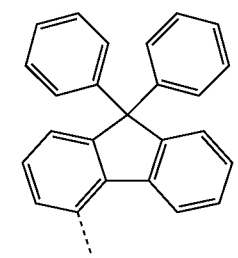 |
| 1-333 | 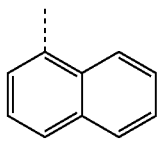 | 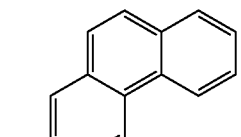 | 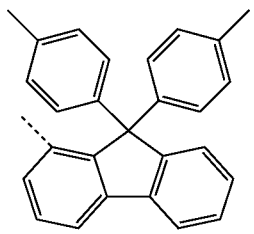 |
| 1-334 | 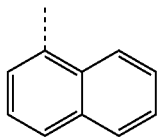 | 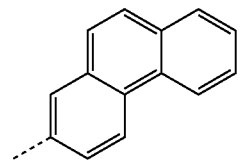 | 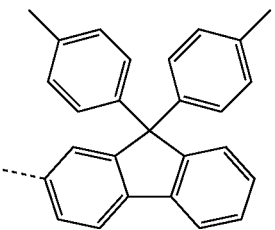 |
| 1-335 | 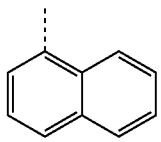 | 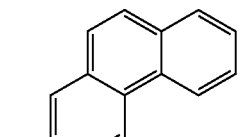 | 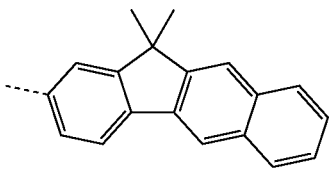 |
| 1-336 | 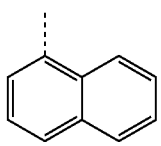 | 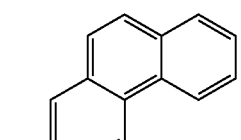 | 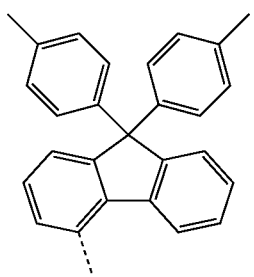 |

-continued
| Formula | - - -Ar1 | - - -Ar2 | - - -Ar3 |
|---|---|---|---|
| 1-337 | 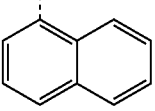 | 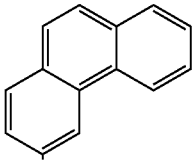 | 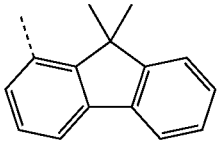 |
| 1-338 | 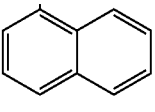 | 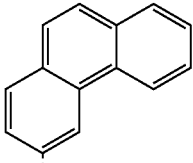 | 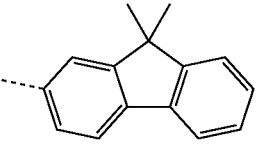 |
| 1-339 | 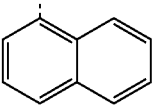 | 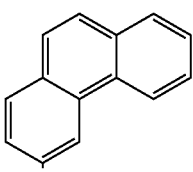 | 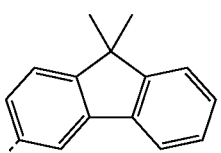 |
| 1-340 | 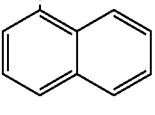 | 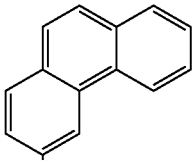 | 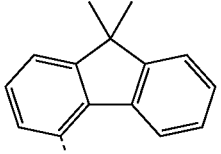 |
| 1-341 | 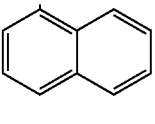 | 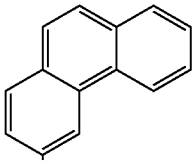 | 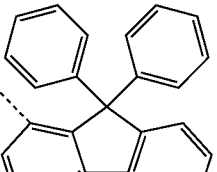 |
| 1-342 | 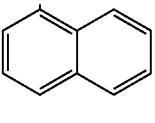 | 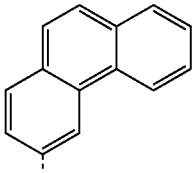 | 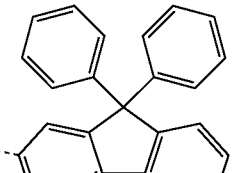 |
| 1-343 | 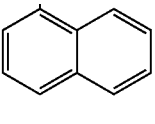 | 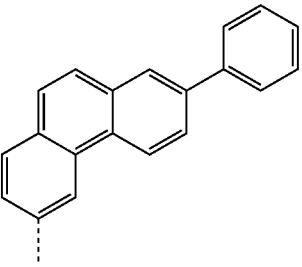 | 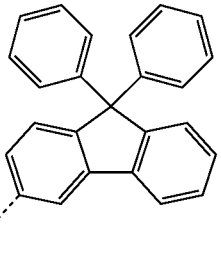 |

-continued
| Formula | ---Ar1 | ---Ar2 | ---Ar3 |
|---|---|---|---|
| 1-344 | 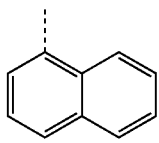 | 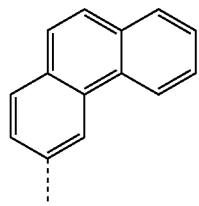 | 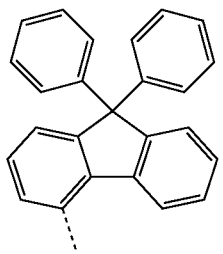 |
| 1-345 | 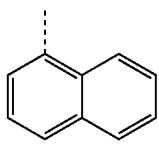 | 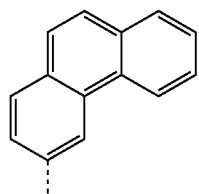 | 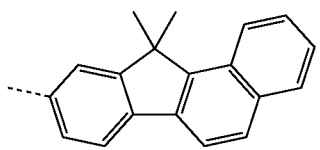 |
| 1-346 | 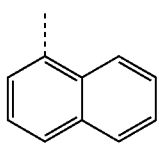 | 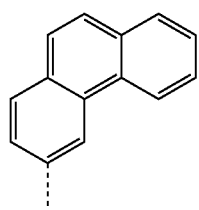 | 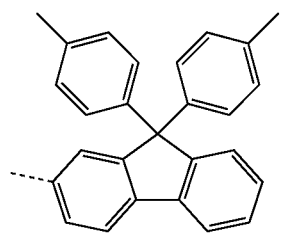 |
| 1-347 | 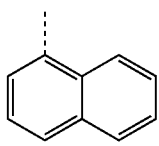 | 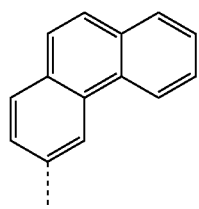 | 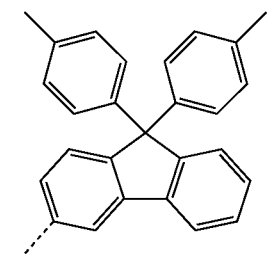 |
| 1-348 | 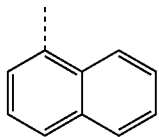 | 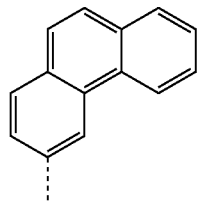 | 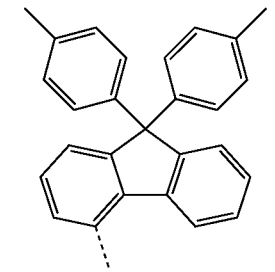 |
| 1-349 | 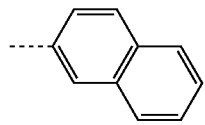 | 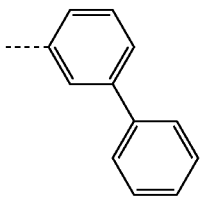 | 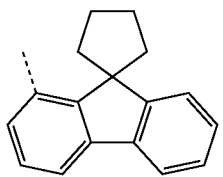 |

-continued
| Formula | - - -Ar1 | - - -Ar2 | - - -Ar3 |
|---|---|---|---|
| 1-350 | 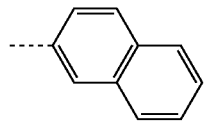 | 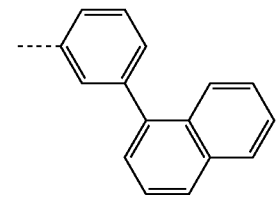 | 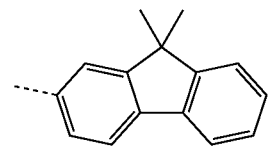 |
| 1-351 | 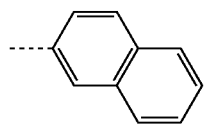 | 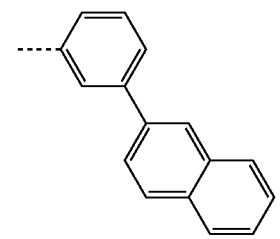 | 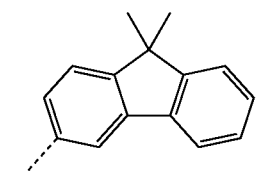 |
| 1-352 | 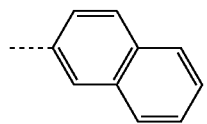 | 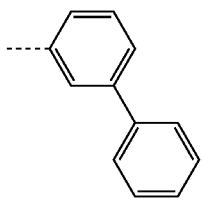 | 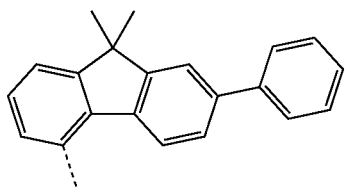 |
| 1-353 | 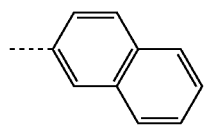 | 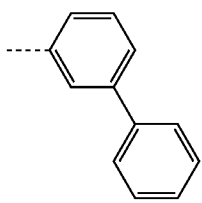 | 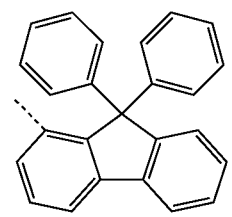 |
| 1-354 | 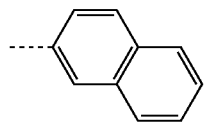 | 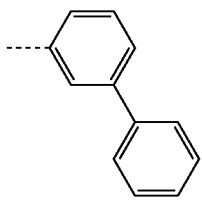 | 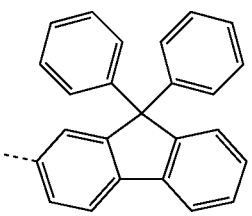 |
| 1-355 | 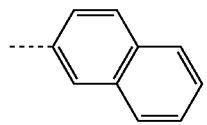 | 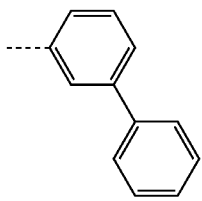 | 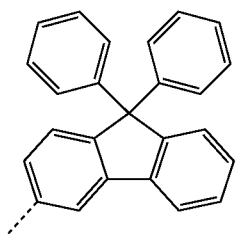 |

US 11,271,167 B2
147                                                                    148
-continued
| Formula | - - -Ar1 | - - -Ar2 | - - -Ar3 |
|---|---|---|---|
| 1-356 | 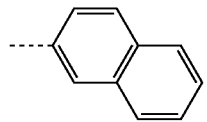 | 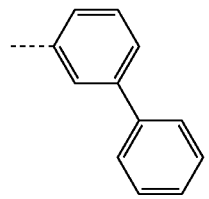 | 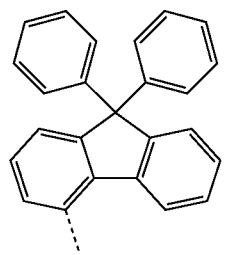 |
| 1-357 | 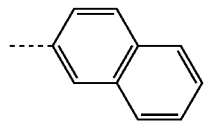 | 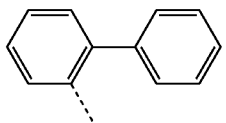 | 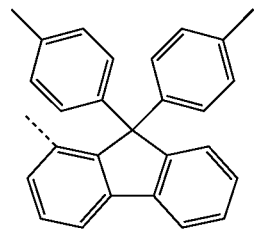 |
| 1-358 | 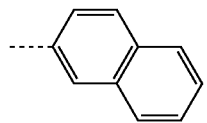 | 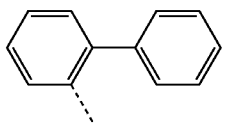 | 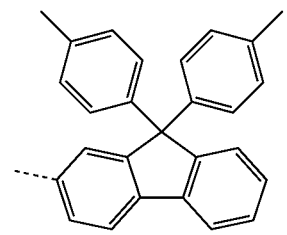 |
| 1-359 | 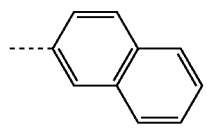 | 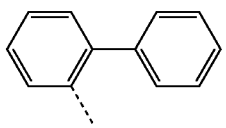 | 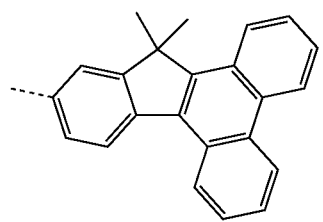 |
| 1-360 | 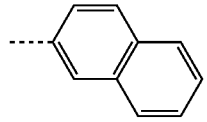 | 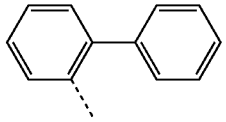 | 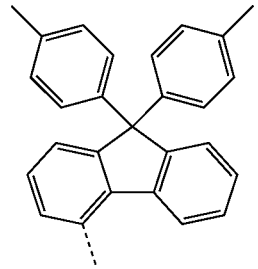 |
| 1-361 | 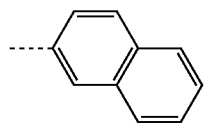 | 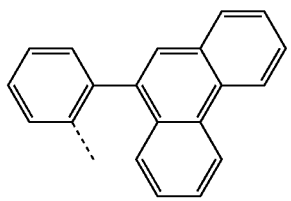 | 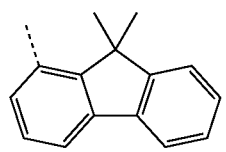 |

-continued
| Formula | - - -Ar1 | - - -Ar2 | - - -Ar3 |
|---|---|---|---|
| 1-362 | 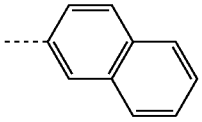 | 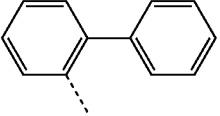 | 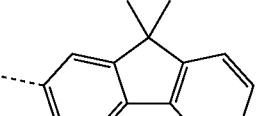 |
| 1-363 | 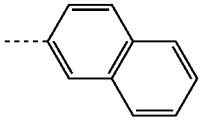 | 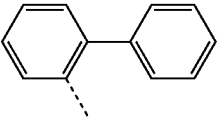 | 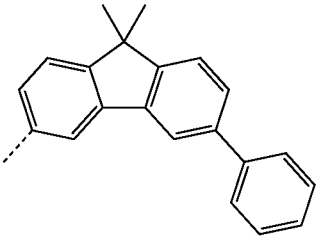 |
| 1-364 | 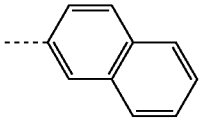 | 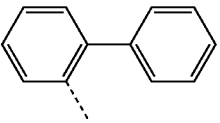 | 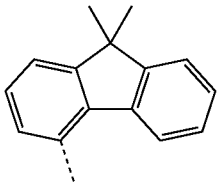 |
| 1-365 | 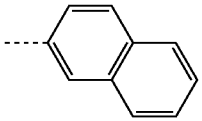 | 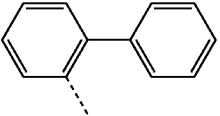 | 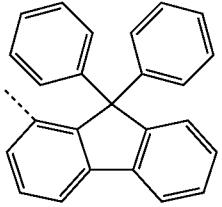 |
| 1-366 | 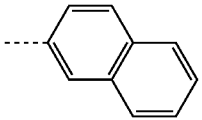 | 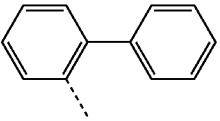 | 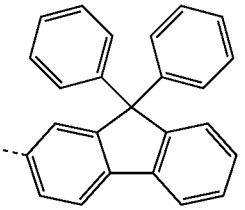 |
| 1-367 | 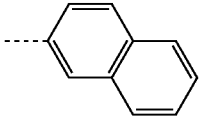 | 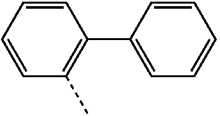 | 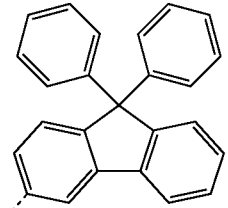 |
| 1-368 | 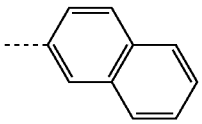 | 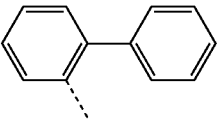 | 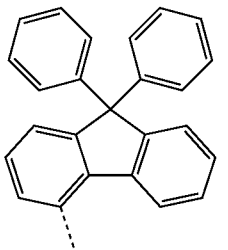 |

-continued
| Formula | - - -Ar1 | - - -Ar2 | - - -Ar3 |
|---|---|---|---|
| 1-369 | 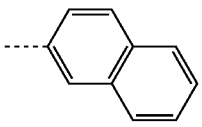 | 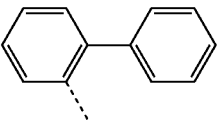 | 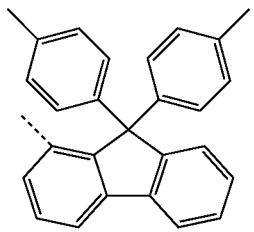 |
| 1-370 | 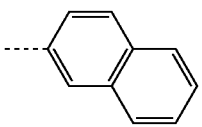 | 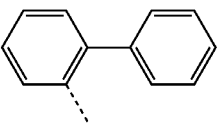 | 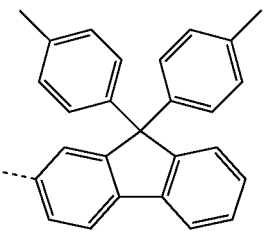 |
| 1-371 | 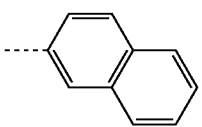 | 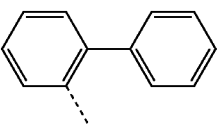 | 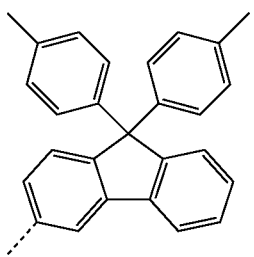 |
| 1-372 | 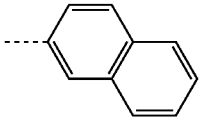 | 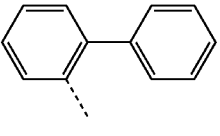 | 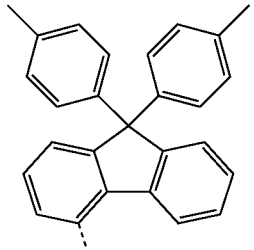 |
| 1-373 | 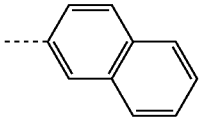 | 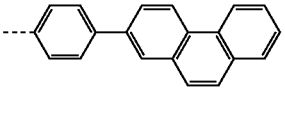 | 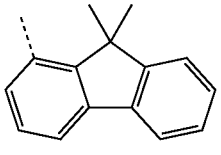 |
| 1-374 | 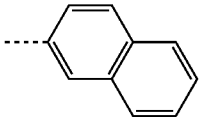 | 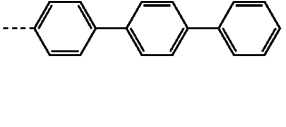 | 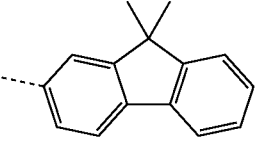 |
| 1-375 | 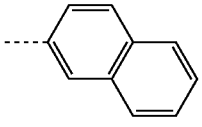 | 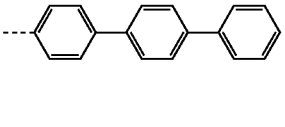 | 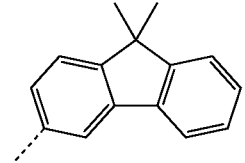 |

-continued
| Formula | - - -Ar1 | - - -Ar2 | - - -Ar3 |
|---|---|---|---|
| 1-376 | 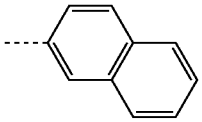 | 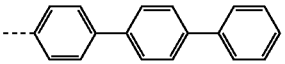 | 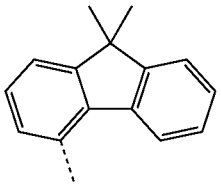 |
| 1-377 | 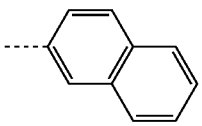 | 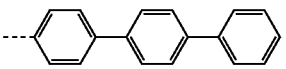 | 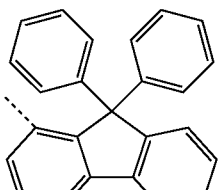 |
| 1-378 | 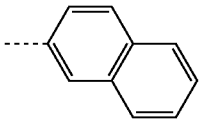 | 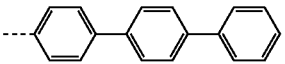 | 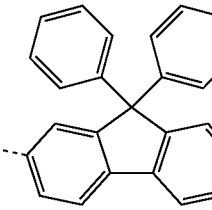 |
| 1-379 | 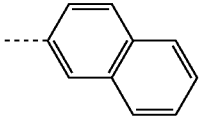 | 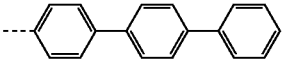 | 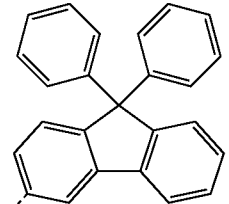 |
| 1-380 | 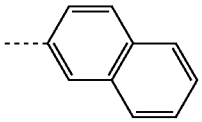 | 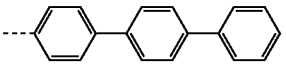 | 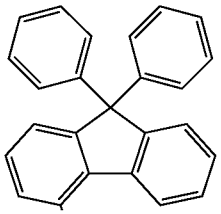 |
| 1-381 | 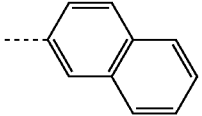 | 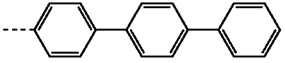 | 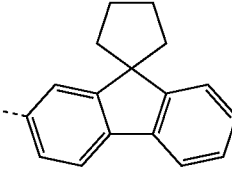 |
| 1-382 | 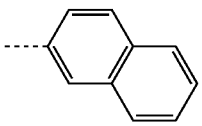 | 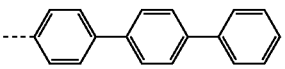 | 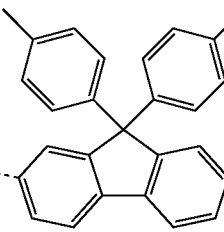 |

| Formula | ---Ar1 | ---Ar2 | ---Ar3 |
|---|---|---|---|
| 1-383 | 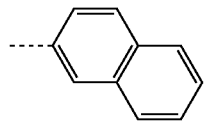 | 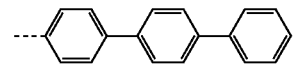 | 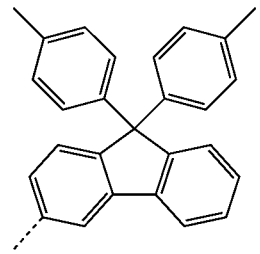 |
| 1-384 | 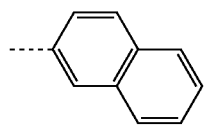 | 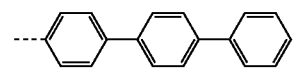 | 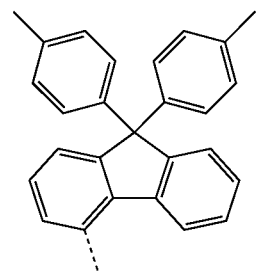 |
| 1-385 | 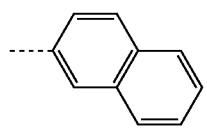 | 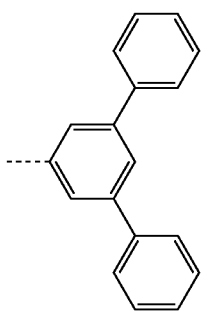 | 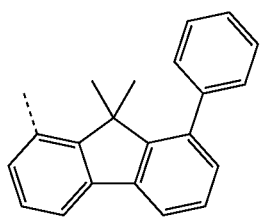 |
| 1-386 | 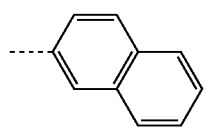 | 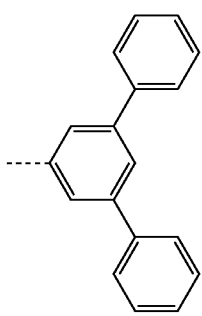 | 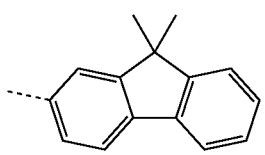 |
| 1-387 | 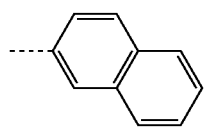 | 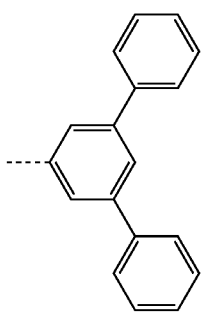 | 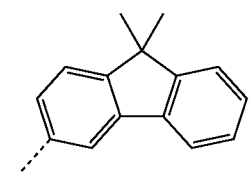 |

-continued

| Formula | - - -Ar1 | - - -Ar2 | - - -Ar3 |
|---|---|---|---|
| 1-388 | 2-naphthyl | 4-(3,5-diphenyl)phenyl-phenyl | 9,9-dimethylfluoren-4-yl |
| 1-389 | 2-naphthyl | 3,5-diphenylphenyl | 2-tert-butyl-9,9-diphenylfluoren-7-yl |
| 1-390 | 2-naphthyl | 3,5-diphenylphenyl | 9,9-diphenylfluoren-2-yl |
| 1-391 | 2-naphthyl | 3,5-diphenylphenyl | 9,9-diphenylfluoren-3-yl |
| 1-392 | 2-naphthyl | 3,5-diphenylphenyl | 9,9-diphenylfluoren-4-yl |

-continued
| Formula | - - -Ar1 | - - -Ar2 | - - -Ar3 |
|---|---|---|---|
| 1-393 | 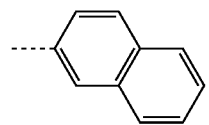 | 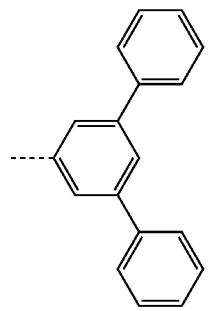 | 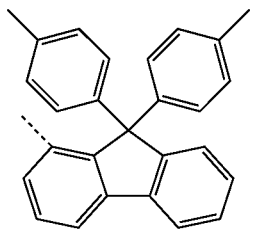 |
| 1-394 | 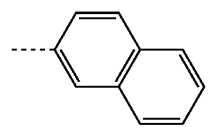 | 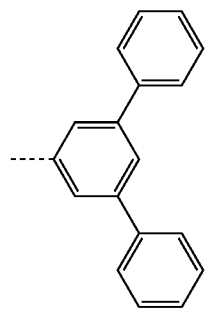 | 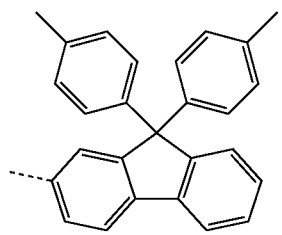 |
| 1-395 | 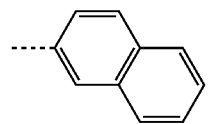 | 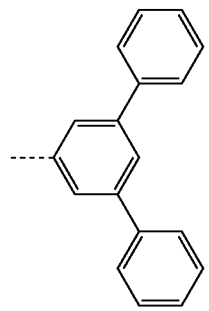 | 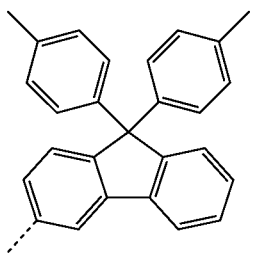 |
| 1-396 | 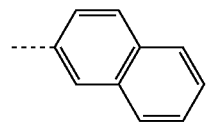 | 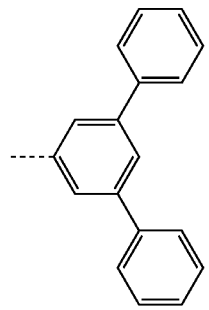 | 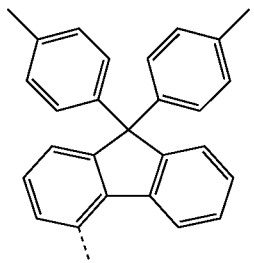 |
| 1-397 | 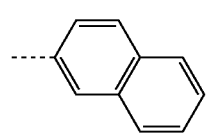 | 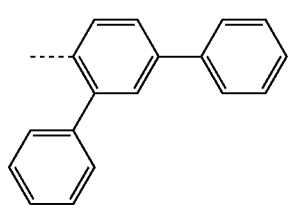 | 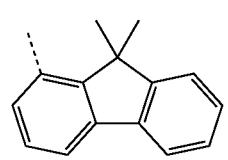 |

-continued
| Formula | - - -Ar1 | - - -Ar2 | - - -Ar3 |
|---|---|---|---|
| 1-398 | 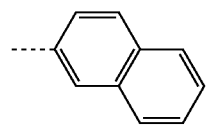 | 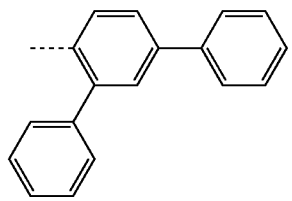 | 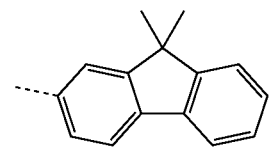 |
| 1-399 | 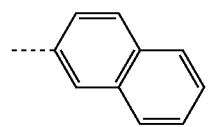 | 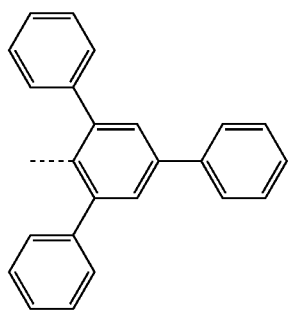 | 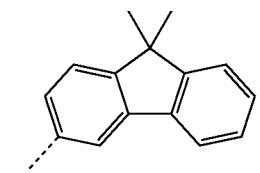 |
| 1-400 | 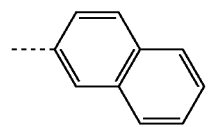 | 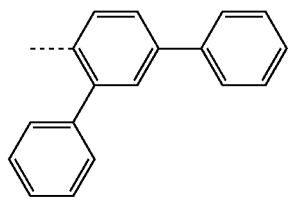 | 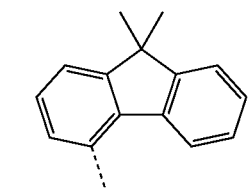 |
| 1-401 | 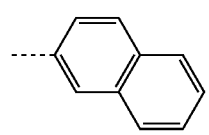 | 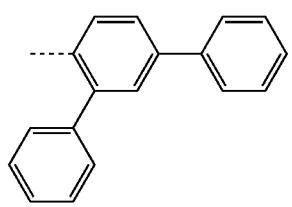 | 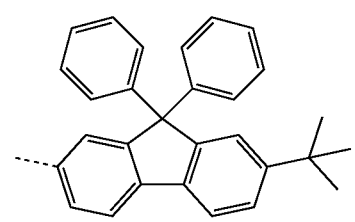 |
| 1-402 | 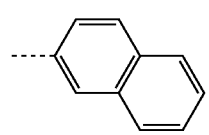 | 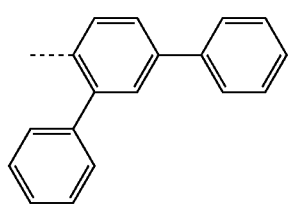 | 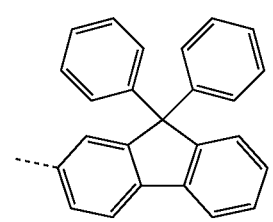 |
| 1-403 | 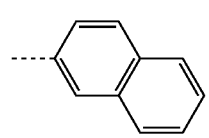 | 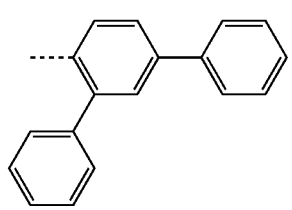 | 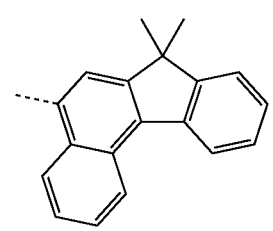 |

| Formula | ---Ar1 | ---Ar2 | ---Ar3 |
|---|---|---|---|
| 1-404 | 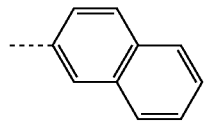 | 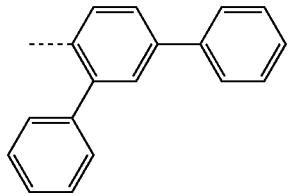 | 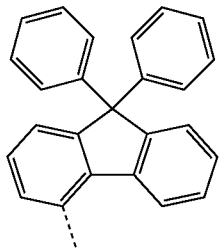 |
| 1-405 | 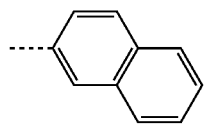 | 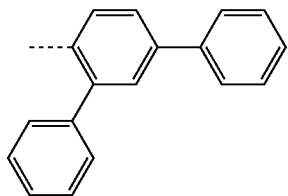 | 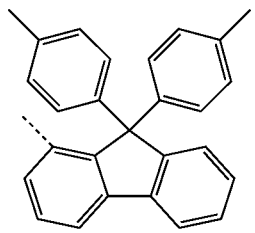 |
| 1-406 | 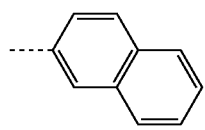 | 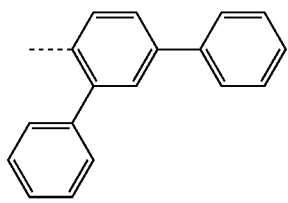 | 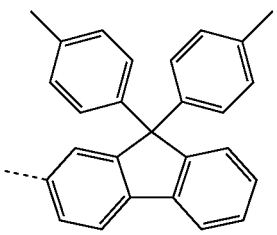 |
| 1-407 | 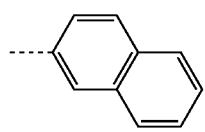 | 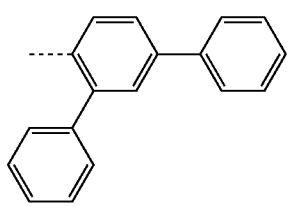 | 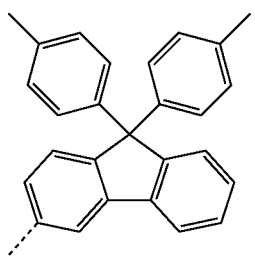 |
| 1-408 | 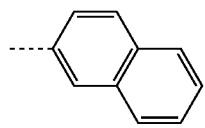 | 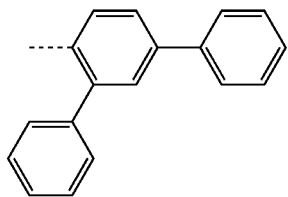 | 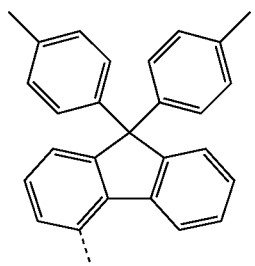 |
| 1-409 | 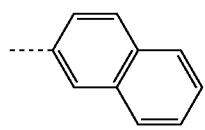 | 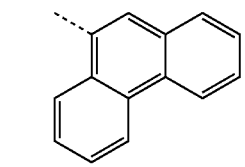 | 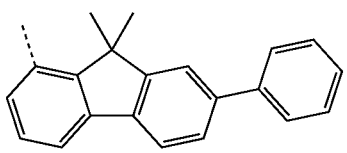 |

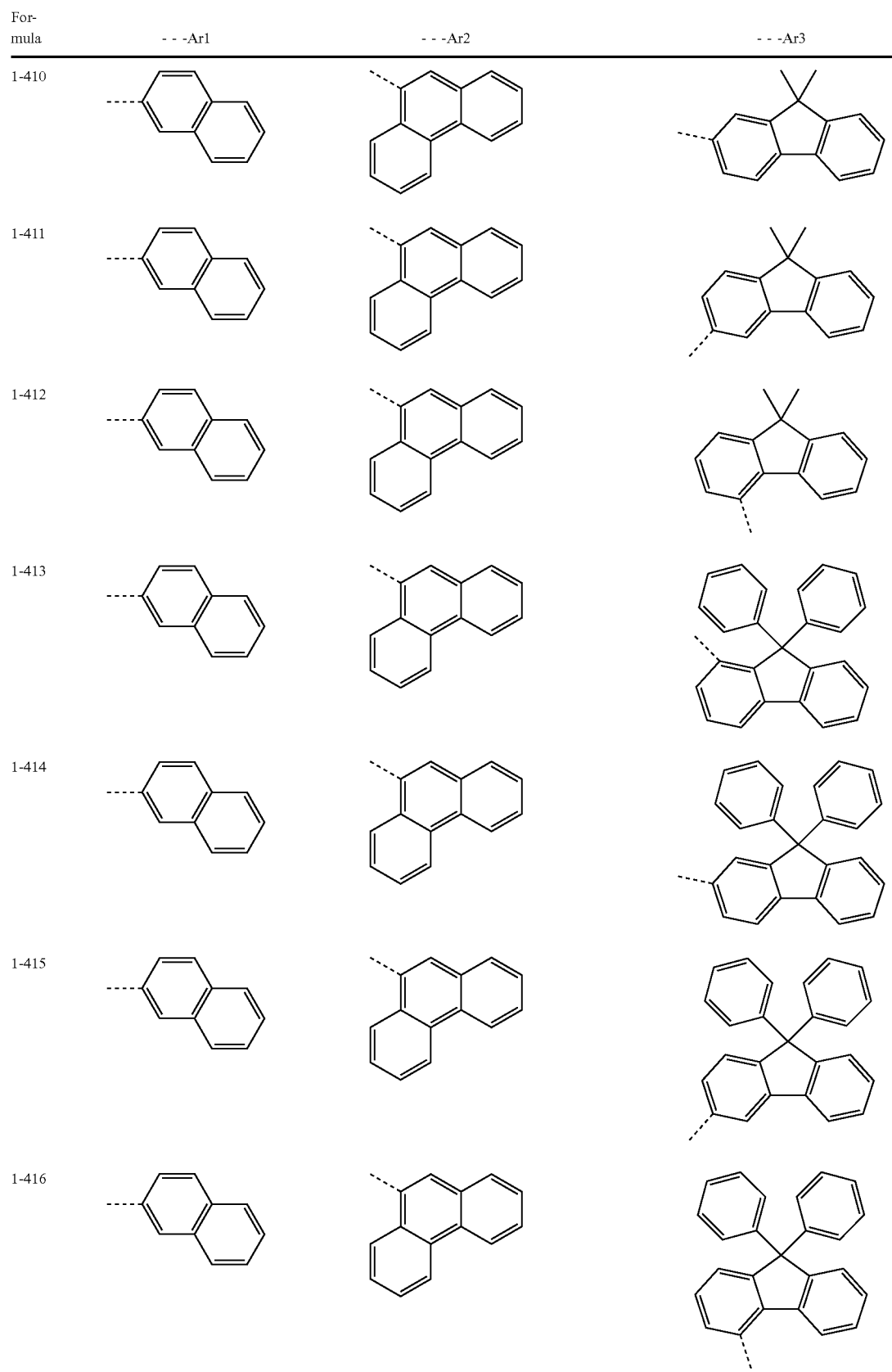

-continued
| Formula | - - -Ar1 | - - -Ar2 | - - -Ar3 |
|---|---|---|---|
| 1-417 | 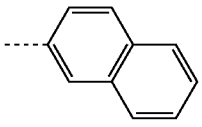 | 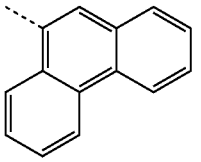 | 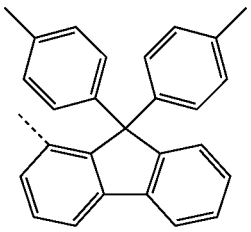 |
| 1-418 | 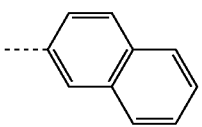 | 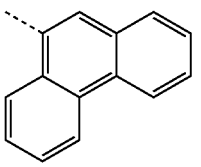 |  |
| 1-419 | 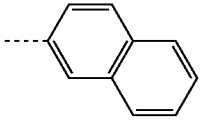 | 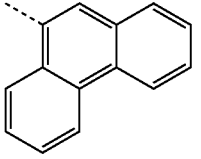 | 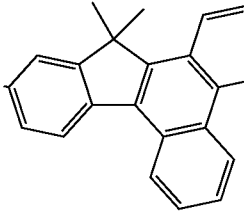 |
| 1-420 | 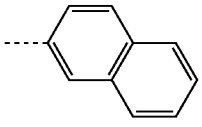 | 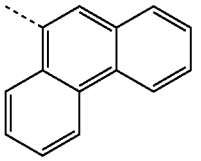 | 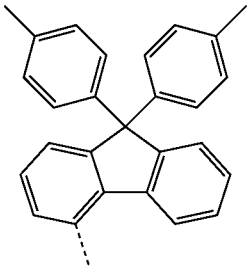 |
| 1-421 | 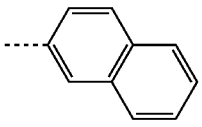 | 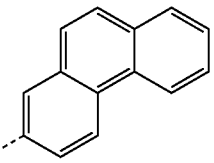 | 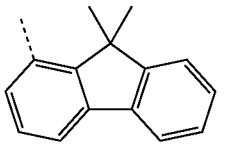 |
| 1-422 | 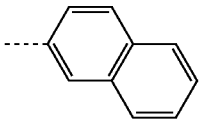 | 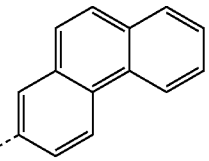 | 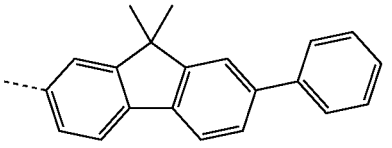 |
| 1-423 | 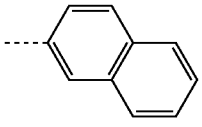 | 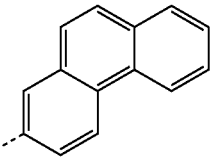 | 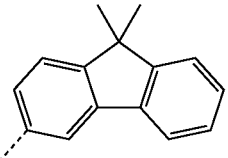 |

-continued
| Formula | ---Ar1 | ---Ar2 | ---Ar3 |
|---|---|---|---|
| 1-424 | 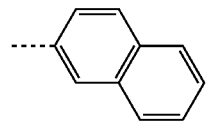 | 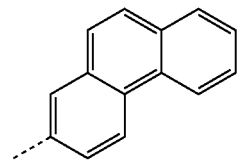 | 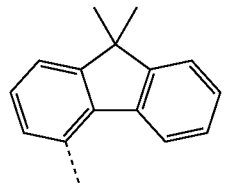 |
| 1-425 | 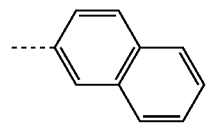 | 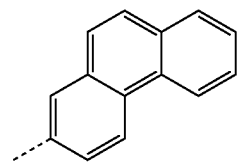 | 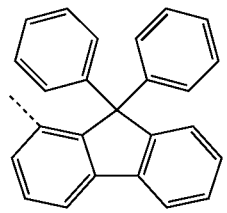 |
| 1-426 | 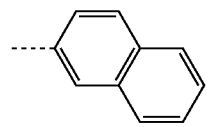 | 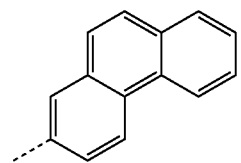 | 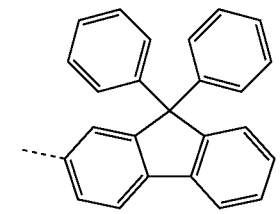 |
| 1-427 | 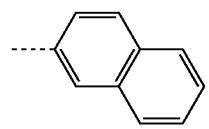 | 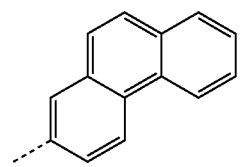 | 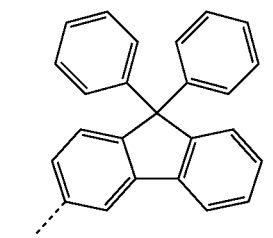 |
| 1-428 | 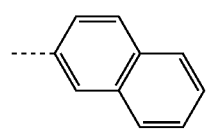 | 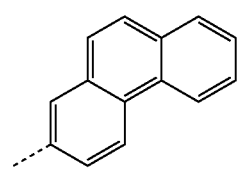 | 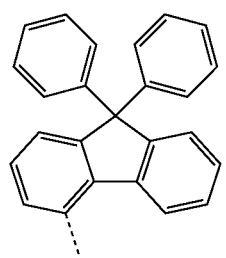 |
| 1-429 | 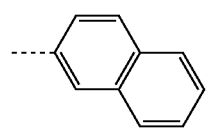 | 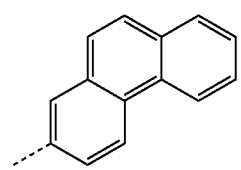 | 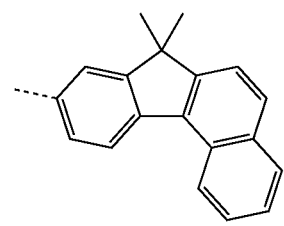 |

-continued
| Formula | - - -Ar1 | - - -Ar2 | - - -Ar3 |
|---|---|---|---|
| 1-430 | 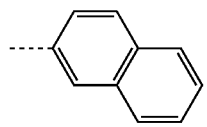 | 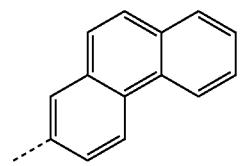 | 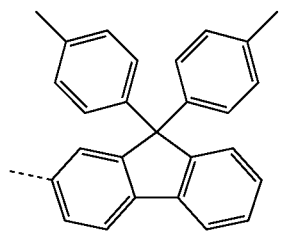 |
| 1-431 | 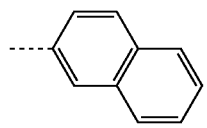 | 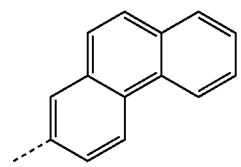 | 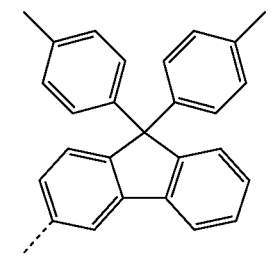 |
| 1-432 | 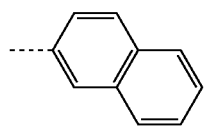 | 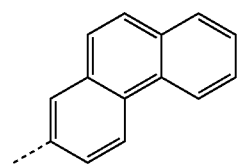 | 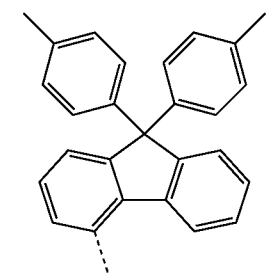 |
| 1-433 | 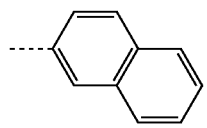 | 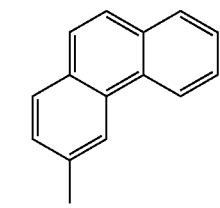 | 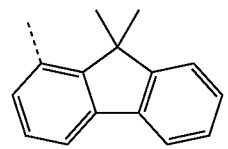 |
| 1-434 | 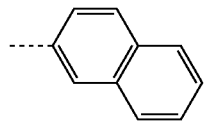 | 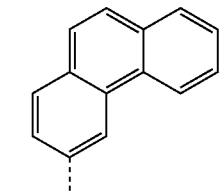 | 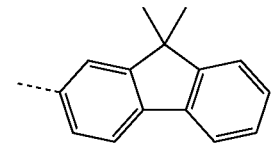 |
| 1-435 | 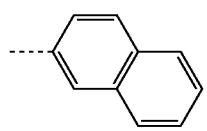 | 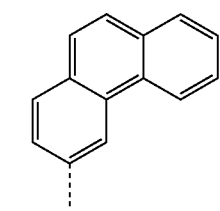 | 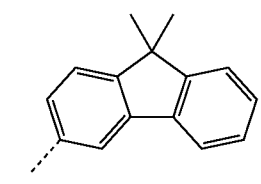 |

-continued
| Formula | ---Ar1 | ---Ar2 | ---Ar3 |
|---|---|---|---|
| 1-436 | 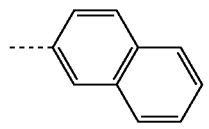 | 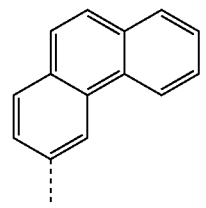 | 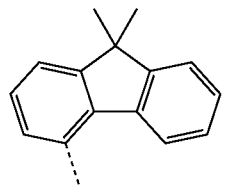 |
| 1-437 | 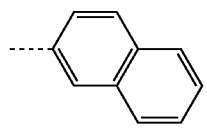 | 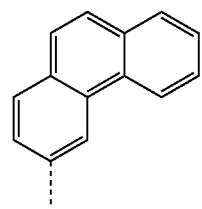 | 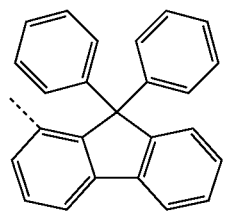 |
| 1-438 | 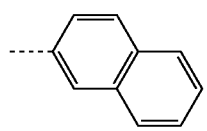 | 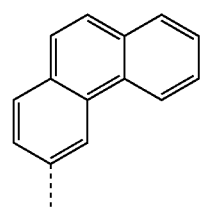 | 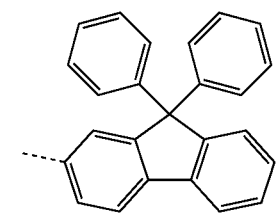 |
| 1-439 | 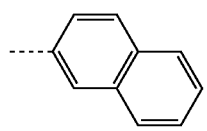 | 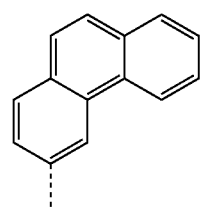 | 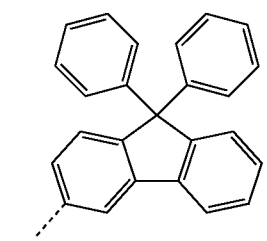 |
| 1-440 | 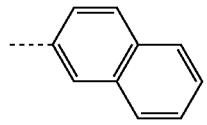 | 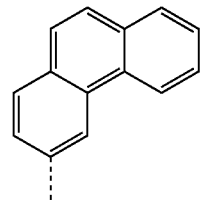 | 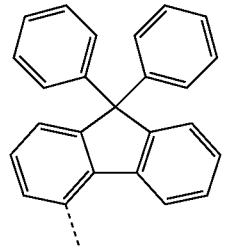 |
| 1-441 | 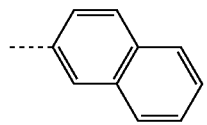 | 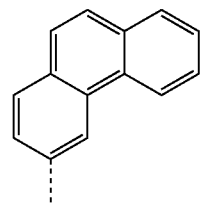 | 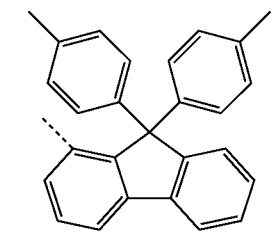 |

-continued
| Formula | ---Ar1 | ---Ar2 | ---Ar3 |
|---|---|---|---|
| 1-442 | 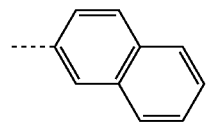 | 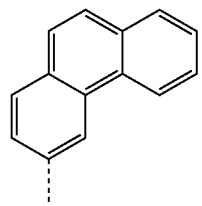 | 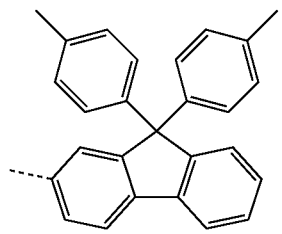 |
| 1-443 | 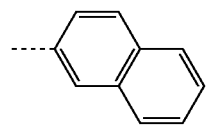 | 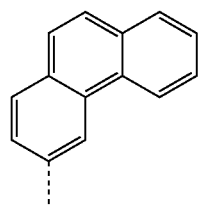 | 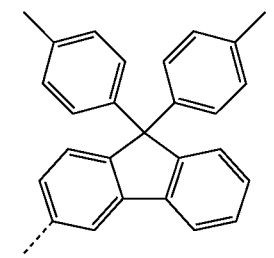 |
| 1-444 | 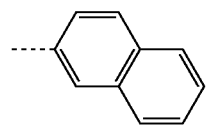 | 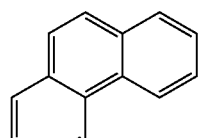 | 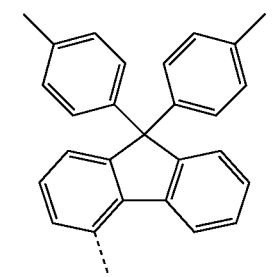 |
| 1-445 | 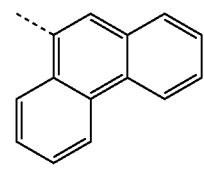 | 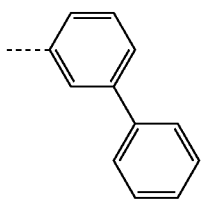 | 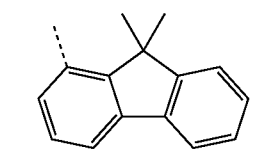 |
| 1-446 | 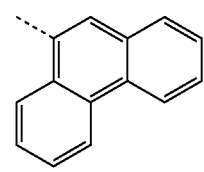 | 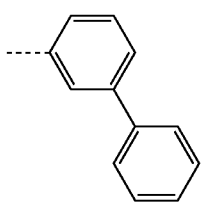 | 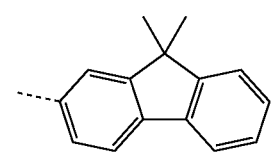 |
| 1-447 | 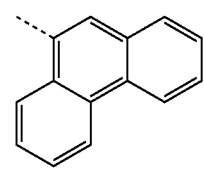 | 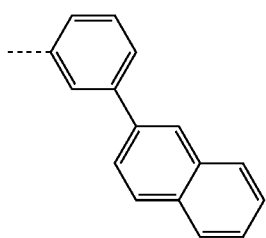 | 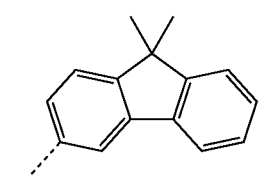 |

-continued
| Formula | - - -Ar1 | - - -Ar2 | - - -Ar3 |
|---|---|---|---|
| 1-448 | 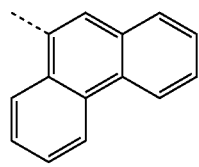 | 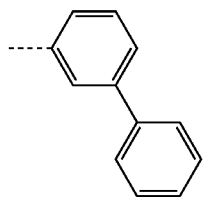 | 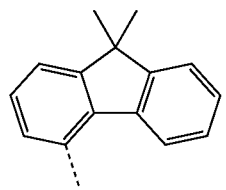 |
| 1-449 | 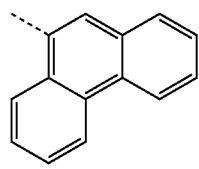 | 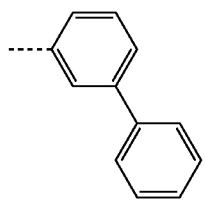 | 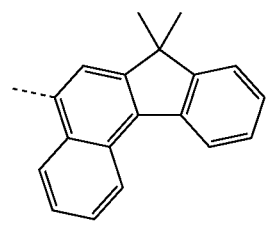 |
| 1-450 | 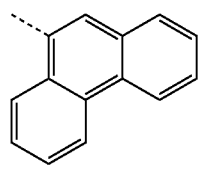 | 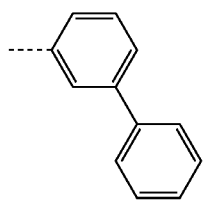 | 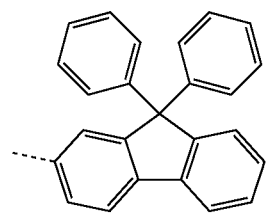 |
| 1-451 | 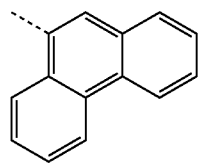 | 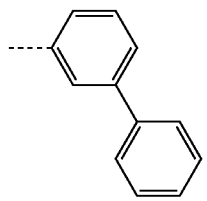 | 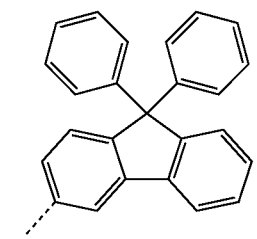 |
| 1-452 | 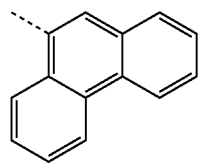 | 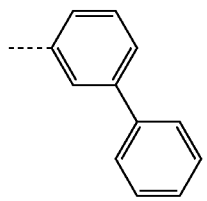 | 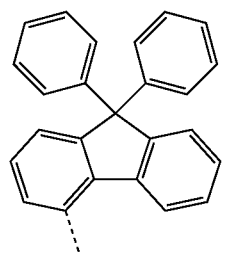 |
| 1-453 | 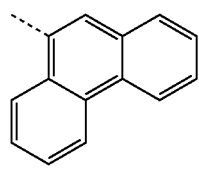 | 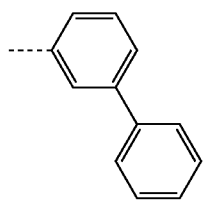 | 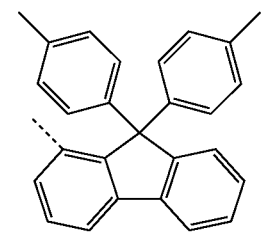 |

-continued
| Formula | - - -Ar1 | - - -Ar2 | - - -Ar3 |
|---|---|---|---|
| 1-454 | 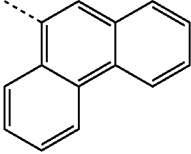 | 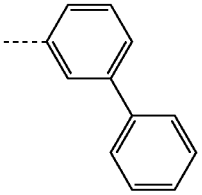 | 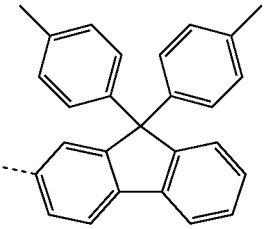 |
| 1-455 | 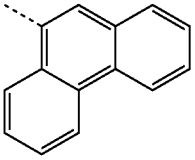 | 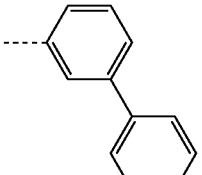 | 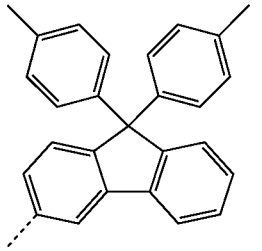 |
| 1-456 | 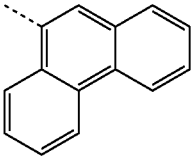 | 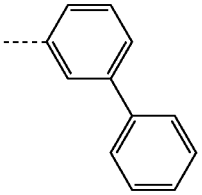 | 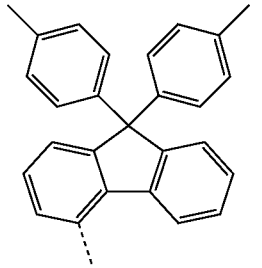 |
| 1-457 | 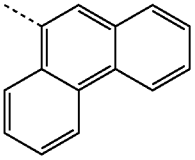 | 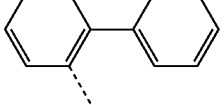 | 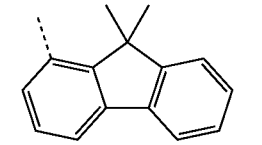 |
| 1-458 | 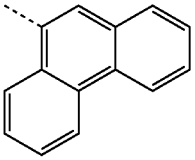 | 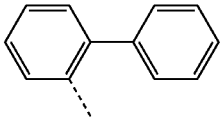 | 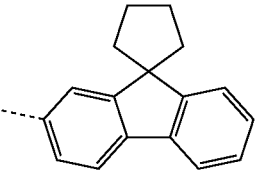 |
| 1-459 | 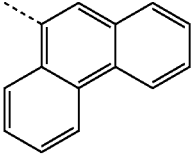 | 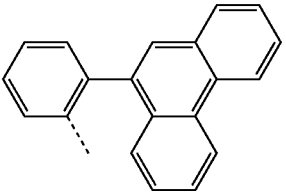 | 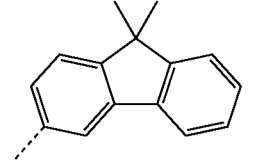 |
| 1-460 | 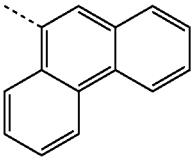 | 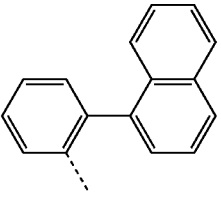 | 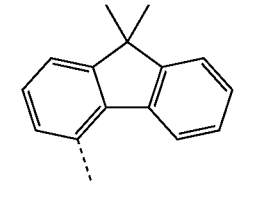 |

| Formula | ---Ar1 | ---Ar2 | ---Ar3 |
|---|---|---|---|
| 1-461 | 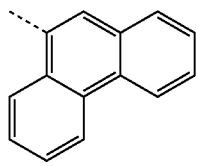 | 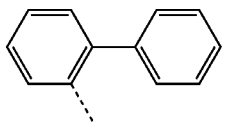 | 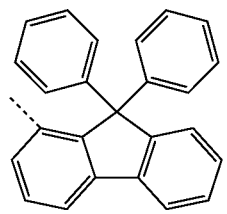 |
| 1-462 | 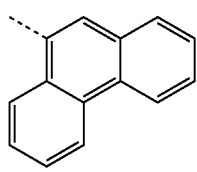 | 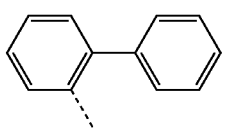 | 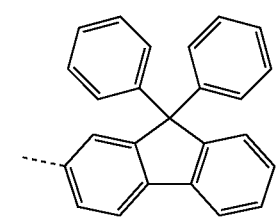 |
| 1-463 | 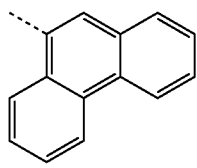 | 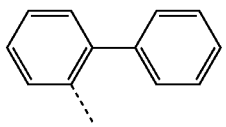 | 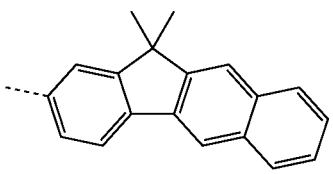 |
| 1-464 | 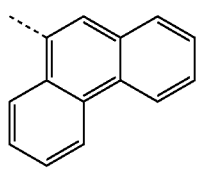 | 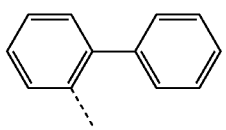 | 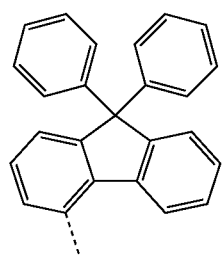 |
| 1-465 | 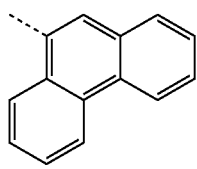 | 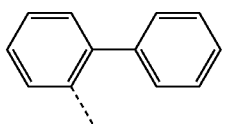 | 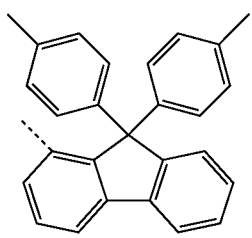 |
| 1-466 | 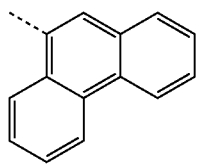 | 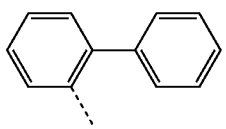 | 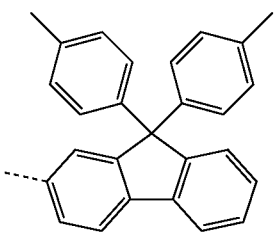 |

-continued
| Formula | ---Ar1 | ---Ar2 | ---Ar3 |
|---|---|---|---|
| 1-467 | 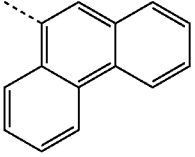 | 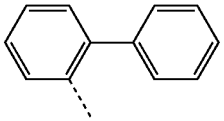 | 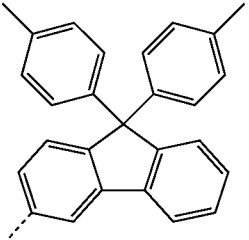 |
| 1-468 | 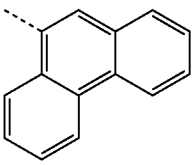 | 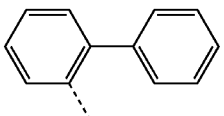 | 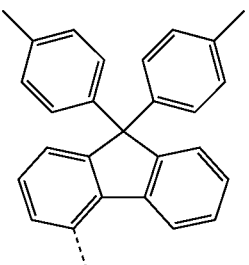 |
| 1-469 | 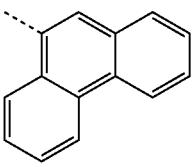 | 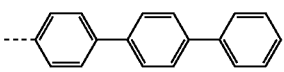 | 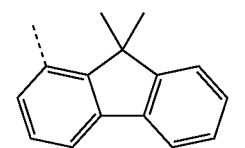 |
| 1-470 | 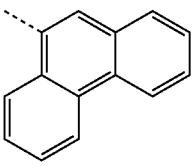 | 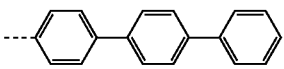 | 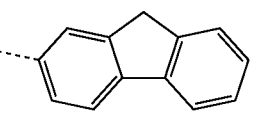 |
| 1-471 | 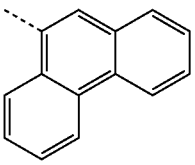 | 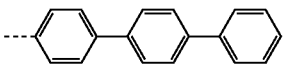 | 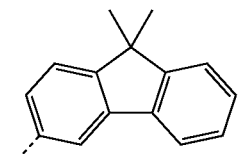 |
| 1-472 | 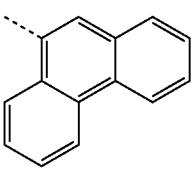 | 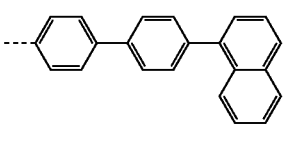 | 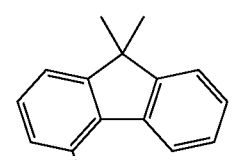 |
| 1-473 | 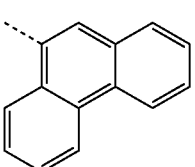 | 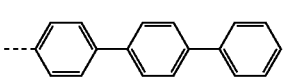 | 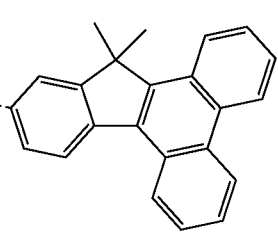 |

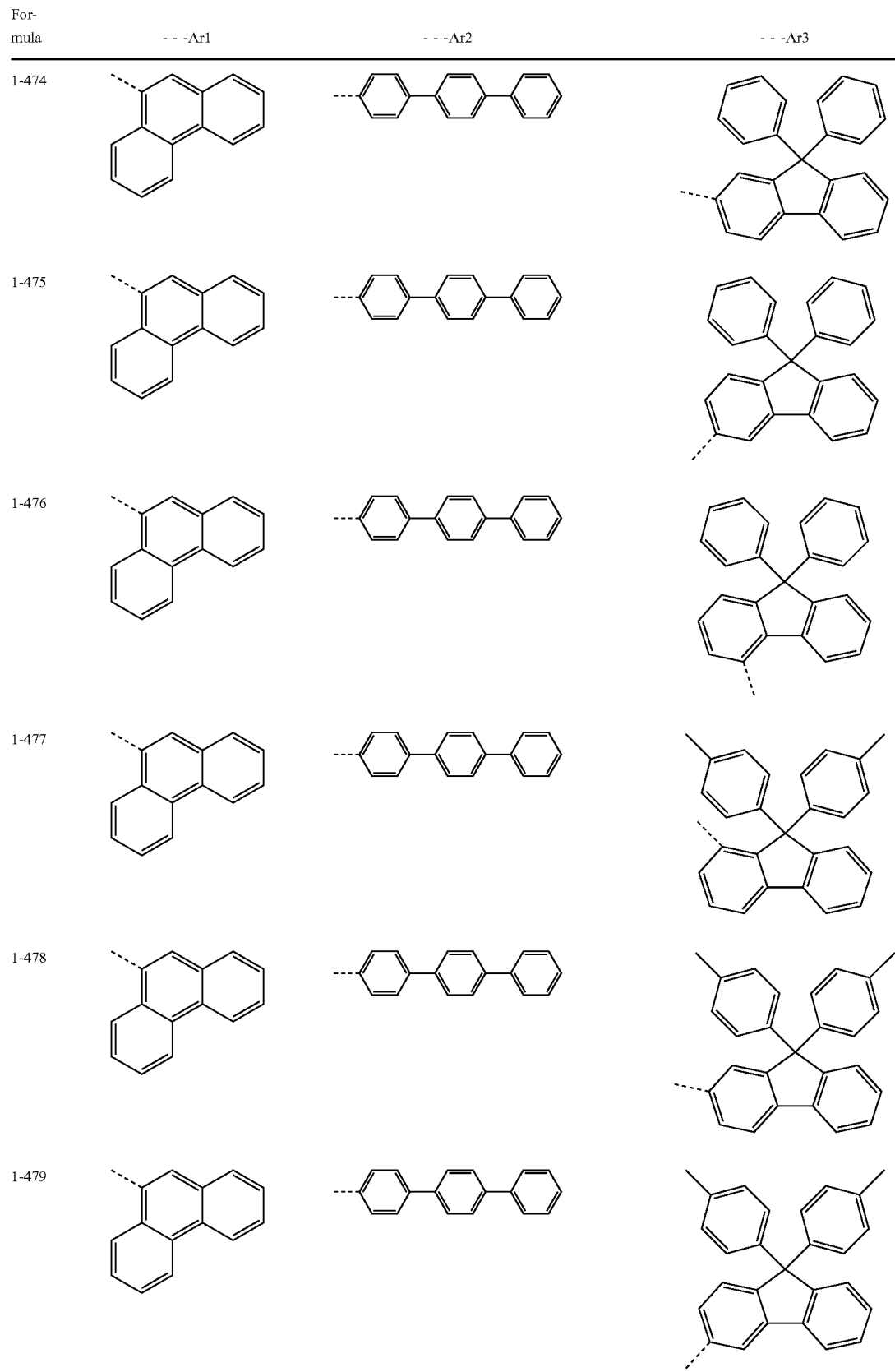

-continued

| Formula | - - -Ar1 | - - -Ar2 | - - -Ar3 |
|---|---|---|---|
| 1-480 | phenanthrene | p-terphenyl | 9,9-di(p-tolyl)fluorene |
| 1-481 | phenanthrene | 1,1':3',1''-terphenyl (meta) | 9,9-dimethylfluorene |
| 1-482 | phenanthrene | 1,3,5-triphenylbenzene derivative | 9,9-dimethylfluorene |
| 1-483 | phenanthrene | 1,1':3',1''-terphenyl (meta) | spiro[cyclopentane-fluorene] |
| 1-484 | phenanthrene | 1,1':3',1''-terphenyl (meta) | 9,9-dimethylfluorene |

-continued

| Formula | ---Ar1 | ---Ar2 | ---Ar3 |
|---|---|---|---|
| 1-485 | | | |
| 1-486 | | | |
| 1-487 | | | |
| 1-488 | | | |
| 1-489 | | | |

| Formula | ---Ar1 | ---Ar2 | ---Ar3 |
|---|---|---|---|
| 1-490 | 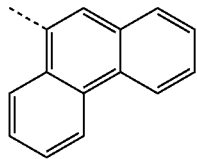 | 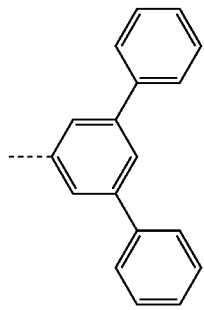 | 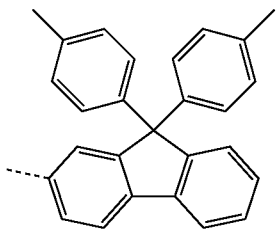 |
| 1-491 | 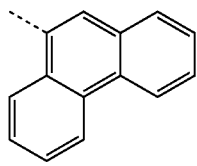 | 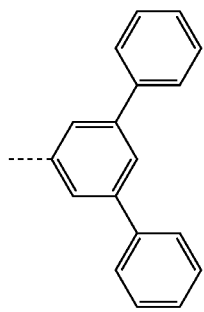 | 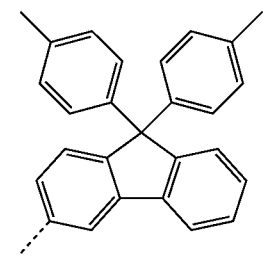 |
| 1-492 | 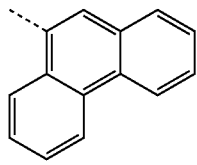 | 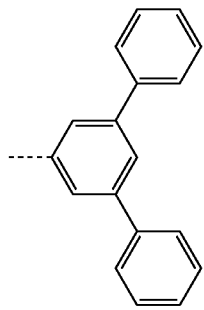 | 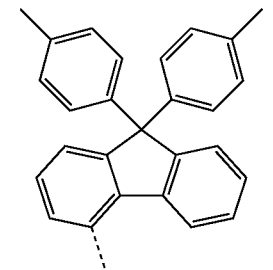 |
| 1-493 | 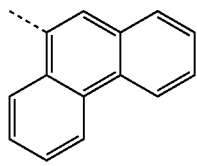 | 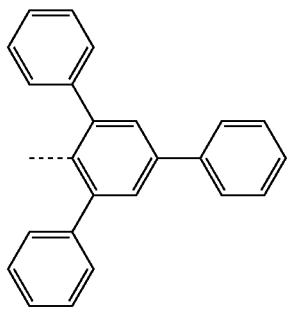 | 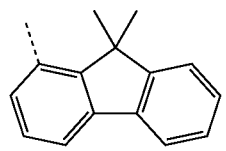 |
| 1-494 | 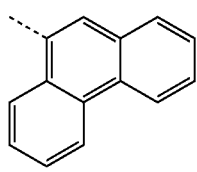 | 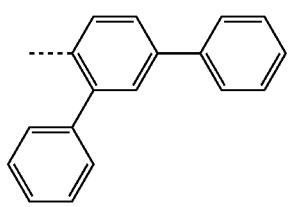 | 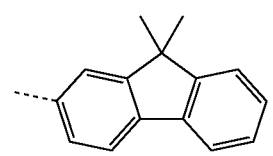 |

-continued
| Formula | ---Ar1 | ---Ar2 | ---Ar3 |
|---|---|---|---|
| 1-495 | 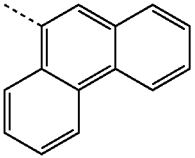 | 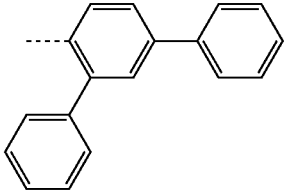 | 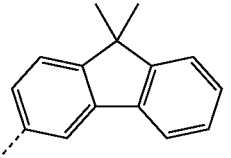 |
| 1-496 | 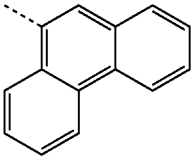 | 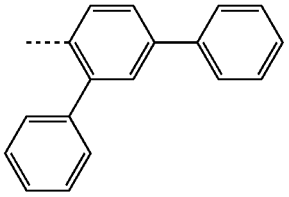 | 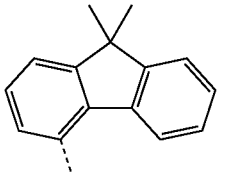 |
| 1-497 | 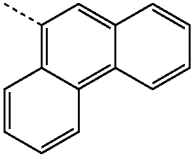 | 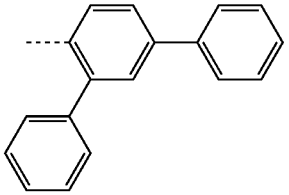 | 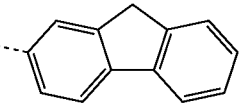 |
| 1-498 | 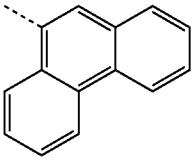 | 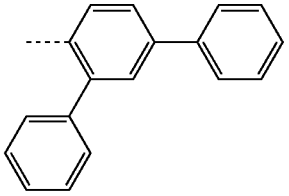 | 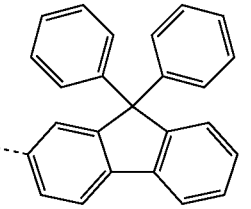 |
| 1-499 | 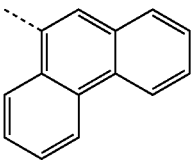 | 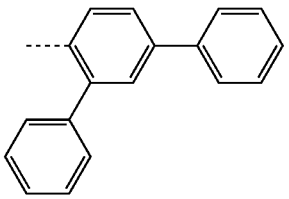 | 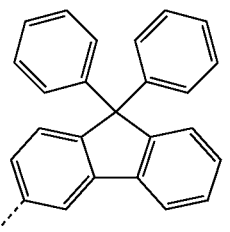 |
| 1-500 | 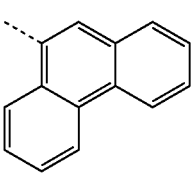 | 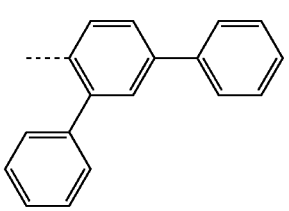 | 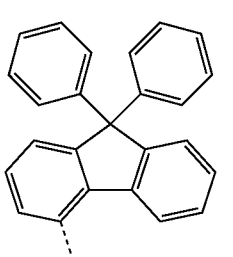 |
| 1-501 | 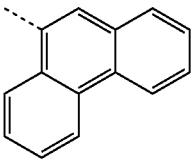 | 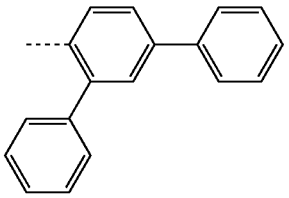 | 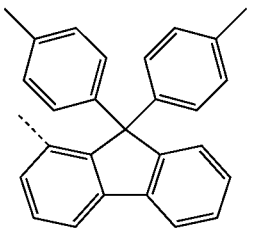 |

-continued
| Formula | - - -Ar1 | - - -Ar2 | - - -Ar3 |
|---|---|---|---|
| 1-502 | 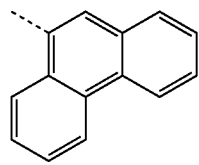 | 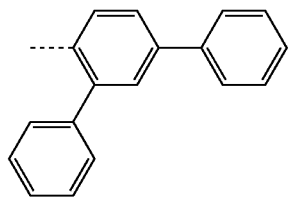 | 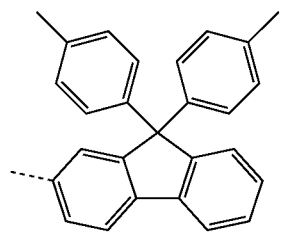 |
| 1-503 | 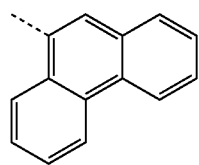 | 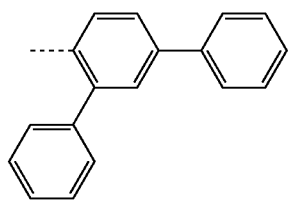 | 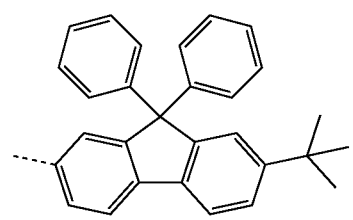 |
| 1-504 | 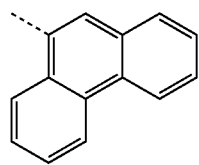 | 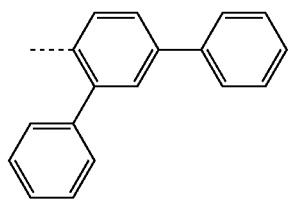 | 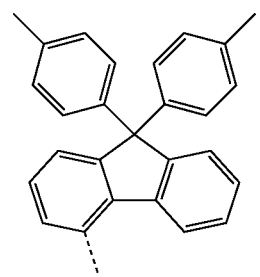 |
| 1-505 | 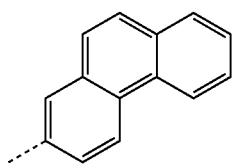 | 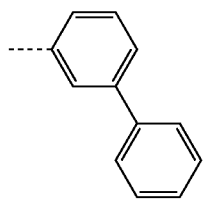 | 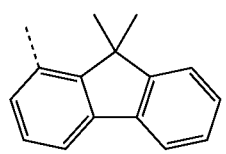 |
| 1-506 | 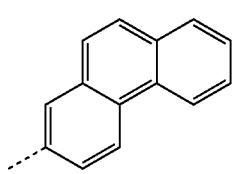 | 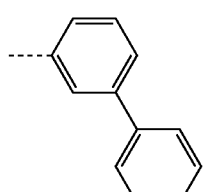 | 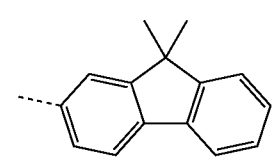 |
| 1-507 | 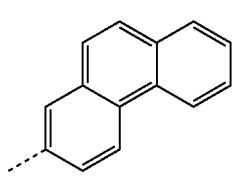 | 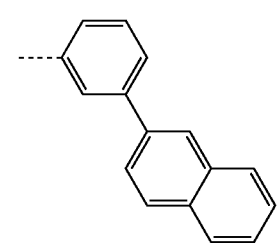 | 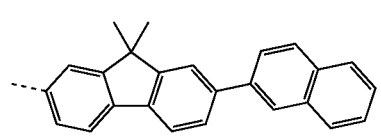 |

-continued
| Formula | - - -Ar1 | - - -Ar2 | - - -Ar3 |
|---|---|---|---|
| 1-508 | 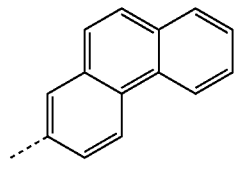 | 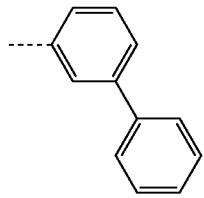 | 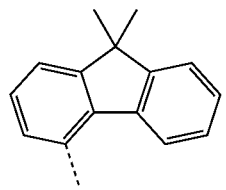 |
| 1-509 | 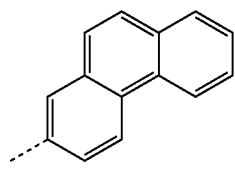 | 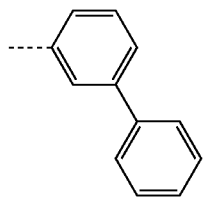 | 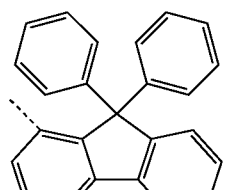 |
| 1-510 | 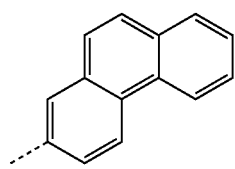 | 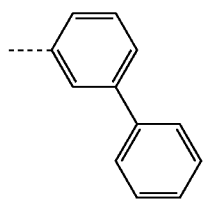 | 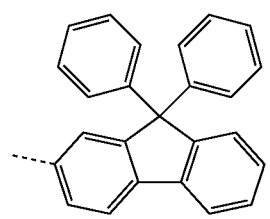 |
| 1-511 | 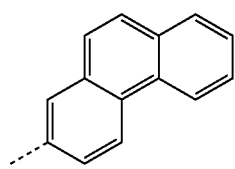 | 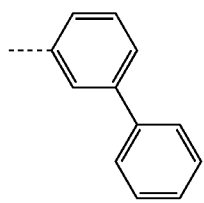 | 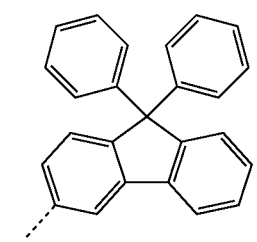 |
| 1-512 | 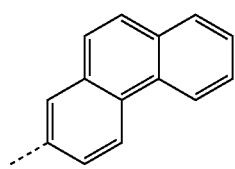 | 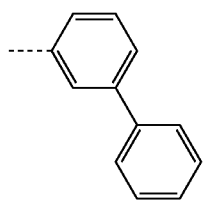 | 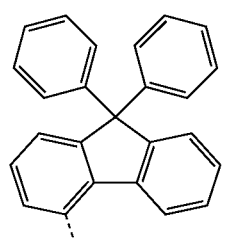 |
| 1-513 | 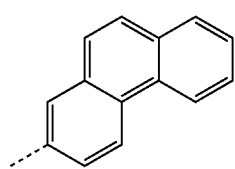 | 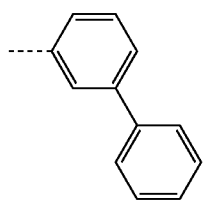 | 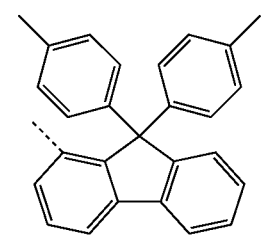 |

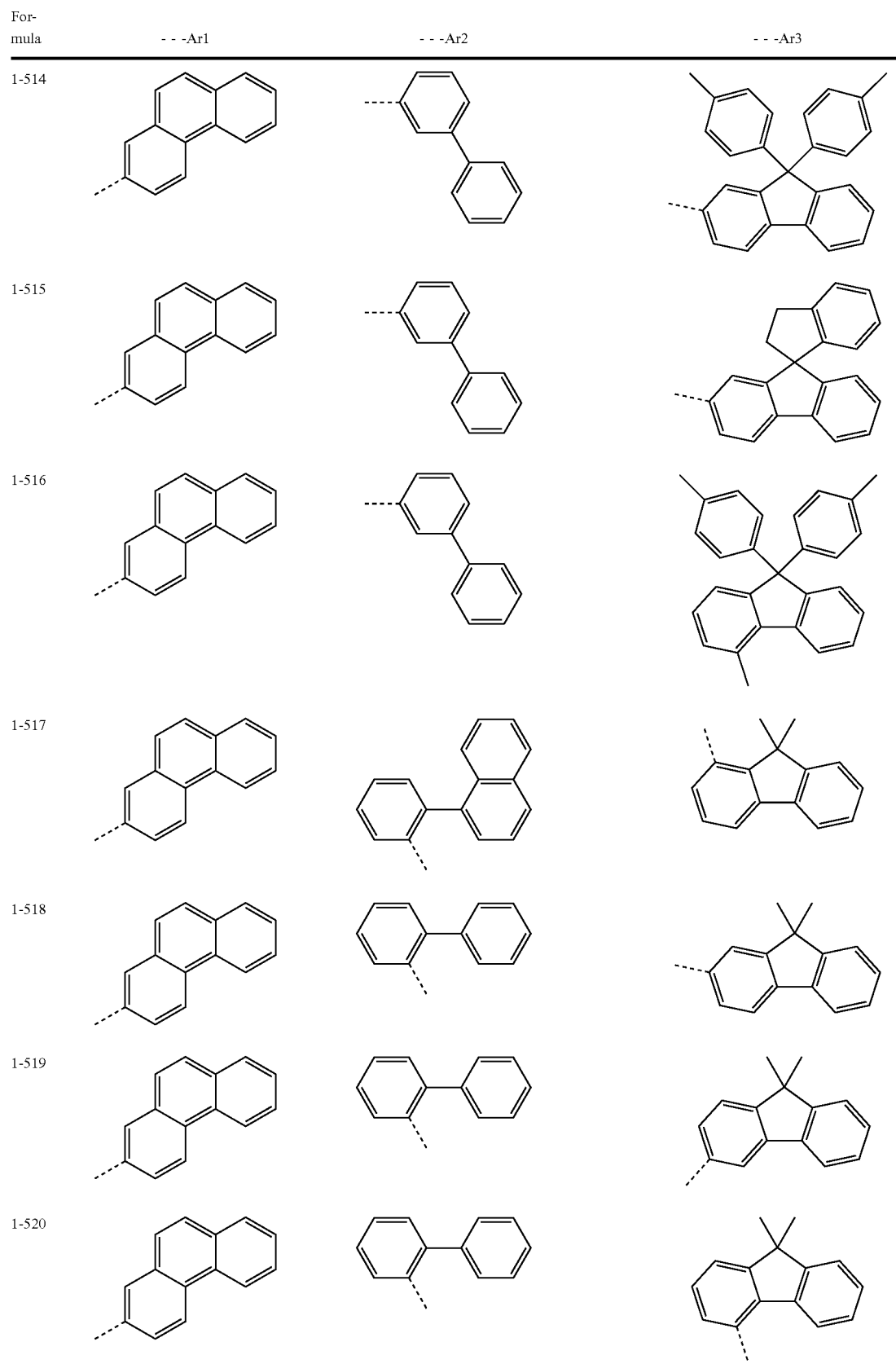

-continued
| Formula | - - -Ar1 | - - -Ar2 | - - -Ar3 |
|---|---|---|---|
| 1-521 | 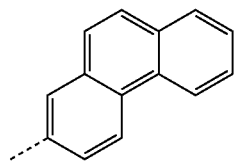 | 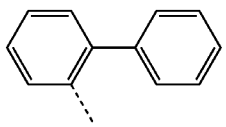 | 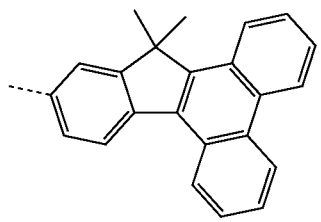 |
| 1-522 | 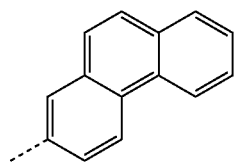 | 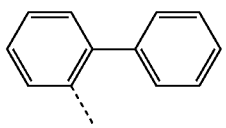 | 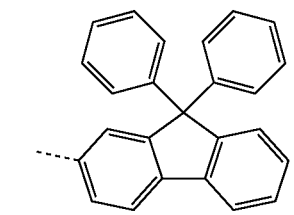 |
| 1-523 | 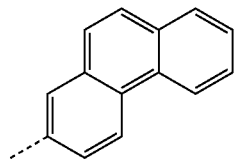 | 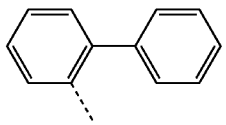 | 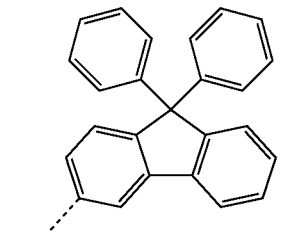 |
| 1-524 | 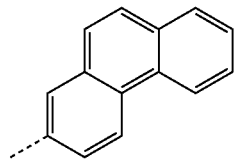 | 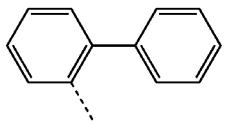 | 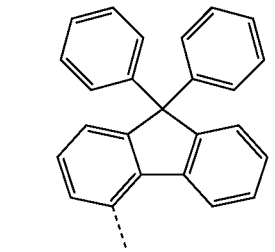 |
| 1-525 | 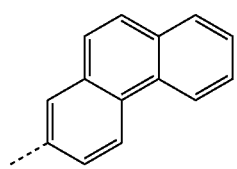 | 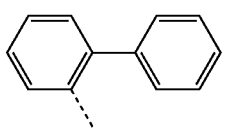 | 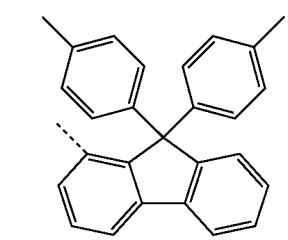 |
| 1-526 | 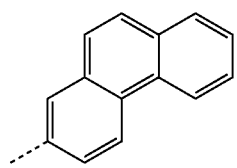 | 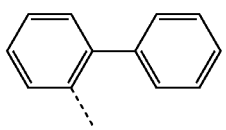 | 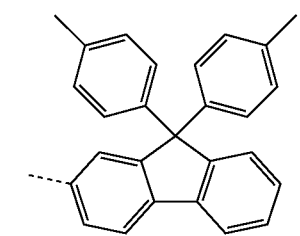 |

-continued
| Formula | ---Ar1 | ---Ar2 | ---Ar3 |
|---|---|---|---|
| 1-527 | 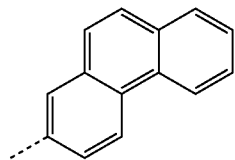 | 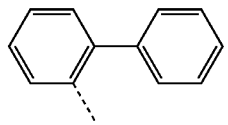 | 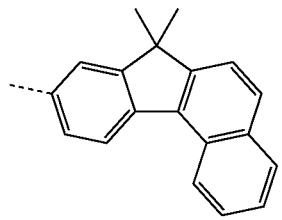 |
| 1-528 | 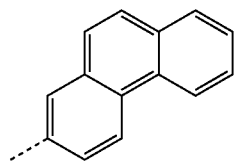 | 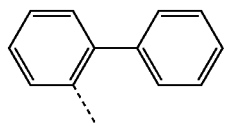 | 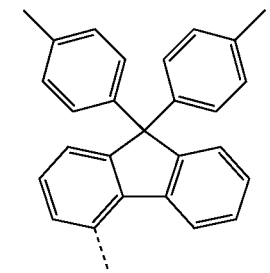 |
| 1-529 | 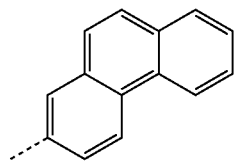 | 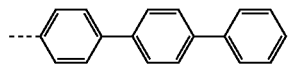 | 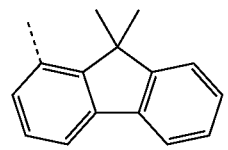 |
| 1-530 | 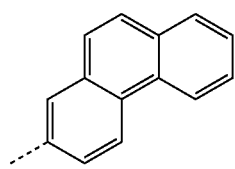 | 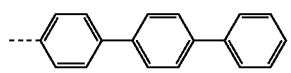 | 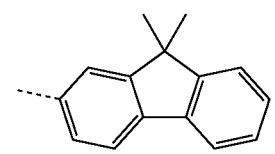 |
| 1-531 | 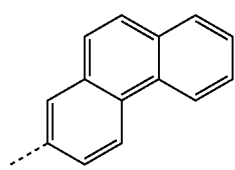 | 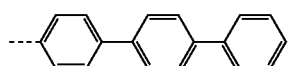 | 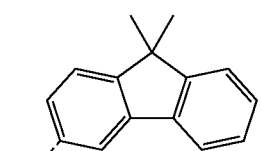 |
| 1-532 | 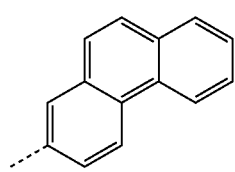 | 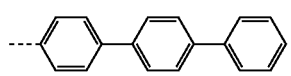 | 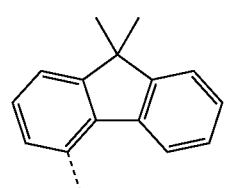 |
| 1-533 | 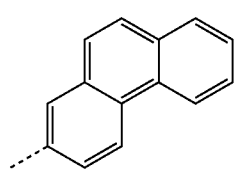 | 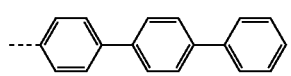 | 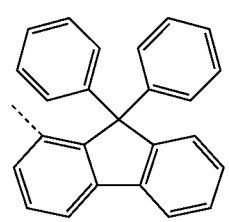 |

-continued
| Formula | ---Ar1 | ---Ar2 | ---Ar3 |
|---|---|---|---|
| 1-534 | 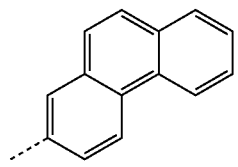 | 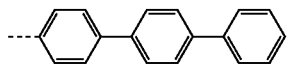 | 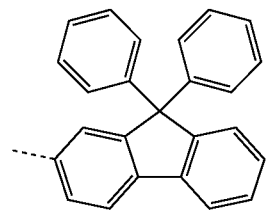 |
| 1-535 | 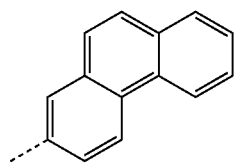 | 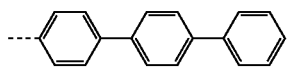 | 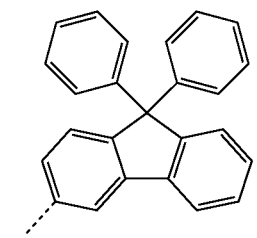 |
| 1-536 | 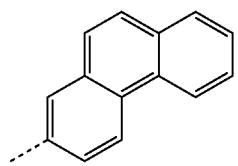 | 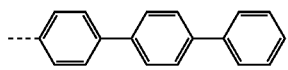 | 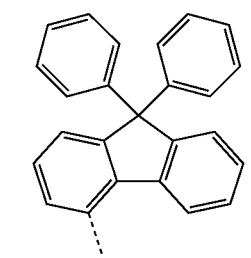 |
| 1-537 | 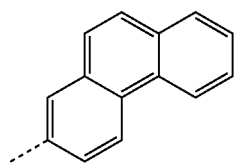 | 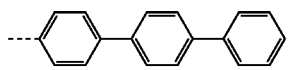 | 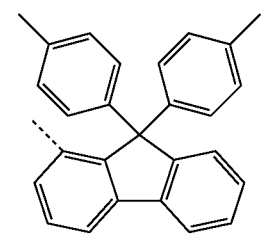 |
| 1-538 | 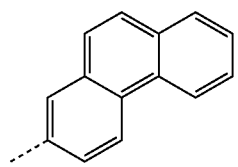 | 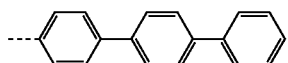 | 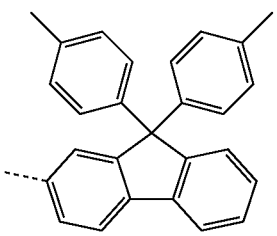 |
| 1-539 | 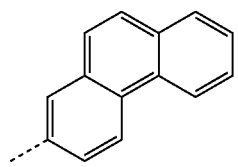 | 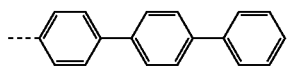 | 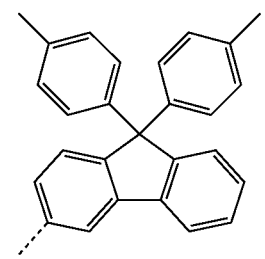 |

| Formula | - - -Ar1 | - - -Ar2 | - - -Ar3 |
|---|---|---|---|
| 1-540 | phenanthrene | -p-C6H4-C6H4-C6H5 | 9,9-di(p-tolyl)fluorene |
| 1-541 | phenanthrene | 3,5-diphenylphenyl | 9,9-dimethylfluorene (1-position) |
| 1-542 | phenanthrene | 3,5-diphenylphenyl | 9,9-dimethylfluorene (2-position) |
| 1-543 | phenanthrene | 3,5-diphenylphenyl | 9,9-dimethylfluorene (3-position) |
| 1-544 | phenanthrene | 3,5-diphenylphenyl | 9,9-dimethylfluorene (4-position) |

-continued

| Formula | - - -Ar1 | - - -Ar2 | - - -Ar3 |
|---|---|---|---|
| 1-545 | | | |
| 1-546 | | | |
| 1-547 | | | |
| 1-548 | | | |
| 1-549 | | | |

| Formula | ---Ar1 | ---Ar2 | ---Ar3 |
|---|---|---|---|
| 1-550 | 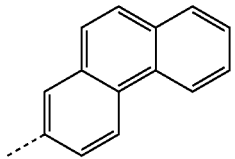 | 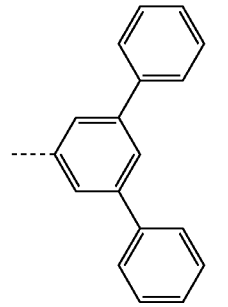 | 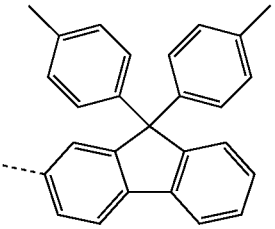 |
| 1-551 | 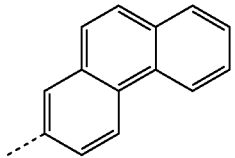 | 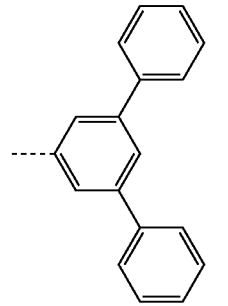 | 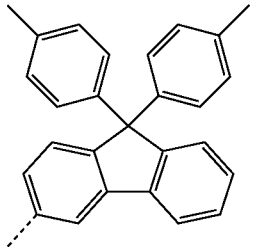 |
| 1-552 | 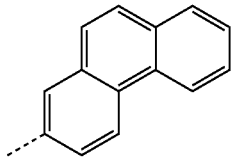 | 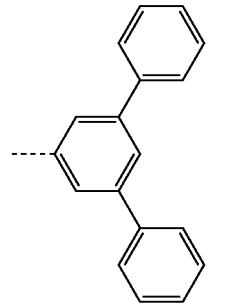 | 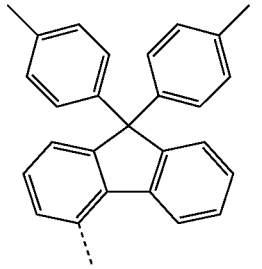 |
| 1-553 | 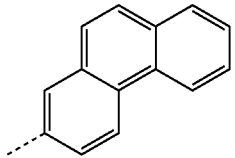 | 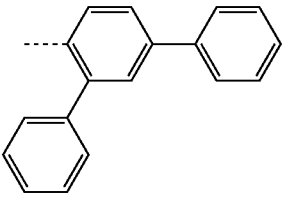 | 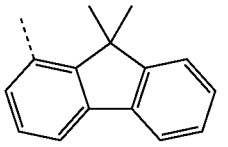 |
| 1-554 | 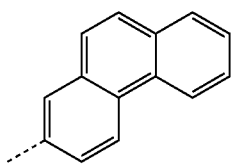 | 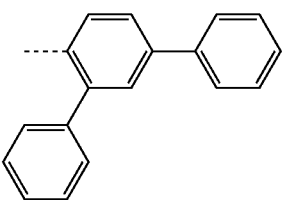 | 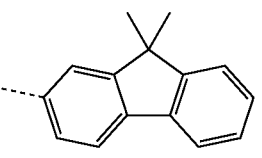 |
| 1-555 | 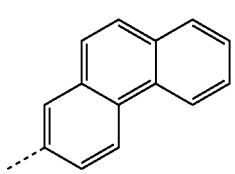 | 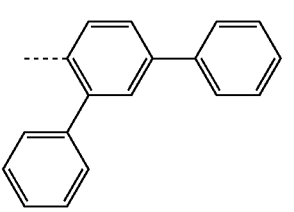 | 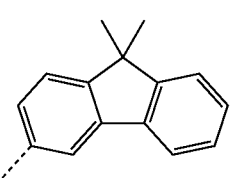 |

-continued
| Formula | ---Ar1 | ---Ar2 | ---Ar3 |
|---|---|---|---|
| 1-556 | 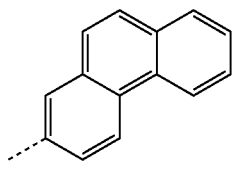 | 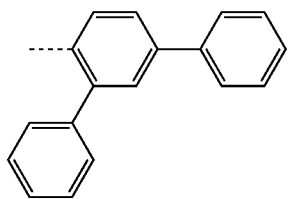 | 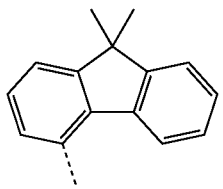 |
| 1-557 | 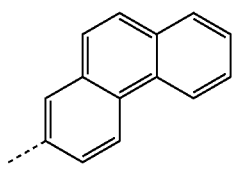 | 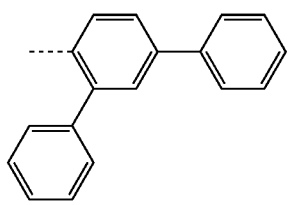 | 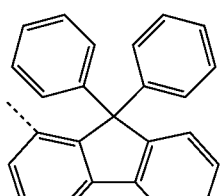 |
| 1-558 | 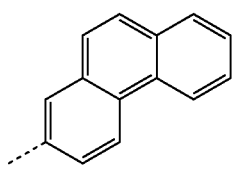 | 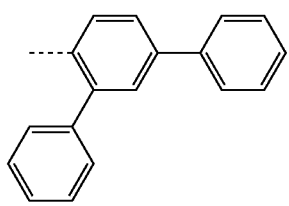 | 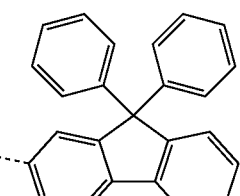 |
| 1-559 | 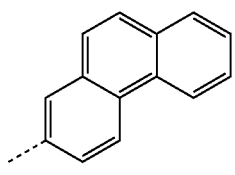 | 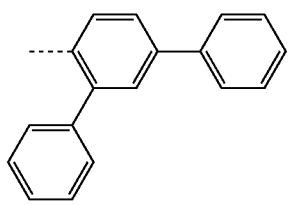 | 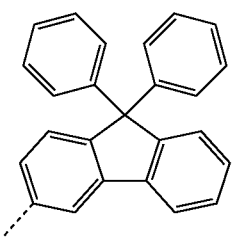 |
| 1-560 | 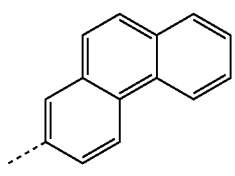 | 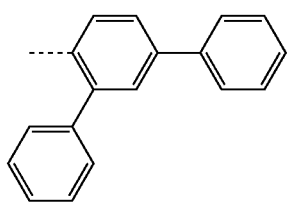 | 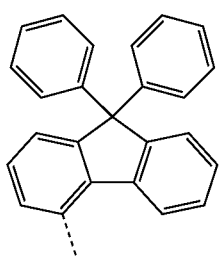 |
| 1-561 | 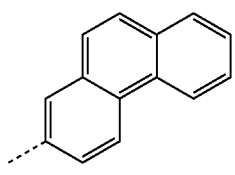 | 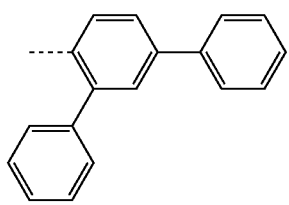 | 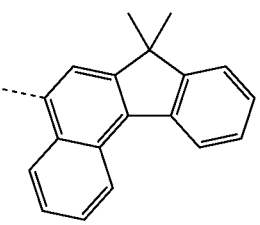 |

-continued
| Formula | - - -Ar1 | - - -Ar2 | - - -Ar3 |
|---|---|---|---|
| 1-562 | 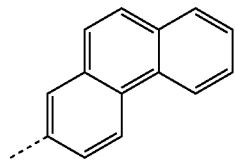 | 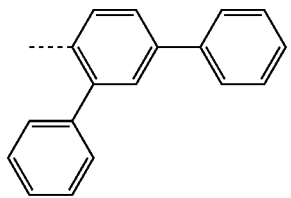 | 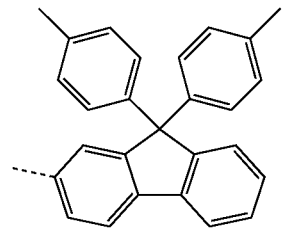 |
| 1-563 | 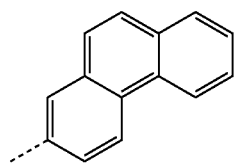 | 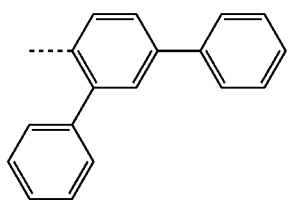 | 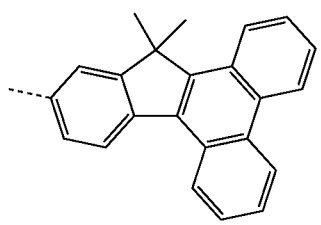 |
| 1-564 | 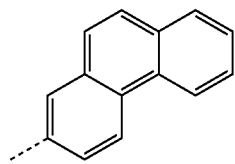 | 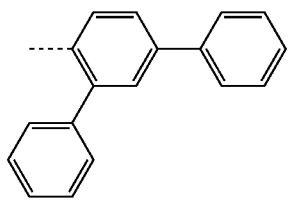 | 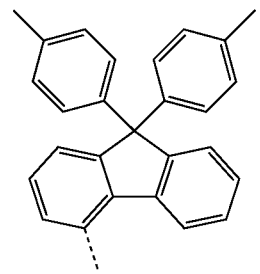 |
| 1-565 | 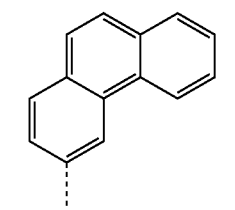 | 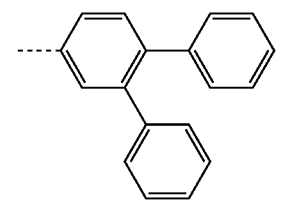 | 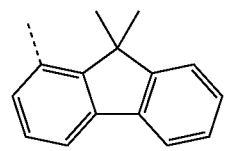 |
| 1-566 | 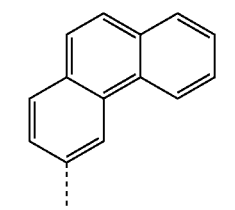 | 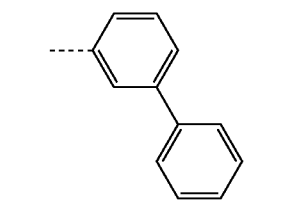 | 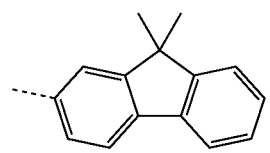 |
| 1-567 | 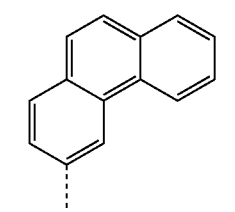 | 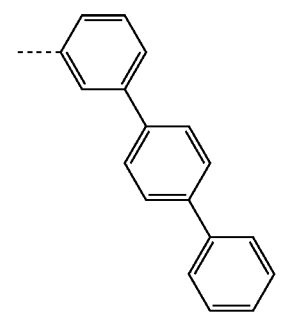 | 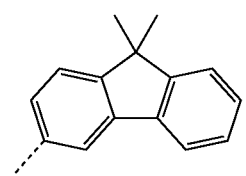 |

| Formula | - - -Ar1 | - - -Ar2 | - - -Ar3 |
|---|---|---|---|
| 1-568 | 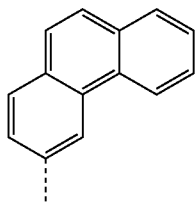 | 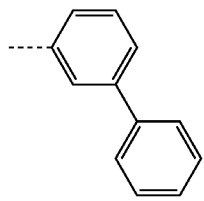 | 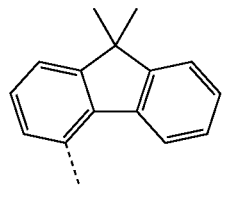 |
| 1-569 | 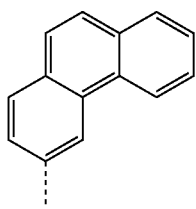 | 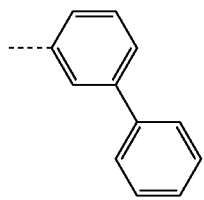 | 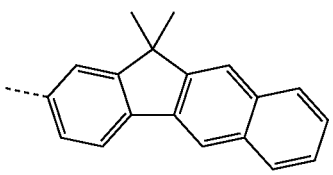 |
| 1-570 | 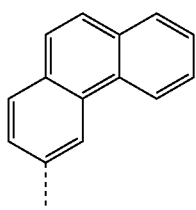 | 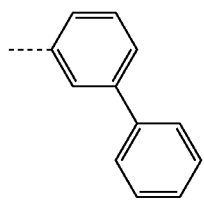 | 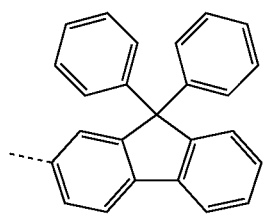 |
| 1-571 | 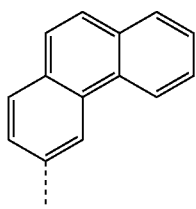 | 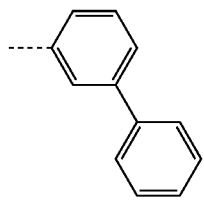 | 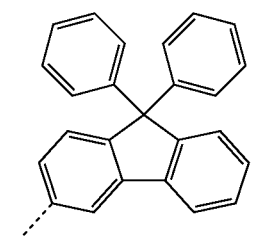 |
| 1-572 | 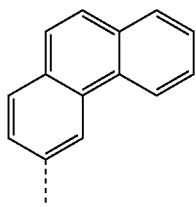 | 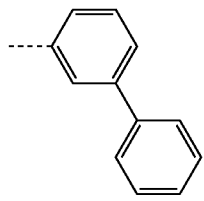 | 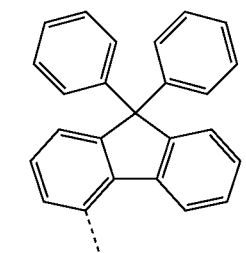 |
| 1-573 | 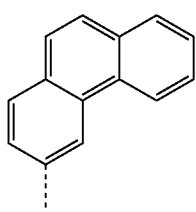 | 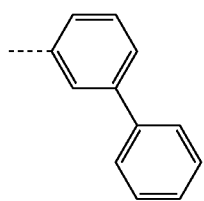 | 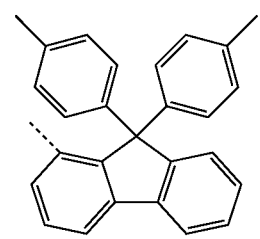 |

| For-mula | - - -Ar1 | - - -Ar2 | - - -Ar3 |
|---|---|---|---|
| 1-574 | 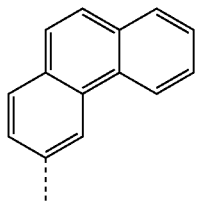 | 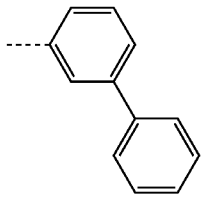 | 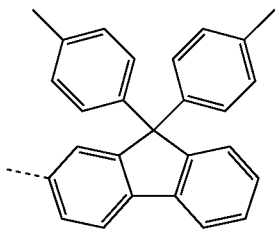 |
| 1-575 | 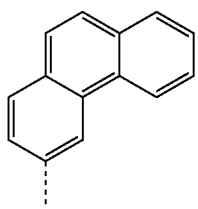 | 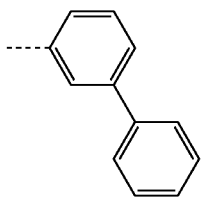 | 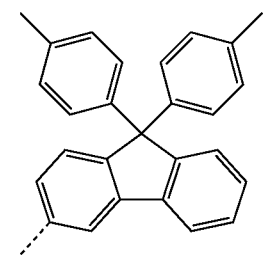 |
| 1-576 | 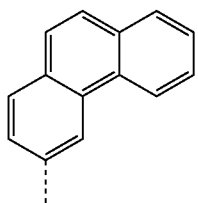 | 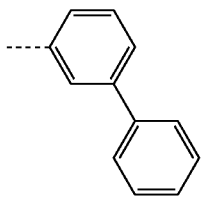 | 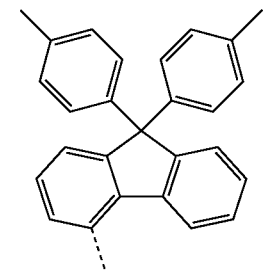 |
| 1-577 | 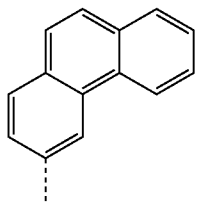 | 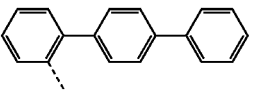 | 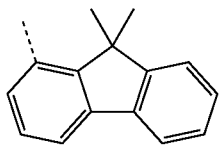 |
| 1-578 | 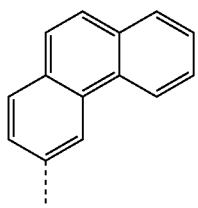 | 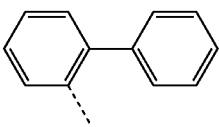 | 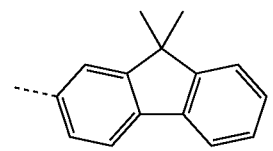 |
| 1-579 | 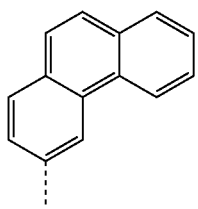 | 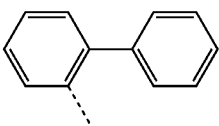 | 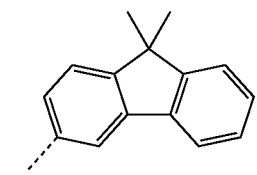 |

-continued
| Formula | - - -Ar1 | - - -Ar2 | - - -Ar3 |
|---|---|---|---|
| 1-580 | 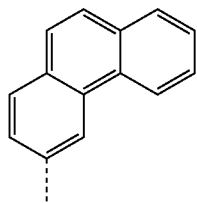 | 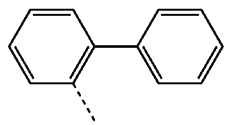 | 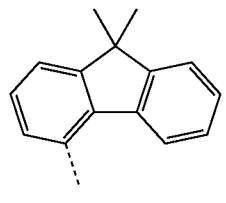 |
| 1-581 | 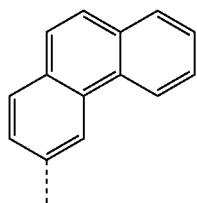 | 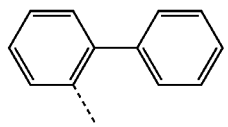 | 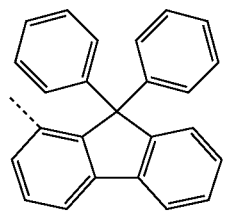 |
| 1-582 | 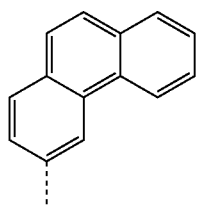 | 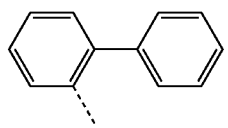 | 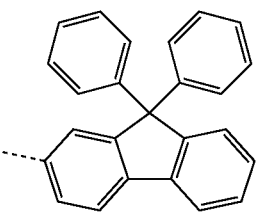 |
| 1-583 | 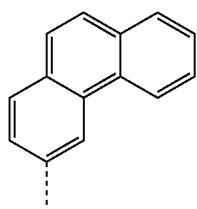 | 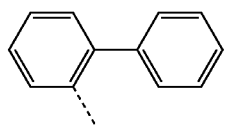 | 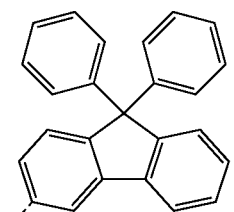 |
| 1-584 | 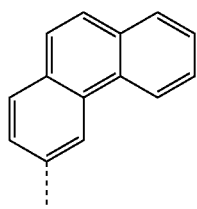 | 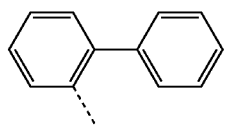 | 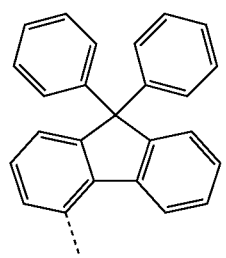 |
| 1-585 | 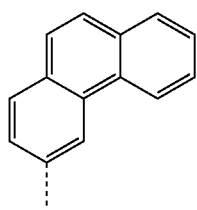 | 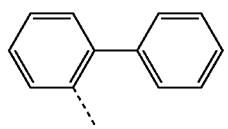 | 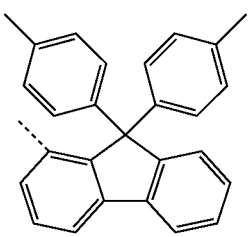 |

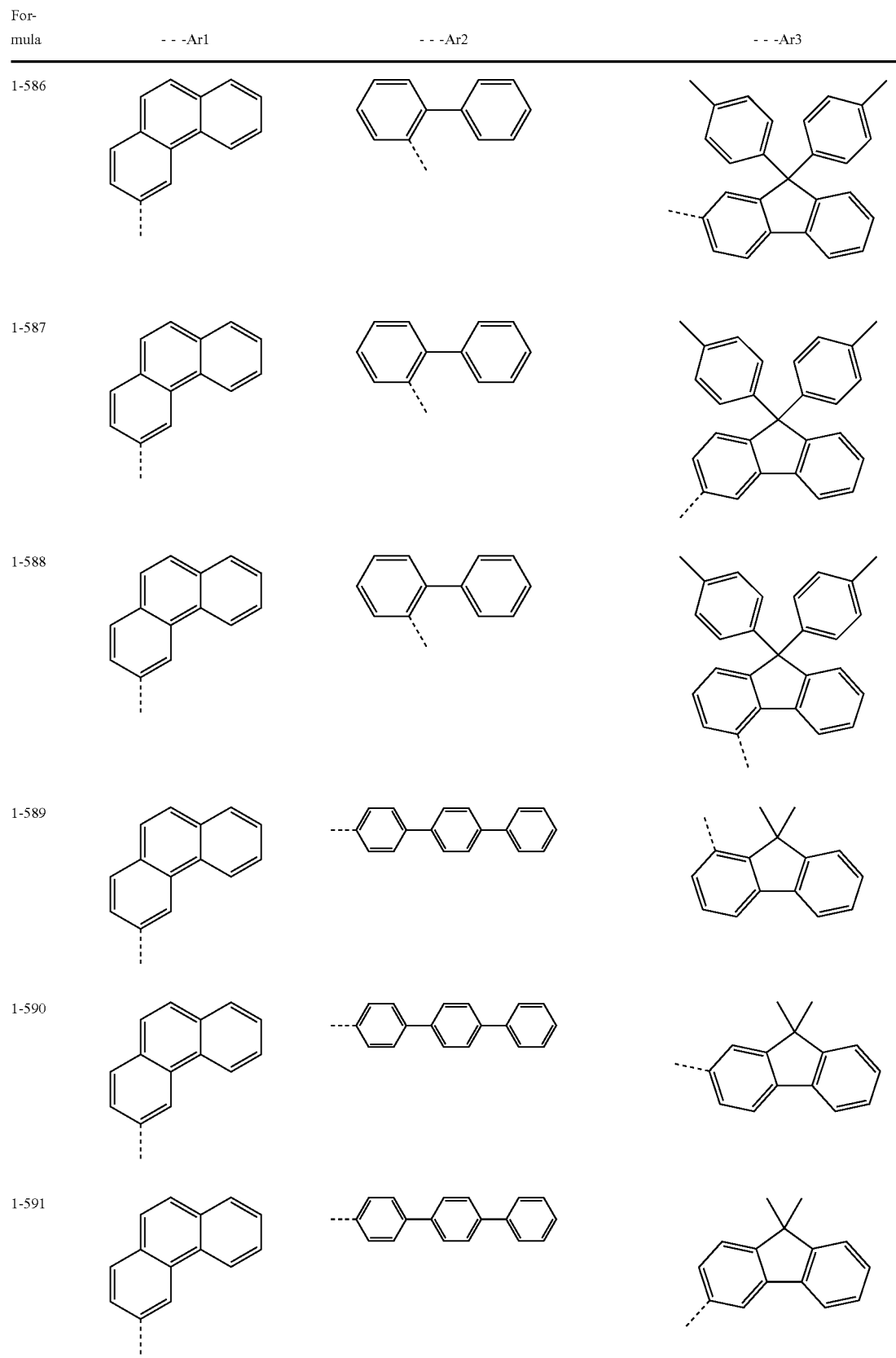

-continued
| For-mula | - - -Ar1 | - - -Ar2 | - - -Ar3 |
|---|---|---|---|
| 1-592 | 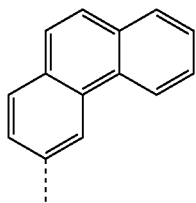 | 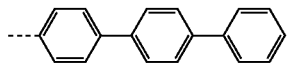 | 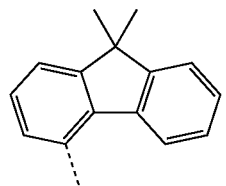 |
| 1-593 | 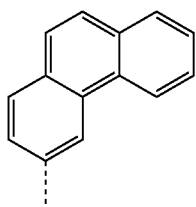 | 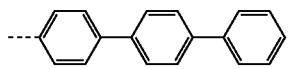 | 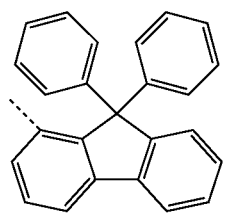 |
| 1-594 | 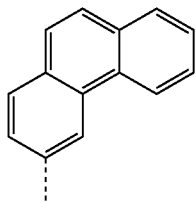 | 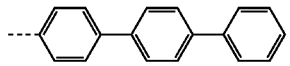 | 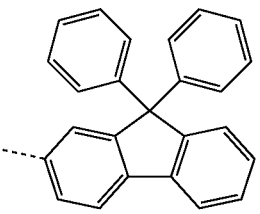 |
| 1-595 | 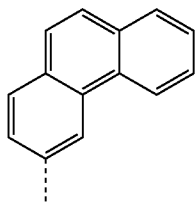 | 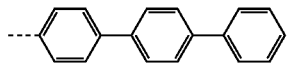 | 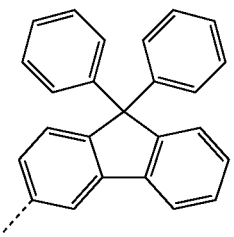 |
| 1-596 | 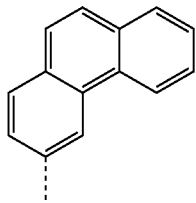 | 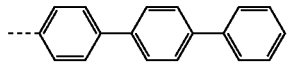 | 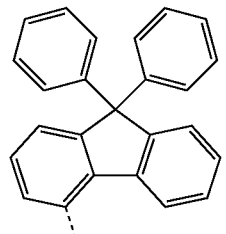 |
| 1-597 | 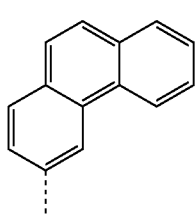 | 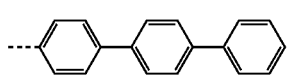 | 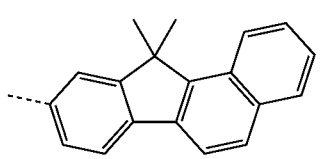 |

-continued
| Formula | - - -Ar1 | - - -Ar2 | - - -Ar3 |
|---|---|---|---|
| 1-598 | 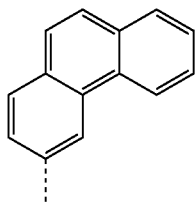 | 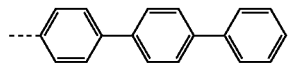 | 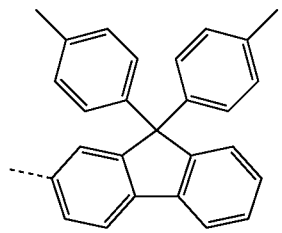 |
| 1-599 | 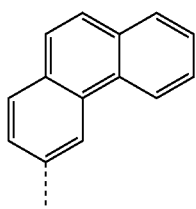 | 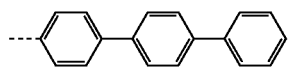 | 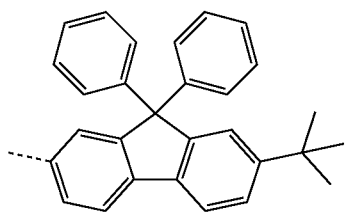 |
| 1-600 | 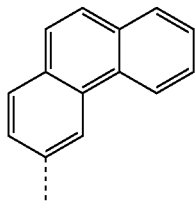 | 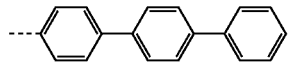 | 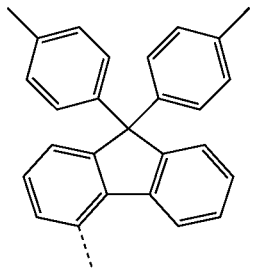 |
| 1-601 | 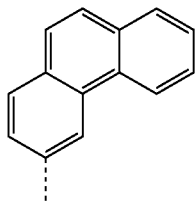 | 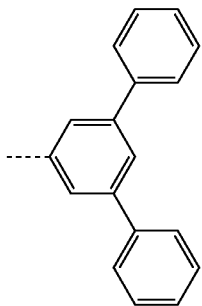 | 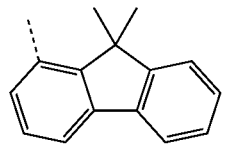 |
| 1-602 | 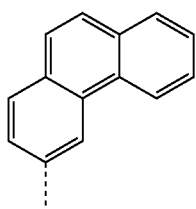 | 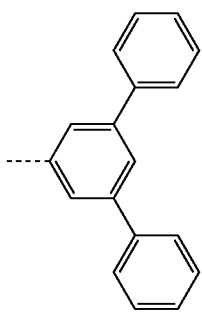 | 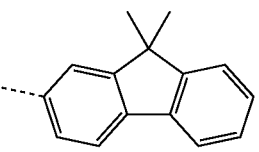 |

| Formula | - - -Ar1 | - - -Ar2 | - - -Ar3 |
|---|---|---|---|
| 1-603 | 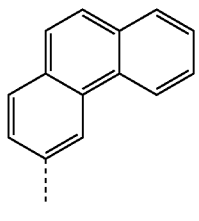 | 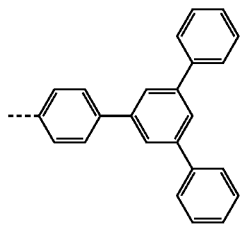 | 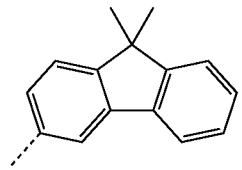 |
| 1-604 | 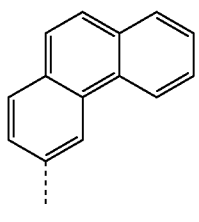 | 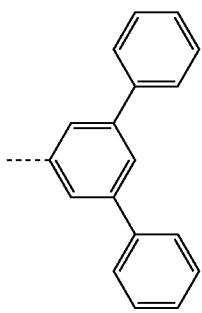 | 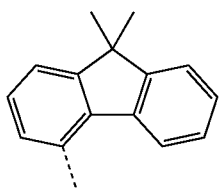 |
| 1-605 | 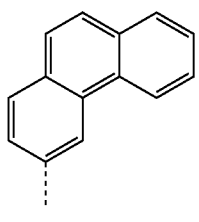 | 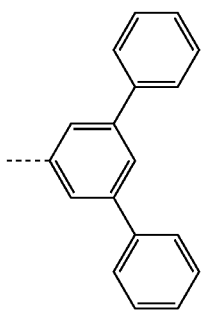 | 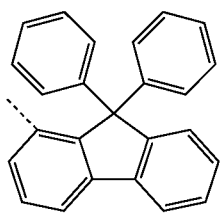 |
| 1-606 | 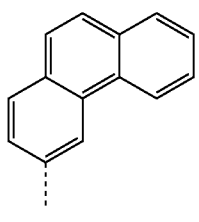 | 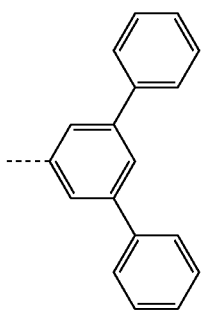 | 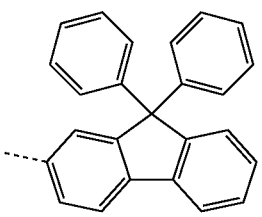 |
| 1-607 | 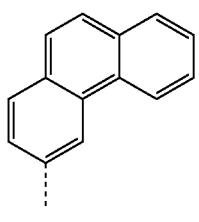 | 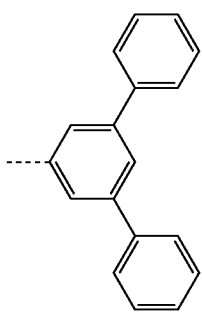 | 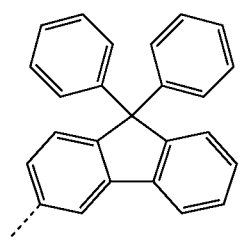 |

-continued

| Formula | - - -Ar1 | - - -Ar2 | - - -Ar3 |
|---|---|---|---|
| 1-608 | | | |
| 1-609 | | | |
| 1-610 | | | |
| 1-611 | | | |
| 1-612 | | | |

| Formula | ---Ar1 | ---Ar2 | ---Ar3 |
|---|---|---|---|
| 1-613 | 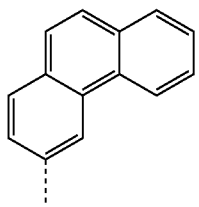 | 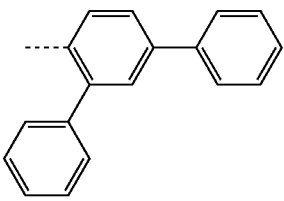 | 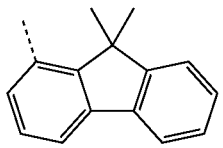 |
| 1-614 | 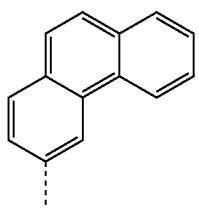 | 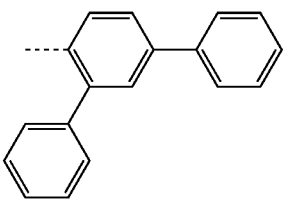 | 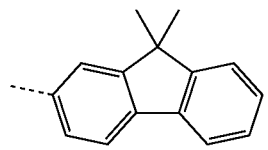 |
| 1-615 | 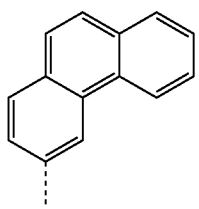 | 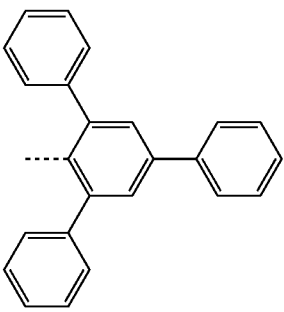 | 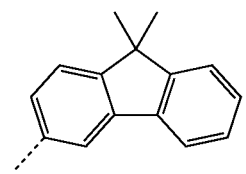 |
| 1-616 | 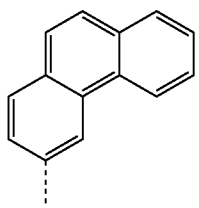 | 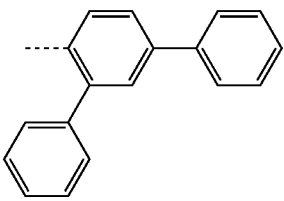 | 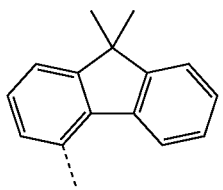 |
| 1-617 | 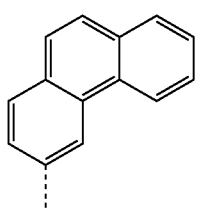 | 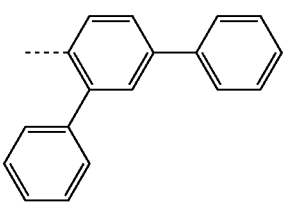 | 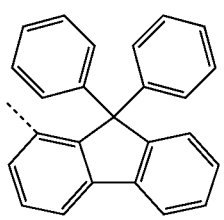 |
| 1-618 | 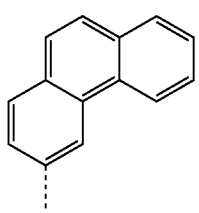 | 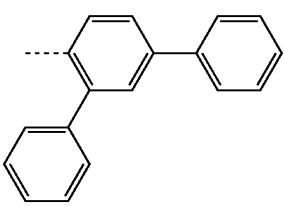 | 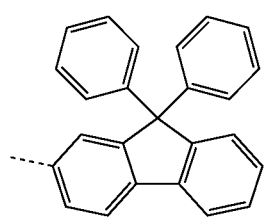 |

-continued
| Formula | - - -Ar1 | - - -Ar2 | - - -Ar3 |
|---|---|---|---|
| 1-619 | 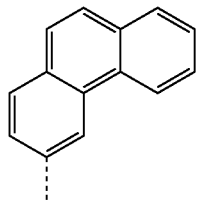 | 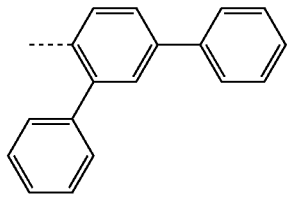 | 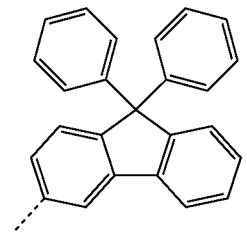 |
| 1-620 | 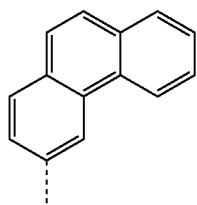 | 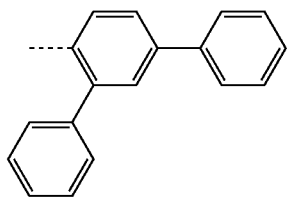 | 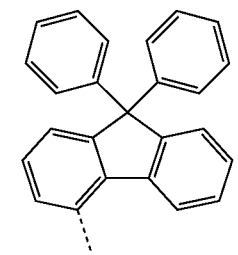 |
| 1-621 | 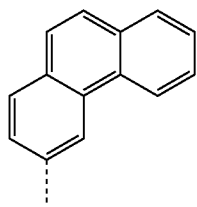 | 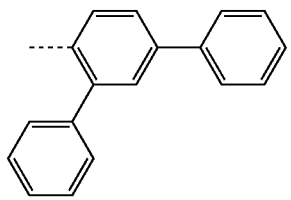 | 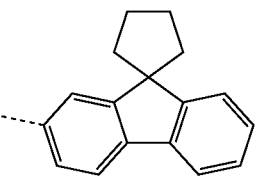 |
| 1-622 | 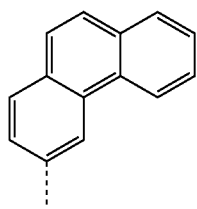 | 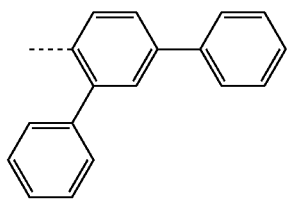 | 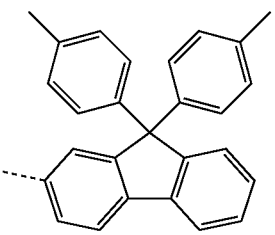 |
| 1-623 | 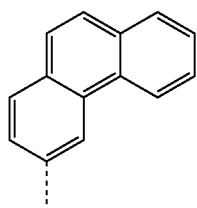 | 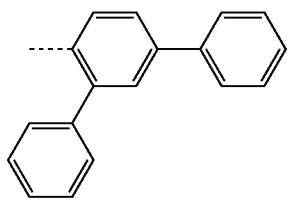 | 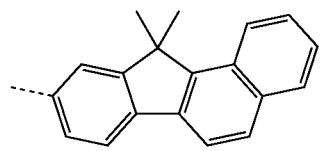 |
| 1-624 | 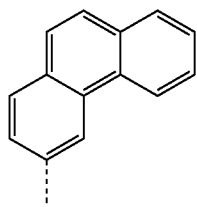 | 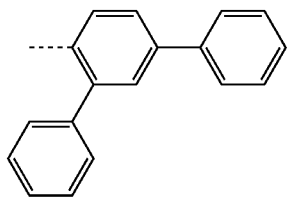 | 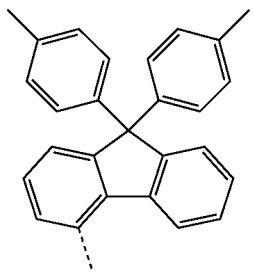 |

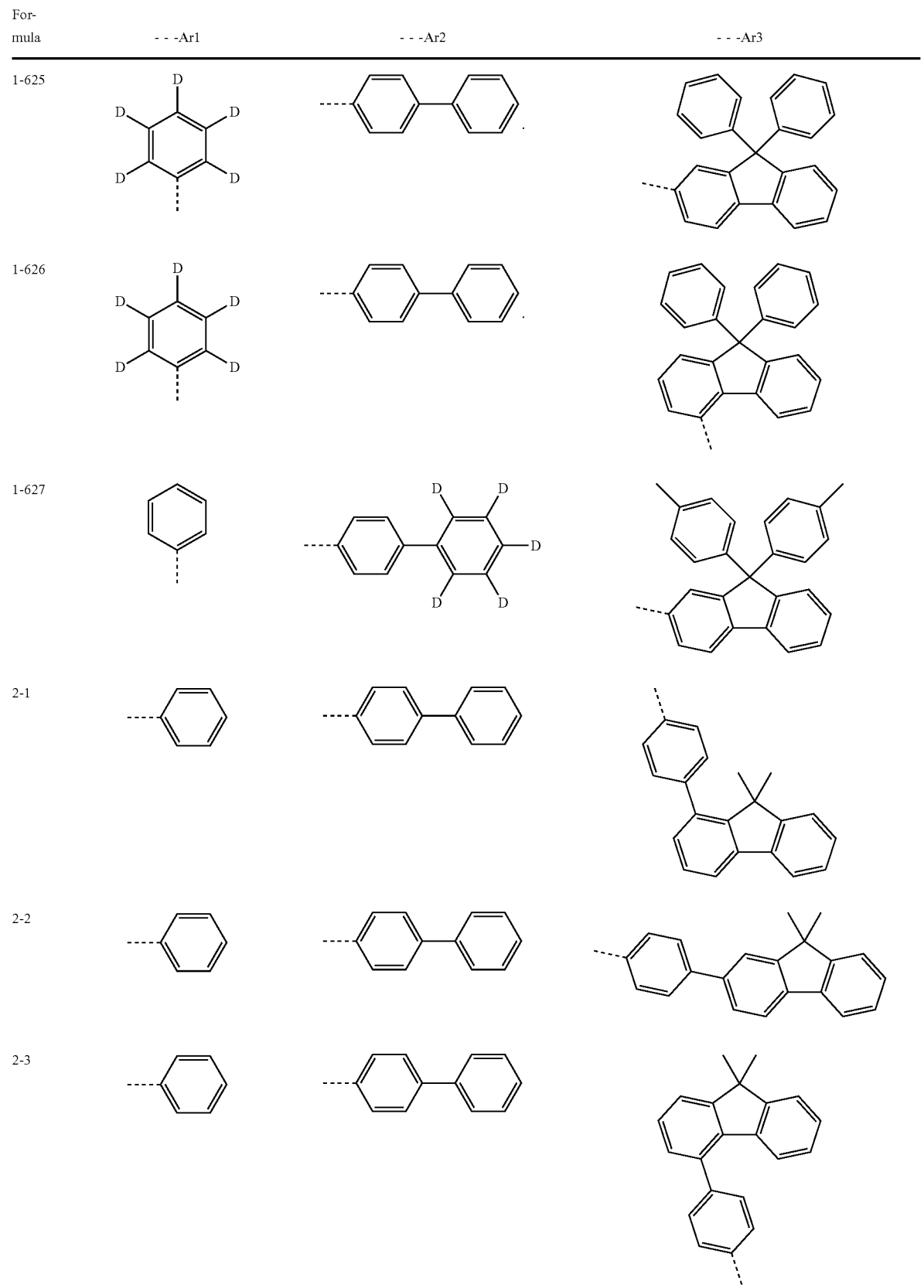

-continued

| Formula | - - -Ar1 | - - -Ar2 | - - -Ar3 |
|---|---|---|---|
| 2-4 | phenyl | biphenyl-4-yl | 2-(9,9-diphenylfluoren-2-yl)-substituted m-phenyl |
| 2-5 | phenyl | biphenyl-4-yl | 4-(9,9-diphenylfluoren-2-yl)phenyl |
| 2-6 | phenyl | biphenyl-4-yl | 4-(9,9-diphenylfluoren-4-yl)phenyl |
| 2-7 | phenyl | biphenyl-4-yl | 4-(9,9-di-p-tolylfluoren-2-yl)phenyl |
| 2-8 | phenyl | biphenyl-4-yl | 4-(dimethylbenzo[c]fluorenyl)phenyl |
| 2-9 | phenyl | biphenyl-2-yl | 4-(9,9-dimethylfluoren-1-yl)phenyl |

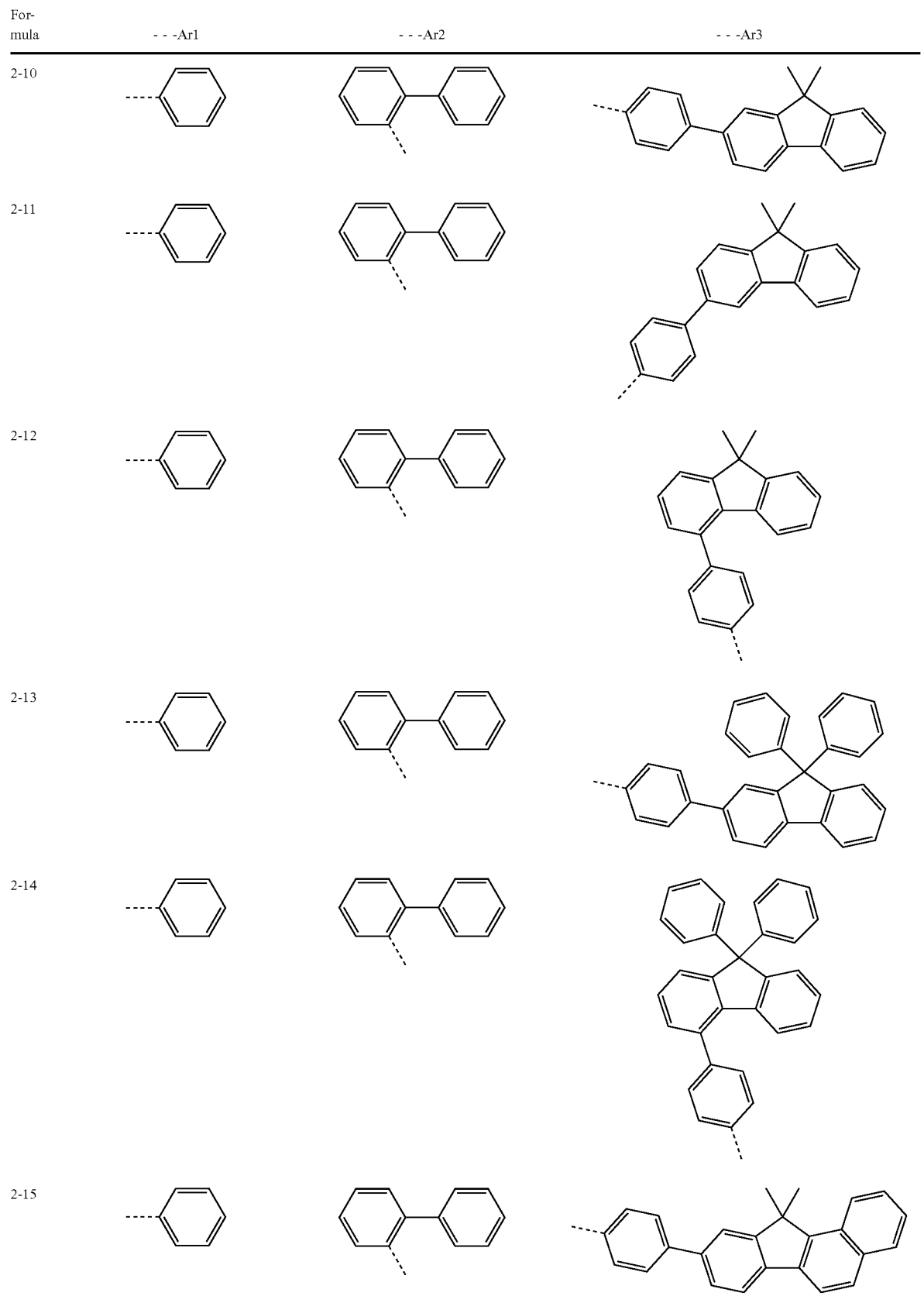

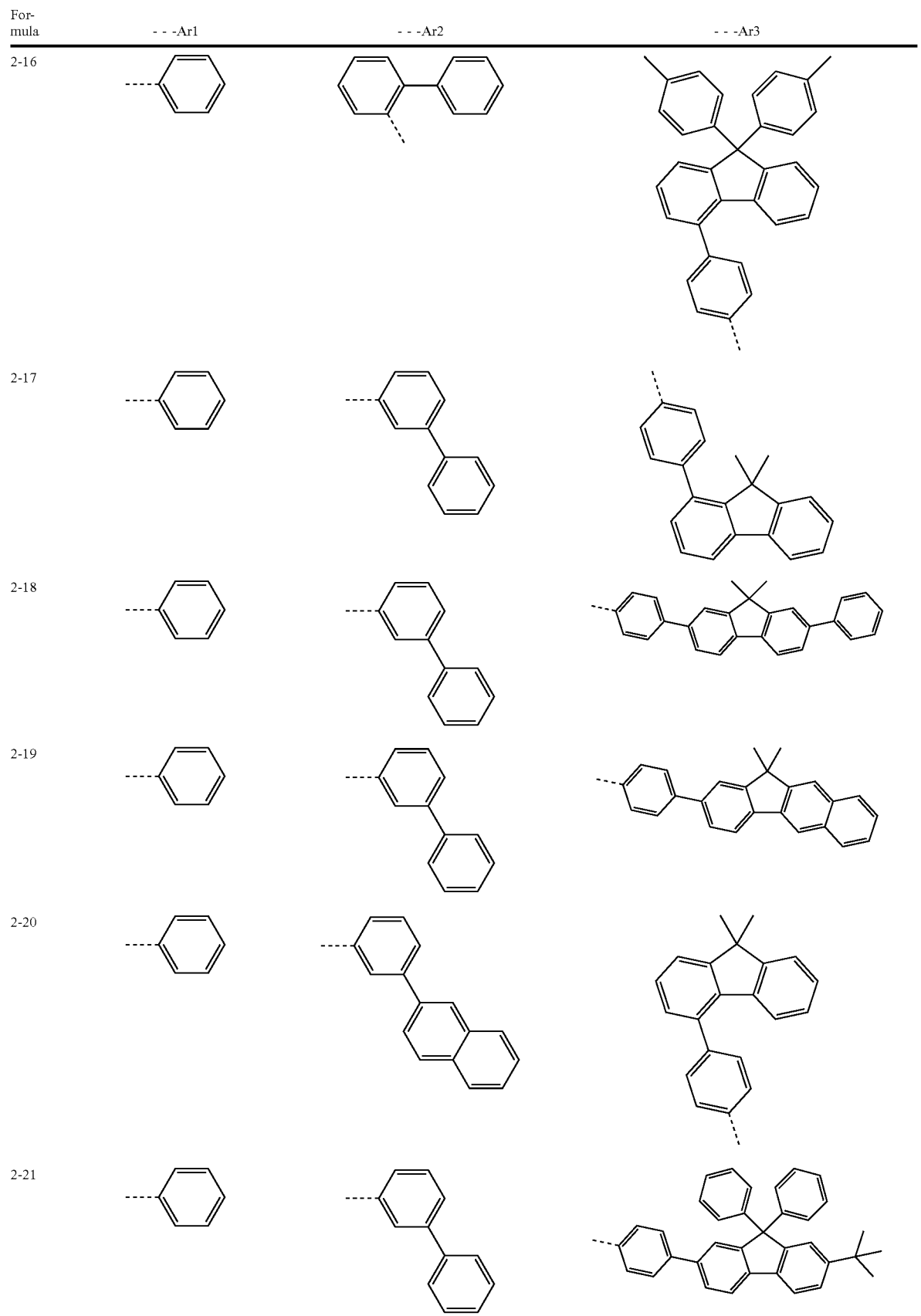

-continued
| Formula | - - -Ar1 | - - -Ar2 | - - -Ar3 |
|---|---|---|---|
| 2-22 | 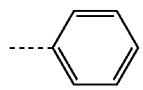 | 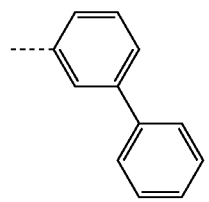 | 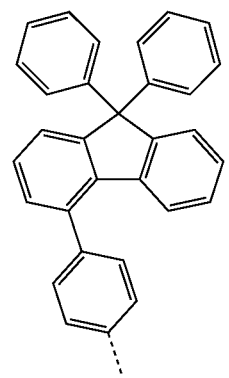 |
| 2-23 | 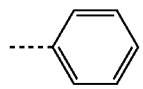 | 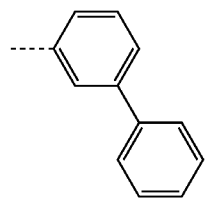 | 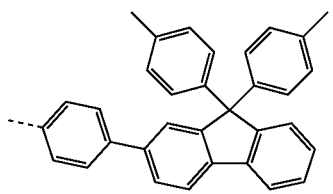 |
| 2-24 | 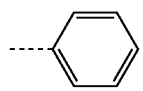 | 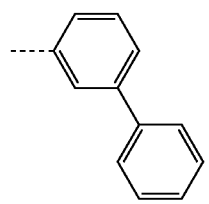 | 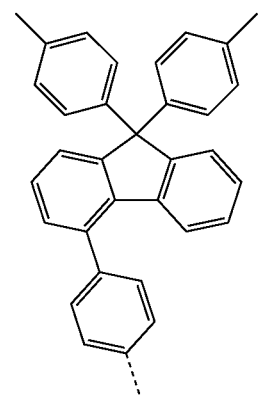 |
| 2-25 | 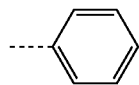 | 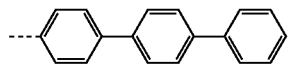 | 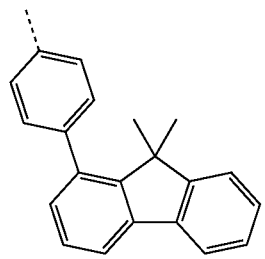 |
| 2-26 | 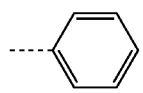 | 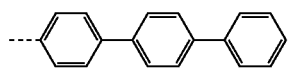 | 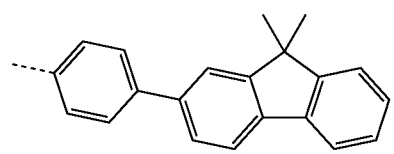 |

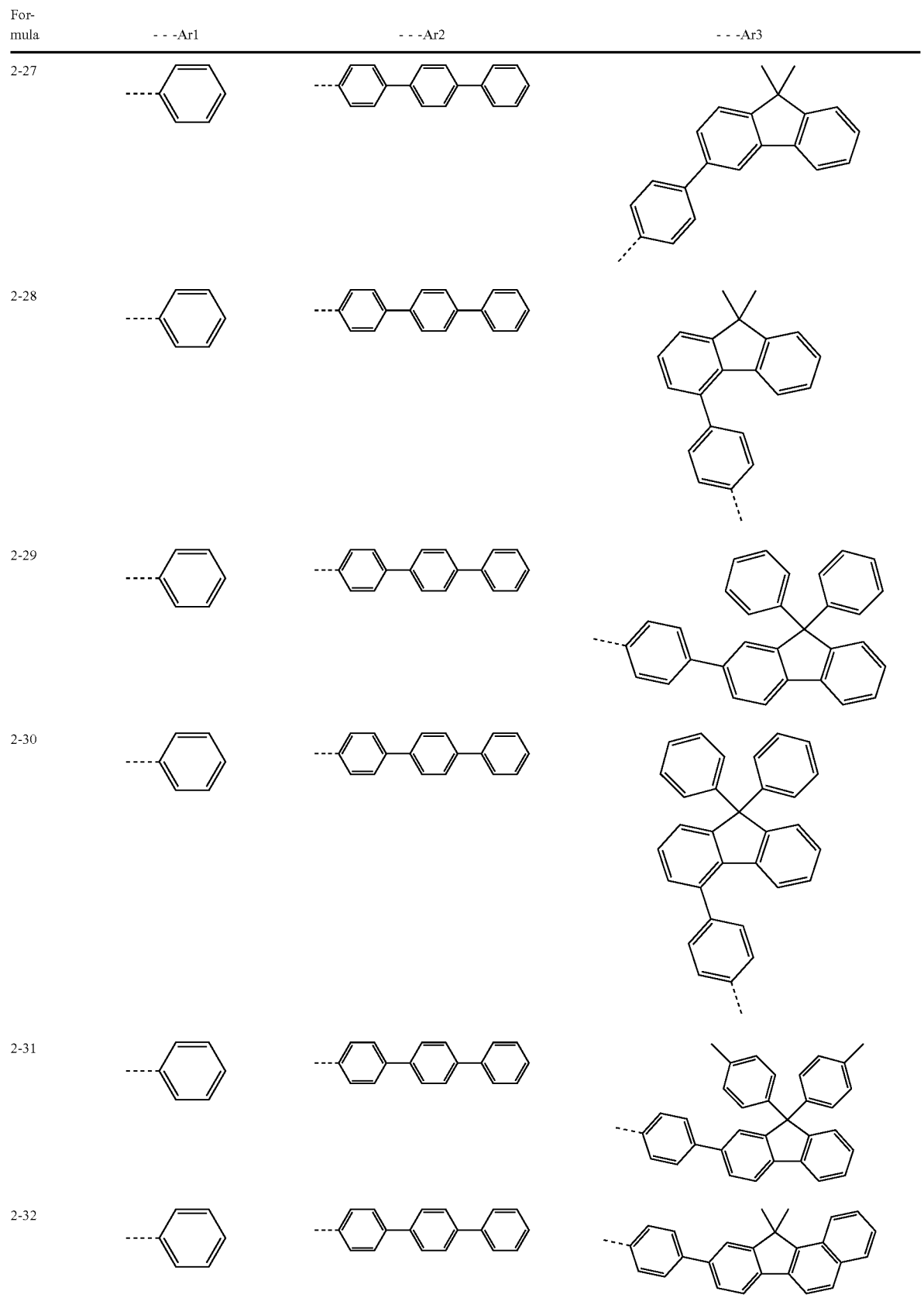

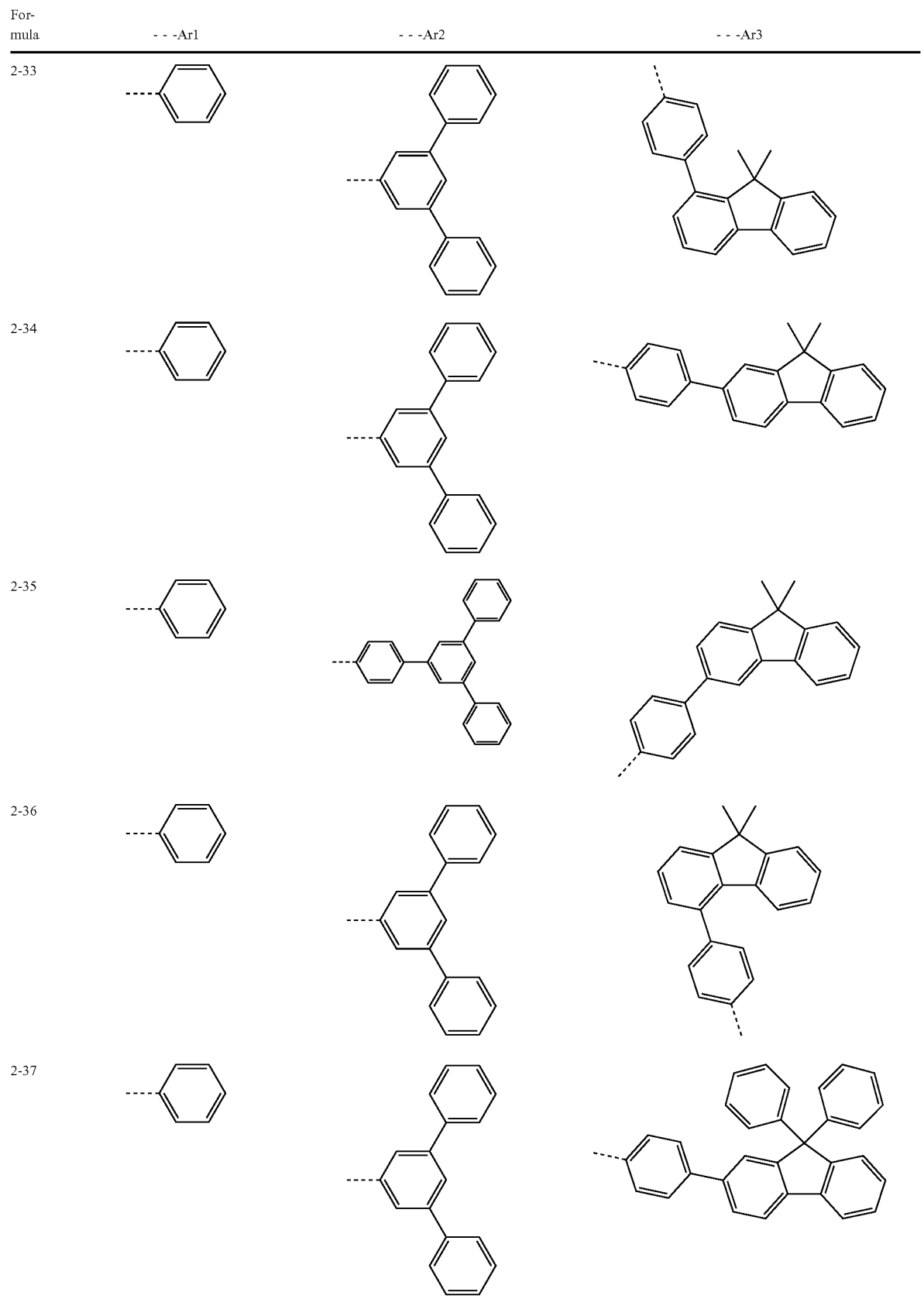

-continued

| Formula | - - -Ar1 | - - -Ar2 | - - -Ar3 |
|---|---|---|---|
| 2-38 | | | |
| 2-39 | | | |
| 2-40 | | | |
| 2-41 | | | |
| 2-42 | | | |

| Formula | ---Ar1 | ---Ar2 | ---Ar3 |
|---|---|---|---|
| 2-43 | 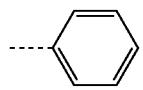 | 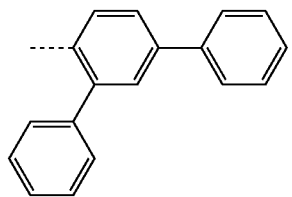 | 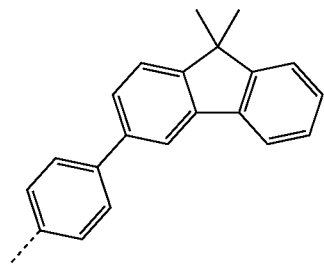 |
| 2-44 | 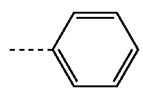 | 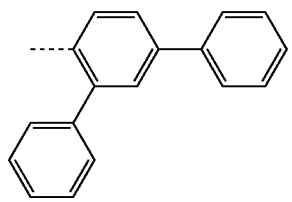 | 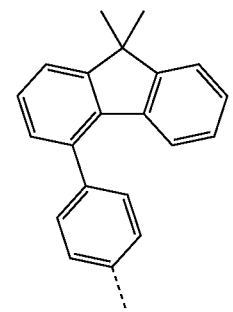 |
| 2-45 | 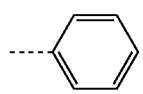 | 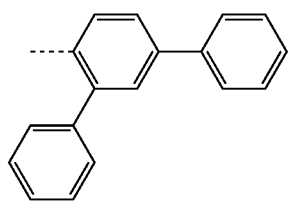 | 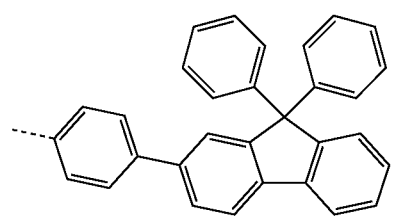 |
| 2-46 | 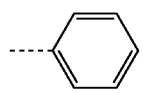 | 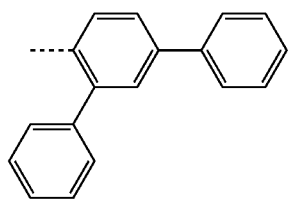 | 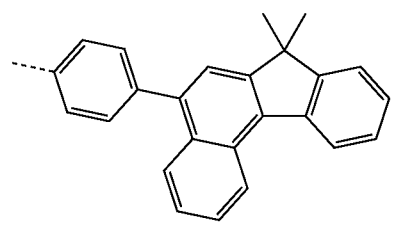 |
| 2-47 | 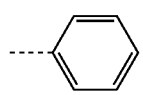 | 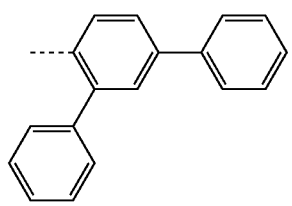 | 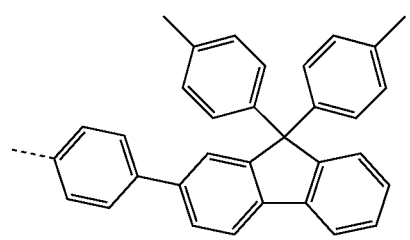 |

-continued
| Formula | - - -Ar1 | - - -Ar2 | - - -Ar3 |
|---|---|---|---|
| 2-48 | | | |
| 2-49 | | | |
| 2-50 | | | |
| 2-51 | | | |
| 2-52 | | | |
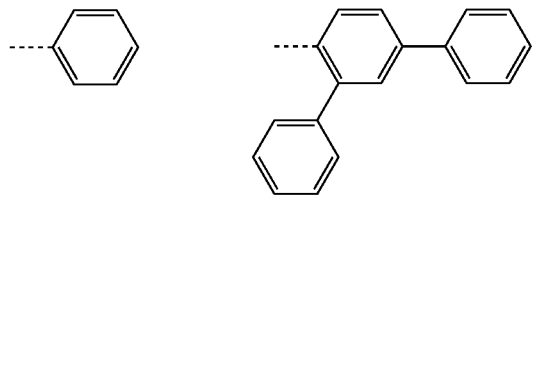
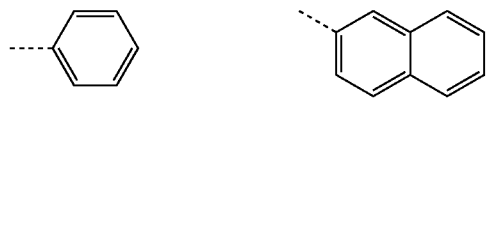
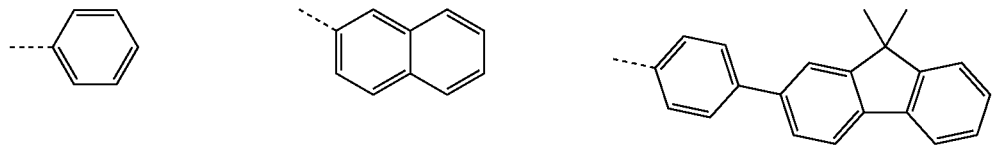
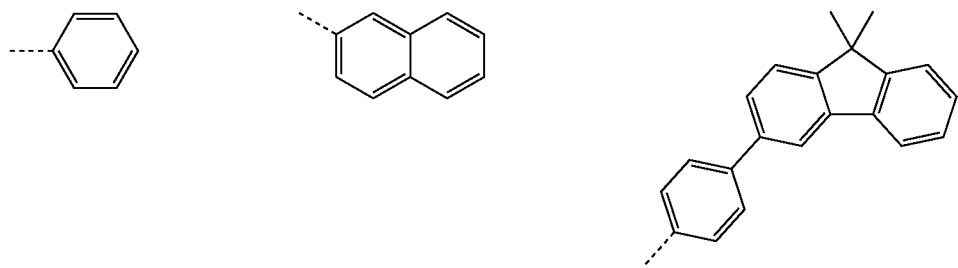
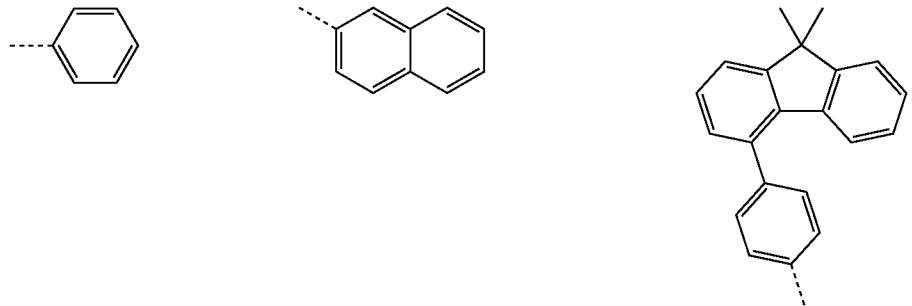

-continued
| Formula | - - -Ar1 | - - -Ar2 | - - -Ar3 |
|---|---|---|---|
| 2-53 | | | |
| 2-54 | | | |
| 2-55 | | | |
| 2-56 | | | |
| 2-57 | | | |
| 2-58 | | | |
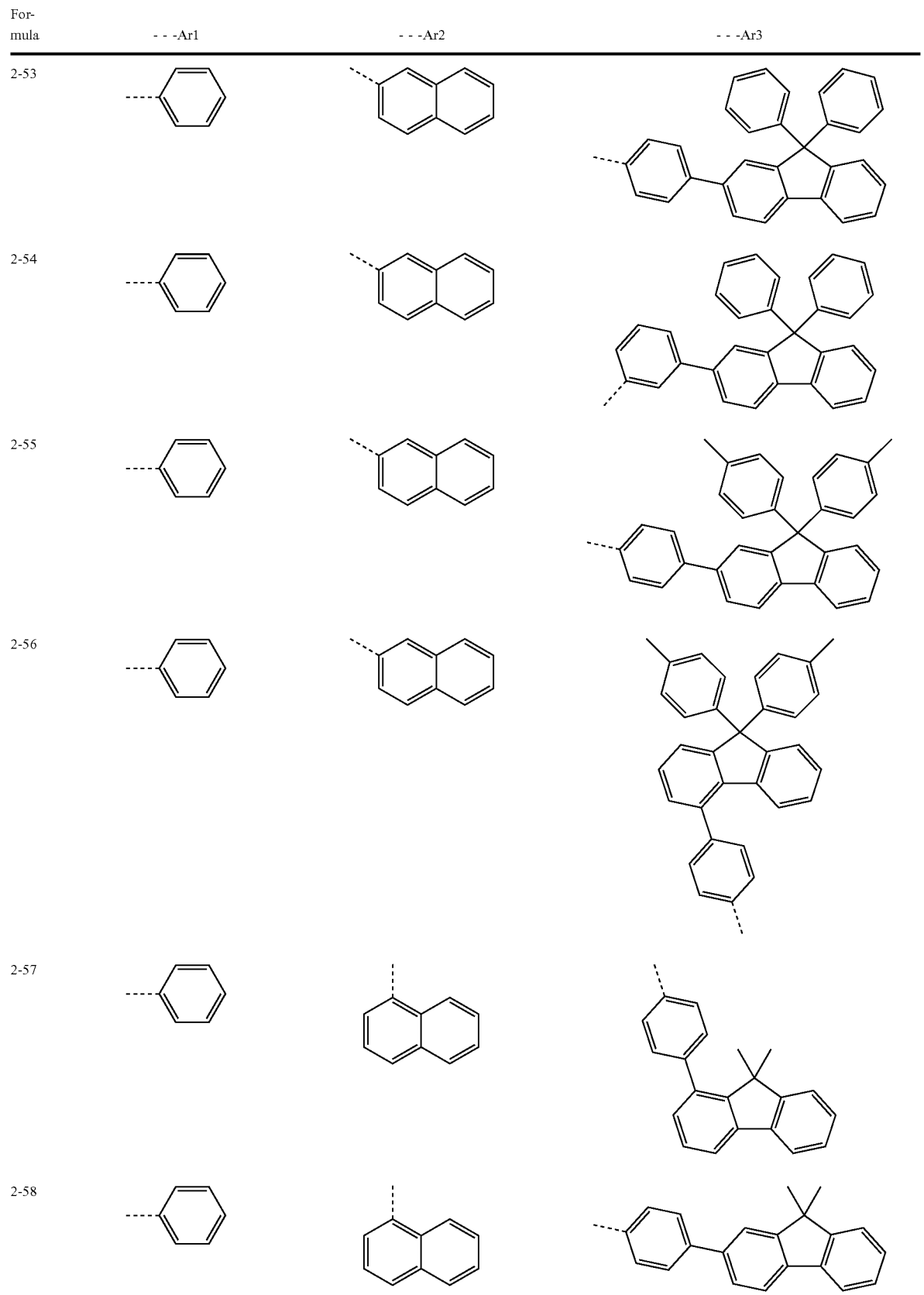

-continued

| Formula | ---Ar1 | ---Ar2 | ---Ar3 |
|---|---|---|---|
| 2-59 | phenyl | 1-naphthyl | 9,9-dimethylfluorene-phenyl |
| 2-60 | phenyl | 1-naphthyl | 9,9-dimethylfluorene-biphenyl |
| 2-61 | phenyl | 1-naphthyl | 9,9-diphenylfluorene-phenyl |
| 2-62 | phenyl | 1-naphthyl | 9,9-diphenylfluorene-phenyl |
| 2-63 | phenyl | 1-naphthyl | 9,9-di(p-tolyl)fluorene-phenyl |

-continued
| Formula | ----Ar1 | ----Ar2 | ----Ar3 |
|---|---|---|---|
| 2-64 | 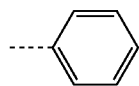 | 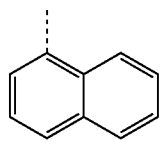 | 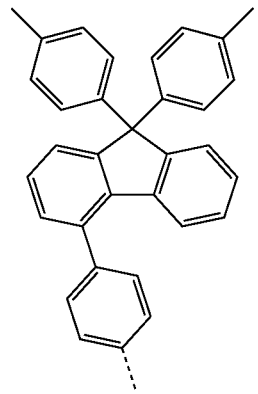 |
| 2-65 | 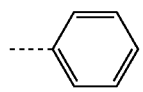 | 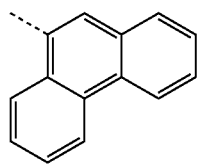 | 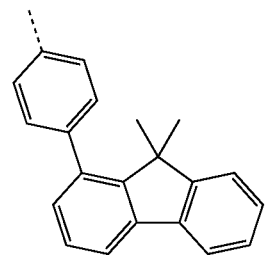 |
| 2-66 | 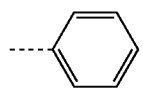 | 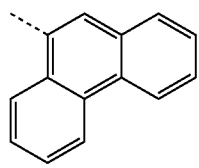 | 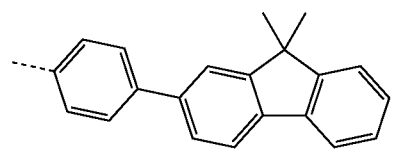 |
| 2-67 | 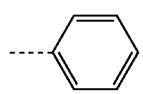 | 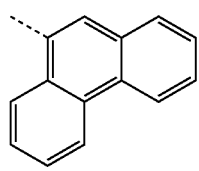 | 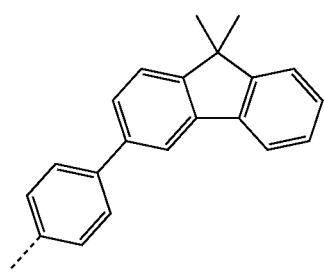 |
| 2-68 | 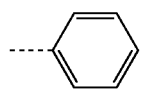 | 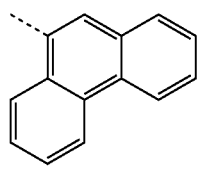 | 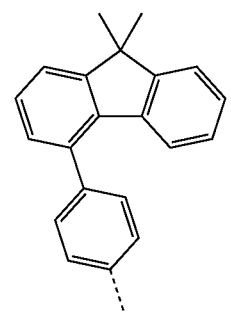 |

-continued
| Formula | - - -Ar1 | - - -Ar2 | - - -Ar3 |
|---|---|---|---|
| 2-69 | | | |
| 2-70 | | | |
| 2-71 | | | |
| 2-72 | | | |
| 2-73 | | | |
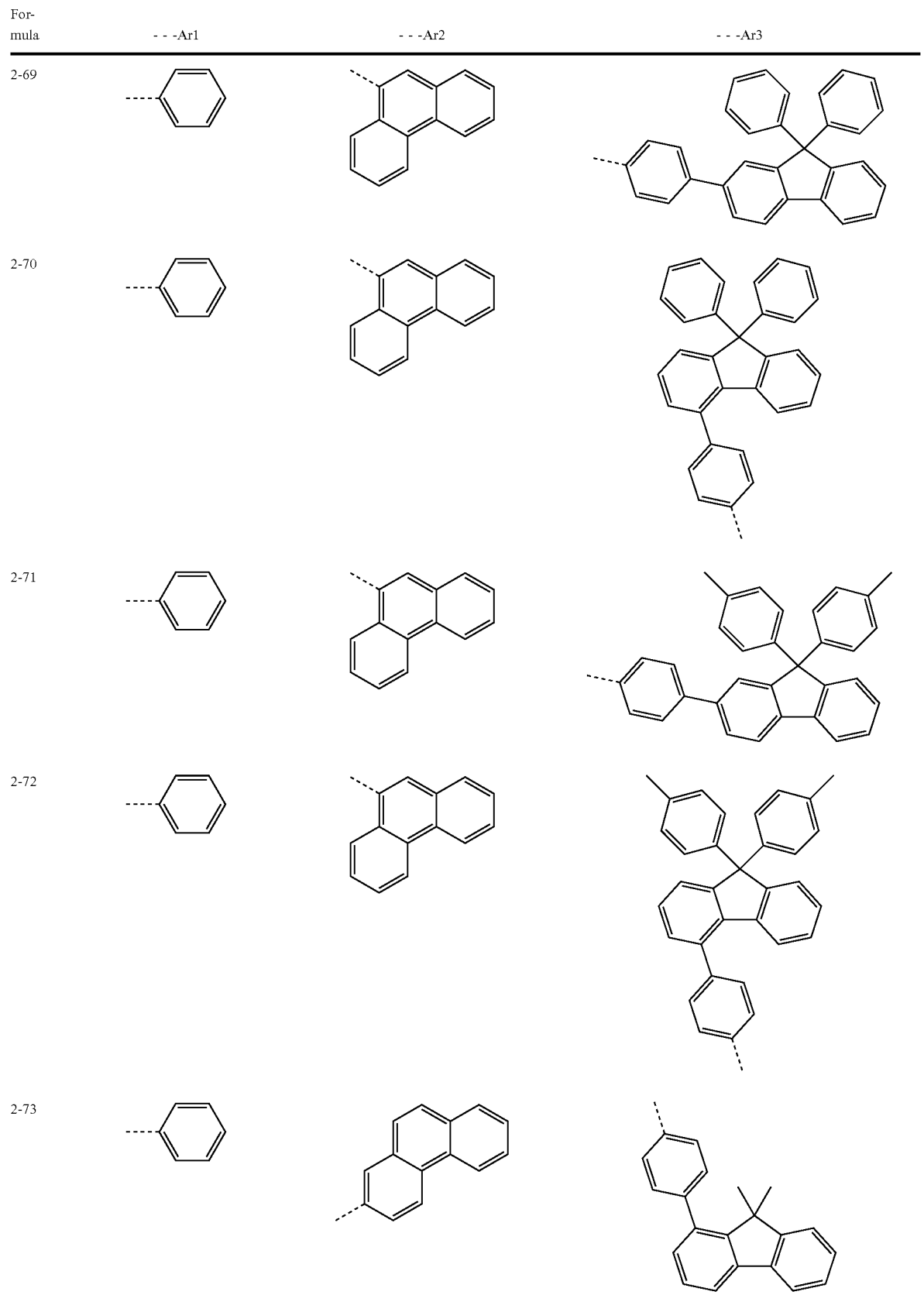

-continued
| Formula | - - -Ar1 | - - -Ar2 | - - -Ar3 |
|---|---|---|---|
| 2-74 | 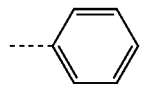 | 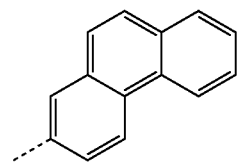 | 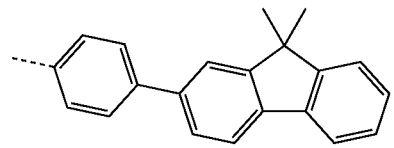 |
| 2-75 | 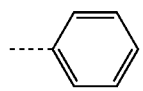 | 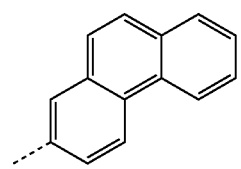 | 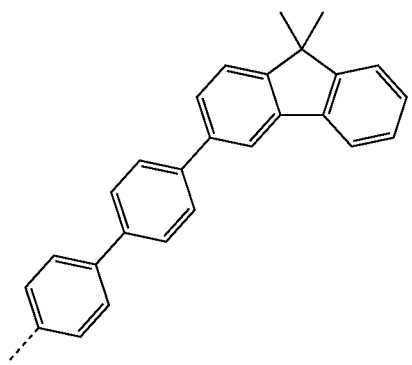 |
| 2-76 | 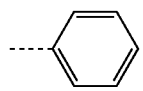 | 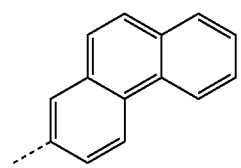 | 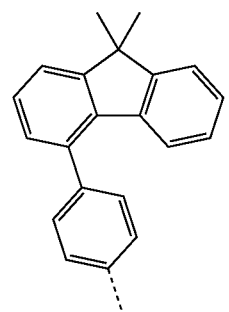 |
| 2-77 | 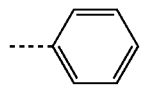 | 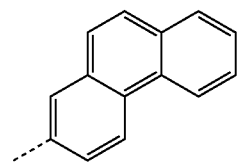 | 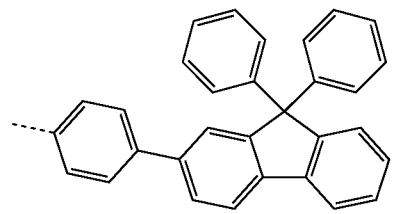 |
| 2-78 | 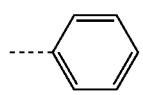 | 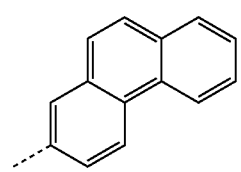 | 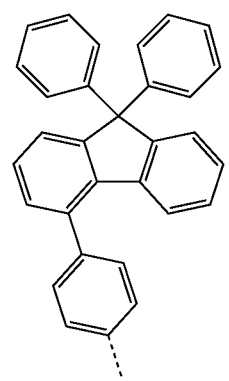 |

-continued

| Formula | ---Ar1 | ---Ar2 | ---Ar3 |
|---|---|---|---|
| 2-79 | | | |
| 2-80 | | | |
| 2-81 | | | |
| 2-82 | | | |
| 2-83 | | | |
| 2-84 | | | |

-continued
| Formula | - - -Ar1 | - - -Ar2 | - - -Ar3 |
|---|---|---|---|
| 2-85 | 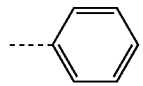 | 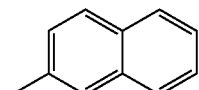 | 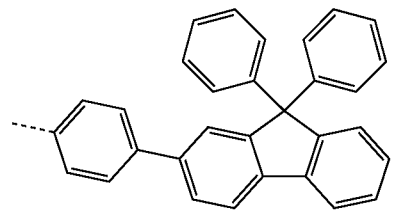 |
| 2-86 | 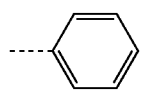 | 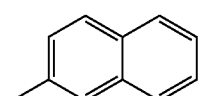 | 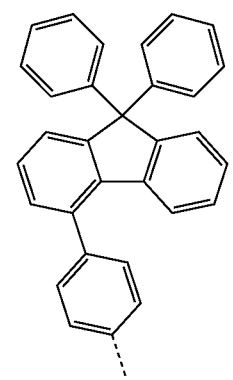 |
| 2-87 | 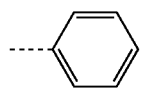 | 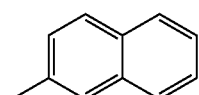 | 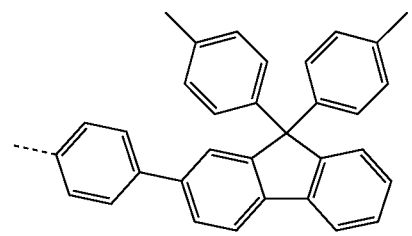 |
| 2-88 | 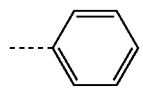 | 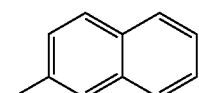 | 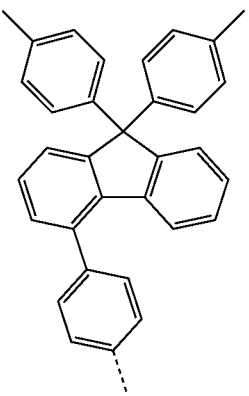 |
| 2-89 | 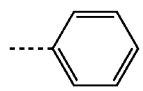 | 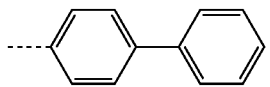 | 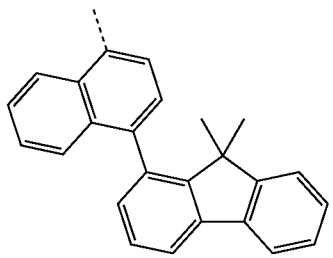 |

-continued
| Formula | ---Ar1 | ---Ar2 | ---Ar3 |
|---|---|---|---|
| 2-90 | 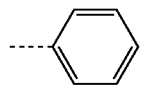 | 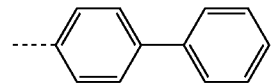 | 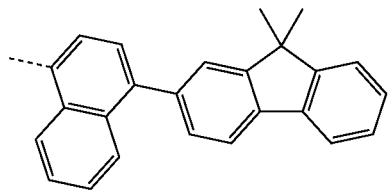 |
| 2-91 | 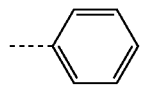 | 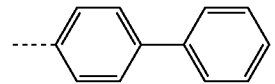 | 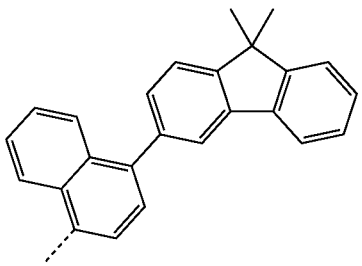 |
| 2-92 | 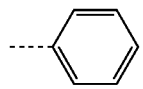 | 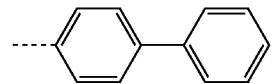 | 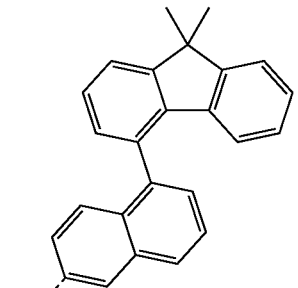 |
| 2-93 | 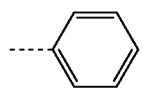 | 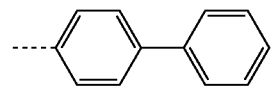 | 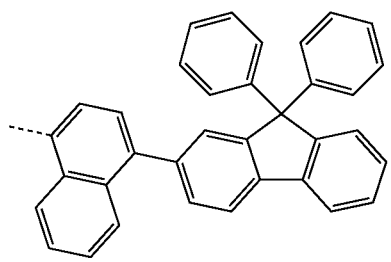 |
| 2-94 | 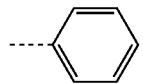 | 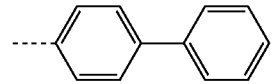 | 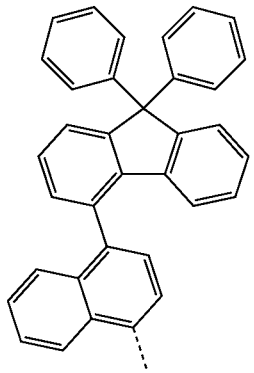 |

-continued
| Formula | - - -Ar1 | - - -Ar2 | - - -Ar3 |
|---|---|---|---|
| 2-95 | 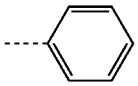 | 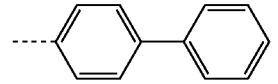 | 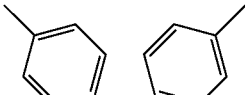 |
| 2-96 | 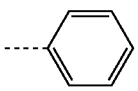 | 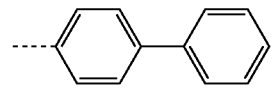 | 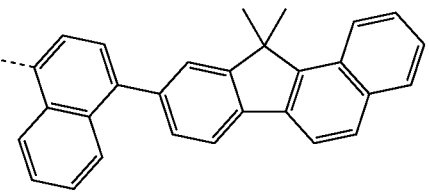 |
| 2-97 | 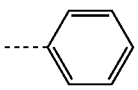 | 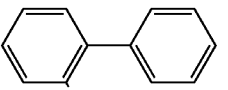 | 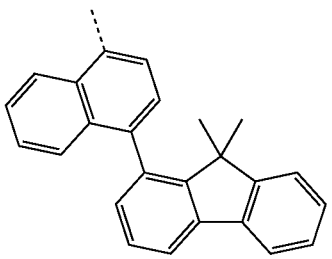 |
| 2-98 | 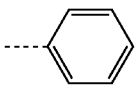 | 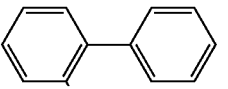 | 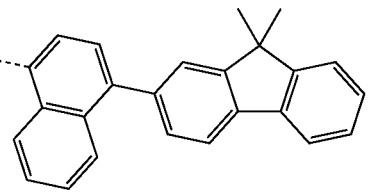 |
| 2-99 | 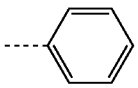 | 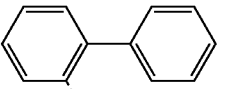 | 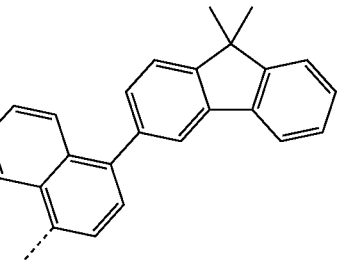 |
| 2-100 | 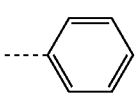 | 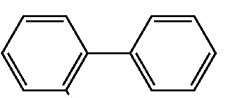 | 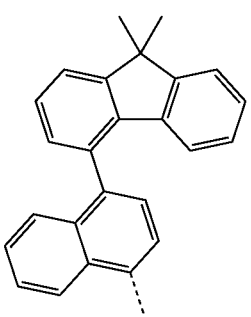 |

-continued
| Formula | - - -Ar1 | - - -Ar2 | - - -Ar3 |
|---|---|---|---|
| 2-101 | 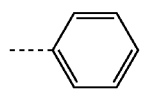 | 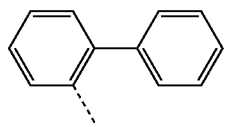 | 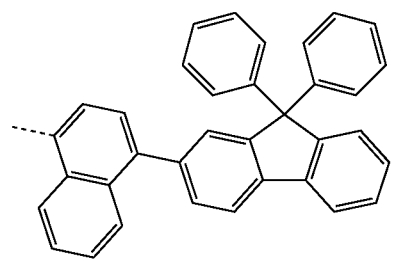 |
| 2-102 | 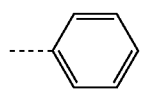 | 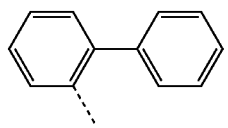 | 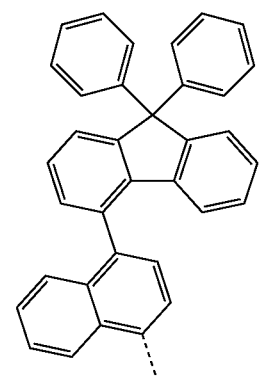 |
| 2-103 | 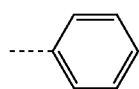 | 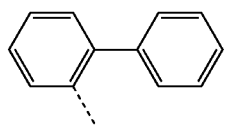 | 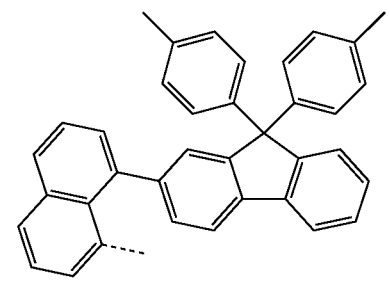 |
| 2-104 | 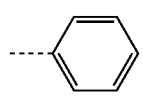 | 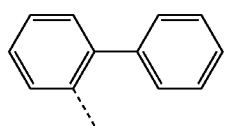 | 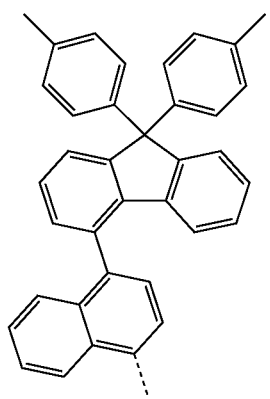 |

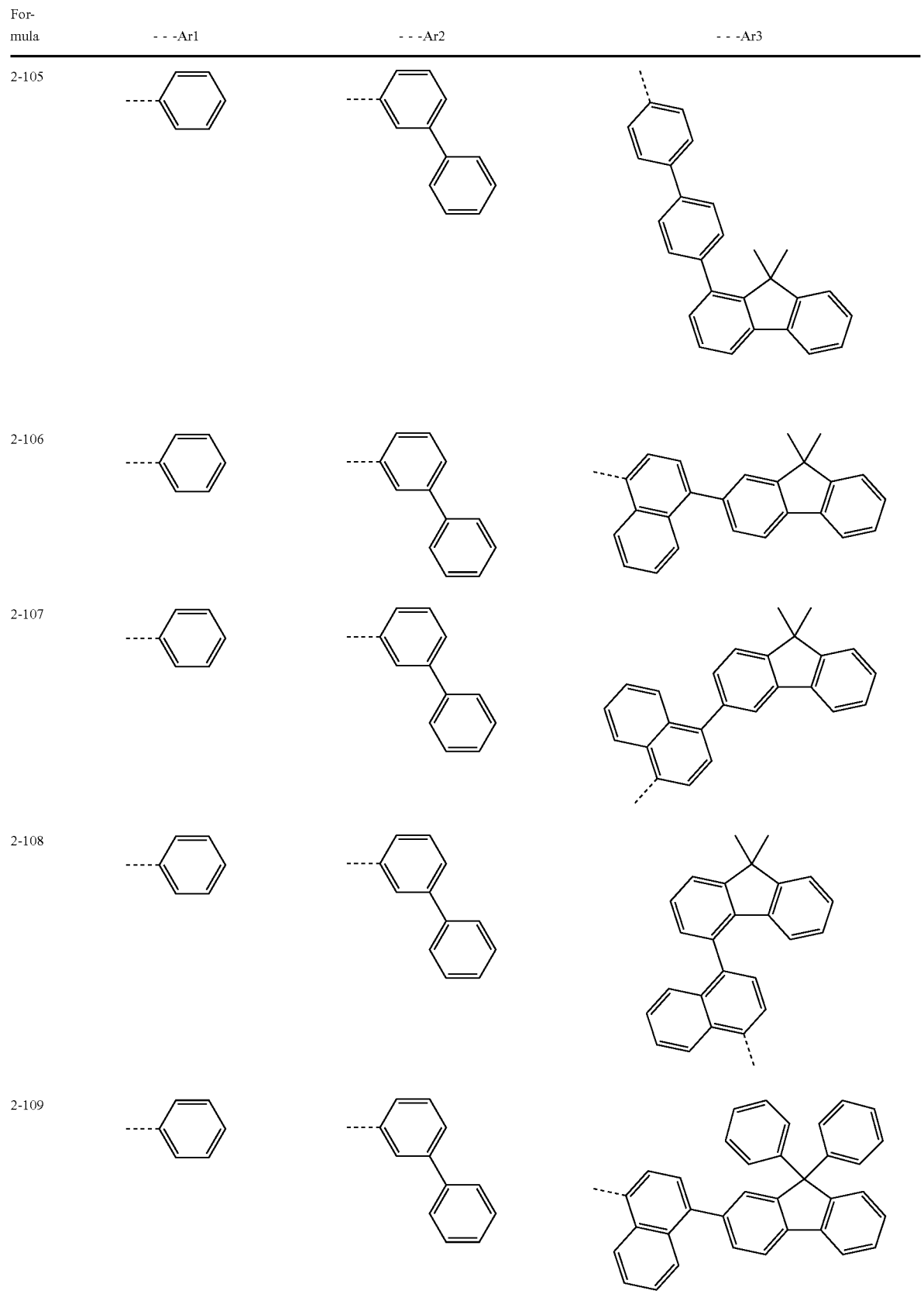

-continued
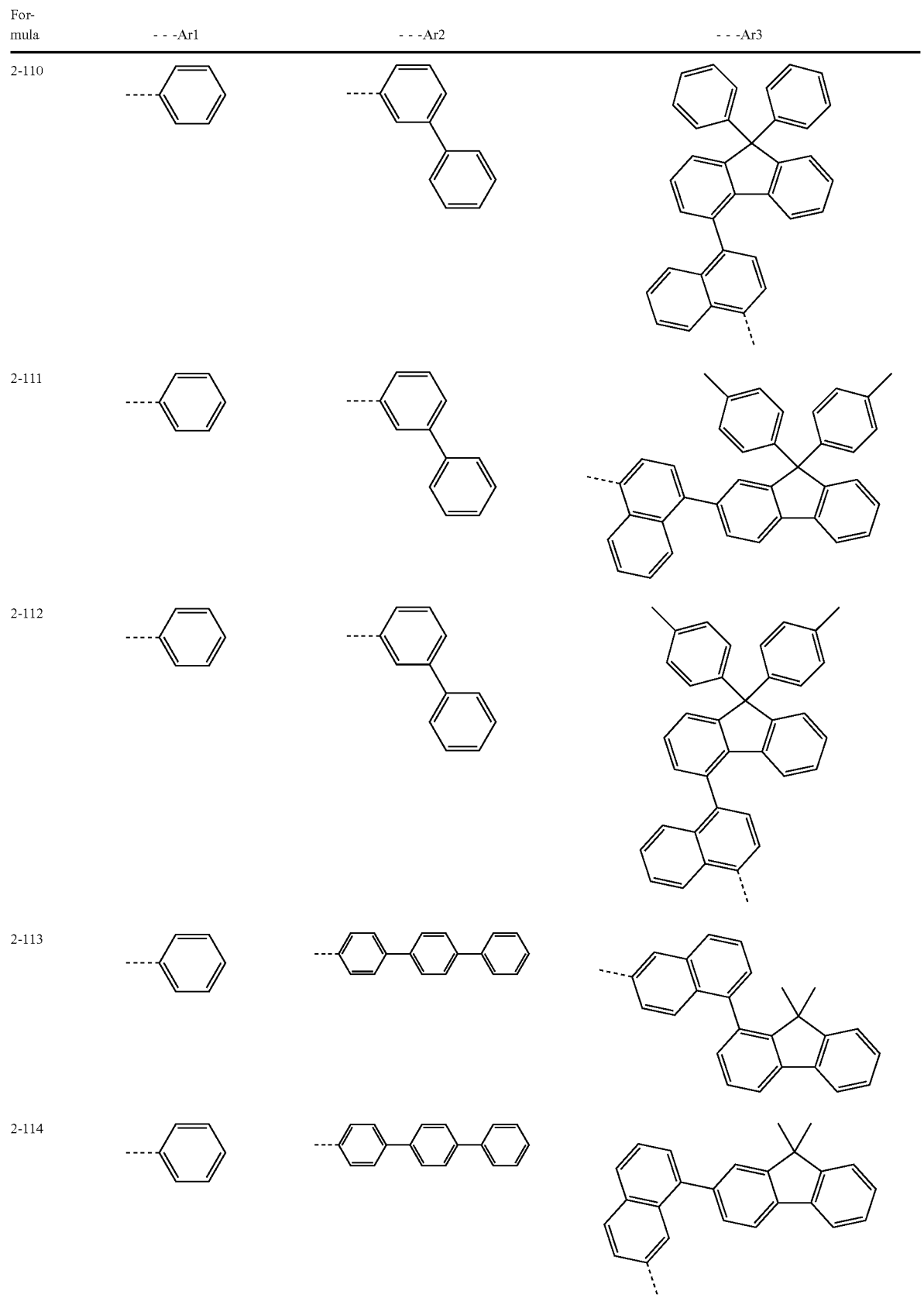

-continued
| Formula | ---Ar1 | ---Ar2 | ---Ar3 |
|---|---|---|---|
| 2-115 | | | |
| 2-116 | | | |
| 2-117 | | | |
| 2-118 | | | |
| 2-119 | | | |
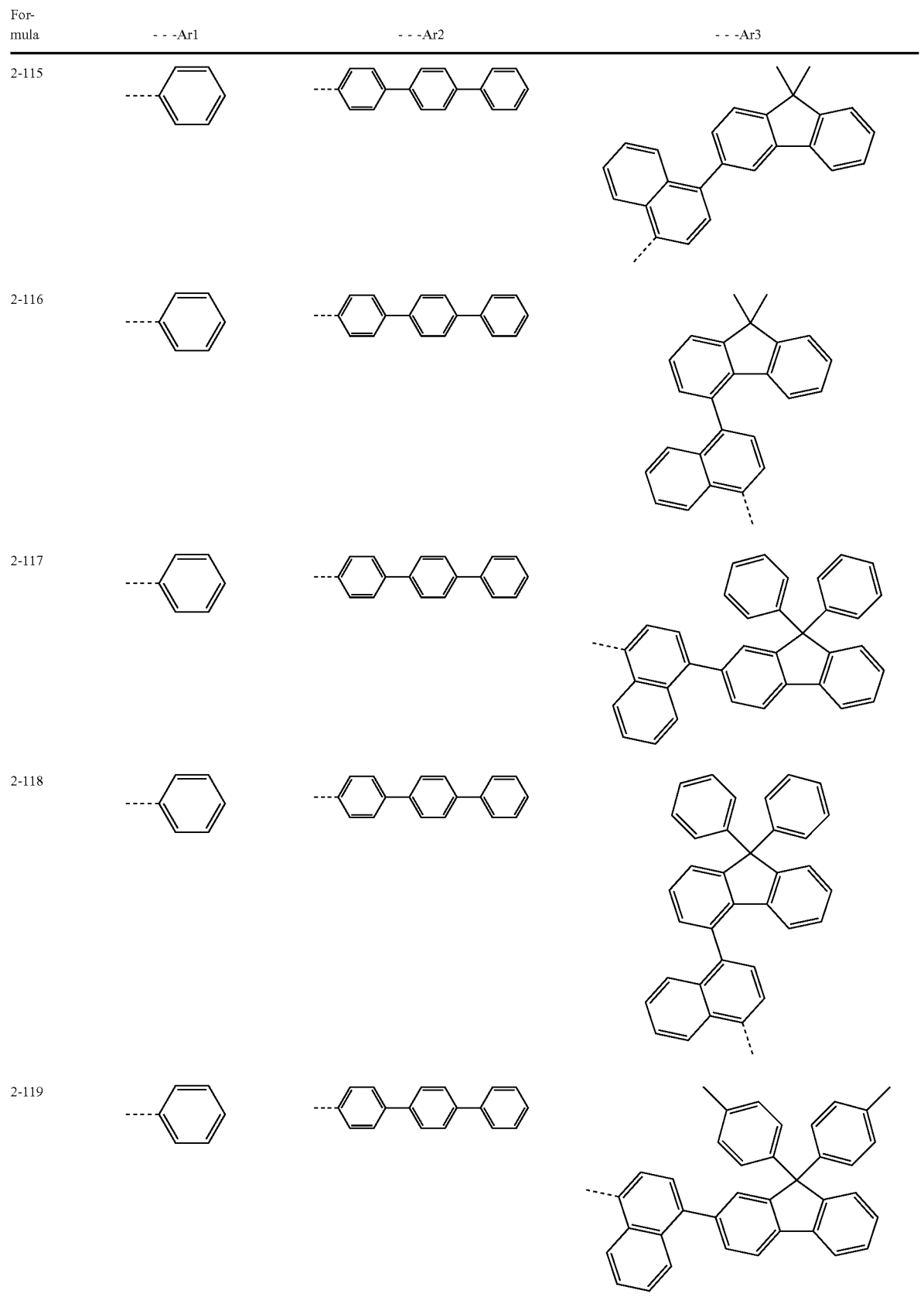

US 11,271,167 B2
-continued
| Formula | - - -Ar1 | - - -Ar2 | - - -Ar3 |
|---|---|---|---|
| 2-120 | 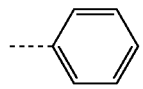 | 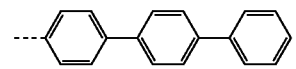 | 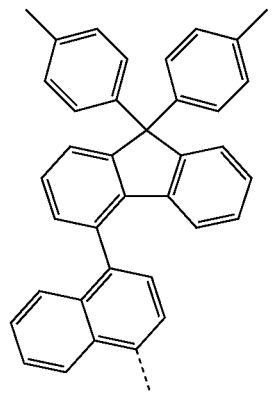 |
| 2-121 | 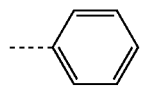 | 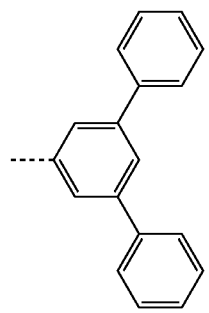 | 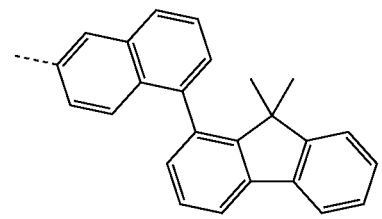 |
| 2-122 | 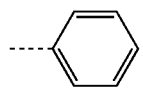 | 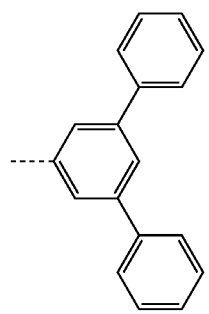 | 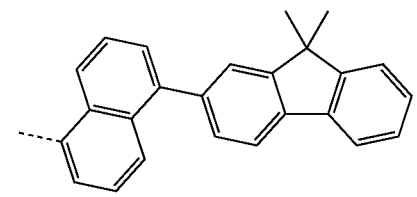 |
| 2-123 | 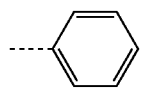 | 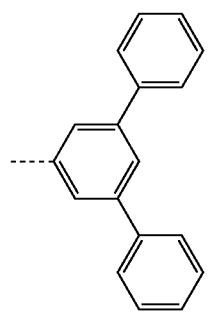 | 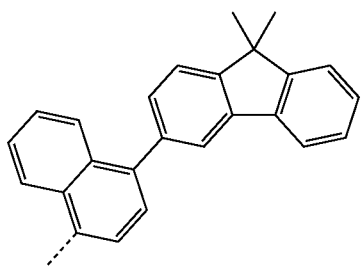 |

-continued
| Formula | ---Ar1 | ---Ar2 | ---Ar3 |
|---|---|---|---|
| 2-124 | 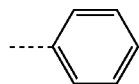 | 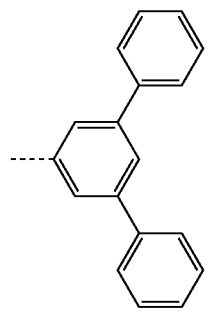 | 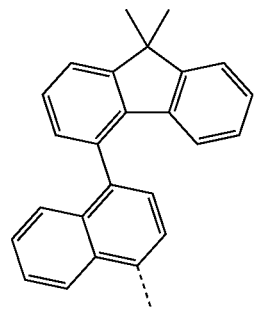 |
| 2-125 | 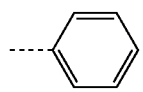 | 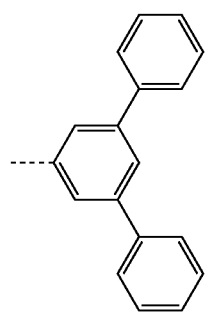 | 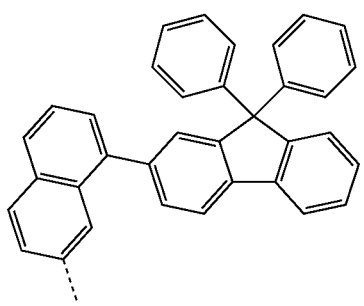 |
| 2-126 | 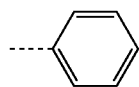 | 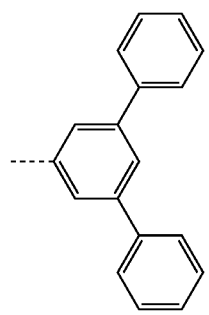 | 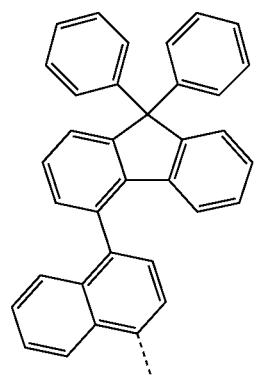 |
| 2-127 | 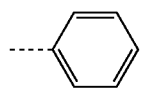 | 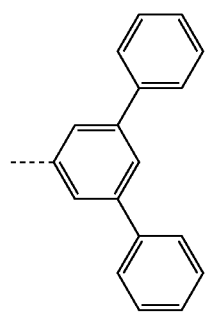 | 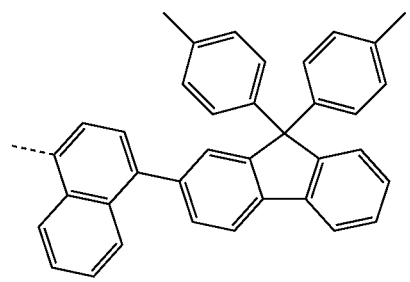 |

-continued
| Formula | ---Ar1 | ---Ar2 | ---Ar3 |
|---|---|---|---|
| 2-128 | 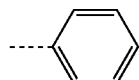 | 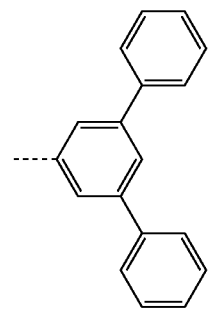 | 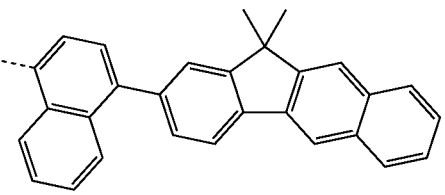 |
| 2-129 | 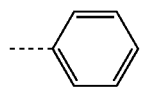 | 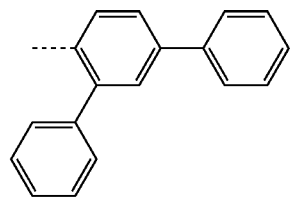 | 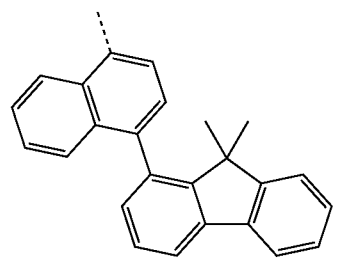 |
| 2-130 | 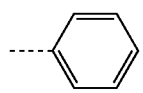 | 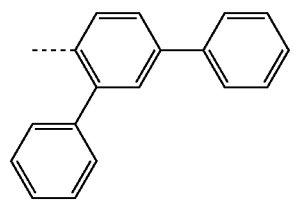 | 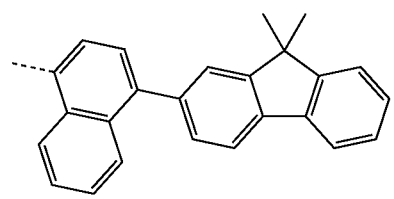 |
| 2-131 | 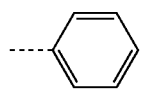 | 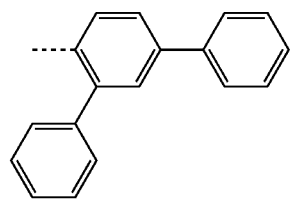 | 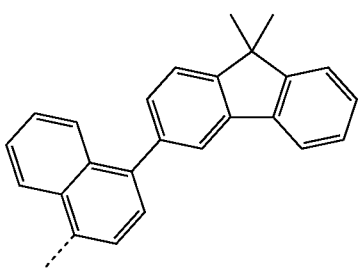 |
| 2-132 | 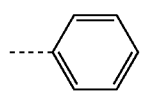 | 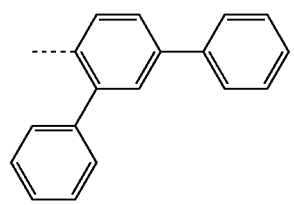 | 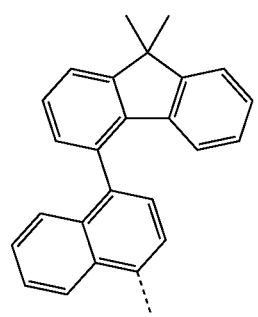 |

-continued
| Formula | - - -Ar1 | - - -Ar2 | - - -Ar3 |
|---|---|---|---|
| 2-133 | 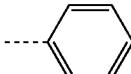 | 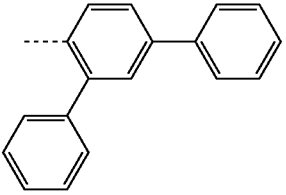 | 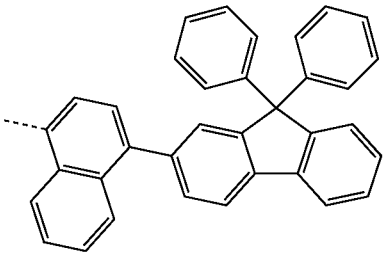 |
| 2-134 | 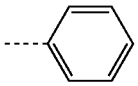 | 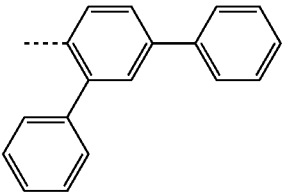 | 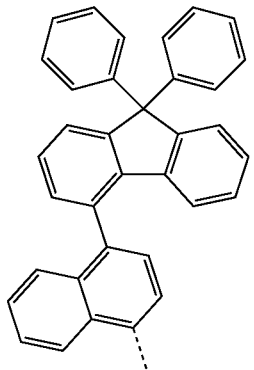 |
| 2-135 | 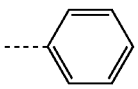 | 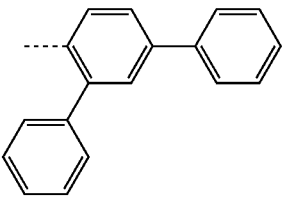 | 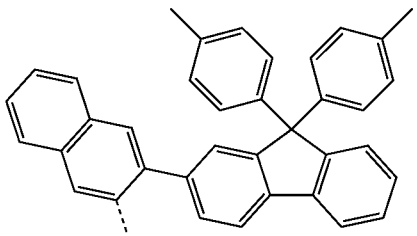 |
| 2-136 | 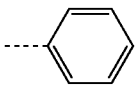 | 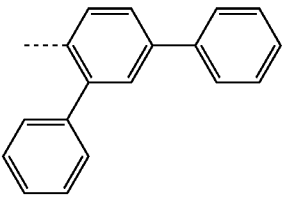 | 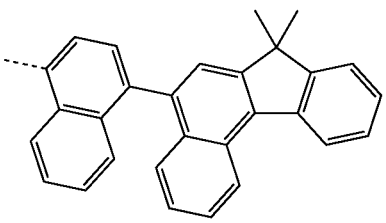 |
| 2-137 | 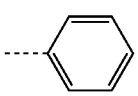 | 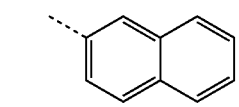 | 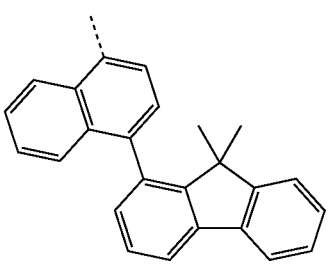 |
| 2-138 | 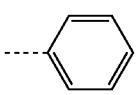 | 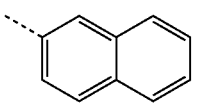 | 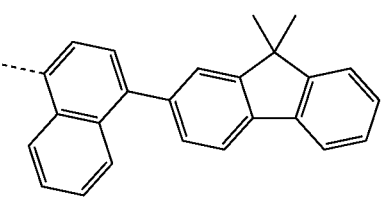 |

| For-mula | - - -Ar1 | - - -Ar2 | - - -Ar3 |
|---|---|---|---|
| 2-139 | 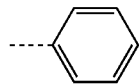 | 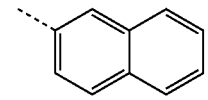 | 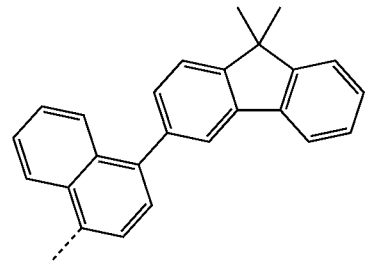 |
| 2-140 | 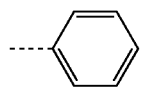 | 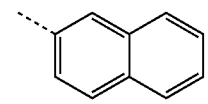 | 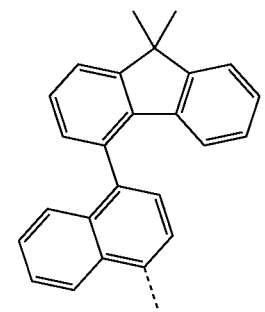 |
| 2-141 | 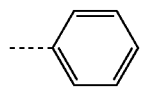 | 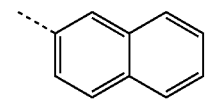 | 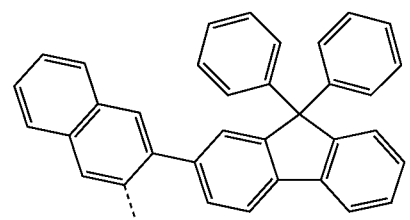 |
| 2-142 | 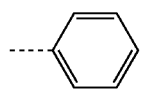 | 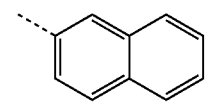 | 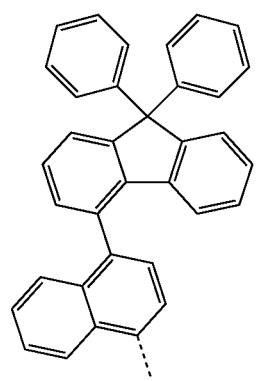 |
| 2-143 | 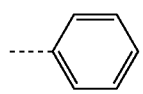 | 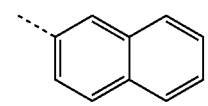 | 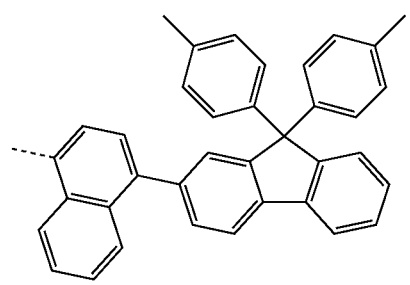 |

-continued
| Formula | - - -Ar1 | - - -Ar2 | - - -Ar3 |
|---|---|---|---|
| 2-144 | 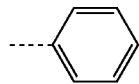 | 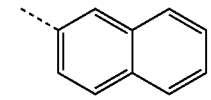 | 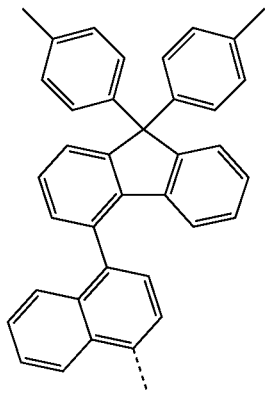 |
| 2-145 | 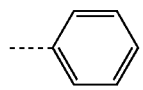 | 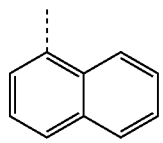 | 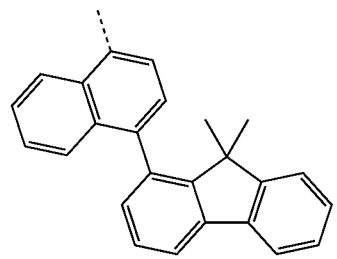 |
| 2-146 | 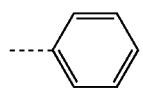 | 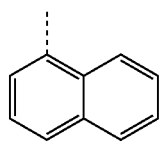 | 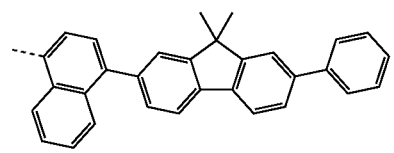 |
| 2-147 | 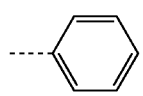 | 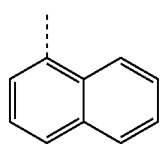 | 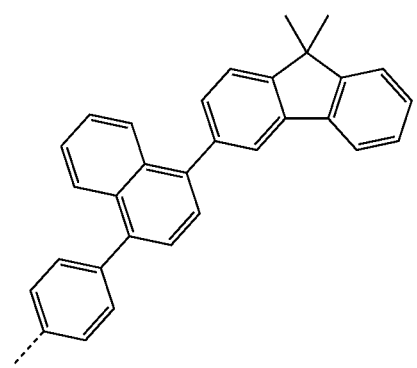 |
| 2-148 | 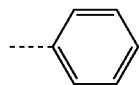 | 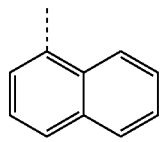 | 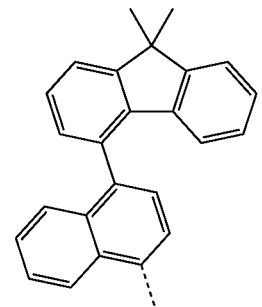 |

| Formula | ---Ar1 | ---Ar2 | ---Ar3 |
|---|---|---|---|
| 2-149 | 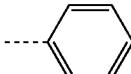 | 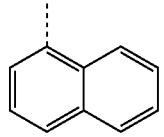 | 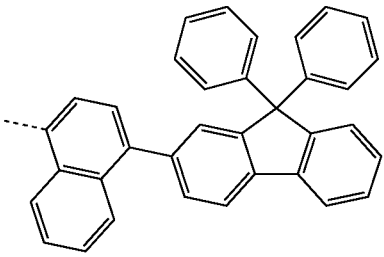 |
| 2-150 | 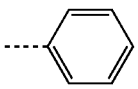 | 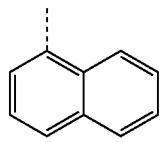 | 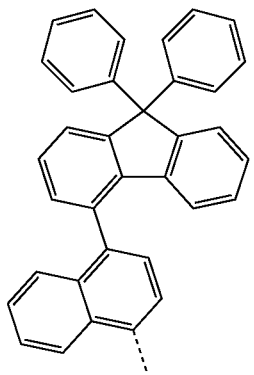 |
| 2-151 | 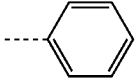 | 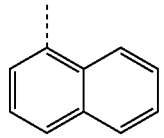 | 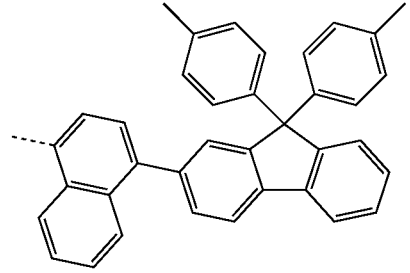 |
| 2-152 | 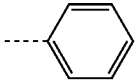 | 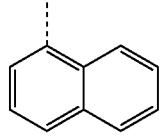 | 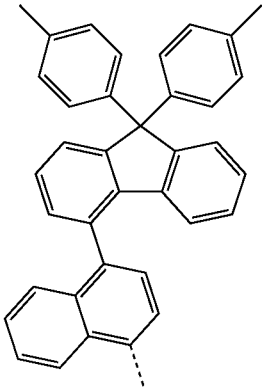 |
| 2-153 | 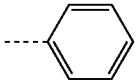 | 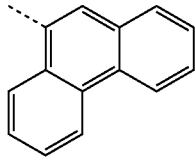 | 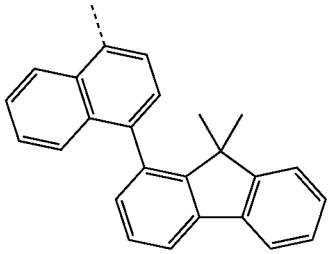 |

-continued
| Formula | ---Ar1 | ---Ar2 | ---Ar3 |
|---|---|---|---|
| 2-154 | 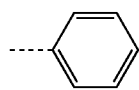 | 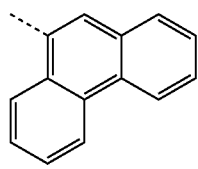 | 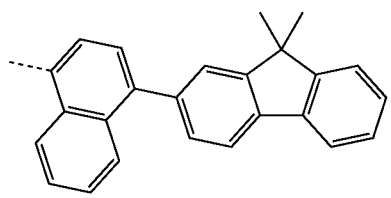 |
| 2-155 | 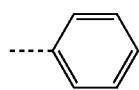 | 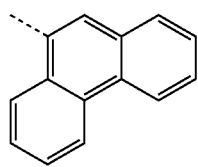 | 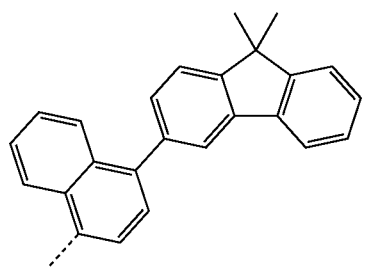 |
| 2-156 | 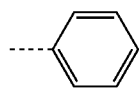 | 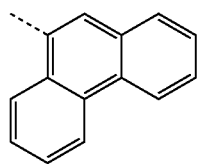 | 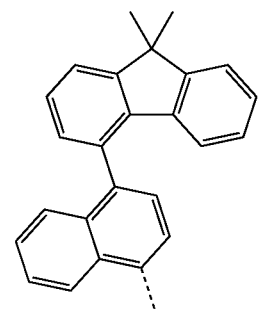 |
| 2-157 | 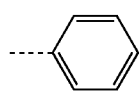 | 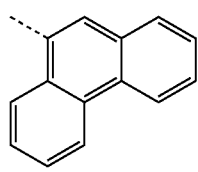 | 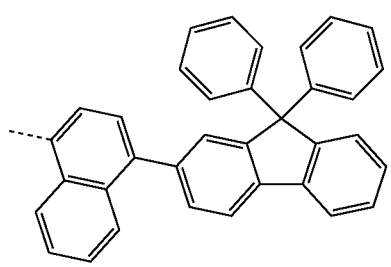 |
| 2-158 | 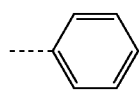 | 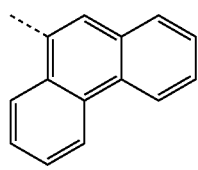 | 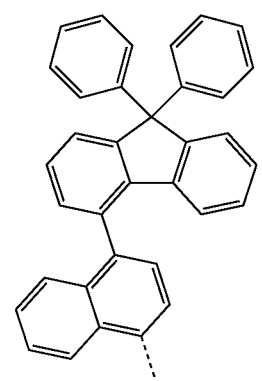 |

| Formula | ---Ar1 | ---Ar2 | ---Ar3 |
|---|---|---|---|
| 2-159 | 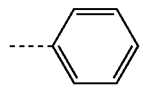 | 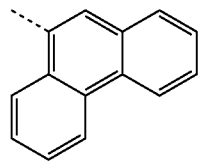 | 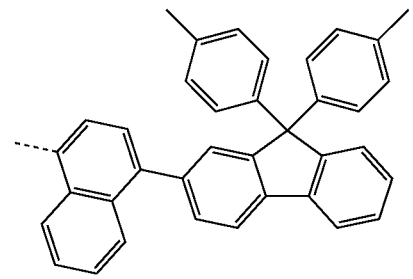 |
| 2-160 | 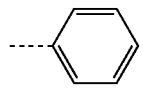 | 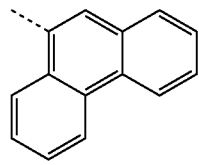 | 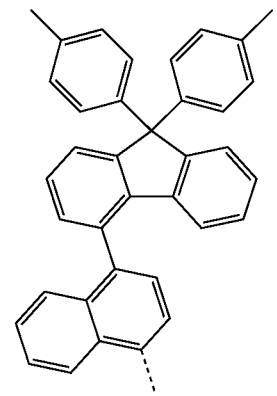 |
| 2-161 | 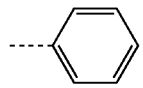 | 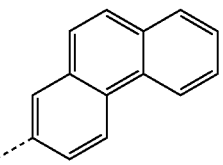 | 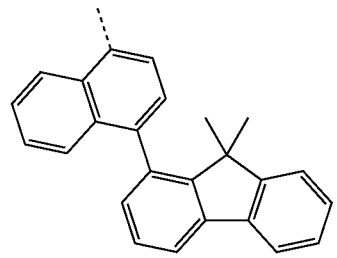 |
| 2-162 | 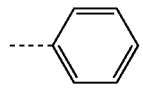 | 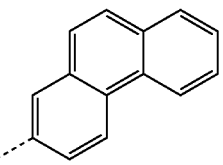 | 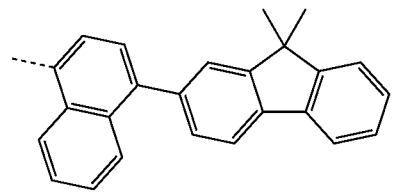 |
| 2-163 | 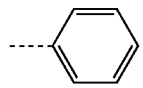 | 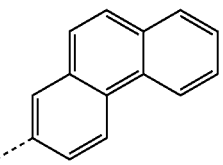 | 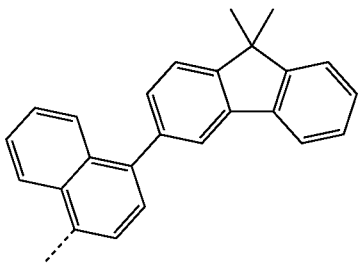 |

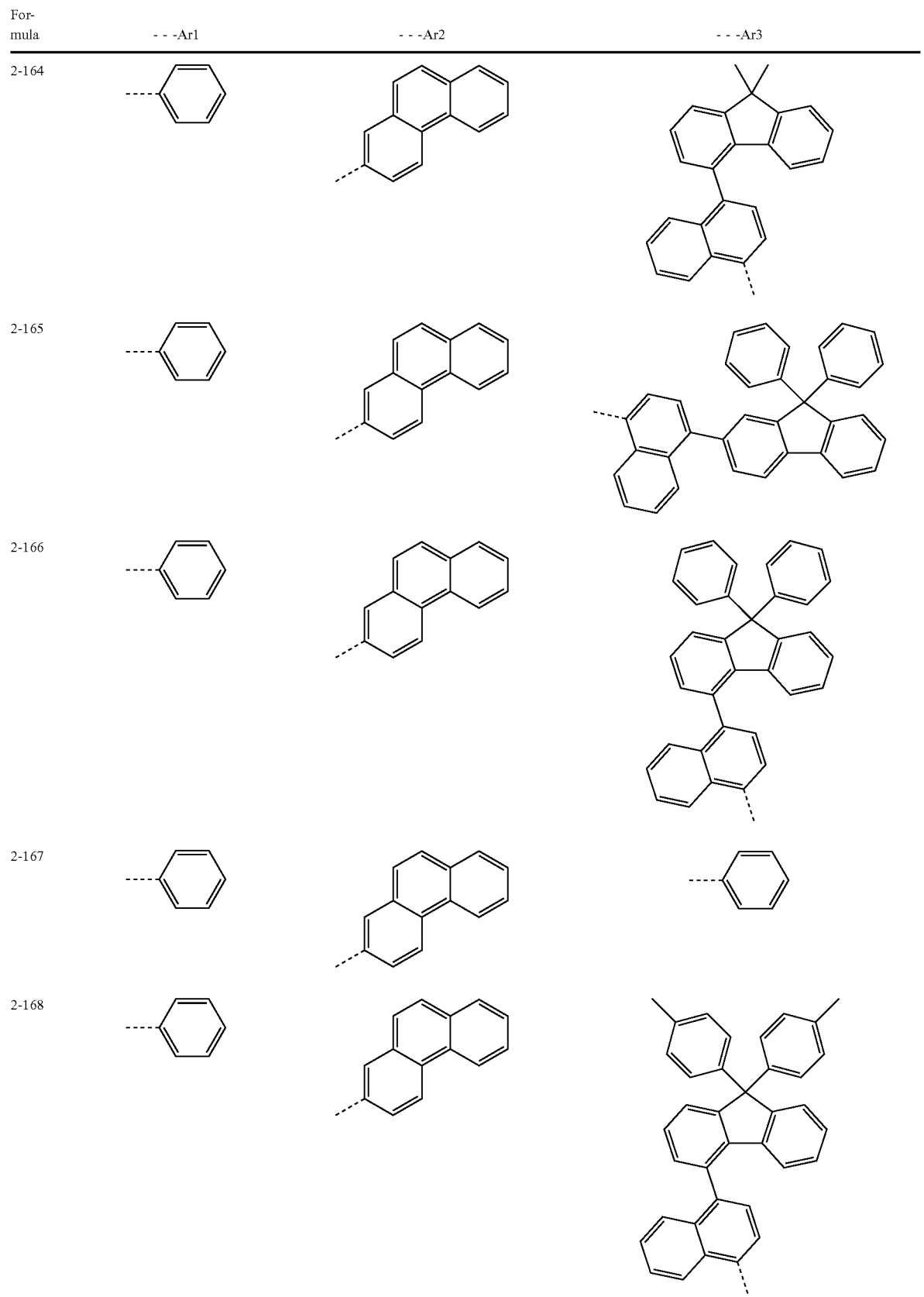

-continued
| Formula | - - -Ar1 | - - -Ar2 | - - -Ar3 |
|---|---|---|---|
| 2-169 | 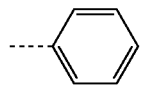 | 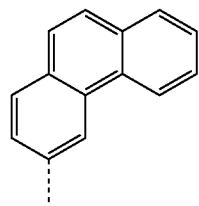 | 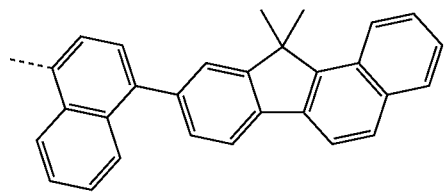 |
| 2-170 | 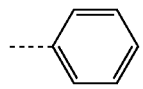 | 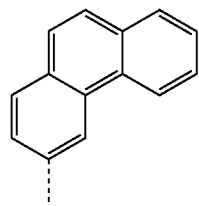 | 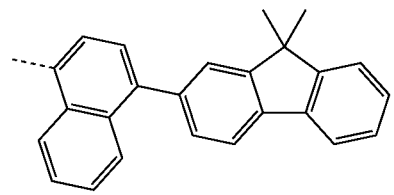 |
| 2-171 | 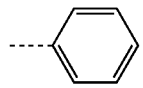 | 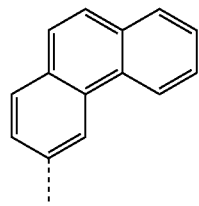 | 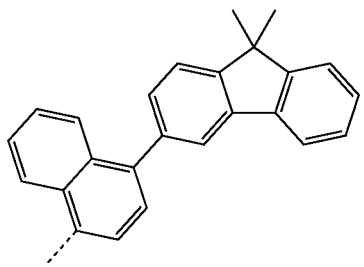 |
| 2-172 | 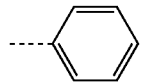 | 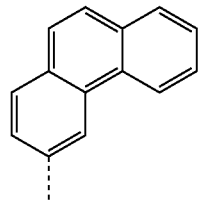 | 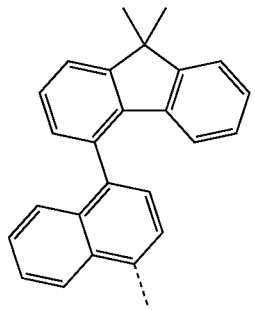 |
| 2-173 | 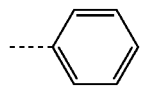 | 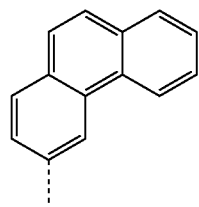 | 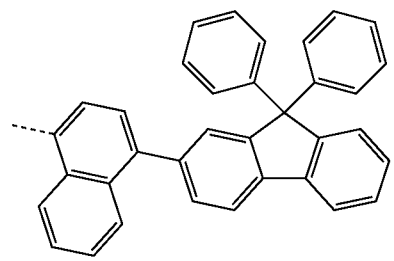 |

-continued
| Formula | ---Ar1 | ---Ar2 | ---Ar3 |
|---|---|---|---|
| 2-174 | 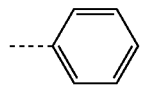 | 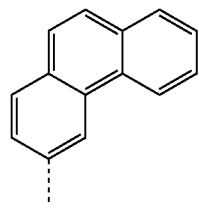 | 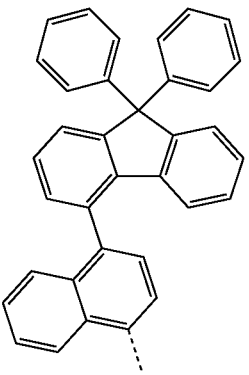 |
| 2-175 | 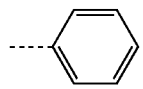 | 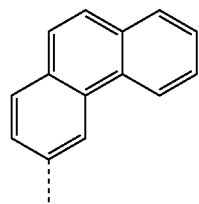 | 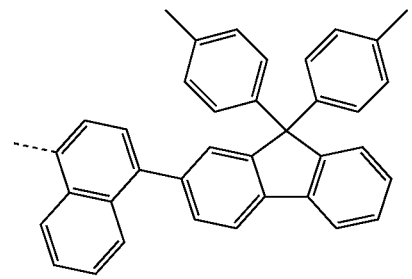 |
| 2-176 | 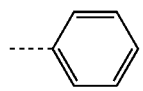 | 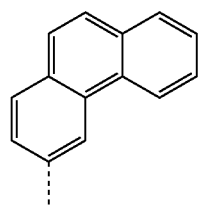 | 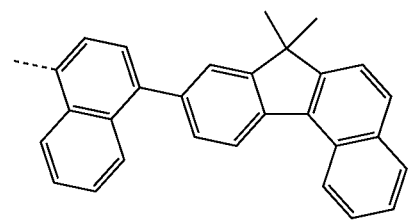 |
| 2-177 | 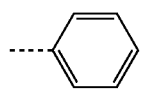 | 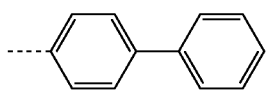 | 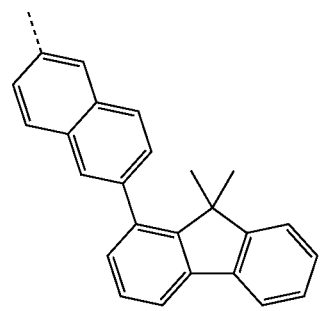 |
| 2-178 | 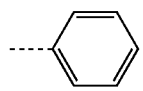 | 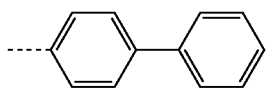 | 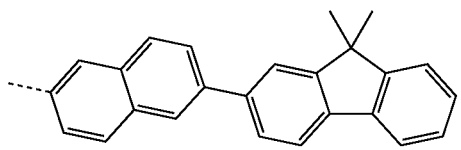 |

-continued

| Formula | - - -Ar1 | - - -Ar2 | - - -Ar3 |
|---|---|---|---|
| 2-179 | phenyl | biphenyl | naphthyl-(9,9-dimethylfluorenyl) |
| 2-180 | phenyl | biphenyl | naphthyl-(9,9-dimethylfluorenyl) |
| 2-181 | phenyl | biphenyl | naphthyl-(9,9-diphenylfluorenyl) |
| 2-182 | phenyl | biphenyl | naphthyl-(9,9-diphenylfluorenyl) |
| 2-183 | phenyl | biphenyl | naphthyl-(9,9-di-p-tolylfluorenyl) |

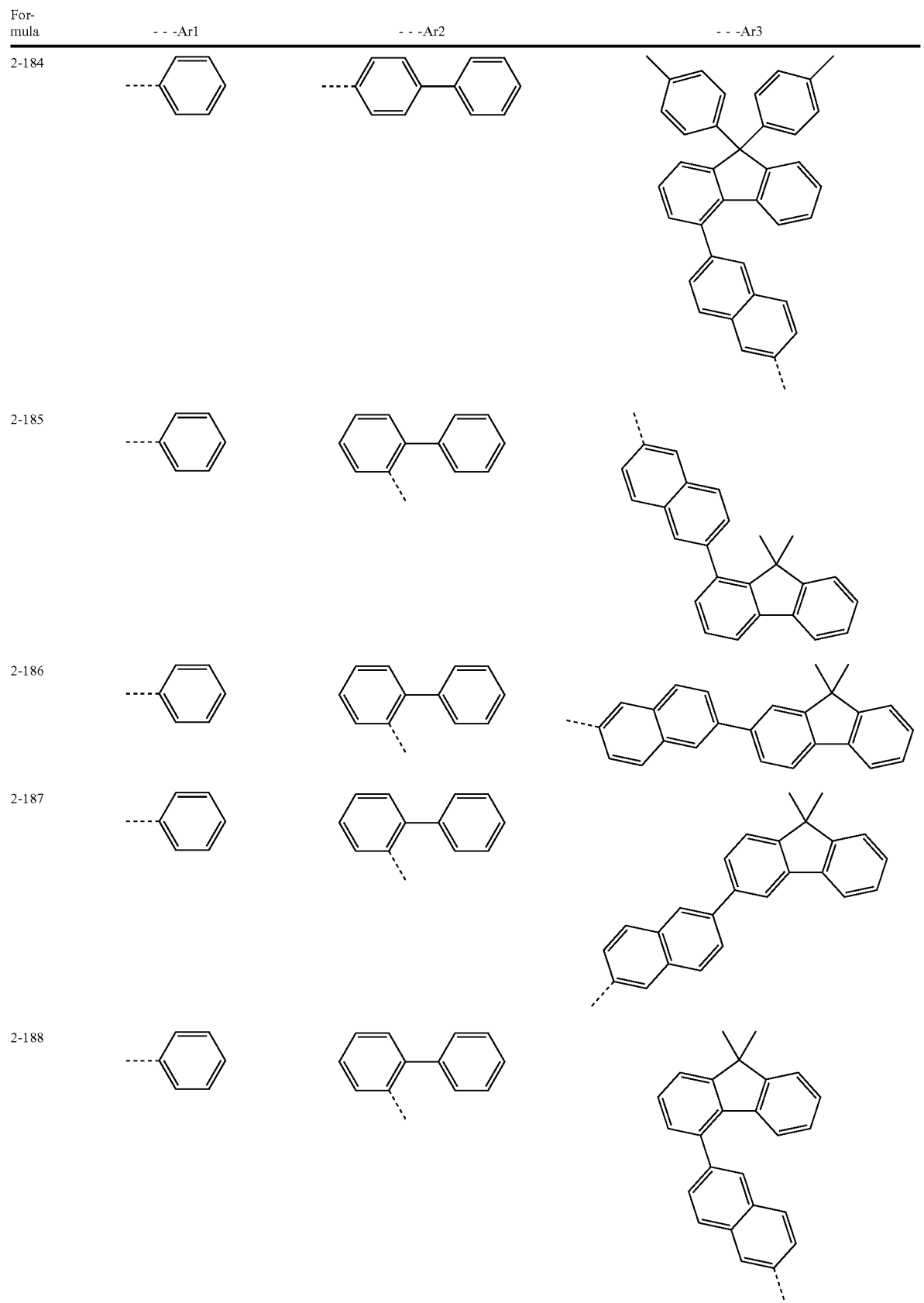

| For-mula | - - -Ar1 | - - -Ar2 | - - -Ar3 |
|---|---|---|---|
| 2-189 | 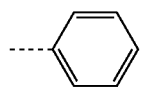 | 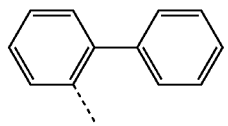 | 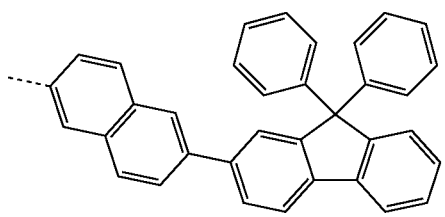 |
| 2-190 | 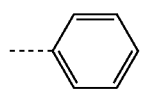 | 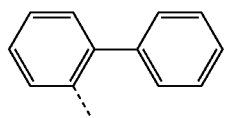 | 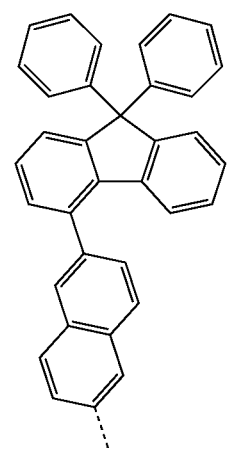 |
| 2-191 | 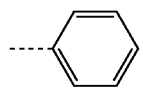 | 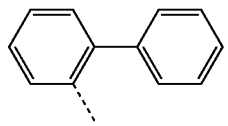 | 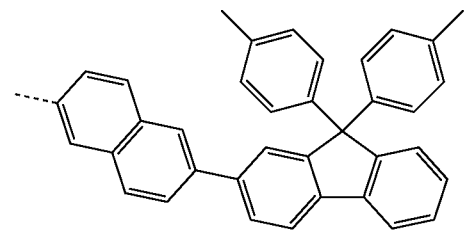 |
| 2-192 | 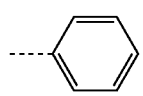 | 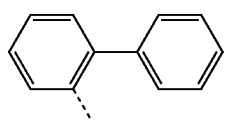 | 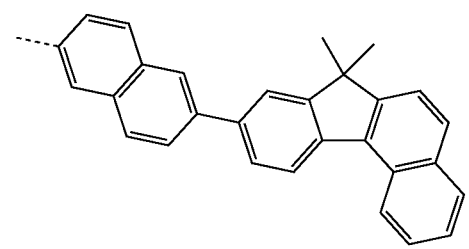 |
| 2-193 | 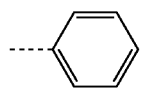 | 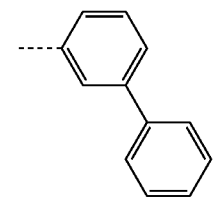 | 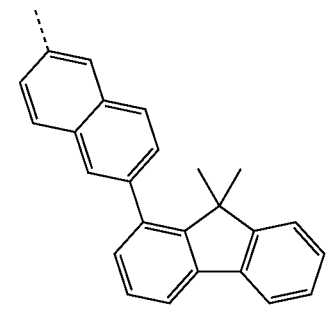 |

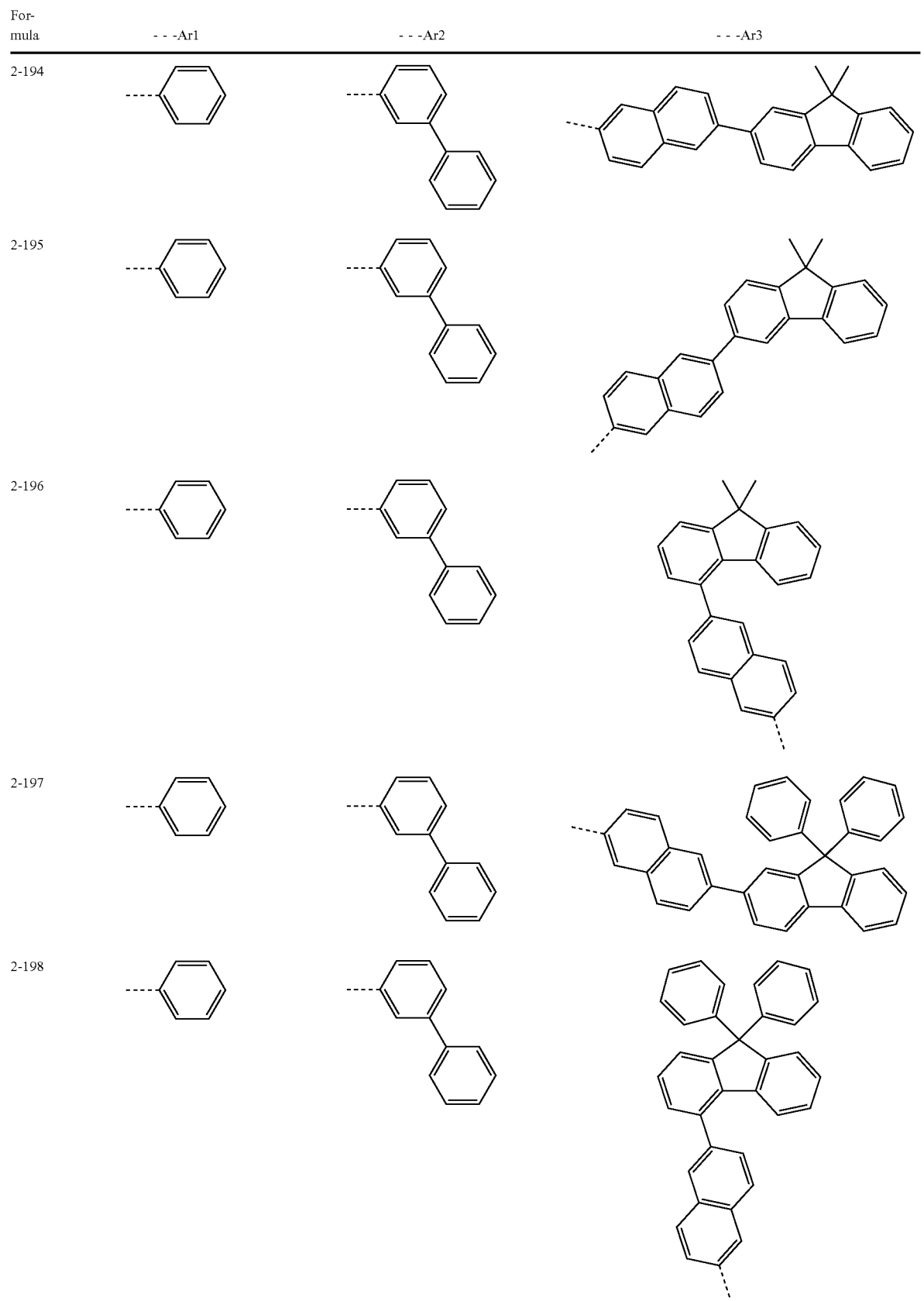

-continued
| Formula | - - -Ar1 | - - -Ar2 | - - -Ar3 |
|---|---|---|---|
| 2-199 | 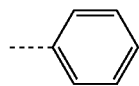 | 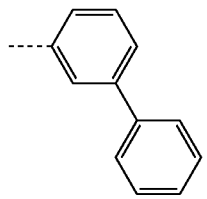 | 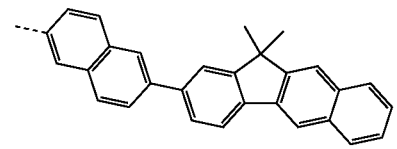 |
| 2-200 | 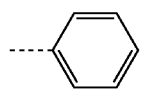 | 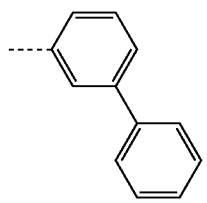 | 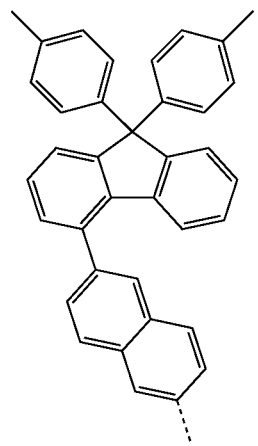 |
| 2-201 | 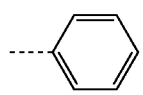 | 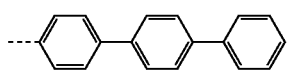 | 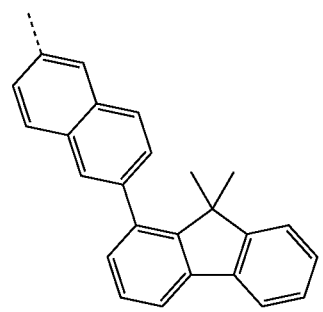 |
| 2-202 | 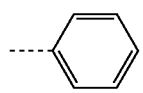 | 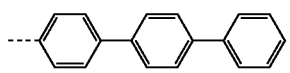 | 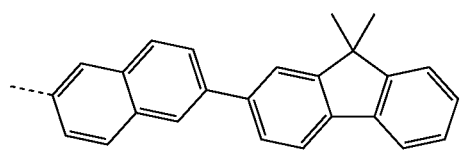 |
| 2-203 | 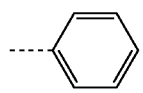 | 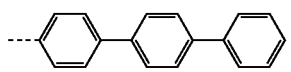 | 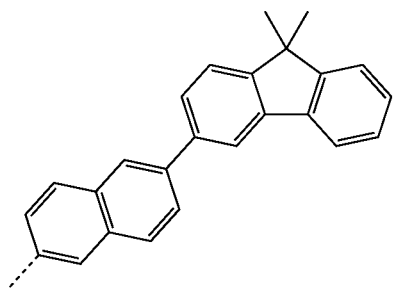 |

-continued
| Formula | - - -Ar1 | - - -Ar2 | - - -Ar3 |
|---|---|---|---|
| 2-204 | 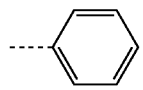 | 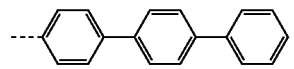 | 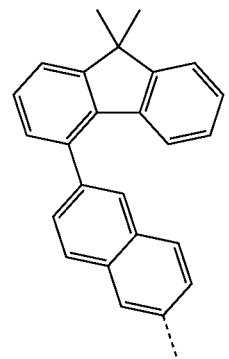 |
| 2-205 | 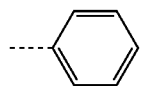 | 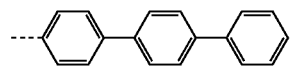 | 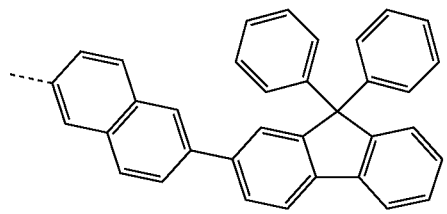 |
| 2-206 | 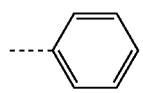 | 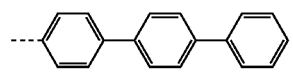 | 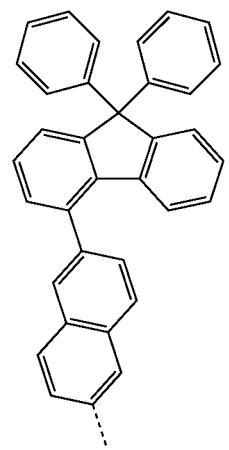 |
| 2-207 | 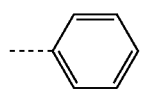 | 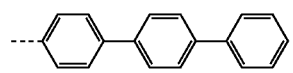 | 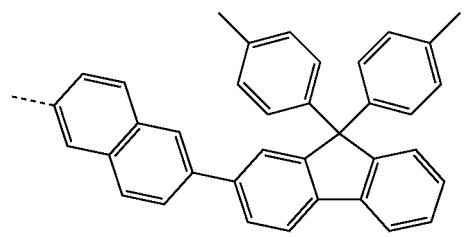 |
| 2-208 | 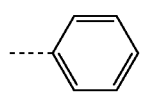 | 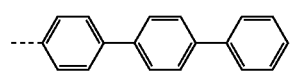 | 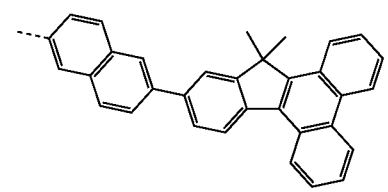 |

-continued
| Formula | ---Ar1 | ---Ar2 | ---Ar3 |
|---|---|---|---|
| 2-209 | 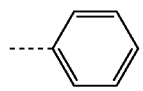 | 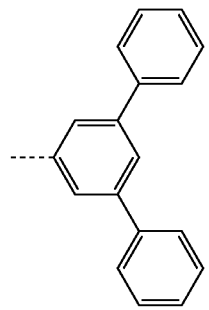 | 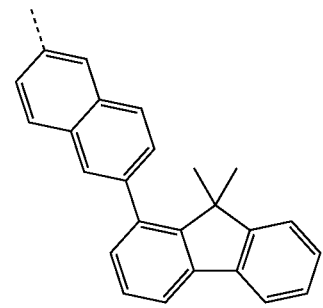 |
| 2-210 | 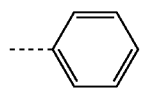 | 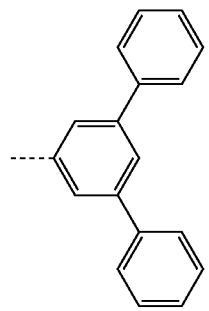 | 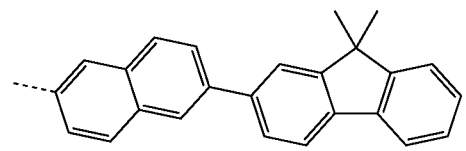 |
| 2-211 | 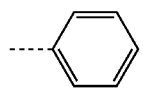 | 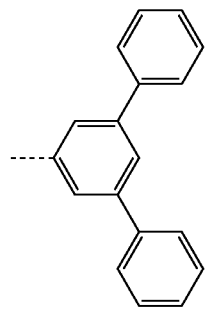 | 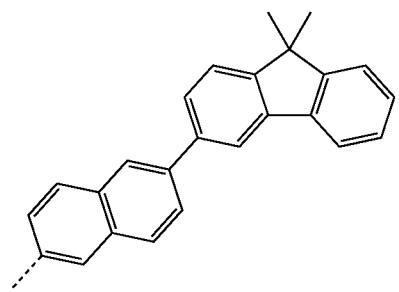 |
| 2-212 | 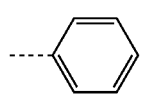 | 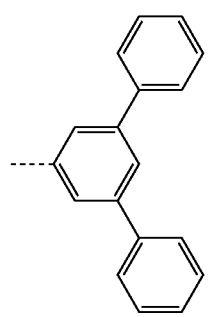 | 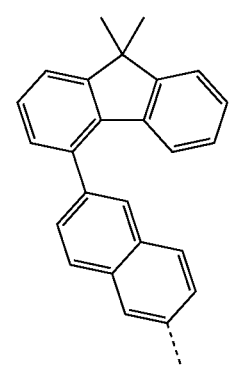 |

-continued
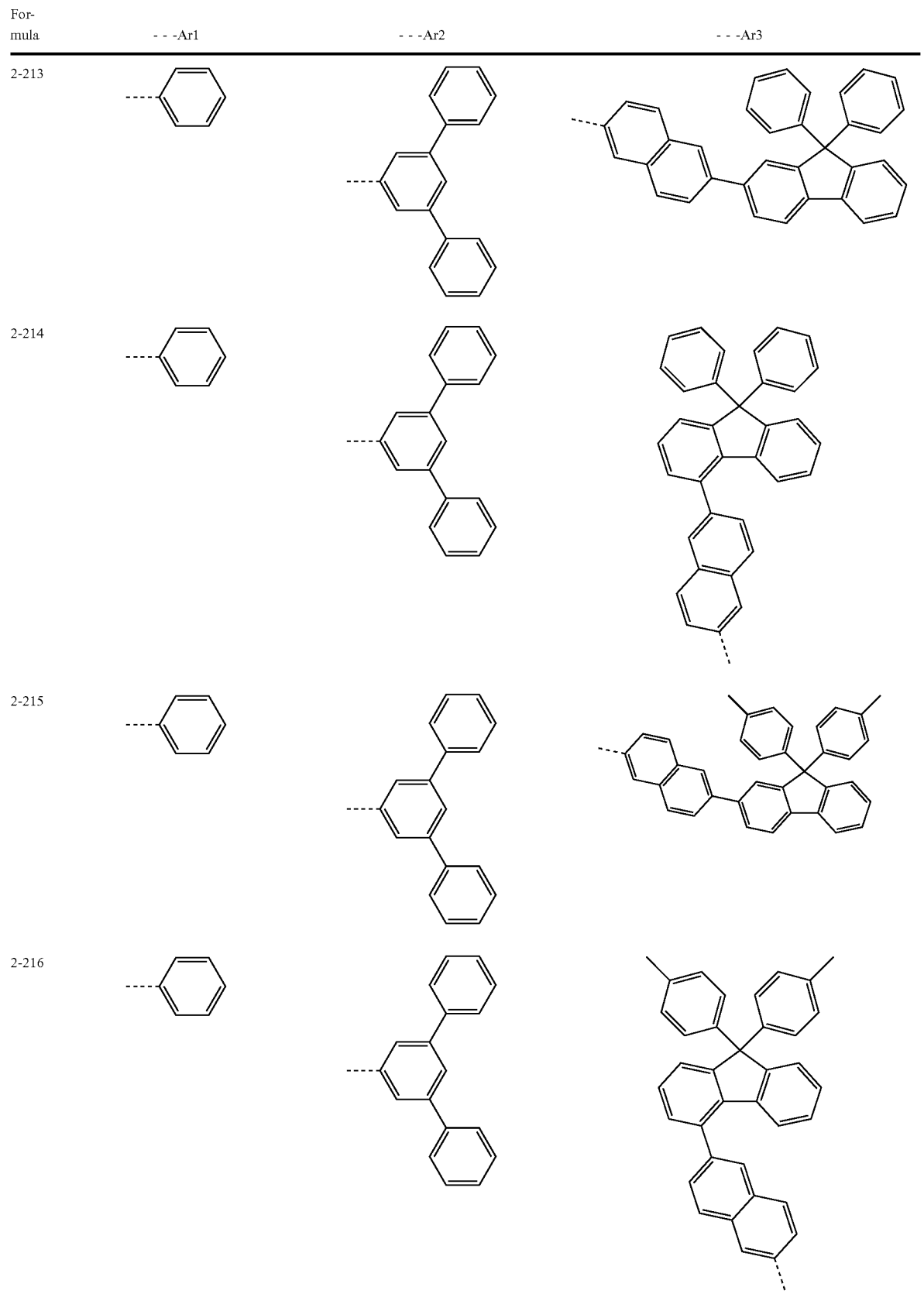

US 11,271,167 B2
-continued
| Formula | - - -Ar1 | - - -Ar2 | - - -Ar3 |
|---|---|---|---|
| 2-217 | 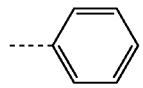 | 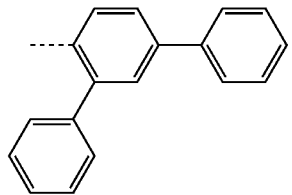 | 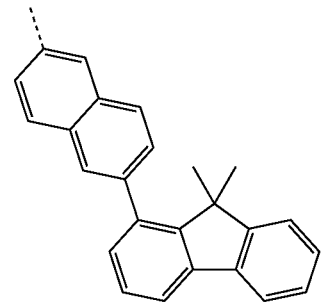 |
| 2-218 | 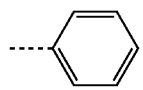 | 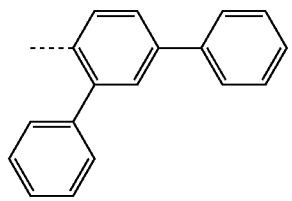 | 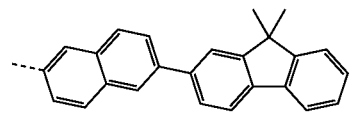 |
| 2-219 | 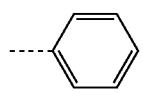 | 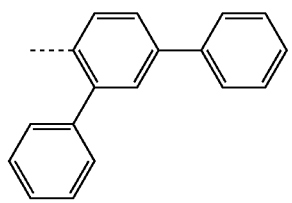 | 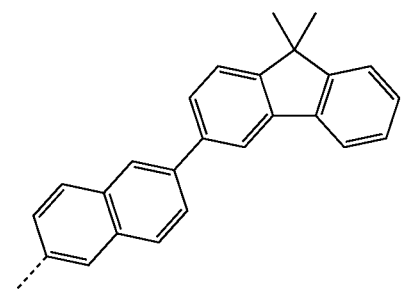 |
| 2-220 | 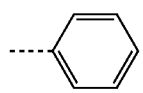 | 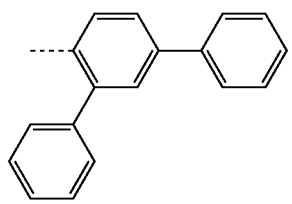 | 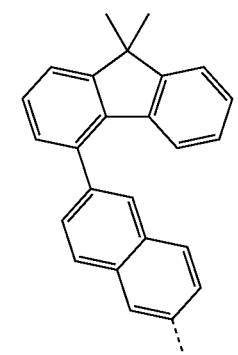 |
| 2-221 | 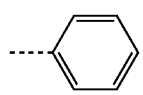 | 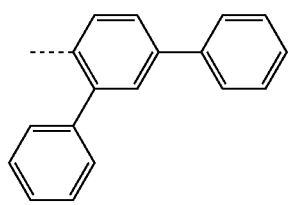 | 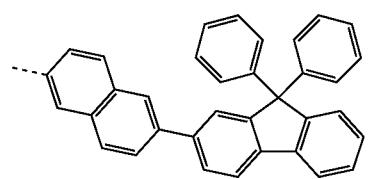 |

-continued

| Formula | - - -Ar1 | - - -Ar2 | - - -Ar3 |
|---|---|---|---|
| 2-222 | phenyl | biphenyl-substituted phenyl | 9,9-diphenylfluorenyl-naphthyl |
| 2-223 | phenyl | biphenyl-substituted phenyl | naphthyl-9,9-di(p-tolyl)fluorenyl |
| 2-224 | phenyl | biphenyl-substituted phenyl | 9,9-di(p-tolyl)fluorenyl-naphthyl |
| 2-225 | phenyl | naphthyl | naphthyl-9,9-dimethylfluorenyl |
| 2-226 | phenyl | naphthyl | naphthyl-9,9-dimethylfluorenyl |

-continued
| Formula | - - -Ar1 | - - -Ar2 | - - -Ar3 |
|---|---|---|---|
| 2-227 | 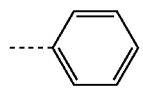 | 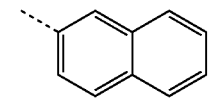 | 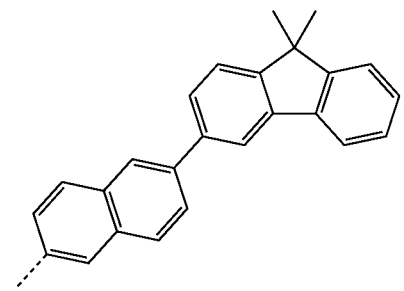 |
| 2-228 | 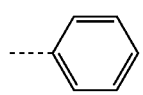 | 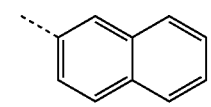 | 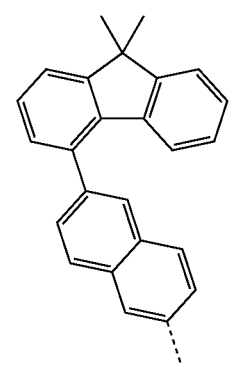 |
| 2-229 | 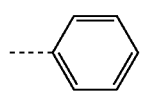 | 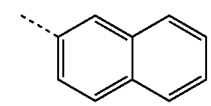 | 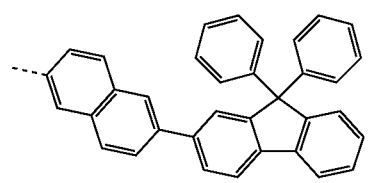 |
| 2-230 | 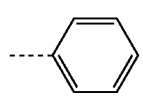 | 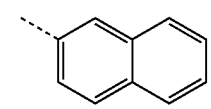 | 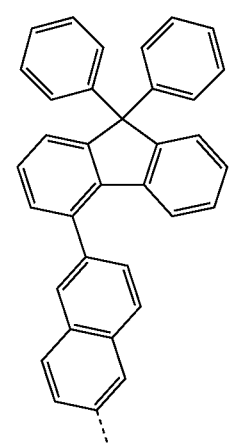 |
| 2-231 | 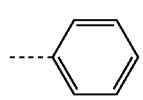 | 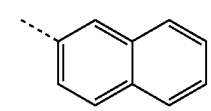 | 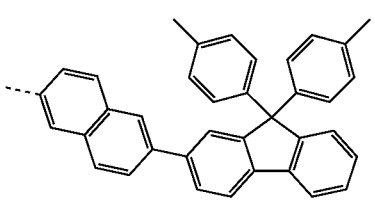 |

-continued
| Formula | - - -Ar1 | - - -Ar2 | - - -Ar3 |
|---|---|---|---|
| 2-232 | 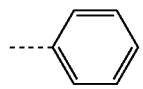 | 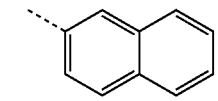 | 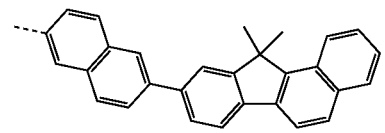 |
| 2-233 | 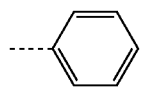 | 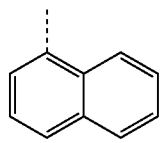 | 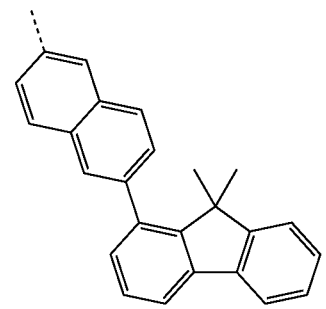 |
| 2-234 | 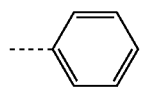 | 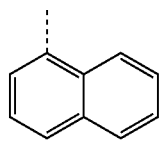 | 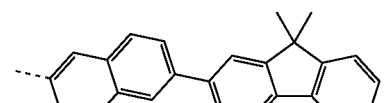 |
| 2-235 | 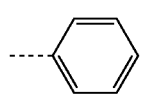 | 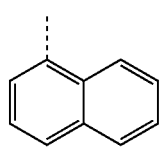 | 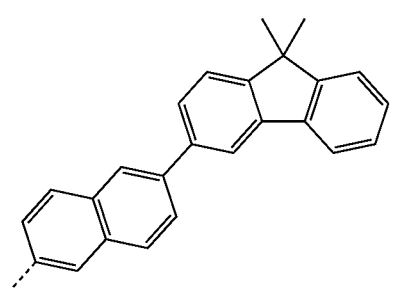 |
| 2-236 | 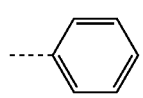 | 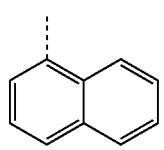 | 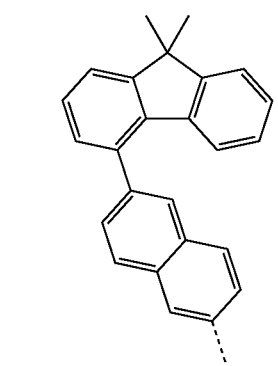 |
| 2-237 | 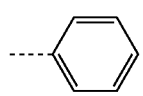 | 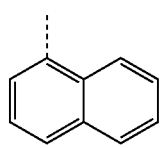 | 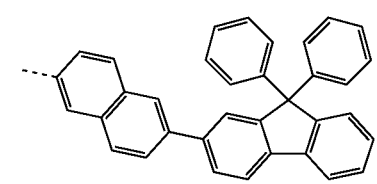 |

| For-mula | - - -Ar1 | - - -Ar2 | - - -Ar3 |
|---|---|---|---|
| 2-238 | 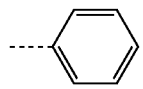 | 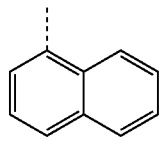 | 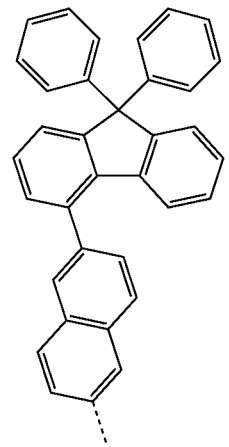 |
| 2-239 | 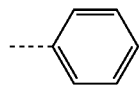 | 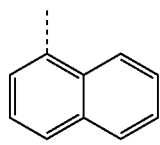 | 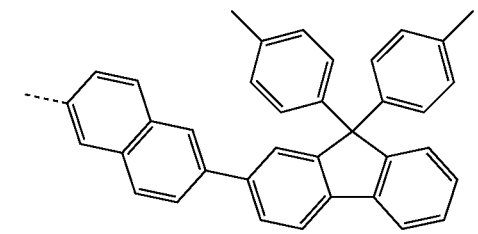 |
| 2-240 | 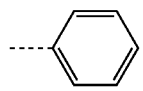 | 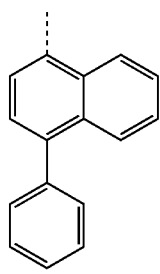 | 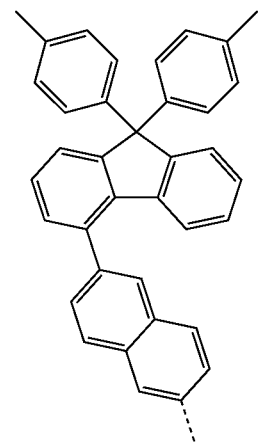 |
| 2-241 | 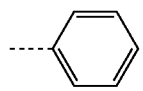 | 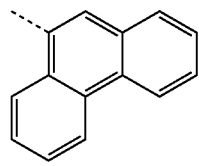 | 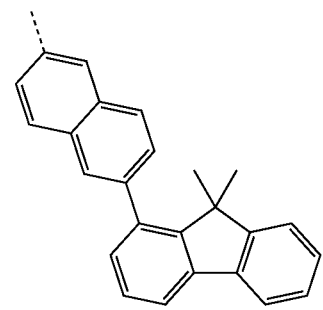 |

-continued
| Formula | - - -Ar1 | - - -Ar2 | - - -Ar3 |
|---|---|---|---|
| 2-242 | 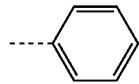 | 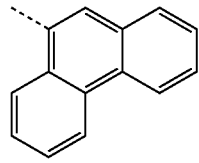 | 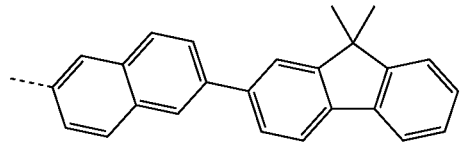 |
| 2-243 | 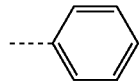 | 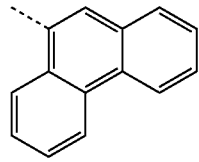 | 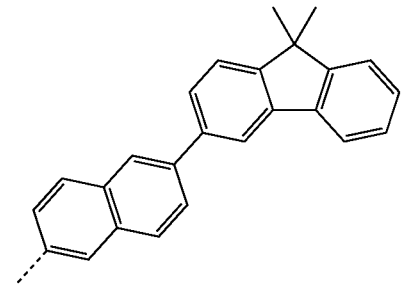 |
| 2-244 | 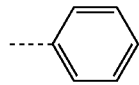 | 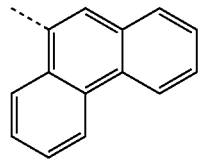 | 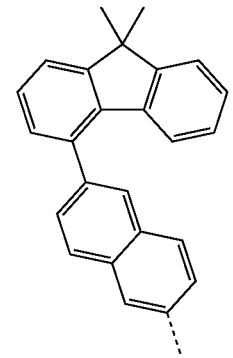 |
| 2-245 | 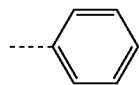 | 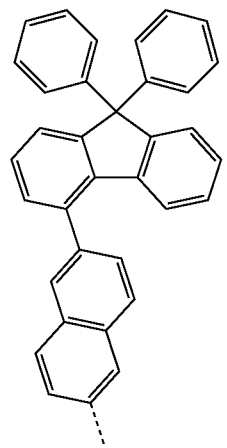 | 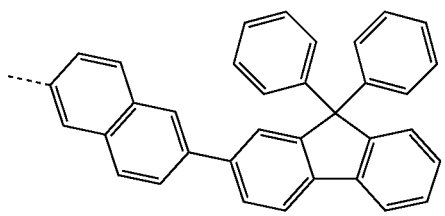 |

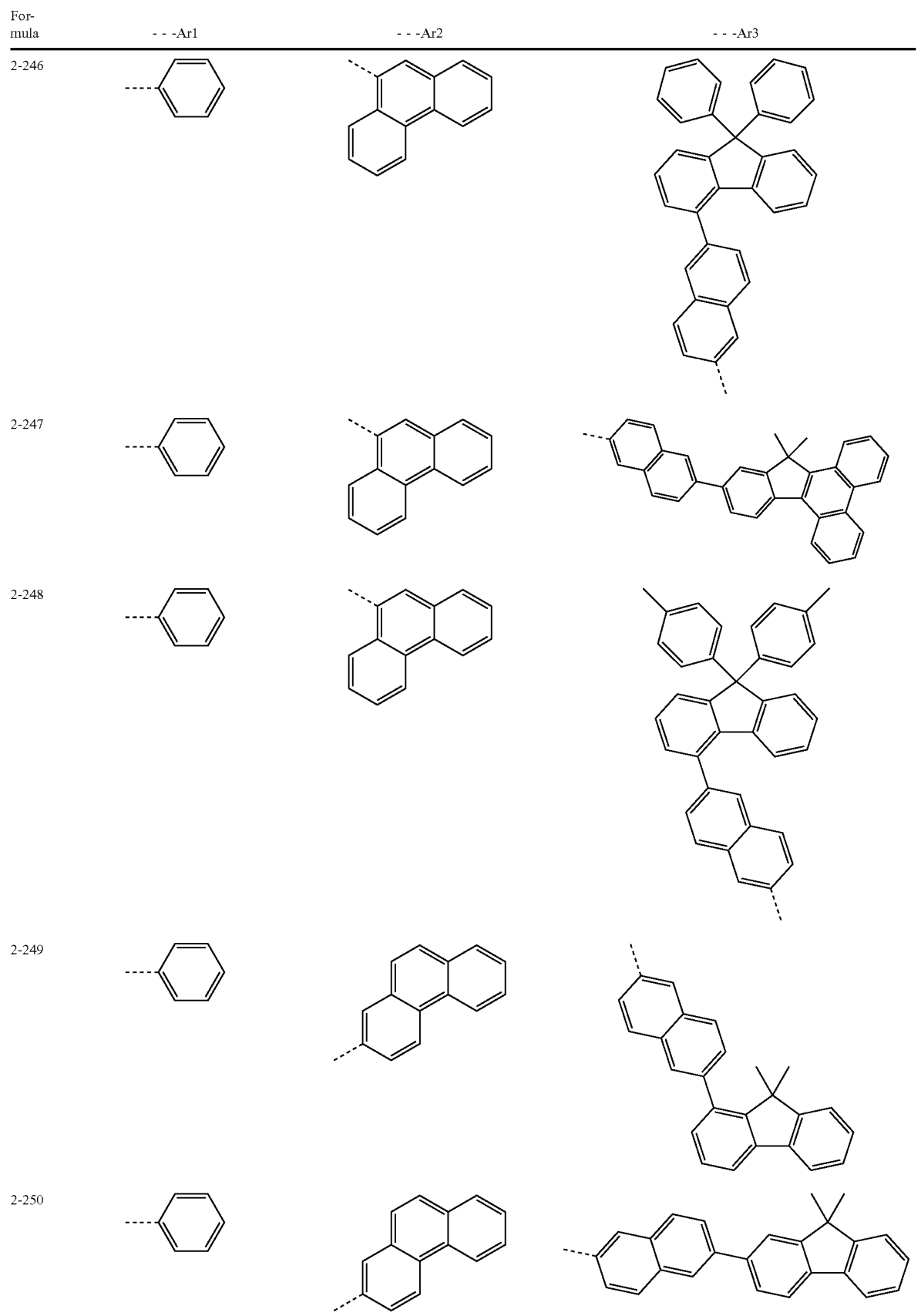

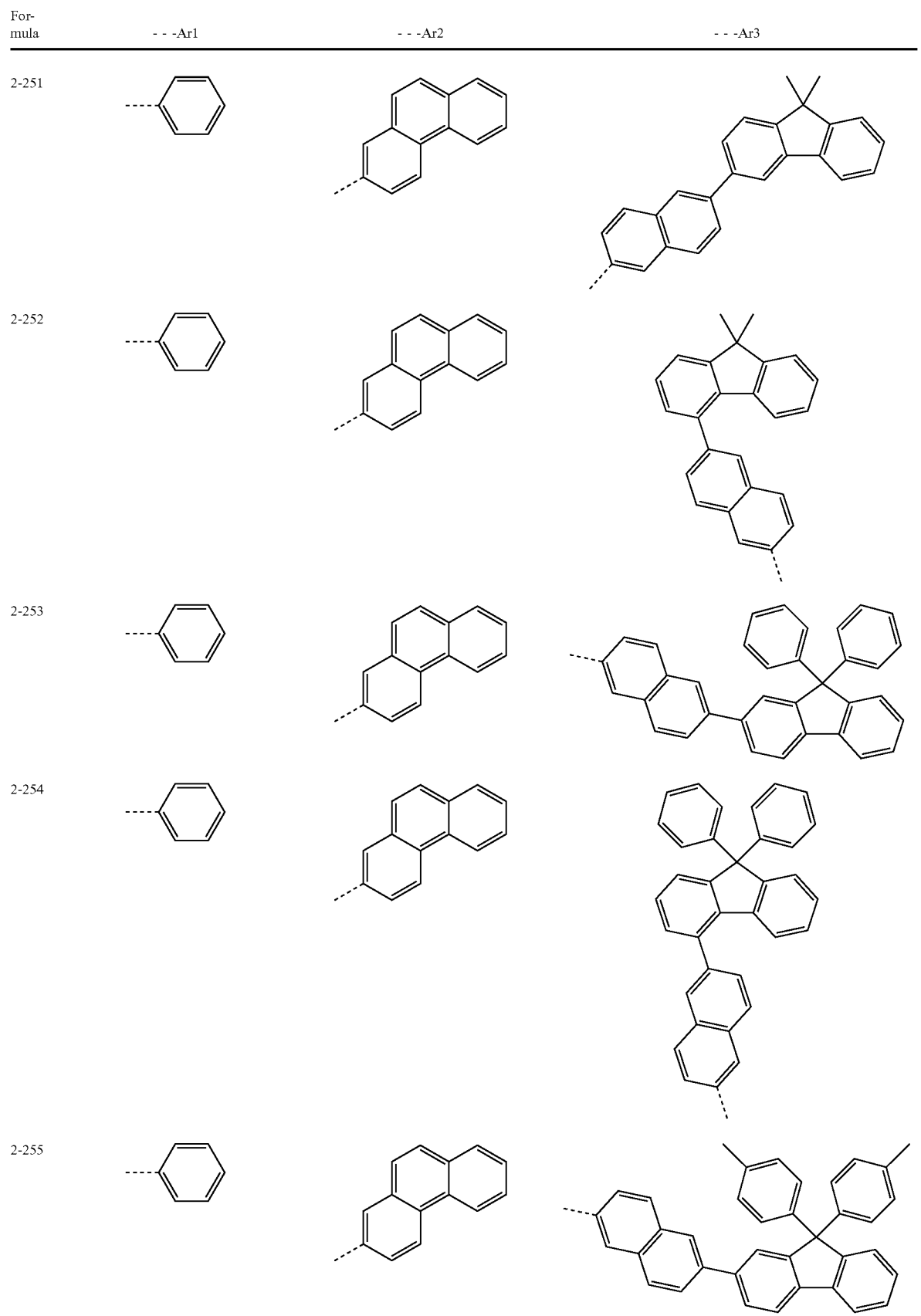

-continued
| Formula | - - -Ar1 | - - -Ar2 | - - -Ar3 |
|---|---|---|---|
| 2-256 | | | 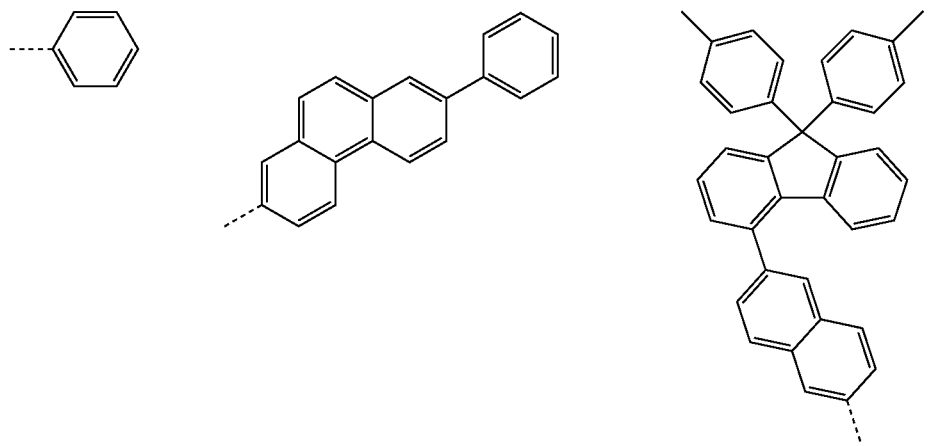 |
| 2-257 | | | 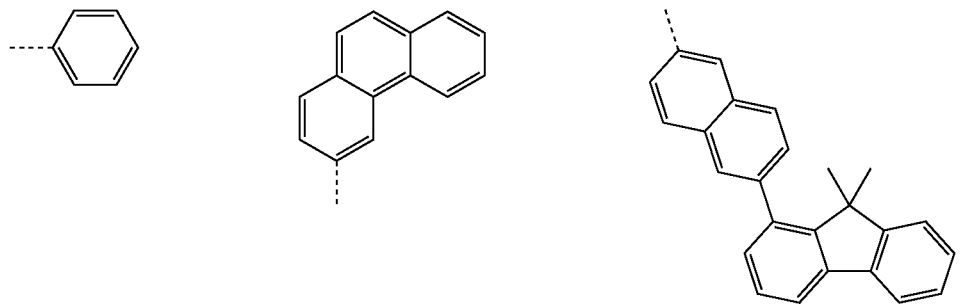 |
| 2-258 | | | 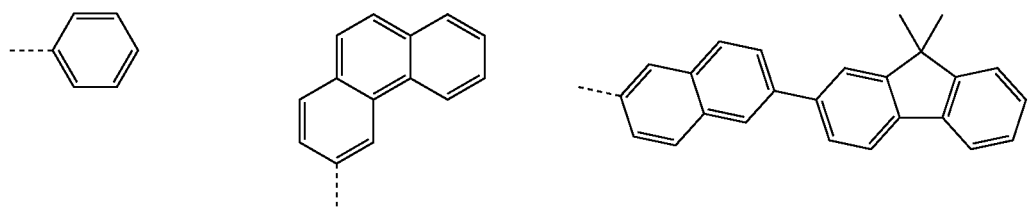 |
| 2-259 | | | 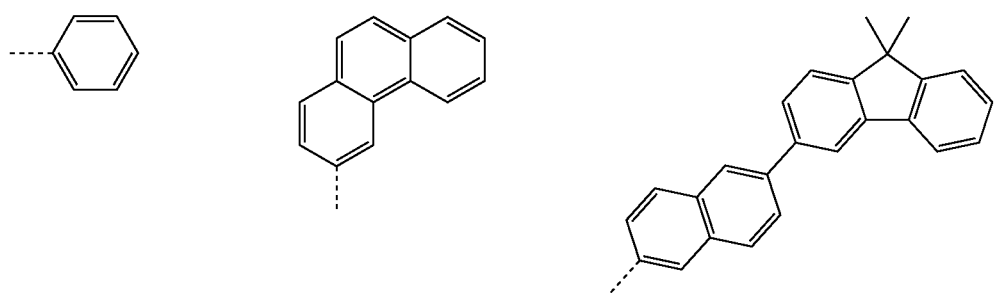 |

-continued
| Formula | - - -Ar1 | - - -Ar2 | - - -Ar3 |
|---|---|---|---|
| 2-260 | 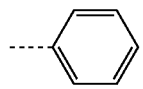 | 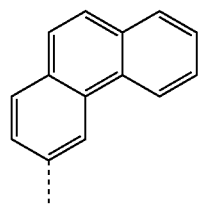 | 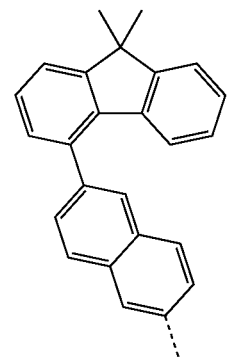 |
| 2-261 | 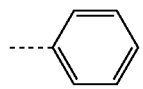 | 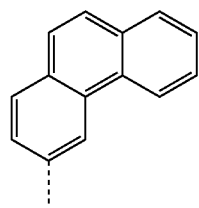 | 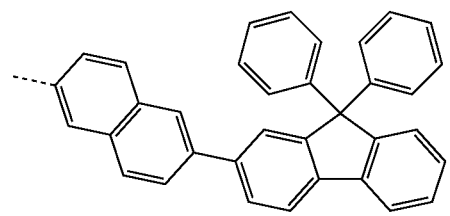 |
| 2-262 | 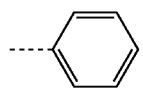 | 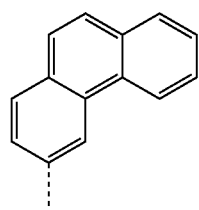 | 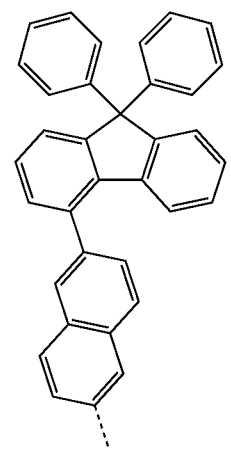 |
| 2-263 | 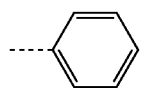 | 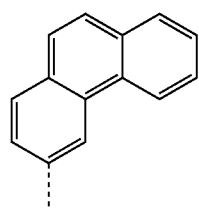 | 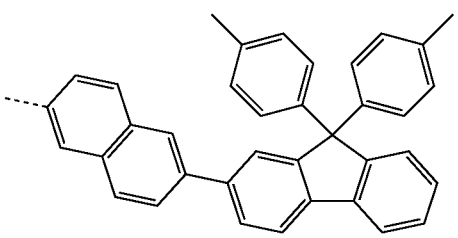 |

US 11,271,167 B2
-continued
| Formula | ---Ar1 | ---Ar2 | ---Ar3 |
|---|---|---|---|
| 2-264 | 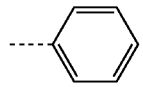 | 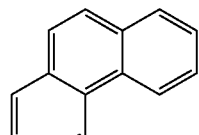 | 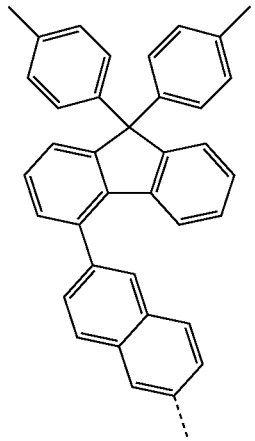 |
| 2-265 | 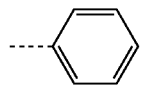 | 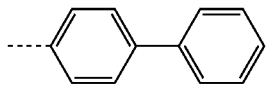 | 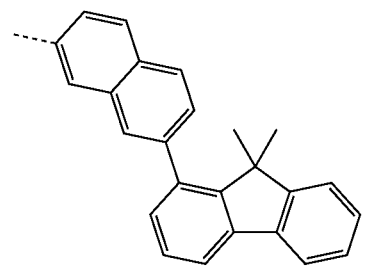 |
| 2-266 | 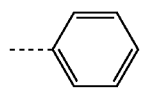 | 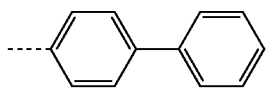 | 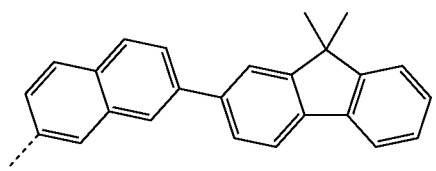 |
| 2-267 | 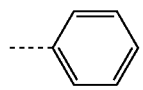 | 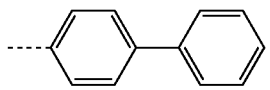 | 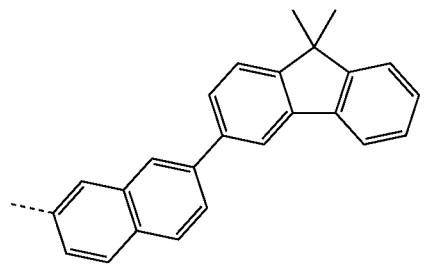 |
| 2-268 | 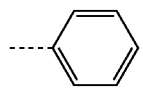 | 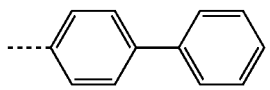 | 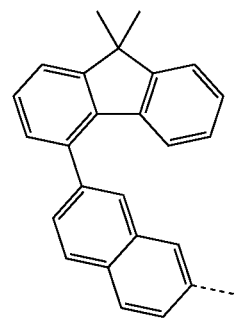 |

-continued
| Formula | - - -Ar1 | - - -Ar2 | - - -Ar3 |
|---|---|---|---|
| 2-269 | 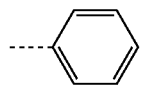 | 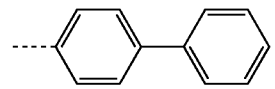 | 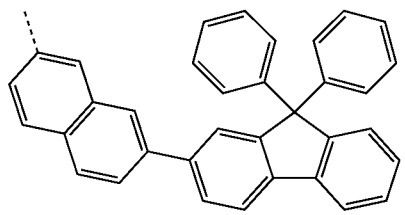 |
| 2-270 | 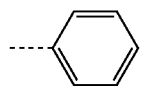 | 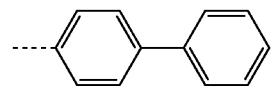 | 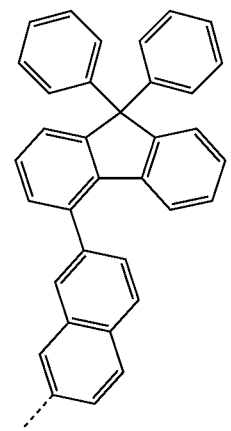 |
| 2-271 | 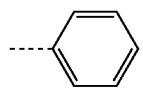 | 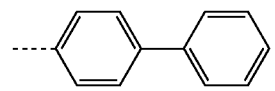 | 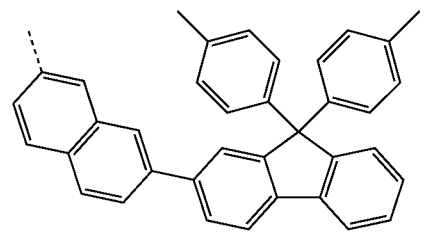 |
| 2-272 | 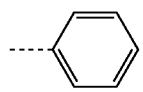 | 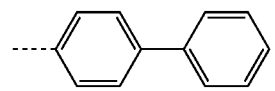 | 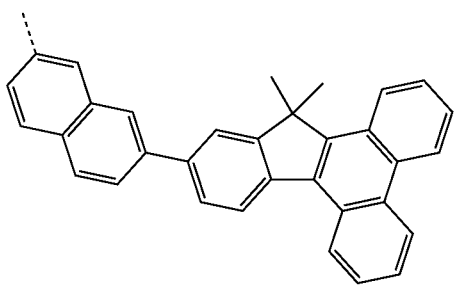 |
| 2-273 | 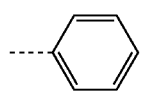 | 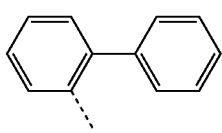 | 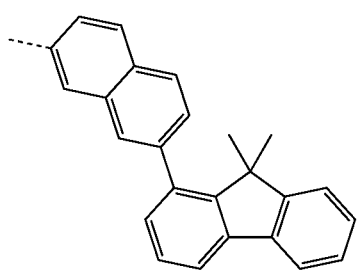 |

| Formula | ---Ar1 | ---Ar2 | ---Ar3 |
|---|---|---|---|
| 2-274 | 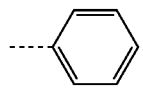 | 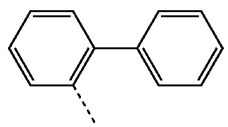 | 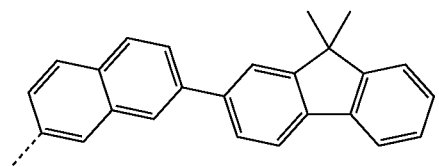 |
| 2-275 | 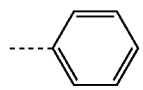 | 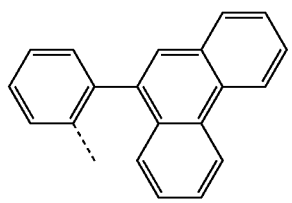 | 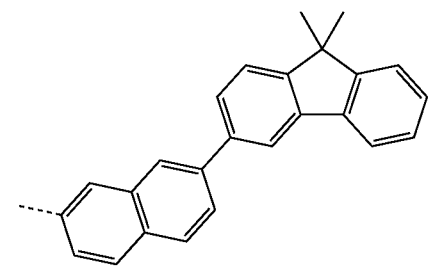 |
| 2-276 | 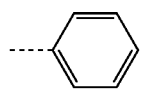 | 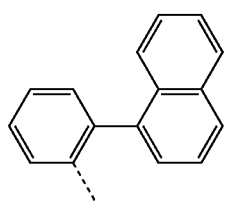 | 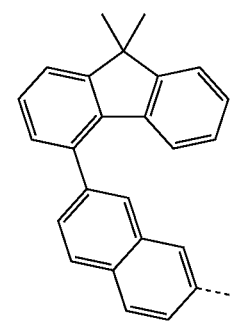 |
| 2-277 | 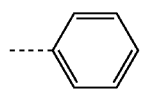 | 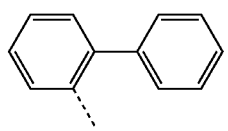 | 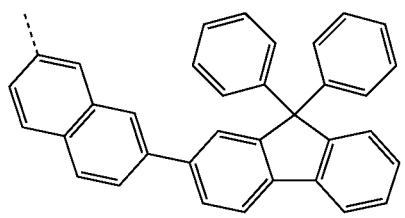 |
| 2-278 | 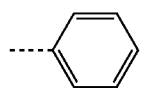 | 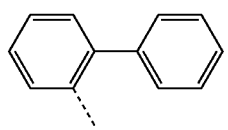 | 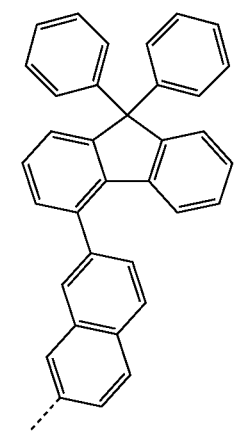 |

-continued
| Formula | - - -Ar1 | - - -Ar2 | - - -Ar3 |
|---|---|---|---|
| 2-279 | 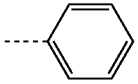 | 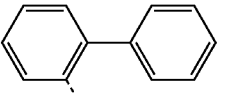 | 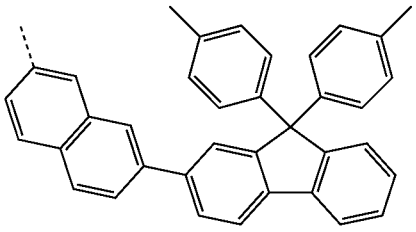 |
| 2-280 | 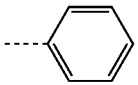 | 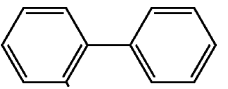 | 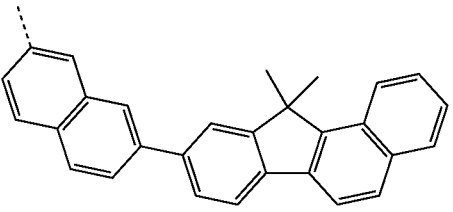 |
| 2-281 | 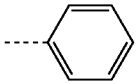 | 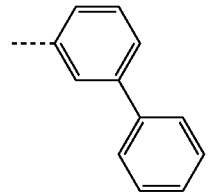 | 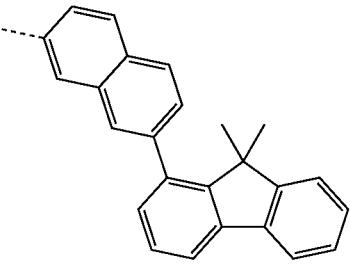 |
| 2-282 | 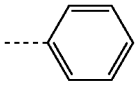 | 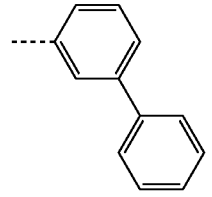 | 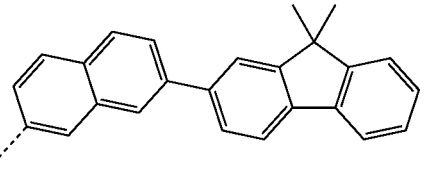 |
| 2-283 | 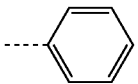 | 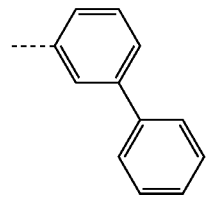 | 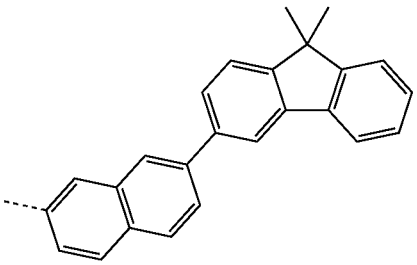 |
| 2-284 | 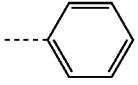 | 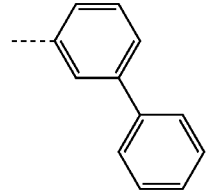 | 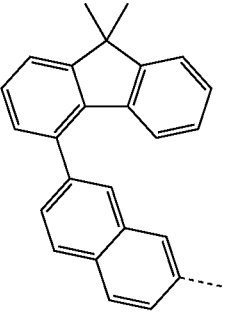 |

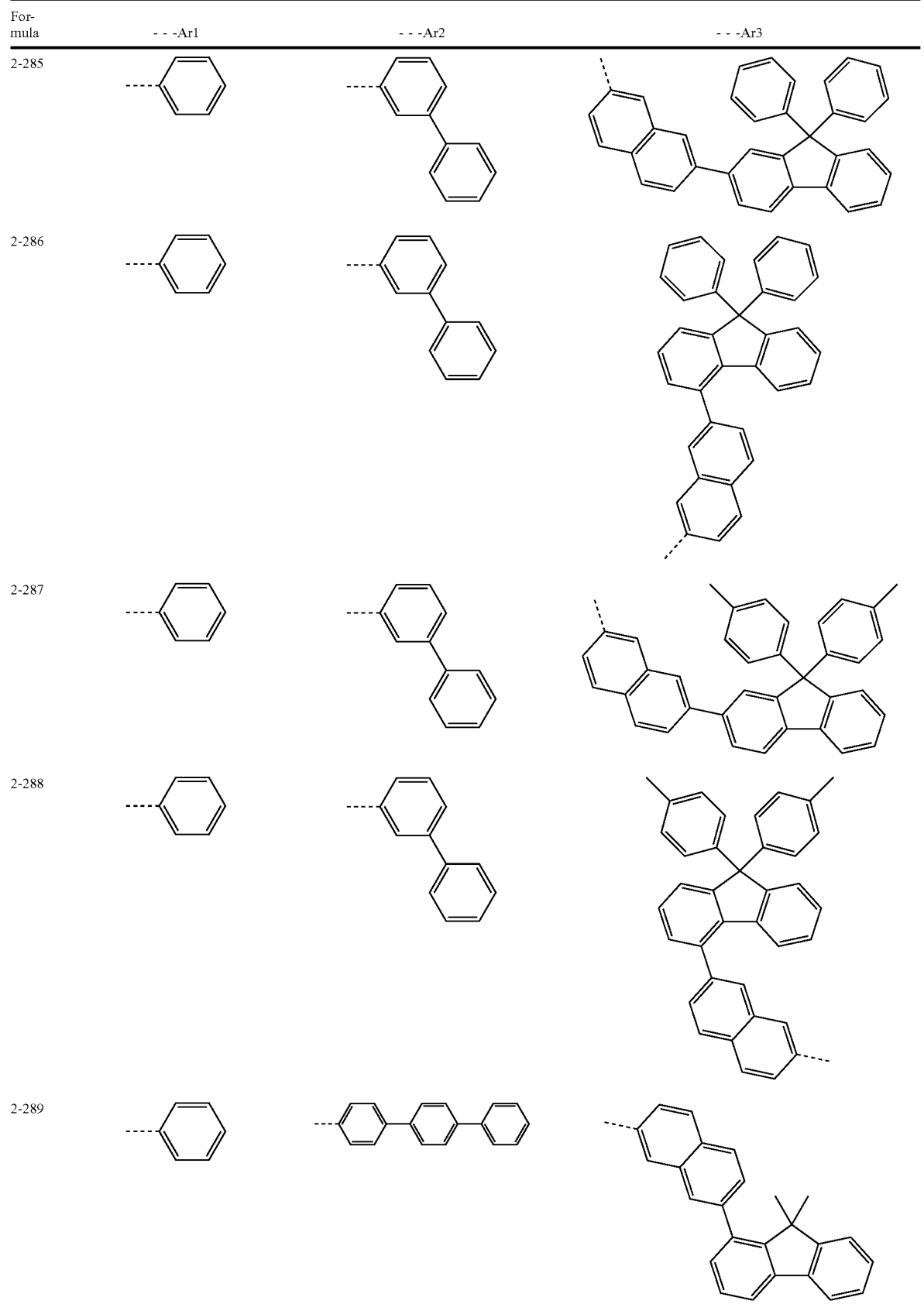

-continued
| Formula | ---Ar1 | ---Ar2 | ---Ar3 |
|---|---|---|---|
| 2-290 | 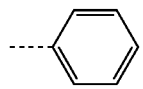 | 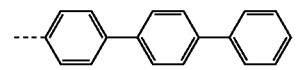 | 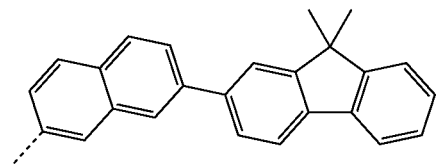 |
| 2-291 | 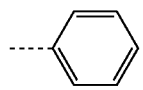 | 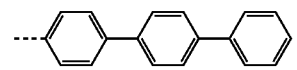 | 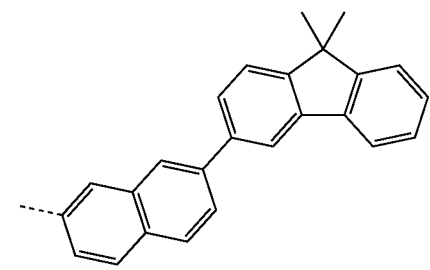 |
| 2-292 | 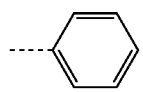 | 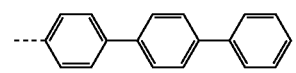 | 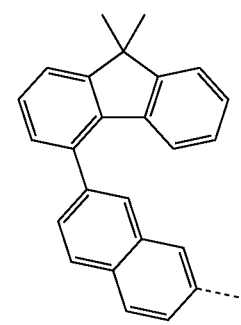 |
| 2-293 | 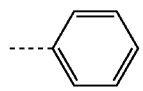 | 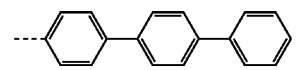 | 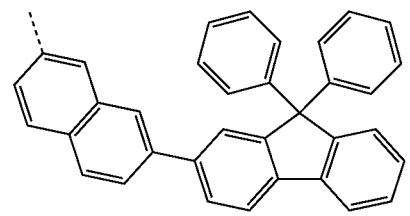 |
| 2-294 | 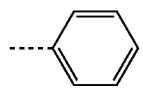 | 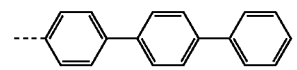 | 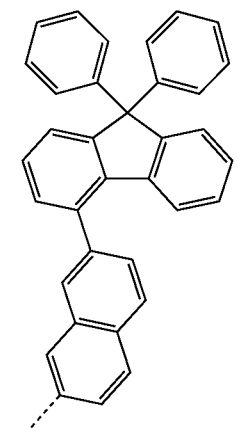 |

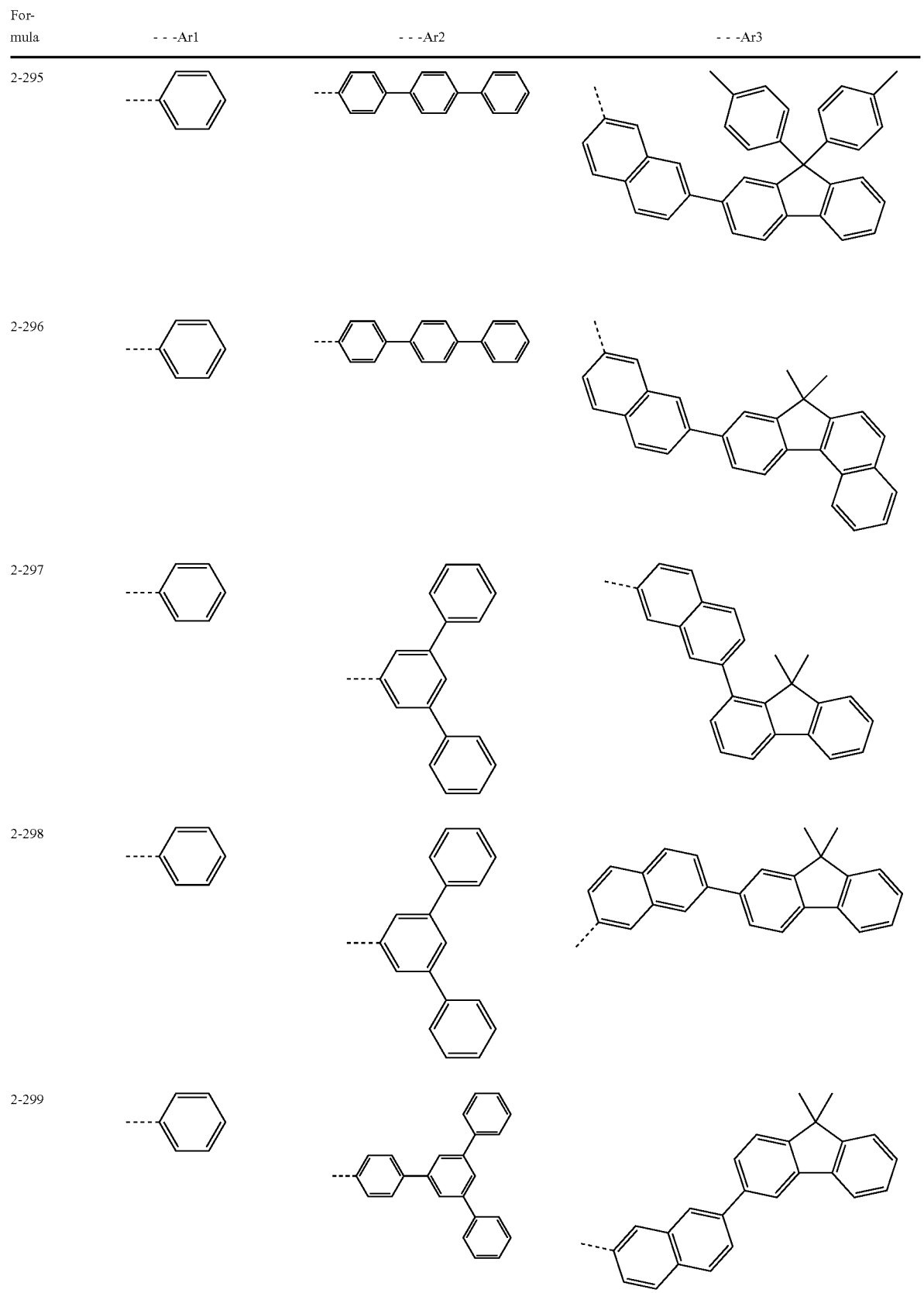

-continued
| Formula | ---Ar1 | ---Ar2 | ---Ar3 |
|---|---|---|---|
| 2-300 | 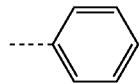 | 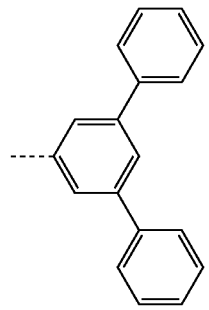 | 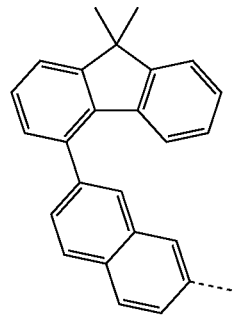 |
| 2-301 | 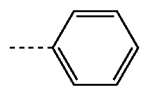 | 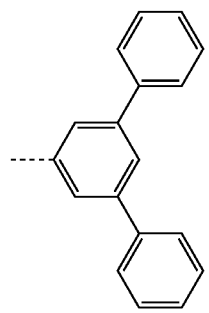 | 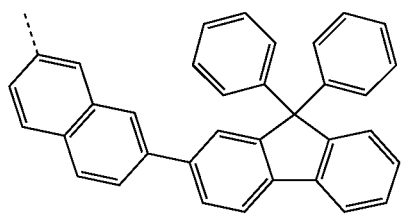 |
| 2-302 | 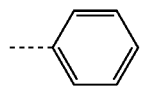 | 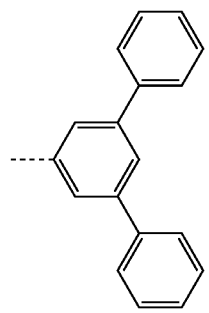 | 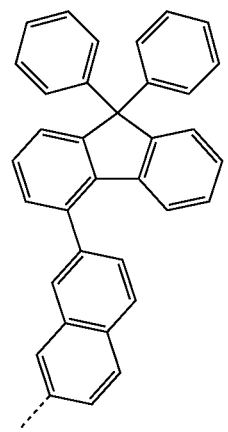 |
| 2-303 | 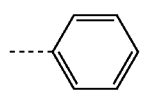 | 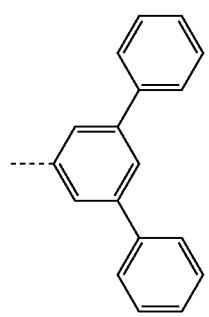 | 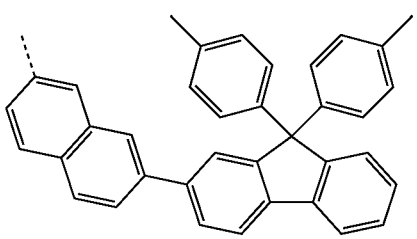 |

-continued
| Formula | - - -Ar1 | - - -Ar2 | - - -Ar3 |
|---|---|---|---|
| 2-304 | 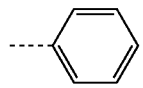 | 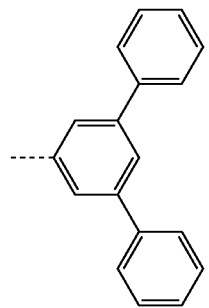 | 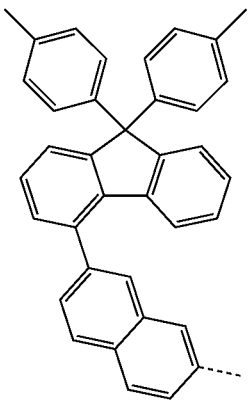 |
| 2-305 | 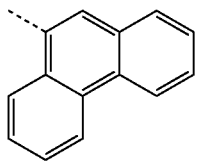 | 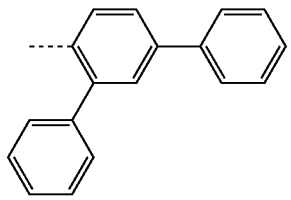 | 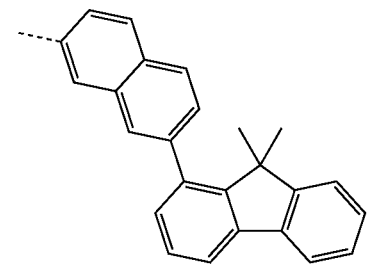 |
| 2-306 | 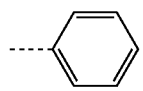 | 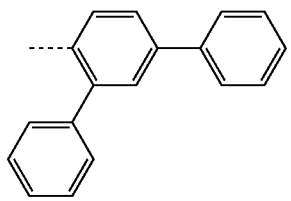 | 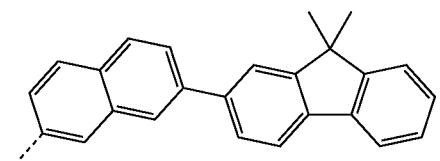 |
| 2-307 | 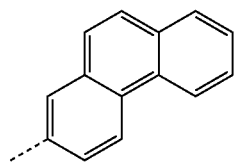 | 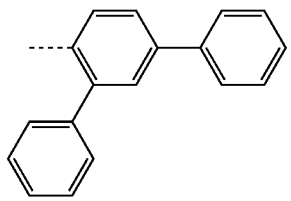 | 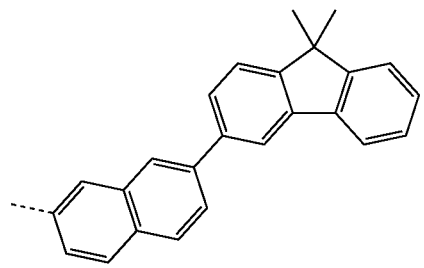 |
| 2-308 | 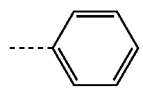 | 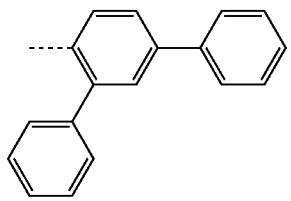 | 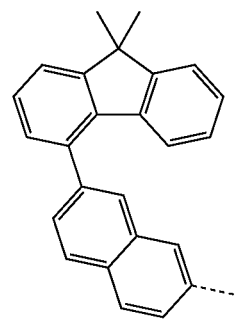 |

-continued
| Formula | ---Ar1 | ---Ar2 | ---Ar3 |
|---|---|---|---|
| 2-309 | 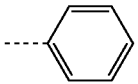 | 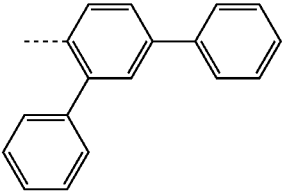 | 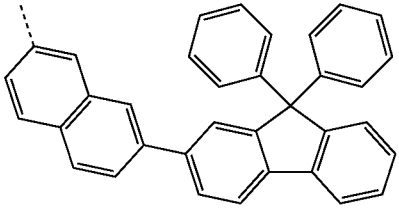 |
| 2-310 | 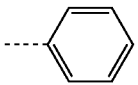 | 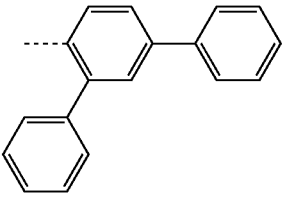 | 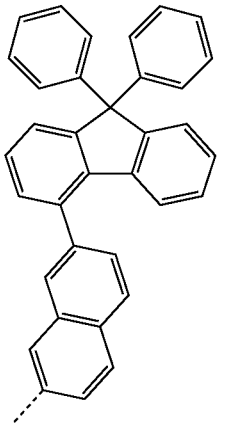 |
| 2-311 | 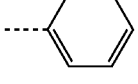 | 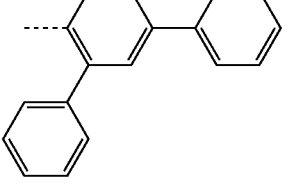 | 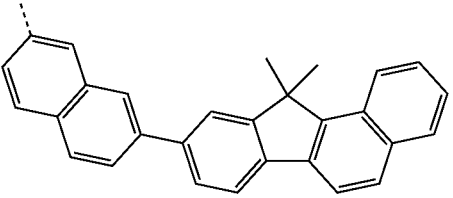 |
| 2-312 | 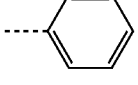 | 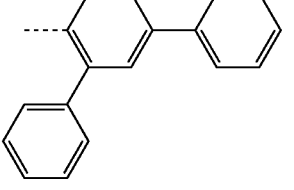 | 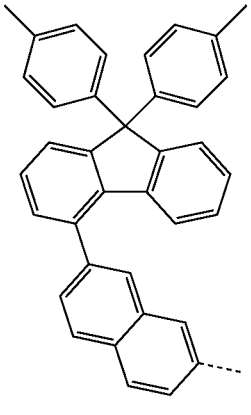 |
| 2-313 | 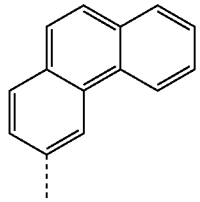 | 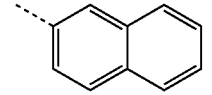 | 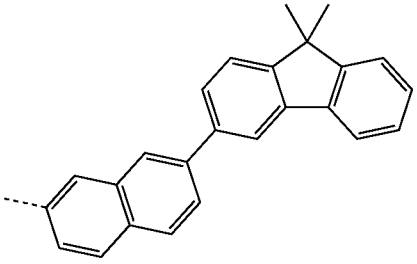 |

-continued
| Formula | ---Ar1 | ---Ar2 | ---Ar3 |
|---|---|---|---|
| 2-314 | 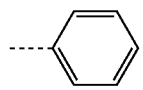 | 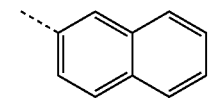 | 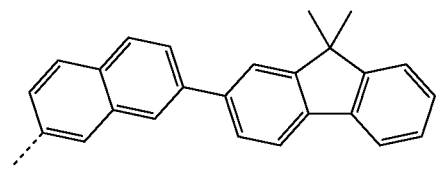 |
| 2-315 | 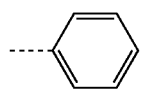 | 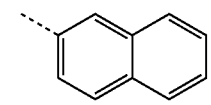 | 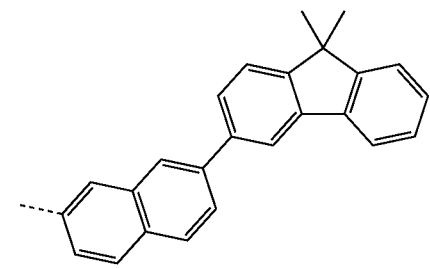 |
| 2-316 | 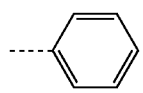 | 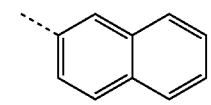 | 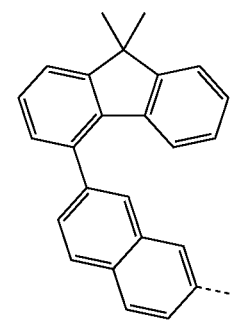 |
| 2-317 | 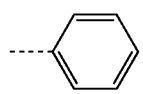 | 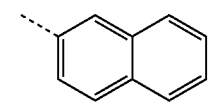 | 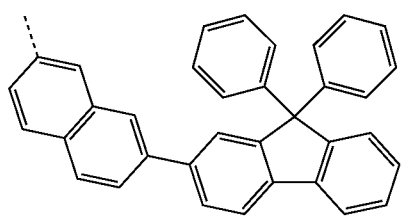 |
| 2-318 | 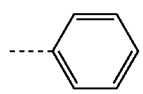 | 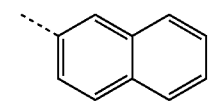 | 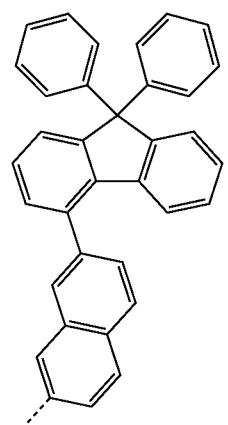 |

-continued
| Formula | ---Ar1 | ---Ar2 | ---Ar3 |
|---|---|---|---|
| 2-319 | 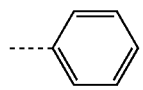 | 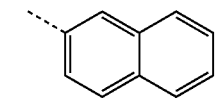 | 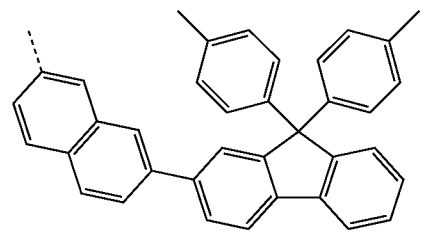 |
| 2-320 | 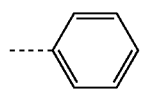 | 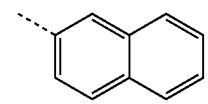 | 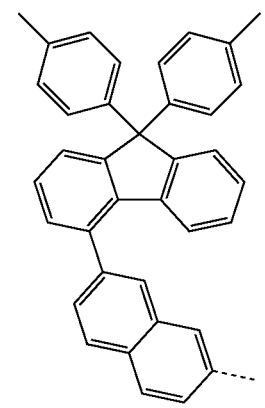 |
| 2-321 | 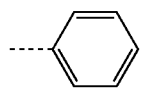 | 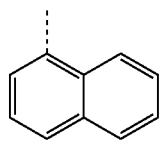 | 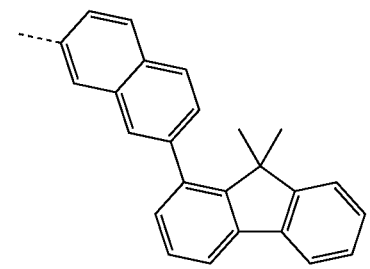 |
| 2-322 | 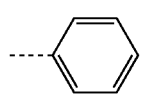 | 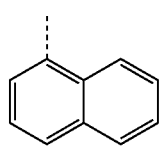 | 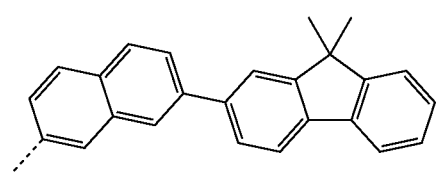 |
| 2-323 | 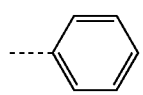 | 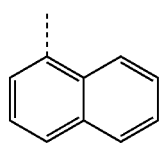 | 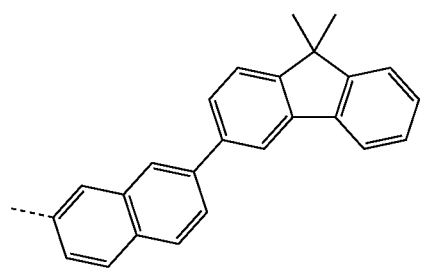 |

-continued
| Formula | - - -Ar1 | - - -Ar2 | - - -Ar3 |
|---|---|---|---|
| 2-324 | 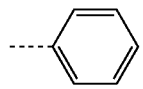 | 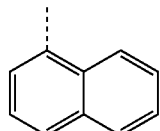 | 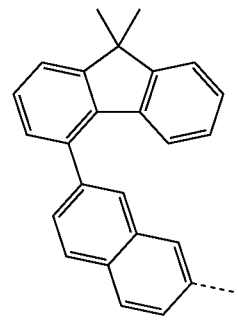 |
| 2-325 | 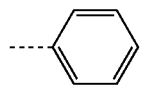 | 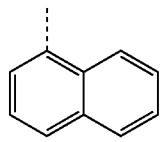 | 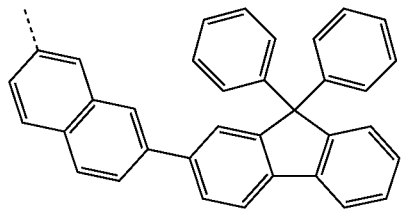 |
| 2-326 | 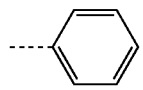 | 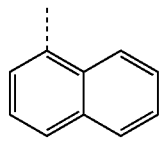 | 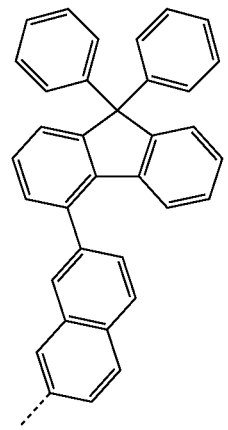 |
| 2-327 | 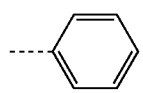 | 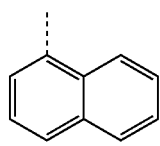 | 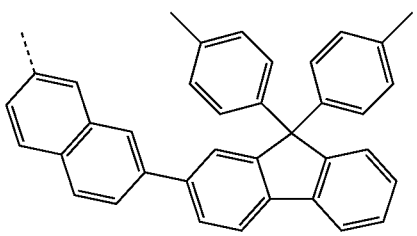 |

-continued
| Formula | - - -Ar1 | - - -Ar2 | - - -Ar3 |
|---|---|---|---|
| 2-328 | 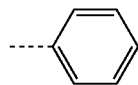 | 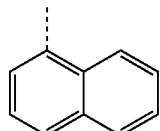 | 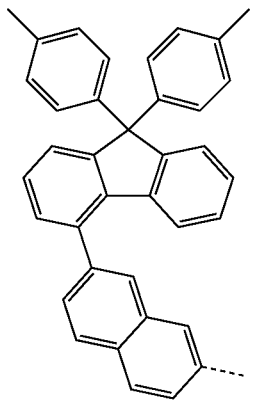 |
| 2-329 | 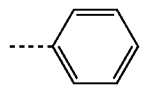 | 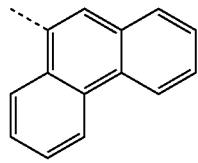 | 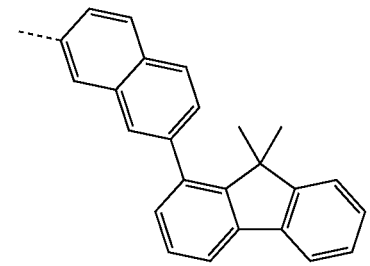 |
| 2-330 | 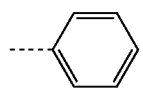 | 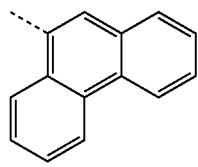 | 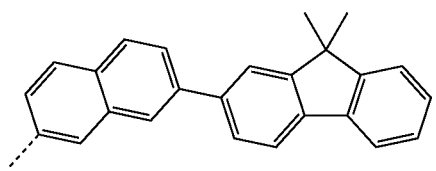 |
| 2-331 | 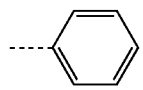 | 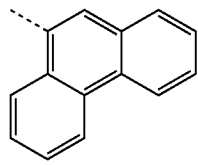 | 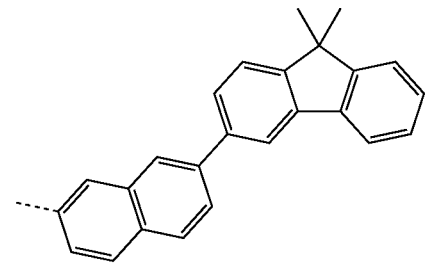 |
| 2-332 | 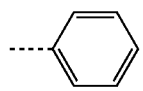 | 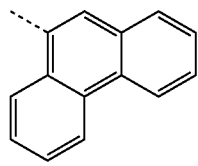 | 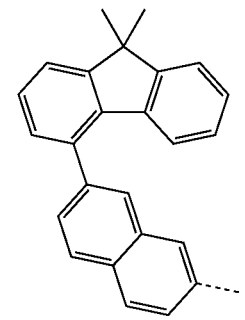 |

-continued

| Formula | - - -Ar1 | - - -Ar2 | - - -Ar3 |
|---|---|---|---|
| 2-333 | phenyl | phenanthrenyl | naphthyl-9,9-diphenylfluorenyl |
| 2-334 | phenyl | phenanthrenyl | 9,9-diphenylfluorenyl-naphthyl |
| 2-335 | phenyl | phenanthrenyl | naphthyl-9,9-di(p-tolyl)fluorenyl |
| 2-336 | phenyl | phenanthrenyl | 9,9-di(p-tolyl)fluorenyl-naphthyl |
| 2-337 | phenyl | phenanthrenyl | naphthyl-9,9-dimethylfluorenyl |

-continued
| Formula | ---Ar1 | ---Ar2 | ---Ar3 |
|---|---|---|---|
| 2-338 | 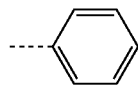 | 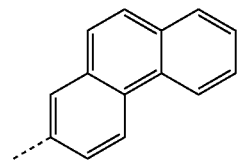 | 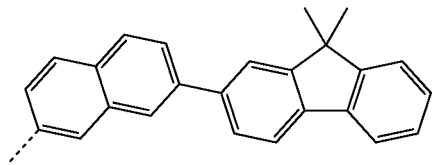 |
| 2-339 | 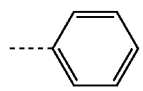 | 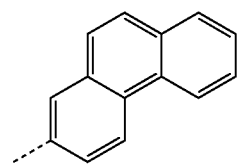 | 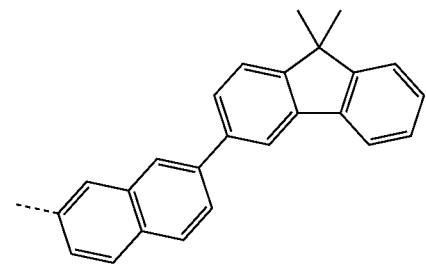 |
| 2-340 | 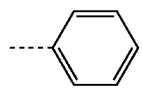 | 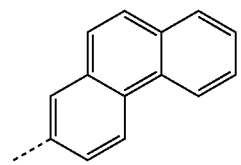 | 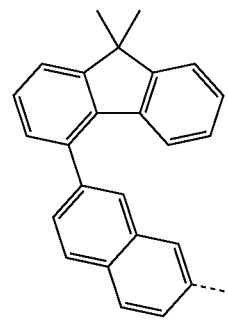 |
| 2-341 | 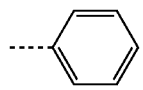 | 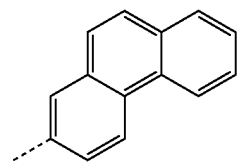 | 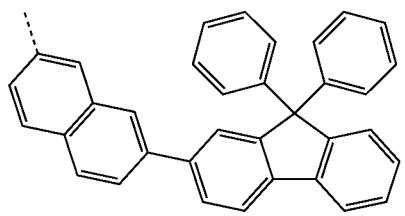 |
| 2-342 | 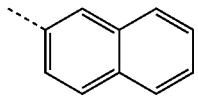 | 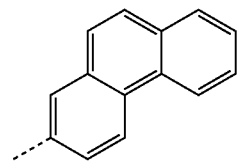 | 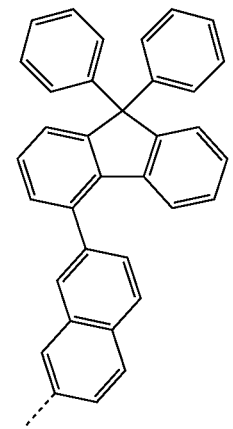 |

-continued
| Formula | - - -Ar1 | - - -Ar2 | - - -Ar3 |
|---|---|---|---|
| 2-343 | 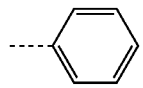 | 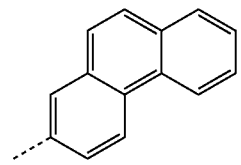 | 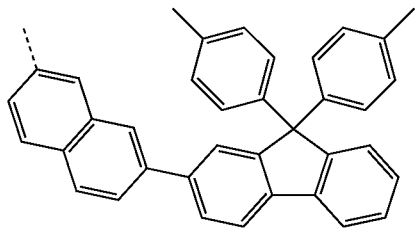 |
| 2-344 | 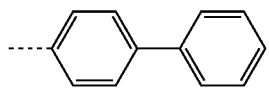 | 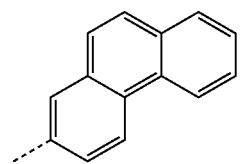 | 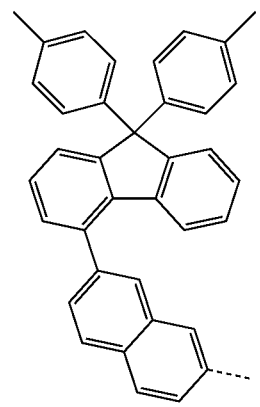 |
| 2-345 | 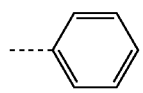 | 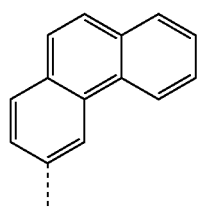 | 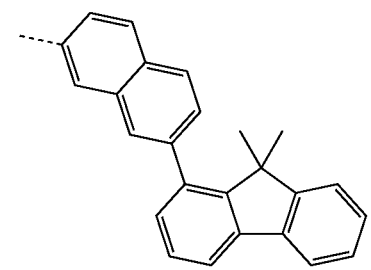 |
| 2-346 | 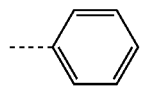 | 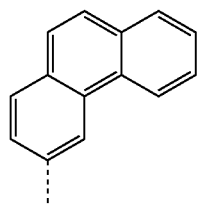 | 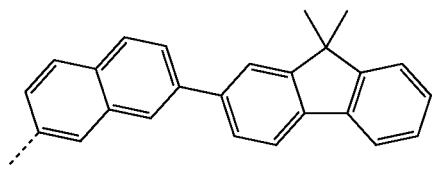 |
| 2-347 | 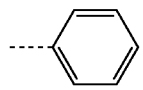 | 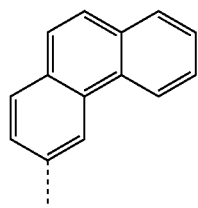 | 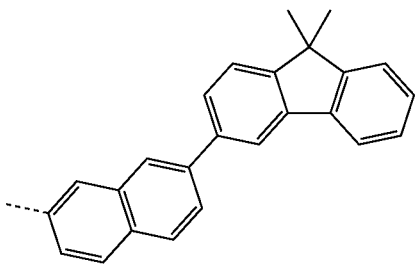 |

| For-mula | - - -Ar1 | - - -Ar2 | - - -Ar3 |
|---|---|---|---|
| 2-348 | 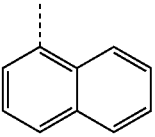 | 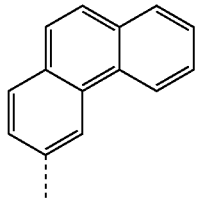 | 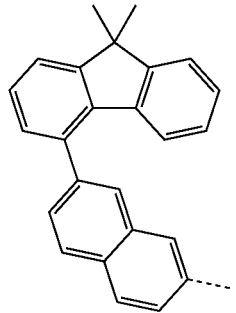 |
| 2-349 | 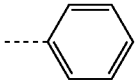 | 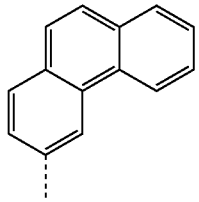 | 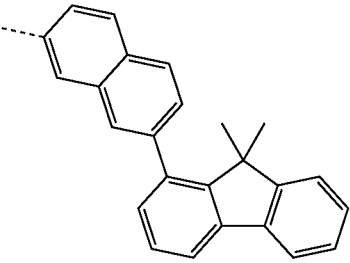 |
| 2-350 | 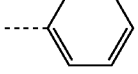 | 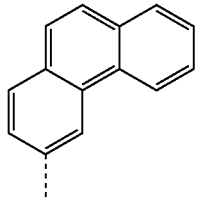 | 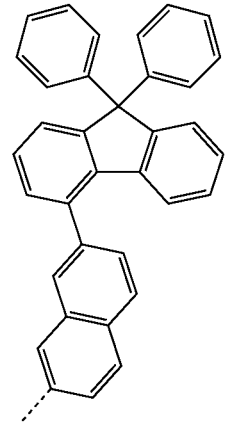 |
| 2-351 | 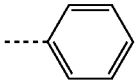 | 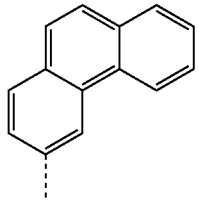 | 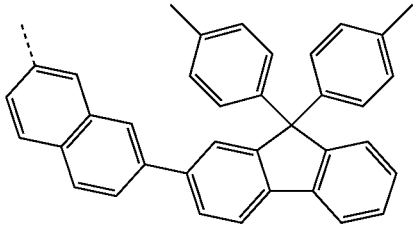 |
| 2-352 | 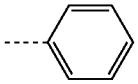 | 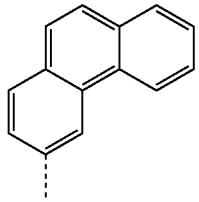 | 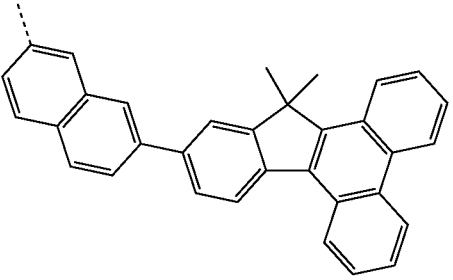 |

-continued
| Formula | - - -Ar1 | - - -Ar2 | - - -Ar3 |
|---|---|---|---|
| 2-353 | 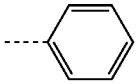 | 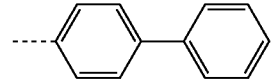 | 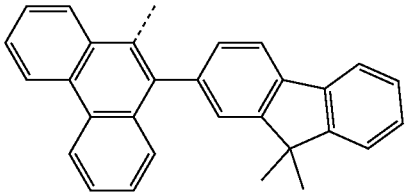 |
| 2-354 | 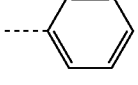 | 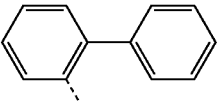 | 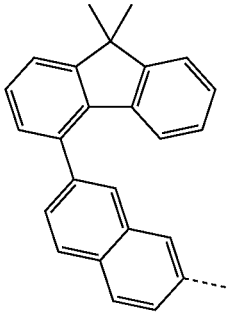 |
| 2-355 | 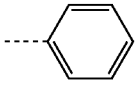 | 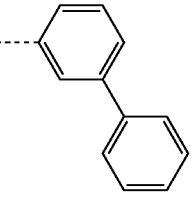 | 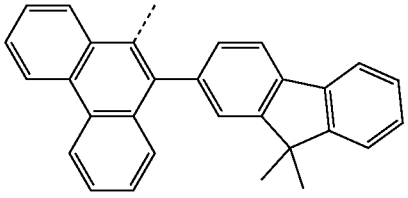 |
| 2-356 | 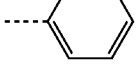 | 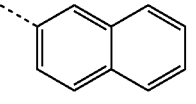 | 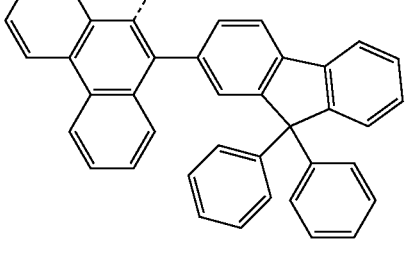 |
| 2-357 | 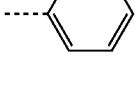 | 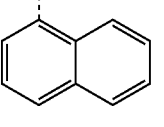 | 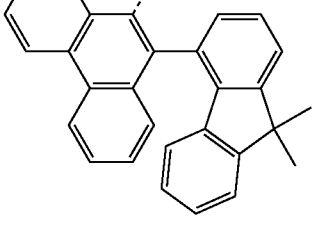 |
| 2-358 | 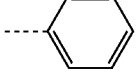 | 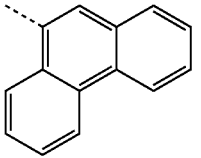 | 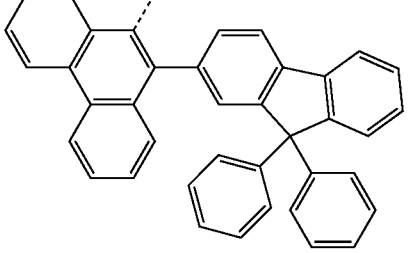 |

| Formula | ---Ar1 | ---Ar2 | ---Ar3 |
|---|---|---|---|
| 2-359 | | | |
| 2-360 | | | |
| 2-361 | | | |
| 2-362 | | | |
| 2-363 | | | |

In an exemplary embodiment of the present specification, the second electron transporting layer includes one or two or more of the compounds represented by Formulae 3 to 6.

In an exemplary embodiment of the present specification, the second electron transporting layer includes the compound represented by Formula 3.

In an exemplary embodiment of the present specification, the second electron transporting layer includes the compound represented by Formula 4.

In an exemplary embodiment of the present specification, the second electron transporting layer includes the compound represented by Formula 5.

Specifically, when the second electron transporting layer includes an imidazole derivative, a pyridine derivative, and a condensed ring derivative of imidazole, an unshared electron pair of a nitrogen atom or an oxygen atom of a phosphine oxide group is effectively bonded to metal, and thus, doping with an n-type dopant may effectively occur. Accordingly, the transport and/or injection of electrons from the cathode is facilitated, and an organic light emitting diode having low driving voltage may be provided.

Further, when the organic light emitting diode is driven, an unshared electron pair of a nitrogen atom or an oxygen atom of a phosphine oxide group may be bonded to metal to prevent metal from moving by a field applied to the organic material layer, thereby suppressing the driving voltage of the organic light emitting diode from being increased, and it is possible to implement an organic light emitting diode having a long service life.

In an exemplary embodiment of the present specification, the second electron transporting layer includes the compound represented by Formula 3.

In an exemplary embodiment of the present specification, A is any one of the following structures which are substituted or unsubstituted.

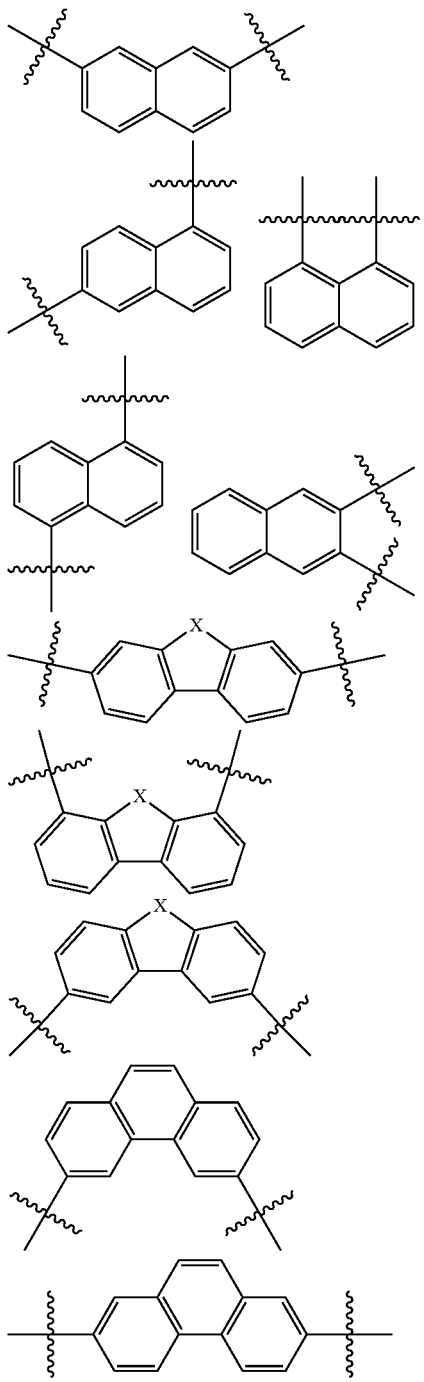

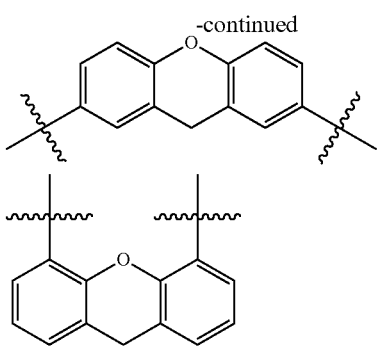

In an exemplary embodiment of the present specification, A is unsubstituted or substituted with a substituent selected from the group consisting of a halogen group; a substituted or unsubstituted alkyl group; and a substituted or unsubstituted aryl group.

In an exemplary embodiment of the present specification, A is unsubstituted or substituted with a substituent selected from the group consisting of fluorine; a methyl group; a phenyl group substituted with an alkyl group; and a phenyl group.

In an exemplary embodiment of the present specification, A is a 2,7-naphthalene group; a 2,7-fluorenylene group; 2,7-dibenzofuranylene; or a 1,6-naphthalene group.

In an exemplary embodiment of the present specification, L2 and L3 are the same as or different from each other, and each independently a direct bond; a substituted or unsubstituted arylene group; or a substituted or unsubstituted divalent hetero ring.

In an exemplary embodiment of the present specification, L2 and L3 are a direct bond; an arylene group; or a divalent heterocyclic group, and the arylene group and the divalent hetero ring are unsubstituted or substituted with an aryl group.

In an exemplary embodiment of the present specification, L2 and L3 are the same as or different from each other, and each independently a direct bond; a substituted or unsubstituted phenylene group; a substituted or unsubstituted naphthalene group; a substituted or unsubstituted biphenylylene group; a substituted or unsubstituted pyridylene group; or a substituted or unsubstituted thiophenylene group.

In an exemplary embodiment of the present specification, L2 and L3 are the same as or different from each other, and each independently a direct bond; a phenylene group; a phenylene group substituted with a phenyl group; a naphthalene group; a biphenylylene group; a pyridylene group; or a thiophenylene group.

In one exemplary embodiment of the present specification, L2 is a phenylene group.

In another exemplary embodiment, L3 is a phenylene group.

In an exemplary embodiment of the present specification, A1 and A2 are the same as or different from each other, and each independently a substituted or unsubstituted alkyl group; or a substituted or unsubstituted aryl group.

In another exemplary embodiment, A1 and A2 are the same as or different from each other, and each independently a methyl group; an ethyl group; an isopropyl group; a t-butyl group; a phenyl group; a naphthyl group; a fluorenyl group substituted with an alkyl group; or a pyridine group.

In an exemplary embodiment of the present specification, A1 and A2 are the same as or different from each other, and each a substituted or unsubstituted alkyl group.

In another exemplary embodiment, A1 and A2 are a substituted or unsubstituted alkyl group having 1 to 10 carbon atoms.

In one exemplary embodiment, A1 and A2 are a methyl group.

In an exemplary embodiment of the present specification, A1 and A2 are the same as or different from each other, and each independently a substituted or unsubstituted aryl group.

In another exemplary embodiment, A1 and A2 are each independently a substituted or unsubstituted aryl group having 6 to 20 carbon atoms.

In an exemplary embodiment of the present specification, A1 and A2 are a naphthyl group.

In an exemplary embodiment of the present specification, T1 to T8 are the same as or different from each other, and each independently hydrogen; a substituted or unsubstituted aryl group; or a substituted or unsubstituted heterocyclic group.

In an exemplary embodiment of the present specification, T1 to T8 are the same as or different from each other, and each independently hydrogen; a substituted or unsubstituted phenyl group; a substituted or unsubstituted naphthyl group; or a substituted or unsubstituted pyridine group.

In an exemplary embodiment of the present specification, T1 to T8 are the same as or different from each other, and each independently hydrogen; a phenyl group; a naphthyl group; or a pyridine group.

In an exemplary embodiment of the present specification, T1 is hydrogen.

In another exemplary embodiment, T2 is hydrogen.

In an exemplary embodiment of the present specification, T3 is a substituted or unsubstituted aryl group.

In another exemplary embodiment, T3 is a substituted or unsubstituted phenyl group.

In still another exemplary embodiment, T3 is a phenyl group.

In yet another exemplary embodiment, T3 is a substituted or unsubstituted naphthyl group.

In still yet another exemplary embodiment, T3 is a naphthyl group.

In an exemplary embodiment of the present specification, T3 is a substituted or unsubstituted heterocyclic group.

In another exemplary embodiment, T3 is a heterocyclic group including nitrogen.

In still another exemplary embodiment, T3 is a monocyclic heterocyclic group including nitrogen.

In an exemplary embodiment of the present specification, T3 is a pyridine group.

In an exemplary embodiment of the present specification, T4 is hydrogen.

In another exemplary embodiment, T5 is hydrogen.

In an exemplary embodiment of the present specification, T6 is a substituted or unsubstituted aryl group.

In another exemplary embodiment, T6 is a substituted or unsubstituted phenyl group.

In still another exemplary embodiment, T6 is a phenyl group.

In yet another exemplary embodiment, T6 is a substituted or unsubstituted naphthyl group.

In still yet another exemplary embodiment, T6 is a naphthyl group.

In an exemplary embodiment of the present specification, T6 is a substituted or unsubstituted heterocyclic group.

In another exemplary embodiment, T6 is a heterocyclic group including nitrogen.

In still another exemplary embodiment, T6 is a monocyclic heterocyclic group including nitrogen.

In an exemplary embodiment of the present specification, T6 is a pyridine group.

In an exemplary embodiment of the present specification, T7 is hydrogen.

In another exemplary embodiment, T8 is hydrogen.

In an exemplary embodiment of the present specification, T1 and T2 combine with each other to form a hydrocarbon ring.

In another exemplary embodiment, T1 and T2 combine with each other to form a benzene ring.

In an exemplary embodiment of the present specification, T3 and T4 combine with each other to form a hydrocarbon ring.

In another exemplary embodiment, T3 and T4 combine with each other to form a benzene ring.

In an exemplary embodiment of the present specification, T5 and T6 combine with each other to form a hydrocarbon ring.

In one exemplary embodiment, T5 and T6 combine with each other to form a benzene ring.

In an exemplary embodiment of the present specification, T7 and T8 combine with each other to form a hydrocarbon ring.

In another exemplary embodiment, T7 and T8 combine with each other to form a benzene ring.

In still another exemplary embodiment, the compound represented by Formula 3 is represented by any one of the following Formulae 3-1 to 3-101.

In an exemplary embodiment of the present specification, the second electron transporting layer includes the compound of Formula 4.

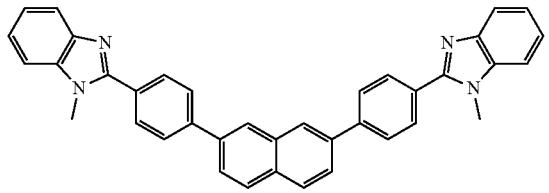

Formula 3-1

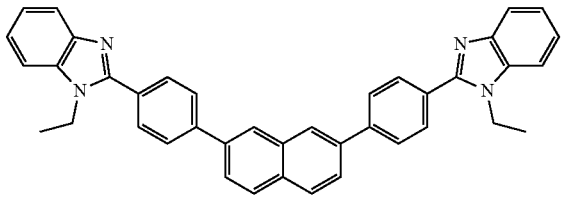

Formula 3-2

-continued
Formula 3-3
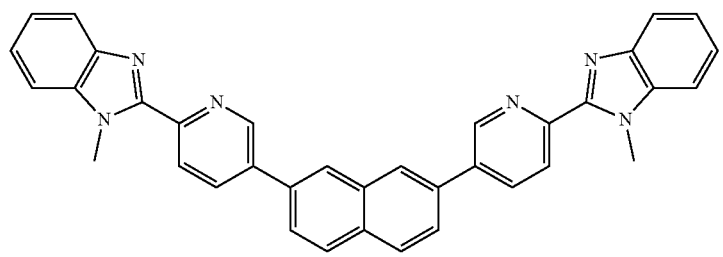
Formula 3-4
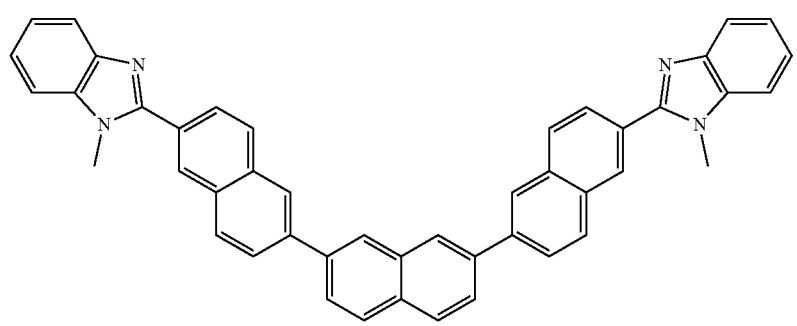
Formula 3-5
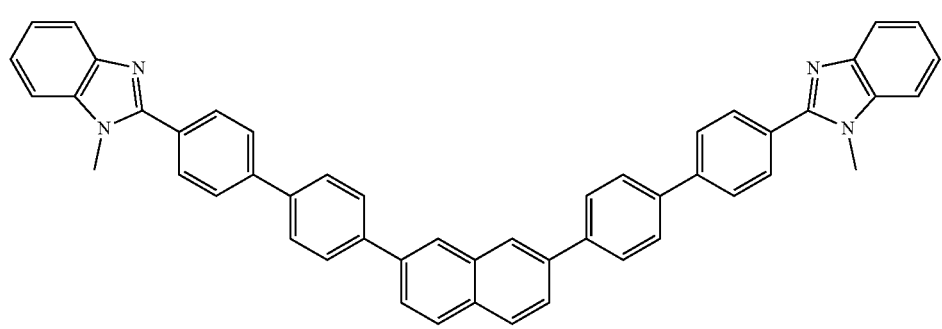
Formula 3-6
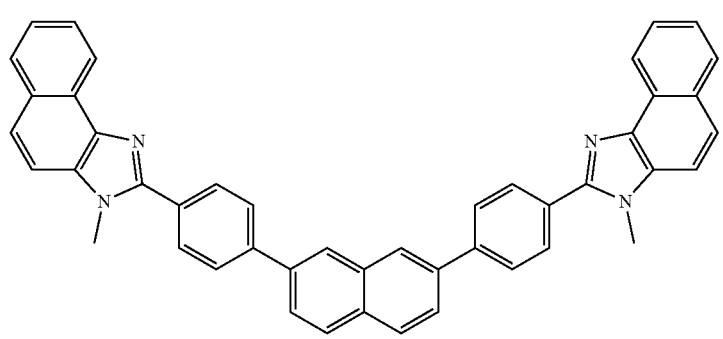
Formula 3-7
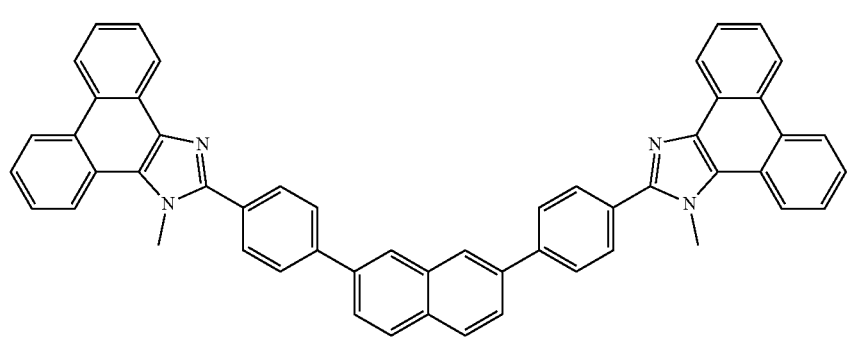

-continued
Formula 3-8
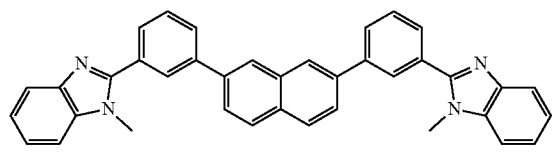
Formula 3-9
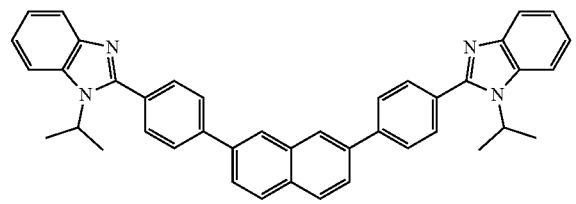
Formula 3-10
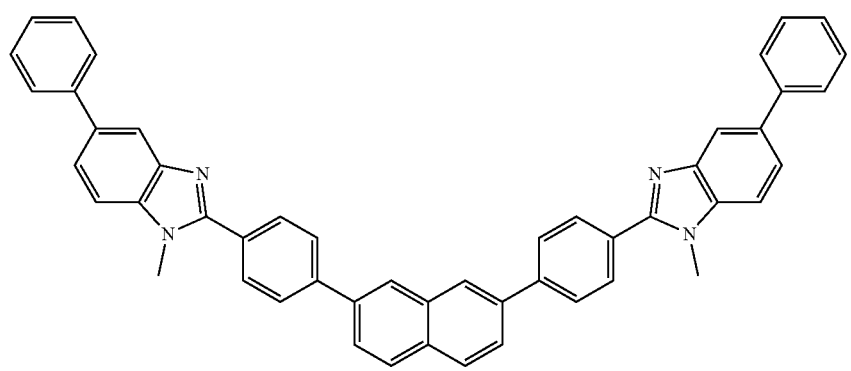
Formula 3-11
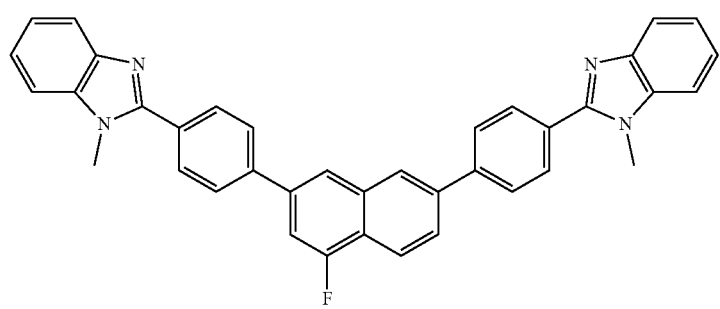
Formula 3-12
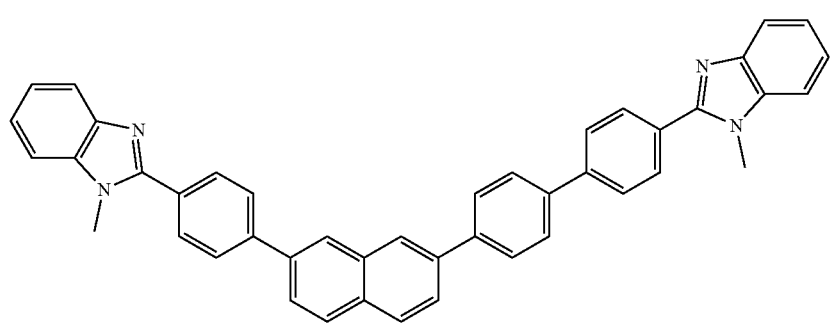
Formula 3-13
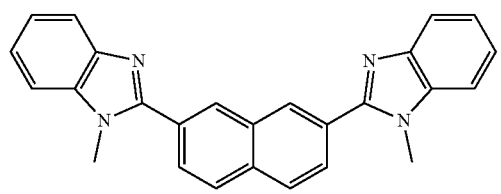
Formula 3-14
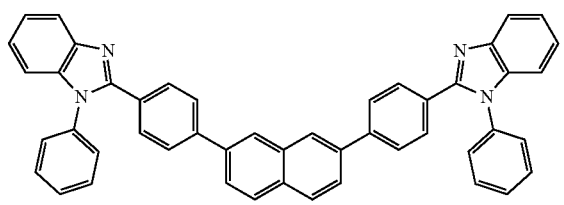

-continued
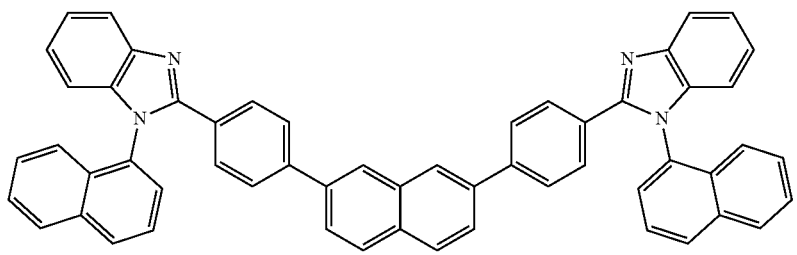
Formula 3-15
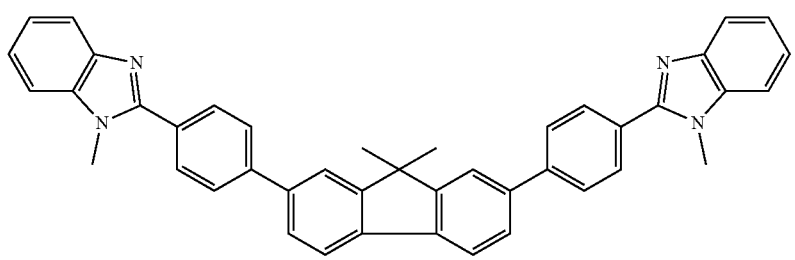
Formula 3-16
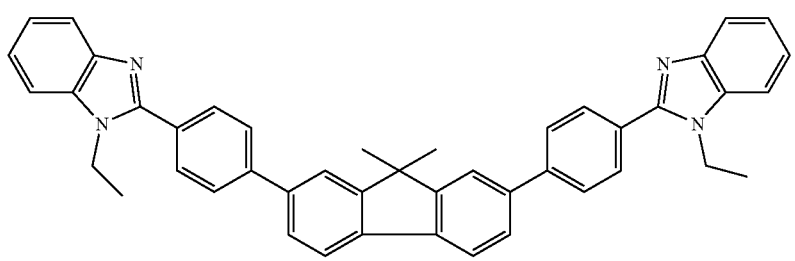
Formula 3-17
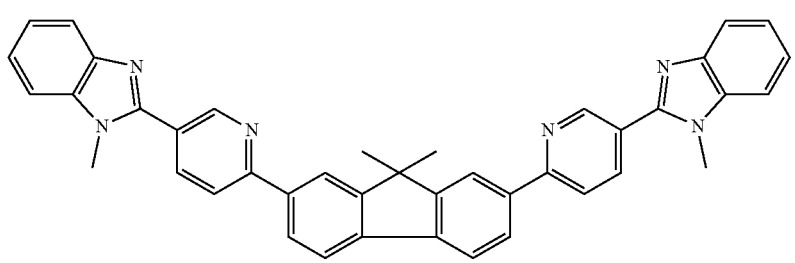
Formula 3-18
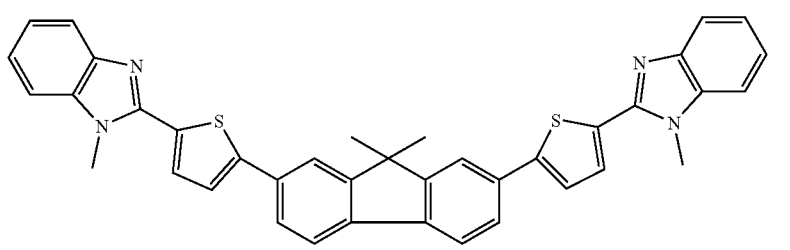
Formula 3-19
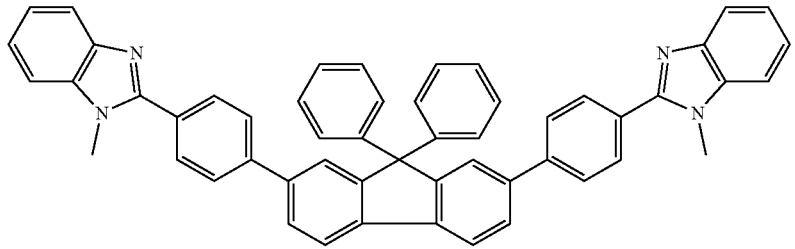
Formula 3-20

-continued
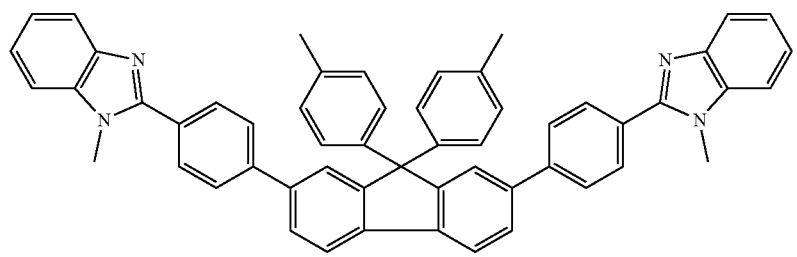
Formula 3-21
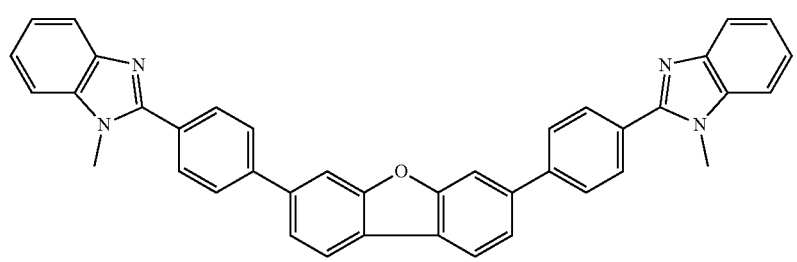
Formula 3-22
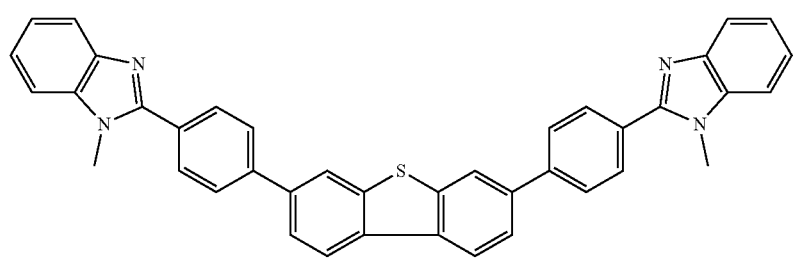
Formula 3-23
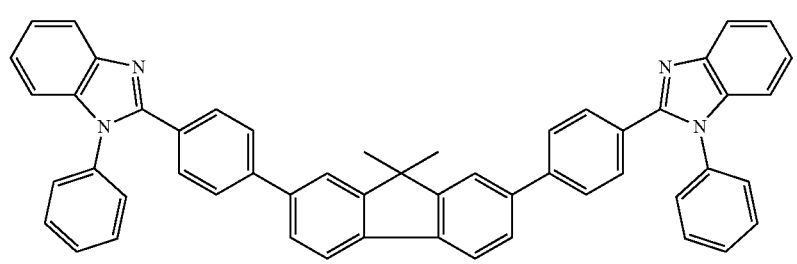
Formula 3-24
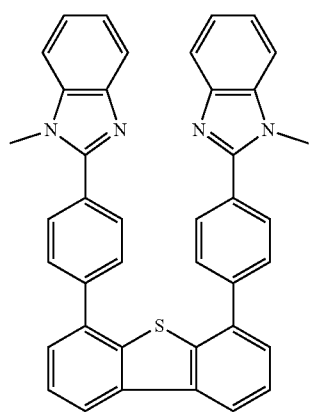
Formula 3-25
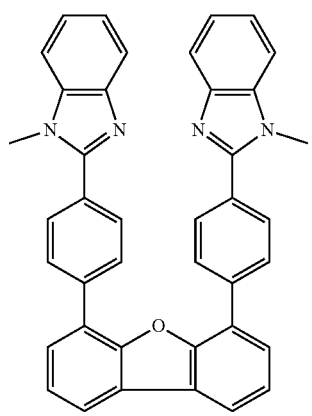
Formula 3-26

-continued
Formula 3-27
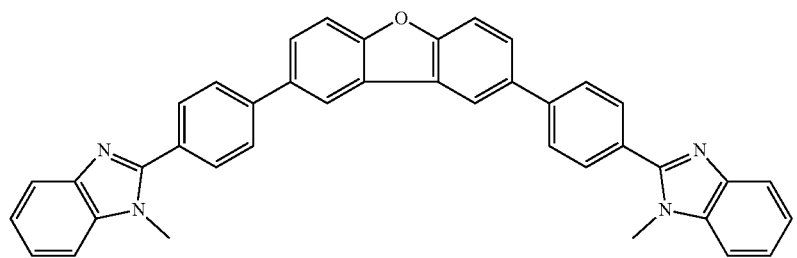
Formula 3-28
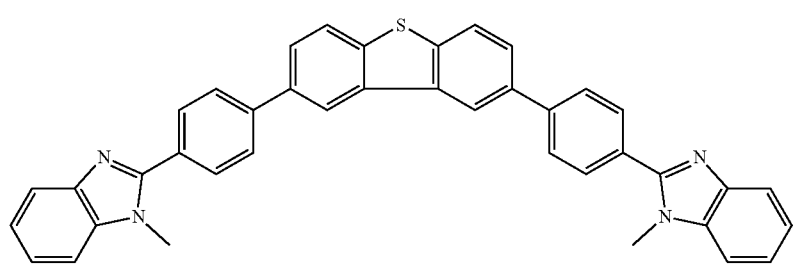
Formula 3-29
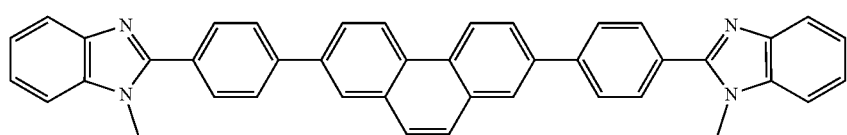
Formula 3-30
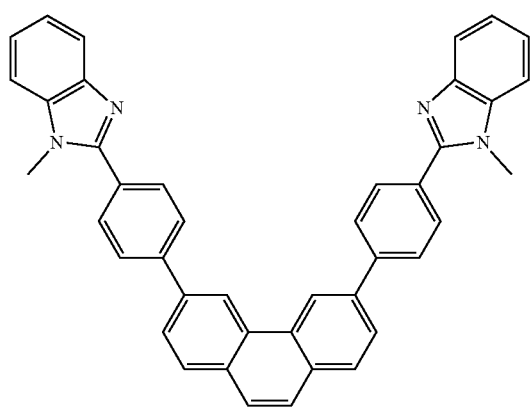
Formula 3-31
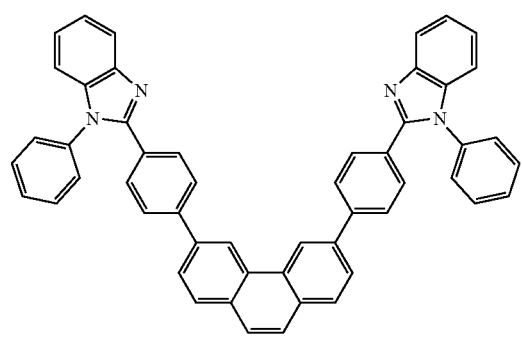

-continued
Formula 3-32
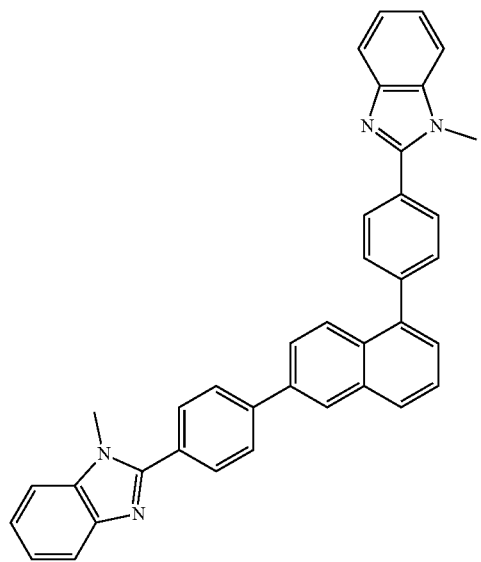
Formula 3-33
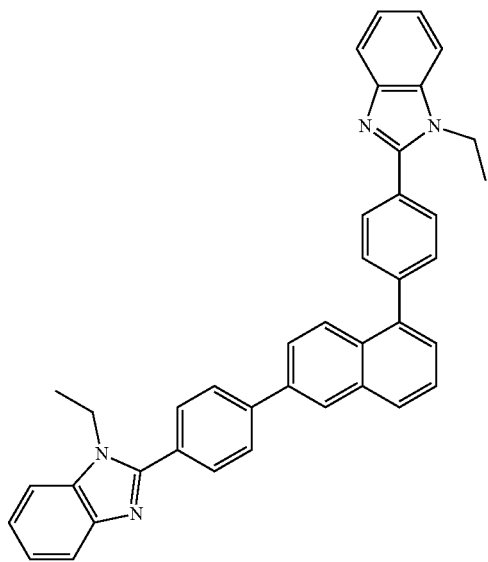
Formula 3-34
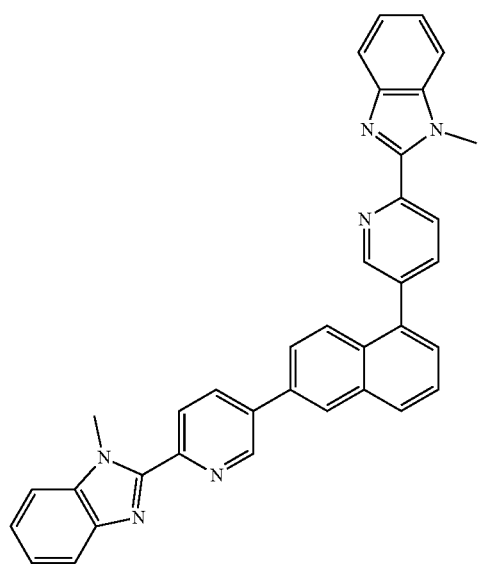
Formula 3-35
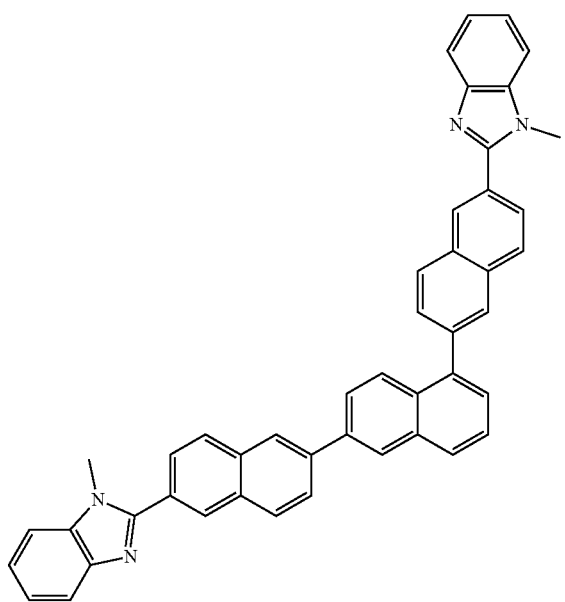

-continued
Formula 3-36
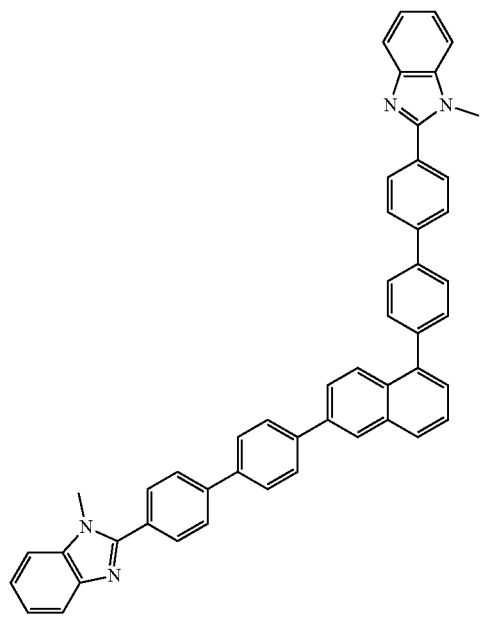
Formula 3-37
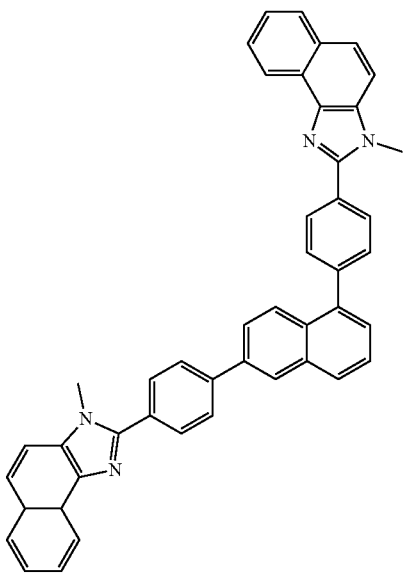
Formula 3-38
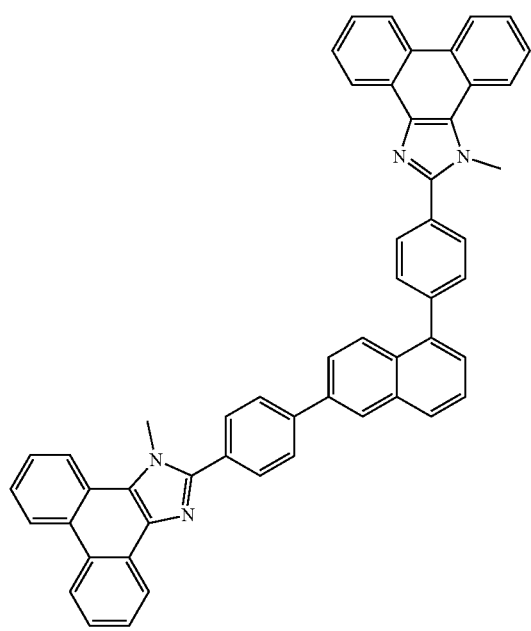
Formula 3-39
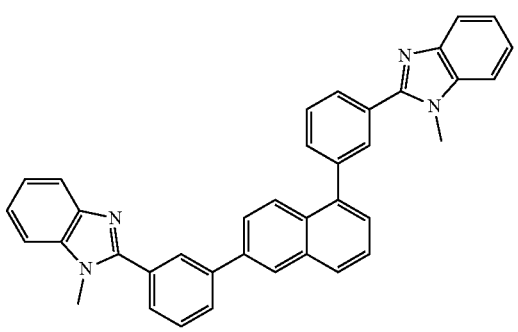

-continued
Formula 3-40
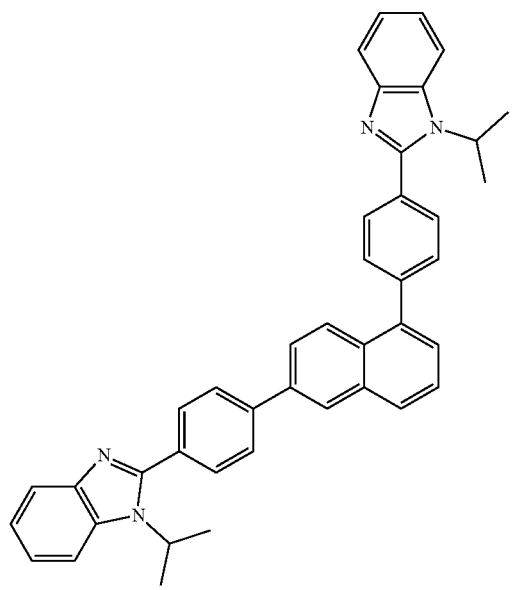
Formula 3-41
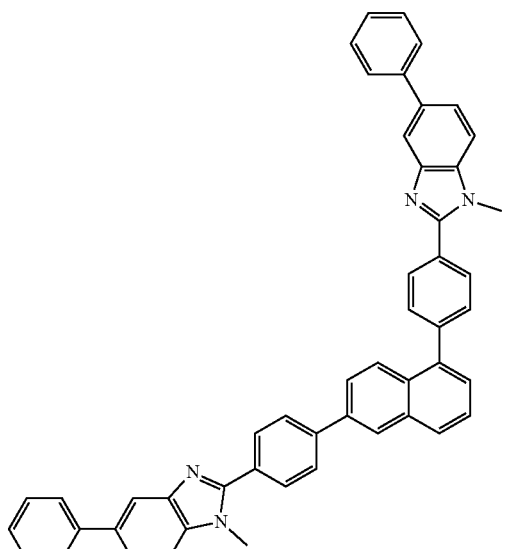
Formula 3-42
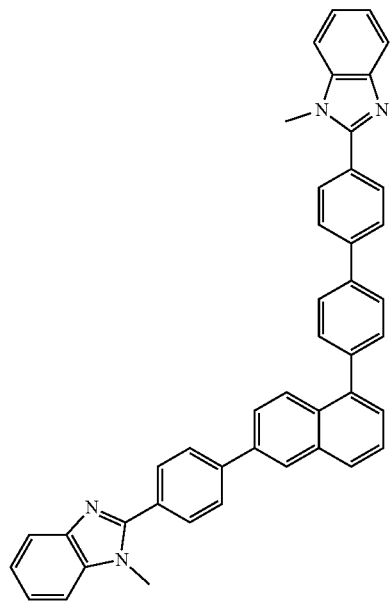
Formula 3-43
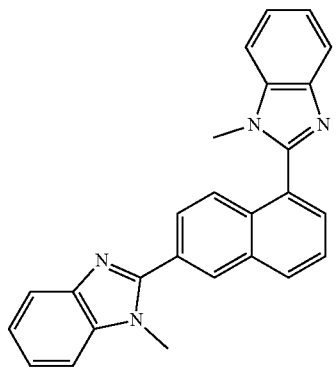

Formula 3-44
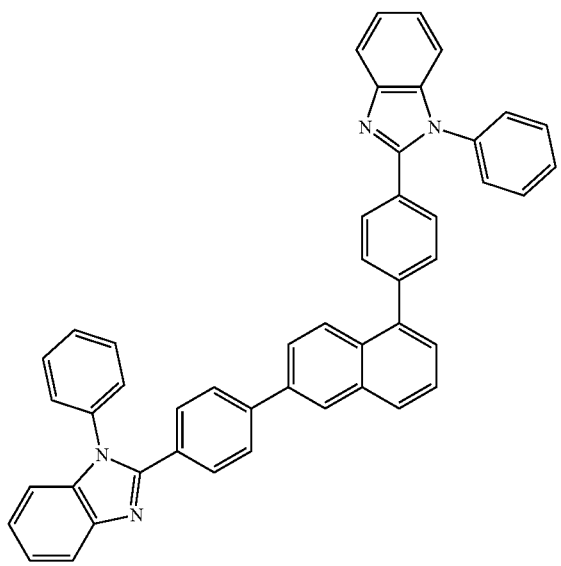
Formula 3-45
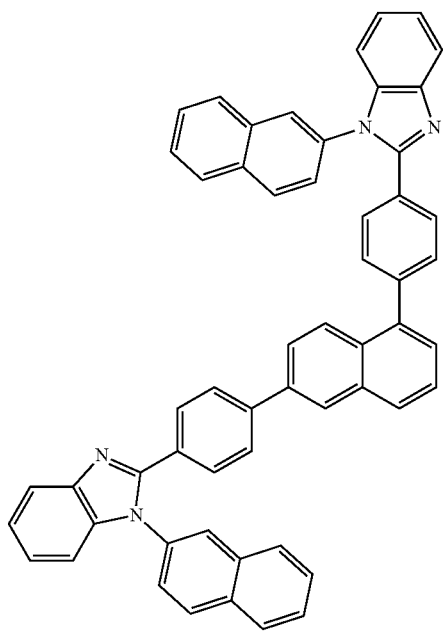
Formula 3-46
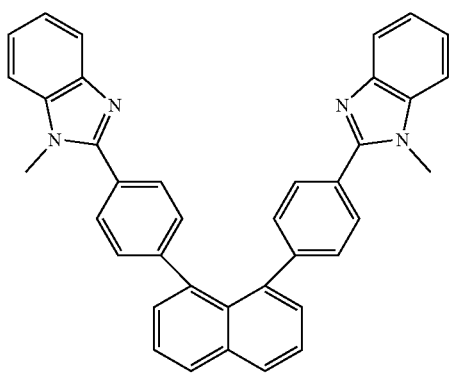
Formula 3-47
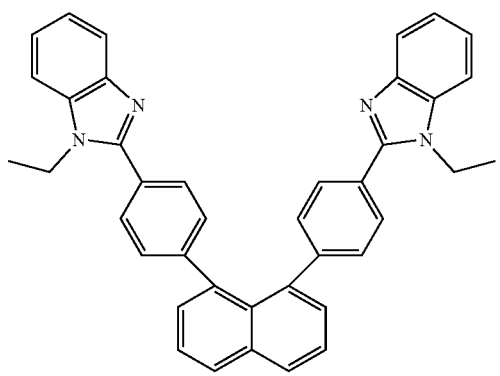
Formula 3-48
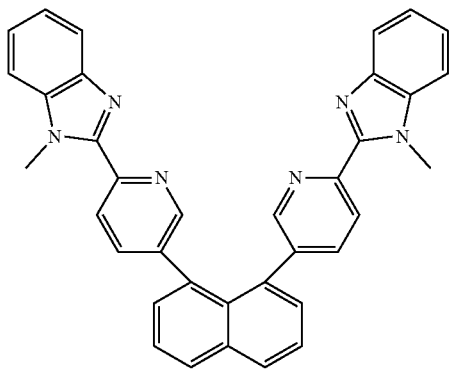
Formula 3-49
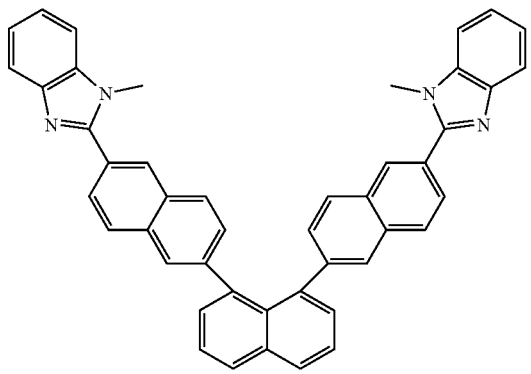

-continued
Formula 3-50
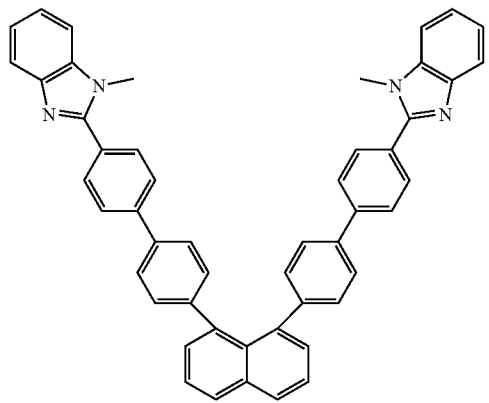
Formula 3-51
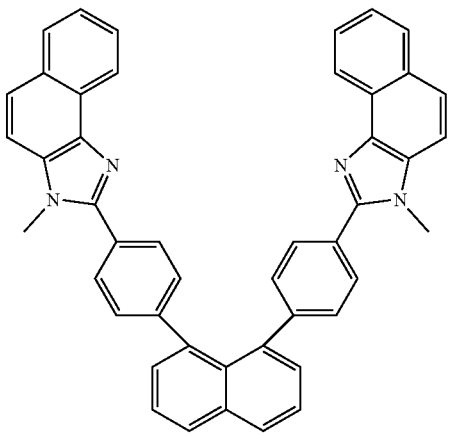
Formula 3-52
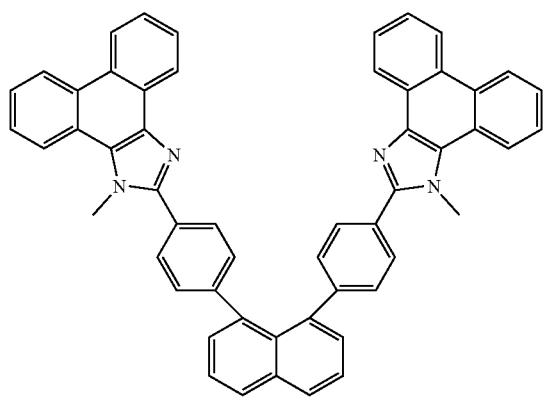
Formula 3-53
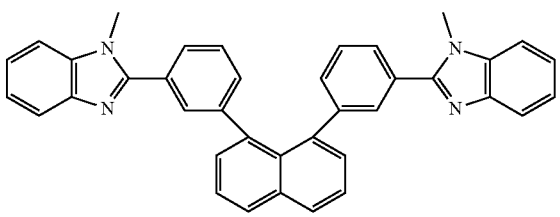
Formula 3-54
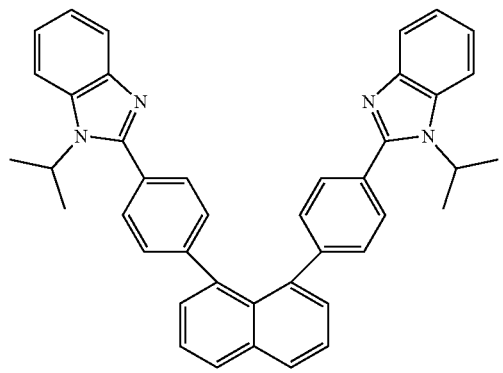
Formula 3-55
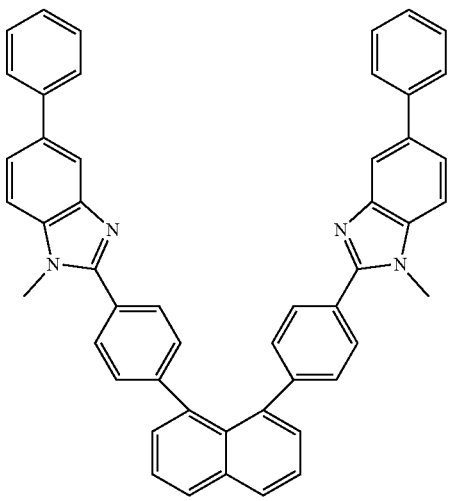

Formula 3-56
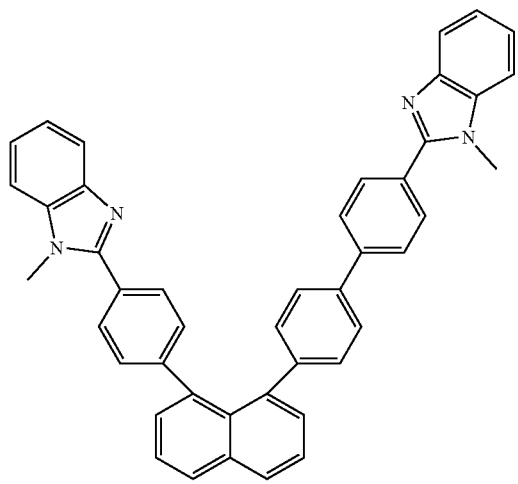
Formula 3-57
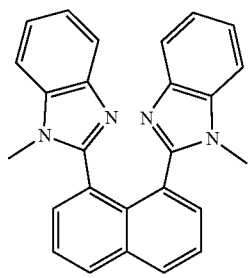
Formula 3-58
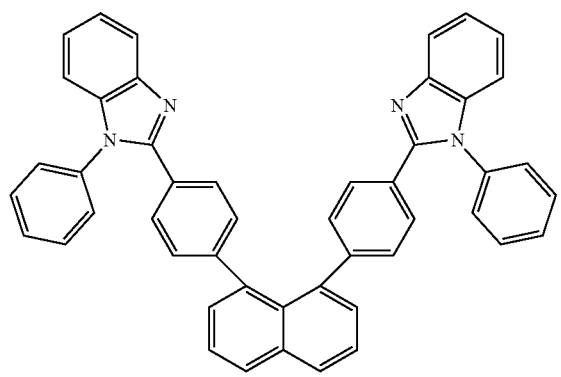
Formula 3-59
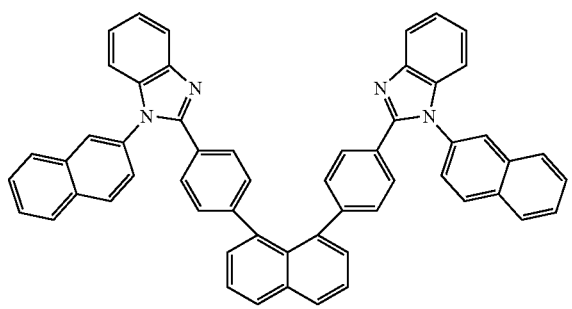
Formula 3-60
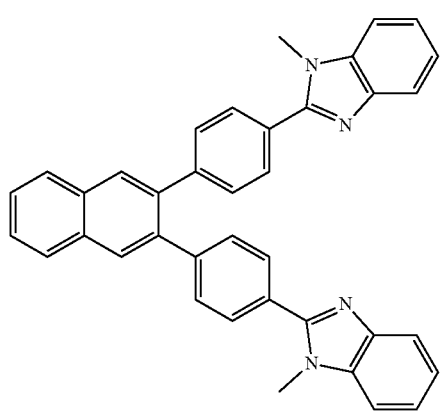
Formula 3-61
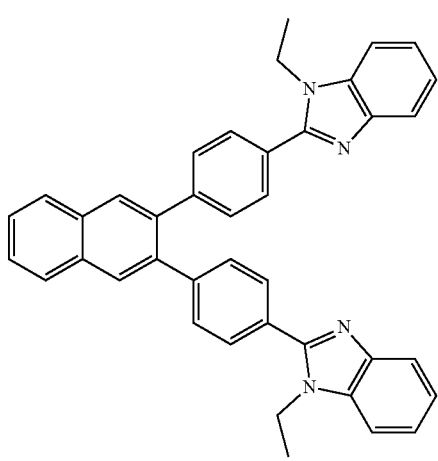

-continued
Formula 3-62
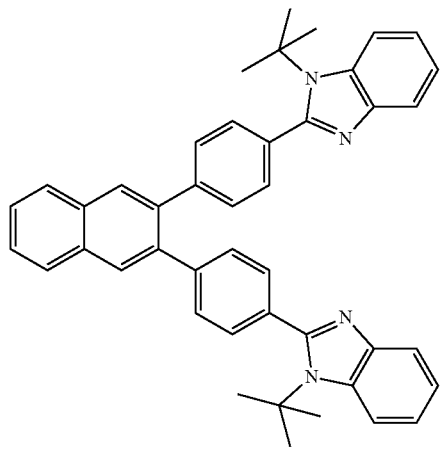
Formula 3-63
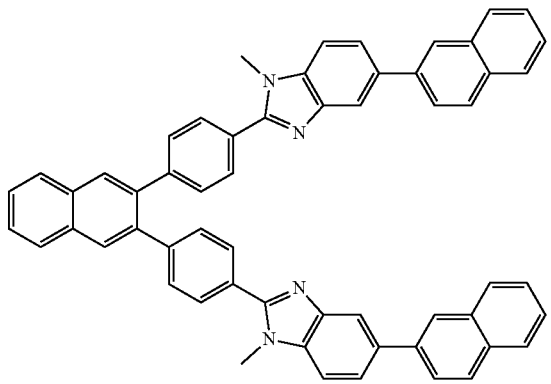
Formula 3-64
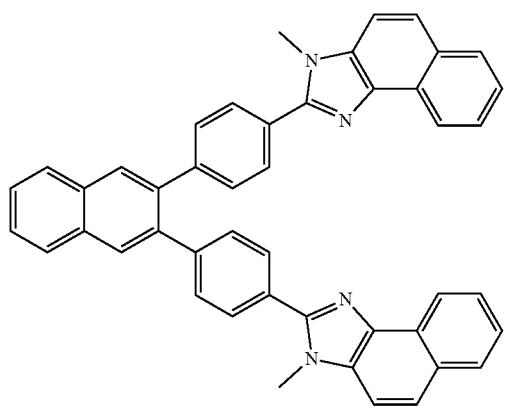
Formula 3-65
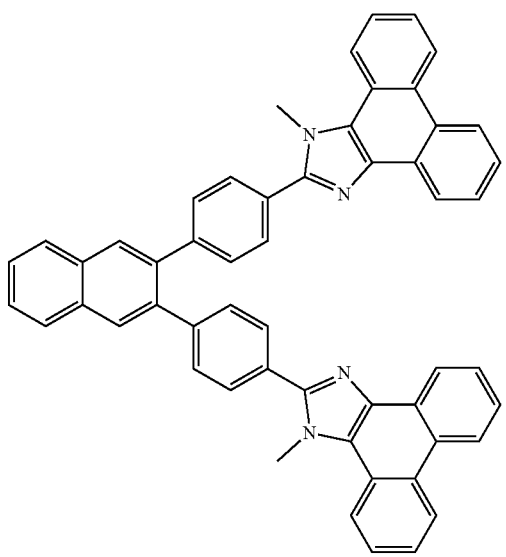
Formula 3-66
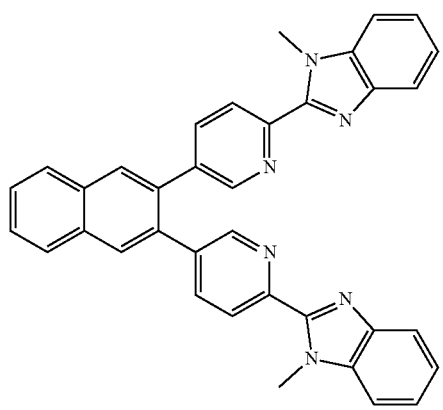
Formula 3-67
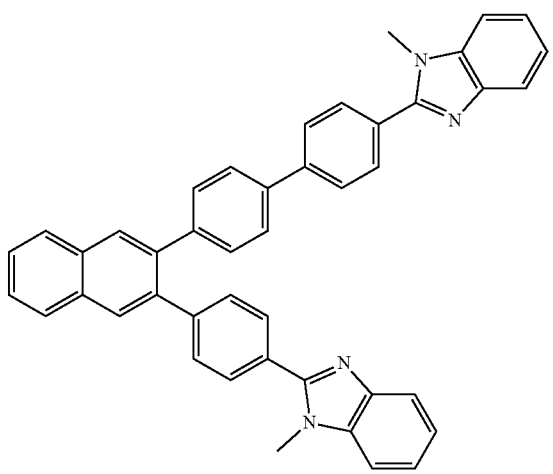

-continued
Formula 3-68
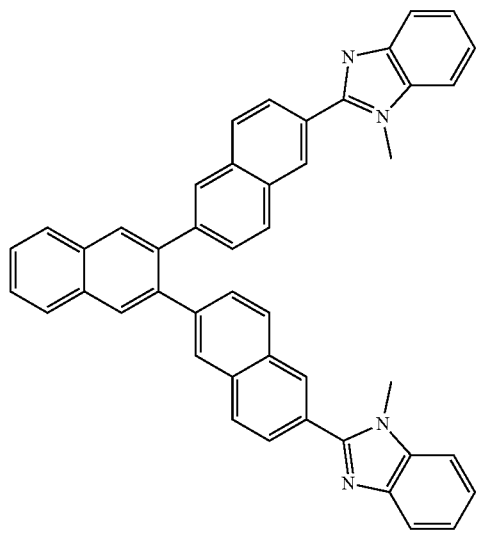
Formula 3-69
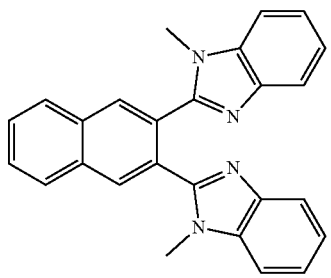
Formula 3-70
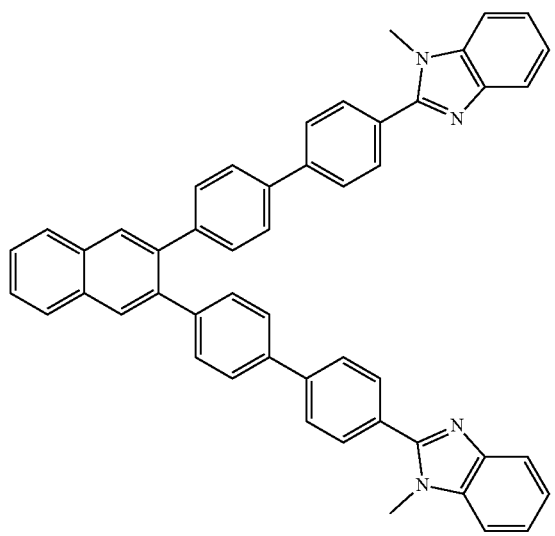
Formula 3-71
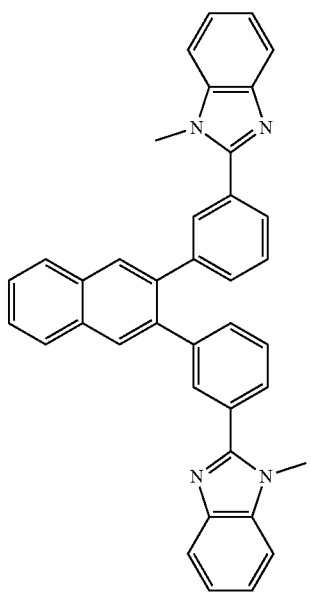
Formula 3-72
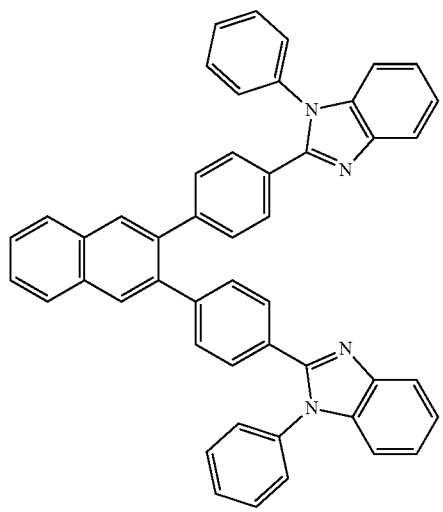
Formula 3-73
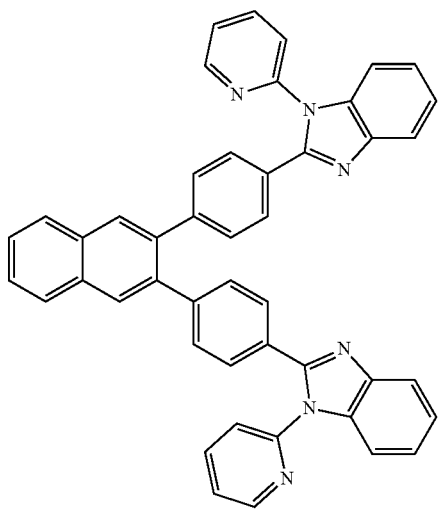

-continued
Formula 3-74
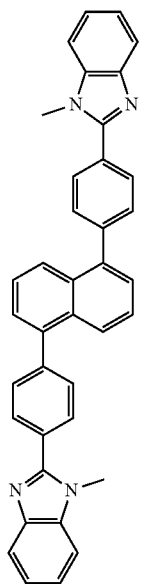
Formula 3-75
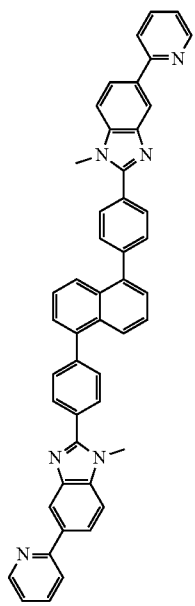
Formula 3-76
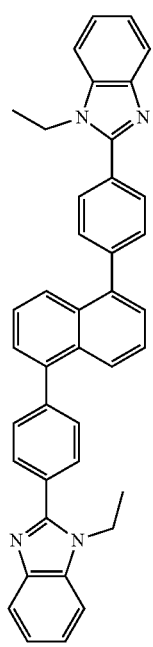
Formula 3-77
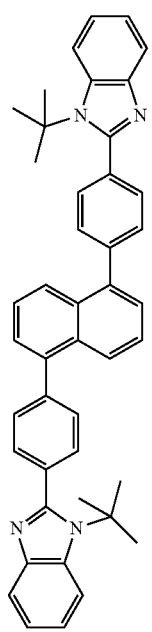

-continued
Formula 3-78
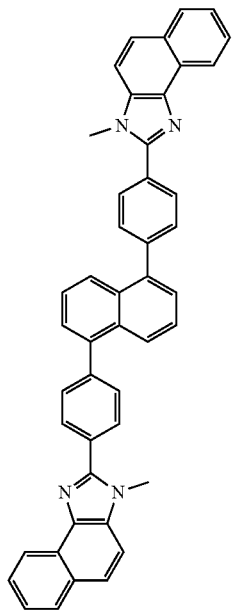
Formula 3-79
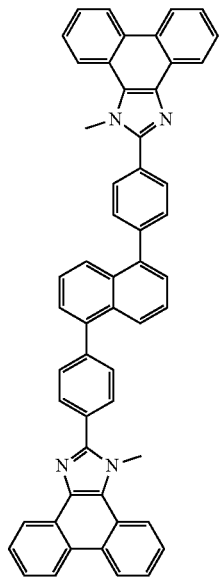
Formula 3-80
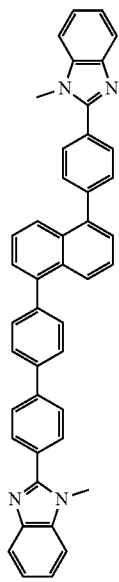
Formula 3-81
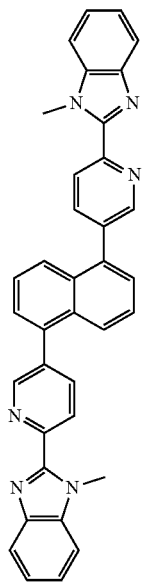

Formula 3-82
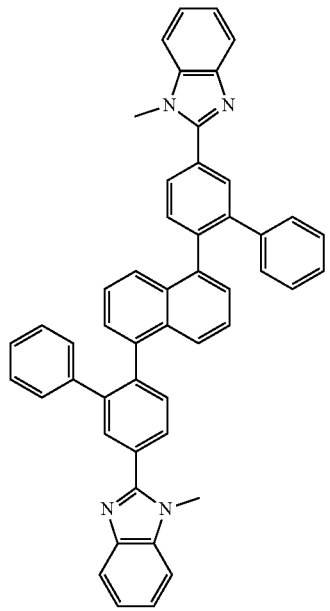
Formula 3-83
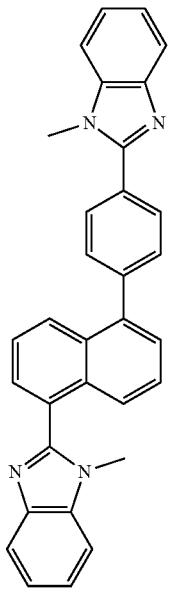
Formula 3-84
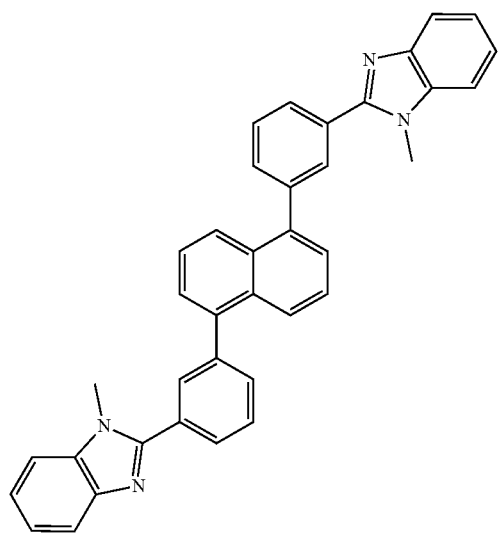
Formula 3-85
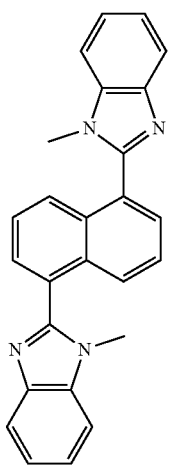

-continued
Formula 3-86
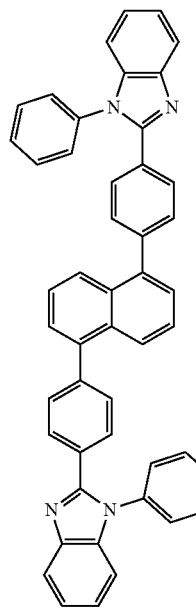
Formula 3-87
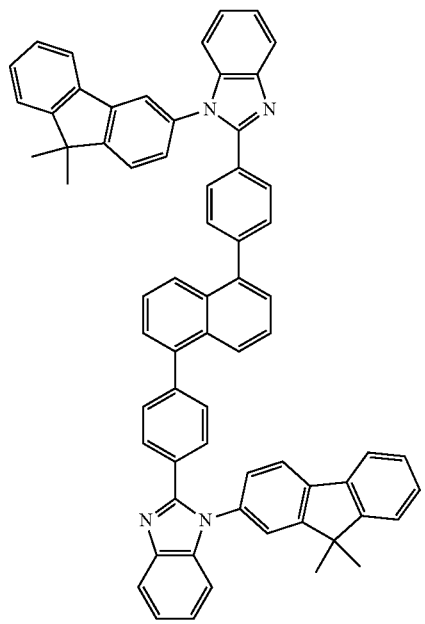
Formula 3-88
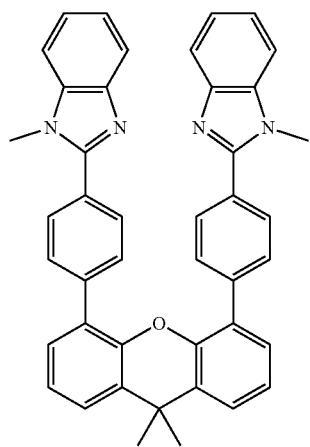
Formula 3-89
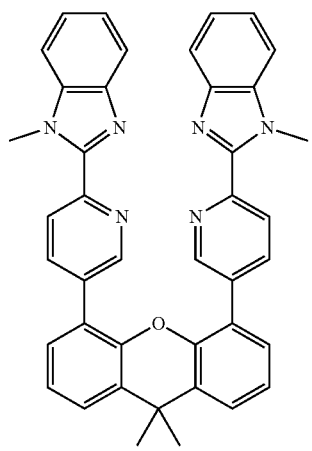
Formula 3-90
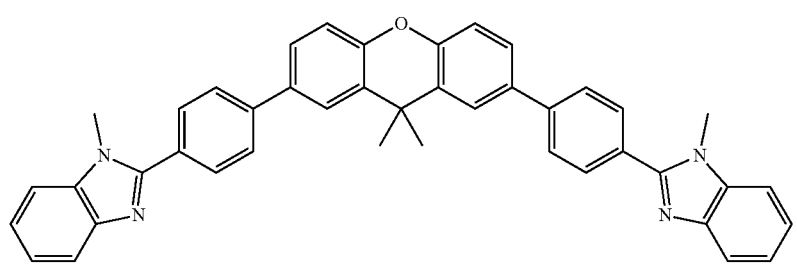
Formula 3-91
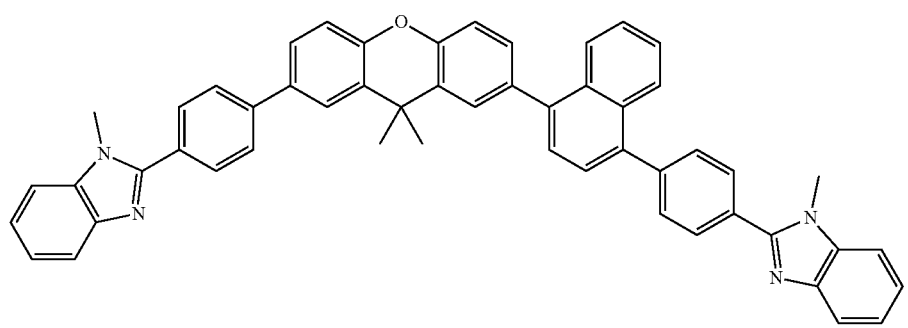

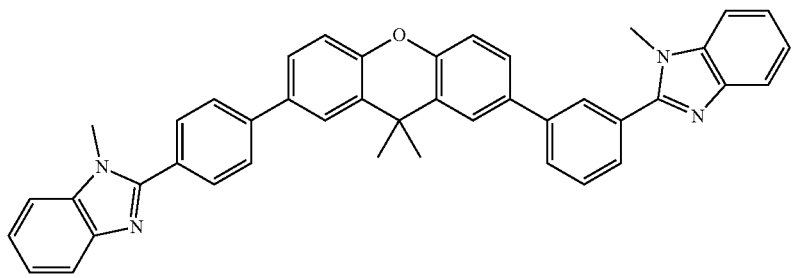
Formula 3-92
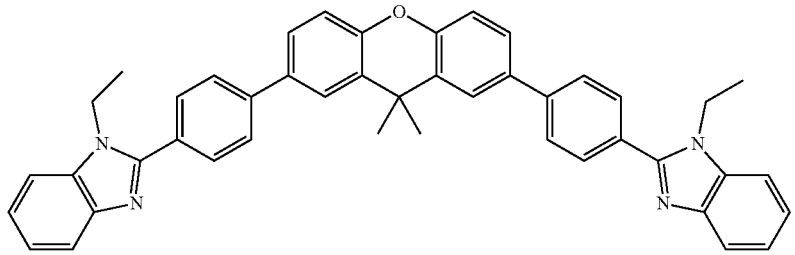
Formula 3-93
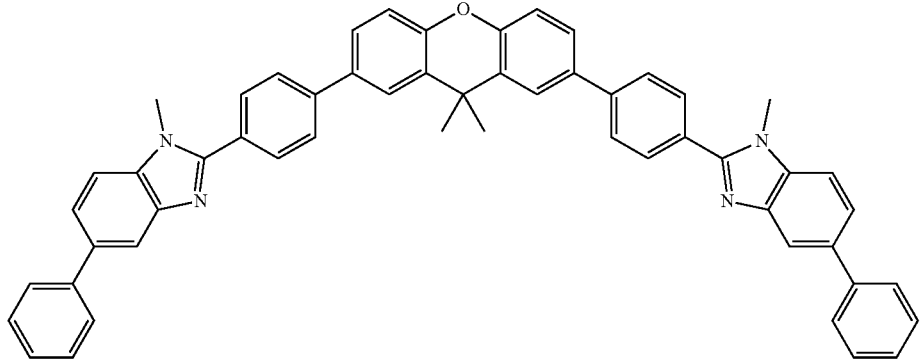
Formula 3-94
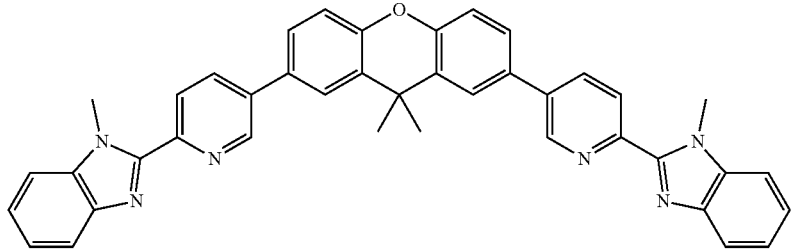
Formula 3-95
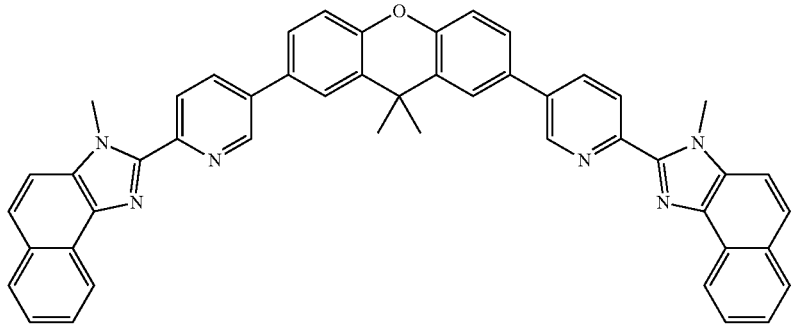
Formula 3-96

-continued
Formula 3-97
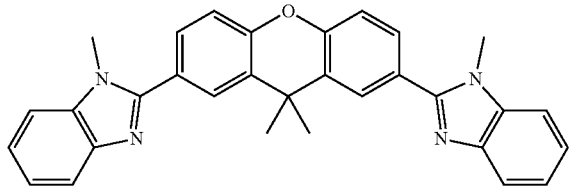
Formula 3-98
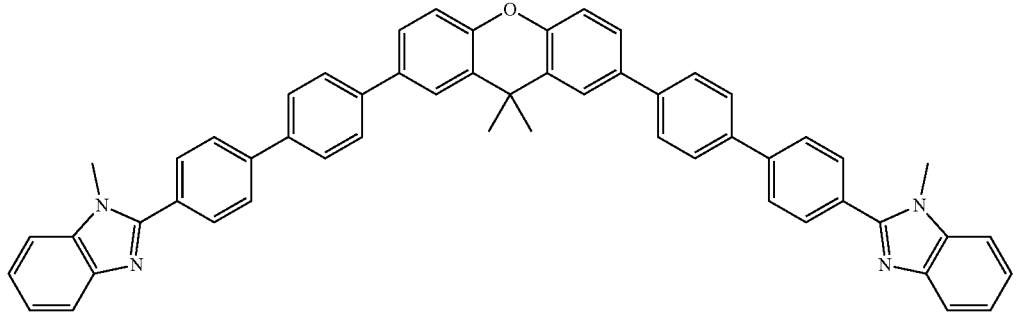
Formula 3-99
Formula 3-100
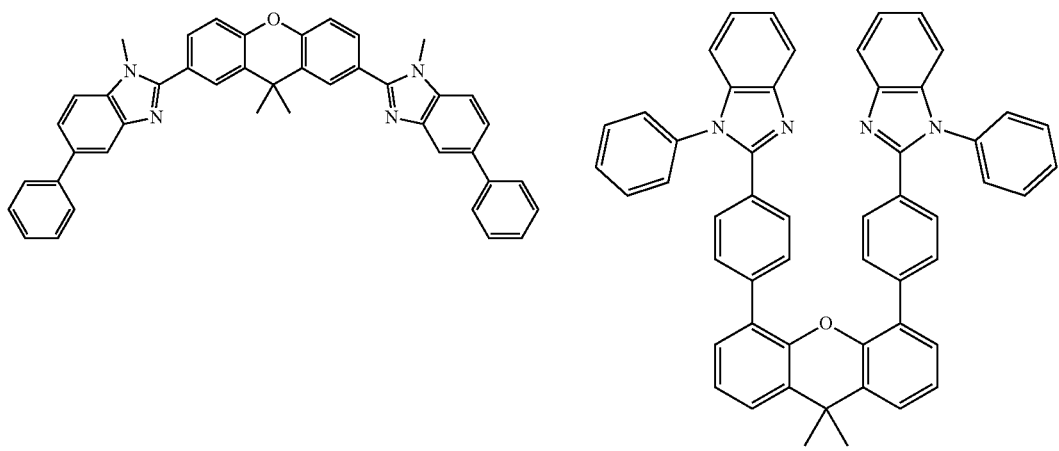
Formula 3-101
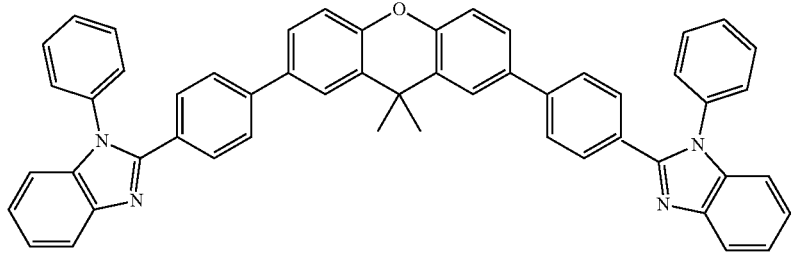
In an exemplary embodiment of the present specification, T9 is hydrogen.
In another exemplary embodiment, T9 is
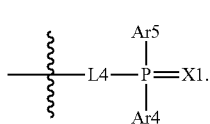
In an exemplary embodiment of the present specification, T10 is hydrogen.
In another exemplary embodiment, T10 is
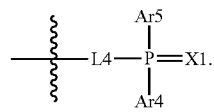
In an exemplary embodiment of the present specification, at least one of T9 and T10 is

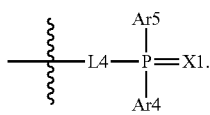

In another exemplary embodiment, one of T9 and T10 is

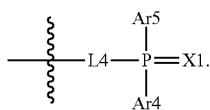

In still another exemplary embodiment, two of T9 and T10 are

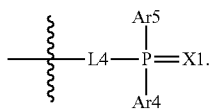

In an exemplary embodiment of the present specification, T9 and T10 combine with an adjacent group to form a substituted or unsubstituted hydrocarbon ring.

In another exemplary embodiment, T9 and T10 combine with an adjacent group to form a substituted or unsubstituted benzene ring.

In still another exemplary embodiment, T9 and T10 combine with an adjacent group to form a benzene ring.

In an exemplary embodiment of the present specification, T10 combine with an adjacent group to form a benzene ring.

In an exemplary embodiment of the present specification, Ar4 and Ar5 are the same as or different from each other, and each independently a substituted or unsubstituted aryl group.

In an exemplary embodiment of the present specification, Ar4 and Ar5 are the same as or different from each other, and each independently a substituted or unsubstituted phenyl group; or a substituted or unsubstituted naphthyl group.

In an exemplary embodiment of the present specification, Ar4 and Ar5 are a phenyl group.

In another exemplary embodiment, Ar4 and Ar5 are a naphthyl group.

In an exemplary embodiment of the present specification, one of Ar4 and Ar5 is a phenyl group, and the other one is a naphthyl group.

In another exemplary embodiment, X1 is O.

In an exemplary embodiment of the present specification, L4 is a direct bond; or a substituted or unsubstituted arylene group.

In an exemplary embodiment of the present specification, L4 is a combination of one or two or more from the group consisting of a direct bond; a substituted or unsubstituted phenylene group; a substituted or unsubstituted biphenylylene group; a substituted or unsubstituted naphthalene group; a substituted or unsubstituted fluorenylene group; and a substituted or unsubstituted pyrenylene group.

In an exemplary embodiment of the present specification, L4 is a phenylene group; a biphenylylene group; a naphthylene group; a fluorenylene group; a pyrenylene group; a phenylene-naphthylene group; a phenylene-pyrenylene group; or a phenylene-fluorenylene group, and L4 is unsubstituted or substituted with a substituent selected from the group consisting of an alkyl group and an aryl group, or forms a spiro structure.

In an exemplary embodiment of the present specification, L4 is a direct bond; a phenylene group; or a biphenylylene group.

In the present specification, the "spiro bond" may mean a structure in which substituents in the same carbon combine with each other, and two ring compounds are linked to each other through one atom.

In the present specification, the spiro structure may form a fluorene structure.

In an exemplary embodiment of the present specification, L4 is a direct bond; a phenylene group; a biphenylylene group; a naphthalene group; a fluorenylene group substituted with a methyl group; a fluorenylene group substituted with a phenyl group; a spirobifluorenylene group; a pyrenylene group; a phenylene-naphthylene group; a phenylene-pyrenylene group; fluorenylene substituted with a phenylene-methyl group; fluorenylene substituted with a phenylene-phenyl group; or a spirofluorenylene group.

In an exemplary embodiment of the present specification, the compound represented by Formula 4 is represented by any one of the following Formulae 4-1 to 4-84.

Formula 4-1

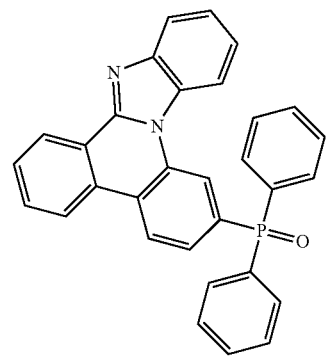

Formula 4-2

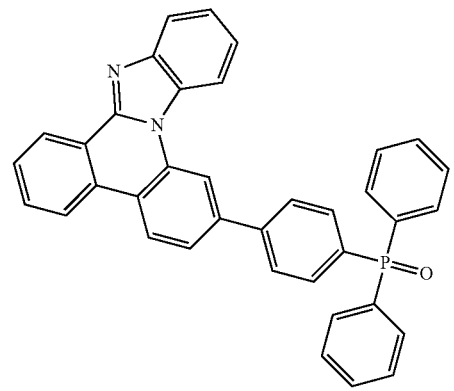

-continued
Formula 4-3
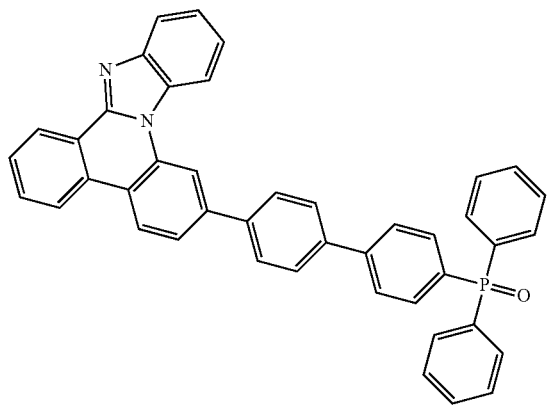
Formula 4-4
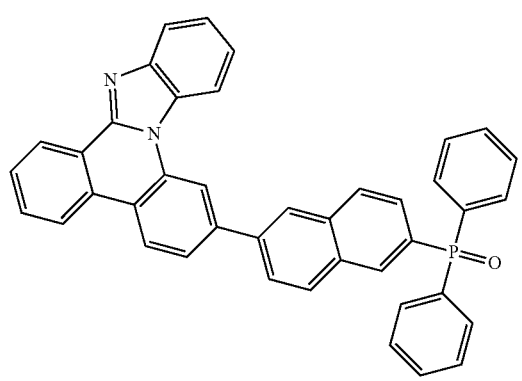
Formula 4-5
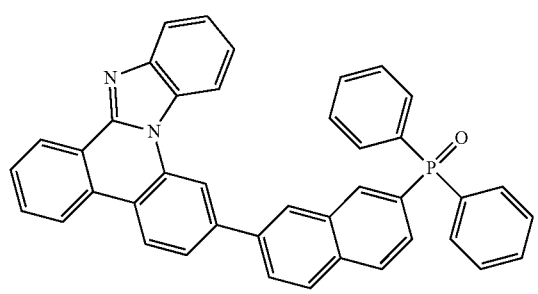
Formula 4-6
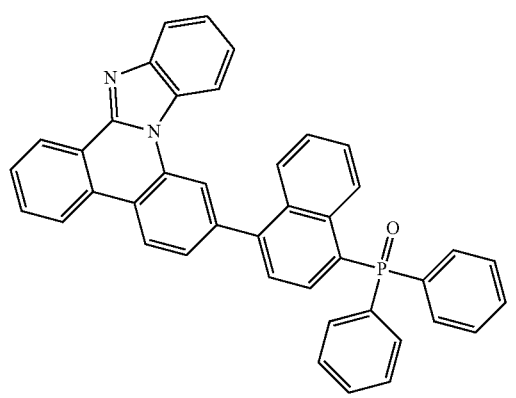
-continued
Formula 4-7
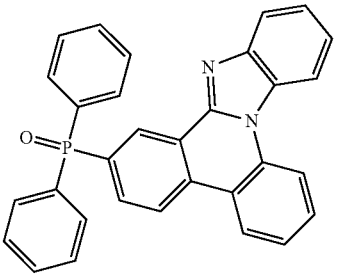
Formula 4-8
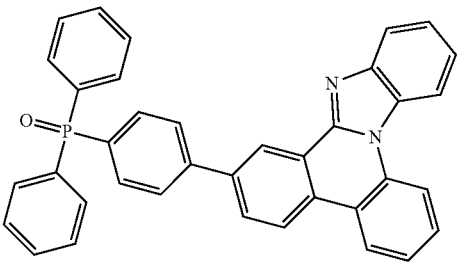
Formula 4-9
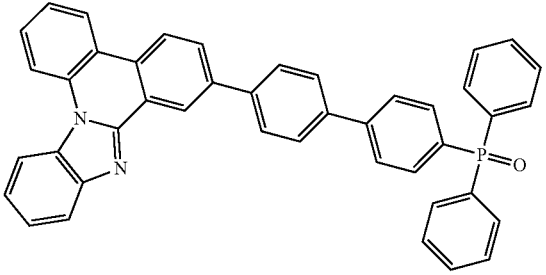
Formula 4-10
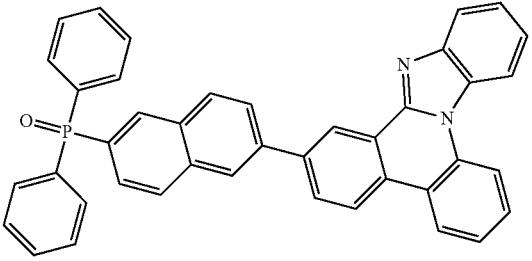
Formula 4-11
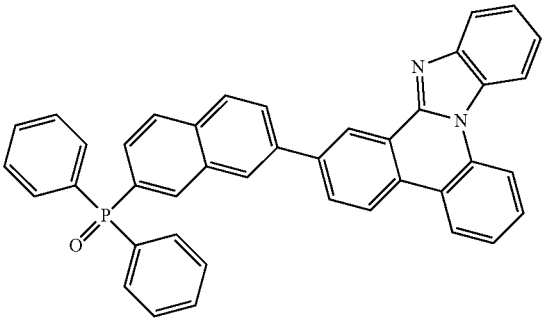

Formula 4-12
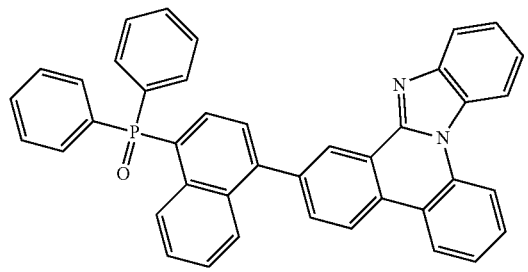
Formula 4-13
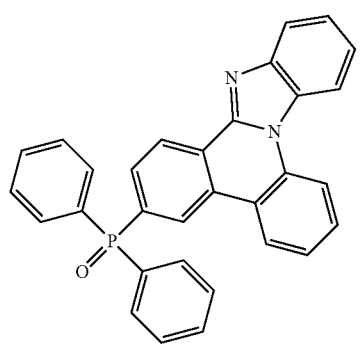
Formula 4-14
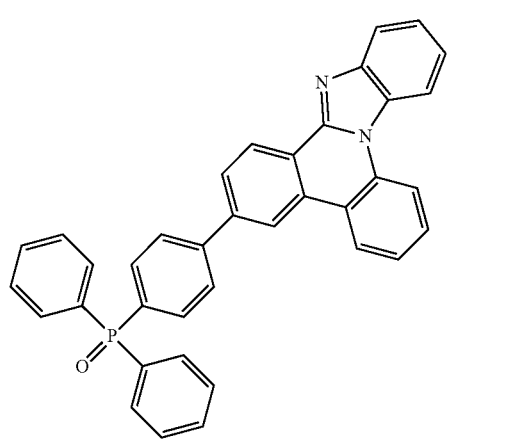
Formula 4-15
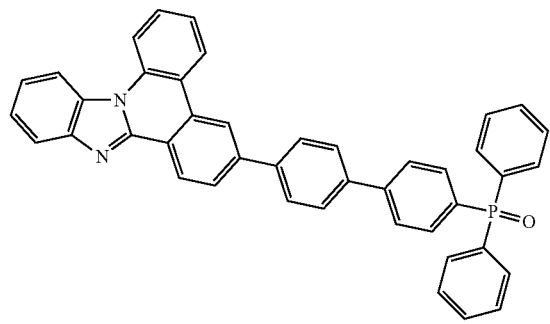
Formula 4-16
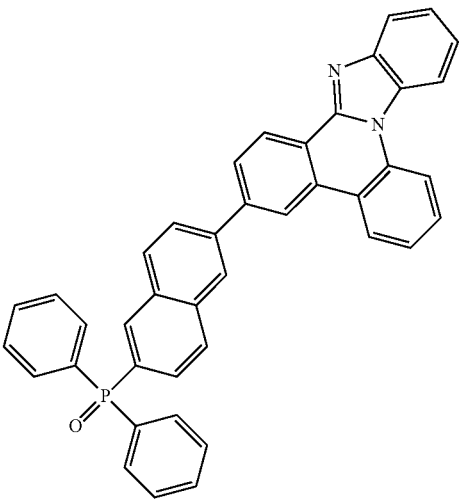
Formula 4-17
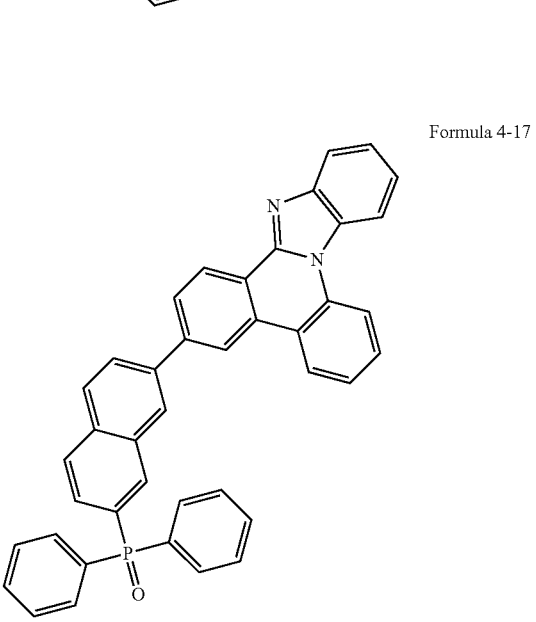
Formula 4-18
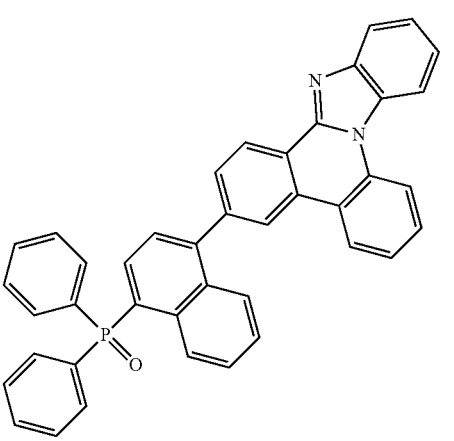

Formula 4-19
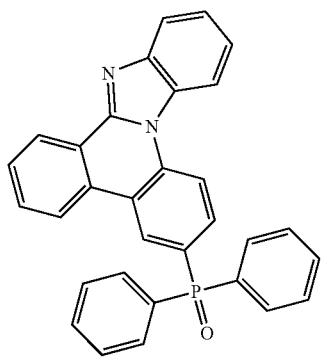
Formula 4-20
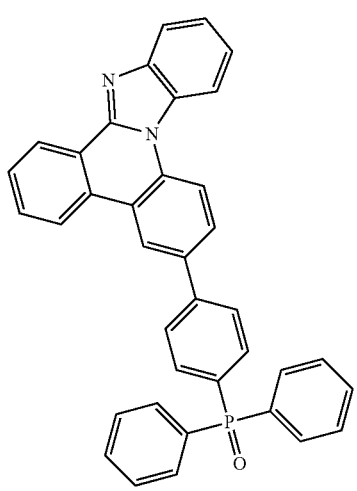
Formula 4-21
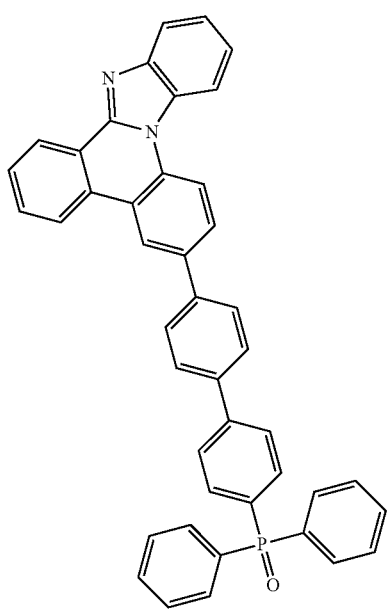
Formula 4-22
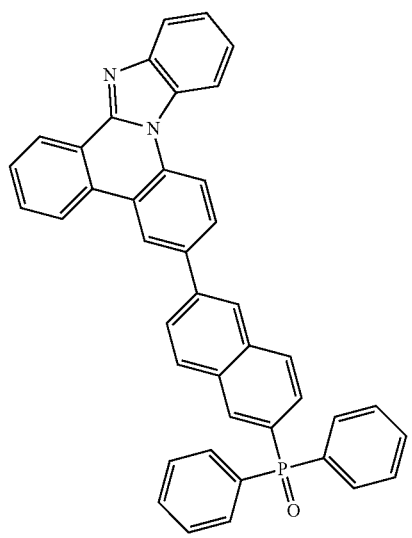
Formula 4-23
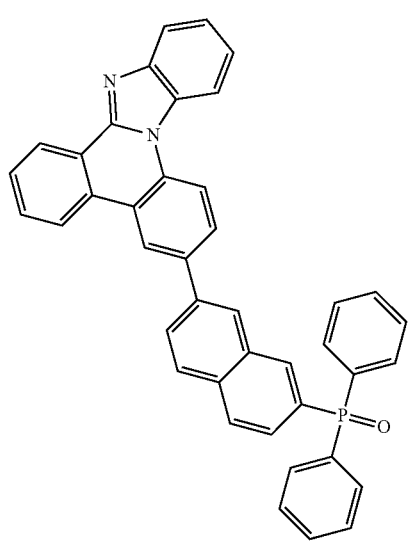
Formula 4-24
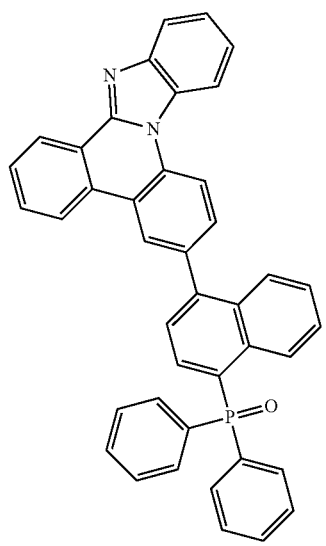

Formula 4-25
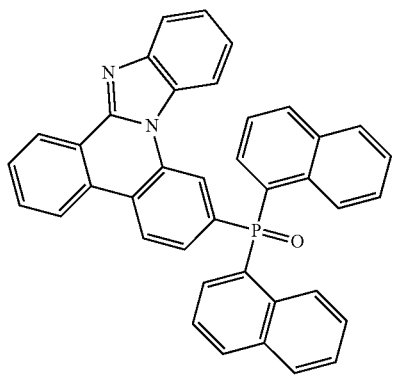
Formula 4-26
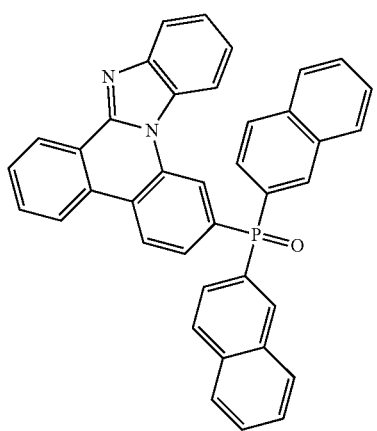
Formula 4-27
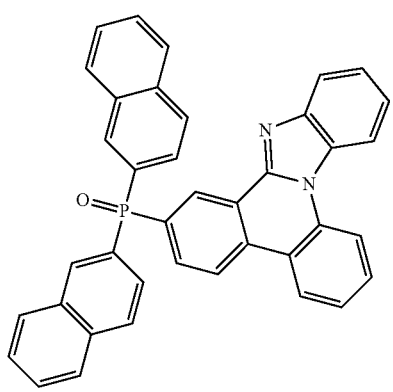
Formula 4-28
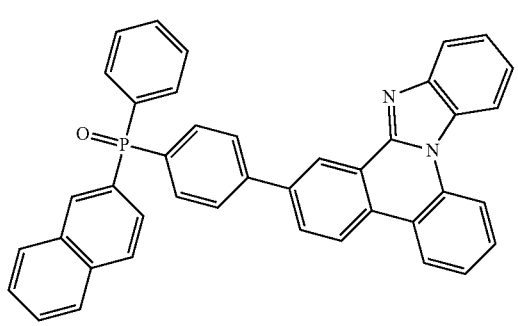
Formula 4-29
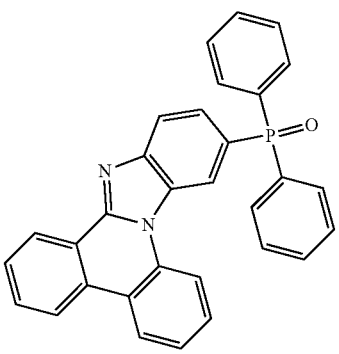
Formula 4-30
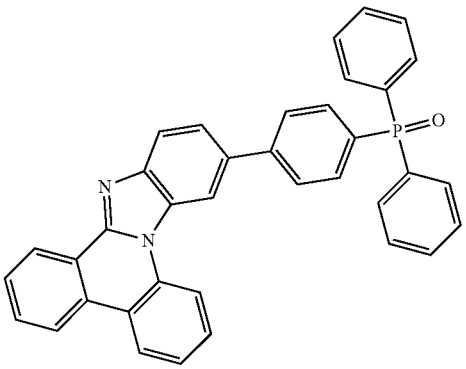
Formula 4-31
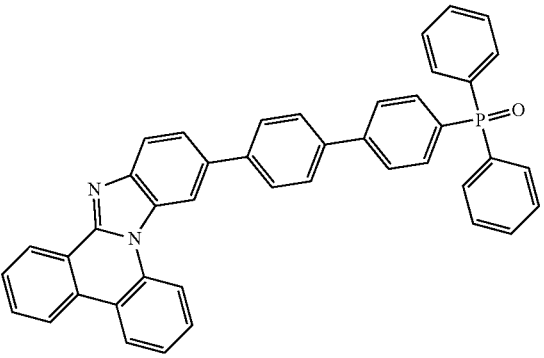
Formula 4-32
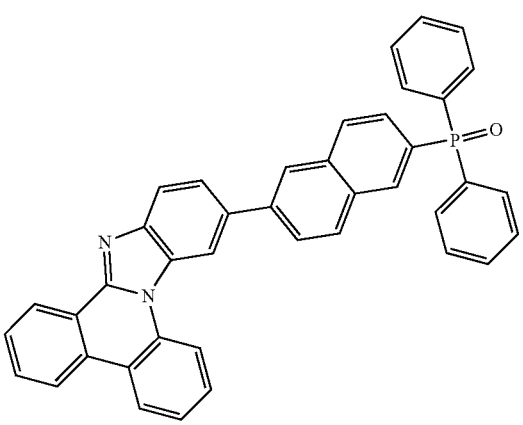

Formula 4-33
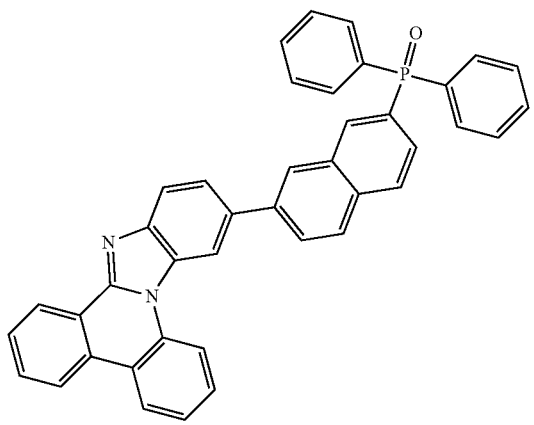
Formula 4-34
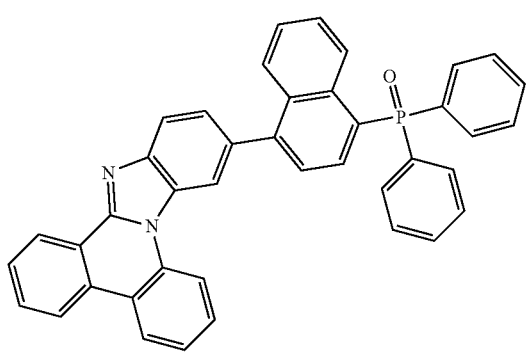
Formula 4-35
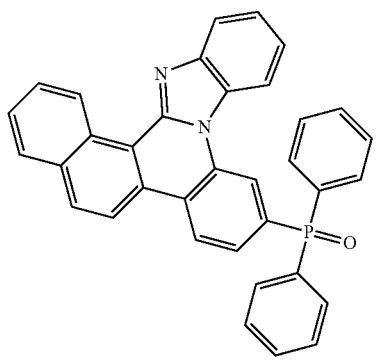
Formula 4-36
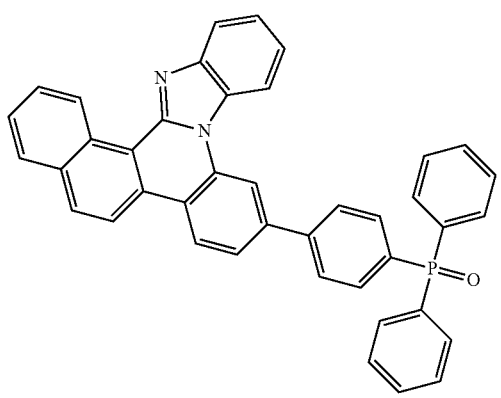
Formula 4-37
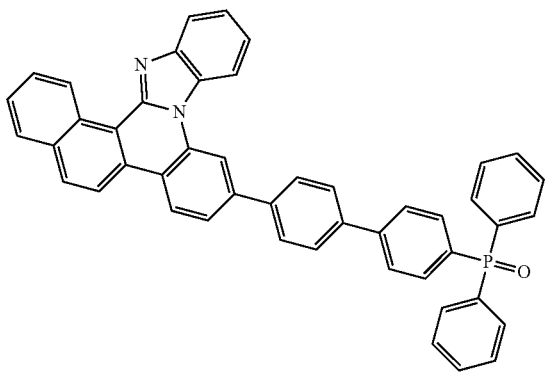
Formula 4-38
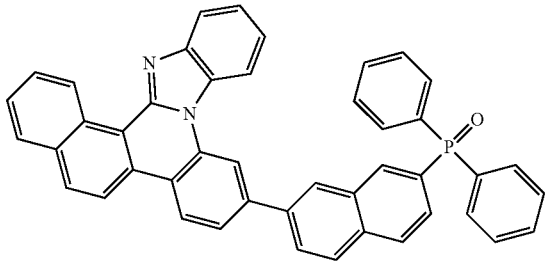
Formula 4-39
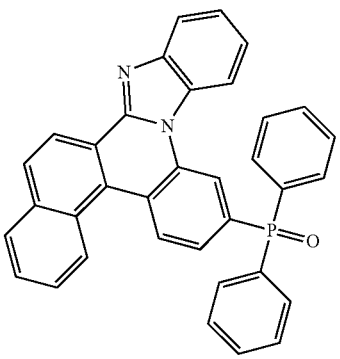
Formula 4-40
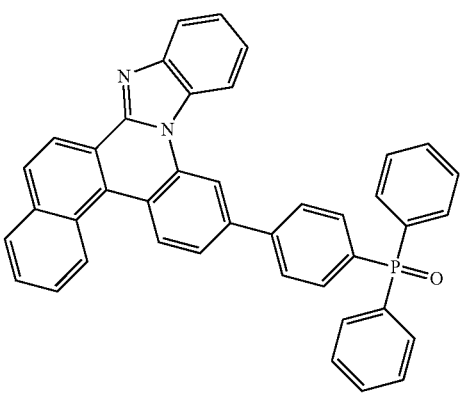

Formula 4-41
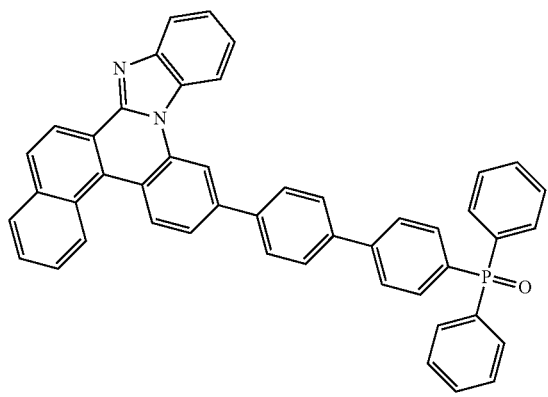
Formula 4-42
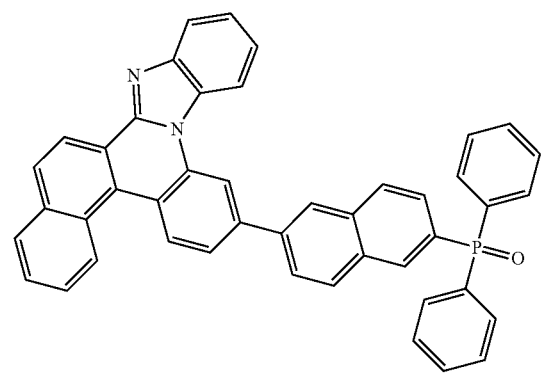
Formula 4-43
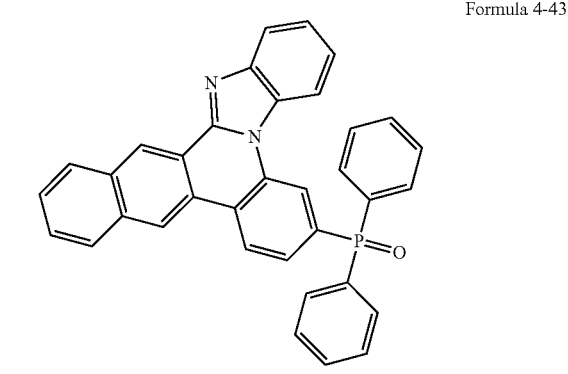
Formula 4-44
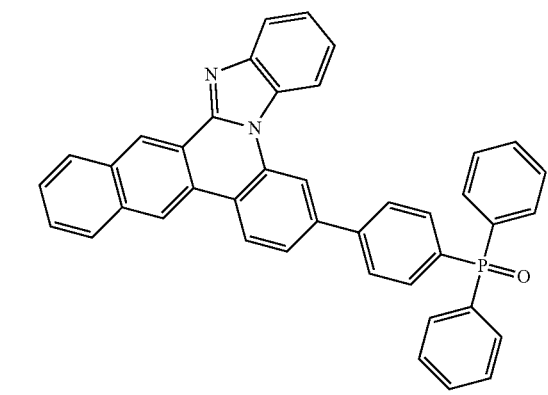
Formula 4-45
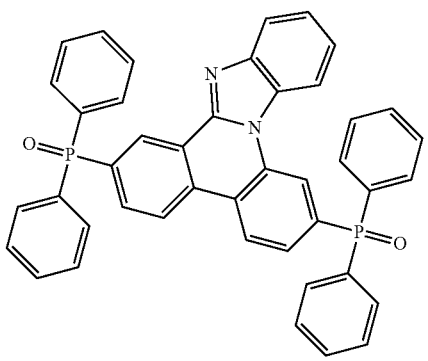
Formula 4-46
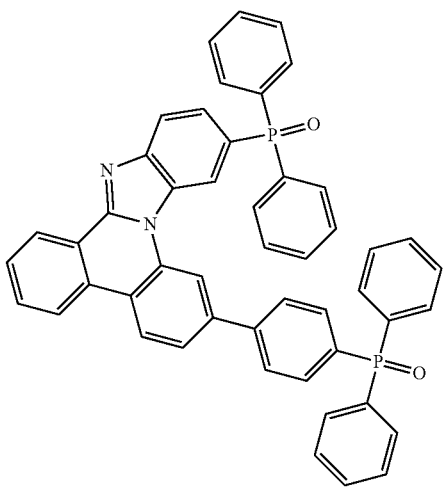
Formula 4-47
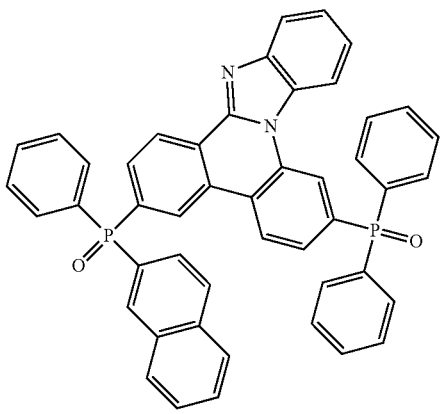

Formula 4-48
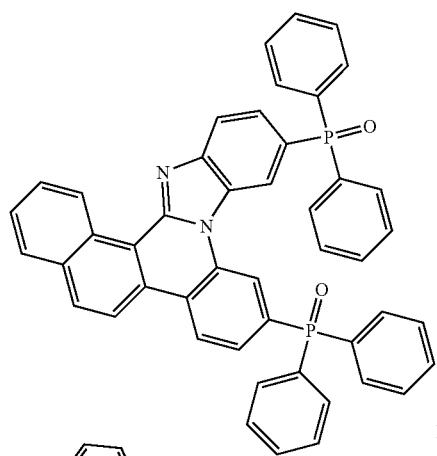
Formula 4-49
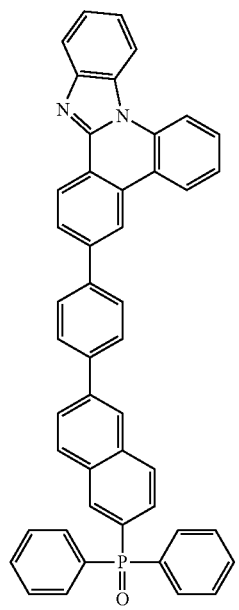
Formula 4-50
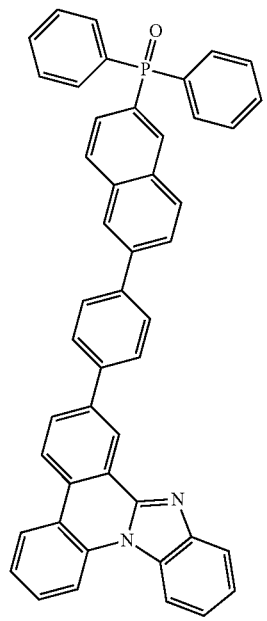
Formula 4-51
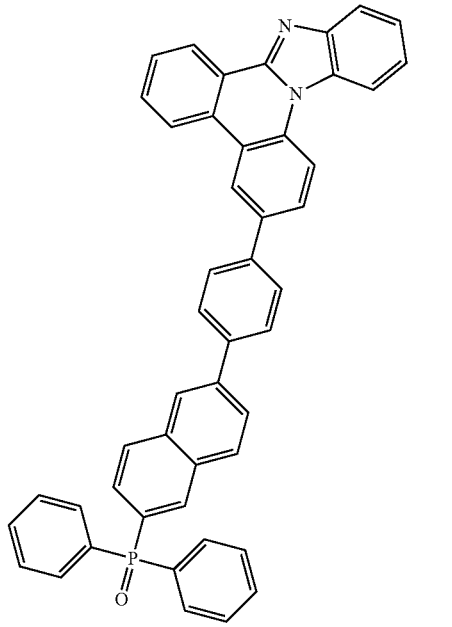
Formula 4-52
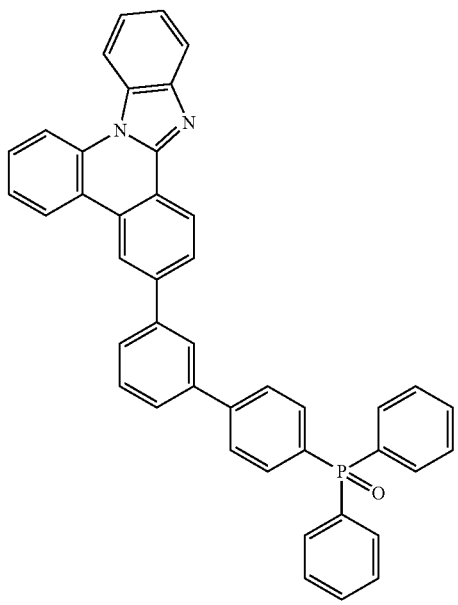

Formula 4-53
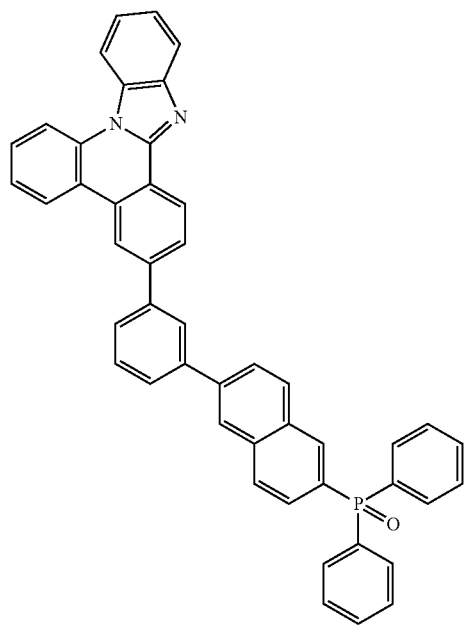
Formula 4-55
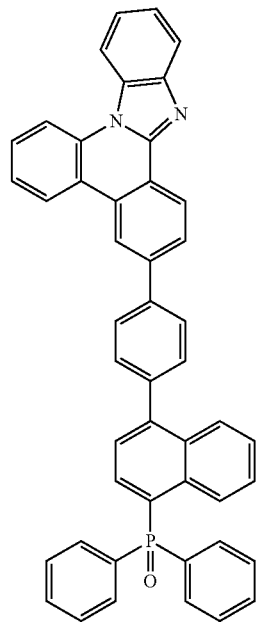
Formula 4-54
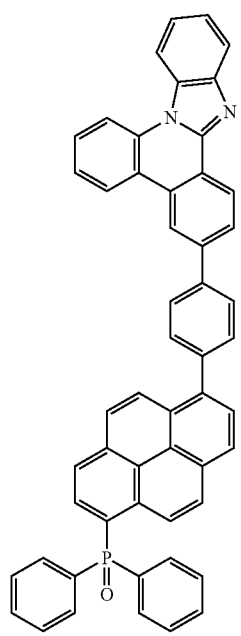
Formula 4-56
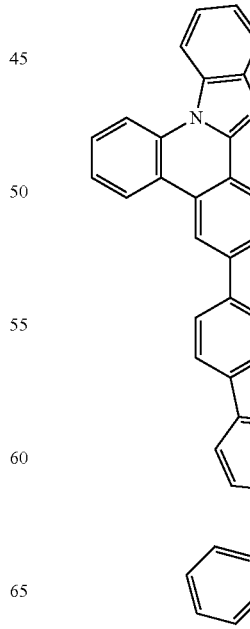

Formula 4-57
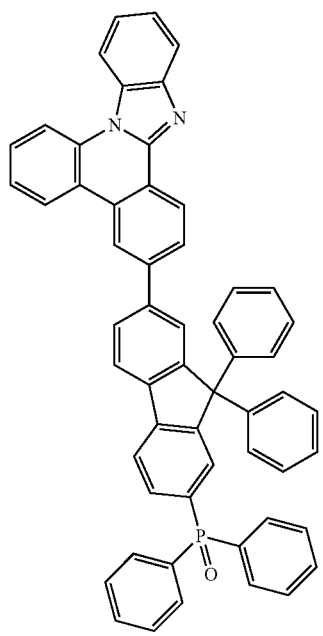
Formula 4-58
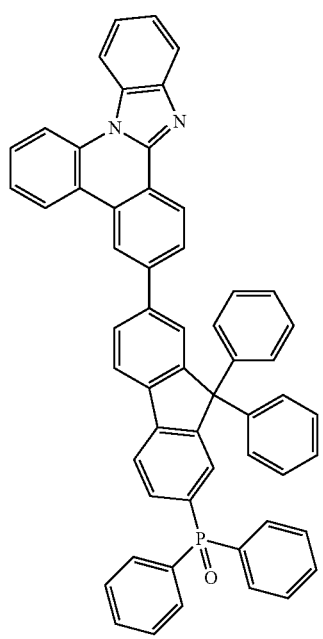
Formula 4-59
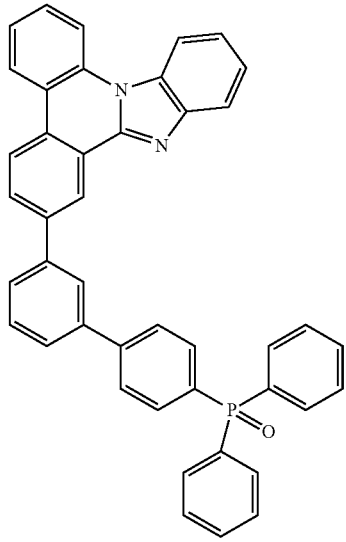
Formula 4-60
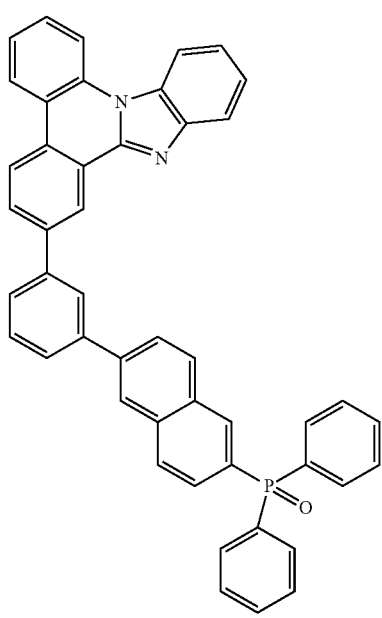

Formula 4-61
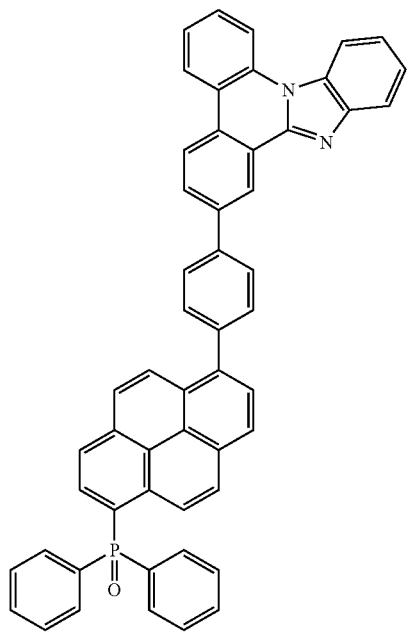
Formula 4-63
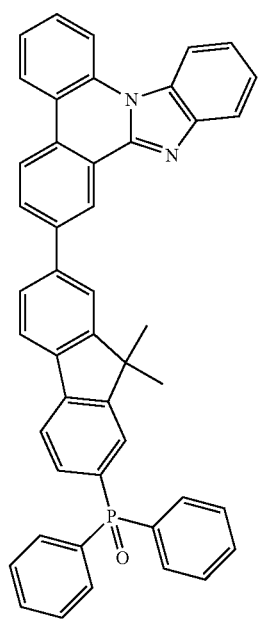
Formula 4-62
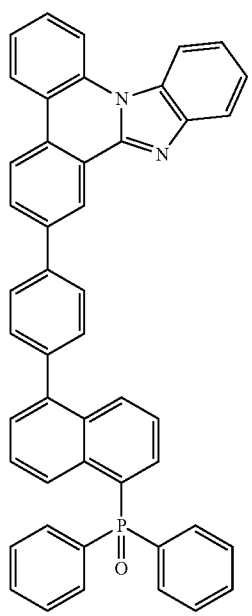
Formula 4-64
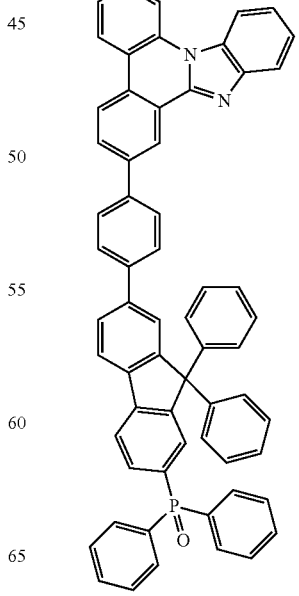

Formula 4-65
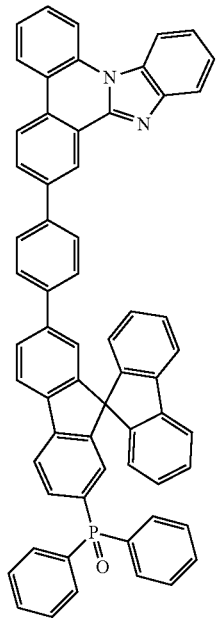
Formula 4-67
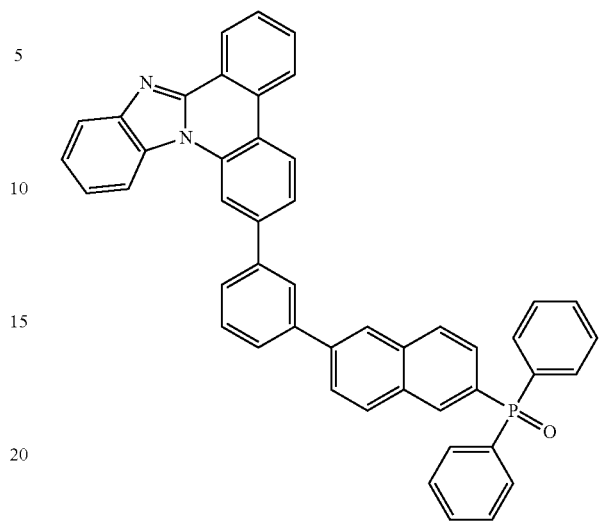
Formula 4-66
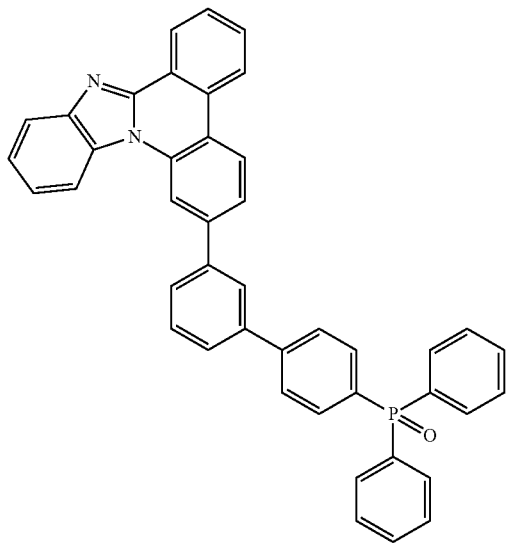
Formula 4-68
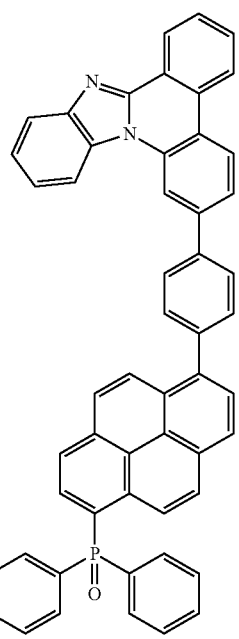

-continued
Formula 4-69
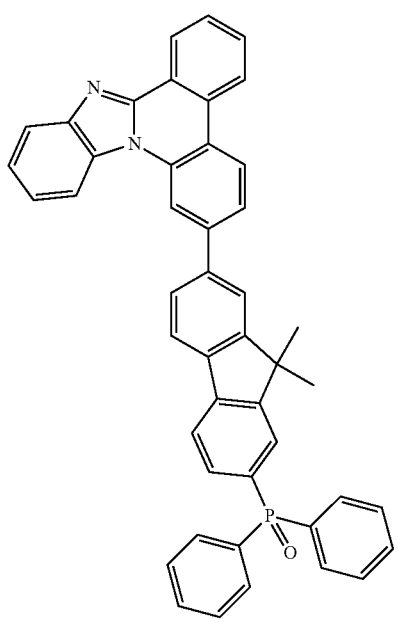
Formula 4-70
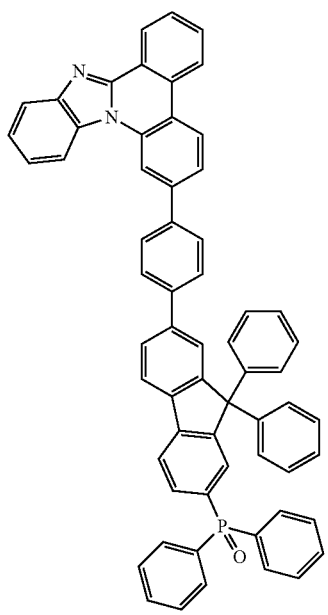
-continued
Formula 4-71
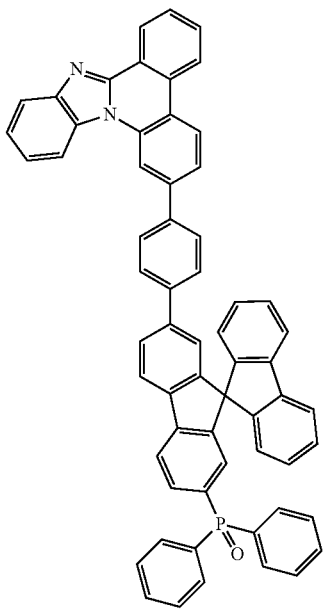
Formula 4-72
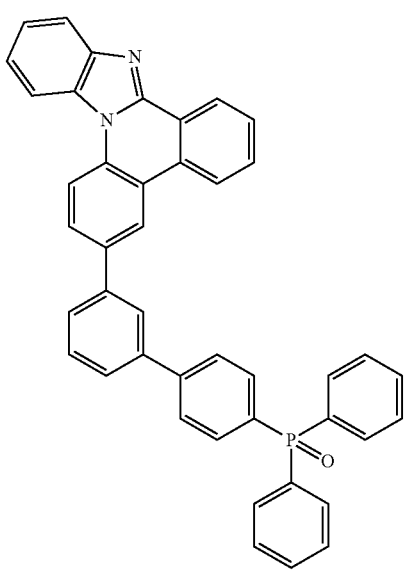

Formula 4-73
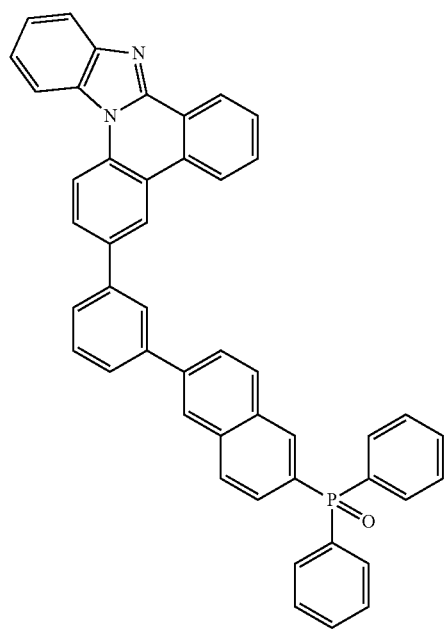
Formula 4-75
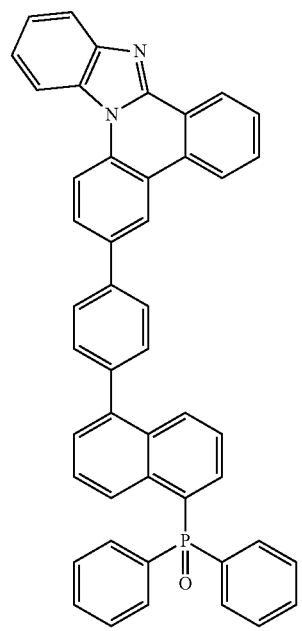
Formula 4-74
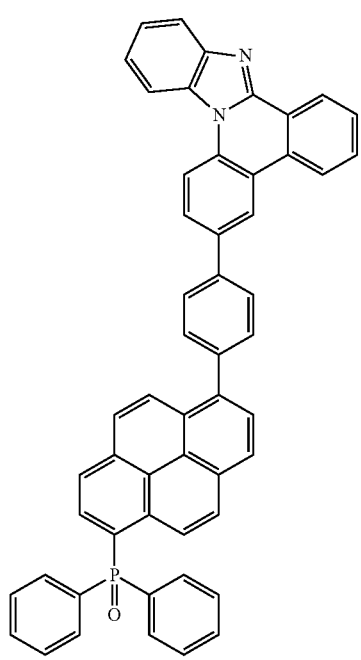
Formula 4-76
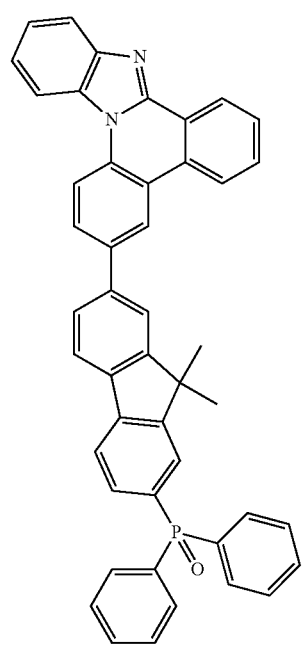

Formula 4-77
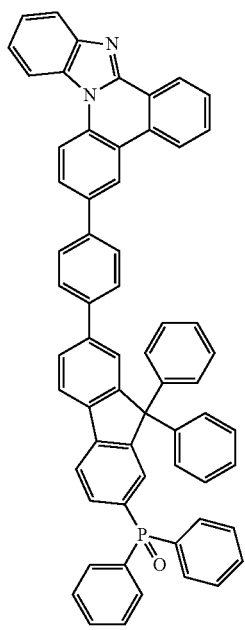
Formula 4-78
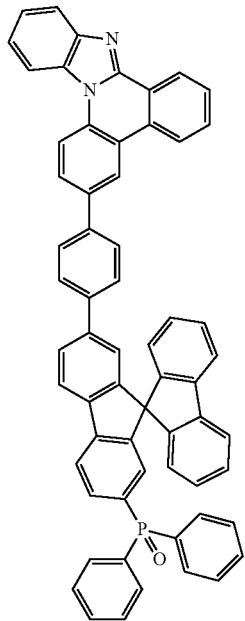
Formula 4-79
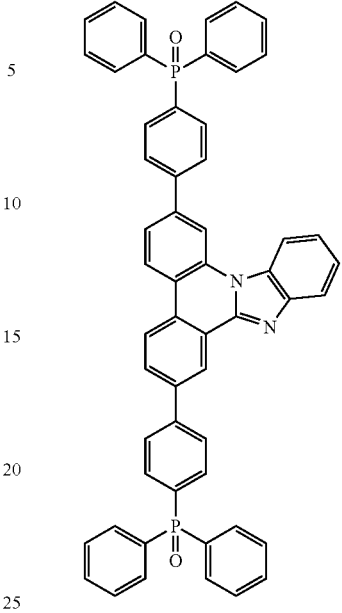
Formula 4-80
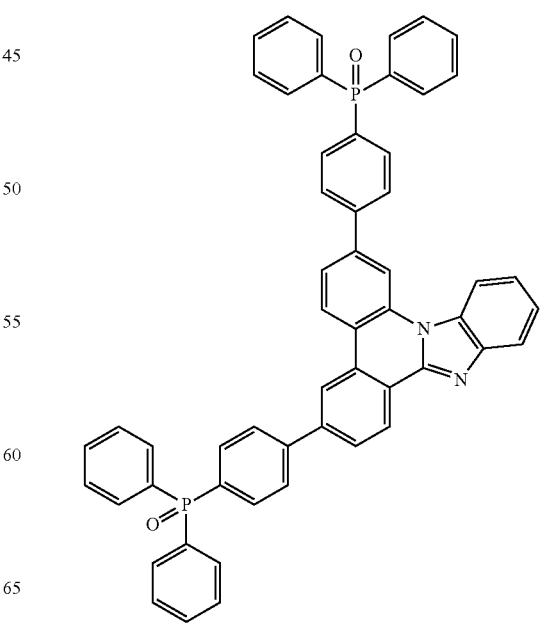

Formula 4-81
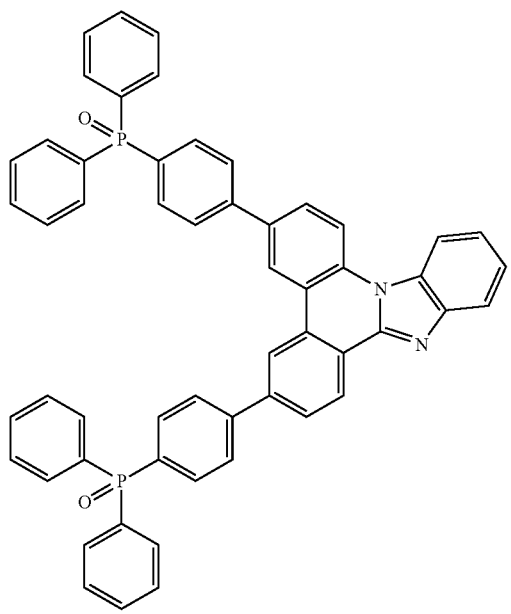
Formula 4-83
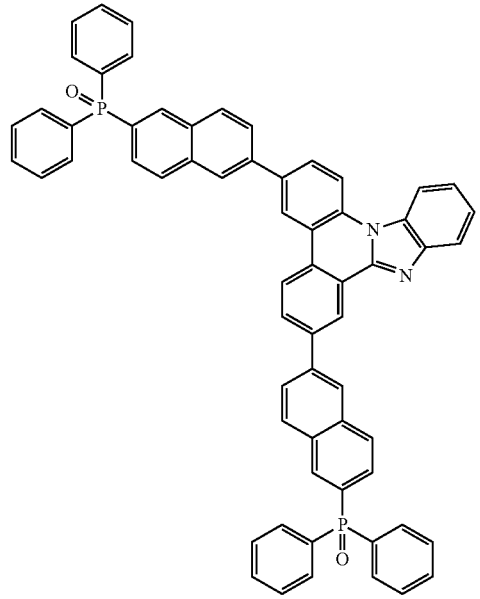
Formula 4-84
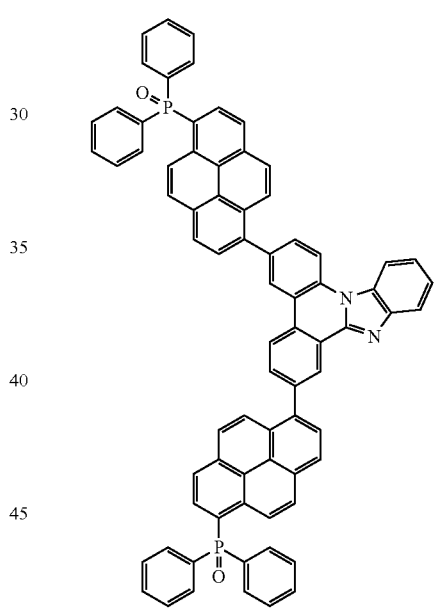
Formula 4-82
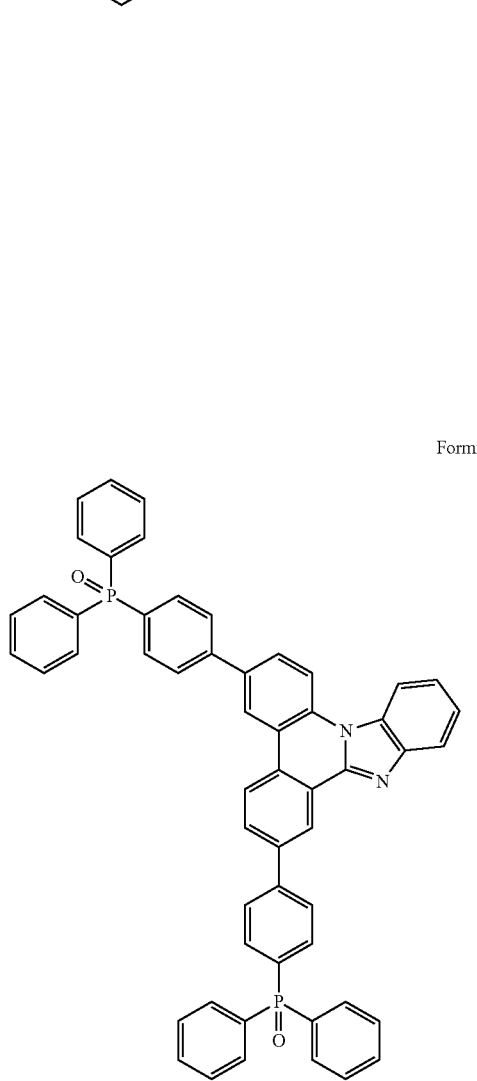
In an exemplary embodiment of the present specification, the second electron transporting layer includes the compound represented by Formula 5.
In an exemplary embodiment of the present specification, Formula 5 is selected from any one of the following Formulae 5A to 5C.
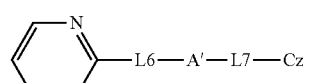
[Formula 5A]
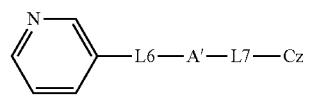
[Formula 5B]

-continued

[Formula 5C]

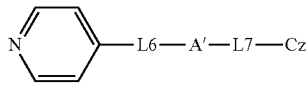

In Formulae 5A to 5C,

A', Cz, L6, and L7 are the same as those defined in Formula 5.

In an exemplary embodiment of the present specification, A' is selected from the following structures.

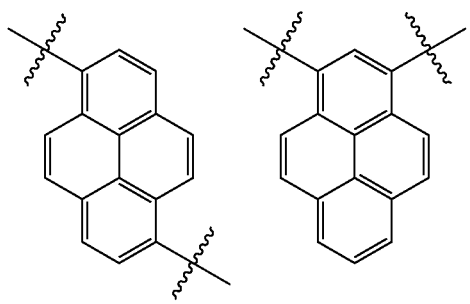 [SMILES: *c1ccc2ccc3c(*)ccc4ccc1c2c43 ; *c1cc(*)c2ccc3cccc4ccc1c2c43]

The structure is unsubstituted or substituted with one or two or more substituents selected from the group consisting of deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; and a substituted or unsubstituted heterocyclic group.

In one exemplary embodiment of the present specification, the pyrenylene structure is unsubstituted or substituted with a substituted or unsubstituted alkyl group. In another exemplary embodiment, the pyrenylene structure is unsubstituted or substituted with a substituted or unsubstituted alkyl group having 1 to 10 carbon atoms.

In an exemplary embodiment of the present specification, the pyrenyl structure is unsubstituted or substituted with a t-butyl group.

In an exemplary embodiment of the present specification, A' is

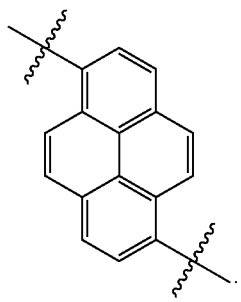 [SMILES: *c1ccc2ccc3c(*)ccc4ccc1c2c43]

In another exemplary embodiment, A' is

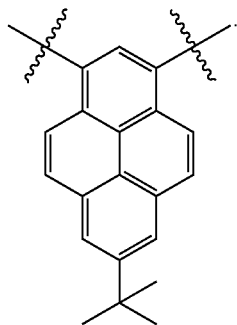 [SMILES: *c1cc(*)c2ccc3cc(C(C)(C)C)cc4ccc1c2c43]

In an exemplary embodiment of the present specification, L6 and L7 are the same as or different from each other, and each independently a direct bond; or a substituted or unsubstituted arylene group.

In another exemplary embodiment, L6 and L7 are the same as or different from each other, and each independently a direct bond; or a substituted or unsubstituted arylene group having 6 to 30 carbon atoms.

In still another exemplary embodiment, L6 and L7 are the same as or different from each other, and each independently a direct bond; or a substituted or unsubstituted phenylene group.

In an exemplary embodiment of the present specification, L6 is a phenylene group.

In another exemplary embodiment, L6 is a direct bond.

In still another exemplary embodiment, L7 is a phenylene group.

The phenylene group of the present specification may be selected from the following structures.

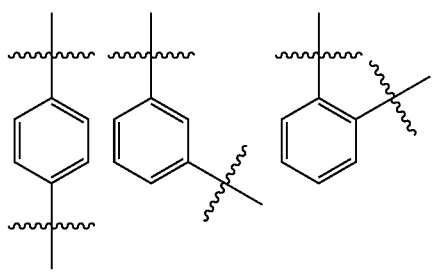

The phenylene group may be unsubstituted or substituted with one or two or more substituents selected from the group consisting of deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; and a substituted or unsubstituted heterocyclic group.

In an exemplary embodiment of the present specification, Cz may be selected from the following structures.

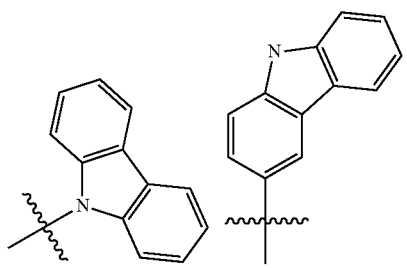

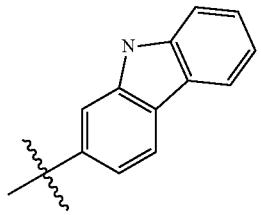

The structure is unsubstituted or substituted with one or two or more substituents selected from the group consisting of deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; and a substituted or unsubstituted heterocyclic group.

In an exemplary embodiment of the present specification, Cz is unsubstituted or substituted with a substituted or unsubstituted aryl group.

In another exemplary embodiment, Cz is unsubstituted or substituted with a substituted or unsubstituted aryl group having 6 to 30 carbon atoms.

In still another exemplary embodiment, Cz is unsubstituted or substituted with a substituted or unsubstituted phenyl group.

In an exemplary embodiment of the present specification, Cz is

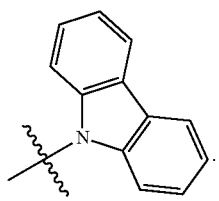 [SMILES: *n1c2ccccc2c2ccccc21]

In an exemplary embodiment of the present specification, the compound represented by Formula 5 is represented by any one of the following Formulae 5-1 to 5-37.

Formula 5-1

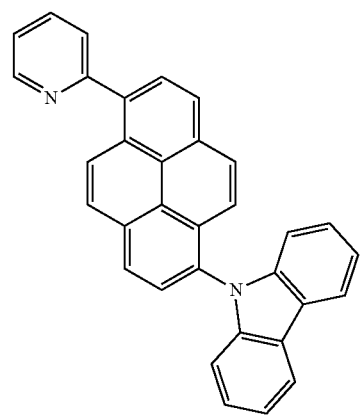

Formula 5-2

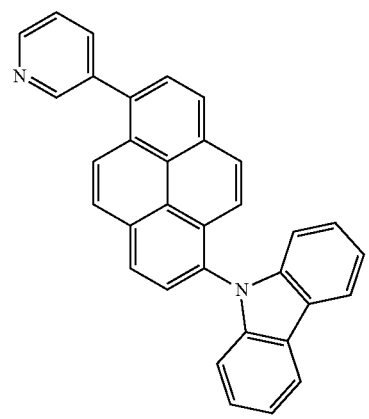

Formula 5-3

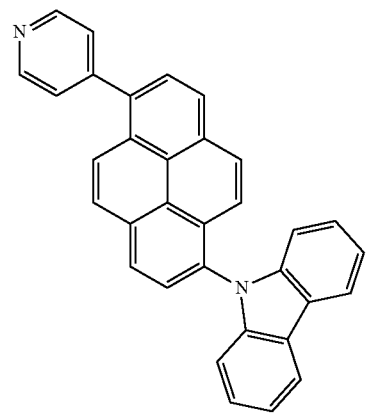

Formula 5-4

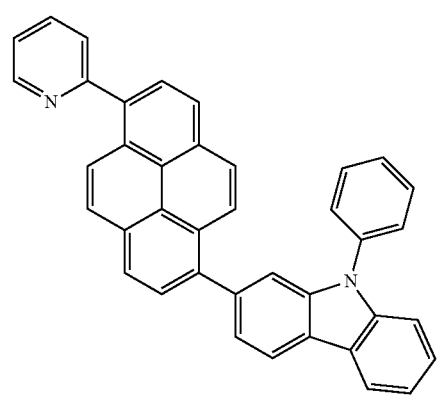

Formula 5-5
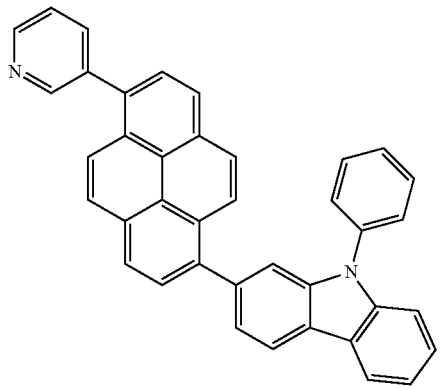
Formula 5-6
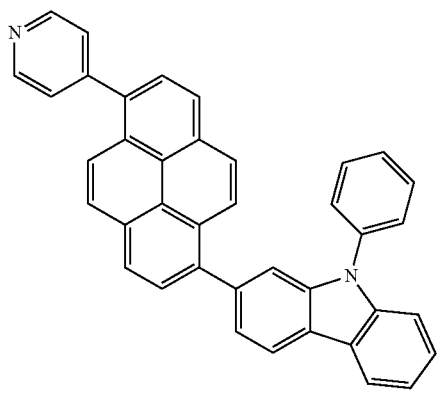
Formula 5-7
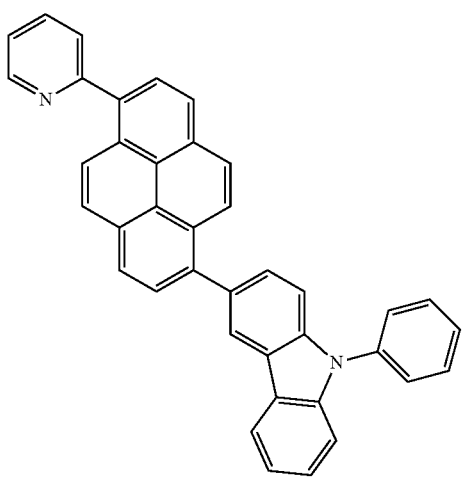
Formula 5-8
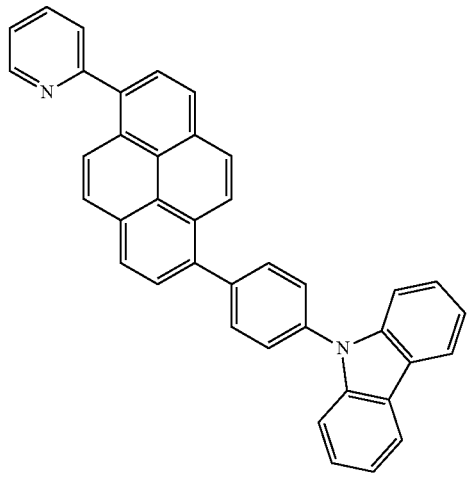
Formula 5-9
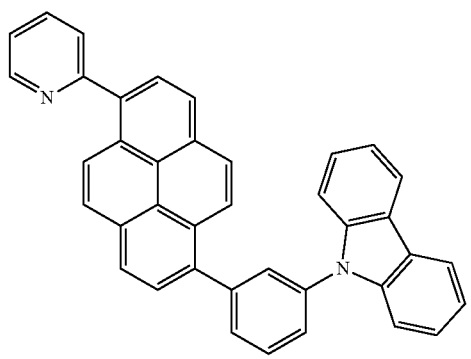
Formula 5-10
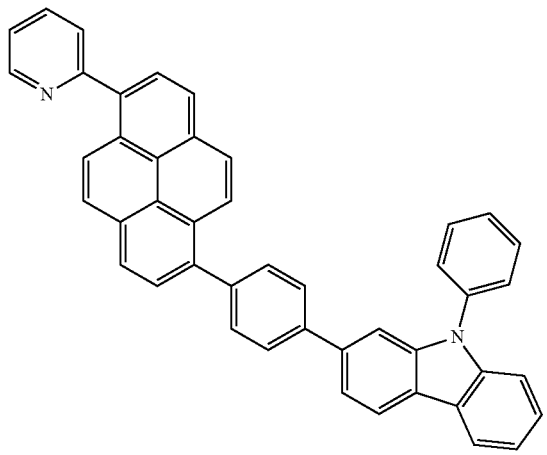

Formula 5-11
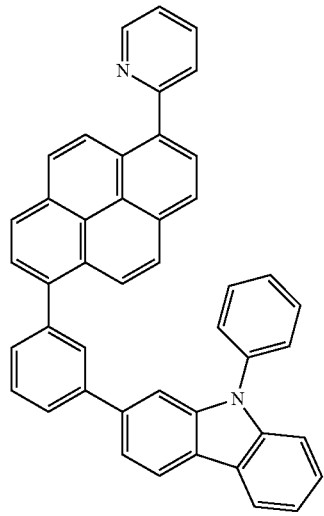
Formula 5-12
Formula 5-13
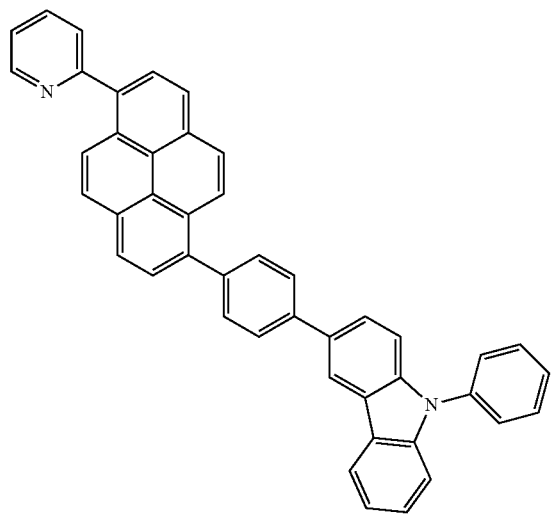
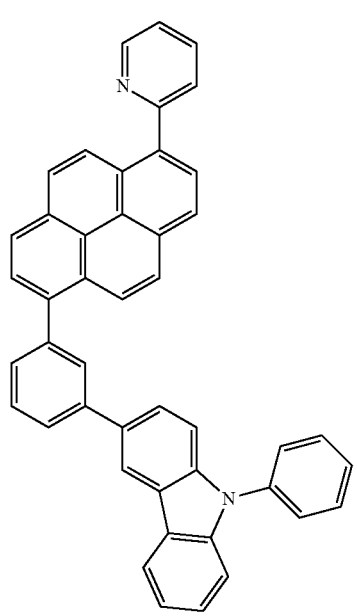
Formula 5-14
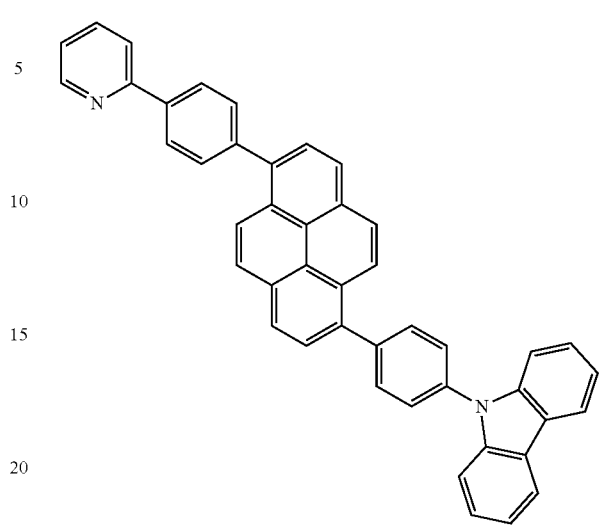
Formula 5-15
Formula 5-16
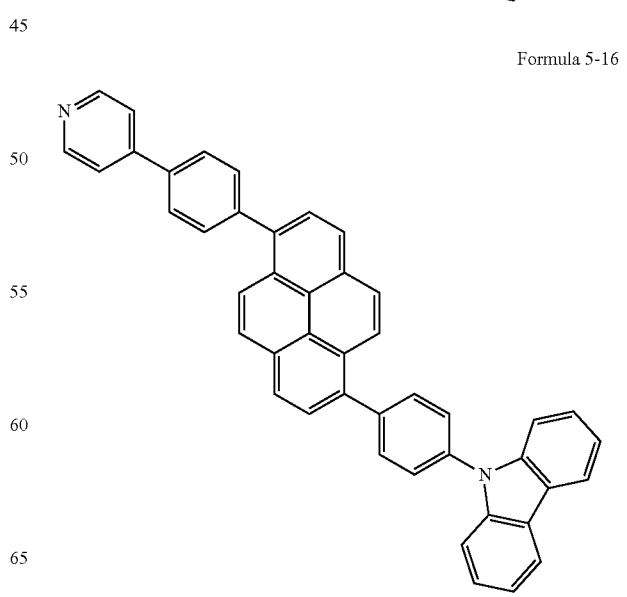

465
-continued
Formula 5-17
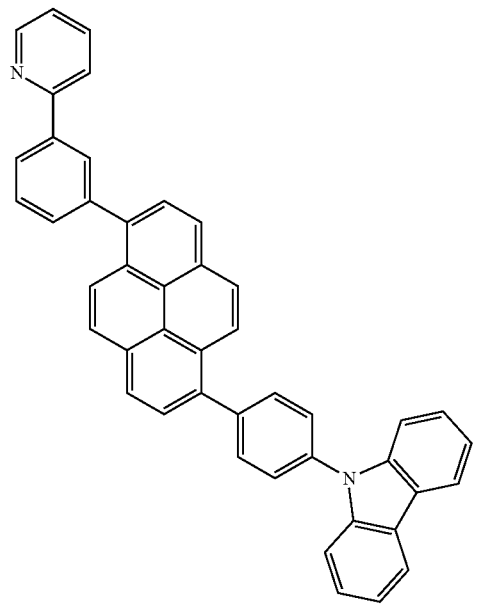
5-18
466
-continued
5-19
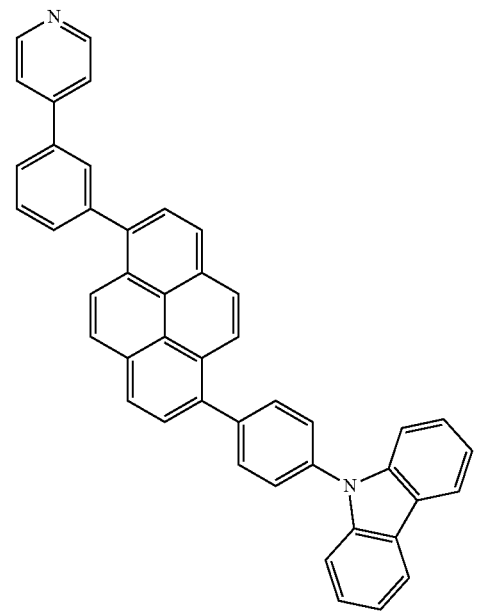
Formula 5-20
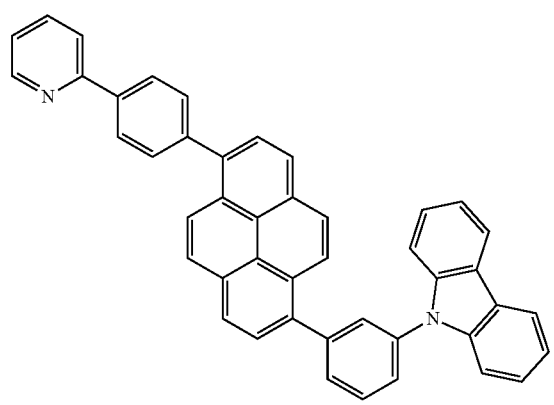
Formula 5-21
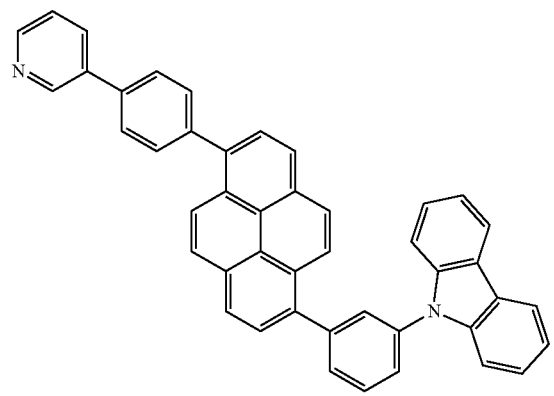

-continued
Formula 5-22
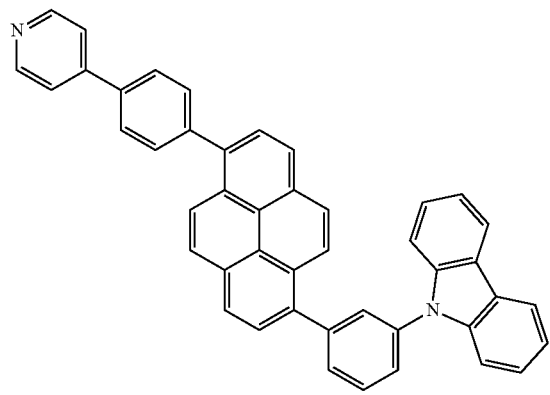
Formula 5-23
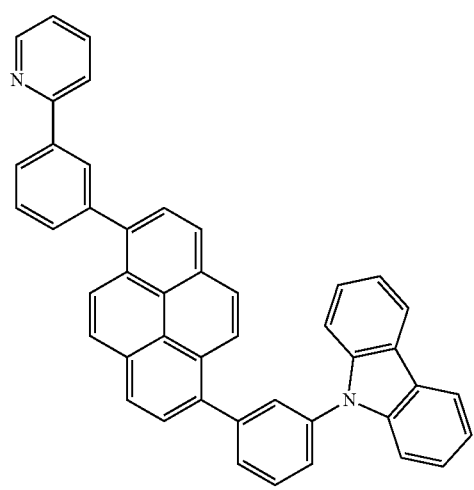
Formula 5-24
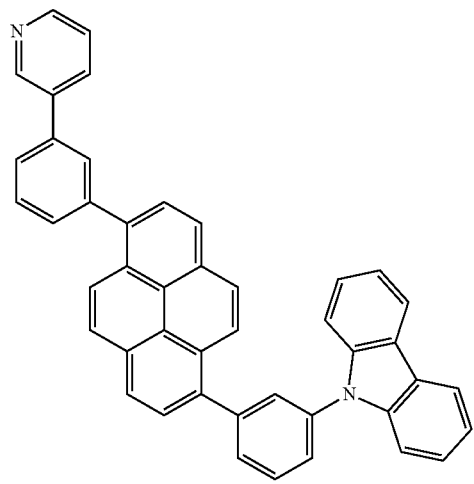
-continued
Formula 5-25
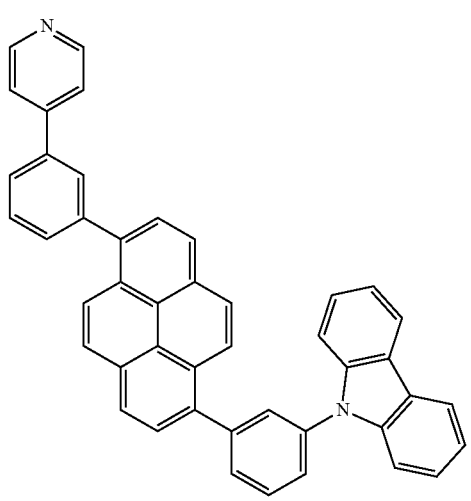
Formula 5-26
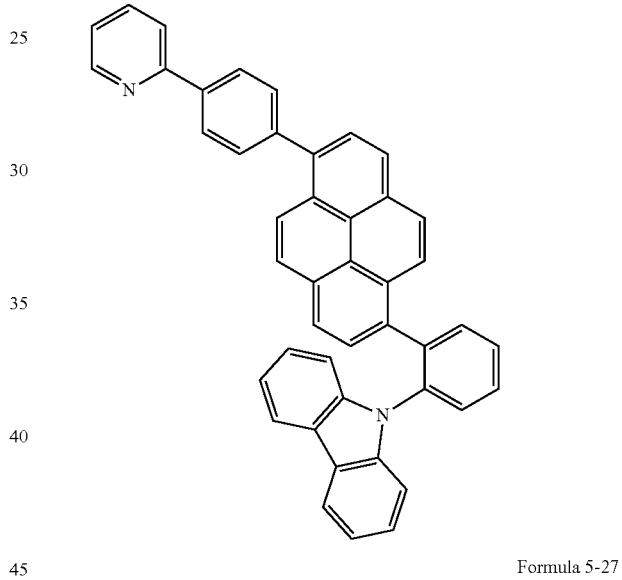
Formula 5-27
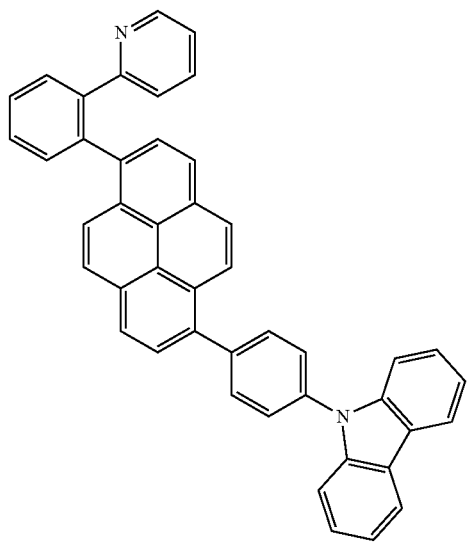

Formula 5-28
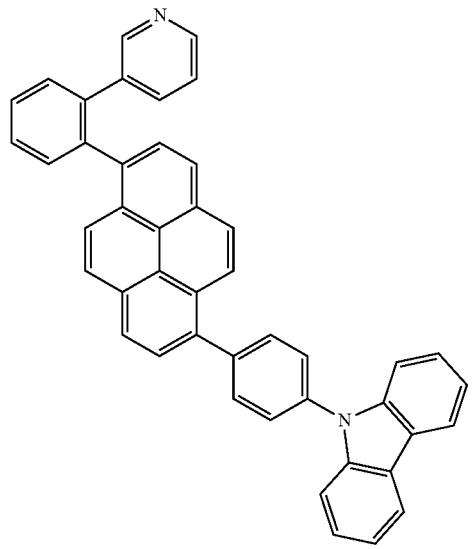
Formula 5-31
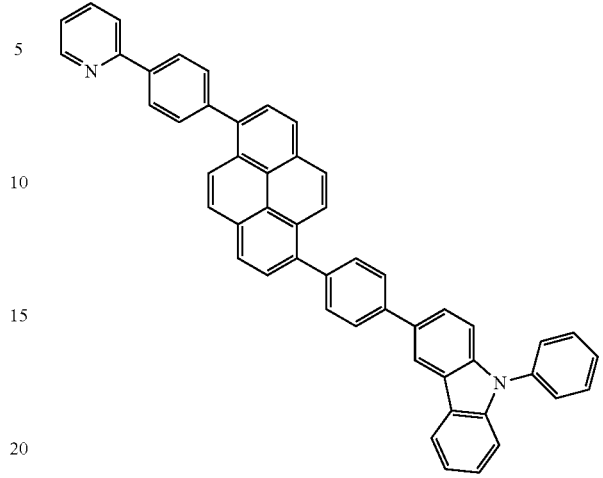
Formula 5-29
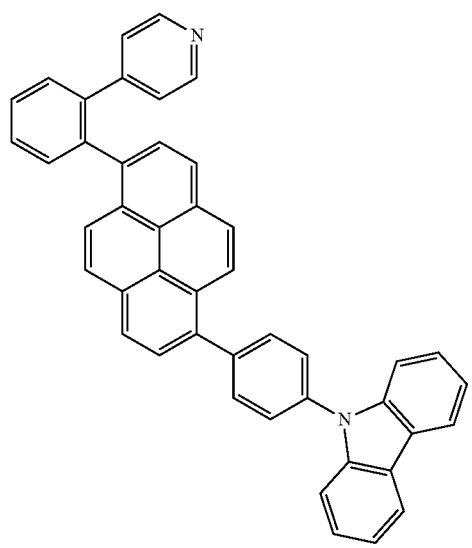
Formula 5-32
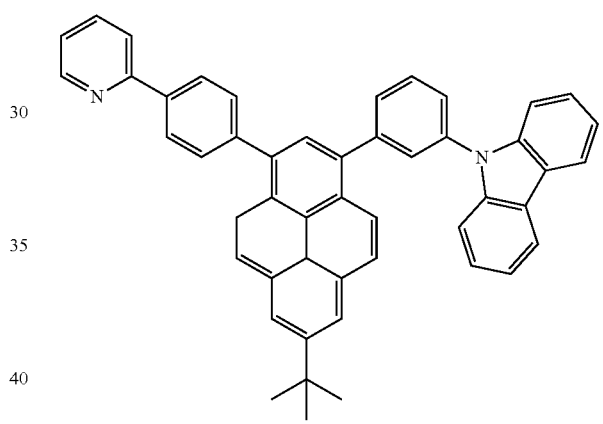
Formula 5-30
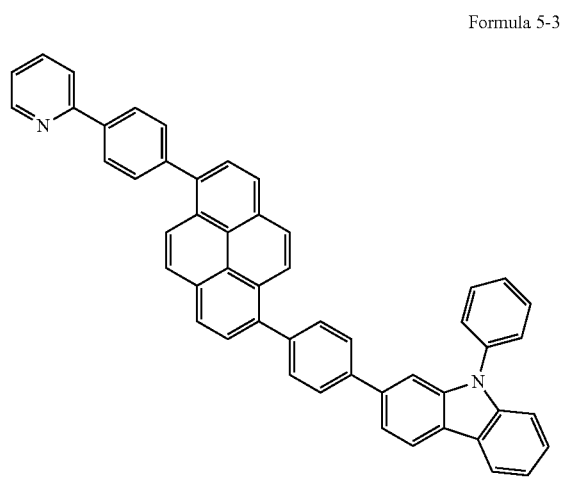
Formula 5-33
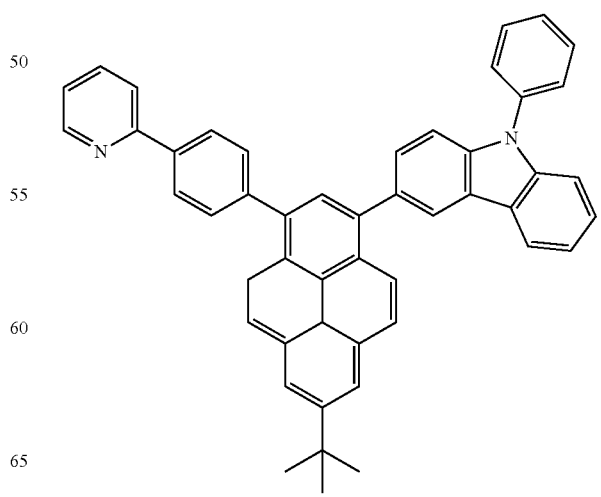

Formula 5-34

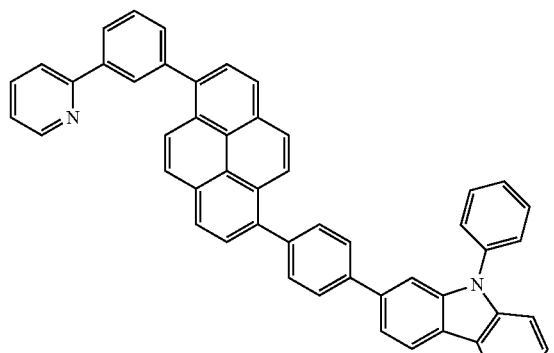

Formula 5-35

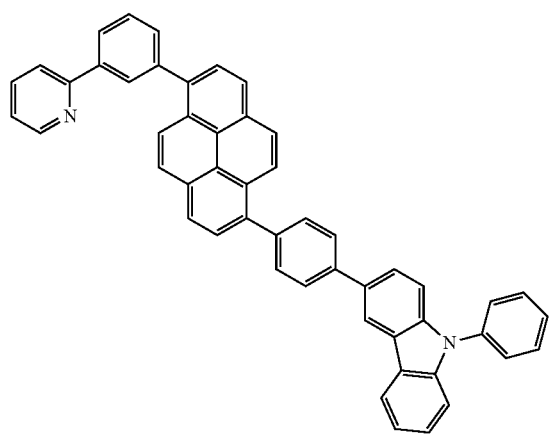

Formula 5-36

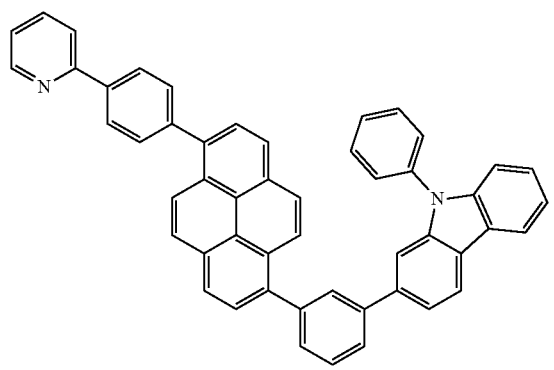

Formula 5-37

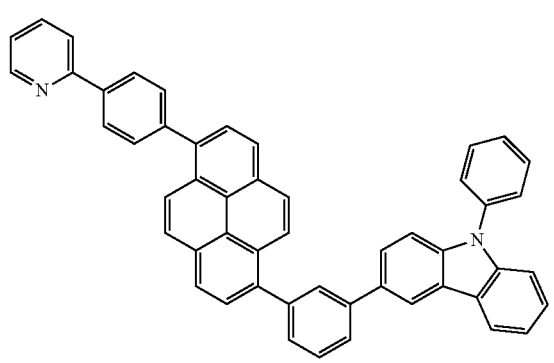

In an exemplary embodiment of the present specification, the organic light emitting diode has a tandem structure. In this case, it is possible to manufacture a white light emitting diode with a stack of a blue fluorescence, a green phosphorescence, and red phosphorescence; and a stack of a blue fluorescence and a greenish yellow phosphorescence. Specifically, the organic light emitting diode according to an exemplary embodiment of the present specification may include a fluorescence light emitting diode and/or a phosphorescence light emitting diode.

In an exemplary embodiment of the present specification, the organic light emitting diode includes two or more light emitting layers, and includes a charge generating layer between the two adjacent light emitting layers in the two or more light emitting layers, the charge generating layer includes the second electron transporting layer and a p-type organic material layer, and the first electron transporting layer is provided between the light emitting layer and the second electron transporting layer.

In another exemplary embodiment, the second electron transporting layer and the p-type organic material layer, which are included in the charge generating layer, form an NP junction.

In an exemplary embodiment of the present specification, the p-type organic material layer is selected from the group consisting of a hole injection layer, a hole transporting layer, an electron blocking layer, and a light emitting layer.

In the present specification, the n-type means n-type semiconductor characteristics. In other words, the n-type is a characteristic in that electrons are injected or transported through the lowest unoccupied molecular orbital (LUMO) energy level, and this may be defined as a characteristic of a material having a larger electron mobility than the hole mobility. In contrast, the p-type means p-type semiconductor characteristics. In other words, the p-type is a characteristic in that holes are injected or transported through the highest occupied molecular orbital (HOMO) energy level, and this may be defined as a characteristic of a material having a larger hole mobility than the electron mobility. In the present specification, a compound or an organic material layer having n-type characteristics may be mentioned as an n-type compound or an n-type organic material layer. Further, a compound or an organic material layer having p-type characteristics may be mentioned as a p-type compound or a p-type organic material layer. In addition, the n-type doping may mean that a doping is conducted so as to have n-type characteristics.

In the present specification, a charge generating layer is a layer of generating charges without the application of an external voltage, and generates charges between adjacent light emitting layers among two or more light emitting layers to allow the two or more light emitting layers included in the organic light emitting diode to be capable of emitting light.

The charge generating layer according to an exemplary embodiment of the present specification includes an n-type organic light emitting layer and a p-type organic material layer, and the n-type organic material layer is the above-described second electron transporting layer.

When the n-type organic material layer is not used in the charge generating layer, holes and electrons are not effectively produced, so that there may occur a problem in that a part of two or more light emitting layers do not emit light. When a second electron transporting layer is used as an n-type organic material layer according to an exemplary embodiment of the present specification, electrons and holes are effectively produced from the charge generating layer, and thus, an efficient light emission may be expected from two or more light emitting layers.

The NP junction in the present specification may mean not only physical contact of the second electron transporting layer, which is an n-type organic material layer, with the p-type organic material layer, but also interaction which may easily generate and transport holes and electrons.

According to an exemplary embodiment of the present specification, when an NP junction is formed, holes or electrons may be easily formed by an external voltage or a light source. Accordingly, it is possible to prevent a driving voltage for injecting holes from being increased.

In an exemplary embodiment of the present specification, the p-type organic material layer includes one or two or more compounds selected from the group consisting of the following Formulae 7 to 9.

[Formula 7]

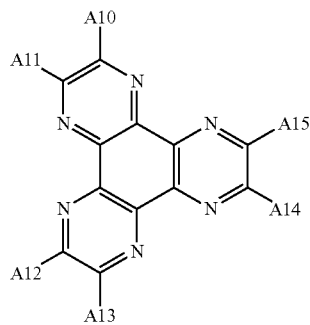

In Formula 7,

A10 to A15 are the same as or different from each other, and each independently hydrogen; a nitrile group; a nitro group; an amide group; a carbonyl group; a substituted or unsubstituted sulfonyl group; a substituted or unsubstituted ester group; a substituted or unsubstituted alkyl group; a substituted or unsubstituted alkenyl group; a substituted or unsubstituted aryl group; or a substituted or unsubstituted heterocyclic group, or combine with an adjacent group to form a substituted or unsubstituted hydrocarbon ring or a substituted or unsubstituted hetero ring,

[Formula 8]

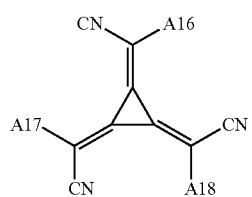

in Formula 8,

A16 to A18 are the same as or different from each other, and each independently an aryl group, which is unsubstituted or substituted with one or two or more substituents selected from the group consisting of a cyano group, a halogen group, and a haloalkyl group; or a heterocyclic group, which is unsubstituted or substituted with one or two or more substituents selected from the group consisting of a cyano group, a halogen group, and a haloalkyl group, and

[Formula 9]

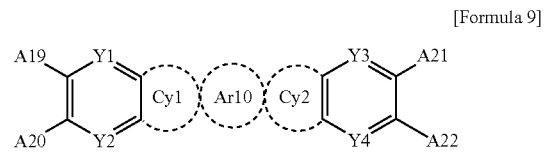

in Formula 9,

Ar10 is a substituted or unsubstituted hydrocarbon ring; or a substituted or unsubstituted hetero ring, Y1 to Y4 are the same as or different from each other, and each independently N; or CA23, A19 to A23 are the same as or different from each other, and each independently hydrogen; a nitrile group; a halogen group; a substituted or unsubstituted alkyl group; a substituted or unsubstituted alkoxy group; a substituted or unsubstituted aryloxy group; a substituted or unsubstituted aryl group; or a substituted or unsubstituted heterocyclic group, or combine with an adjacent group to form a substituted or unsubstituted hydrocarbon ring or a substituted or unsubstituted hetero ring, Cy1 and Cy2 are the same as or different from each other, and each independently any one of the following structures, and

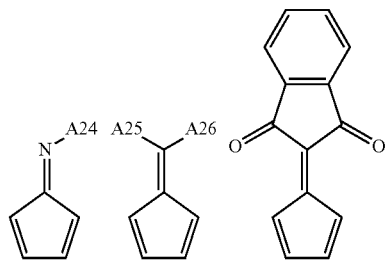

A24 to A26 are the same as or different from each other, and each independently a nitrile group; a substituted or unsubstituted ester group; or a substituted or unsubstituted trifluoroalkyl group.

In an exemplary embodiment of the present specification, the p-type organic material layer includes only a compound of Formula 7.

In another exemplary embodiment, Formula 8 is used as a p-type dopant. Accordingly, a p-type organic material layer including Formula 8 may be used together with a general hole transporting material.

In still another exemplary embodiment, Formula 9 is used as a p-type dopant. Accordingly, a p-type organic material layer including Formula 9 may be used together with a general hole transporting material.

According to an exemplary embodiment of the present specification, when the second electron transporting layer is included as an n-type organic material layer of the charge generating layer and an organic material layer including one or two or more compounds selected from the group consisting of Formulae 7 to 9 is included as a p-type organic material layer of the charge generating layer, electrons and holes are effectively produced from the charge generating layer, so that the light emitting efficiency of two or more light emitting layers, which are used in a tandem structure, may be excellent.

In an exemplary embodiment of the present specification, A10 to A15 are the same as or different from each other, and each independently a nitrile group; a nitro group; a substituted or unsubstituted sulfonyl group ($SO_2R$); a substituted or unsubstituted alkenyl group; or a substituted or unsubstituted aryl group.

R means a substituted or unsubstituted aryl group.

In another exemplary embodiment, A10 to A15 are each an alkenyl group substituted with a nitrile group.

In another exemplary embodiment of the present specification, A10 to A15 are each a nitro group; or an aryl group substituted with a nitrile group.

In another exemplary embodiment, A10 to A15 are each a nitro group; or a phenyl group substituted with a nitrile group.

In an exemplary embodiment of the present specification, the compound represented by Formula 7 may be represented by any one of the following Formulae 7-1 to 7-6.

Formula 7-1
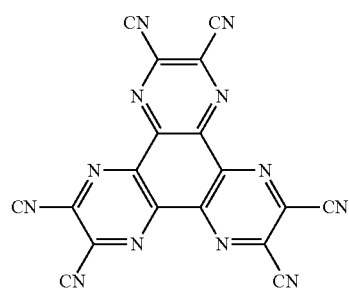

Formula 7-2
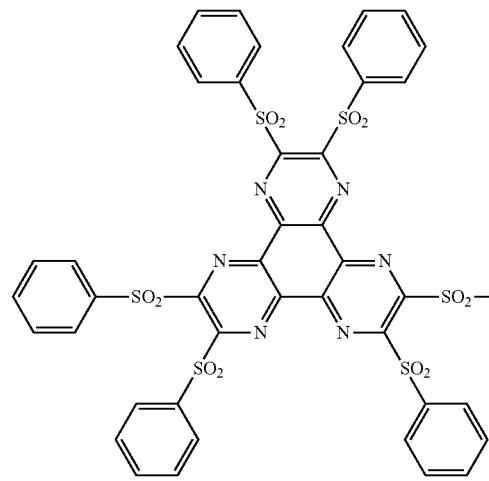

Formula 7-3
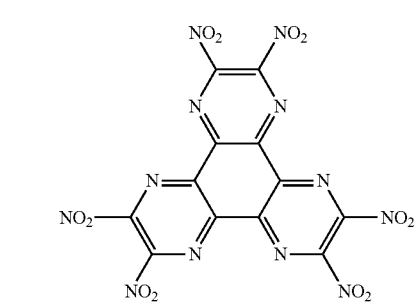

Formula 7-4
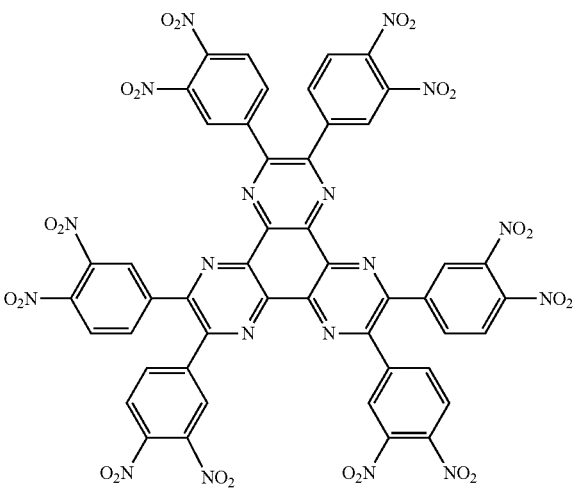

Formula 7-5
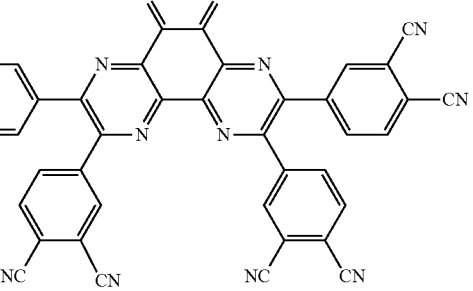

Formula 7-6
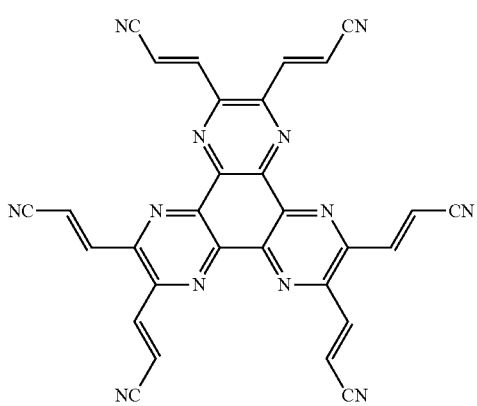

In an exemplary embodiment of the present specification, the p-type organic material layer includes Formula 7-1.

In an exemplary embodiment of the present specification, A16 to A18 are the same as or different from each other, and each independently a phenyl group; a naphthyl group; a pyridine group; a pyrazine group; a pyrimidine group; a quinoline group; or an isoquinoline group, and the phenyl group; the naphthyl group; the pyridine group; the pyrazine group; the pyrimidine group; the quinoline group; and the isoquinoline group may be unsubstituted or substituted with one or two or more substituents selected from the group consisting of a cyano group, a halogen group, and a haloalkyl group.

In an exemplary embodiment of the present specification, A1 to A3 are the same as or different from each other, and each independently a phenyl group substituted with fluorine and a cyano group.

In an exemplary embodiment of the present specification, the compound represented by Formula 8 is represented by the following Formula 8-1.

[Formula 8-1]

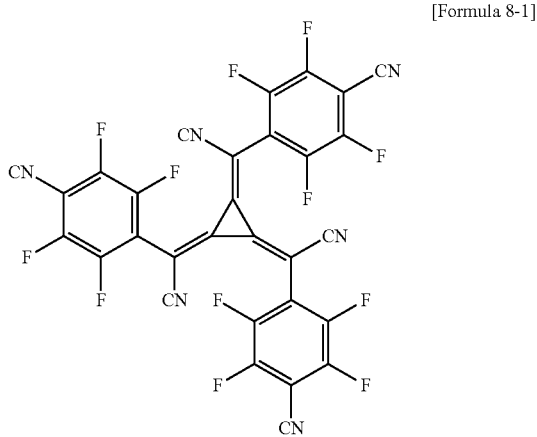

In another exemplary embodiment of the present specification, the p-type organic material layer includes a generally used hole transporting material and Formula 8-1.

In another exemplary embodiment, the p-type organic material layer includes NPB and Formula 8-1.

In an exemplary embodiment of the present specification, Ar10 is a substituted or unsubstituted benzene ring; or a substituted or unsubstituted naphthalene ring.

In another exemplary embodiment, Ar10 is a benzene ring.

In an exemplary embodiment of the present specification, Ar10 is a naphthalene ring.

In an exemplary embodiment of the present specification, Y1 to Y4 are the same as or different from each other, and each independently CA23.

In an exemplary embodiment of the present specification, A19 to A22 are the same as or different from each other, and each independently hydrogen; a halogen group; a substituted or unsubstituted alkyl group; a substituted or unsubstituted alkoxy group; or a substituted or unsubstituted aryl group.

In an exemplary embodiment of the present specification, A19 to A22 are the same as or different from each other, and each independently hydrogen; fluorine; a trifluoroalkyl group; or a trifluoroalkoxy group; or an aryl group substituted once or twice or more with a substituent selected from the group consisting of a halogen group and a trifluoroalkyl group.

In an exemplary embodiment of the present specification, A20 is hydrogen.

In another exemplary embodiment, A22 is hydrogen.

In an exemplary embodiment of the present specification, A19 is a substituted or unsubstituted aryl group.

In another exemplary embodiment, A19 is an aryl group substituted once or twice or more with a substituent selected from the group consisting of a halogen group and a trifluoroalkyl group.

In one exemplary embodiment, A19 is a phenyl group substituted once or twice or more with a substituent selected from the group consisting of fluorine and a trifluoromethyl group.

In an exemplary embodiment of the present specification, A19 is a phenyl group substituted with a trifluoromethyl group.

In another exemplary embodiment, A19 is a phenyl group substituted with fluorine.

In an exemplary embodiment of the present specification, A19 is a halogen group.

In another exemplary embodiment, A19 is fluorine.

In an exemplary embodiment of the present specification, A19 is an alkoxy group substituted with a trifluoroalkyl group.

In another exemplary embodiment, A19 is a trifluoromethyloxy group.

In an exemplary embodiment of the present specification, A20 is a substituted or unsubstituted aryl group.

In another exemplary embodiment, A20 is an aryl group substituted once or twice or more with a substituent selected from the group consisting of a halogen group and a trifluoroalkyl group.

In one exemplary embodiment, A20 is a phenyl group substituted once or twice or more with a substituent selected from the group consisting of fluorine and a trifluoromethyl group.

In an exemplary embodiment of the present specification, A20 is a phenyl group substituted with a trifluoromethyl group.

In another exemplary embodiment, A20 is a phenyl group substituted with fluorine.

In an exemplary embodiment of the present specification, A20 is a halogen group.

In another exemplary embodiment, A20 is fluorine.

In an exemplary embodiment of the present specification, A20 is an alkoxy group substituted with a trifluoroalkyl group.

In another exemplary embodiment, A20 is a trifluoromethyloxy group.

In an exemplary embodiment of the present specification, Cy1 is

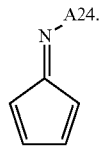

In another exemplary embodiment, Cy2 is

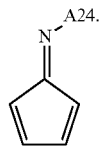

In an exemplary embodiment of the present specification, A24 is a nitrile group.

In an exemplary embodiment of the present specification, Cy1 is

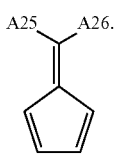

In an exemplary embodiment of the present specification, Cy2 is

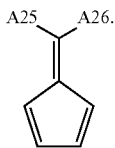

In another exemplary embodiment, A25 and A26 are the same as each other, and each independently a nitrile group. In an exemplary embodiment of the present specification, A23 is hydrogen.

In an exemplary embodiment of the present specification, the compound represented by Formula 9 is represented by the following Formulae 9-1 to 9-7.

Formula 9-1

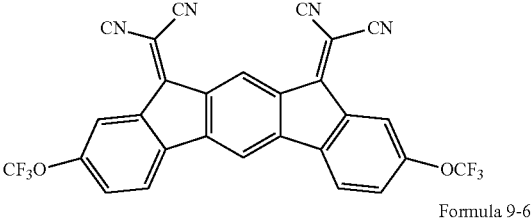

Formula 9-2

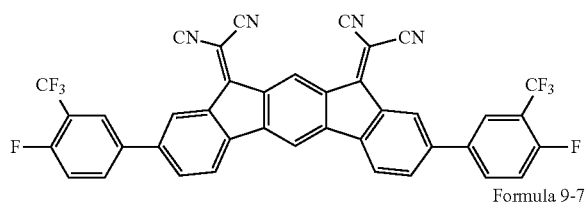

Formula 9-3

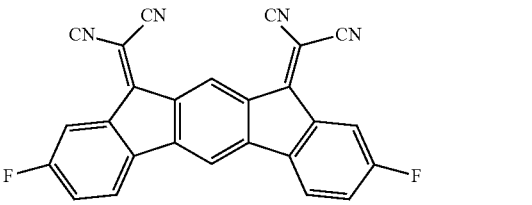

Formula 9-4

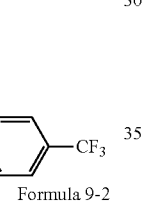

Formula 9-5

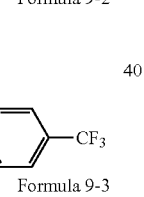

Formula 9-6

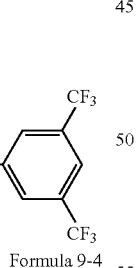

Formula 9-7

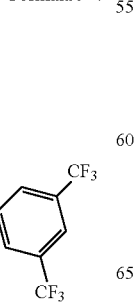

The organic light emitting diode according to an exemplary embodiment of the present specification includes a first electron transporting layer including the above-described heterocyclic compound represented by Formula 1 between a cathode and a light emitting layer, and may be manufactured by materials and methods known in the art, except that the first electron transporting layer and a second electron transporting layer including the compound represented by Formulae 3 to 5 are provided.

For example, the organic light emitting diode of the present specification may be manufactured by sequentially stacking an anode, an organic material layer, and a cathode on a substrate. In this case, the organic light emitting diode may be manufactured by depositing a metal or a metal oxide having conductivity, or an alloy thereof on a substrate to form an anode by using a physical vapor deposition (PVD) method such as sputtering or e-beam evaporation, forming an organic material layer including a hole injection layer, a hole transporting layer, an electron blocking layer, a light emitting layer, an electron transporting layer, and an electron injection layer thereon, and then depositing a material which may be used as a cathode thereon. In addition to the method described above, an organic light emitting diode may be made by subsequently depositing a cathode material, an organic material layer, and an anode material on a substrate. In addition to the method described above, an organic light emitting diode may be made by subsequently depositing an anode material, an organic material layer, and a cathode material on a substrate.

The organic material layer of the organic light emitting diode of the present specification may be composed of a multi-layered structure in which an organic material layer having one or more layers is stacked.

In an exemplary embodiment of the present specification, the organic light emitting diode may further include one or more layers selected from the group consisting of a hole injection layer, a hole transporting layer, an electron transporting layer, an electron injection layer, an electron blocking layer, and a hole blocking layer.

For example, the structure of the organic light emitting diode of the present specification may have the same structures as those illustrated in FIGS. 1 to 4, but is not limited thereto.

FIG. 1 illustrates the structure of an organic light emitting diode in which an anode 201, a hole transporting layer 301, a light emitting layer 401, a first electron transporting layer 501, a second electron transporting layer 601, and a cathode 701 are sequentially stacked on a substrate 101.

In FIG. 1, the heterocyclic compound represented by Formula 1 is included in the first electron transporting layer 501, and one or more of the compounds represented by Formulae 3 to 5 and a metal dopant are included in the second electron transporting layer 601.

FIG. 2 illustrates the structure of a tandem-type organic light emitting diode in which an anode 201, a hole transporting layer 301, a first light emitting layer 401, a first electron transporting layer 501, a second electron transporting layer 601, a p-type organic material layer 801, a second light emitting layer 402, and a cathode 701 are sequentially stacked on a substrate 101.

In FIG. 2, the heterocyclic compound represented by Formula 1 is included in the first electron transporting layer 501, and one or more of the compounds represented by Formulae 3 to 5 and a metal dopant are included in the second electron transporting layer 601. Further, the second electron transporting layer 601 and the p-type organic material layer 801 may constitute a charge generating layer 901.

FIG. 3 illustrates the structure of a tandem-type organic light emitting diode in which an anode 201, a hole injection layer 1001, a first hole transporting layer 301, a first light emitting layer 401, a first electron transporting layer 501, a second electron transporting layer 601, a p-type organic material layer 801, a second hole transporting layer 302, a second light emitting layer 402, an electron transporting layer 1101, and a cathode 701 are sequentially stacked on a substrate 101.

In FIG. 3, the heterocyclic compound represented by Formula 1 is included in the first electron transporting layer 501, and one or more of the compounds represented by Formulae 3 to 5 and a metal dopant are included in the second electron transporting layer 601. In addition, the second electron transporting layer 601 and the p-type organic material layer 801 may constitute a charge generating layer 901.

Furthermore, the materials for the first hole transporting layer 301 and the second hole transporting layer 302 may be the same as or different from each other. FIG. 4 is a view describing a diode in which charge generating layers 901 and 902 are stacked in two or more layers, and illustrates the structure of a tandem-type organic light emitting diode in which an anode 201, a hole injection layer 1001, a first hole transporting layer 301, a first light emitting layer 401, a first electron transporting layer 501, a second electron transporting layer 601, a first p-type organic material layer 801, a second hole transporting layer 302, a second light emitting layer 402, a first electron transporting layer 502, a second electron transporting layer 602, a second p-type organic material layer 802, a third hole transporting layer 303, a third light emitting layer 403, an electron transporting layer 1101, and a cathode 701 are sequentially stacked on a substrate 101.

In FIG. 4, the heterocyclic compound represented by Formula 1 is included in the first electron transporting layers 501 and 502, and one or more of the compounds represented by Formulae 3 to 5 and a metal dopant are included in the second electron transporting layers 601 and 602. Further, the second electron transporting layers 601 and 602 and the p-type organic material layers 801 and 802 may constitute a first charge generating layer 901 and a second charge generating layer 902, respectively.

The materials for the first hole transporting layer 301, the second hole transporting layer 302, and the third hole transporting layer 303 may be the same as or different from each other, and the materials for the first p-type organic material layer 801 and the second p-type organic material layer 802 may be the same as or different from each other.

FIGS. 1 to 4 illustrate exemplified structures according to exemplary embodiments of the present specification, and the structure is not limited thereto.

When the organic light emitting diode includes a plurality of organic material layers, the organic material layer may be formed of the same material or different materials.

As the anode material, a material having a large work function is usually preferred so as to smoothly inject holes into an organic material layer. Examples of an anode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly(3-methylthiophene), poly[3,4-(ethylene-1,2-dioxy)thiophene] (PEDOT), polypyrrole, and polyaniline, and the like, but are not limited thereto.

As the cathode material, a material having a small work function is usually preferred so as to smoothly inject electrons into an organic material layer. Specific examples of a cathode material include: a metal, such as magnesium, calcium, sodium, potassium, titanium, indium, yttrium, lithium, gadolinium, aluminum, silver, tin, or lead, or alloys thereof; a multi-layered structural material, such as LiF/Al or $LiO_2$/Al, and the like, but are not limited thereto.

As the hole injection material, a compound is preferred, in which the hole injection material has a capability of transporting holes to a layer which injects holes from an electrode, and thus has an effect of injecting holes at the anode and an excellent effect of injecting holes for the light emitting layer or the light emitting material, prevents excitons produced from the light emitting layer from moving to an electron injection layer or an electron injection material, and has excellent capability of forming a thin film. It is preferred that the highest occupied molecular orbital (HOMO) of the hole injection material is between the work function of the anode material and the HOMO of the organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The hole transporting layer is a layer which receives holes from the hole injection layer and transports holes to the light emitting layer, and a hole transporting material is suitably a material which may receive holes from an anode or a hole injection layer and may transfer holes to a light emitting layer, and has a large mobility for the holes. Specific examples thereof include an arylamine-based organic material, an electrically conductive polymer, a block copolymer in which a conjugate portion and a non-conjugate portion are present together, and the like, but are not limited thereto.

The light emitting material is a material which may receive holes and electrons from the hole transporting layer and the electron transporting layer, respectively, and combine the holes and the electrons to emit light in a visible ray region, and is preferably a material having good quantum efficiency to fluorescence or phosphorescence. Specific examples thereof comprise a 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but are not limited thereto.

The light emitting layer may include a host material and a dopant material. Examples of the host material include a condensed aromatic ring derivative, or a hetero ring-containing compound, and the like. Specifically, examples of the condensed aromatic ring derivative include an anthracene derivative, a pyrene derivative, a naphthalene derivative, a pentacene derivative, a phenanthrene compound, a fluoranthene compound, and the like, and examples of the hetero ring-containing compound include a carbazole derivative, a dibenzofuran derivative, a ladder-type furan compound, a pyrimidine derivative, and the like, but are not limited thereto.

In the fluorescence light emitting layer, as the host material, one or two or more are selected from the group consisting of distyrylarylene (DSA), a distyrylarylene derivative, distyrylbenzene (DSB), a distyrylbenzene derivative, 4,4'-bis(2,2'-diphenyl vinyl)-1,1'-biphenyl (DPVBi), a DPVBi derivative, spiro-DPVBi, and spiro-6P.

In the fluorescence light emitting layer, as the dopant material, one or two or more are selected from the group consisting of styrylamine-based, pherylene-based, and distyrylbiphenyl (DSBP)-based dopant materials.

The electron injection layer is a layer which injects electrons from an electrode, and a compound is preferred, which has a capability of transporting electrons, has an effect of injecting electrons from a cathode and an excellent effect of injecting electrons into a light emitting layer or a light emitting material, prevents excitons produced from the light emitting layer from moving to the hole injection layer, and is also excellent in capability of forming a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone and derivatives thereof, a metal complex compound, a nitrogen-containing 5-membered derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The hole blocking layer is a layer which blocks holes from reaching a cathode, and may be generally formed under the same conditions as those of the hole injection layer. Specific examples thereof include an oxadiazole derivative or a triazole derivative, a phenanthroline derivative, BCP, an aluminum complex, and the like, but are not limited thereto.

The organic light emitting diode according to the present specification may be a top emission type, a bottom emission type, or a dual emission type according to the material to be used.

In addition, the organic light emitting diode according to the present specification may be a normal type in which a lower electrode is an anode and an upper electrode is a cathode, and may also be an inverted type in which a lower electrode is a cathode and an upper electrode is an anode.

The structure according to an exemplary embodiment of the present specification may be operated by a principle which is similar to the principle applied to an organic light emitting diode, even in an organic electronic diode including an organic solar cell, an organic photoconductor, an organic transistor, and the like.

Mode for Invention

Hereinafter, the present specification will be described in detail with reference to Examples for specifically describing the present specification. However, the Examples according to the present specification may be modified in various forms, and it is not interpreted that the scope of the present specification is limited to the Examples described below in detail. The Examples of the present specification are provided for more completely explaining the present specification to the person with ordinary skill in the art.

Example 1

The values of the HOMO energy level and the triplet energy ($E_T$) of the heterocyclic compound represented by Formula 1 according to an exemplary embodiment of the present specification, and the following Formulae ET-A and ET-B are shown in the following Table 1.

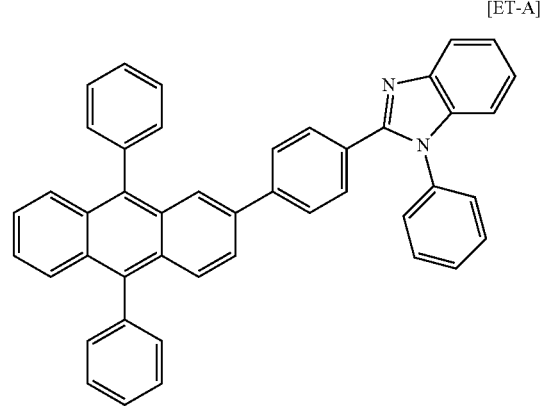

[ET-A]

-continued

[ET-B]

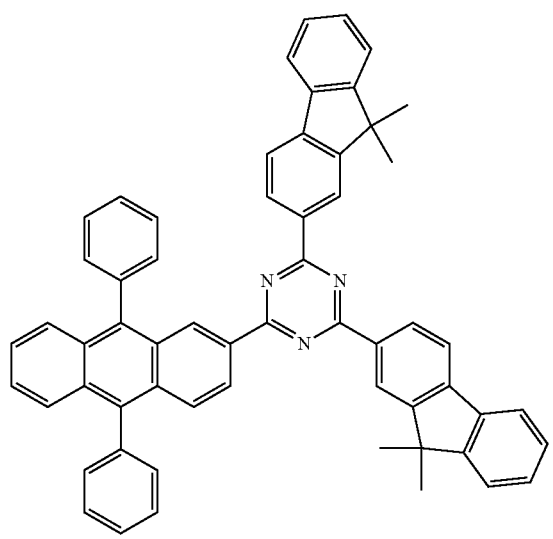

In the Examples of the present specification, the HOMO level was measured by using an atmospheric pressure photoelectron spectrometer AC3 (manufactured by RIKEN KEIKI Co., Ltd.).

Further, the triplet energy ($E_T$) was calculated by using a quantum chemical calculation program Gaussian 03 manufactured by U.S. Gaussian Corporation, and a density functional theory (DFT) was used and the calculated value of the triplet energy was obtained by the time-dependent-density functional theory (TD-DFT) with respect to a structure optimized using B3LYP as a functional and 6-31G* as a basis function.

TABLE 1

| Formula | HOMO (eV) | $E_T$ (eV) |
|---|---|---|
| 1-1 | 6.45 | 2.80 |
| 1-6 | 6.37 | 2.62 |
| 1-8 | 6.38 | 2.78 |
| 1-30 | 6.44 | 2.62 |
| 1-32 | 6.43 | 2.78 |
| 1-54 | 6.35 | 2.62 |
| 1-92 | 6.30 | 2.46 |
| 1-102 | 6.27 | 2.46 |
| 1-116 | 6.29 | 2.57 |
| 1-128 | 6.32 | 2.47 |
| 1-138 | 6.29 | 2.47 |
| 1-160 | 6.37 | 2.79 |
| 1-229 | 6.32 | 2.57 |
| 1-237 | 6.28 | 2.46 |
| 1-279 | 6.31 | 2.46 |
| 2-5 | 6.22 | 2.62 |
| 2-6 | 6.25 | 2.70 |
| 2-28 | 6.32 | 2.71 |
| 2-141 | 6.15 | 2.43 |
| 2-269 | 6.13 | 2.44 |
| 2-282 | 6.19 | 2.45 |
| ET-A | 5.71 | 1.64 |
| ET-B | 5.75 | 1.64 |

Example 2

The dipole moment values of the heterocyclic compound represented by Formula 1 according to an exemplary embodiment of the present specification are shown in Table 2.

TABLE 2

| Formula | Dipole moment (Debye) |
|---|---|
| 1-6 | 0.85 |
| 1-8 | 0.51 |
| 1-30 | 0.8 |

Example 1-1

A glass substrate thinly coated with indium tin oxide (ITO) to have a thickness of 500 Å was put into distilled water in which a detergent was dissolved, and ultrasonically washed. In this case, a product manufactured by Fischer Co. was used as the detergent, and distilled water twice filtered using a filter manufactured by Millipore Co. was used as the distilled water. After the ITO was washed for 30 minutes, ultrasonic washing was conducted twice using distilled water for 10 minutes. After the washing using distilled water was completed, ultrasonic washing was conducted using isopropyl alcohol, acetone, and methanol solvents, and drying was conducted, and then the product was transported to a plasma washing machine. In addition, the substrate was washed using oxygen plasma for 5 min, and then transported to a vacuum evaporator.

The following Formula [HAT] was thermally vacuum deposited to a thickness of 50 Å on a transparent ITO electrode, which was prepared as described above, thereby forming a hole injection layer. The following Formula [NPB] was vacuum deposited to have a thickness of 1,100 Å on the hole injection layer, thereby forming a hole transporting layer. The following Formula [HT-A] was vacuum deposited to have a thickness of 200 Å on the hole transporting layer, thereby forming an electron blocking layer.

Subsequently, the following Formulae [BH] and [BD] were vacuum deposited at a weight ratio of 25:1 to a film thickness of 350 Å on the electron blocking layer, thereby forming a light emitting layer.

Formula 1-1 and the following Formula [LiQ] were vacuum deposited at a weight ratio of 1:1 on the light emitting layer, thereby forming a first electron transporting layer having a thickness of 200 Å. Formula 3-1 and [Li] were vacuum deposited at a weight ratio of 100:1 on the first electron transporting layer, thereby forming a second electron transporting layer having a thickness of 100 Å.

Aluminum was deposited to have a thickness of 1,000 Å on the second electron transporting layer, thereby forming a cathode.

In the aforementioned procedure, the deposition rate of the organic material was maintained at 0.4 to 0.9 Å/sec, the deposition rate of lithium fluoride of the cathode was maintained at 0.3 Å/sec, and the deposition rate of aluminum was maintained at 2 Å/sec, and the degree of vacuum during the deposition was maintained at $1\times10^{-7}$ to $5\times10^{-8}$ torr, thereby manufacturing an organic light emitting diode.

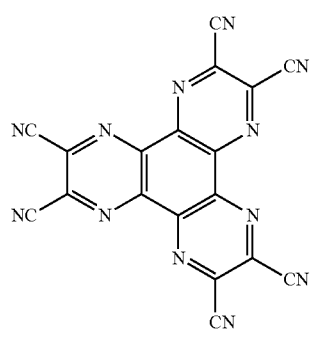
[HAT]
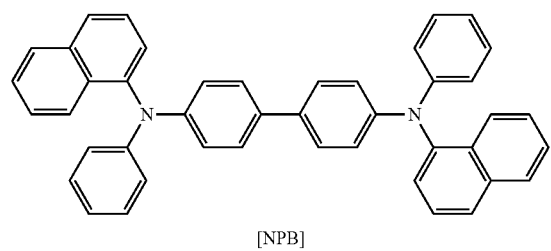
[NPB]
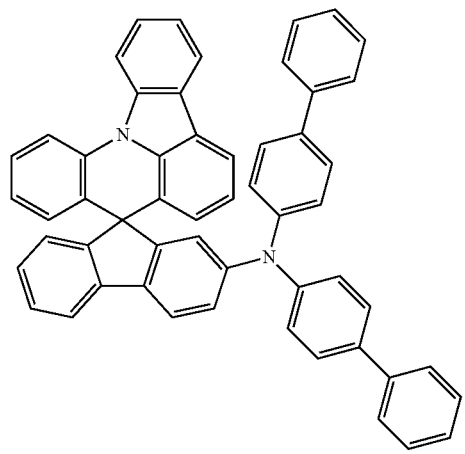
[HT-A]
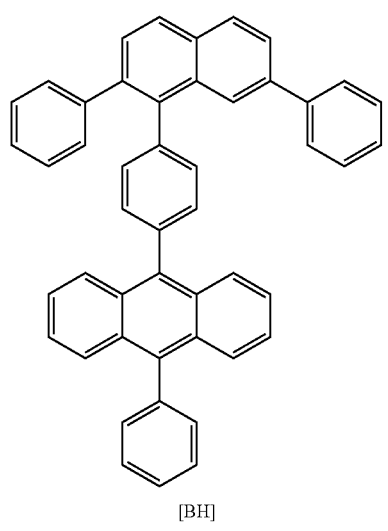
[BH]
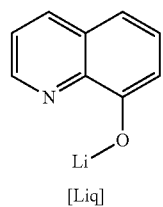
[Liq]
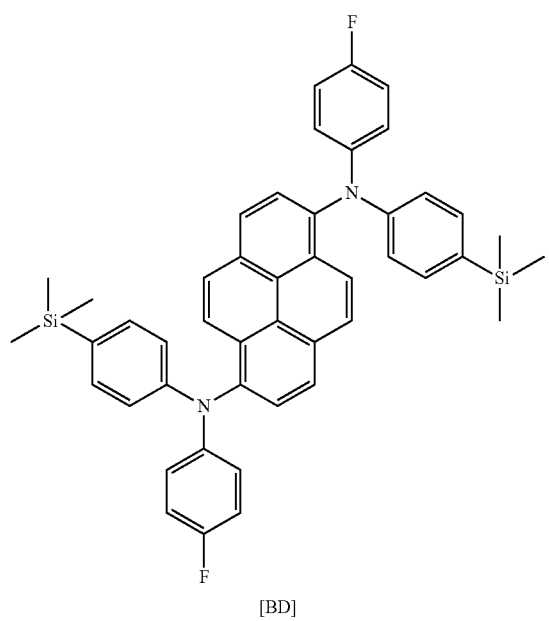
[BD]
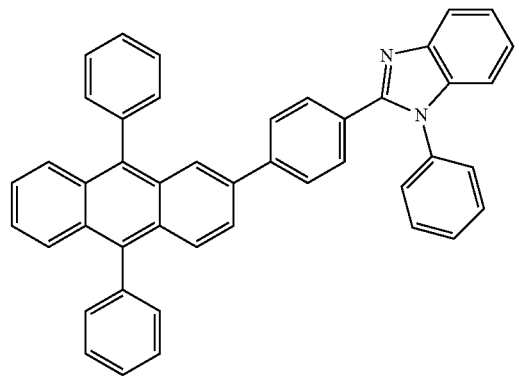
[ET-A]
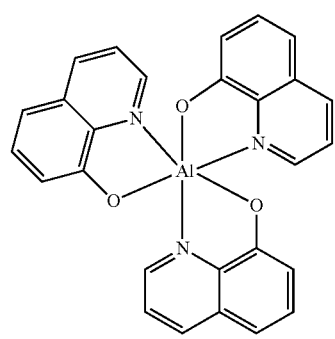
[Alq$_3$]

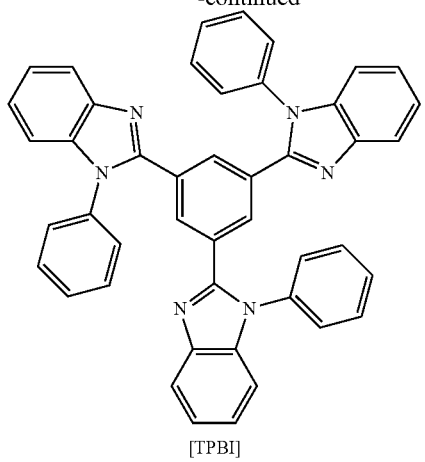

[TPBI]

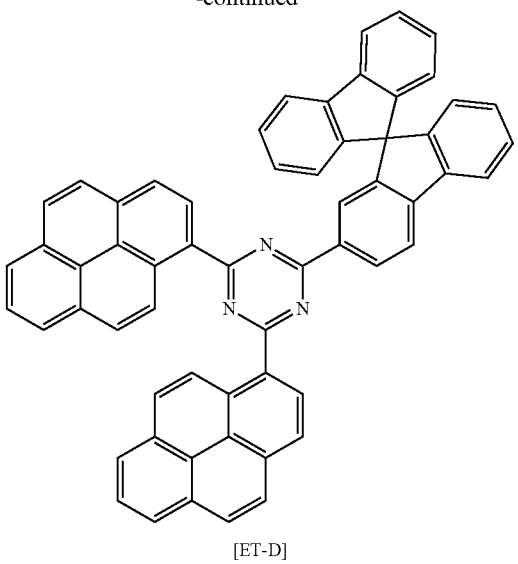

[ET-D]

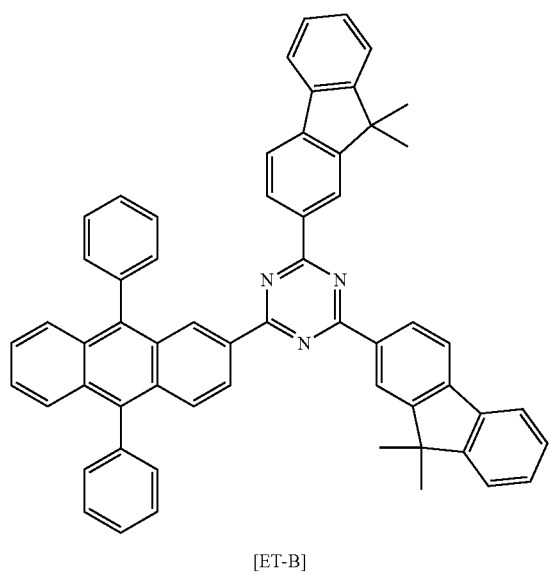

[ET-B]

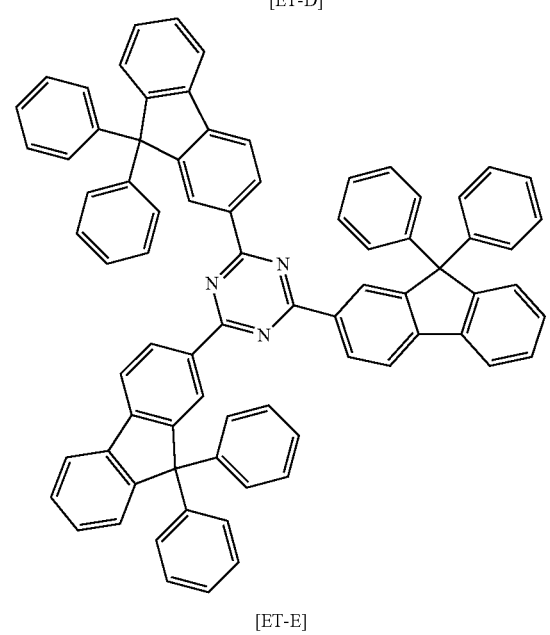

[ET-E]

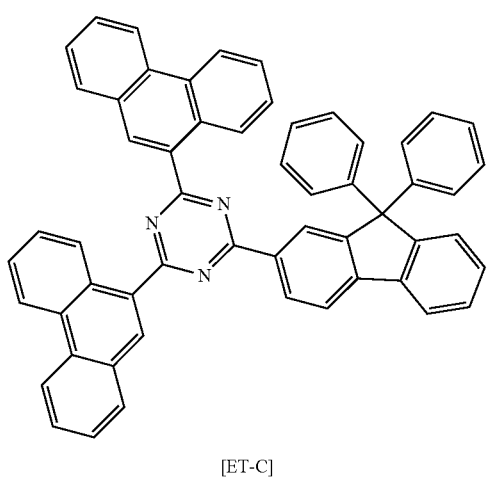

[ET-C]

Example 1-2

An organic light emitting diode was manufactured in the same manner as in [Example 1-1], except that [Formula 1-6] and [Formula 5-14] were used instead of [Formula 1-1] and [Formula 3-1] of [Example 1-1], respectively.

Example 1-3

An organic light emitting diode was manufactured in the same manner as in [Example 1-1], except that [Formula 1-30] and [Formula 3-16] were used instead of [Formula 1-1] and [Formula 3-1] of [Example 1-1], respectively.

Example 1-4

An organic light emitting diode was manufactured in the same manner as in [Example 1-1], except that [Formula 1-32] and [Formula 4-2] were used instead of [Formula 1-1] and [Formula 3-1] of [Example 1-1], respectively.

Example 1-5

An organic light emitting diode was manufactured in the same manner as in [Example 1-1], except that [Formula 1-54] and [Formula 3-32] were used instead of [Formula 1-1] and [Formula 3-1] of [Example 1-1], respectively.

Example 1-6

An organic light emitting diode was manufactured in the same manner as in [Example 1-1], except that [Formula 1-92] and [Formula 3-32] were used instead of [Formula 1-1] and [Formula 3-1] of [Example 1-1], respectively.

Example 1-7

An organic light emitting diode was manufactured in the same manner as in [Example 1-1], except that [Formula 1-102] and [Formula 4-35] were used instead of [Formula 1-1] and [Formula 3-1] of [Example 1-1], respectively.

Example 1-8

An organic light emitting diode was manufactured in the same manner as in [Example 1-1], except that [Formula 1-138] and [Formula 4-3] were used instead of [Formula 1-1] and [Formula 3-1] of [Example 1-1], respectively.

Example 1-9

An organic light emitting diode was manufactured in the same manner as in [Example 1-1], except that [Formula 1-160] was used instead of [Formula 1-1] of [Example 1-1].

Example 1-10

An organic light emitting diode was manufactured in the same manner as in [Example 1-1], except that [Formula 1-237] and [Formula 4-2] were used instead of [Formula 1-1] and [Formula 3-1] of [Example 1-1], respectively.

Example 1-11

An organic light emitting diode was manufactured in the same manner as in [Example 1-1], except that [Formula 2-5] and [Formula 3-15] were used instead of [Formula 1-1] and [Formula 3-1] of [Example 1-1], respectively.

Example 1-12

An organic light emitting diode was manufactured in the same manner as in [Example 1-1], except that [Formula 2-6] and [Formula 5-32] were used instead of [Formula 1-1] and [Formula 3-1] of [Example 1-1], respectively.

Example 1-13

An organic light emitting diode was manufactured in the same manner as in [Example 1-1], except that [Formula 2-28] and [Formula 5-14] were used instead of [Formula 1-1] and [Formula 3-1] of [Example 1-1], respectively.

Example 1-14

An organic light emitting diode was manufactured in the same manner as in [Example 1-1], except that [Formula 2-141] and [Formula 3-22] were used instead of [Formula 1-1] and [Formula 3-1] of [Example 1-1], respectively.

Example 1-15

An organic light emitting diode was manufactured in the same manner as in [Example 1-1], except that [Formula 2-269] and [Formula 5-10] were used instead of [Formula 1-1] and [Formula 3-1] of [Example 1-1], respectively.

Example 1-16

An organic light emitting diode was manufactured in the same manner as in [Example 1-1], except that [Formula 2-282] and [Formula 4-3] were used instead of [Formula 1-1] and [Formula 3-1] of [Example 1-1], respectively.

Example 1-17

An organic light emitting diode was manufactured in the same manner as in [Example 1-2], except for [Liq] of [Example 1-2].

Example 1-18

An organic light emitting diode was manufactured in the same manner as in [Example 1-2], except that [Formula 3-1] was used instead of [Formula 5-14] of [Example 1-2].

Example 1-19

An organic light emitting diode was manufactured in the same manner as in [Example 1-2], except that [Formula 4-2] was used instead of [Formula 5-14] of [Example 1-2].

Example 1-20

An organic light emitting diode was manufactured in the same manner as in [Example 1-2], except that [Formula 1-8] was used instead of [Formula 1-6] of [Example 1-2].

Comparative Example 1-1

An organic light emitting diode was manufactured in the same manner as in [Example 1-1], except that [Formula 3-1] was used instead of [Formula 1-1] of [Example 1-1].

Comparative Example 1-2

An organic light emitting diode was manufactured in the same manner as in [Example 1-4], except that [Formula 4-2] was used instead of [Formula 1-32] of [Example 1-4].

Comparative Example 1-3

An organic light emitting diode was manufactured in the same manner as in [Example 1-2], except that [Formula 5-14] was used instead of [Formula 1-6] of [Example 1-2].

Comparative Example 1-4

An organic light emitting diode was manufactured in the same manner as in [Example 1-4], except for [Li] of [Example 1-4].

Comparative Example 1-5

An organic light emitting diode was manufactured in the same manner as in [Example 1-1], except that [Formula ET-A] was used instead of [Formula 1-1] of [Example 1-1].

Comparative Example 1-6

An organic light emitting diode was manufactured in the same manner as in [Example 1-1], except that [Formula Alq3] was used instead of [Formula 1-1] of [Example 1-1].

Comparative Example 1-7

An organic light emitting diode was manufactured in the same manner as in [Example 1-1], except that [Formula TPBI] was used instead of [Formula 1-1] of [Example 1-1].

Comparative Example 1-8

An organic light emitting diode was manufactured in the same manner as in [Example 1-1], except that [Formula ET-B] was used instead of [Formula 1-1] of [Example 1-1].

Comparative Example 1-9

An organic light emitting diode was manufactured in the same manner as in [Example 1-1], except that [Formula ET-C] was used instead of [Formula 1-1] of [Example 1-1].

Comparative Example 1-10

An organic light emitting diode was manufactured in the same manner as in [Example 1-4], except that [Formula ET-D] was used instead of [Formula 1-32] of [Example 1-4].

Comparative Example 1-11

An organic light emitting diode was manufactured in the same manner as in [Example 1-2], except that [Formula ET-E] was used instead of [Formula 1-6] of [Example 1-2].

Comparative Example 1-12

An organic light emitting diode was manufactured in the same manner as in [Example 1-1], except that [Formula 1-1] was used instead of [Formula 3-1] of [Example 1-1].

For the organic light emitting diodes manufactured by the above-described method, the driving voltage and the light emitting efficiency were measured at a current density of 10 mA/cm$^2$, and a time T90 for reaching a 90% value compared to the initial luminance was measured at a current density of 20 mA/cm$^2$. The results are shown in the following Table 3.

TABLE 3

| | Voltage (V) | Efficiency (Cd/A) | Color Coordinate (x, y) | Service life (h) T$_{90}$ at 20 mA/cm$^2$ |
|---|---|---|---|---|
| Example 1-1 | 4.32 | 6.42 | (0.138, 0.112) | 152 |
| Example 1-2 | 3.92 | 6.95 | (0.138, 0.110) | 192 |
| Example 1-3 | 4.27 | 6.66 | (0.138, 0.111) | 162 |
| Example 1-4 | 4.35 | 6.26 | (0.138, 0.113) | 155 |
| Example 1-5 | 4.22 | 6.53 | (0.138, 0.112) | 182 |
| Example 1-6 | 4.38 | 6.53 | (0.138, 0.112) | 157 |
| Example 1-7 | 4.51 | 6.22 | (0.138, 0.113) | 181 |
| Example 1-8 | 4.21 | 6.65 | (0.138, 0.113) | 192 |
| Example 1-9 | 4.57 | 6.32 | (0.138, 0.114) | 149 |
| Example 1-10 | 4.42 | 6.22 | (0.138, 0.112) | 171 |
| Example 1-11 | 4.26 | 6.58 | (0.138, 0.111) | 166 |
| Example 1-12 | 4.13 | 6.59 | (0.138, 0.111) | 170 |
| Example 1-13 | 4.10 | 6.77 | (0.138, 0.110) | 187 |
| Example 1-14 | 4.52 | 6.30 | (0.138, 0.114) | 199 |
| Example 1-15 | 4.02 | 6.69 | (0.138, 0.111) | 172 |
| Example 1-16 | 4.21 | 6.55 | (0.138, 0.112) | 182 |
| Example 1-17 | 4.05 | 6.75 | (0.138, 0.110) | 152 |
| Example 1-18 | 4.01 | 6.85 | (0.138, 0.110) | 176 |
| Example 1-19 | 4.06 | 6.71 | (0.138, 0.110) | 162 |
| Example 1-20 | 4.09 | 6.73 | (0.138, 0.111) | 172 |
| Comparative Example 1-1 | 4.75 | 5.32 | (0.138, 0.115) | 79 |
| Comparative Example 1-2 | 5.35 | 4.52 | (0.138, 0.114) | 142 |
| Comparative Example 1-3 | 4.92 | 5.20 | (0.138, 0.114) | 132 |
| Comparative Example 1-4 | 7.29 | 3.21 | (0.138, 0.115) | 59 |
| Comparative Example 1-5 | 4.95 | 5.50 | (0.138, 0.113) | 132 |
| Comparative Example 1-6 | 5.1 | 4.42 | (0.138, 0.115) | 95 |
| Comparative Example 1-7 | 4.79 | 5.20 | (0.138, 0.114) | 87 |
| Comparative Example 1-8 | 5.12 | 4.32 | (0.138, 0.115) | 112 |
| Comparative Example 1-9 | 4.72 | 5.52 | (0.138, 0.112) | 124 |
| Comparative Example 1-10 | 4.88 | 5.29 | (0.138, 0.114) | 92 |
| Comparative Example 1-11 | 4.50 | 5.79 | (0.138, 0.111) | 132 |
| Comparative Example 1-12 | 6.21 | 3.20 | (0.138, 0.115) | 53 |

From the result of Table 3, it can be confirmed that the compound represented by Formula 1 according to an exemplary embodiment of the present specification may be used as a first electron transporting layer of the organic light emitting diode, and the compound represented by Formula 3 to 5 according to an exemplary embodiment of the present specification may be used as a second electron transporting layer of the organic light emitting diode.

In particular, the compound represented by Formula 1 according to the present invention was excellent in thermal stability, and had a deep HOMO level of 6.0 eV or more, and high triplet energy ($E_T$) and hole stability, thereby exhibiting excellent characteristics. When the compound represented by Formula 1 is used in the first electron transporting layer, an alkali organic metal compound or an alkaline earth metal organic metal compound may be used in a mixture with an n-type dopant. Accordingly, the compound represented by Formula 1 has low driving voltage and high efficiency, and stability of the diode may be improved by hole stability of the compound.

As a result of Table 1, it can be confirmed that both the compounds represented by Formulae [ET-A] and [ET-B] have a triplet energy of less than 1.9 eV, and as a result of the Examples and the Comparative Examples of Table 3, it can be confirmed that a compound having a triplet energy of less than 2.2 eV has low diode efficiency. These results are because an effect of the triplet-triplet annihilation (TTA) is reduced when a compound having a triplet energy of less than 2.2 eV is used.

Further, it can be confirmed through Table 1 that the compounds represented by Formulae [ET-A] and [ET-B] have a HOMO level of less than 6 eV, and as a result of the evaluation of the diode of Table 3, it can be confirmed that the diode has a short service life when the diode includes the compound. The result as described above is exhibited because an effect of blocking holes transferred from the light emitting layer is reduced in the organic light emitting diode including the compound having a HOMO energy level of less than 6 eV.

Accordingly, it can be confirmed that even for the heterocyclic compound represented by Formula 1 according to an exemplary embodiment of the present invention, those having a HOMO energy level of 6 eV or more and a triplet energy of 2.2 eV are more preferred in terms of driving voltage, efficiency, and/or service life of the diode.

Further, according to the document (J. AM. CHEM. SOC. 2003, 125, 3710-3711), it can be confirmed that a disubstituted fluorenyl group has a higher electron mobility than that of a spirobifluorenyl group. Accordingly, it can be confirmed that the compound represented by Formula 1 may transport electrons more efficiently than Formula [ET-D] used in the Comparative Examples and thus exhibits high efficiency, and also improves the service life.

From the result of Table 3, it can be confirmed that the compound represented by Formula 1 is not suitable for the second electron transporting layer doped with a metal. For the second electron transporting layer doped with the metal, the compound represented by Formulae 3 to 5 instead of Formula 1 exhibited low driving voltage and high efficiency. The result described above may be exhibited because the unshared electron pair of a nitrogen atom or an oxygen atom of a phosphine oxide group of the compound represented by Formulae 3 to 5 may be effectively bonded to a metal, and thus a doping by a metal dopant effectively occurs. Accordingly, when a second electron transporting layer including the compound represented by Formulae 3 to 5 and an n-type dopant of a metal is used, electrons are smoothly transported and/or injected from the cathode, and an organic light emitting diode having low driving voltage may be provided.

Further, when the organic light emitting diode is driven, an unshared electron pair of a nitrogen atom or an oxygen atom of a phosphine oxide group may be bonded to metal to prevent metal from moving by a field applied to the organic material layer, thereby suppressing the driving voltage of the organic light emitting diode from being increased, and it is possible to implement an organic light emitting diode having a long service life.

Example 2-1

A glass substrate thinly coated with indium tin oxide (ITO) to have a thickness of 500 Å was put into distilled water in which a detergent was dissolved, and ultrasonically washed. In this case, a product manufactured by Fischer Co. was used as the detergent, and distilled water twice filtered using a filter manufactured by Millipore Co. was used as the distilled water. After the ITO was washed for 30 minutes, ultrasonic washing was conducted twice using distilled water for 10 minutes. After the washing using distilled water was completed, ultrasonic washing was conducted using isopropyl alcohol, acetone, and methanol solvents, and drying was conducted, and then the product was transported to a plasma washing machine. In addition, the substrate was washed using oxygen plasma for 5 minutes, and then transported to a vacuum evaporator.

Formula [HAT] was thermally vacuum deposited to have a thickness of 50 Å on a transparent ITO electrode, which was prepared as described above, thereby forming a hole injection layer. Formula [NPB] was vacuum deposited to have a thickness of 1,100 Å on the hole injection layer, thereby forming a hole transporting layer. Formula [HT-A] was vacuum deposited to have a thickness of 200 Å on the hole transporting layer, thereby forming an electron blocking layer.

Formulae [BH] and [BD] were vacuum deposited at a weight ratio of 25:1 to have a film thickness of 350 Å on the electron blocking layer, thereby forming a light emitting layer.

Formula 1-6 and Formula [LiQ] were vacuum deposited at a weight ratio of 1:1 on the light emitting layer, thereby forming a first electron transporting layer having a thickness of 200 Å. Formula 5-14 and [Ca] were vacuum deposited at a weight ratio of 97:3 on the first electron transporting layer, thereby forming a second electron transporting layer having a thickness of 100 Å.

Formula [HAT] was thermally vacuum deposited to have a thickness of 50 Å on the second electron transporting layer, thereby forming a p-type organic material layer. Formula [NPB] was vacuum deposited to have a thickness of 200 Å on the p-type organic material layer, thereby forming a hole transporting layer. Formula [HT-A] was vacuum deposited to have a thickness of 200 Å on the hole transporting layer, thereby forming an electron blocking layer.

The following Formulae [YGD] and [YGH] were vacuum deposited at a weight ratio of 1:13 to have a film thickness of 350 Å on the electron blocking layer, thereby forming a light emitting layer.

Formula 1-6 and Formula [LiQ] were vacuum deposited at a weight ratio of 1:1 on the light emitting layer, thereby forming a first electron transporting layer having a thickness of 200 Å. Formula 5-14 and Formula [Ca] were vacuum deposited at a weight ratio of 97:3 on the first electron transporting layer, thereby forming a second electron transporting layer having a thickness of 100 Å. Aluminum was deposited to have a thickness of 1,000 Å on the second electron transporting layer, thereby forming a cathode.

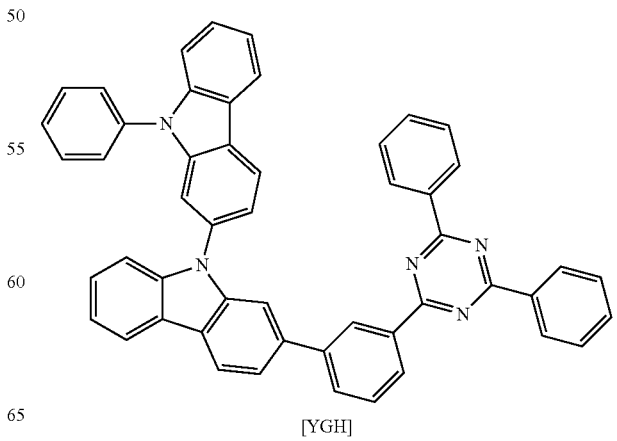

[YGH]

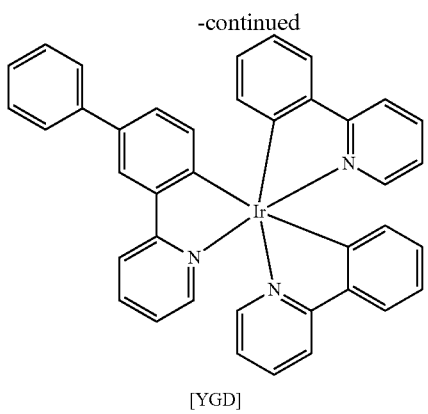

[YGD]

In the aforementioned procedure, the deposition rate of the organic material was maintained at 0.4 to 0.9 Å/sec, the deposition rate of lithium fluoride of the cathode was maintained at 0.3 Å/sec, and the deposition rate of aluminum was maintained at 2 Å/sec, and the degree of vacuum during the deposition was maintained at 1×10-7 to 5×10-8 torr, thereby manufacturing an organic light emitting diode.

Example 2-2

An organic light emitting diode was manufactured in the same manner as in [Example 2-1], except that [NPB] and [Formula 8-1] were deposited at a weight ratio of 95:5 and used instead of [HAT] of [Example 2-1].

Comparative Example 2-1

An organic light emitting diode was manufactured in the same manner as in [Example 2-1], except that [ET-A] was used instead of [Formula 1-6] of [Example 2-1].

Comparative Example 2-2

An organic light emitting diode was manufactured in the same manner as in [Example 2-1], except that [Formula 1-8] was used instead of [Formula 5-14] of [Example 2-1].

For the organic light emitting diodes manufactured by the above-described method, the driving voltage and the light emitting efficiency were measured at a current density of 10 mA/cm², and a time (T90) for reaching a 90% value compared to the initial luminance was measured at a current density of 20 mA/cm². The results are shown in the following Table 4.

TABLE 4

| | Voltage (V) | Efficiency (Cd/A) | Color Coordinate (x, y) | Service life (h) $T_{90}$ at 20 mA/cm² |
|---|---|---|---|---|
| Example 2-1 | 7.9 | 69.15 | (0.365, 0.389) | 251 |
| Example 2-2 | 7.8 | 70.15 | (0.365, 0.380) | 245 |
| Comparative Example 2-1 | 9.5 | 55.15 | (0.366, 0.401) | 152 |
| Comparative Example 2-2 | 13.2 | 28.0 | (0.369, 0.421) | 39 |

From the result of Table 4, it can be confirmed that the compound represented by Formula 1 according to an exemplary embodiment of the present specification may be used as a first electron transporting layer of the organic light emitting diode, and the compound represented by Formula 3 to 5 according to an exemplary embodiment of the present specification may be used as a second electron transporting layer of the organic light emitting diode.

In particular, the compound represented by Formula 1 according to the present invention was excellent in thermal stability, and had a deep HOMO level of 6.0 eV or more, and high triplet energy ($E_T$) and hole stability, thereby exhibiting excellent characteristics. When the compound represented by Formula 1 is used in the first electron transporting layer, an alkali organic metal compound or an alkaline earth metal organic metal compound may be used in a mixture with an n-type dopant. Accordingly, the compound represented by Formula 1 has low driving voltage and high efficiency, and stability of the diode may be improved by hole stability of the compound.

From the result of Table 4, it can be confirmed that when an NP junction is formed by using the compound represented by Formulae 3 to 5 as a second electron transporting layer, which is an n-type organic material layer, and the compound represented by Formulae 7 to 9 as a p-type organic material layer, electrons are smoothly produced from the p-type organic material layer to the second electron transporting layer, and thus it is possible to implement an organic light emitting diode having an effective tandem structure.

The invention claimed is:

1. An organic light emitting diode comprising:

a cathode;

an anode;

a light emitting layer provided between the cathode and the anode;

a first electron transporting layer comprising a heterocyclic compound represented by the following Formula 1 and provided between the cathode and the light emitting layer to be in physical contact with the light emitting layer; and a second electron transporting layer provided between the cathode and the first electron transporting layer, wherein the light emitting layer comprises a host and a dopant, and a difference between a HOMO energy level of the host and a HOMO energy level of the heterocyclic compound represented by Formula 1 is 0.2 eV or more, wherein the second electron transporting layer includes a host material including one or two or more of compounds represented by the following Formula 3, and one or two or more n-type dopants selected from alkali metals and alkaline earth metals, wherein the organic light emitting diode comprises two or more light emitting layers, and comprises a charge generating layer between two adjacent light emitting layers among the two or more light emitting layers, wherein the charge generating layer comprises the second electron transporting layer and a p-type organic material layer, and wherein the first electron transporting layer is provided between an adjacent light emitting layer among the two or more light emitting layers and the second electron transporting layer:

[Formula 1]

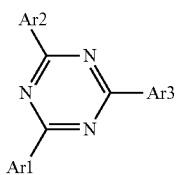

in Formula 1,
Ar1 to Ar3 are different from each other,
Ar1 and Ar2 are different from each other, and are each independently a phenyl group; a biphenyl group; a terphenyl group; a naphthyl group; or a phenanthryl group, which is unsubstituted or substituted with deuterium; a phenyl group; a naphthyl group; or a phenanthryl group,
Ar3 is represented by the following Formula 2,

[Formula 2]

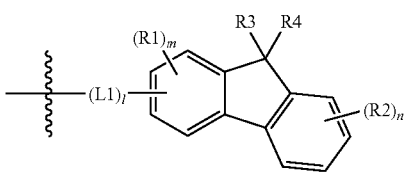

in Formula 2,
R1 and R2 are each independently hydrogen or deuterium, or optionally combine with an adjacent R1 or R2 respectively to form a fused benzene ring,
R3 and R4 are the same as or different from each other, and each independently hydrogen; deuterium; a C1 to C10 alkyl group; or a phenyl group,
L1 is a direct bond; a phenylene group unsubstituted or substituted with a deuterium; a divalent biphenyl group; a naphthylene group; or a phenanthrylene group,
l is an integer of 1 to 5,
m is an integer of 1 to 3,
n is an integer of 1 to 4,
when l, m, and n are each an integer of 2 or more, two or more structures in the parenthesis are the same as or different from each other,

[Formula 3]

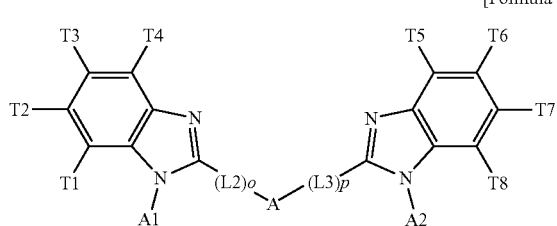

in Formula 3,
A1 and A2 are the same as or different from each other, and each independently an alkyl group having 1 to 10 carbon atoms; a phenyl group; a naphthyl group; or a fluorenyl group substituted with an alkyl group having 1 to 10 carbon atoms,
L2 and L3 are the same as or different from each other, and each independently a direct bond; a phenylene group unsubstituted or substituted with a phenyl group; a naphthylene group; or a divalent biphenyl group,
A is any one of the following substituted or unsubstituted structures,

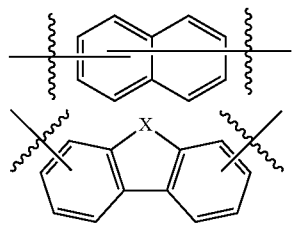

X is O; S; or CT12T13,
and p are an integer of 1 to 3, and
when o and p are an integer of 2 or more, two or more structures in the parenthesis are the same as or different from each other,
T1 to T8 are hydrogen,
T12 and T13 are the same as or different from each other, and each independently hydrogen or a C1 to C10 alkyl group.

2. The organic light emitting diode of claim 1, wherein the first electron transporting layer further comprises an n-type dopant represented by the following Formula 10:

[Formula 10]

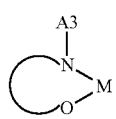

A3 is hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or substituted or unsubstituted heterocyclic group,
a curved line represents two or three carbon atoms required for forming a 5-membered or 6-membered ring having M, and each of the two or three carbon atoms are unsubstituted or substituted with one or two substituents having the same definition as A3, and
M is an alkali metal or an alkaline earth metal,
wherein the A3 on nitrogen atom and the substituents on the two or three carbon atoms in the curved line optionally combine with each other to form a fused ring, and
wherein the substituents on the two or three carbon atoms in the curved line optionally combine with each other to form a fused ring.

3. The organic light emitting diode of claim 2, wherein the n-type dopant represented by Formula 10 is represented by the following Formula 10-1 or 10-2:

[Formula 10-1]

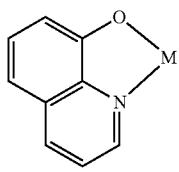

[Formula 10-2]

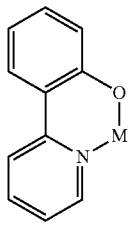

in Formulae 10-1 and 10-2,

M is the same as that defined in Formula 10, and

Formulae 10-1 and 10-2 are each independently unsubstituted or substituted with one or two or more substituents selected from the group consisting of hydrogen; deuterium; a halogen; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; and a substituted or unsubstituted heterocyclic group, or adjacent substituents combine with each other to form a substituted or unsubstituted hydrocarbon ring or a substituted or unsubstituted hetero ring.

4. The organic light emitting diode of claim 1, wherein a triplet energy of the heterocyclic compound represented by Formula 1 is 2.2 eV or more.

5. The organic light emitting diode of claim 1, wherein a dipole moment of the heterocyclic compound represented by Formula 1 is 2 debye or less.

6. The organic light emitting diode of claim 1, wherein an electron mobility of the heterocyclic compound represented by Formula 1 is $10^{-6}$ cm$^2$/Vs or more.

7. The organic light emitting diode of claim 1, wherein the heterocyclic compound represented by Formula 1 is represented by the following Formula 1-B:

[Formula 1-B]

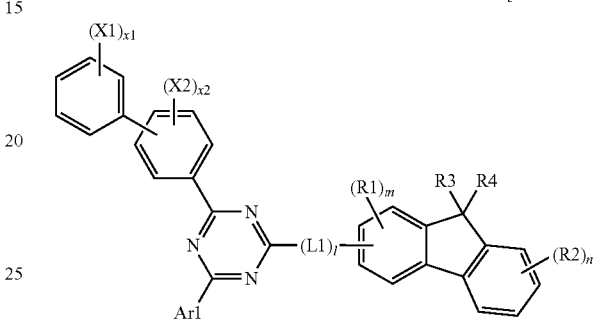

R1 to R4, Ar1, L1, 1, m, and n are the same as defined in Formula 1, x1 is an integer of 1 to 5, x2 is an integer of 1 to 4, and when x1 and x2 are an integer of 2 or more, two or more structures in the parenthesis are the same as or different from each other, and X1 and X2 are the same as or different from each other, and each independently hydrogen; deuterium; or a phenyl group, or two or more adjacent groups combine with each other to form a fused benzene ring.

8. The organic light emitting diode of claim 1, wherein the heterocyclic compound represented by Formula 1 is represented by any one of the following Formulae:

| Formula | ---Ar1 | ---Ar2 | ---Ar3 |
|---|---|---|---|
| 1-1 | | | |
| 1-2 | | | |
| 1-3 | | | |

-continued

| Formula | ---Ar1 | ---Ar2 | ---Ar3 |
|---|---|---|---|
| 1-4 | phenyl | biphenyl | 9,9-dimethylfluorenyl |
| 1-5 | phenyl | biphenyl | 9,9-diphenylfluorenyl |
| 1-6 | phenyl | biphenyl | 9,9-diphenylfluorenyl |
| 1-7 | phenyl | biphenyl | benzofluorenyl (methyl) |
| 1-8 | phenyl | biphenyl | 9,9-diphenylfluorenyl |
| 1-9 | phenyl | biphenyl | benzofluorenyl (methyl) |
| 1-13 | phenyl | m-biphenyl | 9,9-dimethylfluorenyl |

-continued

| Formula | ---Ar1 | ---Ar2 | ---Ar3 |
|---|---|---|---|
| 1-14 | phenyl | 3-biphenyl | 9,9-dimethylfluoren-2-yl |
| 1-17 | phenyl | 3-biphenyl | 9,9-diphenylfluoren-1-yl |
| 1-18 | phenyl | 3-biphenyl | 9,9-diphenylfluoren-2-yl |
| 1-19 | phenyl | 3-biphenyl | 9,9-diphenylfluoren-3-yl |
| 1-20 | phenyl | 3-biphenyl | 9,9-diphenylfluoren-4-yl |
| 1-23 | phenyl | 3-biphenyl | 11,11-dimethyl-11H-benzo[b]fluoren-2-yl |
| 1-25 | phenyl | 2-biphenyl | 9,9-dimethylfluoren-4-yl |

-continued
| Formula | ---Ar1 | ---Ar2 | ---Ar3 |
|---|---|---|---|
| 1-27 | 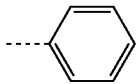 | 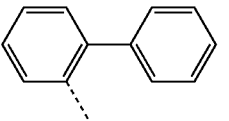 | 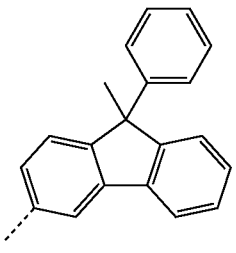 |
| 1-28 | 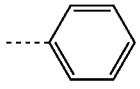 | 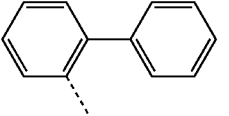 | 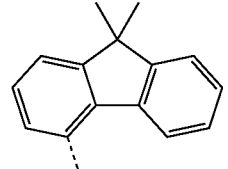 |
| 1-29 | 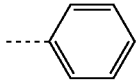 | 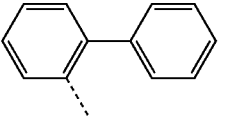 | 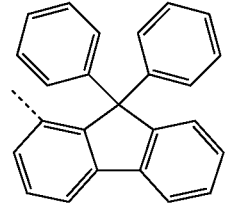 |
| 1-30 | 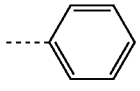 | 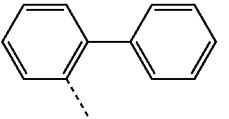 | 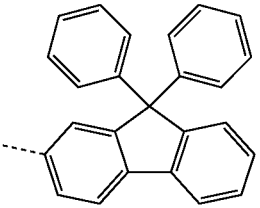 |
| 1-31 | 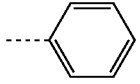 | 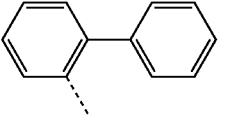 | 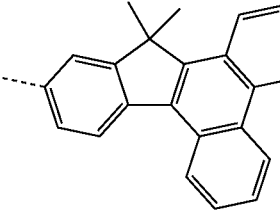 |
| 1-32 | 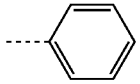 | 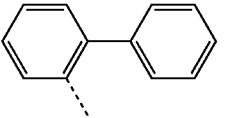 | 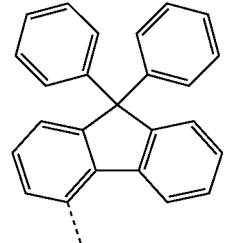 |
| 1-33 | 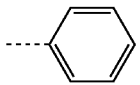 | 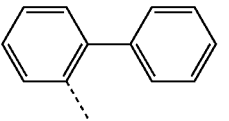 | 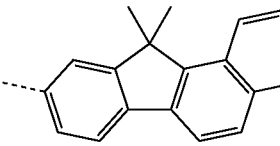 |

-continued

| Formula | ---Ar1 | ---Ar2 | ---Ar3 |
|---|---|---|---|
| 1-37 | phenyl | p-terphenyl | 9,9-dimethylfluorenyl (1-position) |
| 1-38 | phenyl | p-terphenyl | 9,9-dimethylfluorenyl (1-position) |
| 1-39 | phenyl | p-terphenyl | 9,9-dimethylfluorenyl (3-position) |
| 1-40 | phenyl | p-terphenyl | 9,9-dimethylfluorenyl (4-position) |
| 1-41 | phenyl | p-terphenyl | 9,9-diphenylfluorenyl (1-position) |
| 1-43 | phenyl | p-terphenyl | 9,9-diphenylfluorenyl (3-position) |
| 1-44 | phenyl | p-terphenyl | 9,9-diphenylfluorenyl (4-position) |

-continued
| Formula | ---Ar1 | ---Ar2 | ---Ar3 |
|---|---|---|---|
| 1-45 | 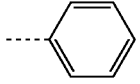 | 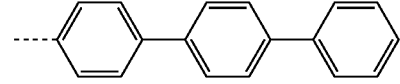 | 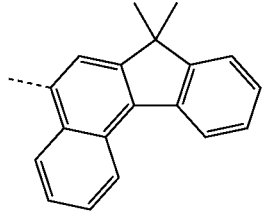 |
| 1-49 | 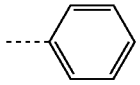 | 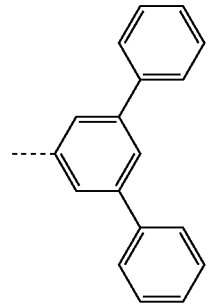 | 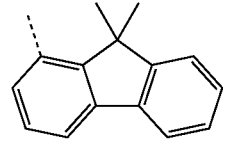 |
| 1-50 | 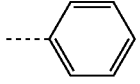 | 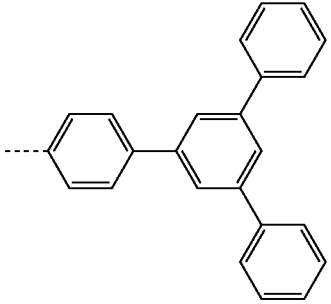 | 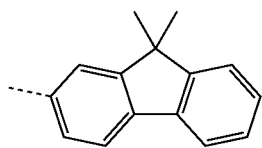 |
| 1-51 | 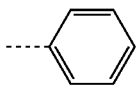 | 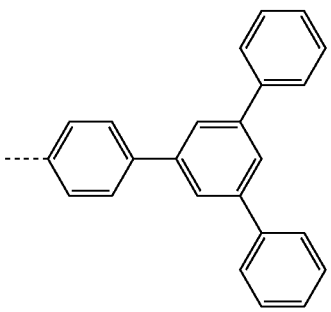 | 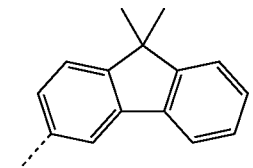 |
| 1-52 | 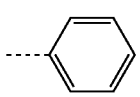 | 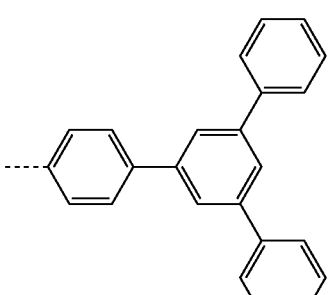 | 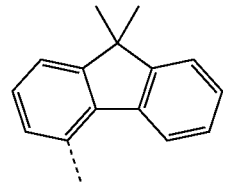 |

-continued

| Formula | ---Ar1 | ---Ar2 | ---Ar3 |
|---|---|---|---|
| 1-53 | phenyl | 3,5-diphenylphenyl | 9,9-diphenylfluoren-1-yl |
| 1-54 | phenyl | 3,5-diphenylphenyl | 9,9-diphenylfluoren-2-yl |
| 1-55 | phenyl | 3,5-diphenylphenyl | 9,9-diphenylfluoren-3-yl |
| 1-56 | phenyl | 3,5-diphenylphenyl | 9,9-diphenylfluoren-4-yl |
| 1-57 | phenyl | 3,5-diphenylphenyl | 9,9-dimethyl-9H-benzo[b]fluoren-2-yl |

-continued

| Formula | ---Ar1 | ---Ar2 | ---Ar3 |
|---|---|---|---|
| 1-61 | phenyl | m-terphenyl | 9,9-dimethylfluoren-1-yl |
| 1-62 | phenyl | m-terphenyl | 9,9-dimethylfluoren-2-yl |
| 1-64 | phenyl | m-terphenyl | 9,9-dimethylfluoren-4-yl |
| 1-65 | phenyl | m-terphenyl | 9,9-dimethyl-benzo[c]fluorenyl |
| 1-66 | phenyl | m-terphenyl | 9,9-diphenylfluoren-2-yl |
| 1-67 | phenyl | m-terphenyl | 9,9-diphenylfluoren-3-yl |
| 1-68 | phenyl | m-terphenyl | 9,9-diphenylfluoren-4-yl |

-continued
| Formula | ---Ar1 | ---Ar2 | ---Ar3 |
|---|---|---|---|
| 1-69 | 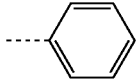 | 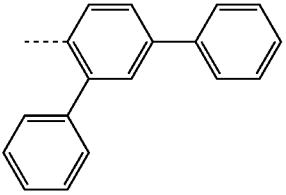 | 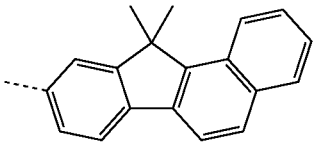 |
| 1-73 | 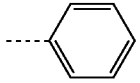 | 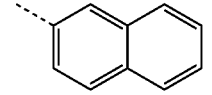 | 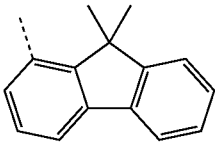 |
| 1-75 | 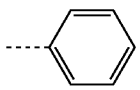 | 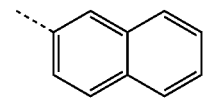 | 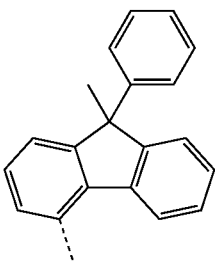 |
| 1-76 | 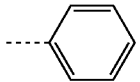 | 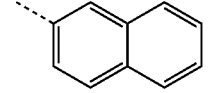 | 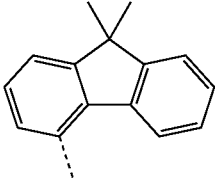 |
| 1-77 | 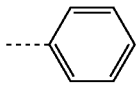 | 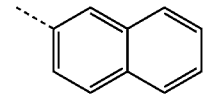 | 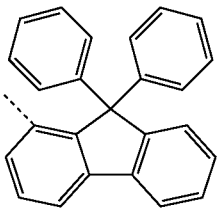 |
| 1-78 | 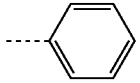 | 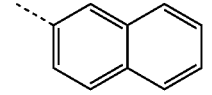 | 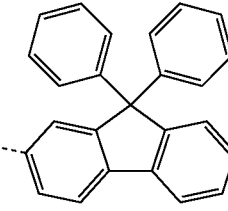 |
| 1-79 | 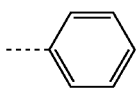 | 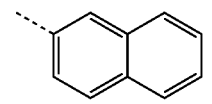 | 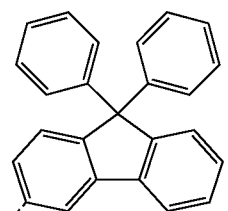 |

-continued
| Formula | ---Ar1 | ---Ar2 | ---Ar3 |
|---|---|---|---|
| 1-80 | 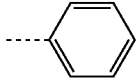 | 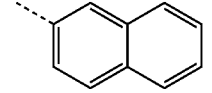 | 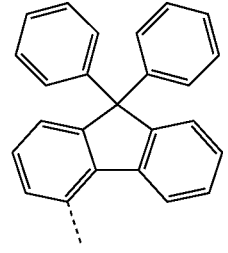 |
| 1-85 | 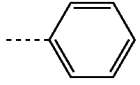 | 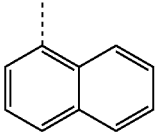 | 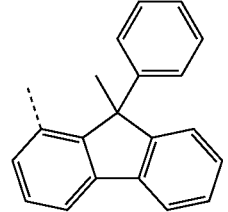 |
| 1-87 | 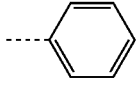 | 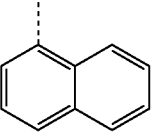 | 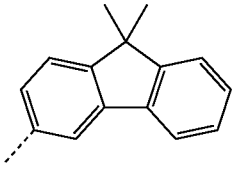 |
| 1-88 | 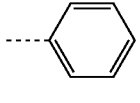 | 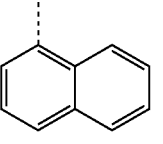 | 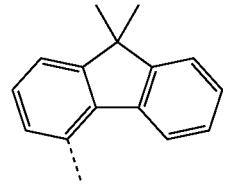 |
| 1-89 | 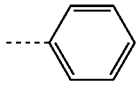 | 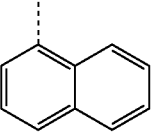 | 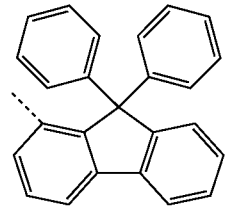 |
| 1-90 | 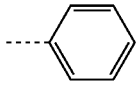 | 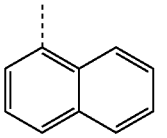 | 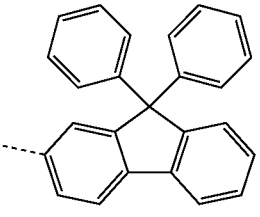 |
| 1-91 | 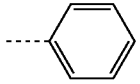 | 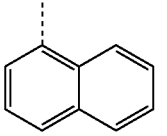 | 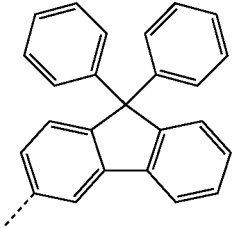 |

-continued

| Formula | ---Ar1 | ---Ar2 | ---Ar3 |
|---|---|---|---|
| 1-92 | phenyl | 1-naphthyl | 9,9-diphenylfluoren-4-yl |
| 1-97 | phenyl | 9-phenanthryl | 9,9-dimethylfluoren-1-yl |
| 1-98 | phenyl | 9-phenanthryl | 9,9-dimethylfluoren-2-yl |
| 1-100 | phenyl | 9-phenanthryl | 9,9-dimethylfluoren-4-yl |
| 1-101 | phenyl | 9-phenanthryl | 9,9-diphenylfluoren-1-yl |
| 1-102 | phenyl | 9-phenanthryl | 9,9-diphenylfluoren-2-yl |
| 1-103 | phenyl | 9-phenanthryl | 9,9-diphenylfluoren-3-yl |

-continued
| Formula | ---Ar1 | ---Ar2 | ---Ar3 |
|---|---|---|---|
| 1-104 | 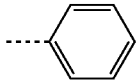 | 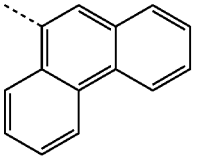 | 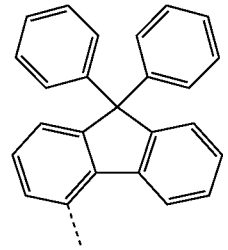 |
| 1-105 | 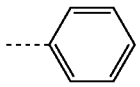 | 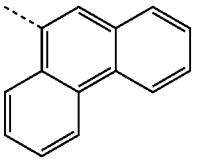 | 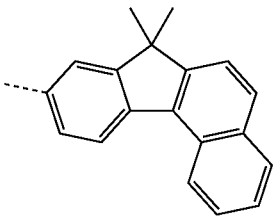 |
| 1-109 | 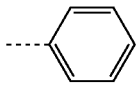 | 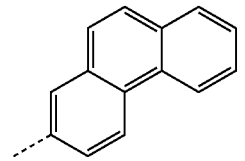 | 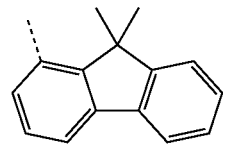 |
| 1-110 | 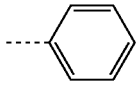 | 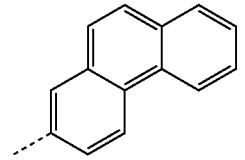 | 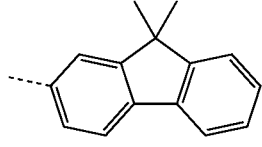 |
| 1-112 | 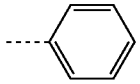 | 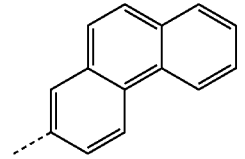 | 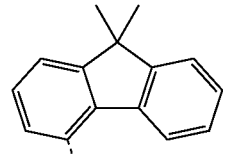 |
| 1-113 | 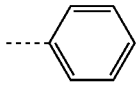 | 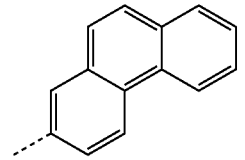 | 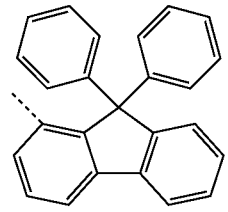 |
| 1-114 | 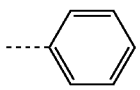 | 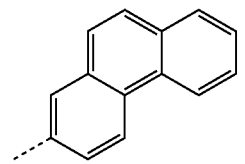 | 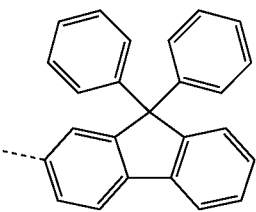 |

-continued
| Formula | ---Ar1 | ---Ar2 | ---Ar3 |
|---|---|---|---|
| 1-115 | 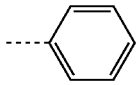 | 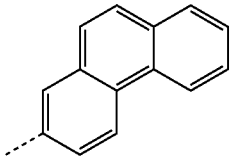 | 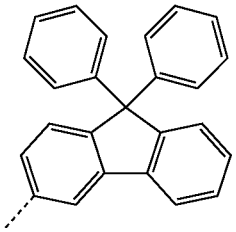 |
| 1-116 | 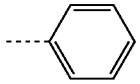 | 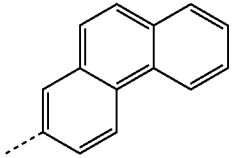 | 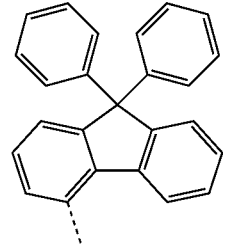 |
| 1-119 | 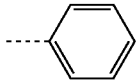 | 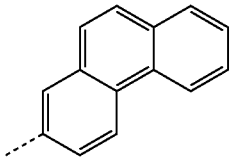 | 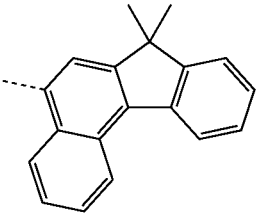 |
| 1-121 | 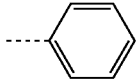 | 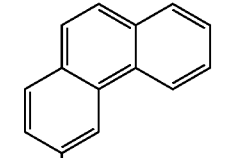 | 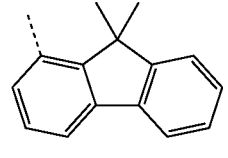 |
| 1-123 | 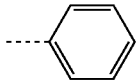 | 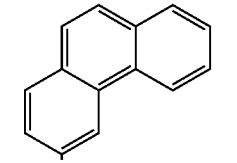 | 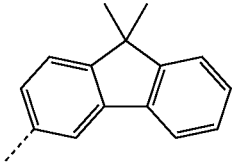 |
| 1-124 | 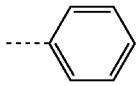 | 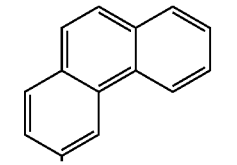 | 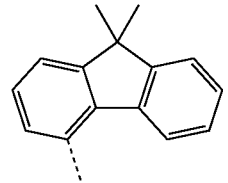 |
| 1-125 | 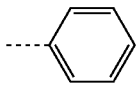 | 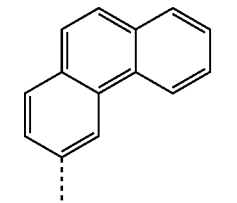 | 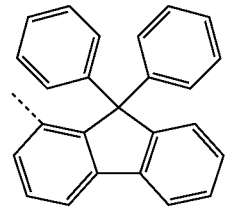 |

-continued

| Formula | ---Ar1 | ---Ar2 | ---Ar3 |
|---|---|---|---|
| 1-126 | phenyl | phenanthrenyl | 9,9-diphenylfluoren-2-yl |
| 1-127 | phenyl | phenanthrenyl | dimethyl-benzofluorenyl |
| 1-128 | phenyl | phenanthrenyl | 9,9-diphenylfluoren-4-yl |
| 1-134 | biphenyl-4-yl | biphenyl-3-yl | 9,9-dimethylfluoren-2-yl |
| 1-135 | biphenyl-4-yl | biphenyl-3-yl | 9,9-dimethylfluoren-3-yl |
| 1-136 | biphenyl-4-yl | biphenyl-3-yl | 9,9-dimethylfluoren-4-yl |
| 1-137 | biphenyl-4-yl | biphenyl-3-yl | 9,9-diphenylfluoren-1-yl |

-continued

| Formula | ---Ar1 | ---Ar2 | ---Ar3 |
|---|---|---|---|
| 1-138 | phenyl | 4-(2-naphthyl)phenyl | 9,9-diphenylfluoren-2-yl |
| 1-139 | 4-biphenyl | 3-biphenyl | 9,9-diphenylfluoren-3-yl |
| 1-140 | 4-biphenyl | 3-biphenyl | 9,9-diphenylfluoren-4-yl |
| 1-143 | 4-biphenyl | 3-(1-naphthyl)phenyl | 9,9-diphenylfluoren-2-yl |
| 1-145 | 4-biphenyl | 2-biphenyl | 9,9-dimethylfluoren-1-yl |
| 1-146 | 4-biphenyl | 2-biphenyl | 9,9-dimethylfluoren-2-yl |
| 1-147 | 4-biphenyl | 2-biphenyl | 9,9-dimethylfluoren-3-yl |

-continued

| Formula | ---Ar1 | ---Ar2 | ---Ar3 |
|---|---|---|---|
| 1-148 | | | |
| 1-150 | | | |
| 1-151 | | | |
| 1-152 | | | |
| 1-153 | | | |
| 1-157 | | | |
| 1-158 | | | |
| 1-159 | | | |

-continued

| Formula | ---Ar1 | ---Ar2 | ---Ar3 |
|---|---|---|---|
| 1-160 | biphenyl | p-terphenyl | 9,9-dimethylfluorene (4-yl) |
| 1-161 | biphenyl | phenanthren-2-yl-phenyl | 9,9-diphenylfluorene |
| 1-162 | biphenyl | p-terphenyl | 9,9-diphenylfluoren-2-yl |
| 1-163 | biphenyl | p-terphenyl | 9,9-diphenylfluoren-3-yl |
| 1-164 | biphenyl | p-terphenyl | 9,9-diphenylfluoren-4-yl |
| 1-167 | biphenyl | p-terphenyl | 11,11-dimethylbenzo[a]fluorenyl |
| 1-169 | biphenyl | 1,3-diphenylbenzen-5-yl | 9,9-dimethylfluoren-1-yl |

-continued

| Formula | ---Ar1 | ---Ar2 | ---Ar3 |
|---|---|---|---|
| 1-170 | biphenyl | 1,3,5-triphenylbenzene (meta) | 9,9-dimethylfluorene (2-position) |
| 1-172 | biphenyl | 1,3,5-triphenylbenzene (meta) | 9,9-dimethylfluorene (4-position) |
| 1-173 | biphenyl | 1,3,5-triphenylbenzene (meta) | 9,9-diphenylfluorene (1-position) |
| 1-174 | biphenyl | 1,3,5-triphenylbenzene (meta) | 9,9-diphenylfluorene (2-position) |
| 1-175 | biphenyl | 1,3,5-triphenylbenzene (meta) | 9,9-diphenylfluorene (3-position) |

-continued
| Formula | ---Ar1 | ---Ar2 | ---Ar3 |
|---|---|---|---|
| 1-176 | 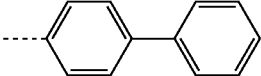 | 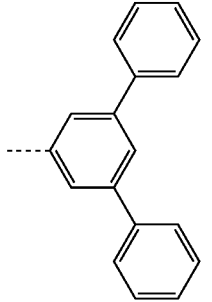 | 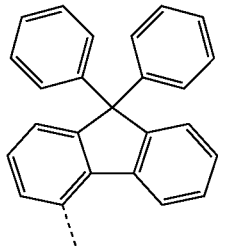 |
| 1-177 | 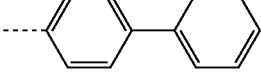 | 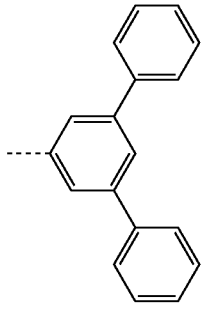 | 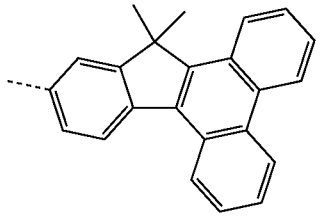 |
| 1-179 | 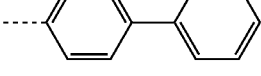 | 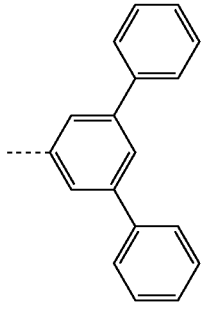 | 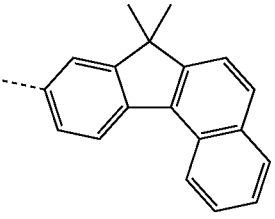 |
| 1-181 | 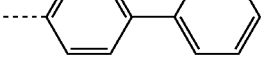 | 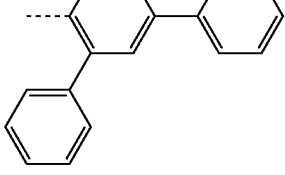 | 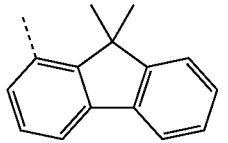 |
| 1-182 | 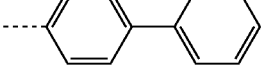 | 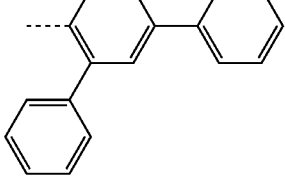 | 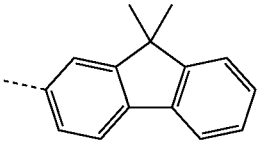 |
| 1-183 | 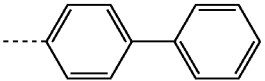 | 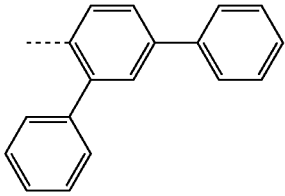 | 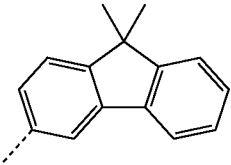 |

-continued

| Formula | ---Ar1 | ---Ar2 | ---Ar3 |
|---|---|---|---|
| 1-184 | biphenyl | m-terphenyl | 9,9-dimethylfluorene (4-yl) |
| 1-185 | biphenyl | m-terphenyl | 9,9-diphenylfluorene (1-yl) |
| 1-186 | biphenyl | m-terphenyl | 9,9-diphenylfluorene (2-yl) |
| 1-187 | biphenyl | m-terphenyl | 9,9-diphenylfluorene (3-yl) |
| 1-188 | biphenyl | m-terphenyl | 9,9-diphenylfluorene (4-yl) |
| 1-193 | biphenyl | 2-naphthyl | 9,9-dimethylfluorene (1-yl) |
| 1-194 | biphenyl | 2-naphthyl | 9,9-dimethylfluorene (2-yl) |

-continued
| Formula | ---Ar1 | ---Ar2 | ---Ar3 |
| --- | --- | --- | --- |
| 1-195 | 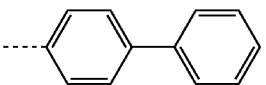 | 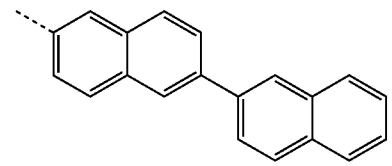 | 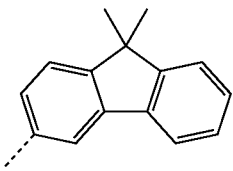 |
| 1-196 | 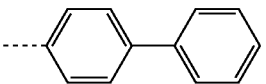 | 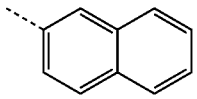 | 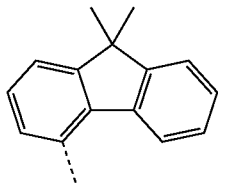 |
| 1-197 | 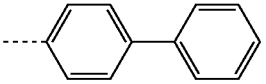 | 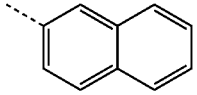 | 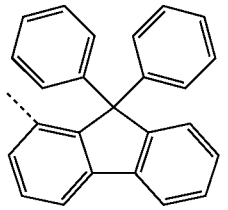 |
| 1-198 | 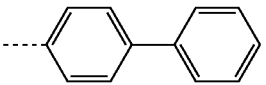 | 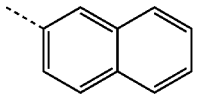 | 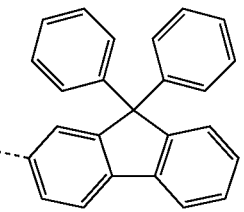 |
| 1-199 | 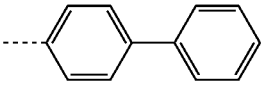 | 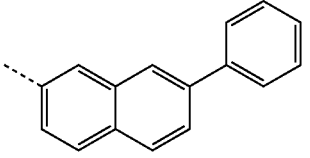 | 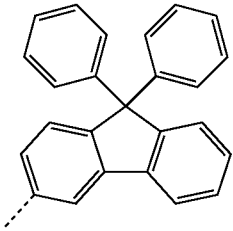 |
| 1-200 | 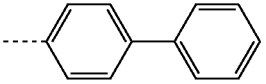 | 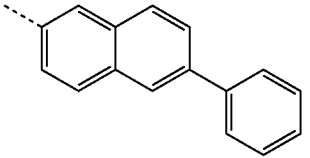 | 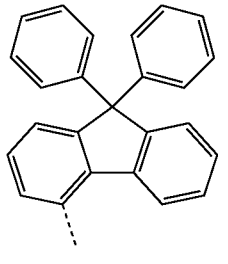 |
| 1-205 | 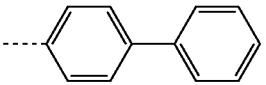 | 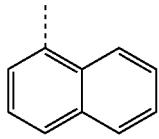 | 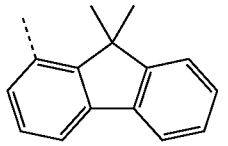 |

-continued

| Formula | ---Ar1 | ---Ar2 | ---Ar3 |
| --- | --- | --- | --- |
| 1-206 | biphenyl | 1-naphthyl | 9,9-dimethylfluoren-2-yl |
| 1-209 | biphenyl | 1-naphthyl | 9,9-diphenylfluoren-1-yl |
| 1-210 | biphenyl | 1-naphthyl | 9,9-diphenylfluoren-2-yl |
| 1-211 | biphenyl | 1-naphthyl | 9,9-diphenylfluoren-3-yl |
| 1-212 | biphenyl | 1-naphthyl | 9,9-diphenylfluoren-4-yl |
| 1-217 | biphenyl | phenanthren-9-yl | 9,9-dimethylfluoren-1-yl |
| 1-218 | biphenyl | phenanthren-9-yl | 9,9-dimethylfluoren-2-yl |

-continued

| Formula | ---Ar1 | ---Ar2 | ---Ar3 |
|---|---|---|---|
| 1-219 | biphenyl | phenanthrene | 9,9-dimethylfluorene |
| 1-220 | biphenyl | 9-phenylphenanthrene | 9,9-dimethylfluorene |
| 1-221 | biphenyl | phenanthrene | 9,9-diphenylfluorene |
| 1-222 | biphenyl | phenanthrene | 9,9-diphenylfluorene |
| 1-223 | biphenyl | phenanthrene | 9,9-diphenylfluorene |
| 1-224 | biphenyl | phenanthrene | 9,9-diphenylfluorene |

-continued

| Formula | ---Ar1 | ---Ar2 | ---Ar3 |
|---|---|---|---|
| 1-227 | biphenyl | phenanthrene | 9,9-dimethyl-benzo-fluorene |
| 1-229 | biphenyl | phenanthrene | 9,9-dimethylfluorene |
| 1-230 | biphenyl | phenanthrene | 9,9-dimethylfluorene |
| 1-231 | biphenyl | phenanthrene | 9,9-dimethylfluorene |
| 1-232 | biphenyl | phenanthrene | 9,9-dimethylfluorene |
| 1-233 | biphenyl | phenanthrene | 9,9-diphenylfluorene |
| 1-234 | biphenyl | phenanthrene | 9,9-diphenylfluorene |

-continued

| Formula | ---Ar1 | ---Ar2 | ---Ar3 |
|---|---|---|---|
| 1-235 | biphenyl | phenanthrene | 9,9-diphenylfluorene |
| 1-236 | biphenyl | phenanthrene | 9,9-diphenylfluorene |
| 1-237 | biphenyl | phenanthrene | benzofluorene |
| 1-241 | biphenyl | phenanthrene | 9,9-dimethylfluorene |
| 1-242 | biphenyl | phenanthrene | 9,9-dimethylfluorene |
| 1-243 | biphenyl | phenanthrene | 9,9-dimethylfluorene |
| 1-244 | biphenyl | phenanthrene | 9,9-dimethylfluorene |

-continued

| Formula | ---Ar1 | ---Ar2 | ---Ar3 |
|---|---|---|---|
| 1-245 | biphenyl | phenanthrene | 9,9-diphenylfluorene (1-position) |
| 1-246 | biphenyl | phenanthrene | 9,9-diphenylfluorene (2-position) |
| 1-248 | biphenyl | phenanthrene | 9,9-diphenylfluorene (4-position) |
| 1-249 | biphenyl | phenanthrene | 11,11-dimethyl-benzo[b]fluorene |
| 1-253 | 1-naphthyl | 3-biphenyl | 9,9-dimethylfluorene (1-position) |
| 1-254 | 1-naphthyl | 3-biphenyl | 9,9-dimethylfluorene (2-position) |
| 1-255 | 1-naphthyl | 3-biphenyl | 9,9-dimethylfluorene (3-position) |

-continued
| Formula | ---Ar1 | ---Ar2 | ---Ar3 |
|---|---|---|---|
| 1-256 | 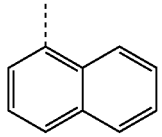 | 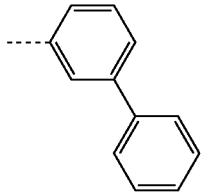 | 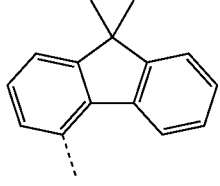 |
| 1-257 | 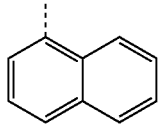 | 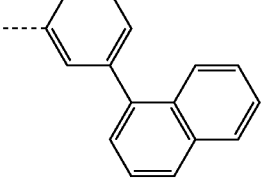 | 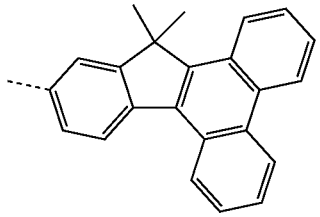 |
| 1-258 | 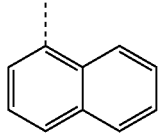 | 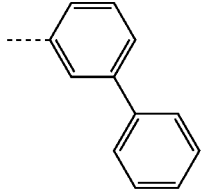 | 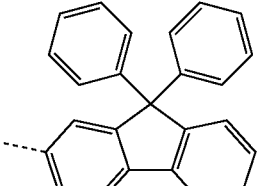 |
| 1-259 | 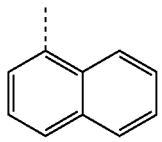 | 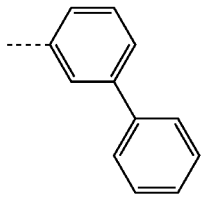 | 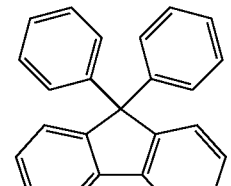 |
| 1-260 | 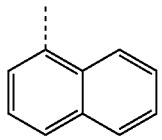 | 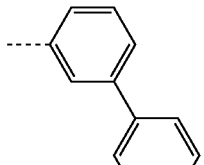 | 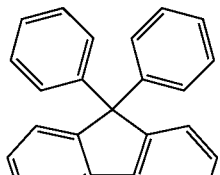 |
| 1-261 | 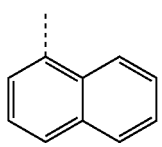 | 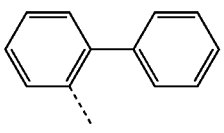 | 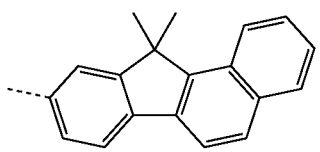 |
| 1-265 | 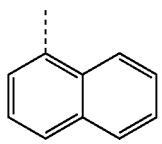 | 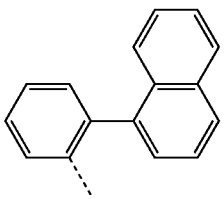 | 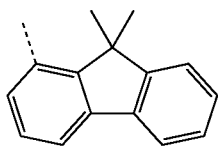 |

-continued

| Formula | ---Ar1 | ---Ar2 | ---Ar3 |
| --- | --- | --- | --- |
| 1-266 | 1-naphthyl | 2-biphenyl | 9,9-dimethylfluoren-2-yl |
| 1-267 | 1-naphthyl | 2-biphenyl | 9,9-dimethylfluoren-3-yl |
| 1-268 | 1-naphthyl | 2-biphenyl | 9,9-dimethylfluoren-4-yl |
| 1-269 | 1-naphthyl | 2-biphenyl | 9,9-diphenylfluoren-1-yl |
| 1-270 | 1-naphthyl | 2-biphenyl | 9,9-diphenylfluoren-2-yl |
| 1-271 | 1-naphthyl | 2-biphenyl | 9,9-diphenylfluoren-3-yl |
| 1-272 | 1-naphthyl | 2-(phenanthren-9-yl)phenyl | 9,9-diphenylfluoren-4-yl |

-continued
| Formula | ---Ar1 | ---Ar2 | ---Ar3 |
|---|---|---|---|
| 1-273 | 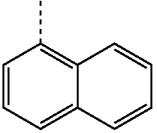 | 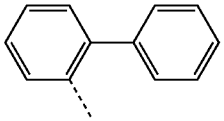 | 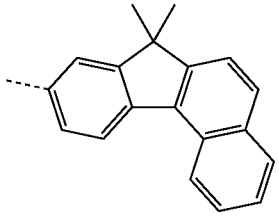 |
| 1-278 | 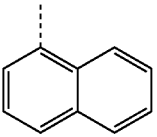 | 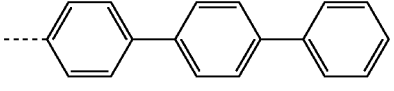 | 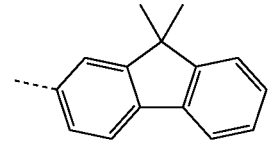 |
| 1-279 | 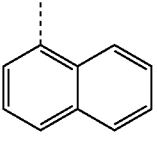 | 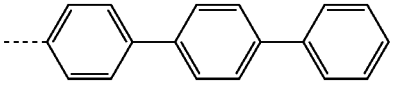 | 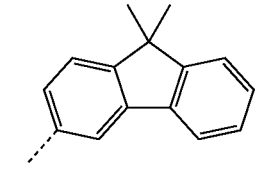 |
| 1-280 | 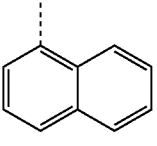 | 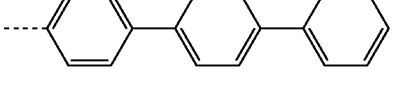 | 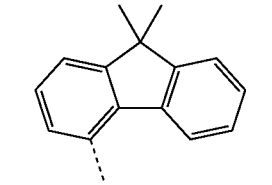 |
| 1-281 | 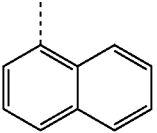 | 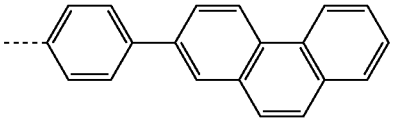 | 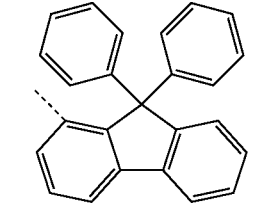 |
| 1-282 | 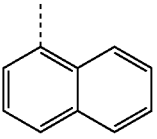 | 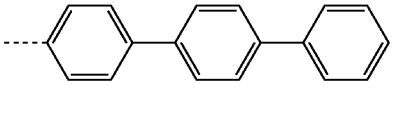 | 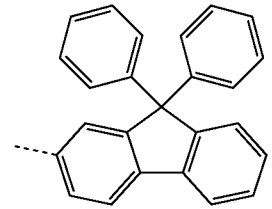 |
| 1-283 | 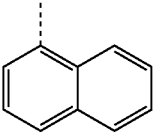 | 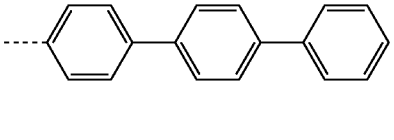 | 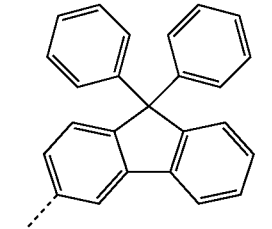 |

| Formula | ---Ar1 | ---Ar2 | ---Ar3 |
|---|---|---|---|
| 1-284 | 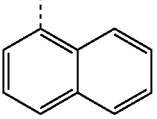 | 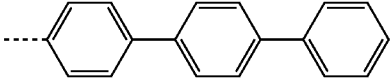 | 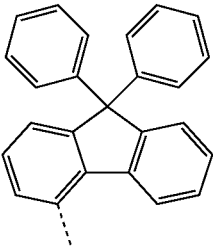 |
| 1-289 | 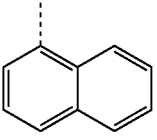 | 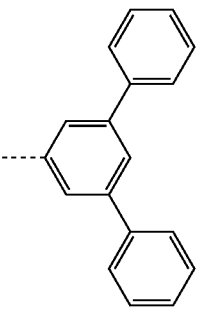 | 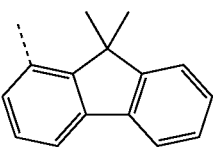 |
| 1-290 | 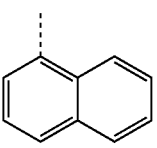 | 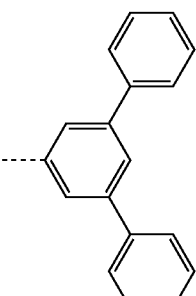 | 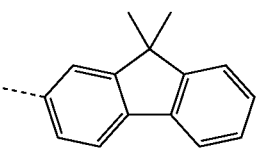 |
| 1-292 | 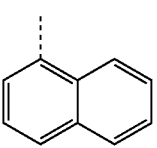 | 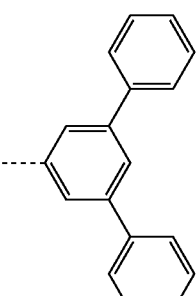 | 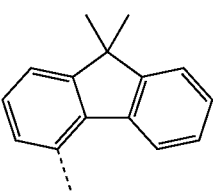 |
| 1-293 | 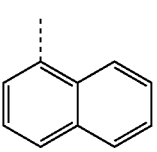 | 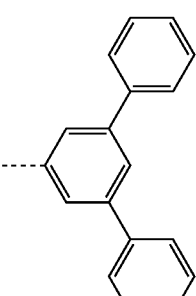 | 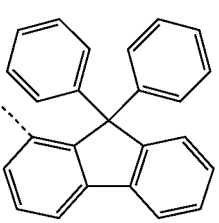 |

-continued
| Formula | ---Ar1 | ---Ar2 | ---Ar3 |
|---|---|---|---|
| 1-294 | 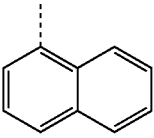 | 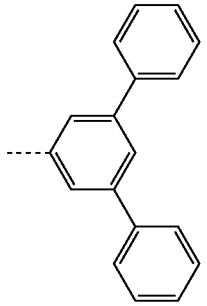 | 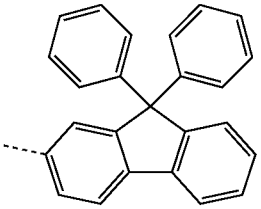 |
| 1-295 | 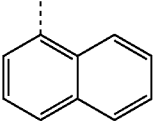 | 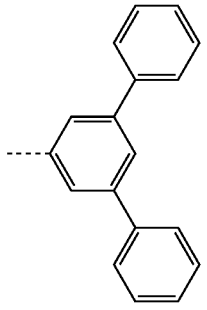 | 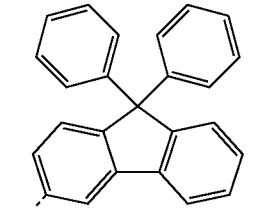 |
| 1-296 | 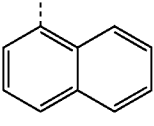 | 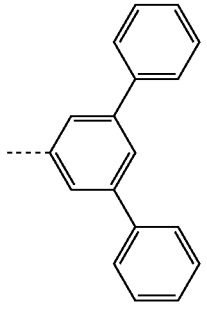 | 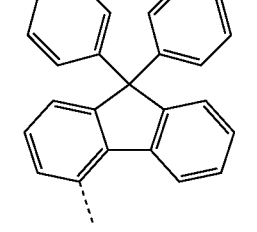 |
| 1-301 | 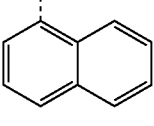 | 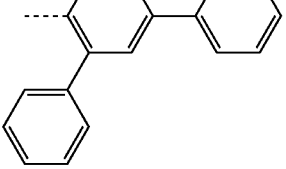 | 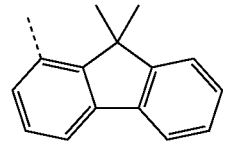 |
| 1-302 | 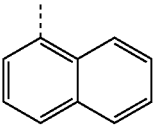 | 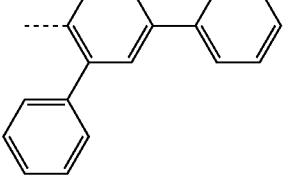 | 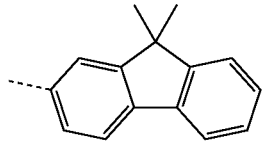 |
| 1-303 | 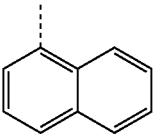 | 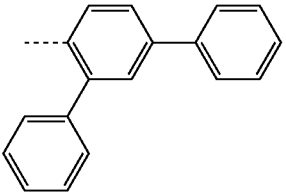 | 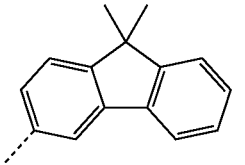 |

-continued
| Formula | ---Ar1 | ---Ar2 | ---Ar3 |
|---|---|---|---|
| 1-304 | 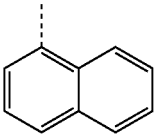 | 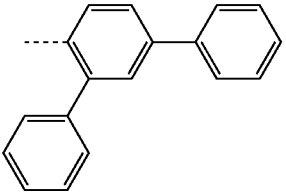 | 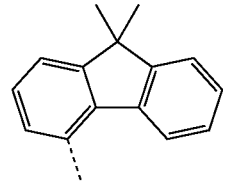 |
| 1-305 | 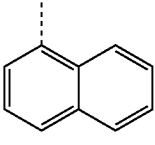 | 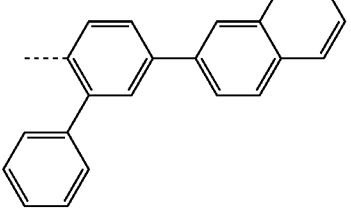 | 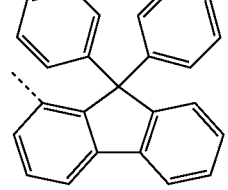 |
| 1-306 | 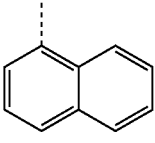 | 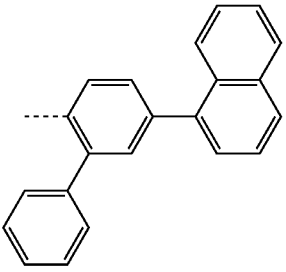 | 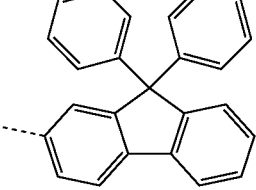 |
| 1-307 | 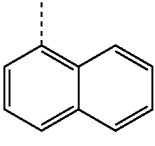 | 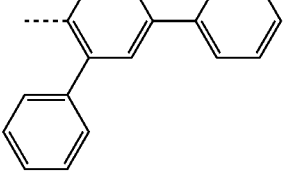 | 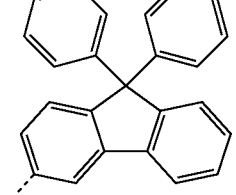 |
| 1-308 | 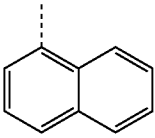 | 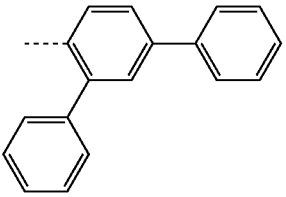 | 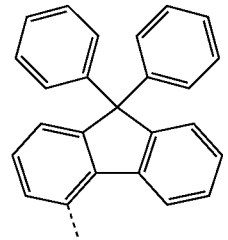 |
| 1-313 | 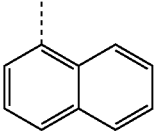 | 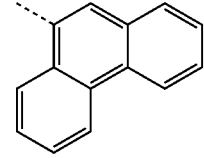 | 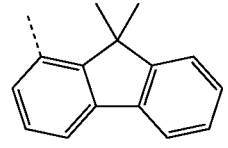 |
| 1-314 | 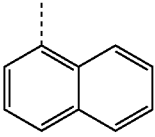 | 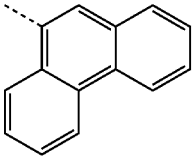 | 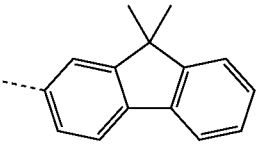 |

-continued
| Formula | ---Ar1 | ---Ar2 | ---Ar3 |
|---|---|---|---|
| 1-315 | 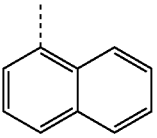 | 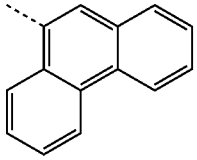 | 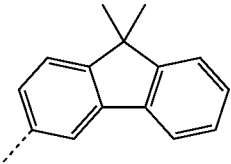 |
| 1-316 | 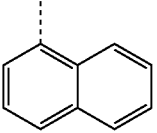 | 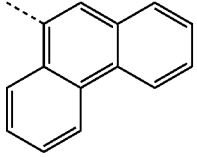 | 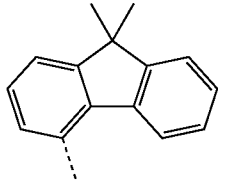 |
| 1-317 | 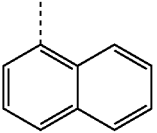 | 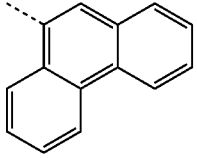 | 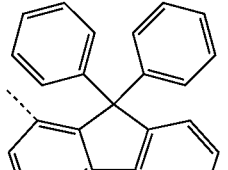 |
| 1-318 | 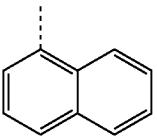 | 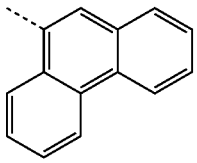 | 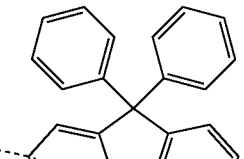 |
| 1-319 | 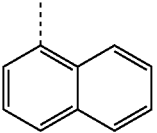 | 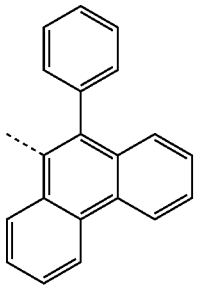 | 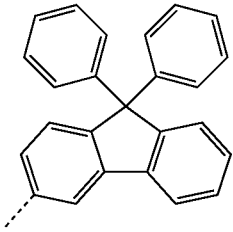 |
| 1-320 | 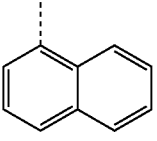 | 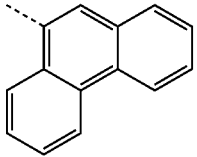 | 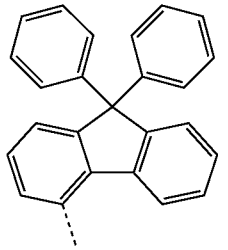 |

-continued
| Formula | ---Ar1 | ---Ar2 | ---Ar3 |
|---|---|---|---|
| 1-321 | 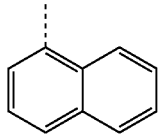 | 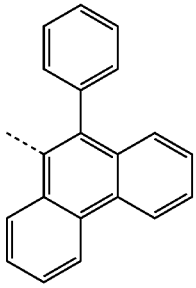 | 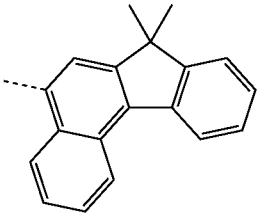 |
| 1-325 | 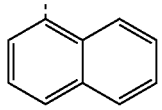 | 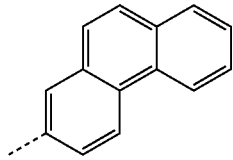 |  |
| 1-326 | 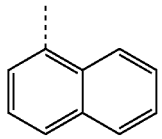 | 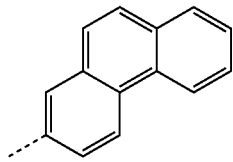 | 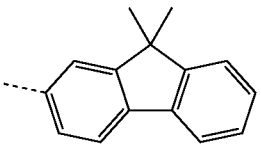 |
| 1-328 | 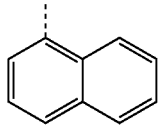 | 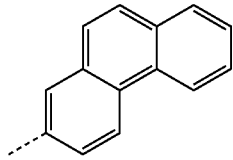 | 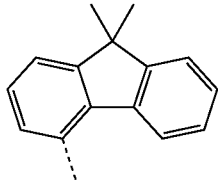 |
| 1-329 | 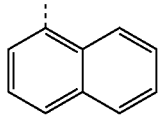 | 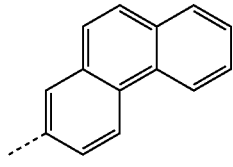 | 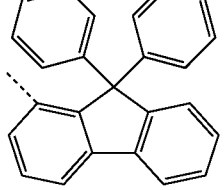 |
| 1-330 | 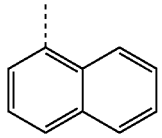 | 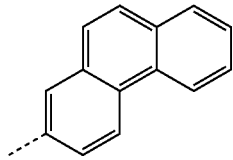 | 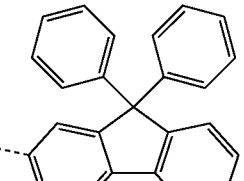 |
| 1-331 | 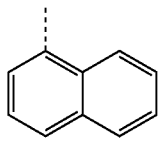 | 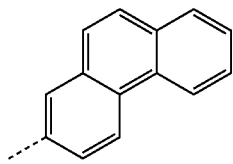 | 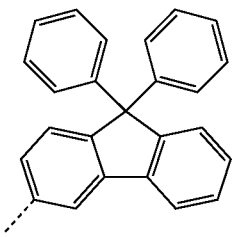 |

-continued
| Formula | ---Ar1 | ---Ar2 | ---Ar3 |
|---|---|---|---|
| 1-332 | 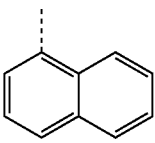 | 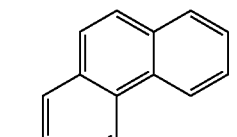 | 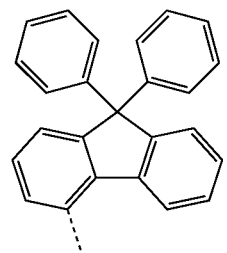 |
| 1-335 | 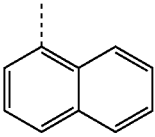 | 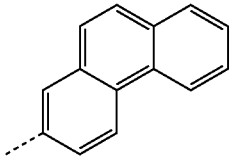 | 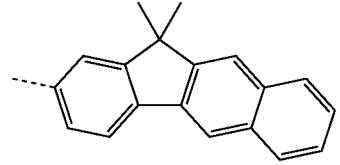 |
| 1-337 | 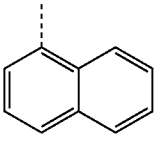 | 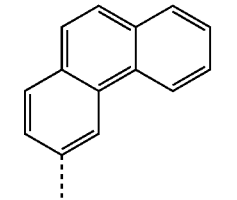 | 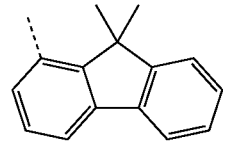 |
| 1-338 | 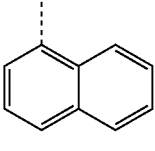 | 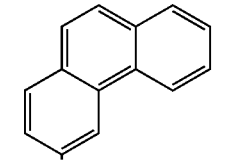 | 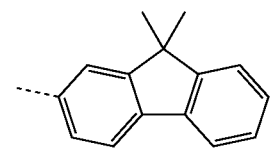 |
| 1-339 | 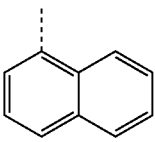 | 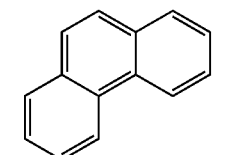 | 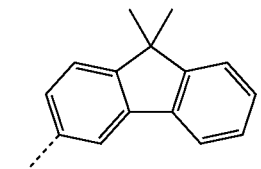 |
| 1-340 | 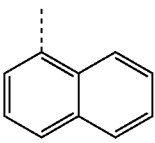 | 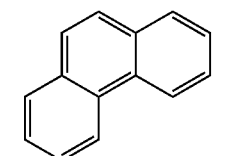 | 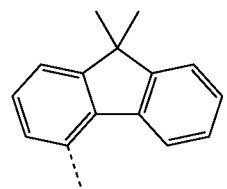 |
| 1-341 | 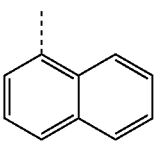 | 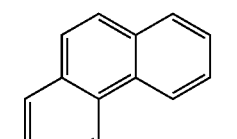 | 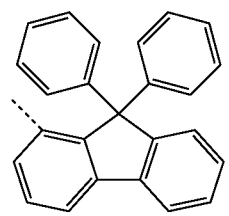 |

-continued
| Formula | ---Ar1 | ---Ar2 | ---Ar3 |
|---|---|---|---|
| 1-342 | 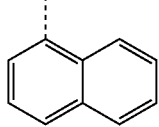 | 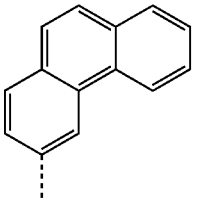 | 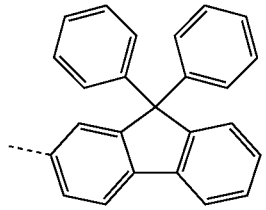 |
| 1-343 | 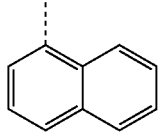 | 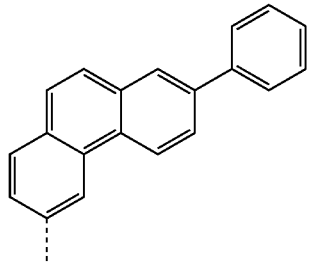 | 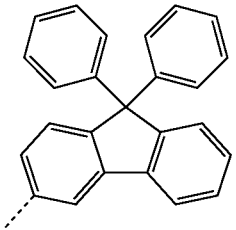 |
| 1-344 | 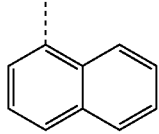 | 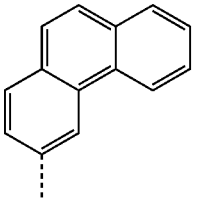 | 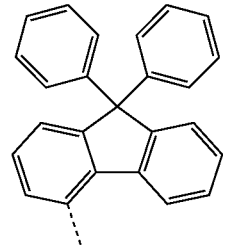 |
| 1-345 | 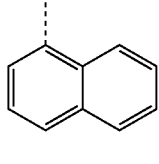 | 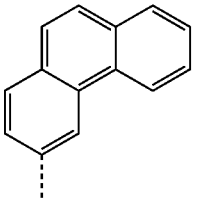 | 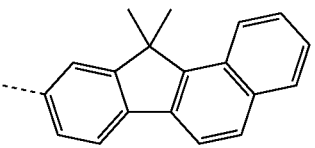 |
| 1-350 | 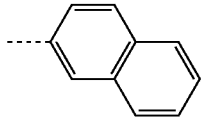 | 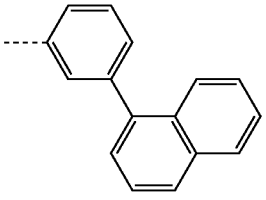 | 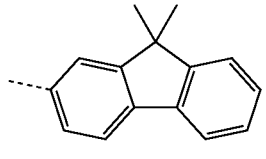 |
| 1-351 | 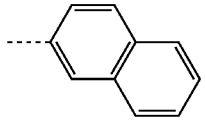 | 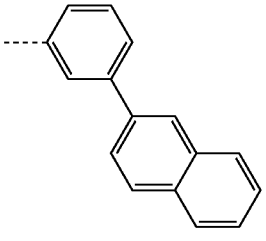 | 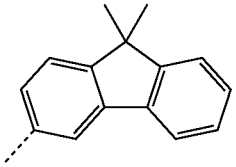 |

-continued

| Formula | ---Ar1 | ---Ar2 | ---Ar3 |
|---|---|---|---|
| 1-353 | naphthyl | biphenyl | 9,9-diphenylfluorenyl |
| 1-354 | naphthyl | biphenyl | 9,9-diphenylfluorenyl |
| 1-355 | naphthyl | biphenyl | 9,9-diphenylfluorenyl |
| 1-356 | naphthyl | biphenyl | 9,9-diphenylfluorenyl |
| 1-359 | naphthyl | 2-biphenyl | 9,9-dimethylbenzo[c]fluorenyl |
| 1-361 | naphthyl | 9-phenanthrenyl-phenyl | 9,9-dimethylfluorenyl |
| 1-362 | naphthyl | 2-biphenyl | 9,9-dimethylfluorenyl |

-continued
| Formula | ---Ar1 | ---Ar2 | ---Ar3 |
|---|---|---|---|
| 1-364 | 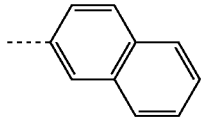 | 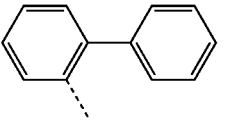 | 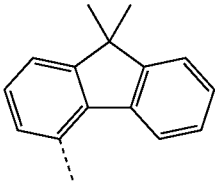 |
| 1-365 | 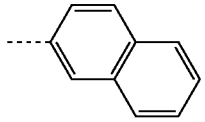 | 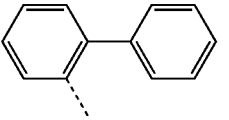 | 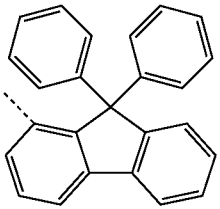 |
| 1-366 | 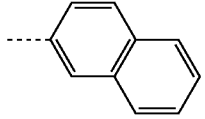 | 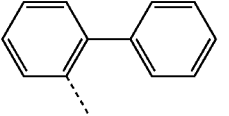 | 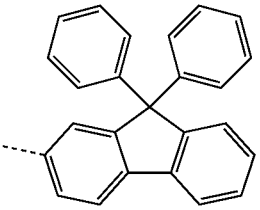 |
| 1-367 | 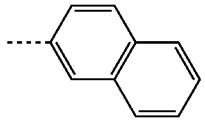 | 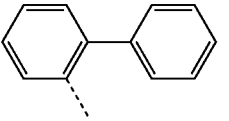 | 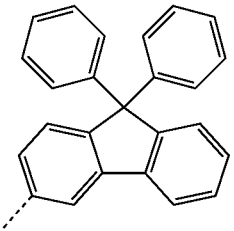 |
| 1-368 | 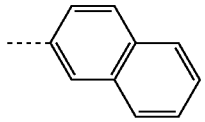 | 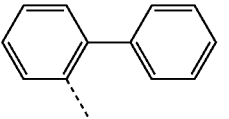 | 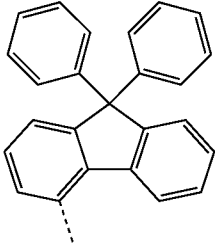 |
| 1-373 | 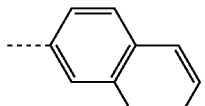 | 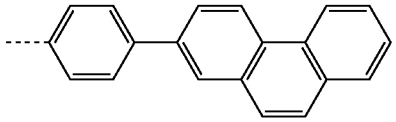 | 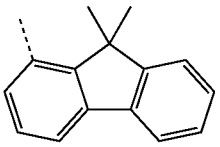 |
| 1-374 | 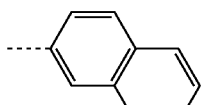 | 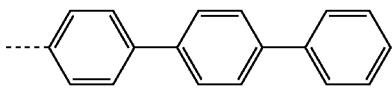 | 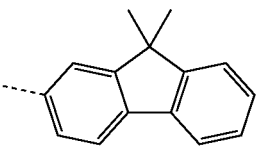 |

-continued
| Formula | ---Ar1 | ---Ar2 | ---Ar3 |
|---|---|---|---|
| 1-375 | 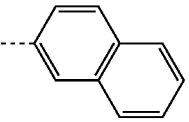 | 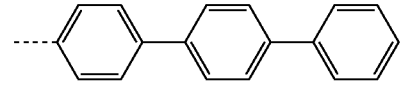 | 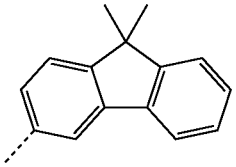 |
| 1-376 | 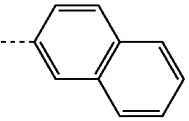 | 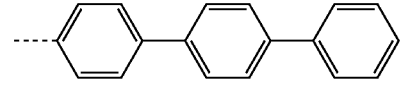 | 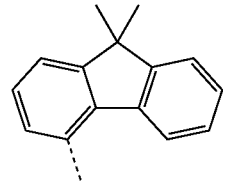 |
| 1-377 | 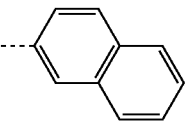 | 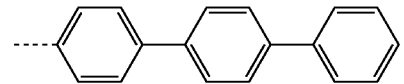 | 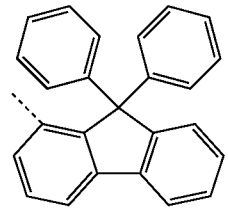 |
| 1-378 | 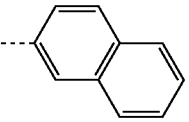 | 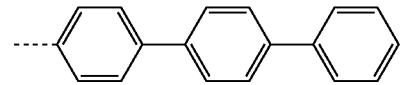 | 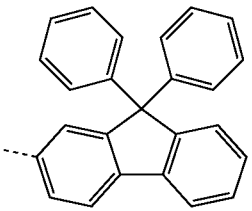 |
| 1-379 | 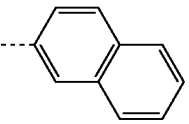 | 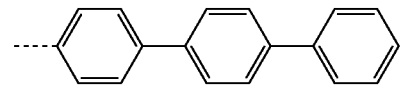 | 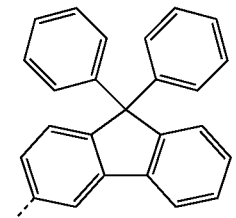 |
| 1-380 | 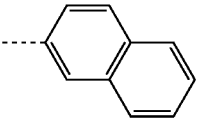 | 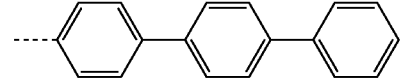 | 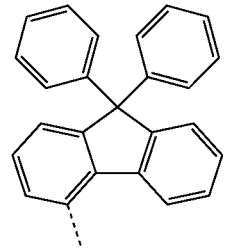 |

-continued
| Formula | ---Ar1 | ---Ar2 | ---Ar3 |
|---|---|---|---|
| 1-386 | 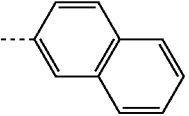 | 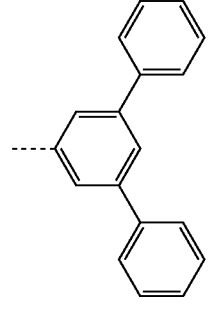 | 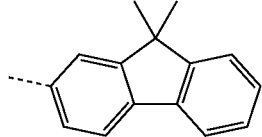 |
| 1-387 | 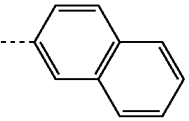 | 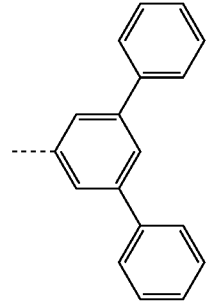 | 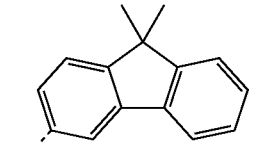 |
| 1-388 | 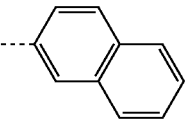 | 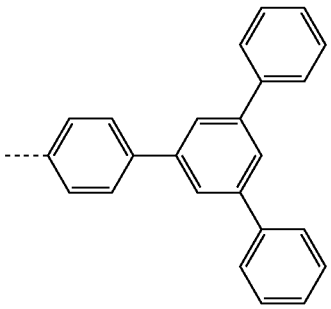 | 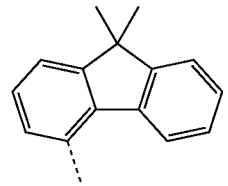 |
| 1-390 | 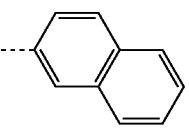 | 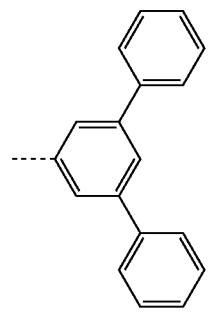 | 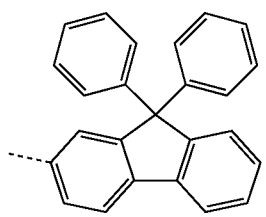 |
| 1-391 | 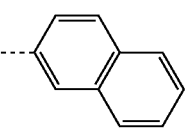 | 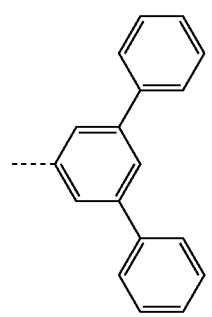 | 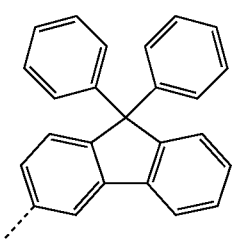 |

-continued
| Formula | ---Ar1 | ---Ar2 | ---Ar3 |
|---|---|---|---|
| 1-392 | 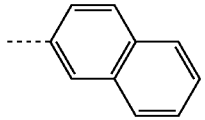 | 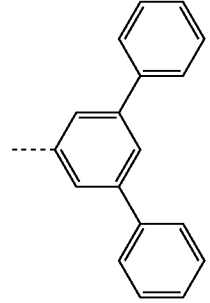 | 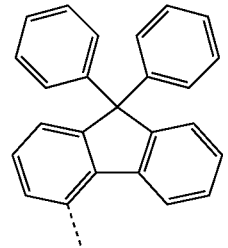 |
| 1-397 | 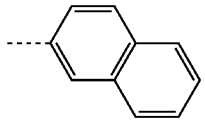 | 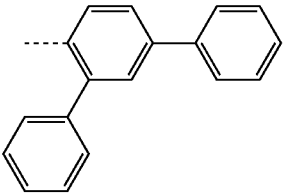 | 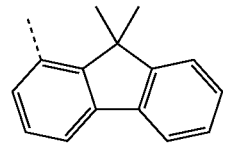 |
| 1-398 | 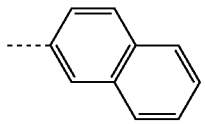 | 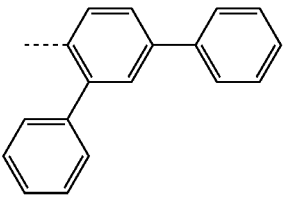 | 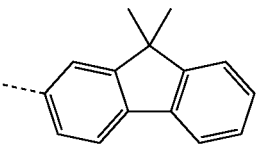 |
| 1-399 | 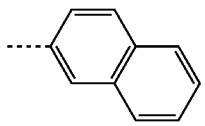 | 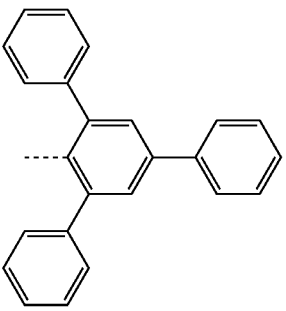 | 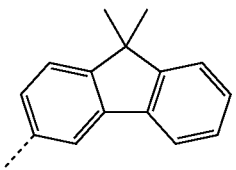 |
| 1-400 | 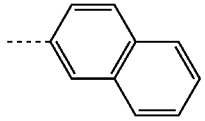 | 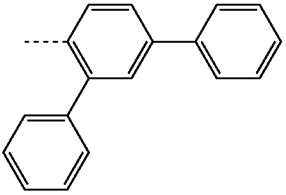 | 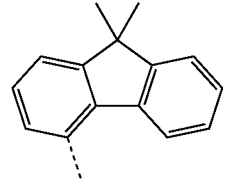 |
| 1-402 | 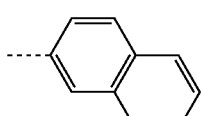 | 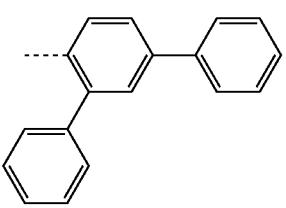 | 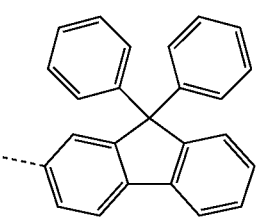 |

-continued
| Formula | ---Ar1 | ---Ar2 | ---Ar3 |
| --- | --- | --- | --- |
| 1-403 | 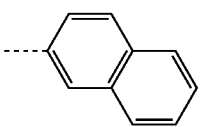 | 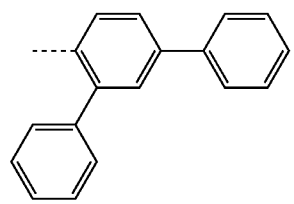 | 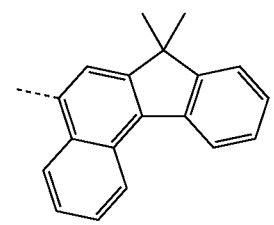 |
| 1-404 | 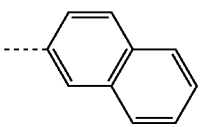 | 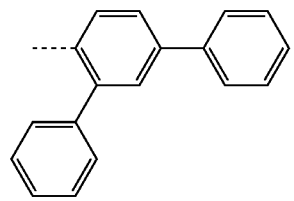 | 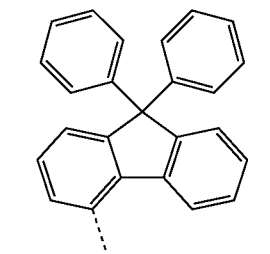 |
| 1-410 | 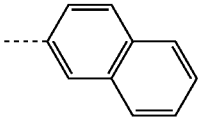 | 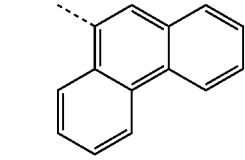 | 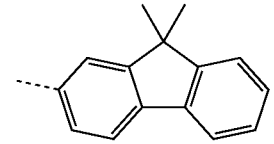 |
| 1-411 | 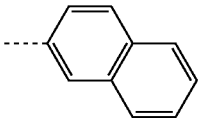 | 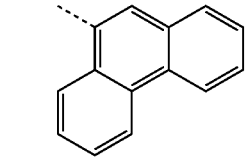 | 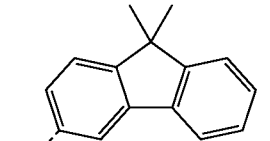 |
| 1-412 | 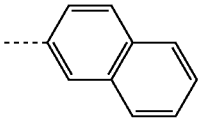 | 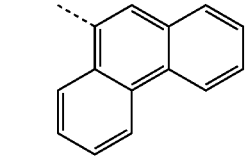 | 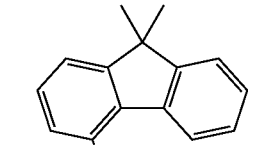 |
| 1-413 | 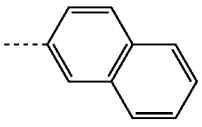 | 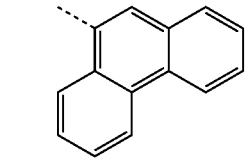 | 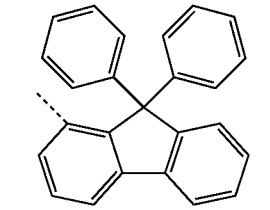 |
| 1-414 | 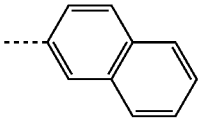 | 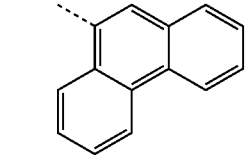 | 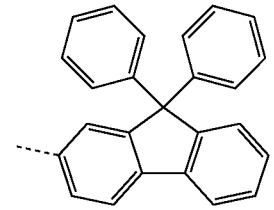 |

-continued
| Formula | ---Ar1 | ---Ar2 | ---Ar3 |
|---|---|---|---|
| 1-415 | 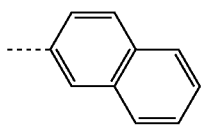 | 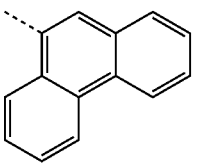 | 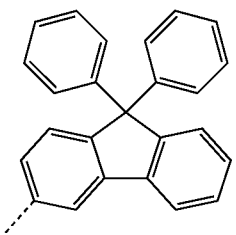 |
| 1-416 | 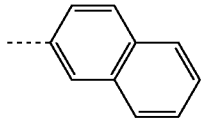 | 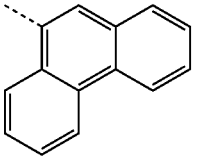 | 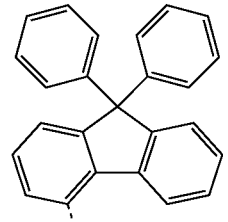 |
| 1-419 | 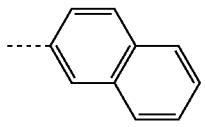 | 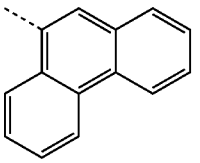 | 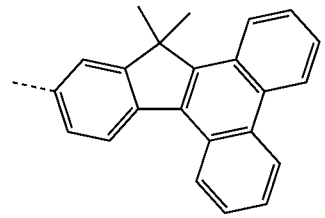 |
| 1-421 | 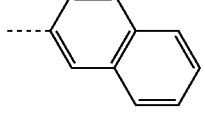 | 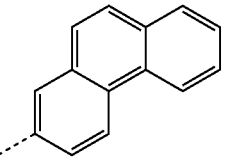 | 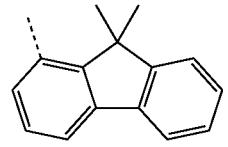 |
| 1-423 | 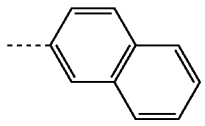 | 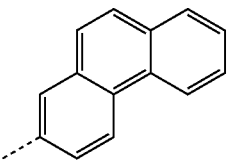 | 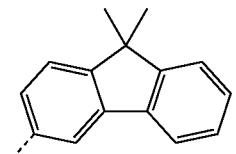 |
| 1-424 | 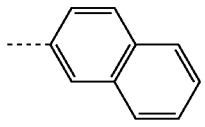 | 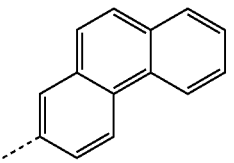 | 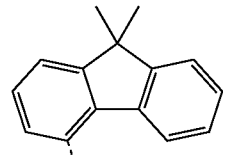 |
| 1-425 | 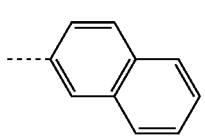 | 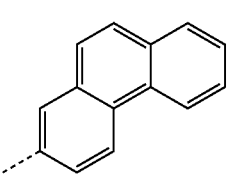 | 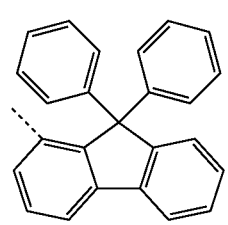 |

-continued
| Formula | ---Ar1 | ---Ar2 | ---Ar3 |
|---|---|---|---|
| 1-426 | 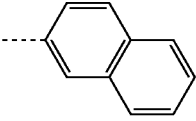 | 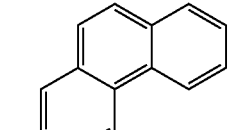 | 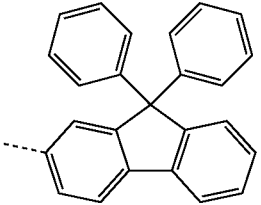 |
| 1-427 | 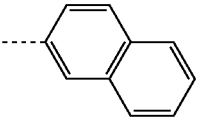 | 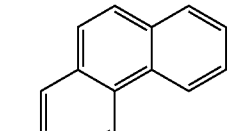 | 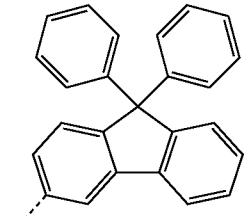 |
| 1-428 | 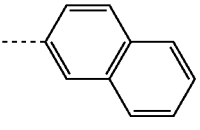 | 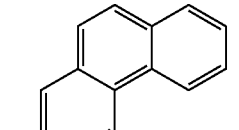 | 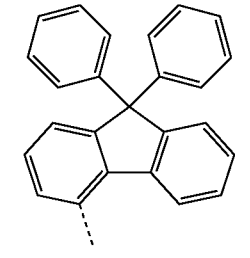 |
| 1-429 | 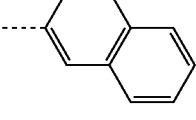 | 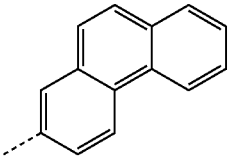 | 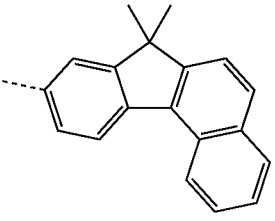 |
| 1-433 | 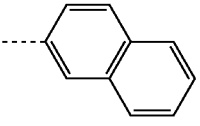 | 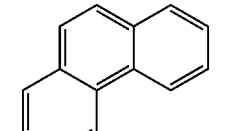 | 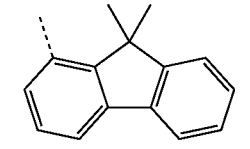 |
| 1-434 | 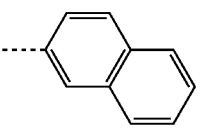 | 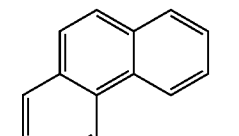 | 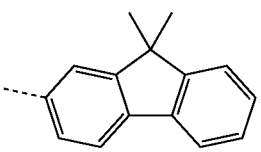 |
| 1-435 | 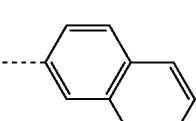 | 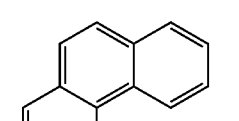 | 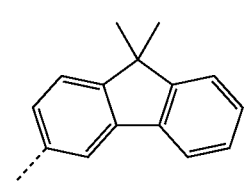 |

-continued
| Formula | ---Ar1 | ---Ar2 | ---Ar3 |
|---|---|---|---|
| 1-436 | 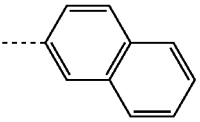 | 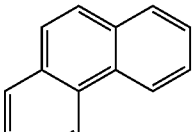 | 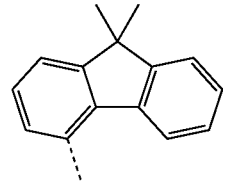 |
| 1-437 | 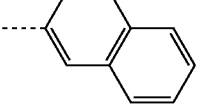 | 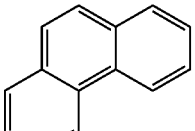 | 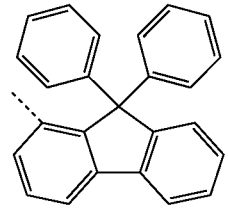 |
| 1-438 | 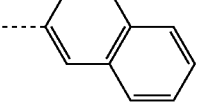 | 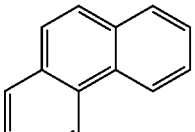 | 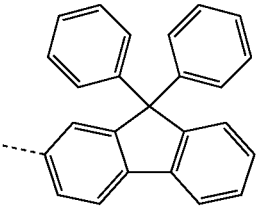 |
| 1-439 | 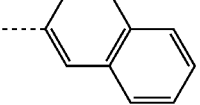 | 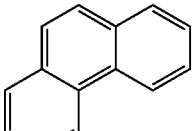 | 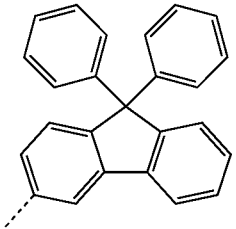 |
| 1-440 | 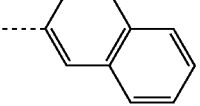 | 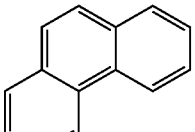 | 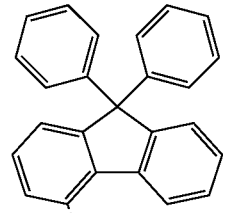 |
| 1-445 | 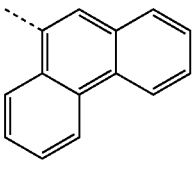 | 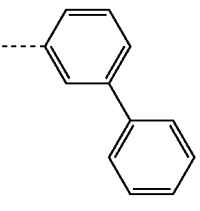 | 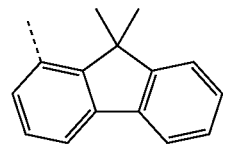 |
| 1-446 | 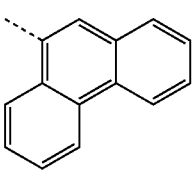 | 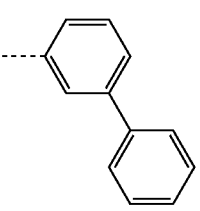 | 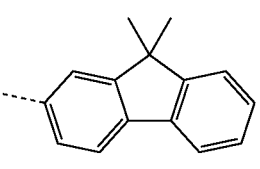 |

-continued

| Formula | ---Ar1 | ---Ar2 | ---Ar3 |
|---|---|---|---|
| 1-447 | phenanthrene | phenyl-naphthalene | 9,9-dimethylfluorene |
| 1-448 | phenanthrene | biphenyl | 9,9-dimethylfluorene |
| 1-449 | phenanthrene | biphenyl | benzo-fused 9,9-dimethylfluorene |
| 1-450 | phenanthrene | biphenyl | 9,9-diphenylfluorene |
| 1-451 | phenanthrene | biphenyl | 9,9-diphenylfluorene |
| 1-452 | phenanthrene | biphenyl | 9,9-diphenylfluorene |
| 1-457 | phenanthrene | biphenyl | 9,9-dimethylfluorene |

-continued
| Formula | ---Ar1 | ---Ar2 | ---Ar3 |
|---|---|---|---|
| 1-459 | 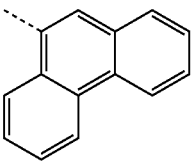 | 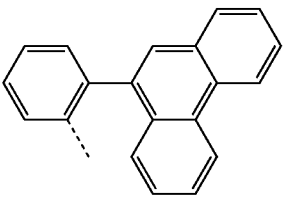 | 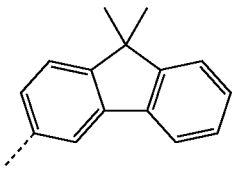 |
| 1-460 | 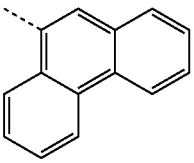 | 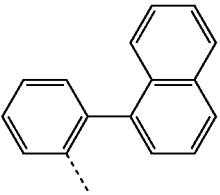 | 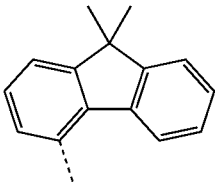 |
| 1-461 | 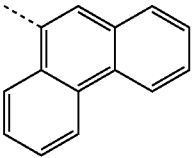 | 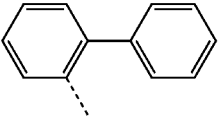 | 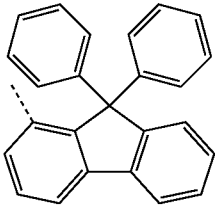 |
| 1-462 | 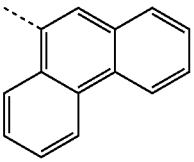 | 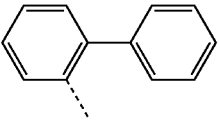 | 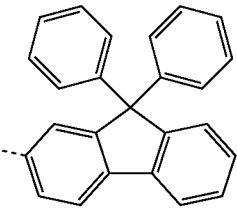 |
| 1-463 | 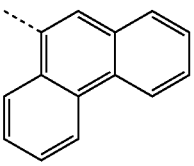 | 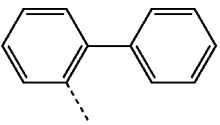 | 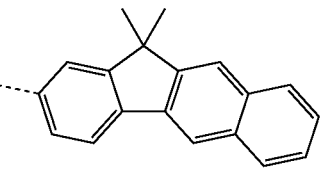 |
| 1-464 | 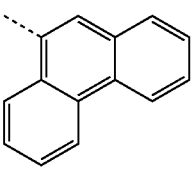 | 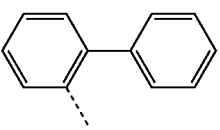 | 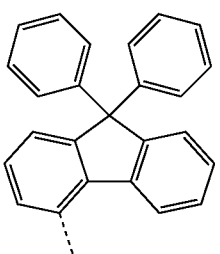 |
| 1-469 | 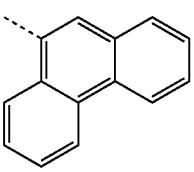 | 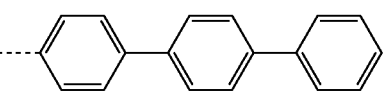 | 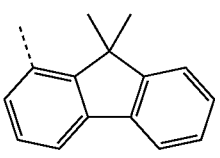 |

-continued
| Formula | ---Ar1 | ---Ar2 | ---Ar3 |
|---|---|---|---|
| 1-470 | 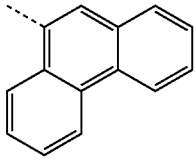 | 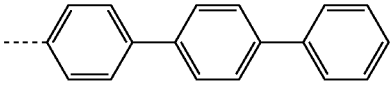 | 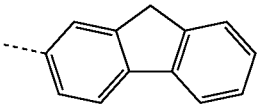 |
| 1-471 | 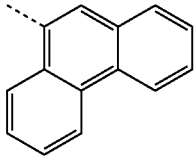 | 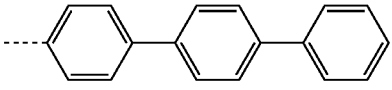 | 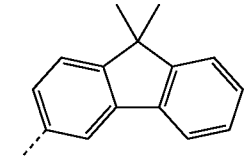 |
| 1-472 | 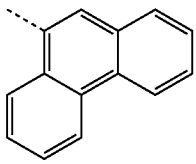 | 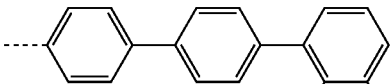 | 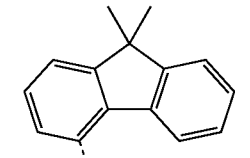 |
| 1-473 | 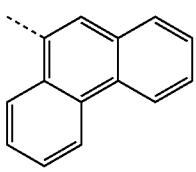 | 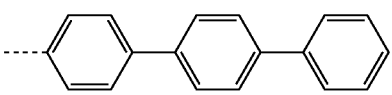 | 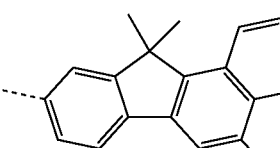 |
| 1-474 | 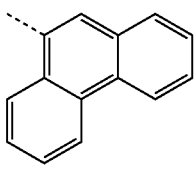 | 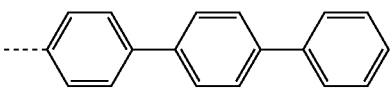 |  |
| 1-475 | 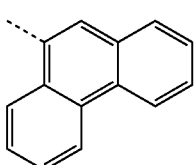 | 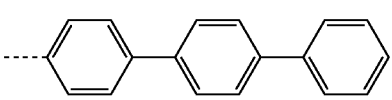 | 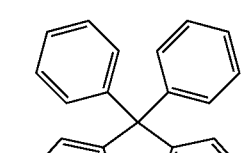 |
| 1-476 | 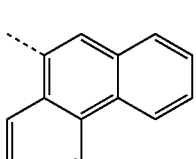 | 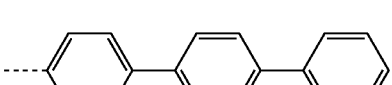 | 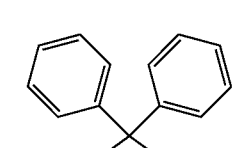 |

-continued
| Formula | ---Ar1 | ---Ar2 | ---Ar3 |
|---|---|---|---|
| 1-481 | 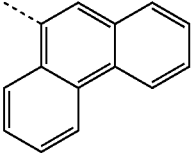 | 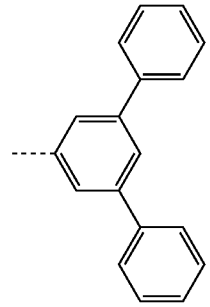 | 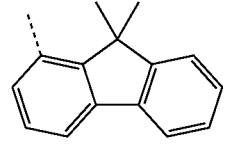 |
| 1-482 | 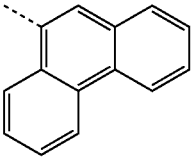 | 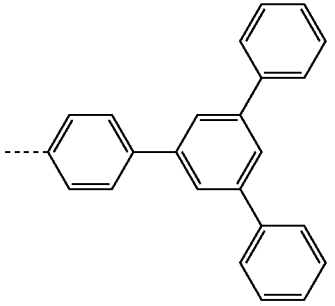 | 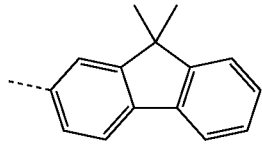 |
| 1-484 | 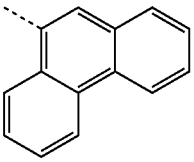 | 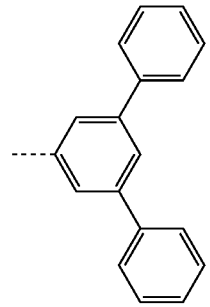 | 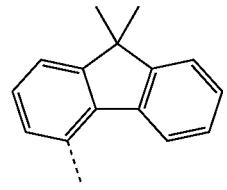 |
| 1-485 | 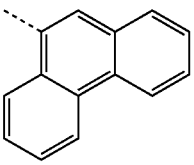 | 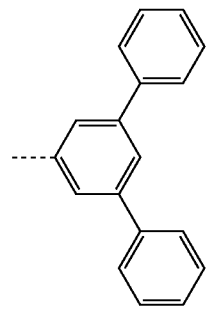 | 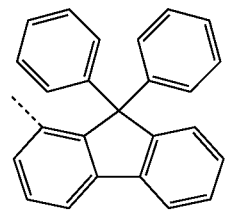 |
| 1-486 | 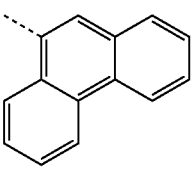 | 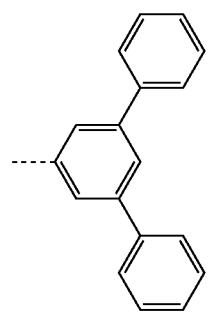 | 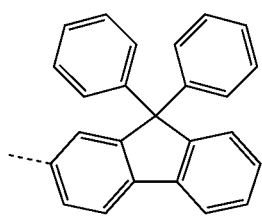 |

-continued
| Formula | ---Ar1 | ---Ar2 | ---Ar3 |
|---|---|---|---|
| 1-487 | 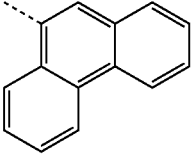 | 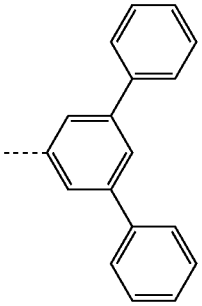 | 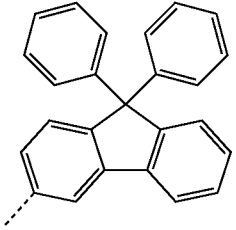 |
| 1-488 | 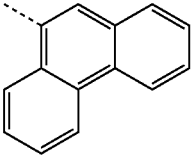 | 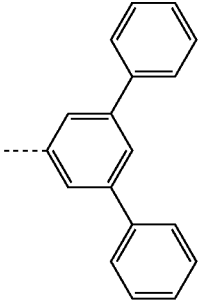 | 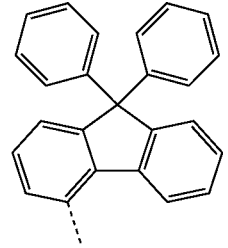 |
| 1-489 | 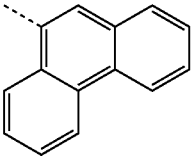 | 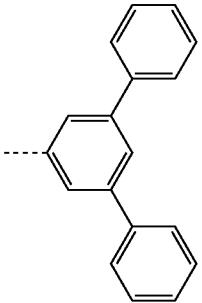 | 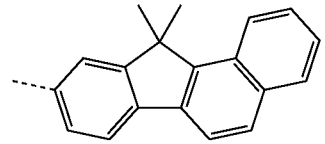 |
| 1-493 | 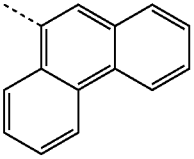 | 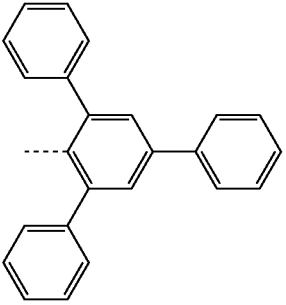 | 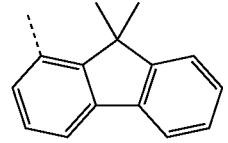 |
| 1-494 | 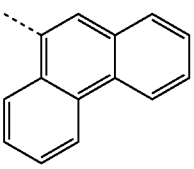 | 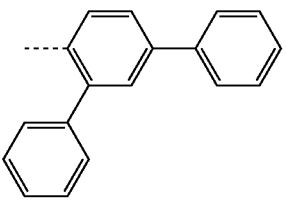 | 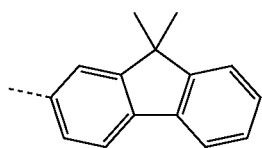 |

-continued
| Formula | ---Ar1 | ---Ar2 | ---Ar3 |
|---|---|---|---|
| 1-495 | 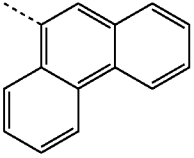 | 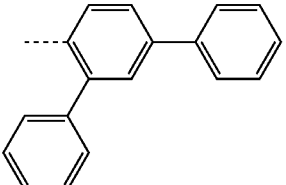 | 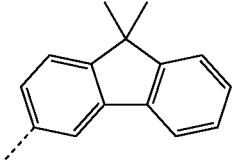 |
| 1-496 | 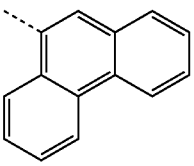 | 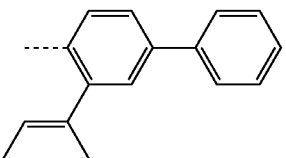 | 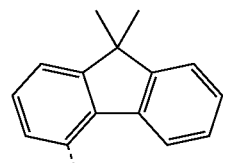 |
| 1-497 | 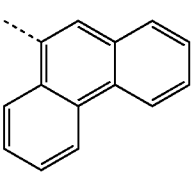 | 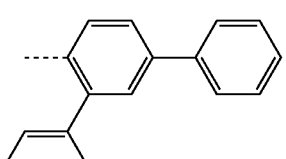 | 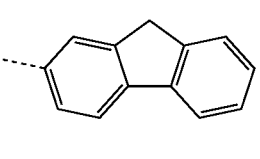 |
| 1-498 | 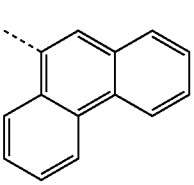 | 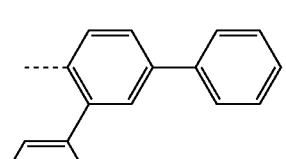 | 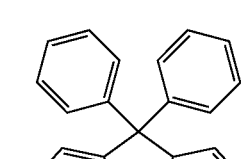 |
| 1-499 | 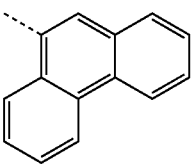 | 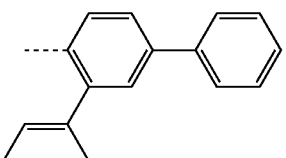 | 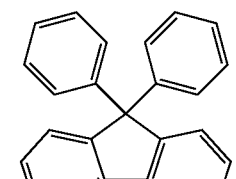 |
| 1-500 | 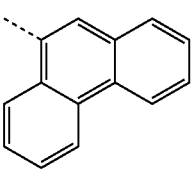 | 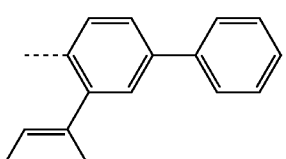 | 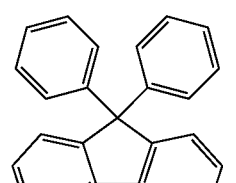 |
| 1-505 | 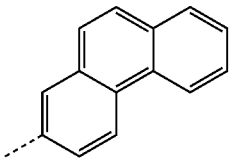 | 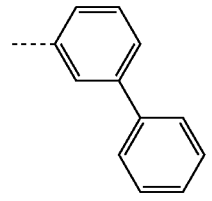 | 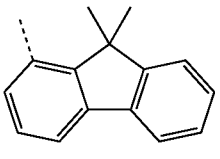 |

-continued
| Formula | ---Ar1 | ---Ar2 | ---Ar3 |
|---|---|---|---|
| 1-506 | 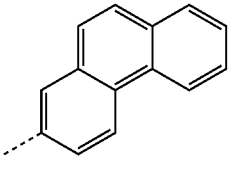 | 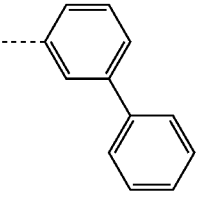 | 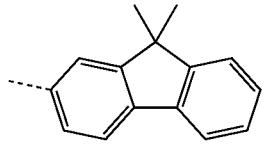 |
| 1-508 | 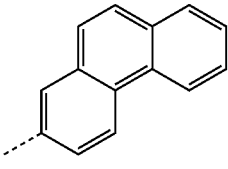 | 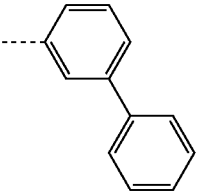 | 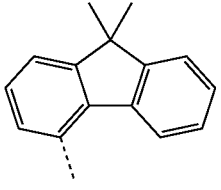 |
| 1-509 | 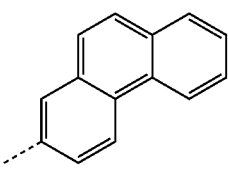 | 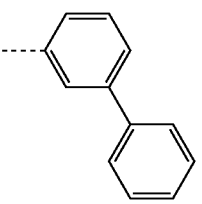 | 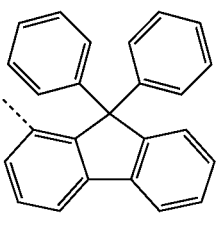 |
| 1-510 | 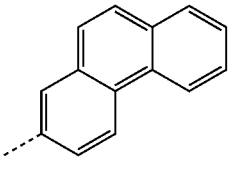 | 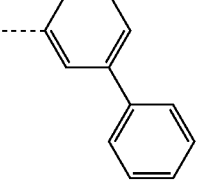 | 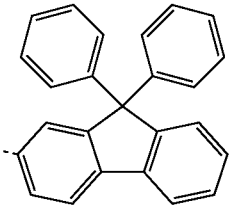 |
| 1-511 | 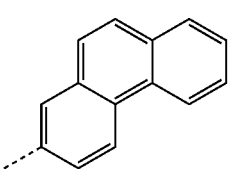 | 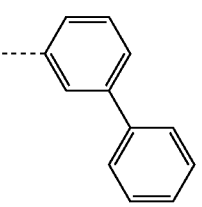 | 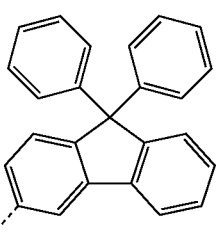 |
| 1-512 | 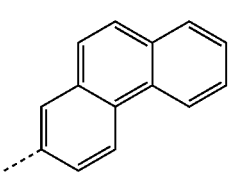 | 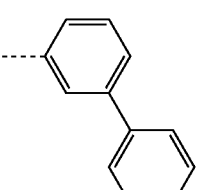 | 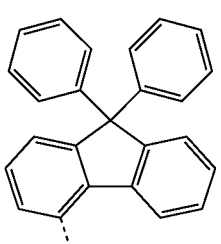 |
| 1-517 | 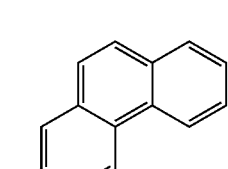 | 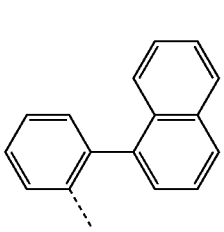 | 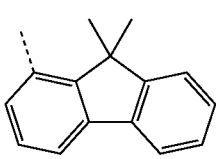 |

-continued
| Formula | ---Ar1 | ---Ar2 | ---Ar3 |
|---|---|---|---|
| 1-518 | 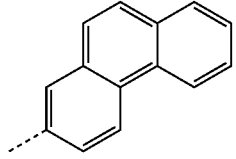 | 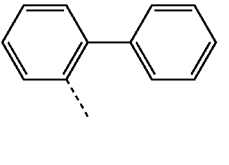 | 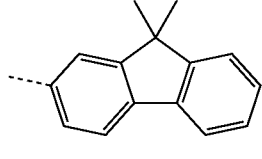 |
| 1-519 | 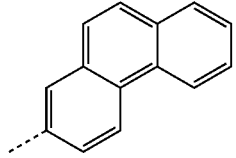 | 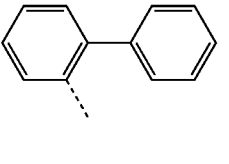 | 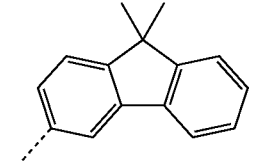 |
| 1-520 | 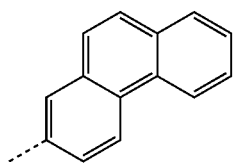 | 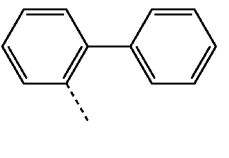 | 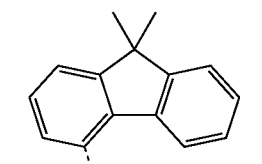 |
| 1-521 | 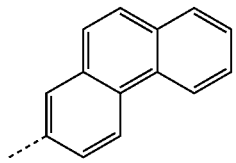 | 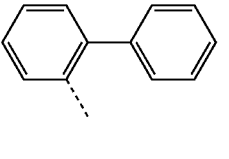 | 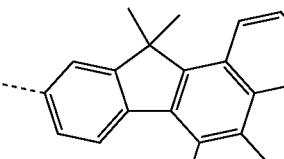 |
| 1-522 | 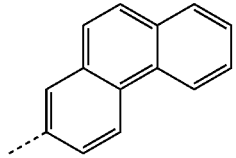 | 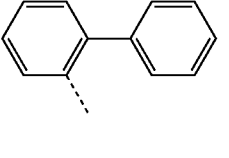 | 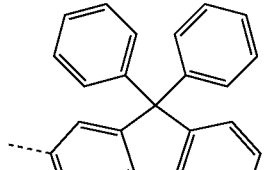 |
| 1-523 | 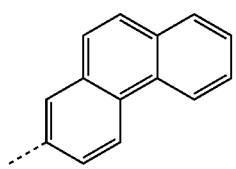 | 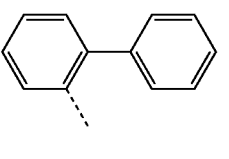 | 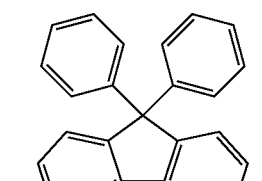 |
| 1-524 | 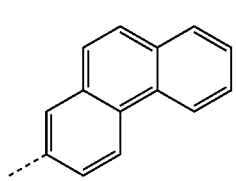 | 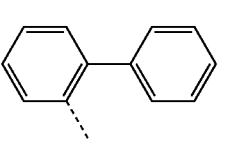 | 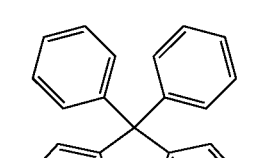 |

| Formula | ---Ar1 | ---Ar2 | ---Ar3 |
|---|---|---|---|
| 1-527 | 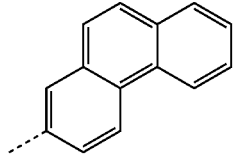 | 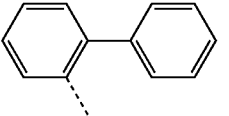 | 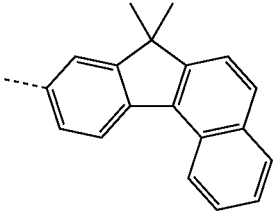 |
| 1-529 | 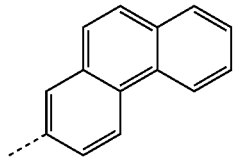 | 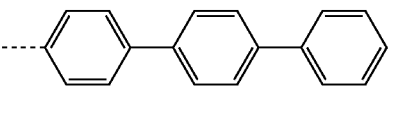 | 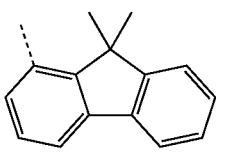 |
| 1-530 | 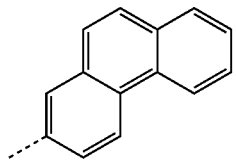 | 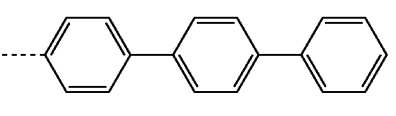 | 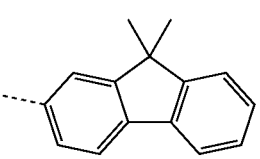 |
| 1-531 | 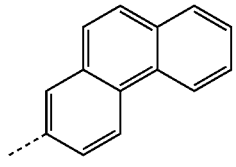 | 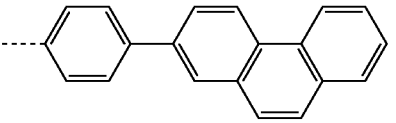 | 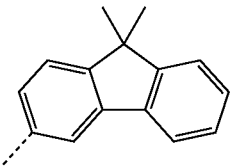 |
| 1-532 | 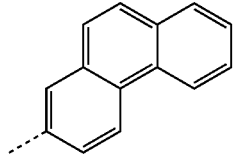 | 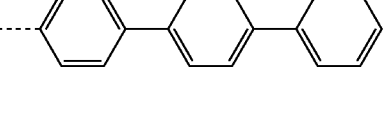 | 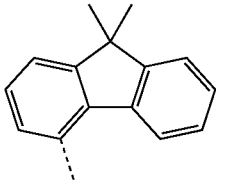 |
| 1-533 | 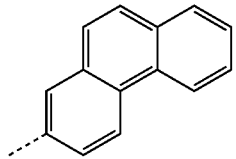 | 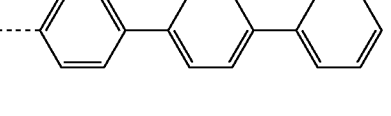 | 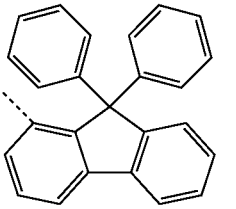 |
| 1-534 | 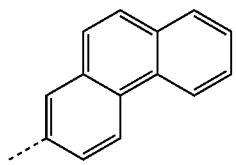 | 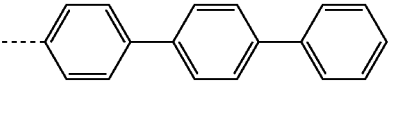 | 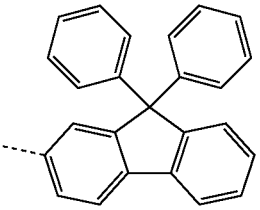 |

-continued
| Formula | ---Ar1 | ---Ar2 | ---Ar3 |
|---|---|---|---|
| 1-535 | 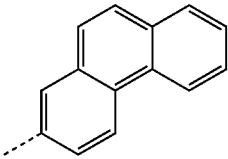 | 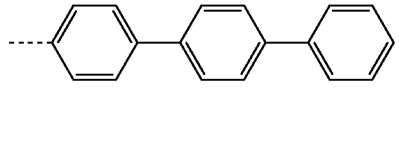 | 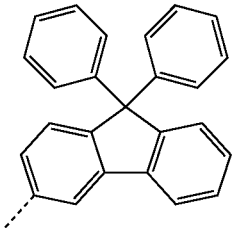 |
| 1-536 | 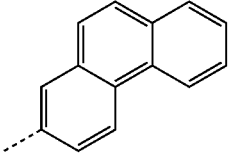 | 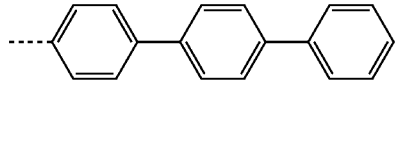 | 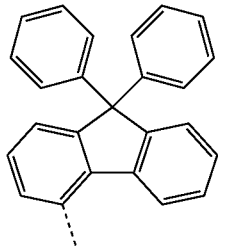 |
| 1-541 | 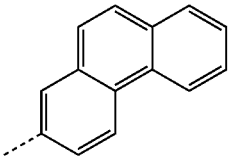 | 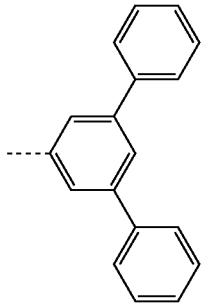 | 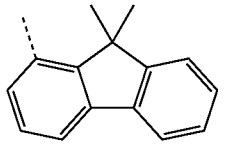 |
| 1-542 | 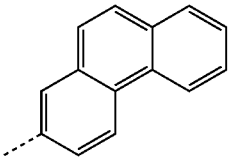 | 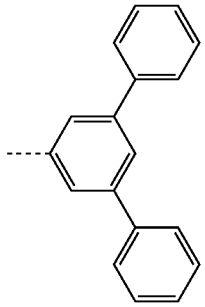 | 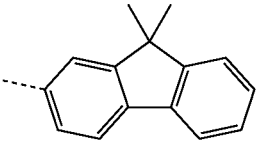 |
| 1-543 | 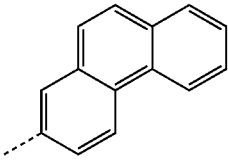 | 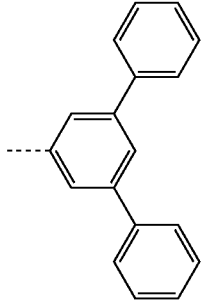 | 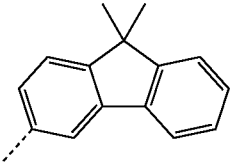 |

| Formula | ---Ar1 | ---Ar2 | ---Ar3 |
|---|---|---|---|
| 1-544 | | | |
| 1-545 | | | |
| 1-546 | | | |
| 1-547 | | | |
| 1-548 | | | |

| Formula | ---Ar1 | ---Ar2 | ---Ar3 |
|---|---|---|---|
| 1-553 | 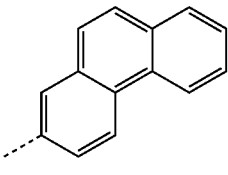 | 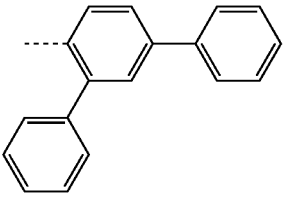 | 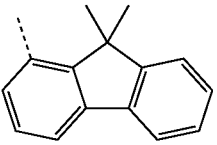 |
| 1-554 | 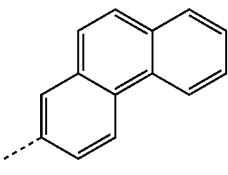 | 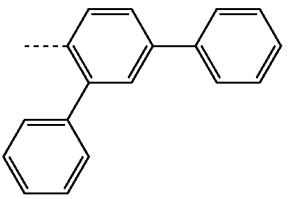 | 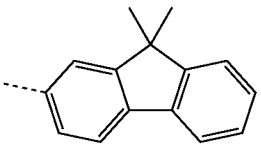 |
| 1-555 | 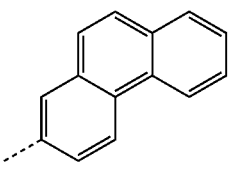 | 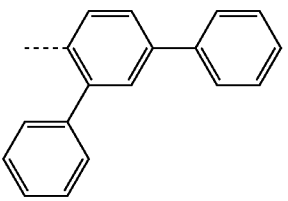 | 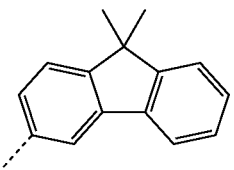 |
| 1-556 | 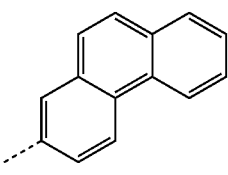 | 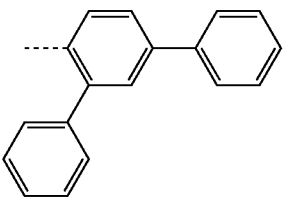 | 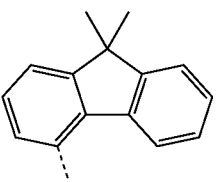 |
| 1-557 | 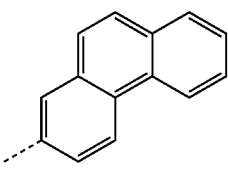 | 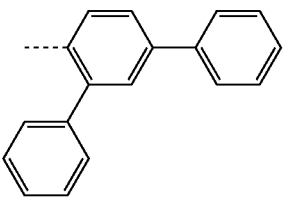 | 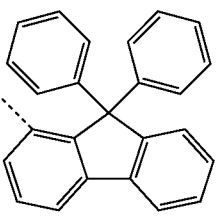 |
| 1-558 | 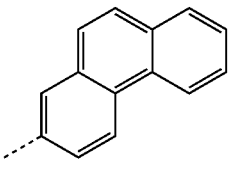 | 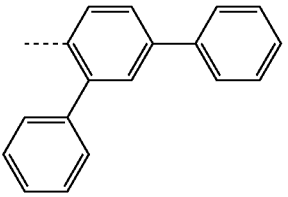 | 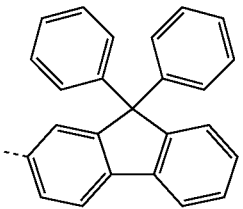 |
| 1-559 | 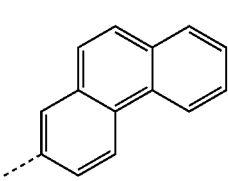 | 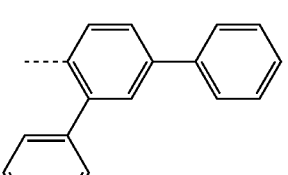 | 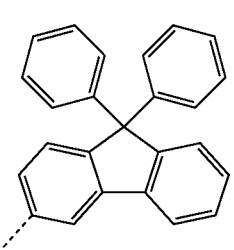 |

-continued
| Formula | ---Ar1 | ---Ar2 | ---Ar3 |
| --- | --- | --- | --- |
| 1-560 | 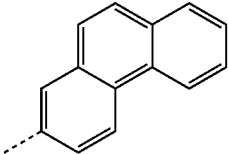 | 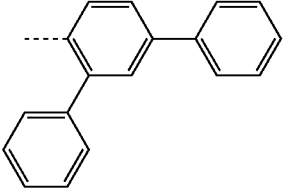 | 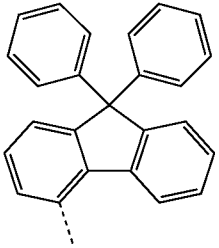 |
| 1-561 | 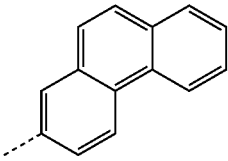 | 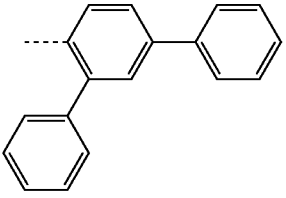 | 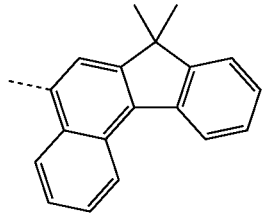 |
| 1-563 | 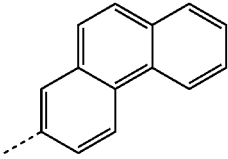 | 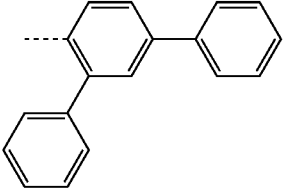 | 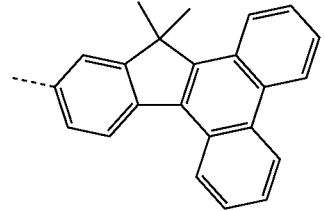 |
| 1-565 | 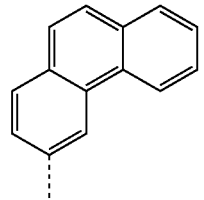 | 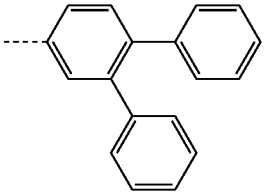 | 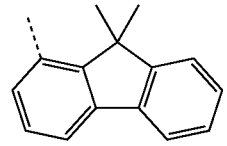 |
| 1-566 | 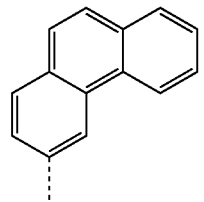 | 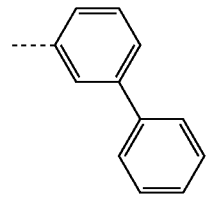 | 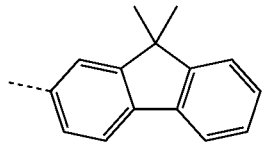 |
| 1-567 | 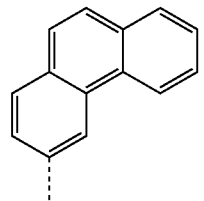 | 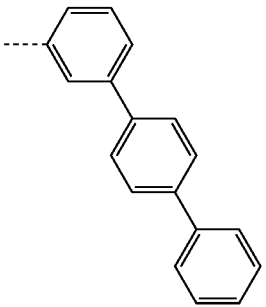 | 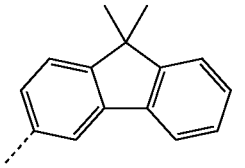 |

-continued
| Formula | ---Ar1 | ---Ar2 | ---Ar3 |
|---|---|---|---|
| 1-568 | 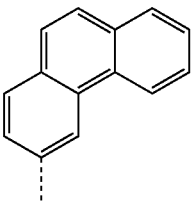 | 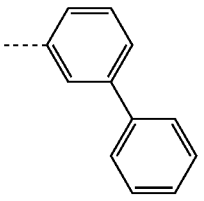 | 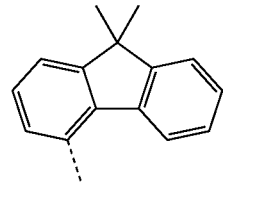 |
| 1-569 | 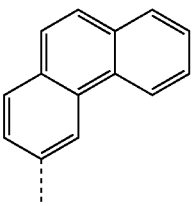 | 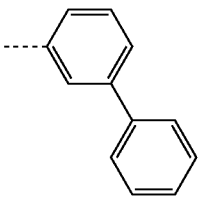 | 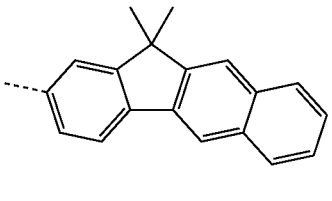 |
| 1-570 | 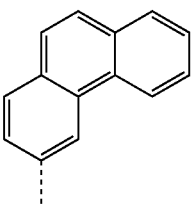 | 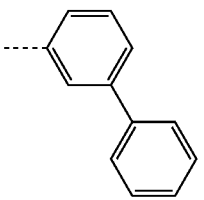 | 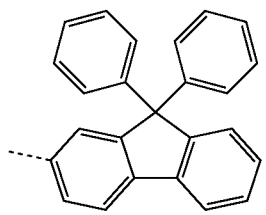 |
| 1-571 | 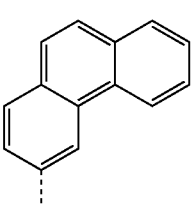 | 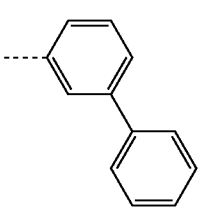 | 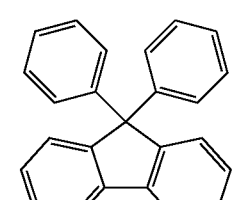 |
| 1-572 | 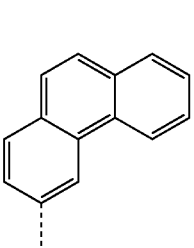 | 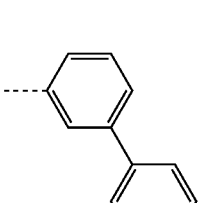 | 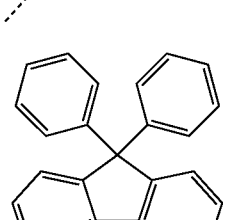 |
| 1-577 | 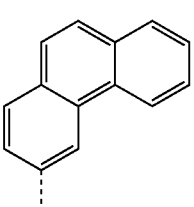 | 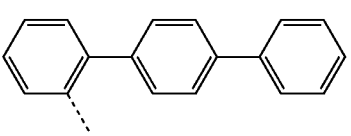 | 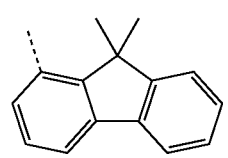 |
| 1-578 | 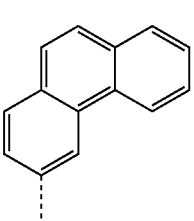 | 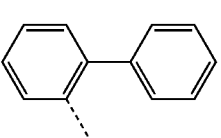 | 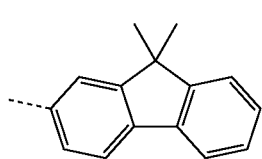 |

-continued
| Formula | ---Ar1 | ---Ar2 | ---Ar3 |
|---|---|---|---|
| 1-579 | 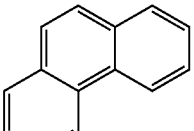 | 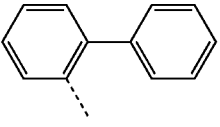 | 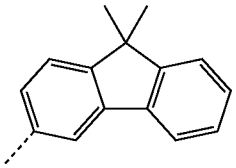 |
| 1-580 | 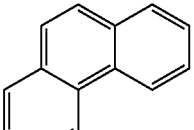 | 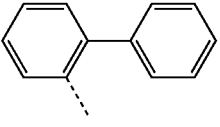 | 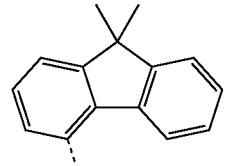 |
| 1-581 | 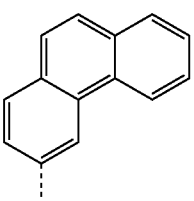 | 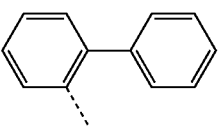 | 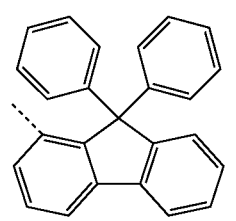 |
| 1-582 | 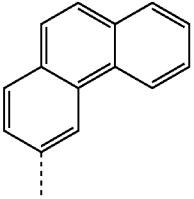 | 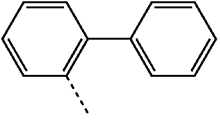 | 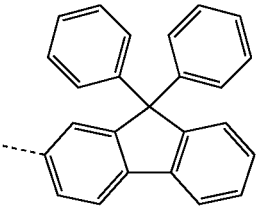 |
| 1-583 | 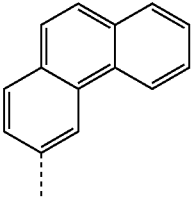 | 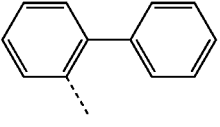 | 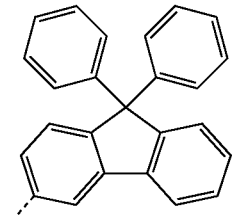 |
| 1-584 | 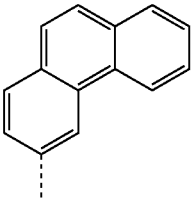 | 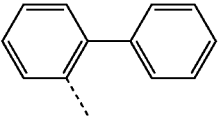 | 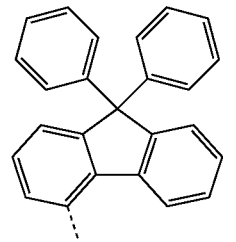 |
| 1-589 | 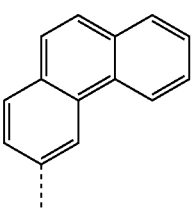 | 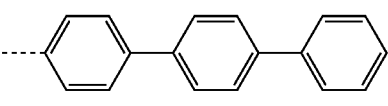 | 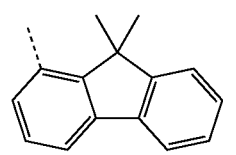 |

-continued
| Formula | ---Ar1 | ---Ar2 | ---Ar3 |
|---|---|---|---|
| 1-590 | 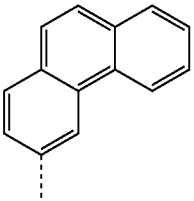 | 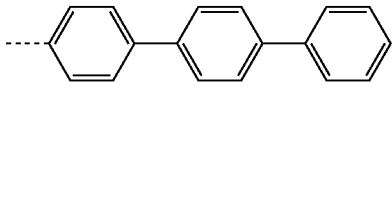 | 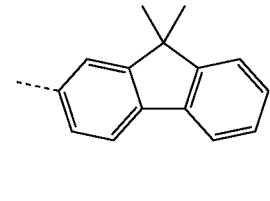 |
| 1-591 | 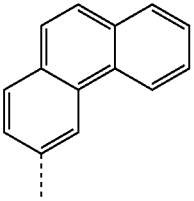 | 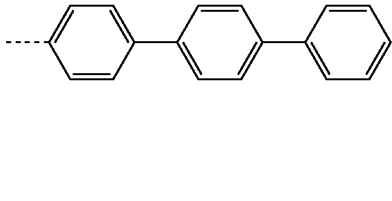 | 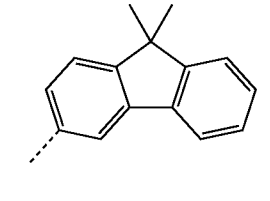 |
| 1-592 | 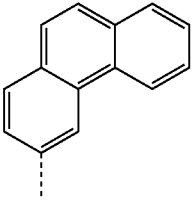 | 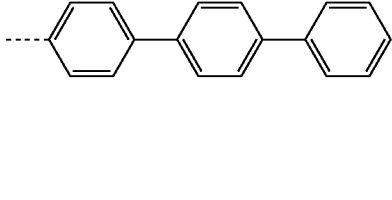 | 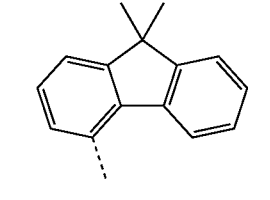 |
| 1-593 | 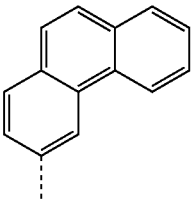 | 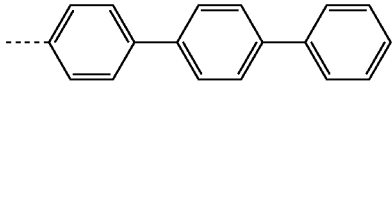 | 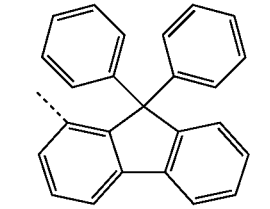 |
| 1-594 | 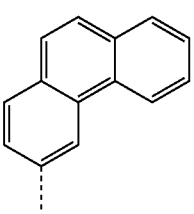 | 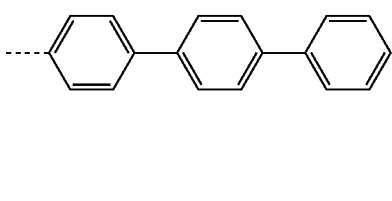 | 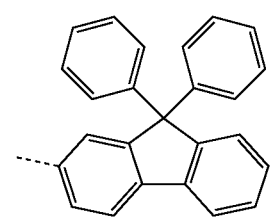 |
| 1-595 | 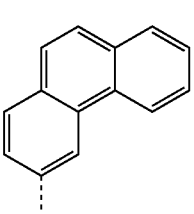 | 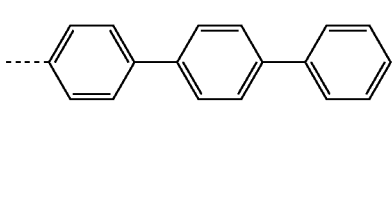 | 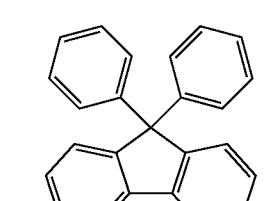 |
| 1-596 | 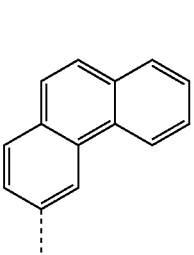 | 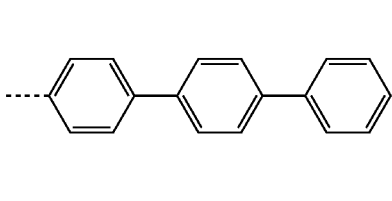 | 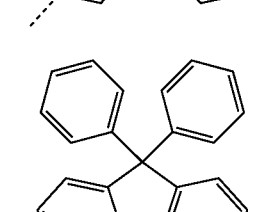 |

-continued
| Formula | ---Ar1 | ---Ar2 | ---Ar3 |
|---|---|---|---|
| 1-597 | 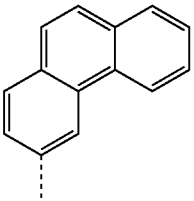 | 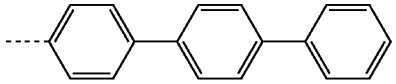 | 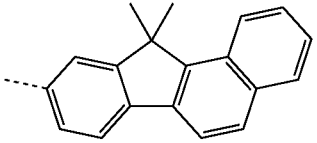 |
| 1-601 | 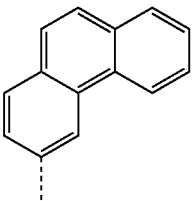 | 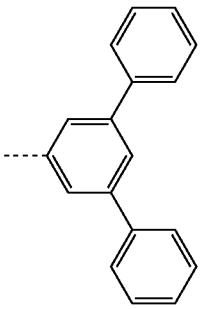 | 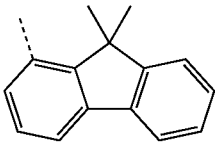 |
| 1-602 | 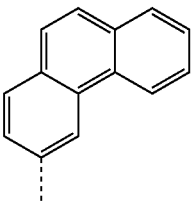 | 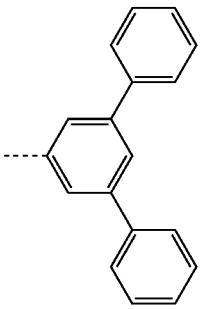 | 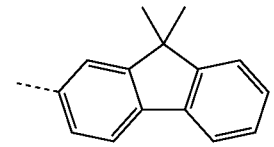 |
| 1-603 | 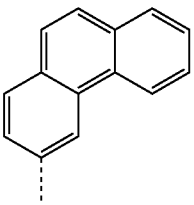 | 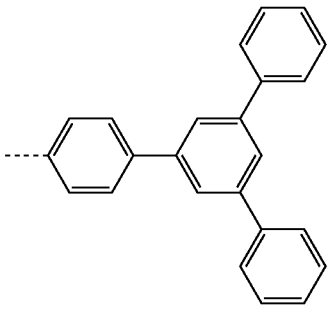 | 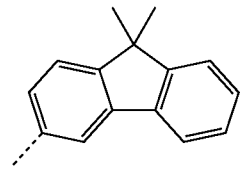 |
| 1-604 | 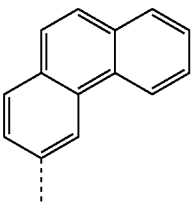 | 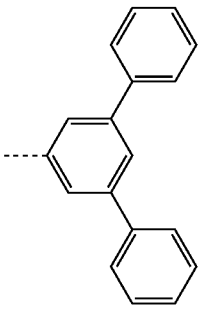 | 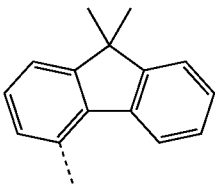 |

-continued
| Formula | ---Ar1 | ---Ar2 | ---Ar3 |
|---|---|---|---|
| 1-605 | 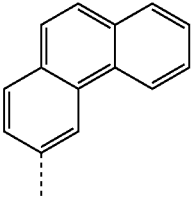 | 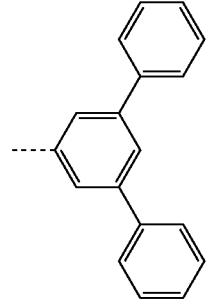 | 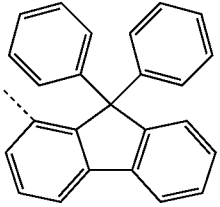 |
| 1-606 | 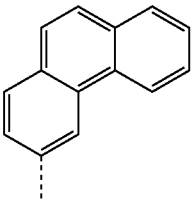 | 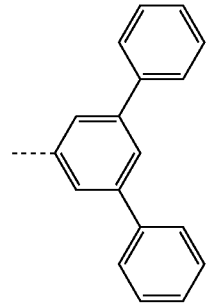 | 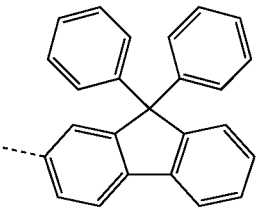 |
| 1-607 | 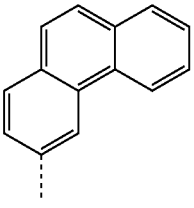 | 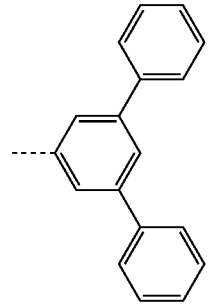 | 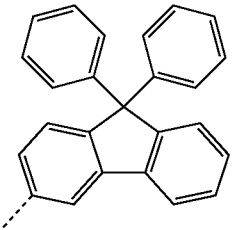 |
| 1-608 | 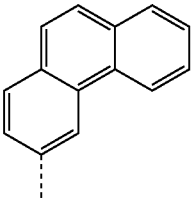 | 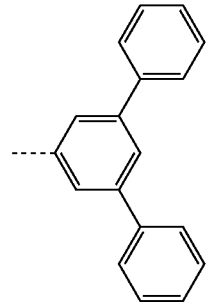 | 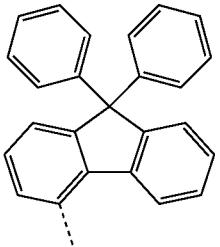 |
| 1-609 | 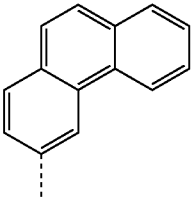 | 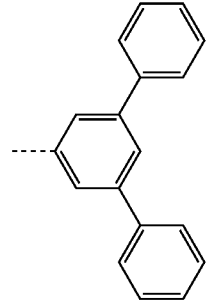 | 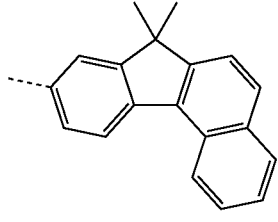 |

-continued

| Formula | ---Ar1 | ---Ar2 | ---Ar3 |
|---|---|---|---|
| 1-611 | | | |
| 1-613 | | | |
| 1-614 | | | |
| 1-615 | | | |
| 1-616 | | | |
| 1-617 | | | |

| Formula | ---Ar1 | ---Ar2 | ---Ar3 |
|---|---|---|---|
| 1-618 | 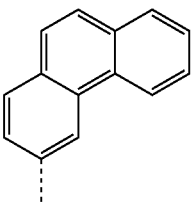 | 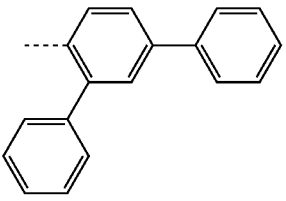 | 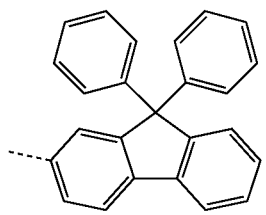 |
| 1-619 | 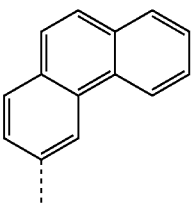 | 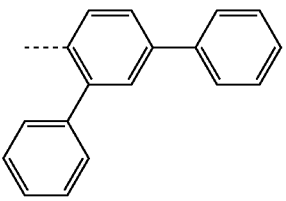 | 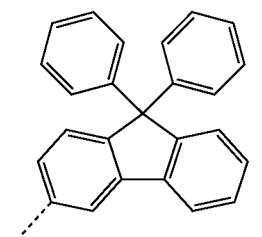 |
| 1-620 | 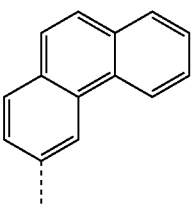 | 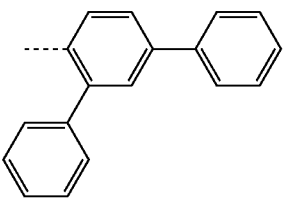 | 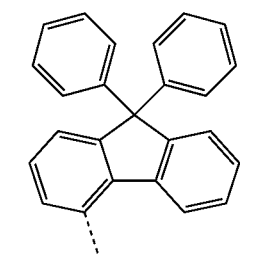 |
| 1-623 | 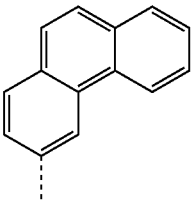 | 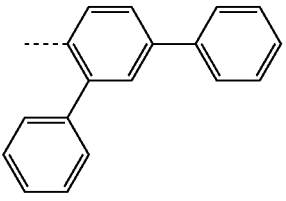 | 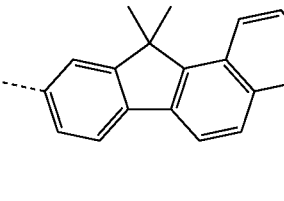 |
| 1-623 | 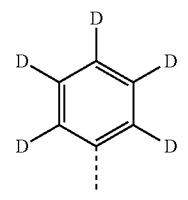 | 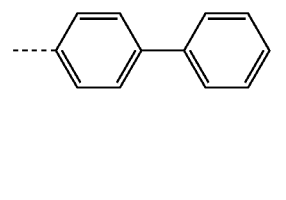 | 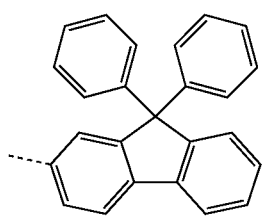 |
| 1-626 | 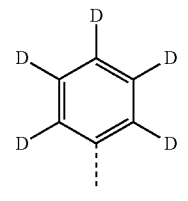 | 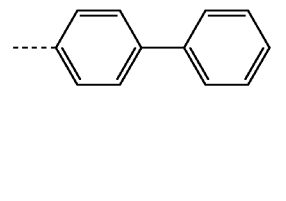 | 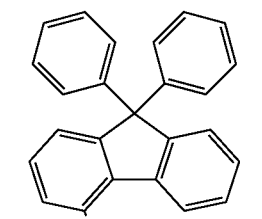 |

| Formula | ---Ar1 | ---Ar2 | ---Ar3 |
|---|---|---|---|
| 2-1 |  |  |  |
| 2-2 |  | 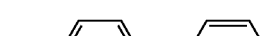 |  |
| 2-3 |  | 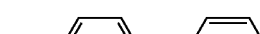 |  |
| 2-4 |  | 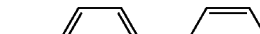 | 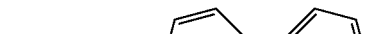 |
| 2-5 |  |  | 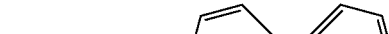 |
| 2-6 |  | 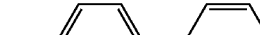 |  |

-continued
| Formula | ---Ar1 | ---Ar2 | ---Ar3 |
|---|---|---|---|
| 2-8 | 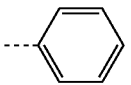 | 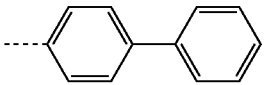 | 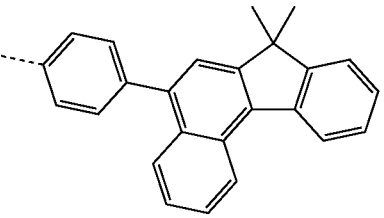 |
| 2-9 | 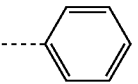 | 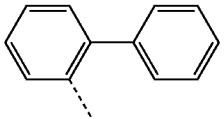 | 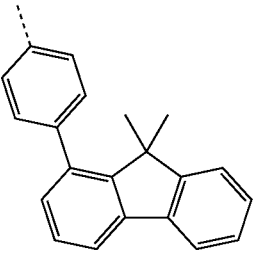 |
| 2-10 | 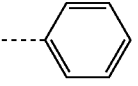 | 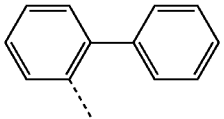 | 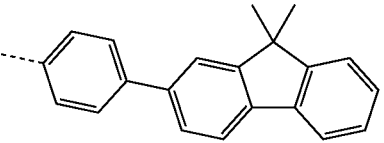 |
| 2-11 | 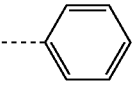 | 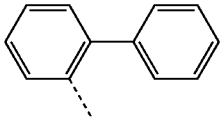 | 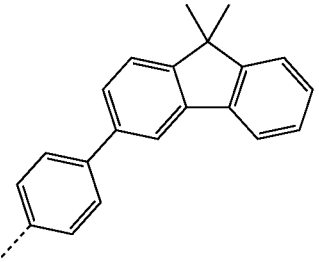 |
| 2-12 | 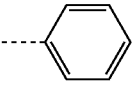 | 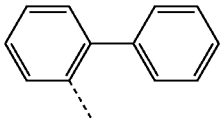 | 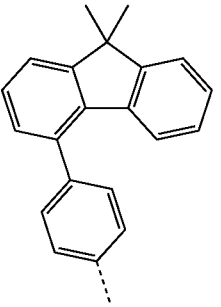 |
| 2-13 | 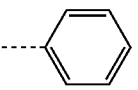 | 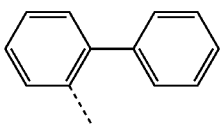 | 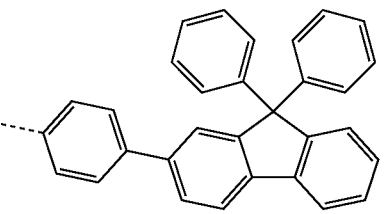 |

-continued
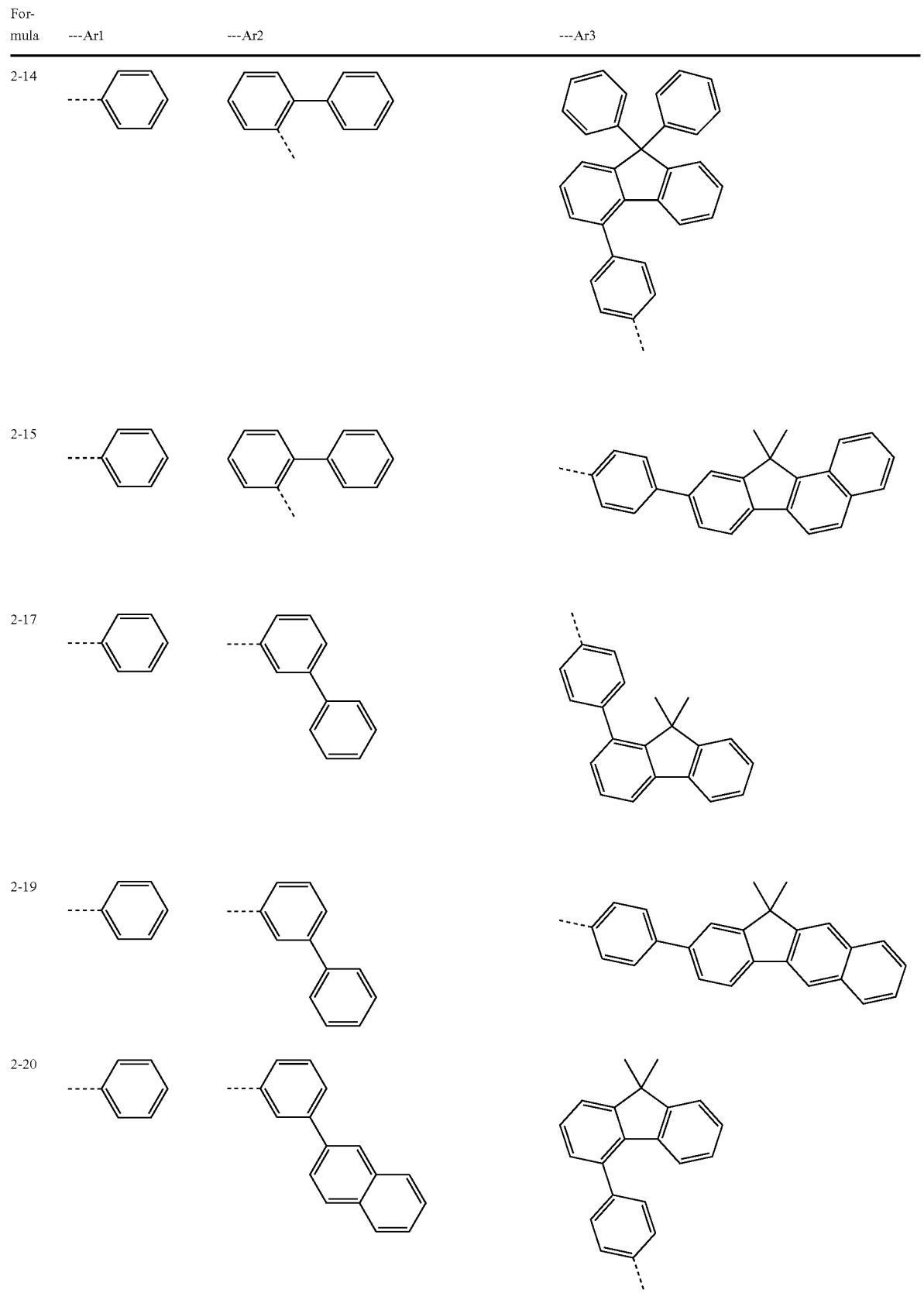

-continued
| Formula | ---Ar1 | ---Ar2 | ---Ar3 |
|---|---|---|---|
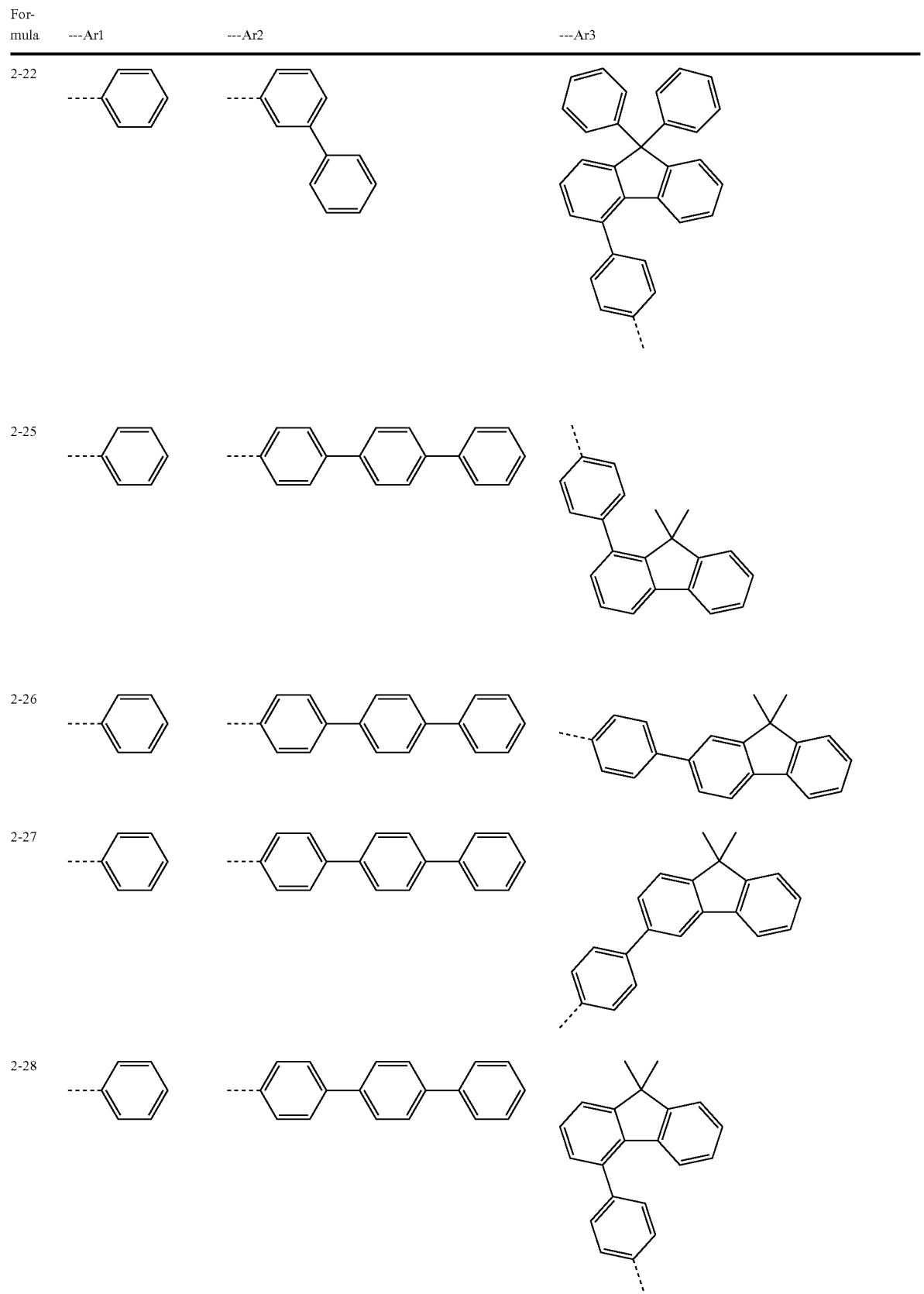

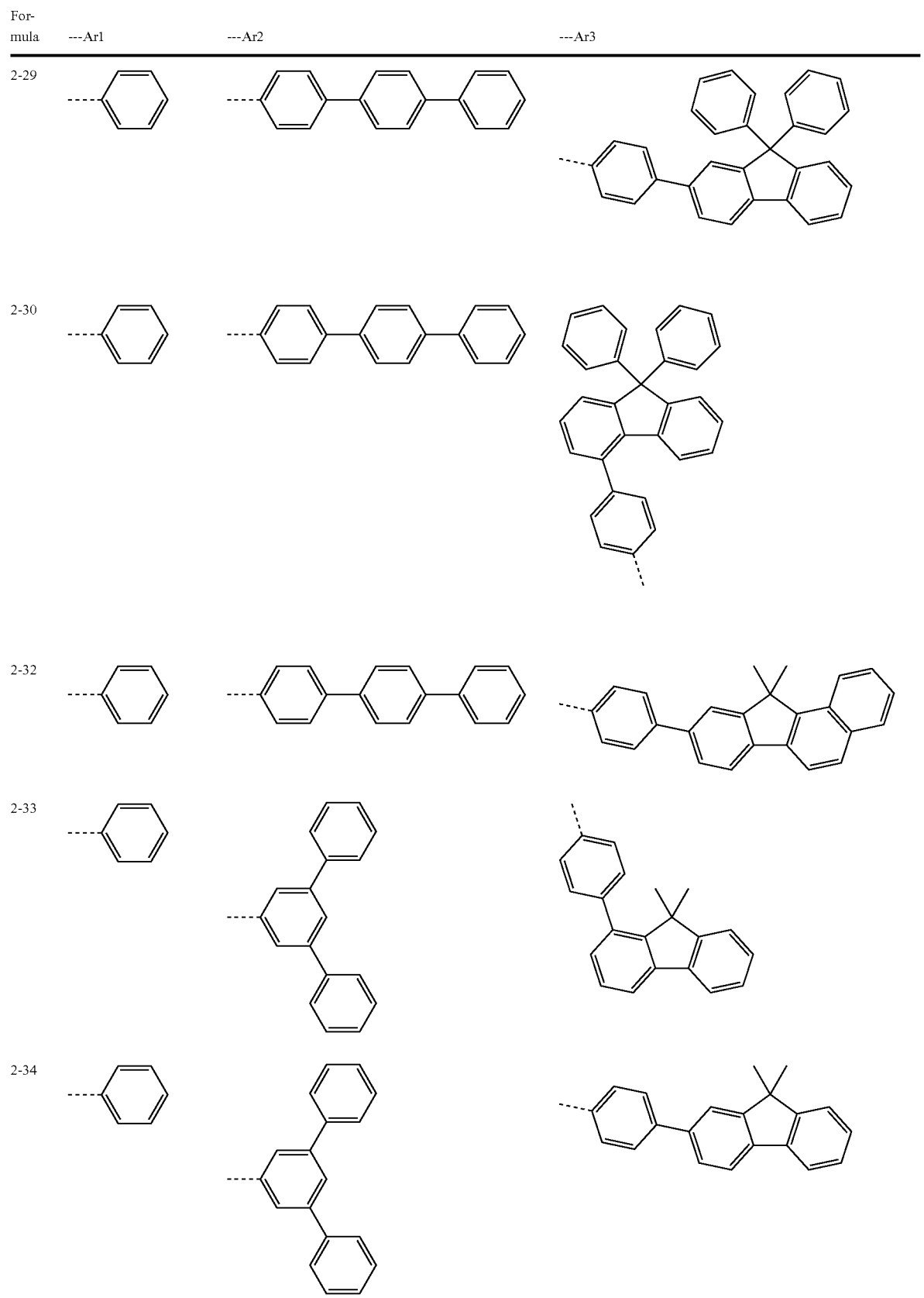

-continued
| Formula | ---Ar1 | ---Ar2 | ---Ar3 |
|---|---|---|---|
| 2-35 | 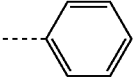 | 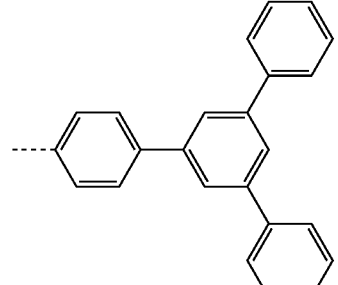 | 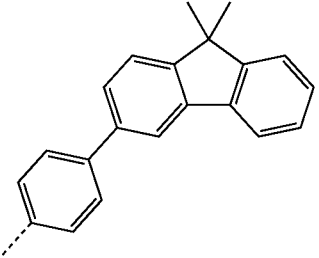 |
| 2-36 | 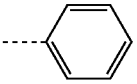 | 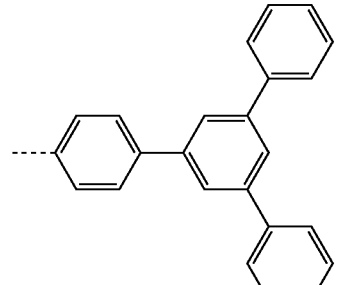 | 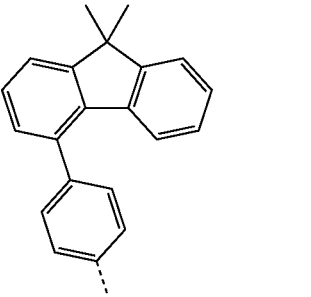 |
| 2-37 | 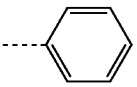 | 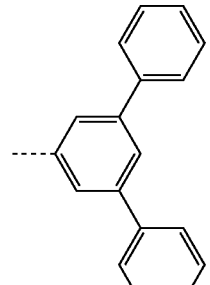 | 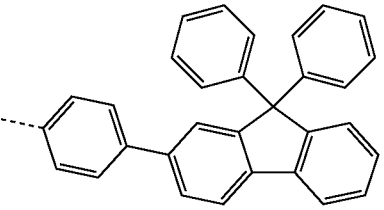 |
| 2-38 | 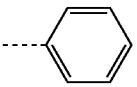 | 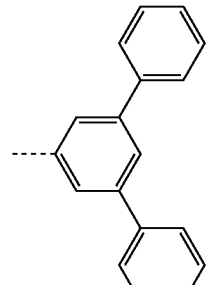 | 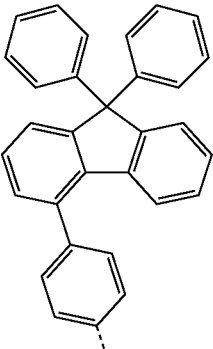 |
| 2-41 | 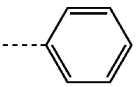 | 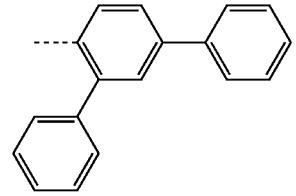 | 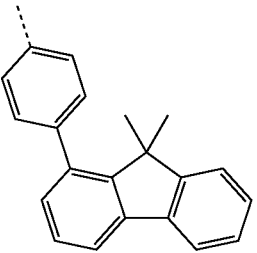 |

US 11,271,167 B2
643                                                                                          644
-continued
| Formula | ---Ar1 | ---Ar2 | ---Ar3 |
|---|---|---|---|
| 2-42 | 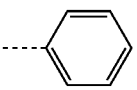 | 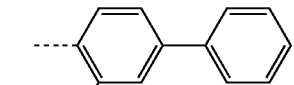 | 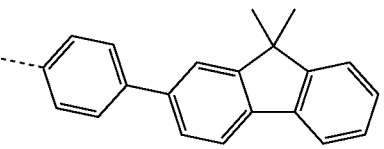 |
| 2-43 | 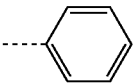 | 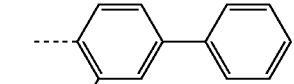 | 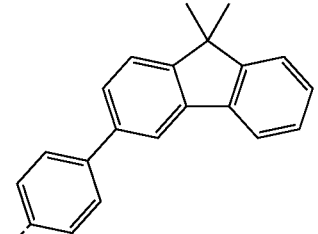 |
| 2-44 | 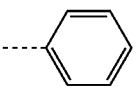 | 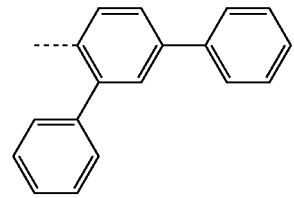 | 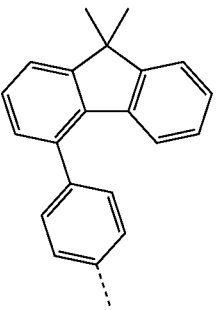 |
| 2-45 | 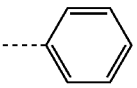 | 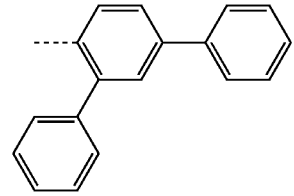 | 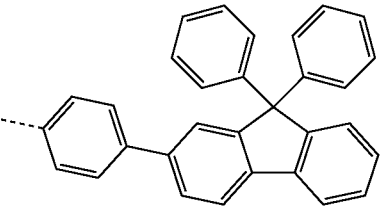 |
| 2-46 | 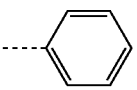 | 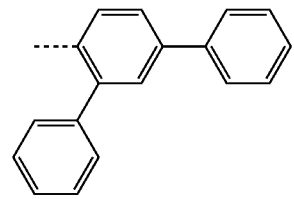 | 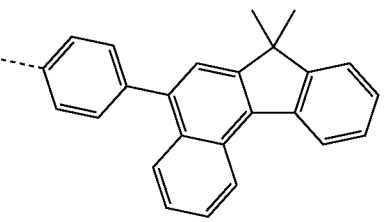 |
| 2-49 | 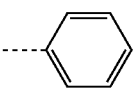 | 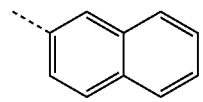 | 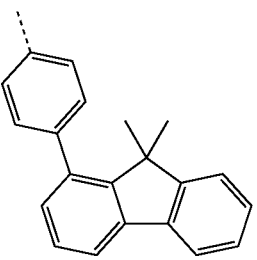 |

-continued
| Formula | ---Ar1 | ---Ar2 | ---Ar3 |
|---|---|---|---|
| 2-50 | 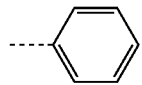 | 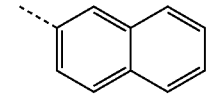 | 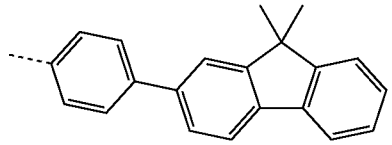 |
| 2-51 | 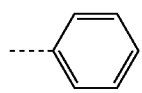 | 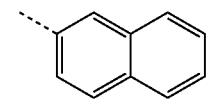 | 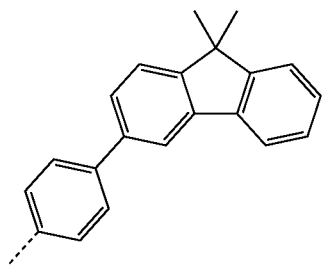 |
| 2-52 | 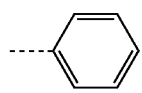 | 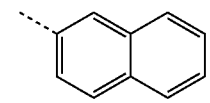 | 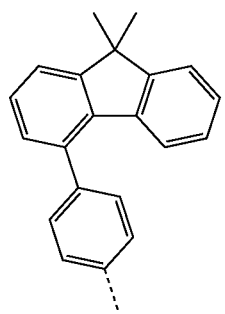 |
| 2-53 | 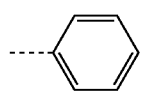 | 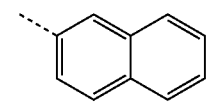 | 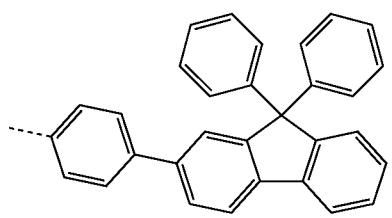 |
| 2-54 | 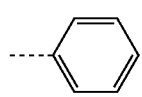 | 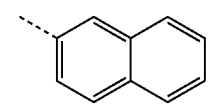 | 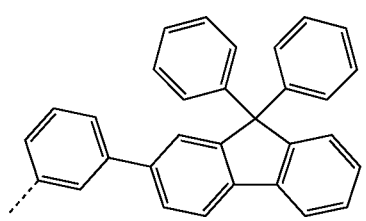 |
| 2-57 | 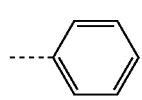 | 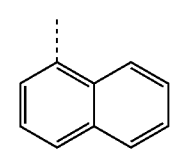 | 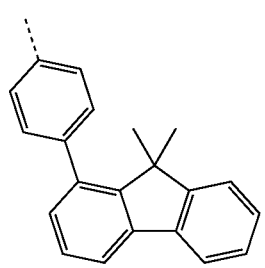 |

-continued
| Formula | ---Ar1 | ---Ar2 | ---Ar3 |
|---|---|---|---|
| 2-58 | 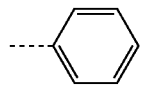 | 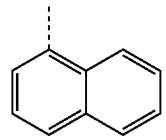 | 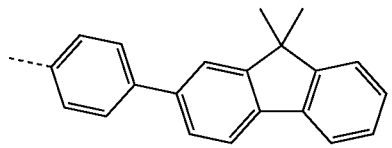 |
| 2-59 | 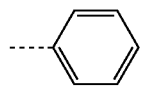 | 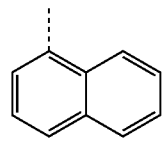 | 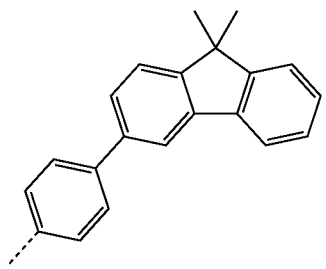 |
| 2-60 | 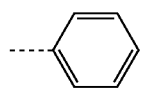 | 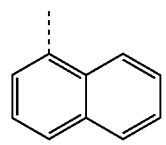 | 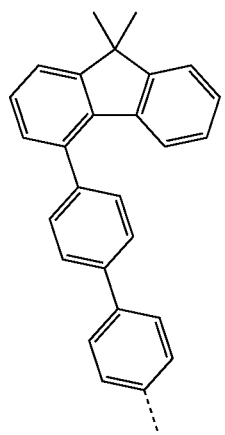 |
| 2-61 | 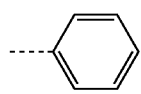 | 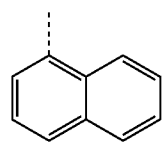 | 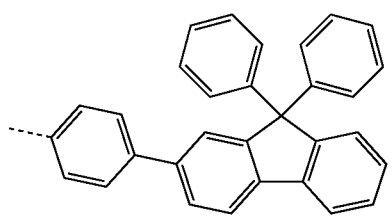 |
| 2-62 | 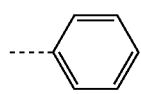 | 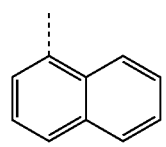 | 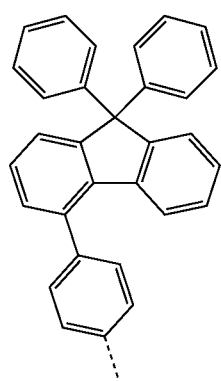 |

-continued
| Formula | ---Ar1 | ---Ar2 | ---Ar3 |
|---|---|---|---|
| 2-65 | 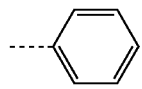 | 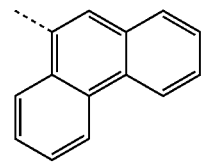 | 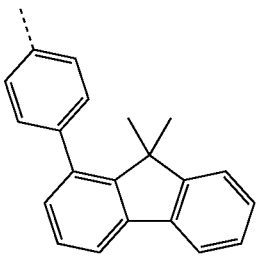 |
| 2-66 | 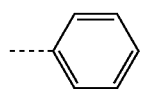 | 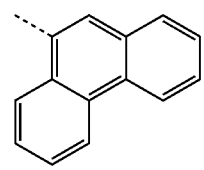 | 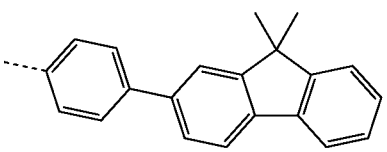 |
| 2-67 | 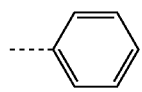 | 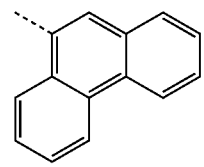 | 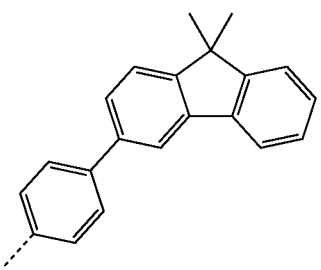 |
| 2-68 | 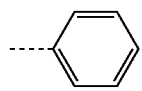 | 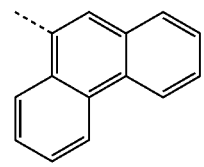 | 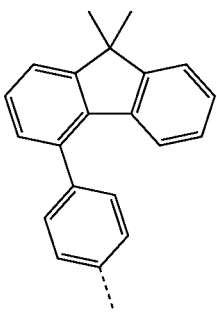 |
| 2-69 | 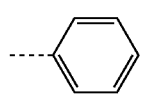 | 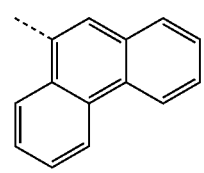 | 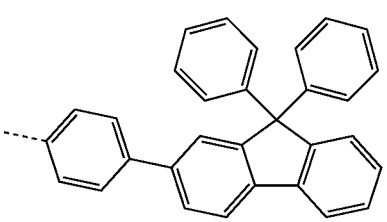 |

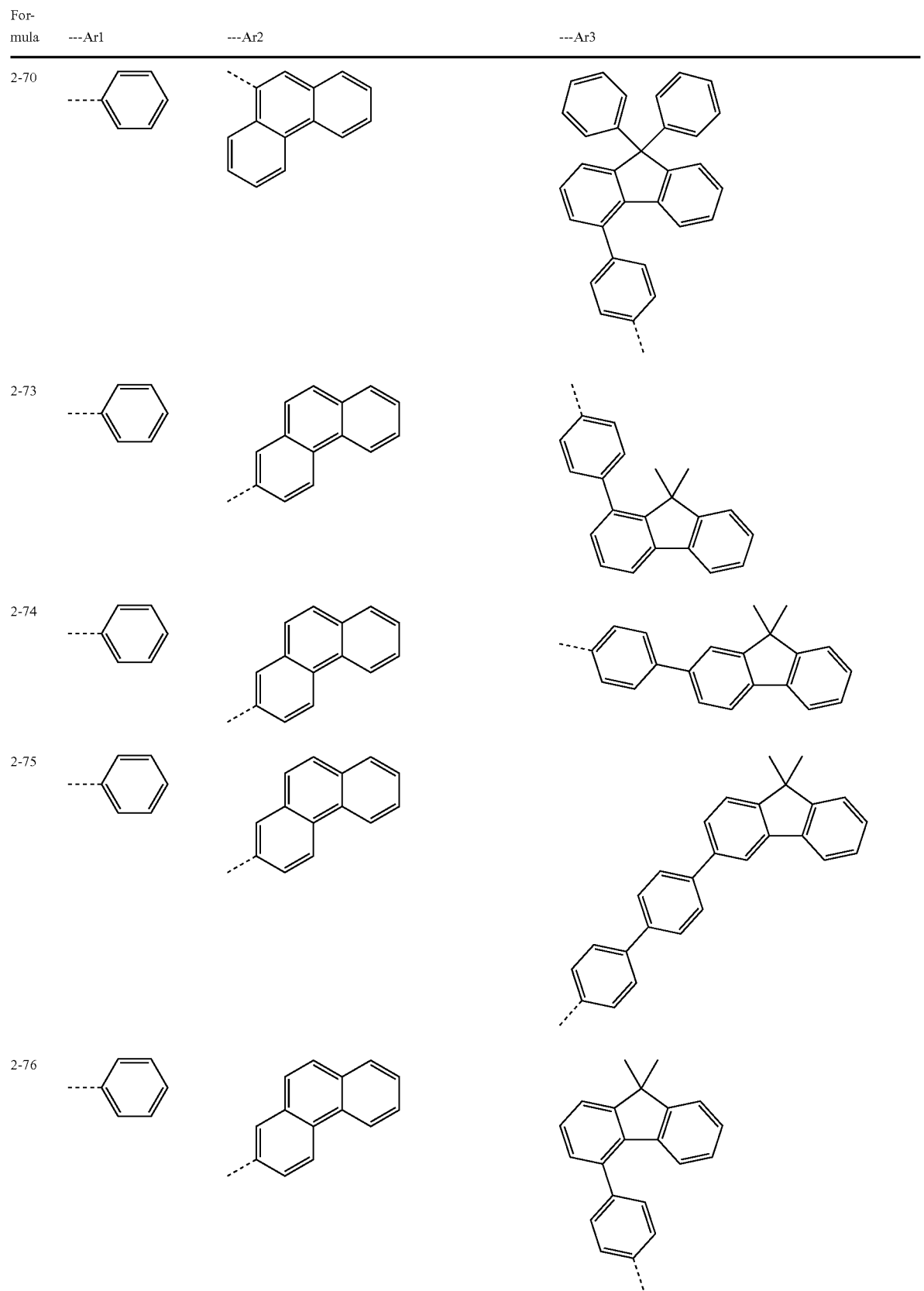

| Formula | ---Ar1 | ---Ar2 | ---Ar3 |
|---|---|---|---|
| 2-77 | 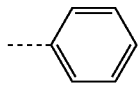 | 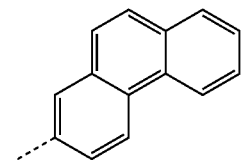 | 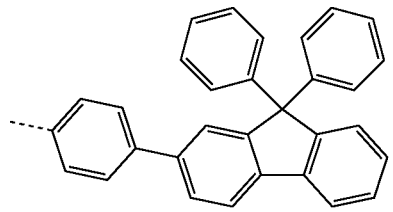 |
| 2-78 | 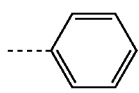 | 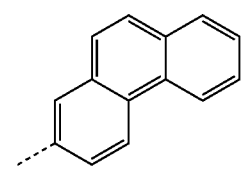 | 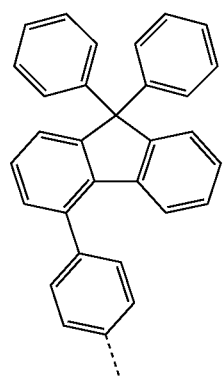 |
| 2-80 | 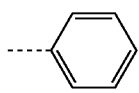 | 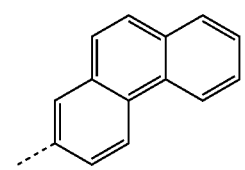 | 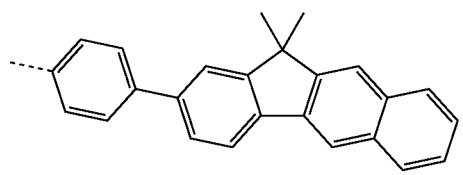 |
| 2-81 | 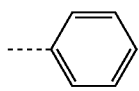 | 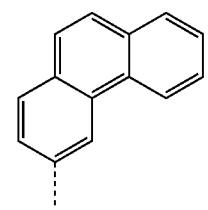 | 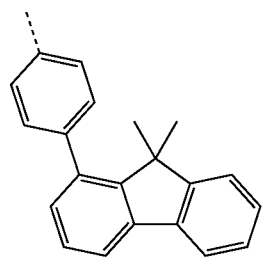 |
| 2-82 | 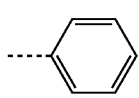 | 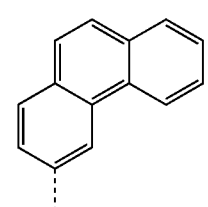 | 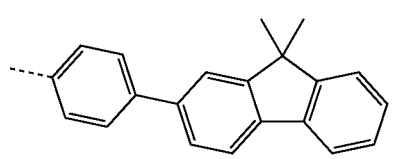 |

-continued
| Formula | ---Ar1 | ---Ar2 | ---Ar3 |
|---|---|---|---|
| 2-83 | 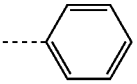 | 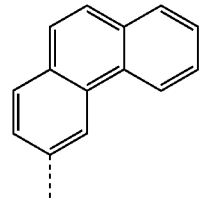 | 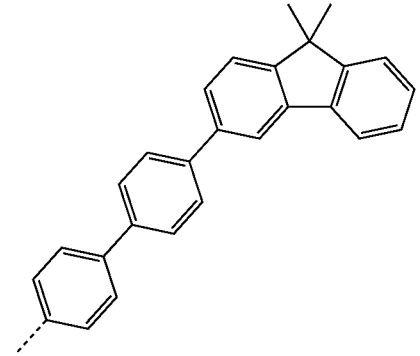 |
| 2-84 | 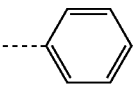 | 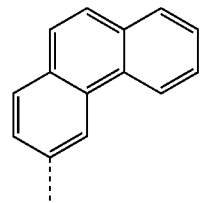 | 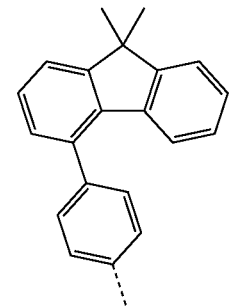 |
| 2-85 | 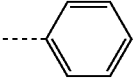 | 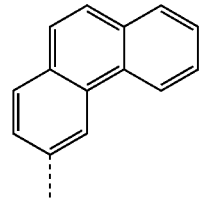 | 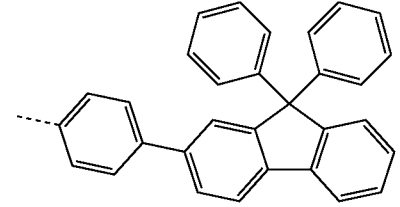 |
| 2-86 | 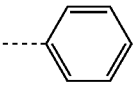 | 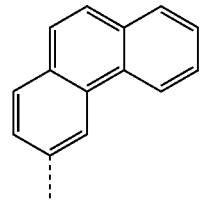 | 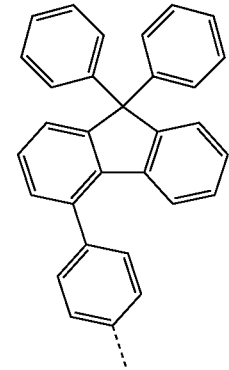 |
| 2-89 | 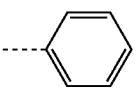 | 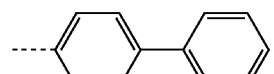 | 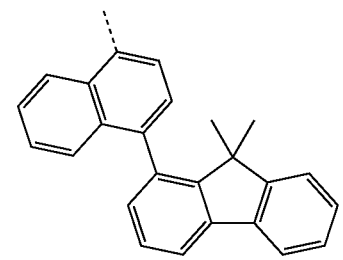 |

-continued
| Formula | ---Ar1 | ---Ar2 | ---Ar3 |
|---|---|---|---|
| 2-90 | 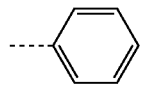 | 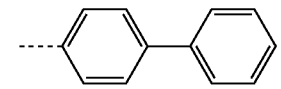 | 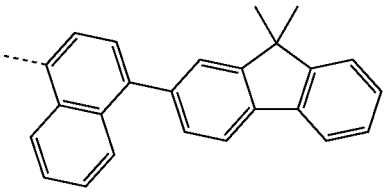 |
| 2-91 | 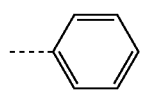 | 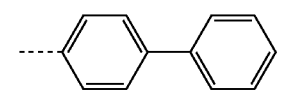 | 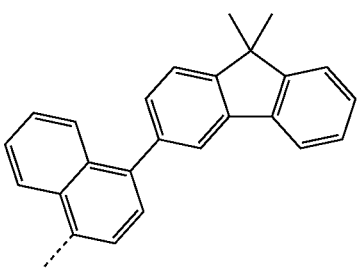 |
| 2-92 | 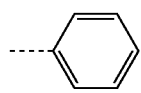 | 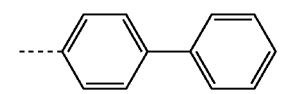 | 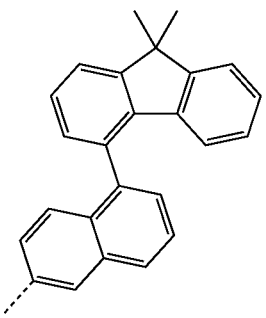 |
| 2-93 | 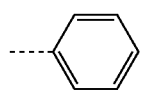 | 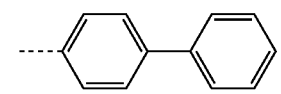 | 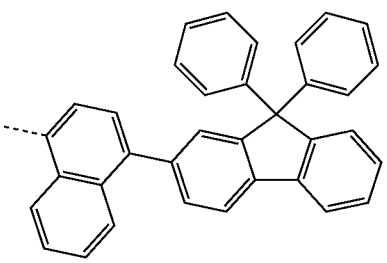 |
| 2-94 | 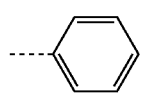 | 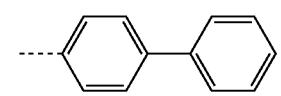 | 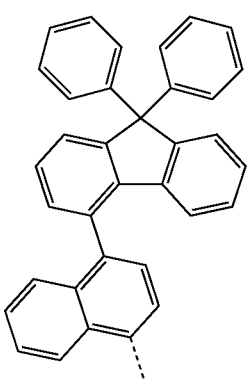 |

-continued

| Formula | ---Ar1 | ---Ar2 | ---Ar3 |
|---|---|---|---|
| 2-96 | phenyl | 4-biphenyl | naphthyl-(9,9-dimethyl-benzo-fluorenyl) |
| 2-97 | phenyl | 2-biphenyl | naphthyl-(9,9-dimethylfluorenyl) |
| 2-98 | phenyl | 2-biphenyl | naphthyl-(9,9-dimethylfluorenyl) |
| 2-99 | phenyl | 2-biphenyl | naphthyl-(9,9-dimethylfluorenyl) |
| 2-100 | phenyl | 2-biphenyl | naphthyl-(9,9-dimethylfluorenyl) |
| 2-101 | phenyl | 2-biphenyl | naphthyl-(9,9-diphenylfluorenyl) |

-continued

| Formula | ---Ar1 | ---Ar2 | ---Ar3 |
|---|---|---|---|
| 2-102 | phenyl | 2-biphenyl | 4-(9,9-diphenylfluoren-4-yl)naphthalen-1-yl |
| 2-105 | phenyl | 3-biphenyl | 1-(9,9-dimethylfluoren-1-yl)-4-biphenyl |
| 2-106 | phenyl | 3-biphenyl | 4-(9,9-dimethylfluoren-2-yl)naphthalen-1-yl |
| 2-107 | phenyl | 3-biphenyl | 4-(9,9-dimethylfluoren-2-yl)naphthalen-1-yl |
| 2-108 | phenyl | 3-biphenyl | 4-(9,9-dimethylfluoren-4-yl)naphthalen-1-yl |

-continued
| Formula | ---Ar1 | ---Ar2 | ---Ar3 |
|---|---|---|---|
| 2-109 | 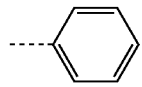 | 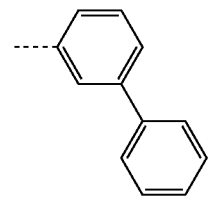 | 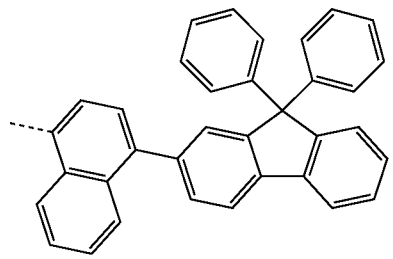 |
| 2-110 | 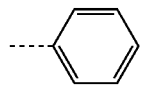 | 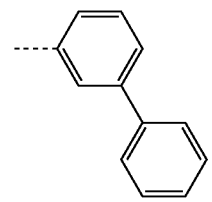 | 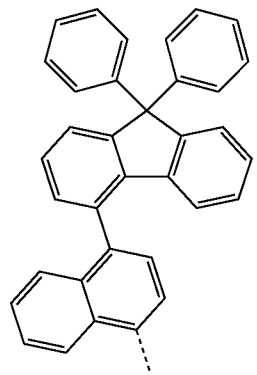 |
| 2-113 | 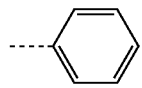 | 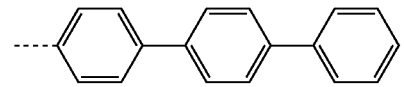 | 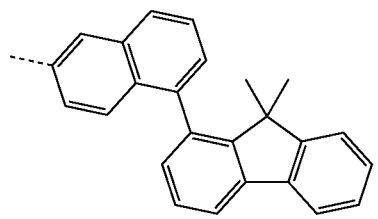 |
| 2-114 | 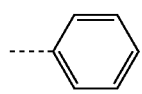 | 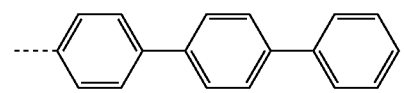 | 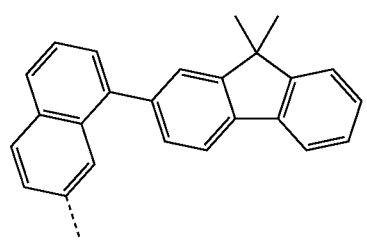 |
| 2-115 | 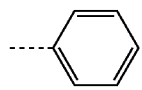 | 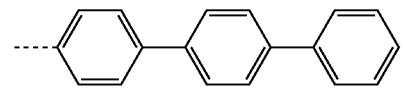 | 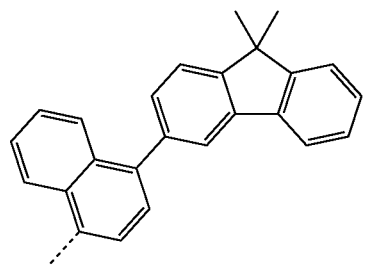 |

-continued
| Formula | ---Ar1 | ---Ar2 | ---Ar3 |
|---|---|---|---|
| 2-116 |  | 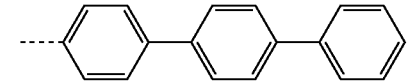 | 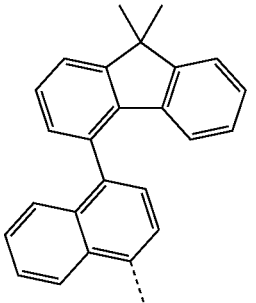 |
| 2-117 | 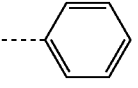 | 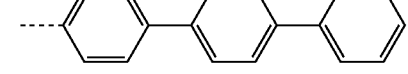 | 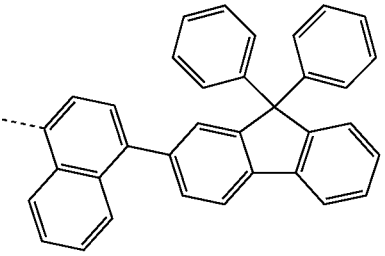 |
| 2-118 |  | 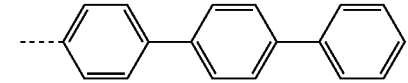 | 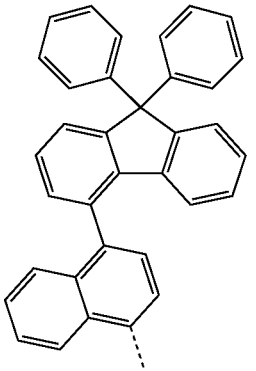 |
| 2-121 |  | 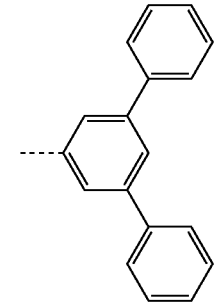 | 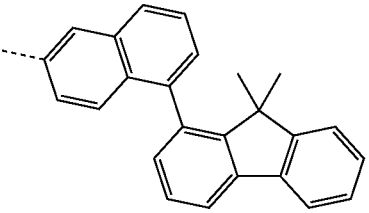 |
| 2-122 | 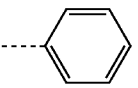 | 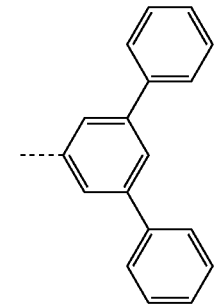 | 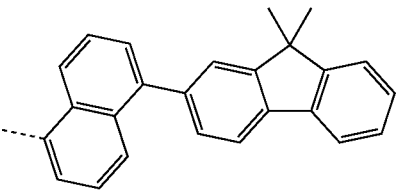 |

-continued
| Formula | ---Ar1 | ---Ar2 | ---Ar3 |
|---|---|---|---|
| 2-123 | 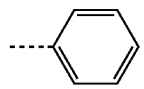 | 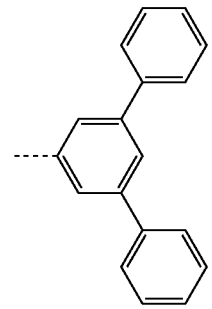 | 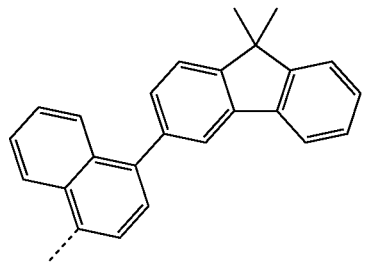 |
| 2-124 | 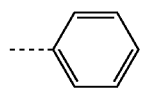 | 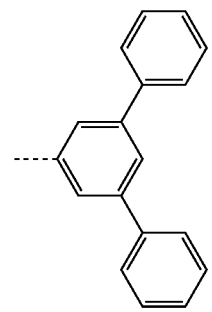 | 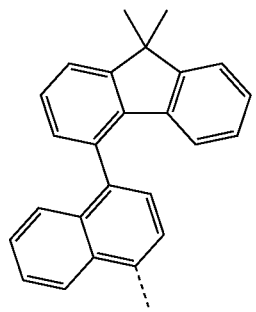 |
| 2-125 | 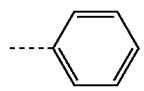 | 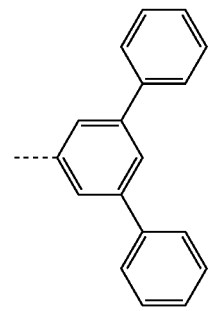 | 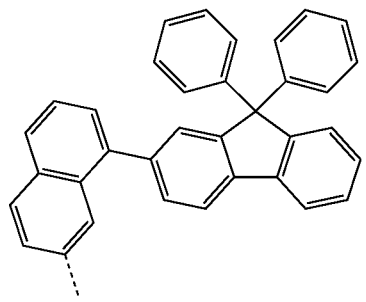 |
| 2-126 | 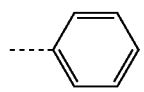 | 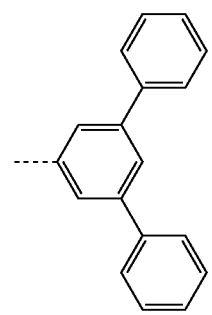 | 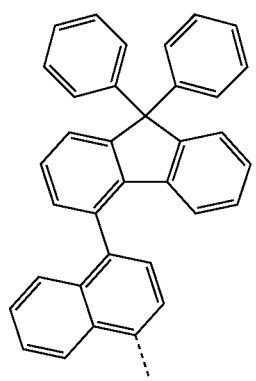 |

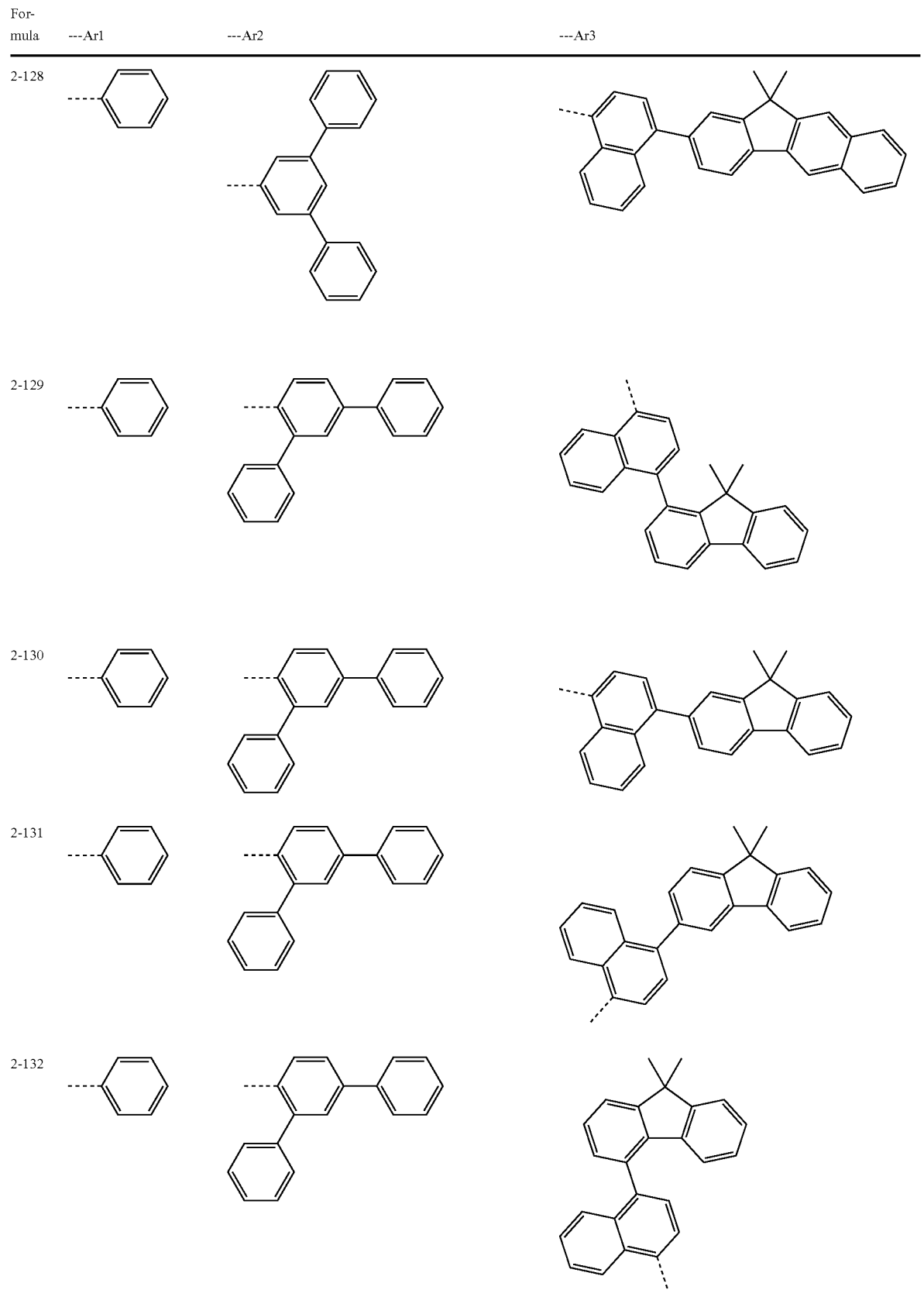

-continued

| Formula | ---Ar1 | ---Ar2 | ---Ar3 |
|---|---|---|---|
| 2-133 | | | |
| 2-134 | | | |
| 2-136 | | | |
| 2-137 | | | |
| 2-138 | | | |

-continued
| Formula | ---Ar1 | ---Ar2 | ---Ar3 |
|---|---|---|---|
| 2-139 | 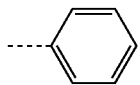 | 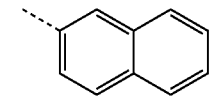 | 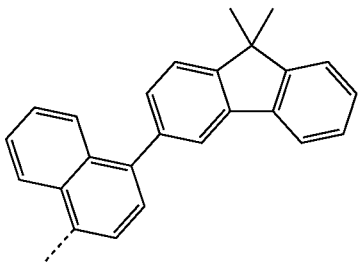 |
| 2-140 | 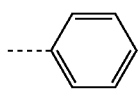 | 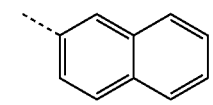 | 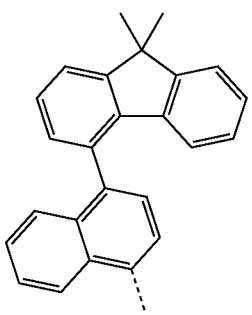 |
| 2-141 | 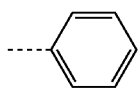 | 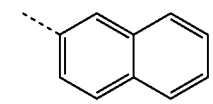 | 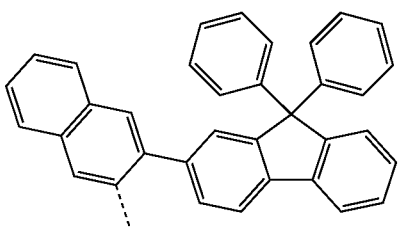 |
| 2-142 | 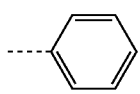 | 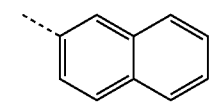 | 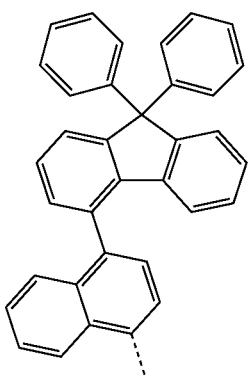 |
| 2-145 | 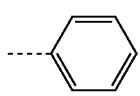 | 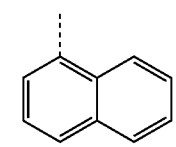 | 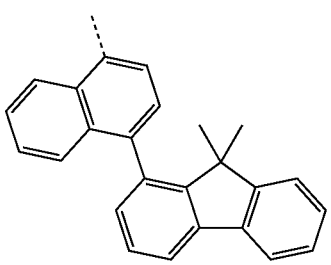 |

-continued
| Formula | ---Ar1 | ---Ar2 | ---Ar3 |
|---|---|---|---|
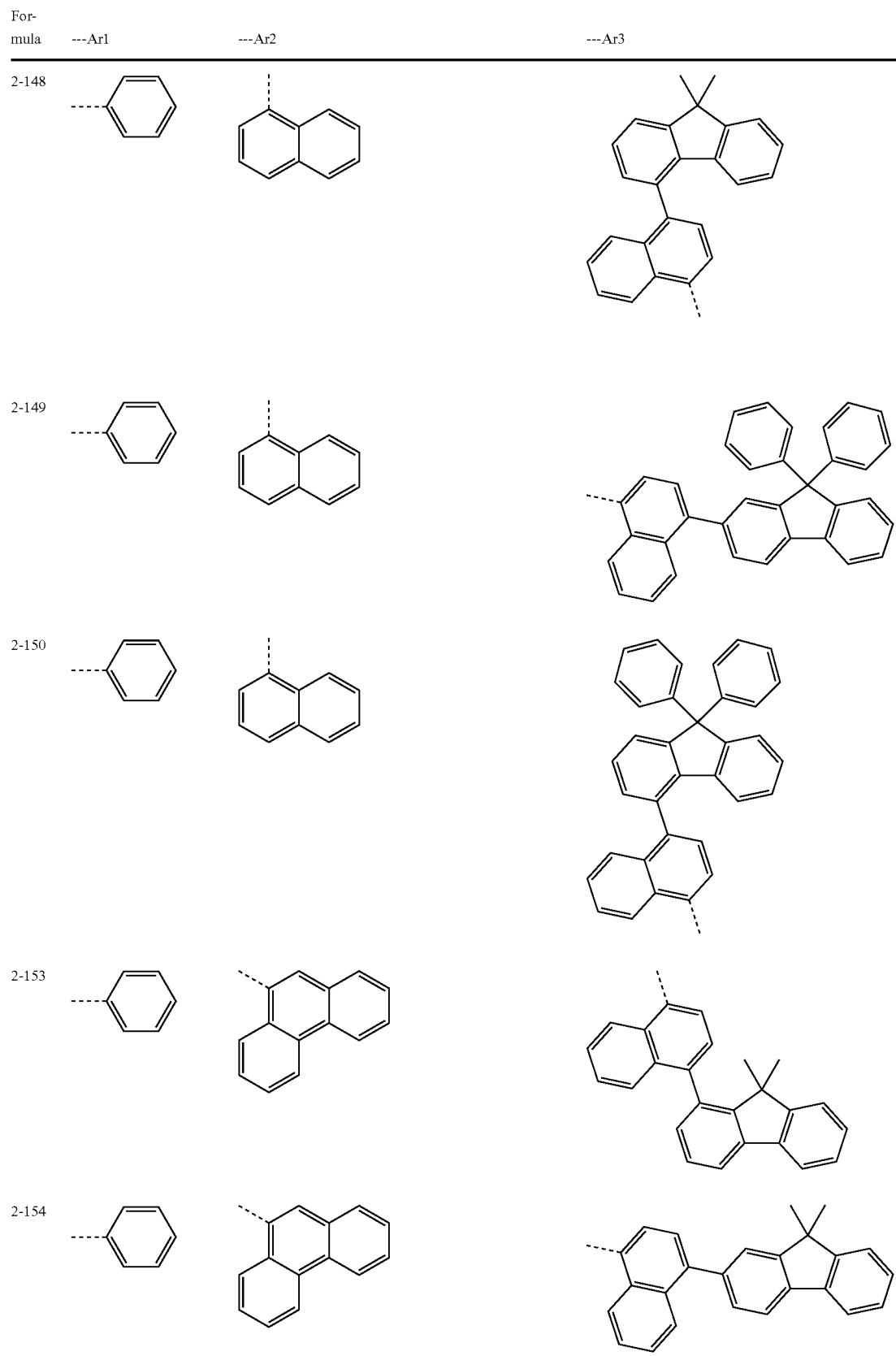

-continued
| Formula | ---Ar1 | ---Ar2 | ---Ar3 |
|---|---|---|---|
| 2-155 | 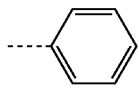 | 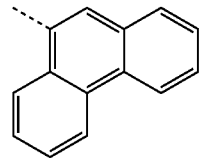 | 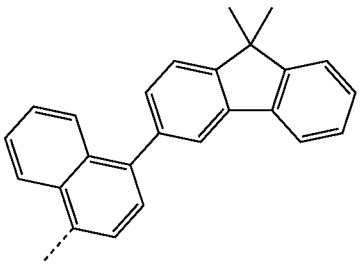 |
| 2-156 | 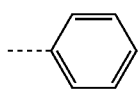 | 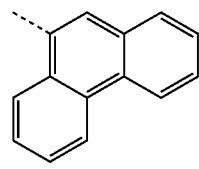 | 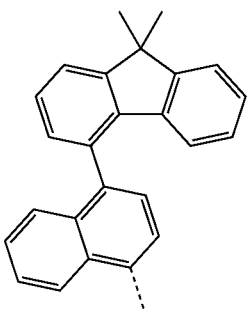 |
| 2-157 | 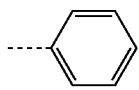 | 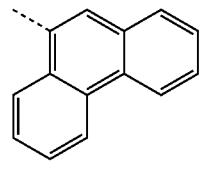 | 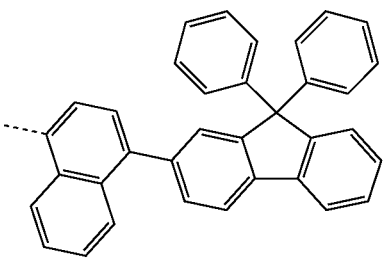 |
| 2-158 | 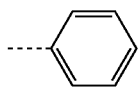 | 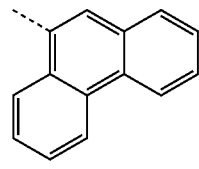 | 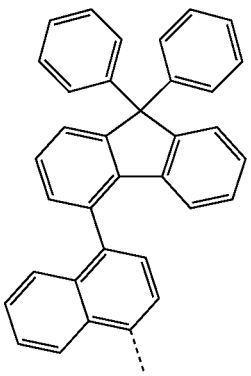 |
| 2-159 | 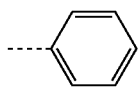 | 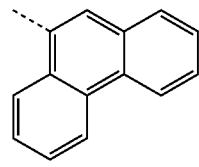 | 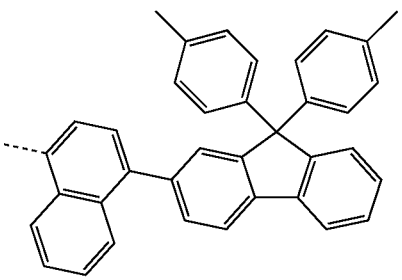 |

-continued
| Formula | ---Ar1 | ---Ar2 | ---Ar3 |
|---|---|---|---|
| 2-160 | 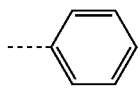 | 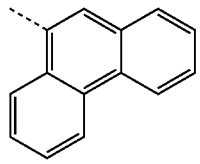 | 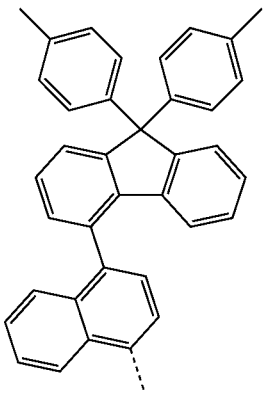 |
| 2-161 | 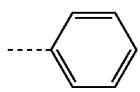 | 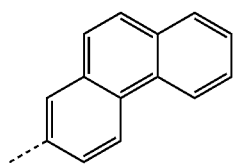 | 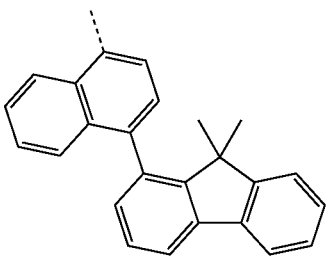 |
| 2-162 | 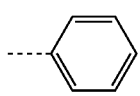 | 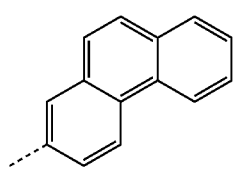 | 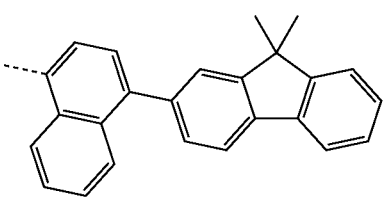 |
| 2-164 | 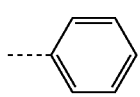 | 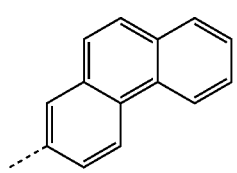 | 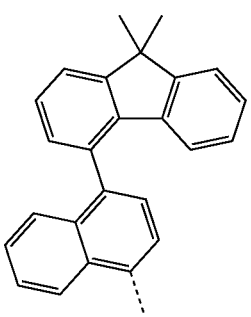 |
| 2-165 | 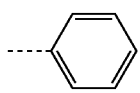 | 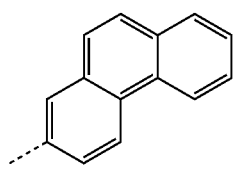 | 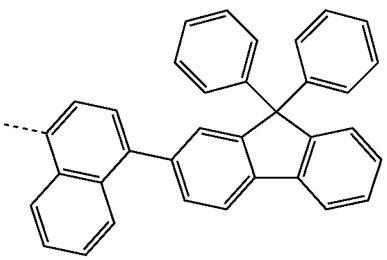 |

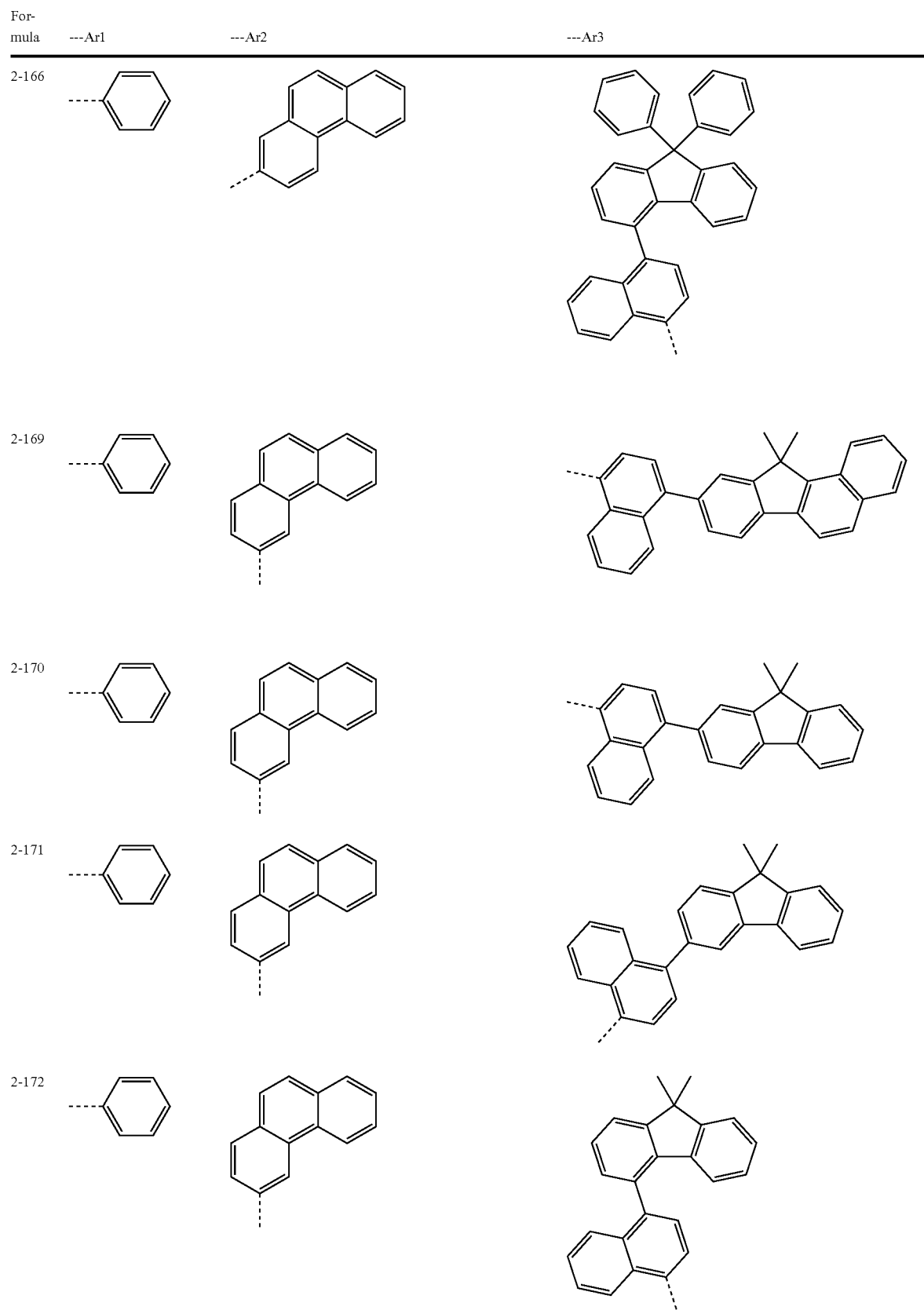

-continued
| Formula | ---Ar1 | ---Ar2 | ---Ar3 |
|---|---|---|---|
| 2-173 | 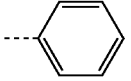 | 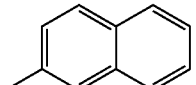 | 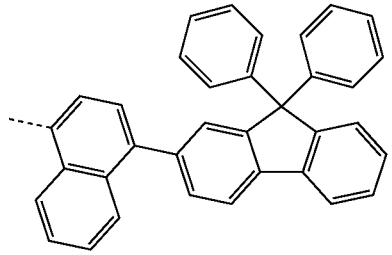 |
| 2-174 | 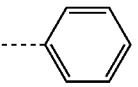 | 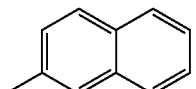 | 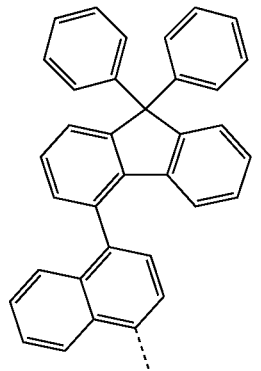 |
| 2-176 | 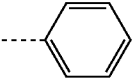 | 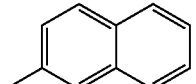 | 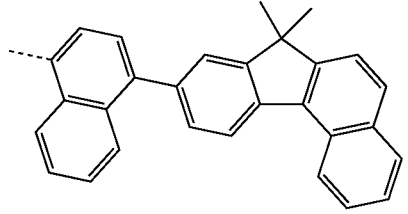 |
| 2-177 | 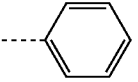 | 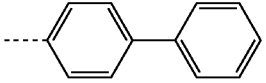 | 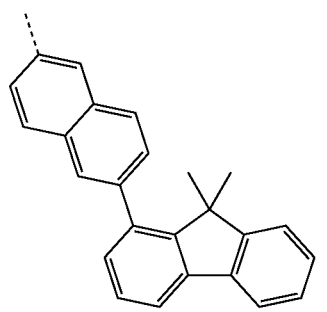 |
| 2-178 | 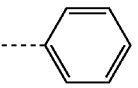 | 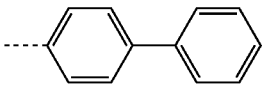 | 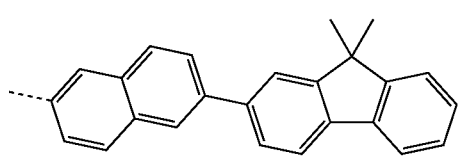 |

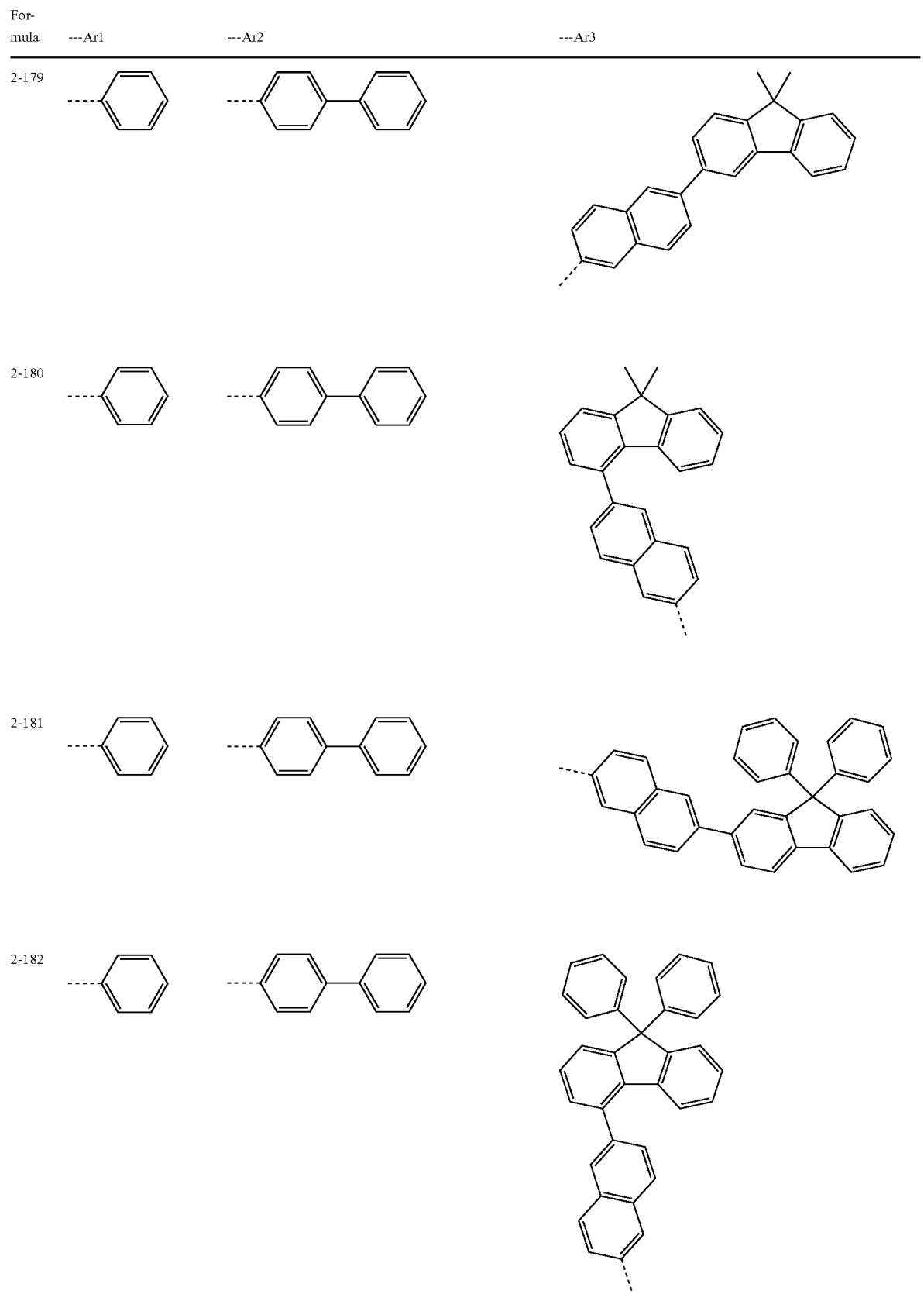

-continued
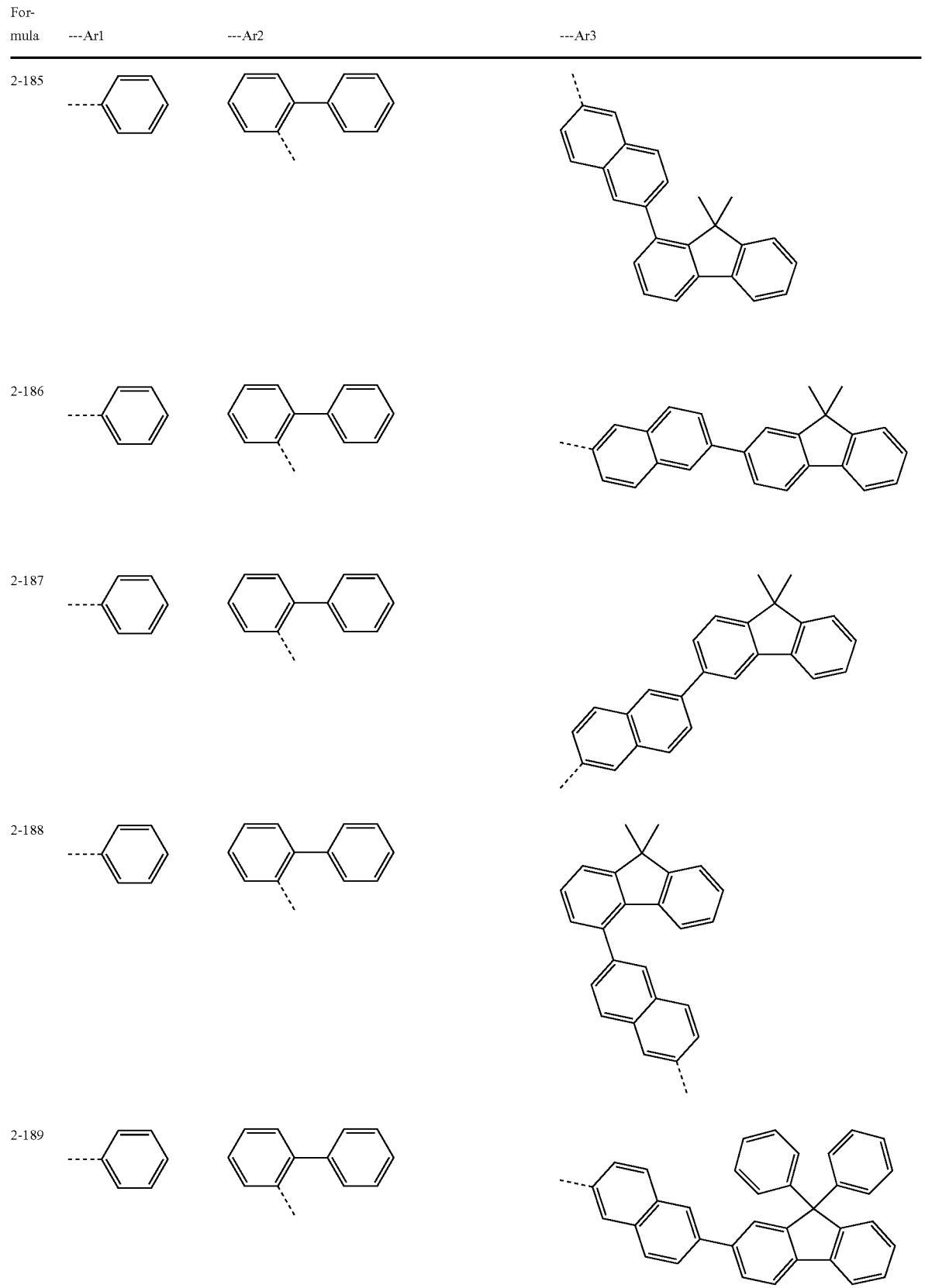

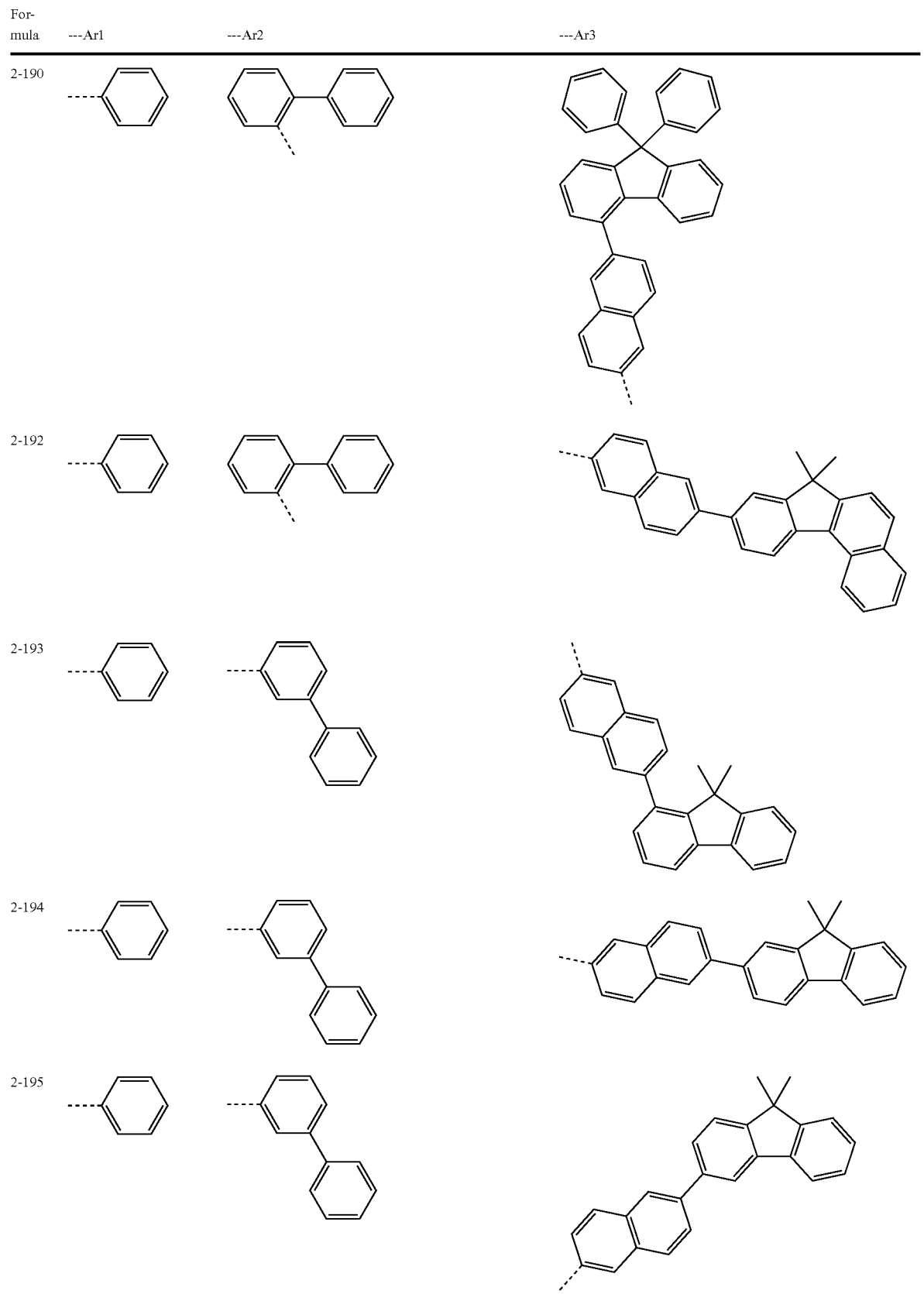

-continued

| Formula | ---Ar1 | ---Ar2 | ---Ar3 |
|---|---|---|---|
| 2-196 | | | |
| 2-197 | | | |
| 2-198 | | | |
| 2-199 | | | |
| 2-201 | | | |

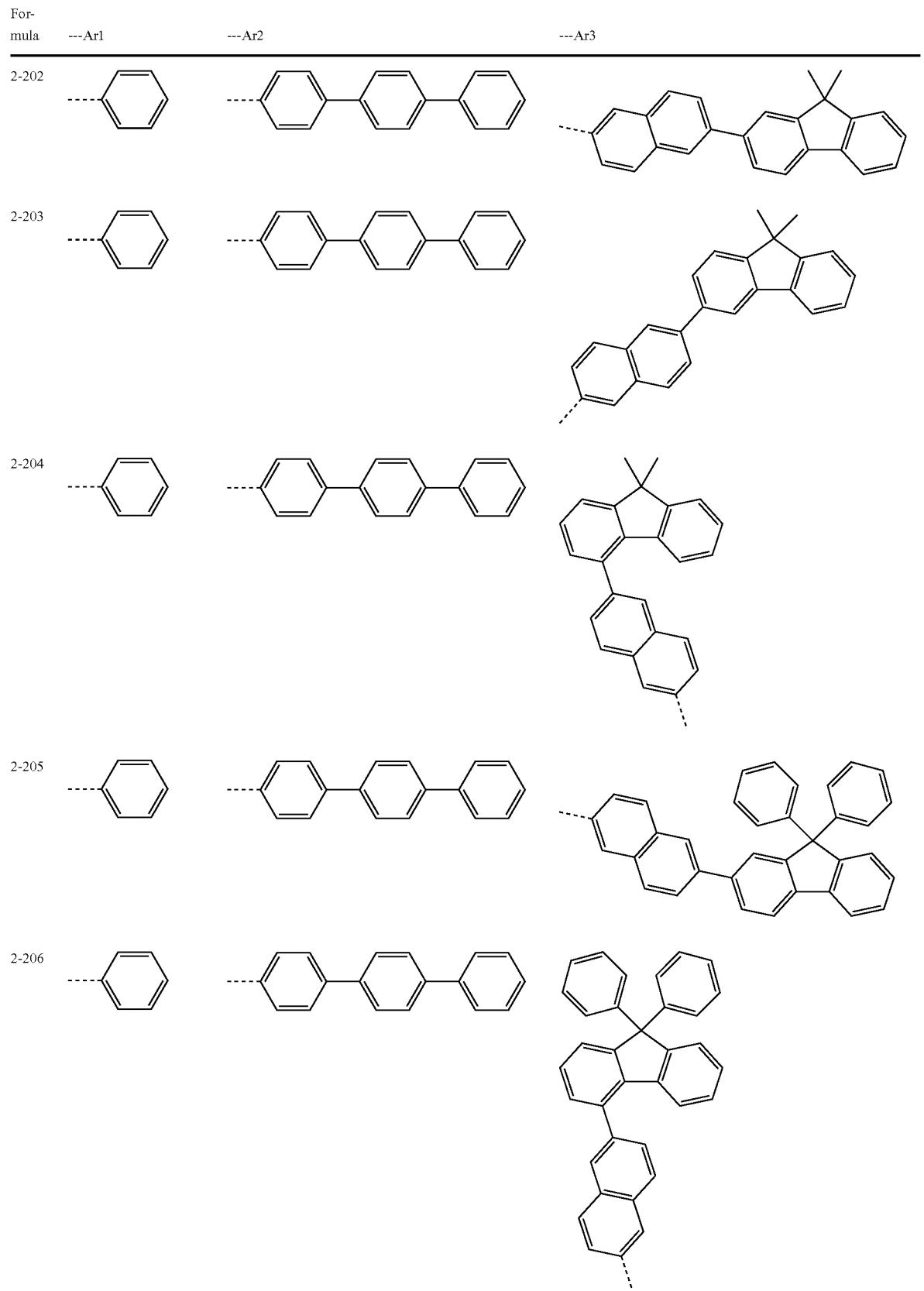

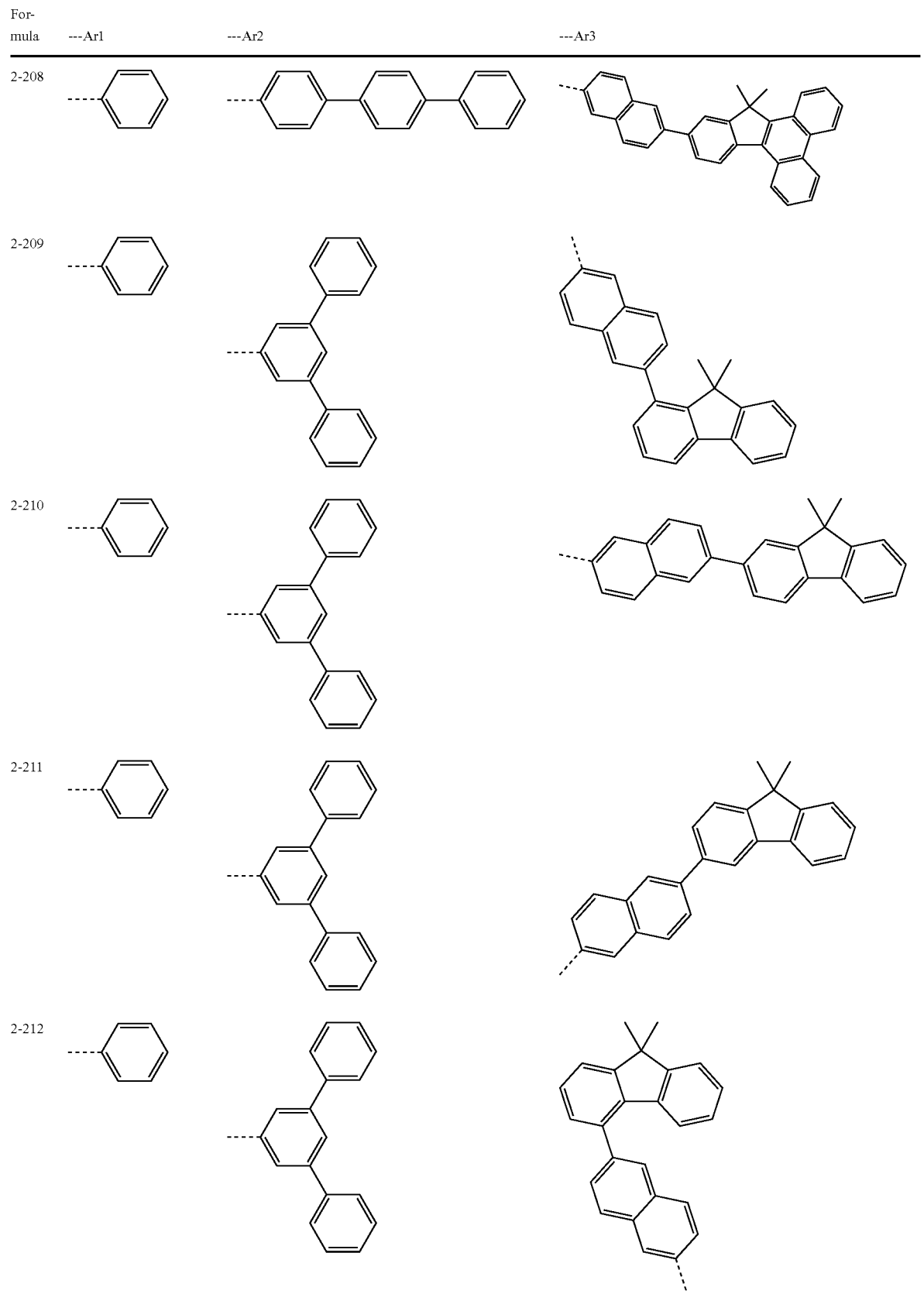

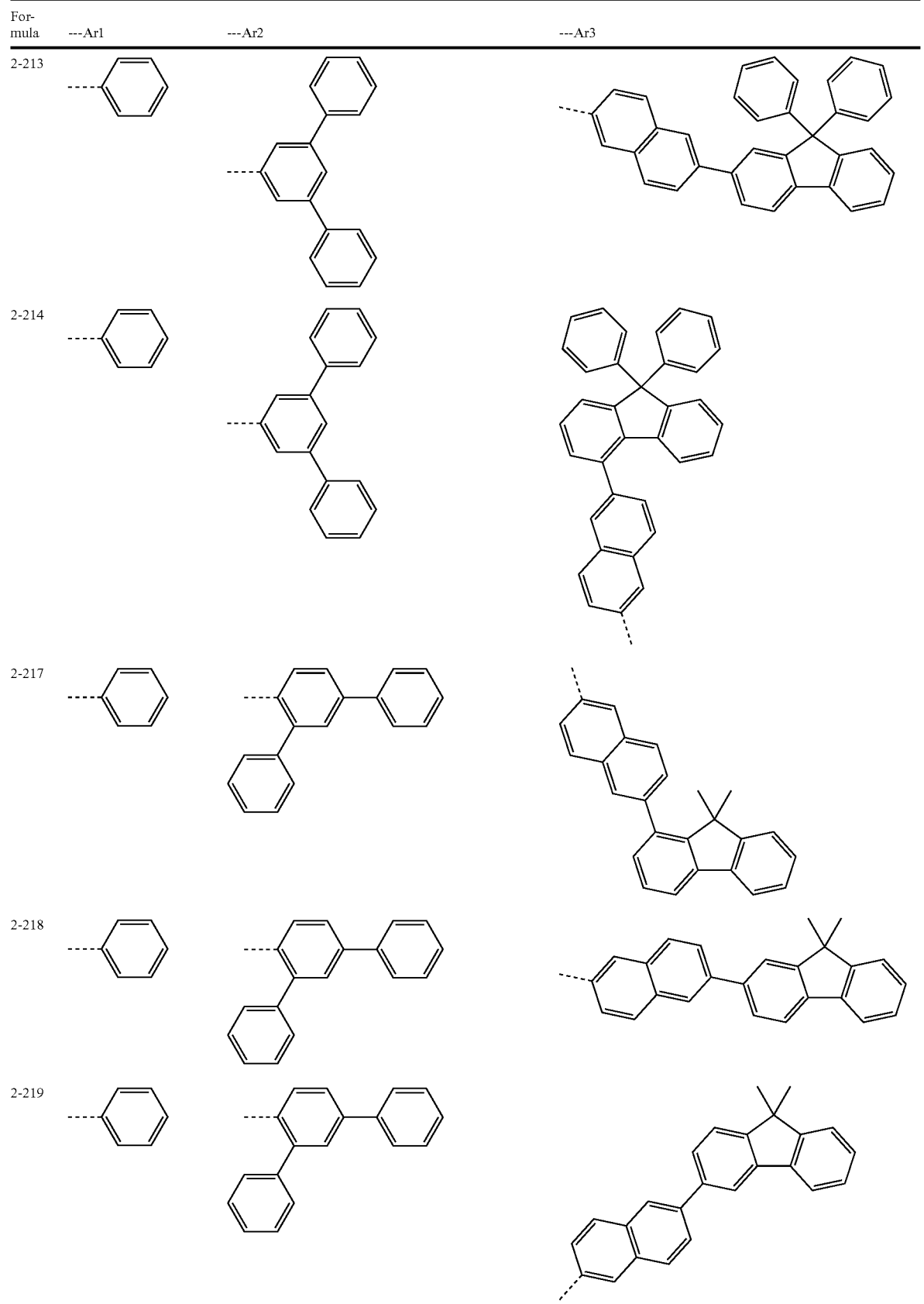

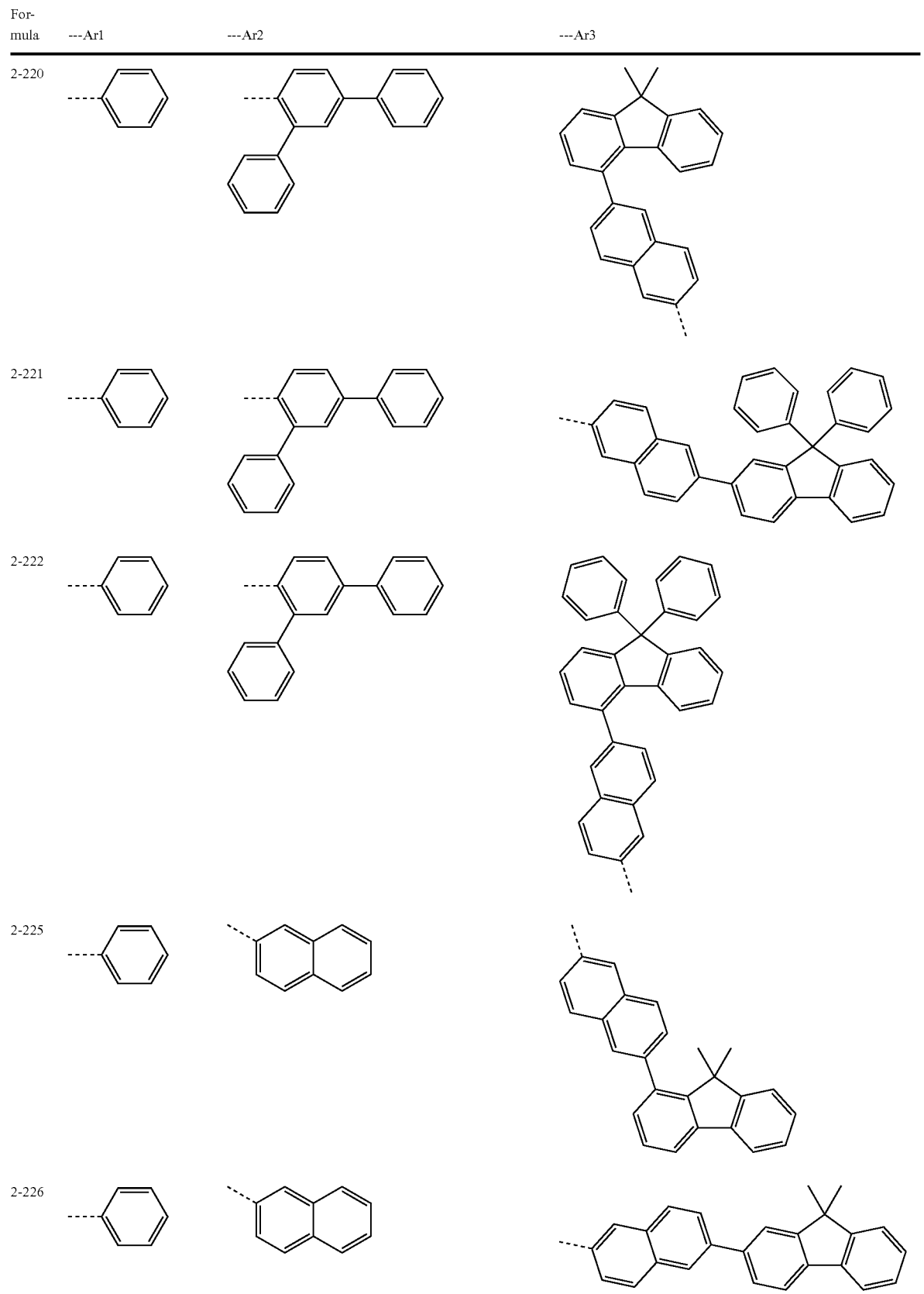

-continued
| Formula | ---Ar1 | ---Ar2 | ---Ar3 |
|---|---|---|---|
| 2-227 | 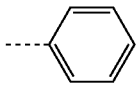 | 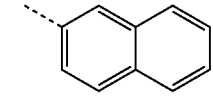 | 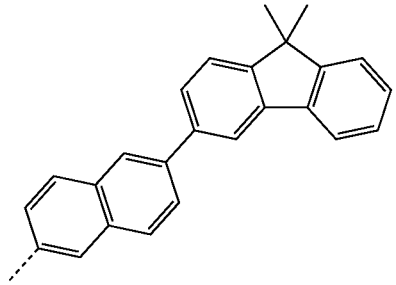 |
| 2-228 | 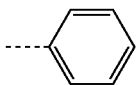 | 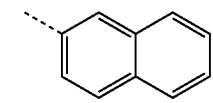 | 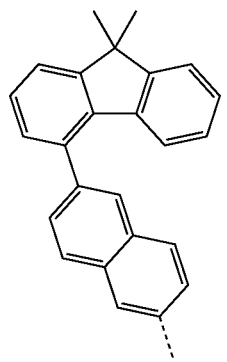 |
| 2-229 | 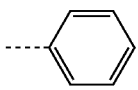 | 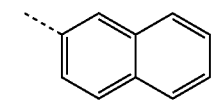 | 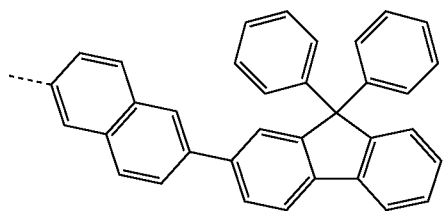 |
| 2-230 | 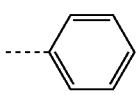 | 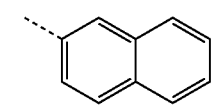 | 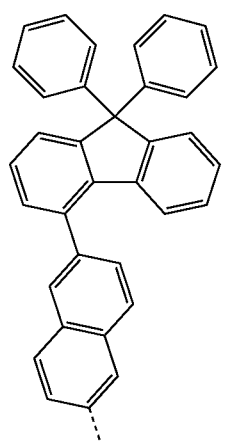 |
| 2-232 | 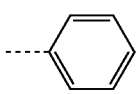 | 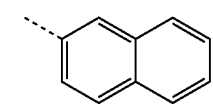 | 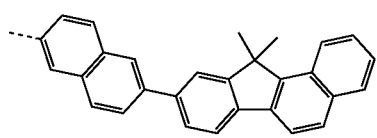 |

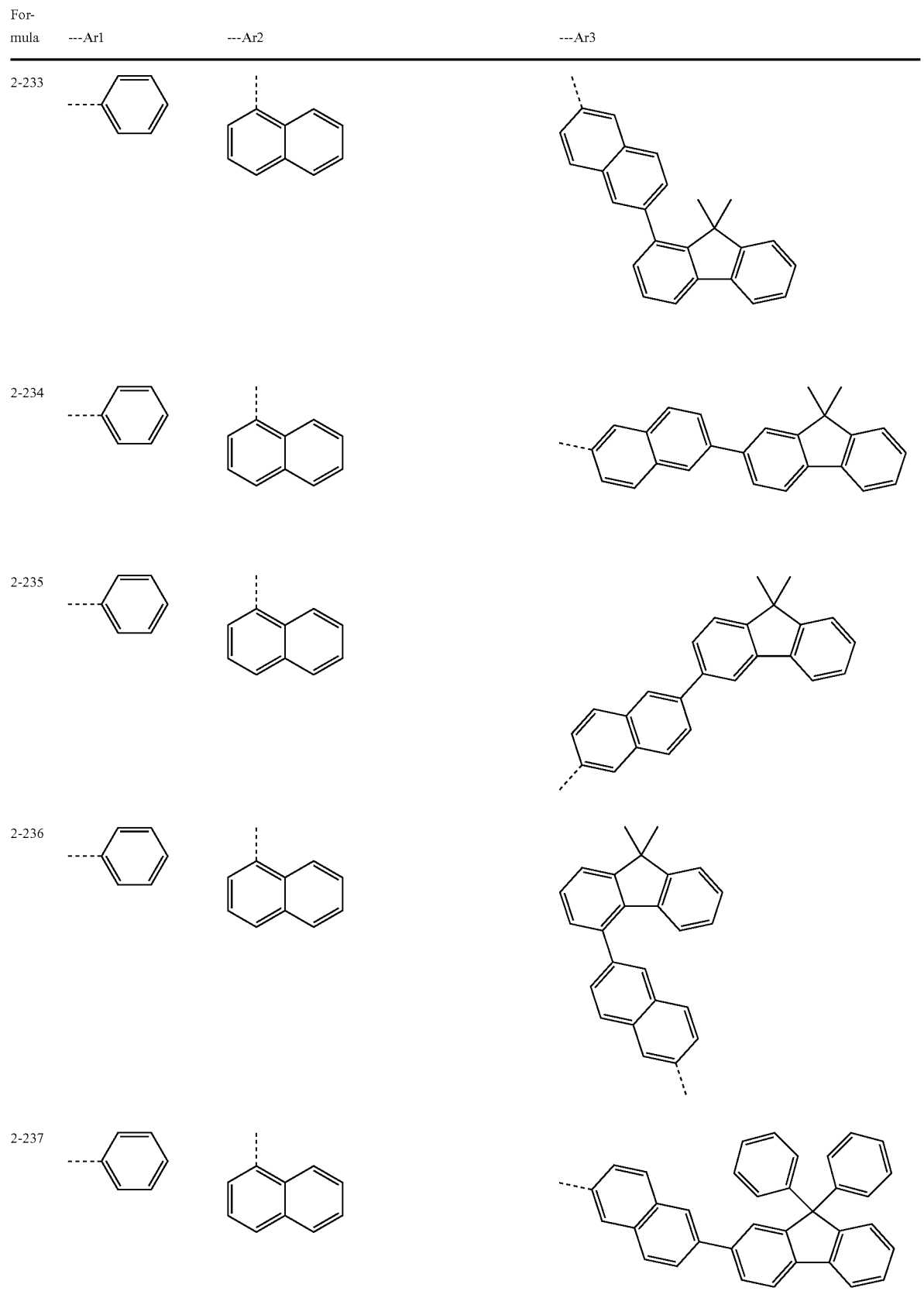

-continued
| Formula | ---Ar1 | ---Ar2 | ---Ar3 |
|---|---|---|---|
| 2-238 | 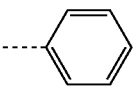 | 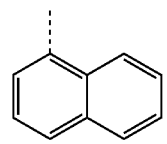 | 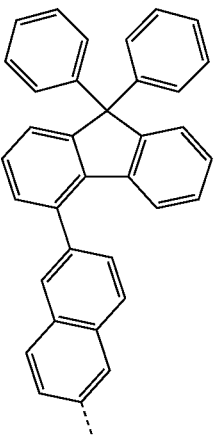 |
| 2-241 | 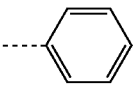 | 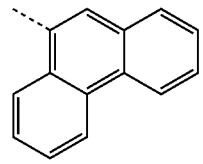 | 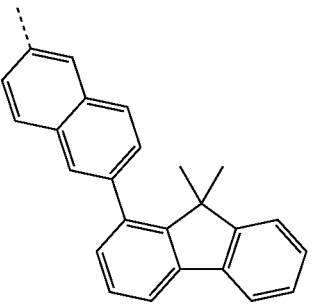 |
| 2-242 | 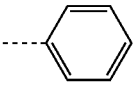 | 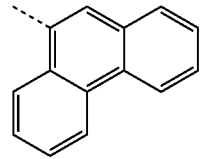 | 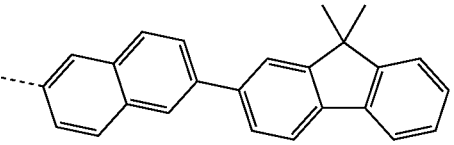 |
| 2-243 | 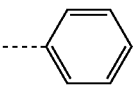 | 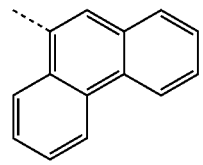 | 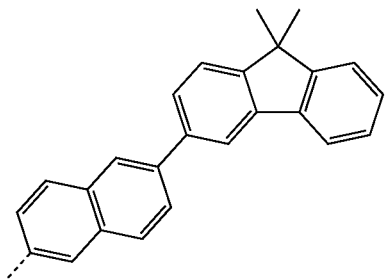 |
| 2-244 | 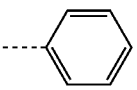 | 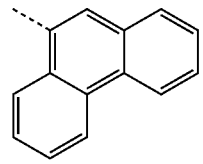 | 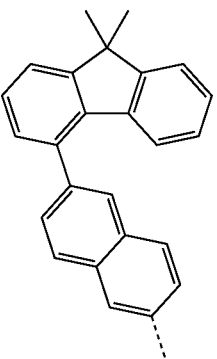 |

-continued
| Formula | ---Ar1 | ---Ar2 | ---Ar3 |
|---|---|---|---|
| 2-245 | 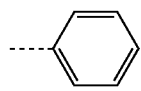 | 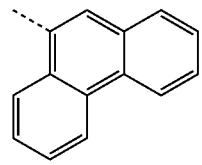 | 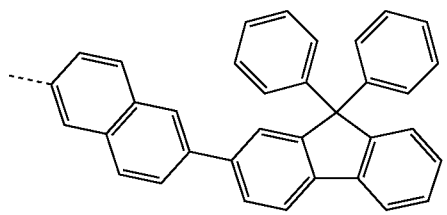 |
| 2-246 | 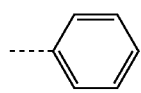 | 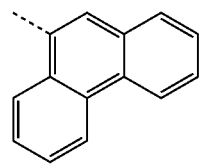 | 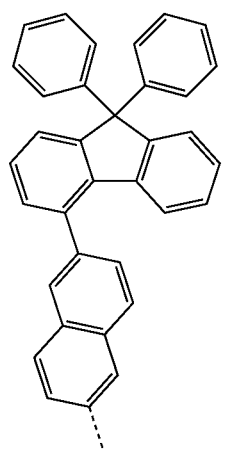 |
| 2-247 | 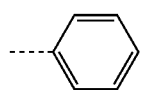 | 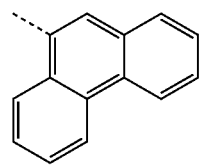 | 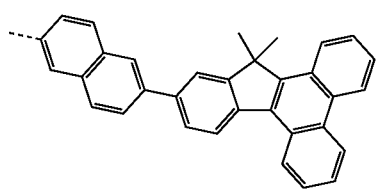 |
| 2-249 | 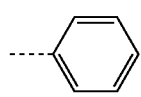 | 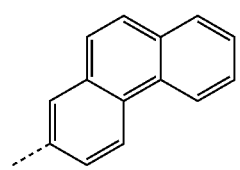 | 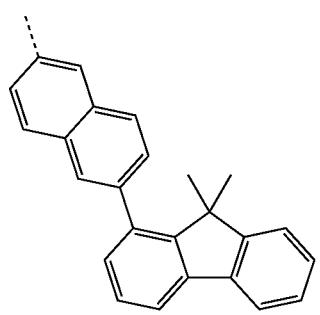 |
| 2-250 | 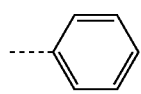 | 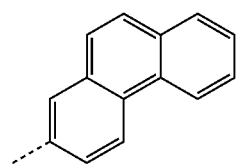 | 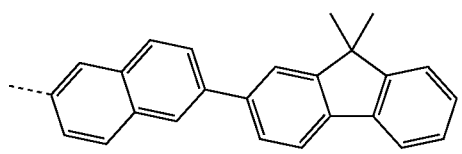 |

-continued
| Formula | ---Ar1 | ---Ar2 | ---Ar3 |
|---|---|---|---|
| 2-251 | 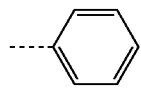 | 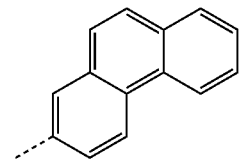 | 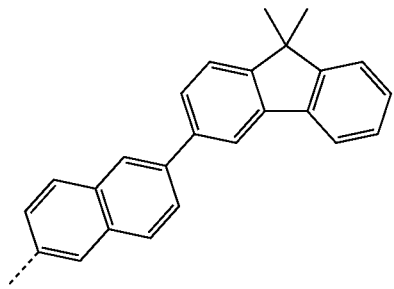 |
| 2-252 | 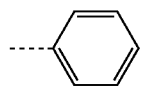 | 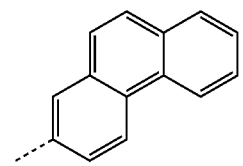 | 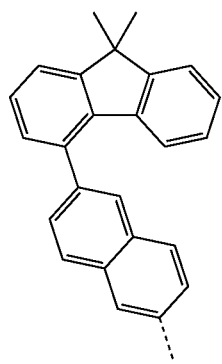 |
| 2-253 | 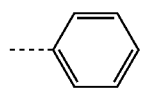 | 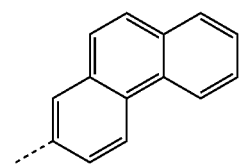 | 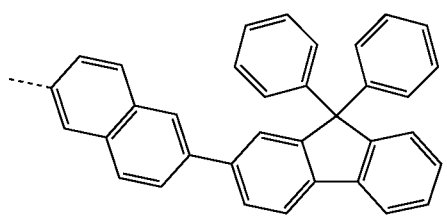 |
| 2-254 | 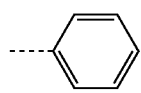 | 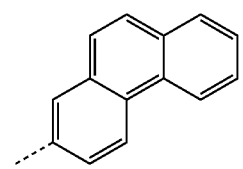 | 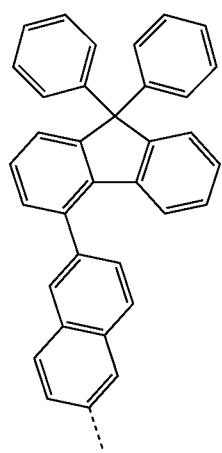 |

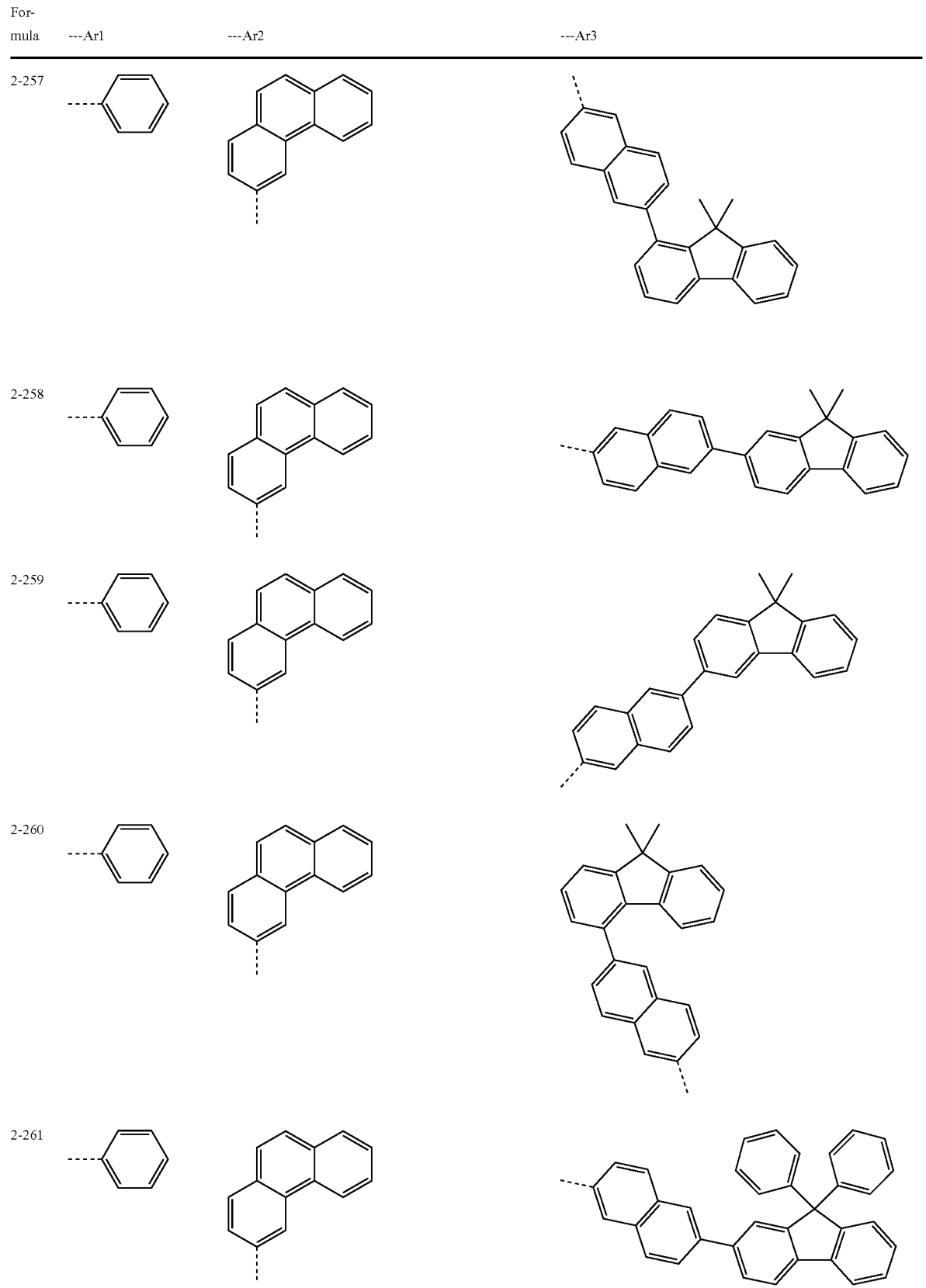

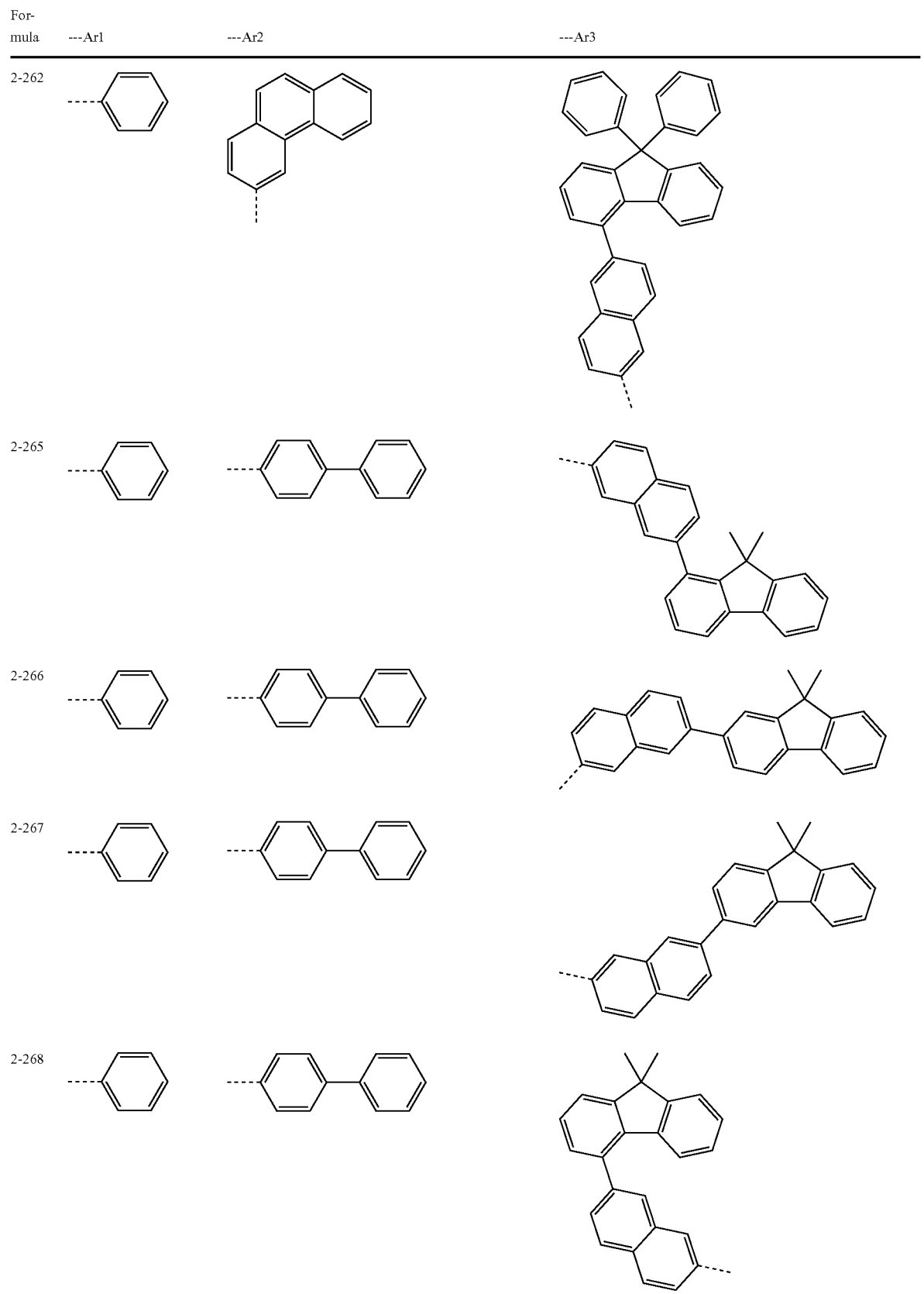

-continued

| Formula | ---Ar1 | ---Ar2 | ---Ar3 |
|---|---|---|---|
| 2-269 | phenyl | 4-biphenyl | 2-(9,9-diphenylfluoren-2-yl)naphthalene |
| 2-270 | phenyl | 4-biphenyl | 4-(6-naphthalen-2-yl)-9,9-diphenylfluorene |
| 2-272 | phenyl | 4-biphenyl | naphthyl-dibenzo[g,p]chrysene/methylfluorene derivative |
| 2-273 | phenyl | 2-biphenyl | 1-(naphthalen-2-yl)-9,9-dimethylfluorene |
| 2-274 | phenyl | 2-biphenyl | 1-(naphthalen-2-yl)-9,9-dimethylfluorene |

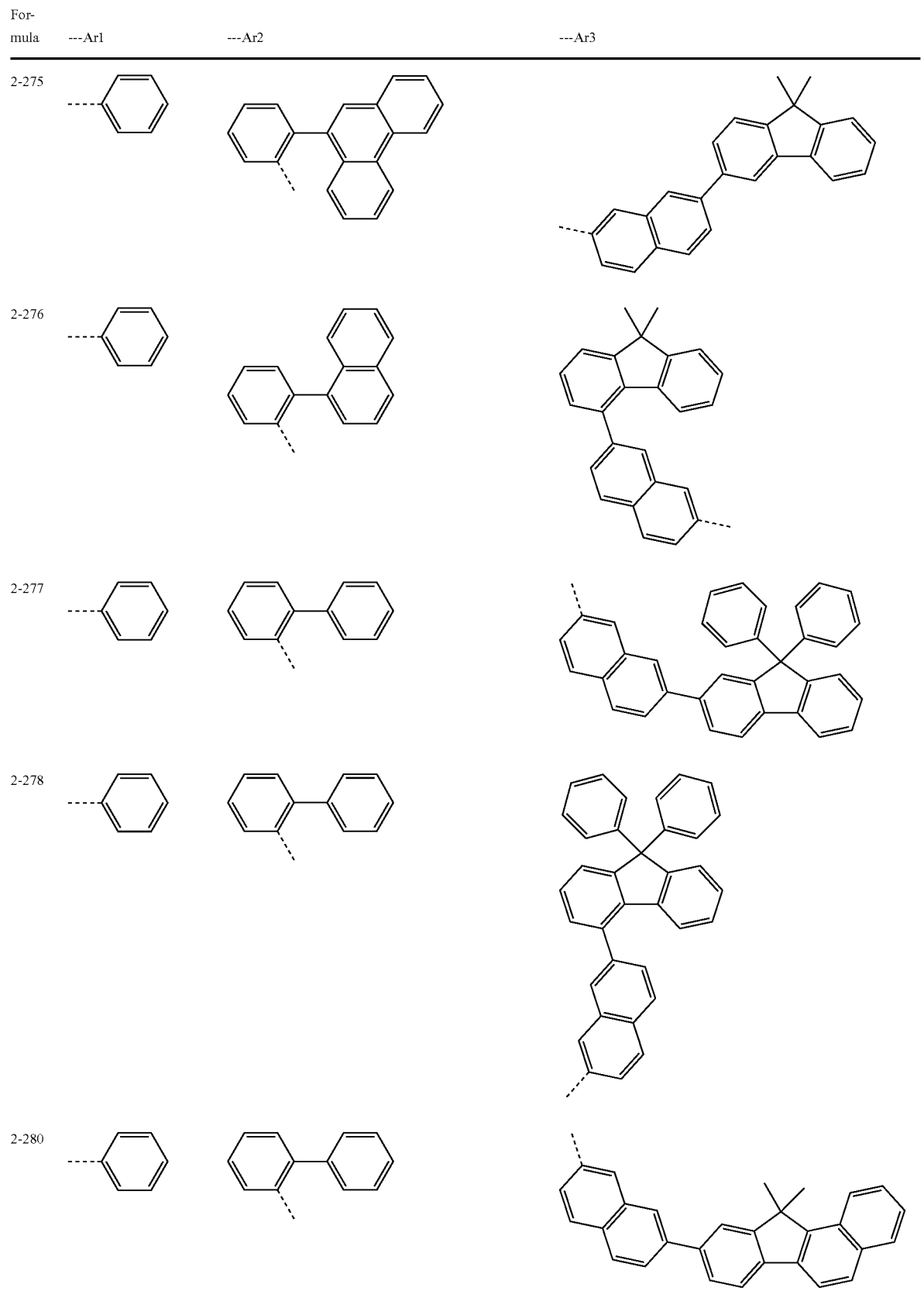

-continued
| Formula | ---Ar1 | ---Ar2 | ---Ar3 |
|---|---|---|---|
| 2-281 | 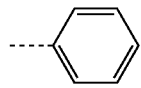 | 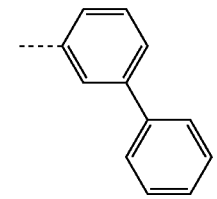 | 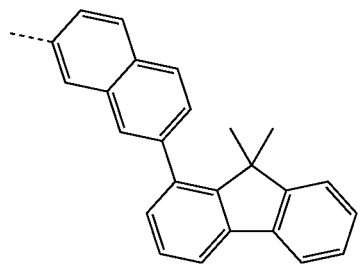 |
| 2-282 | 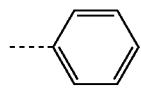 | 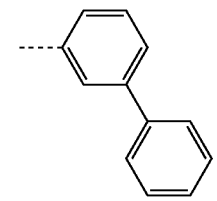 | 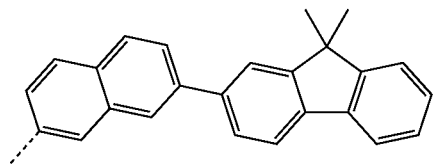 |
| 2-283 | 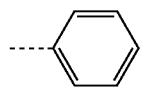 | 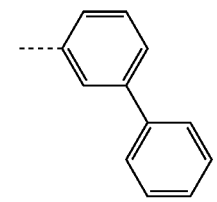 | 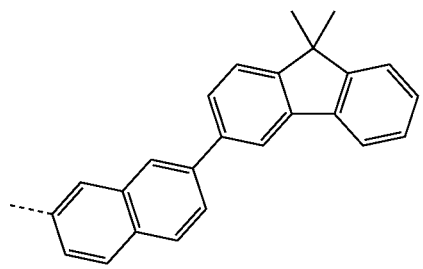 |
| 2-284 | 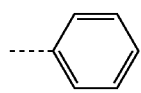 | 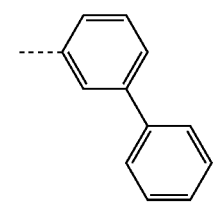 | 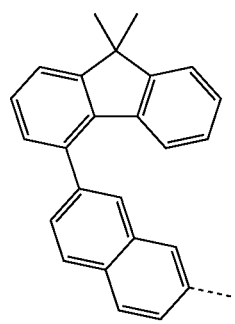 |
| 2-285 | 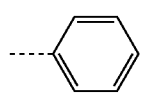 | 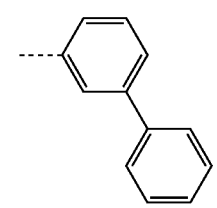 | 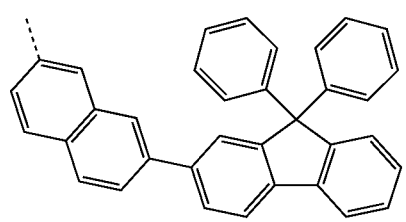 |

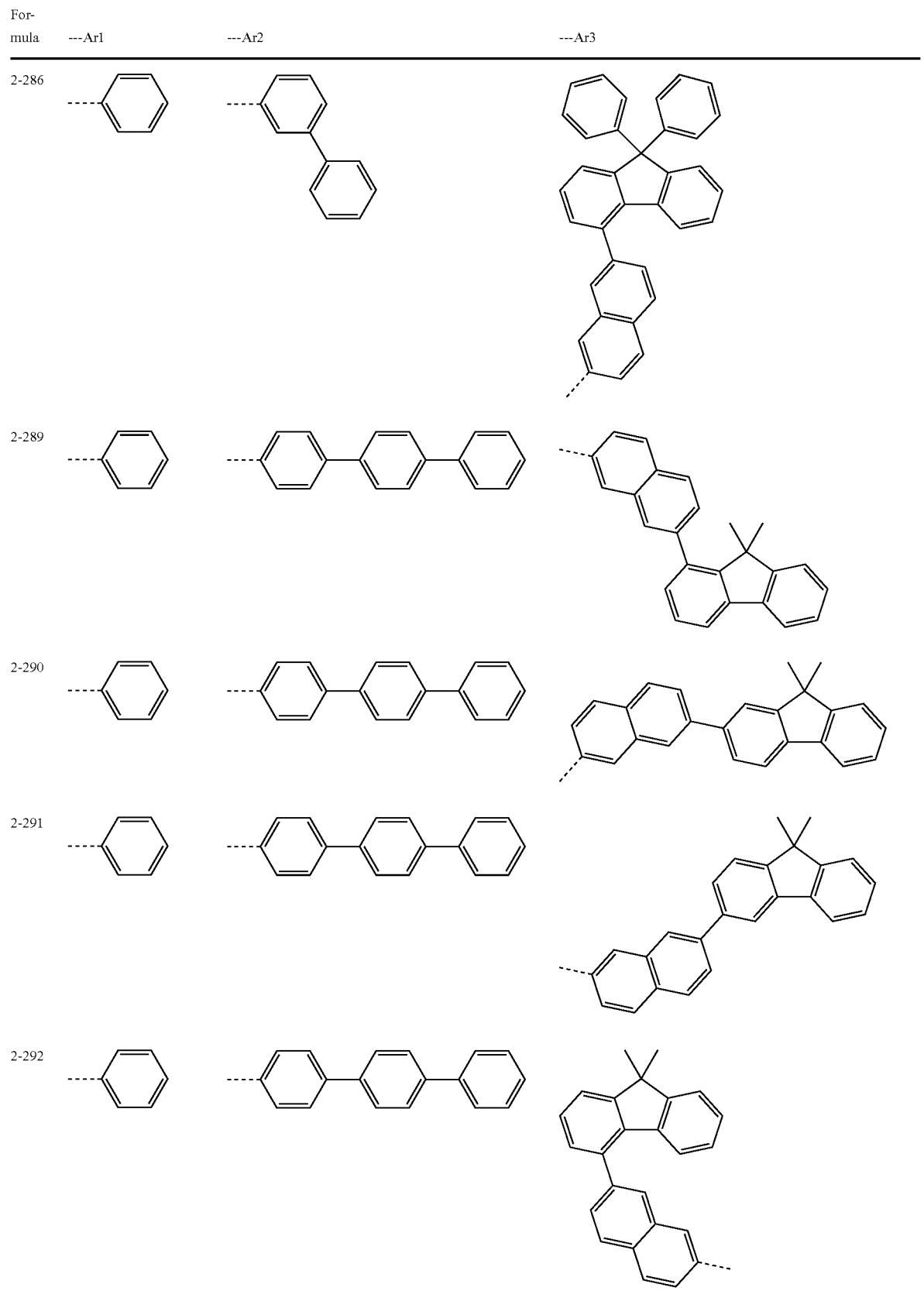

| Formula | ---Ar1 | ---Ar2 | ---Ar3 |
|---|---|---|---|
| 2-293 | 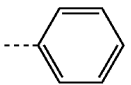 | 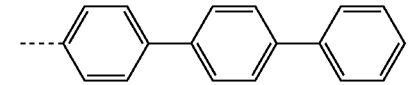 | 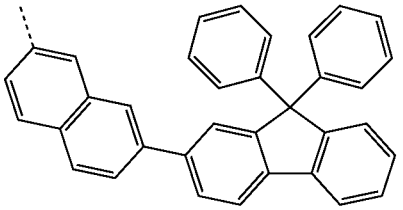 |
| 2-294 | 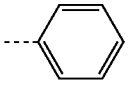 | 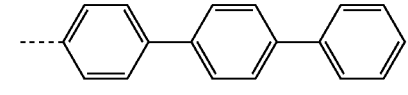 | 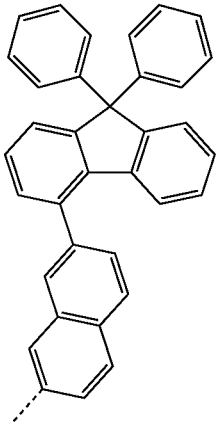 |
| 2-296 | 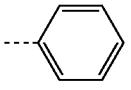 | 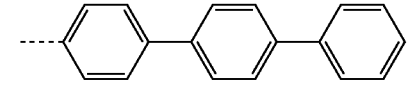 | 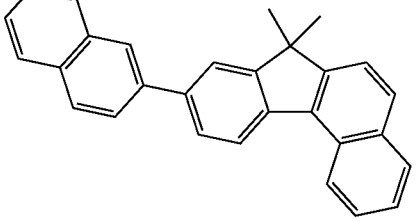 |
| 2-297 | 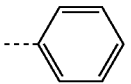 | 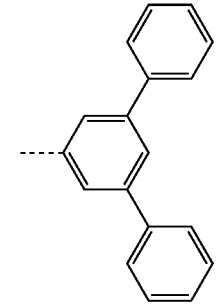 | 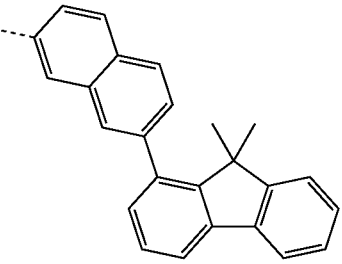 |
| 2-298 | 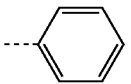 | 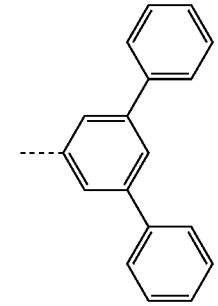 | 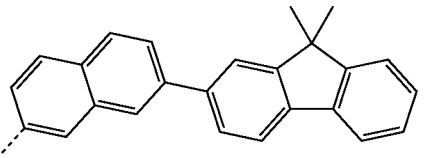 |

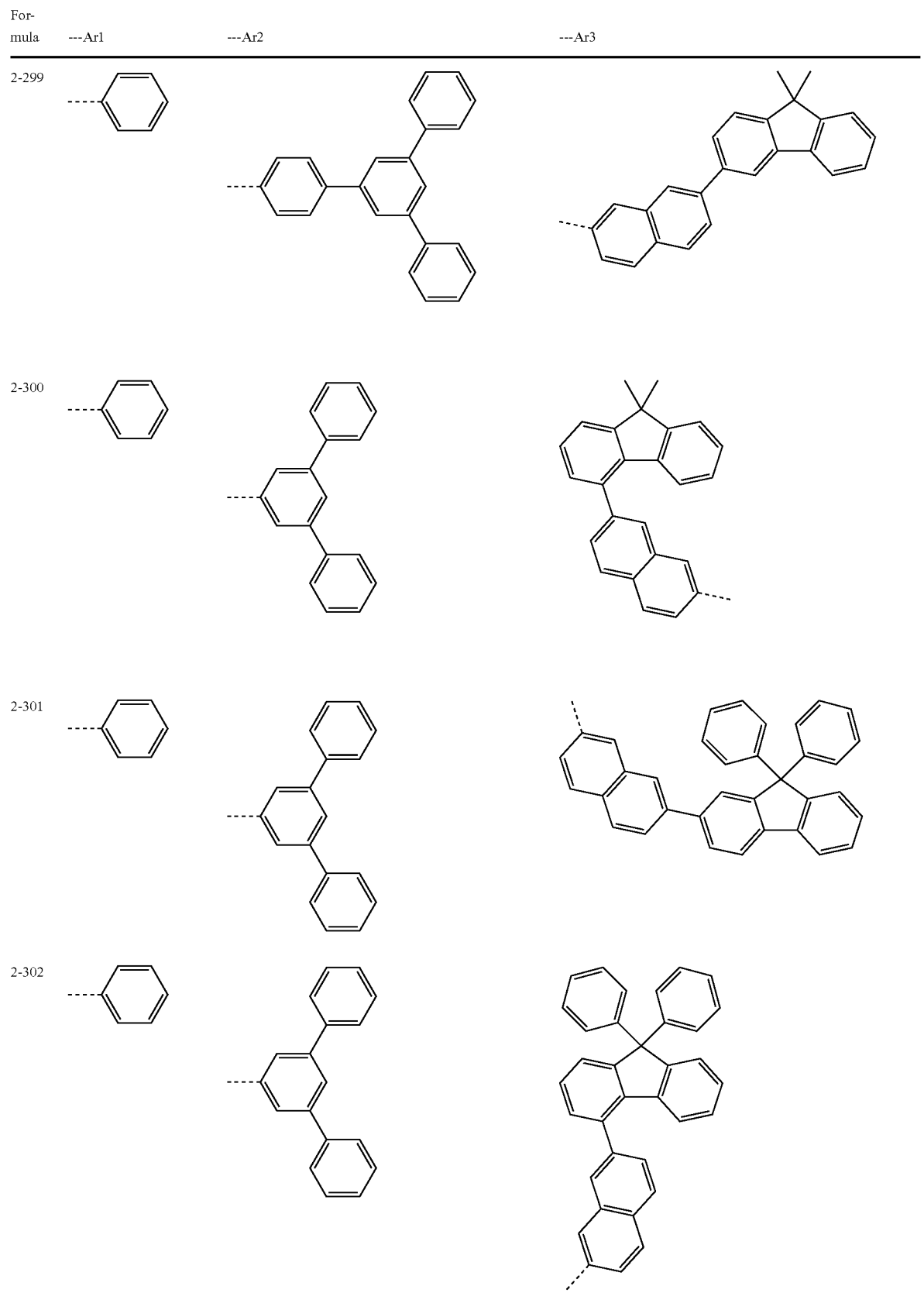

-continued
| Formula | ---Ar1 | ---Ar2 | ---Ar3 |
|---|---|---|---|
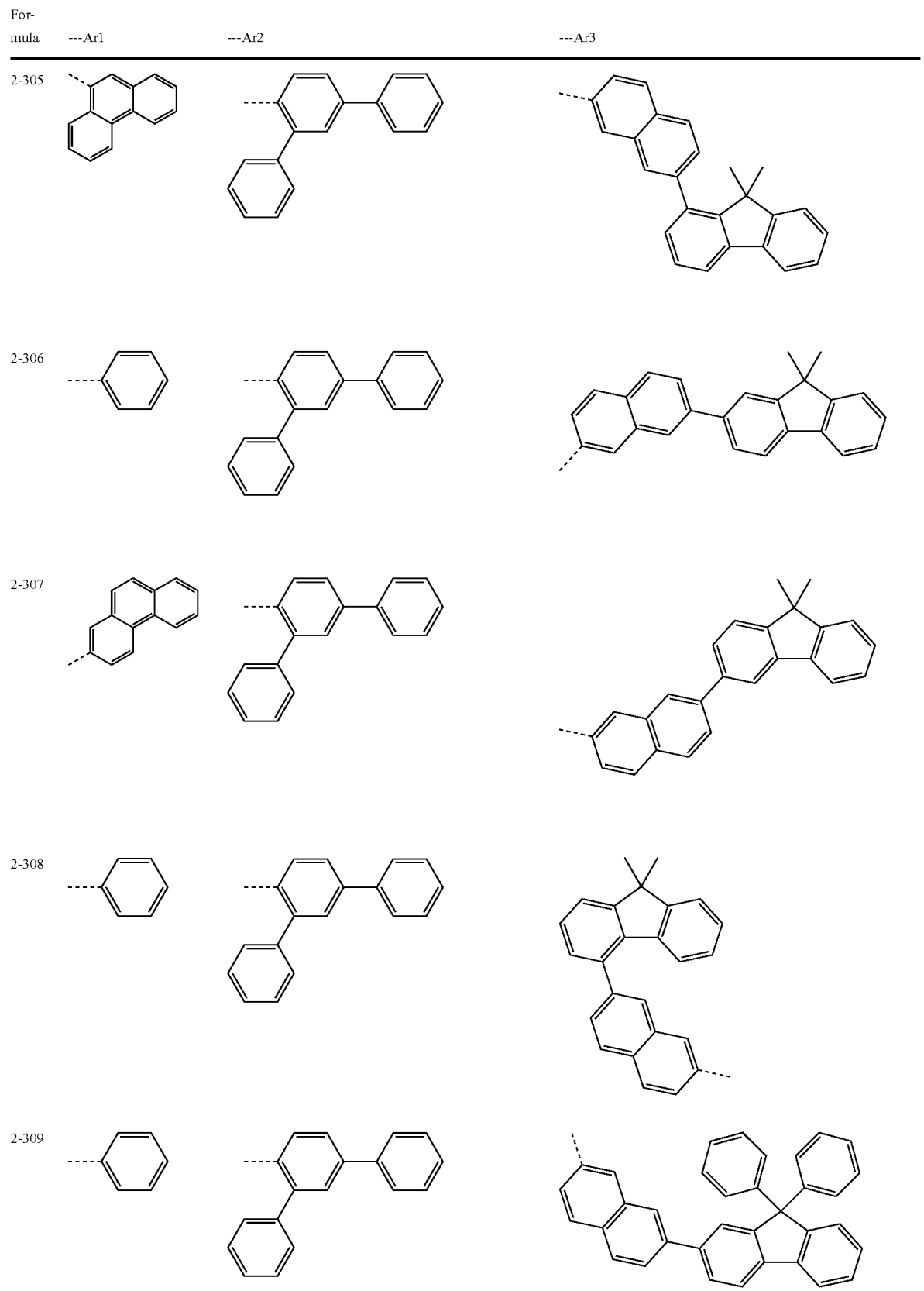

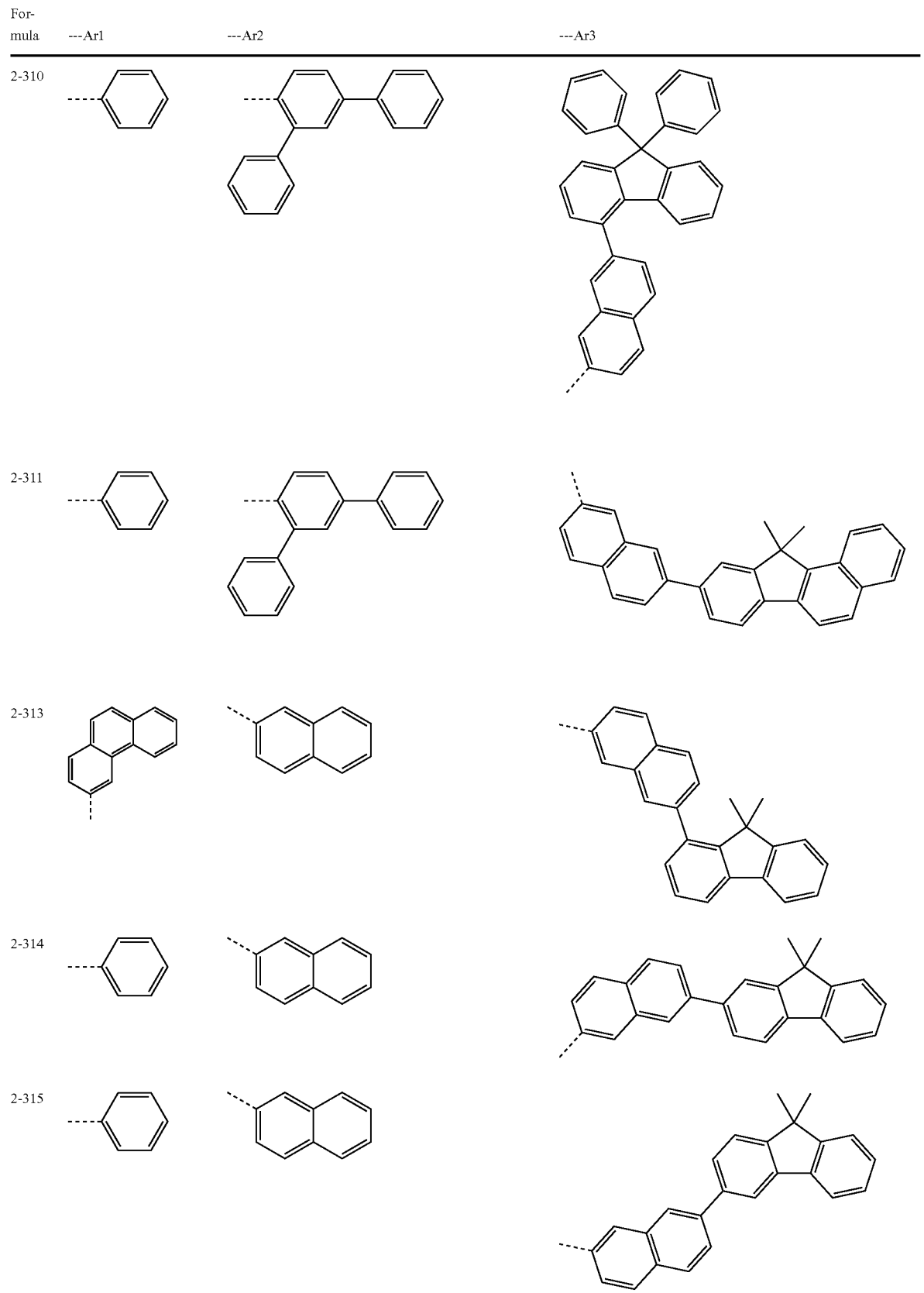

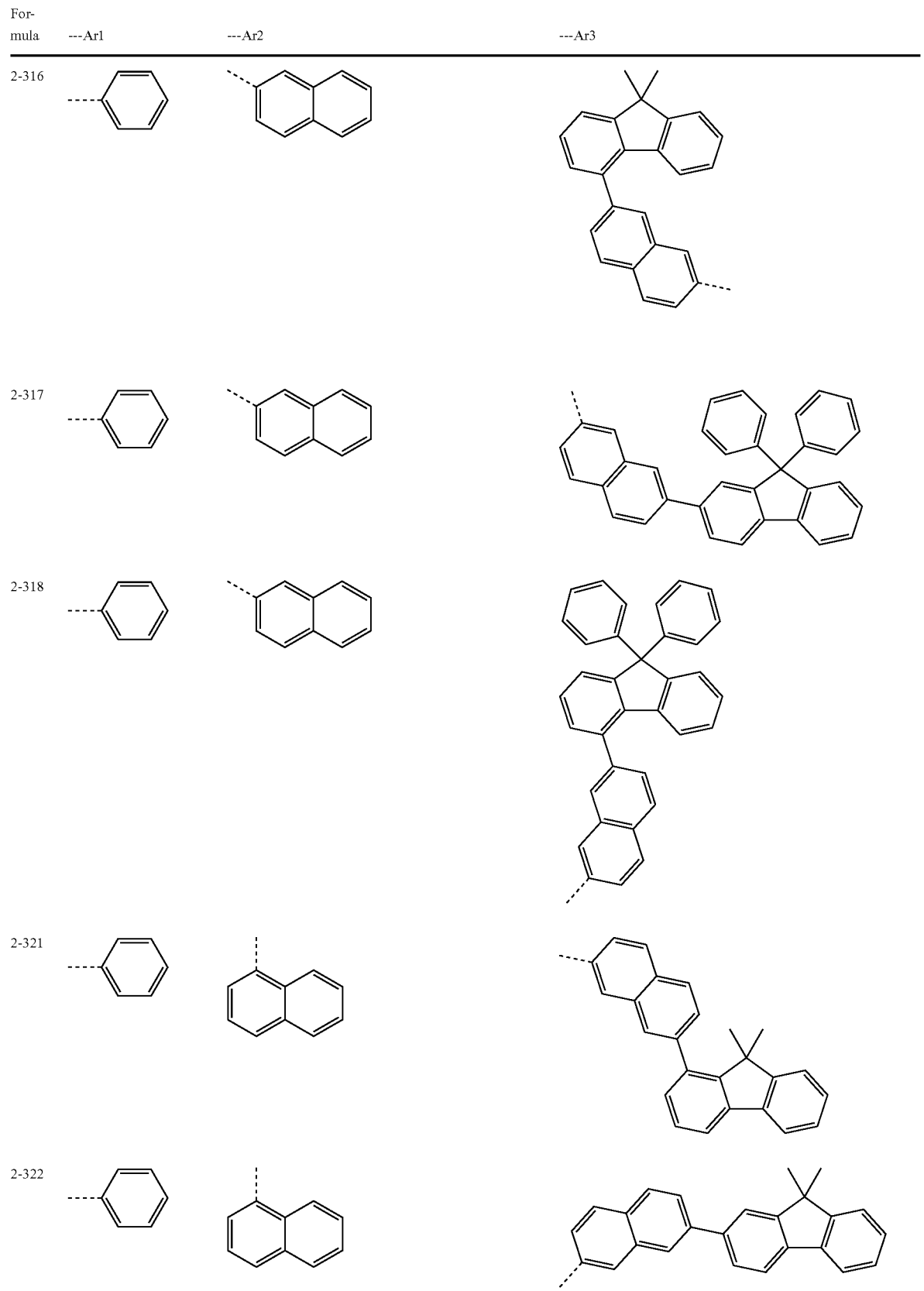

-continued

| Formula | ---Ar1 | ---Ar2 | ---Ar3 |
|---|---|---|---|
| 2-323 | phenyl | 1-naphthyl | 2-naphthyl-(9,9-dimethylfluoren-3-yl) |
| 2-324 | phenyl | 1-naphthyl | 2-naphthyl-(9,9-dimethylfluoren-4-yl) |
| 2-325 | phenyl | 1-naphthyl | 2-naphthyl-(9,9-diphenylfluoren-2-yl) |
| 2-326 | phenyl | 1-naphthyl | 2-naphthyl-(9,9-diphenylfluoren-4-yl) |
| 2-329 | phenyl | 9-phenanthryl | 2-naphthyl-(9,9-dimethylfluoren-4-yl) |

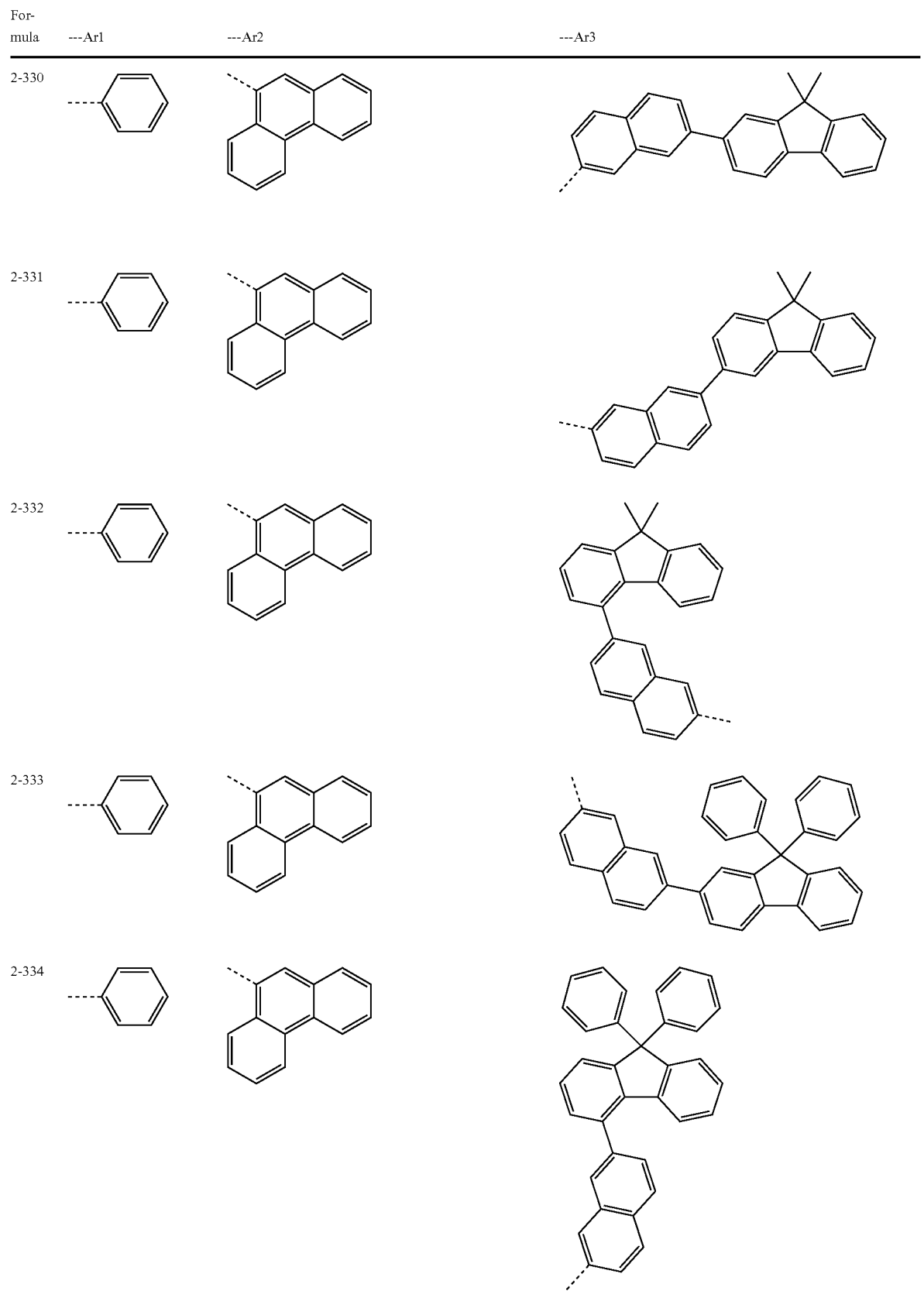

| Formula | ---Ar1 | ---Ar2 | ---Ar3 |
|---|---|---|---|
| 2-337 | 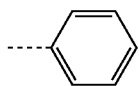 | 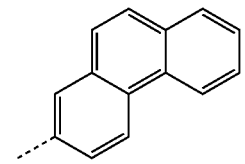 | 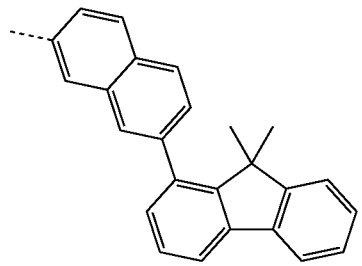 |
| 2-338 | 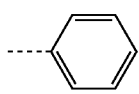 | 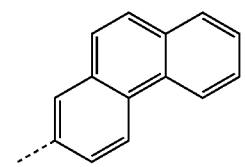 | 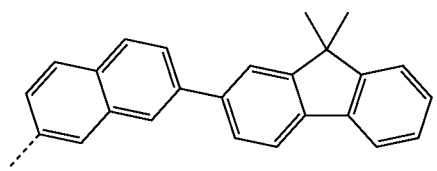 |
| 2-339 | 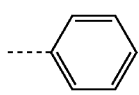 | 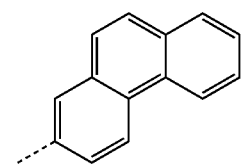 | 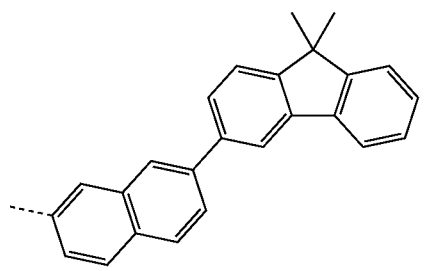 |
| 2-340 | 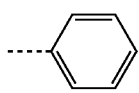 | 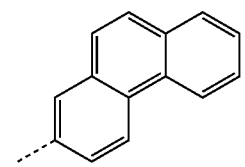 | 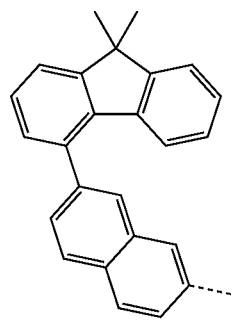 |
| 2-341 | 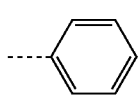 | 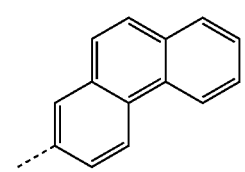 | 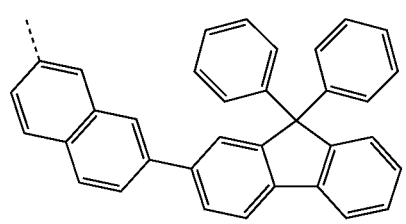 |

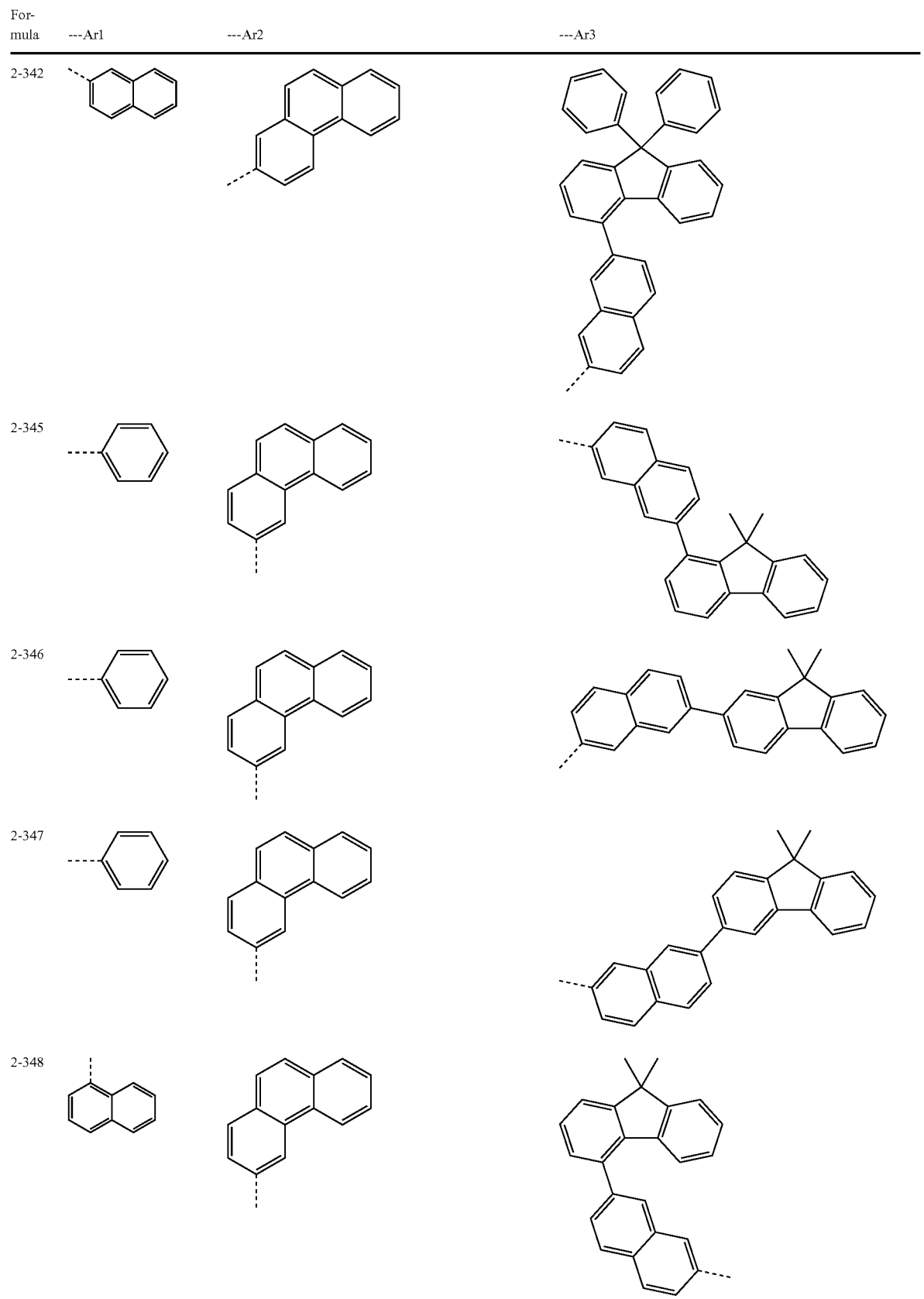

-continued
| Formula | ---Ar1 | ---Ar2 | ---Ar3 |
|---|---|---|---|
| 2-349 | 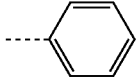 | 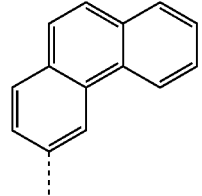 | 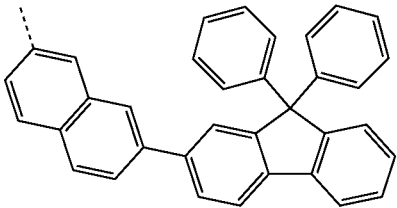 |
| 2-350 | 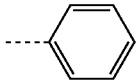 | 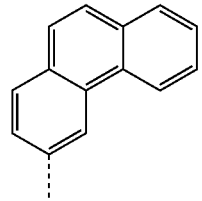 | 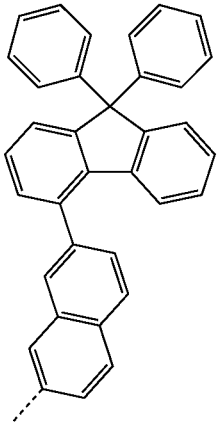 |
| 2-352 | 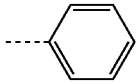 | 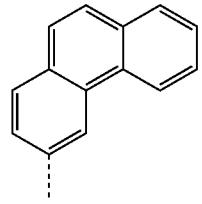 | 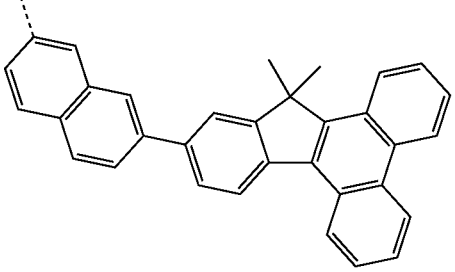 |
| 2-353 | 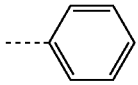 | 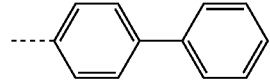 | 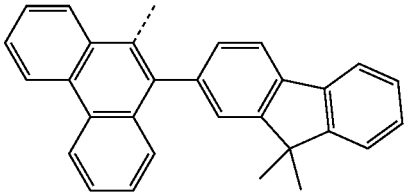 |
| 2-354 | 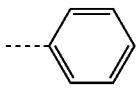 | 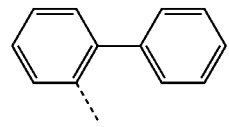 | 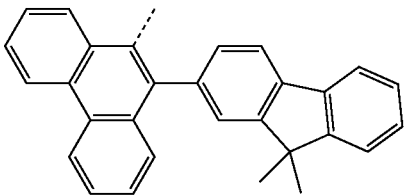 |
| 2-355 | 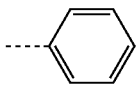 | 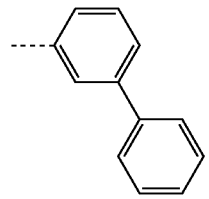 | 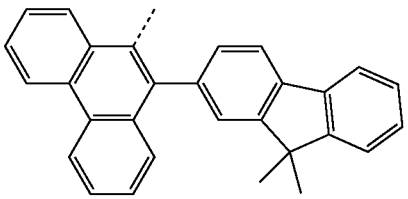 |

-continued
| Formula | ---Ar1 | ---Ar2 | ---Ar3 |
|---|---|---|---|
| 2-356 | 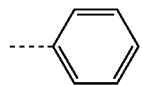 | 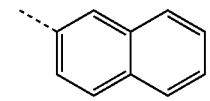 | 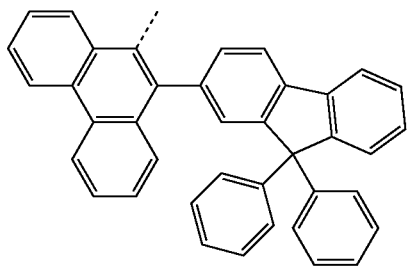 |
| 2-357 | 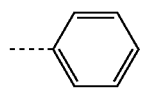 | 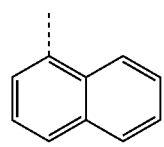 | 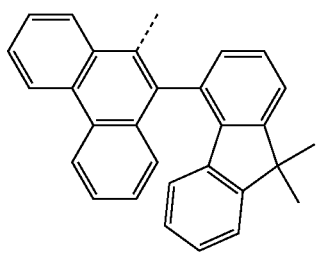 |
| 2-358 | 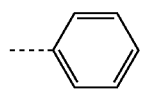 | 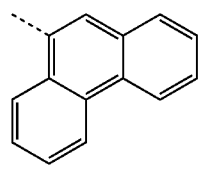 | 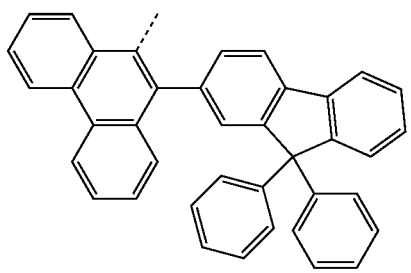 |
| 2-359 | 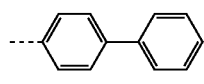 | 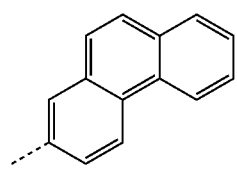 | 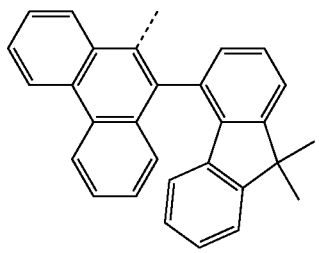 |
| 2-360 | 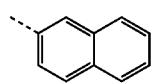 | 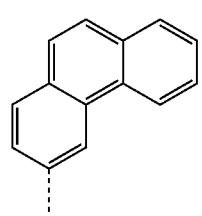 | 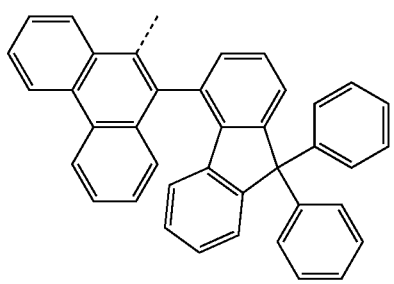 |

| For-mula | ---Ar1 | ---Ar2 | ---Ar3 |
|---|---|---|---|
| 2-361 | 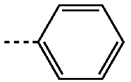 | 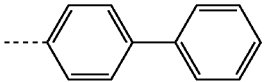 | 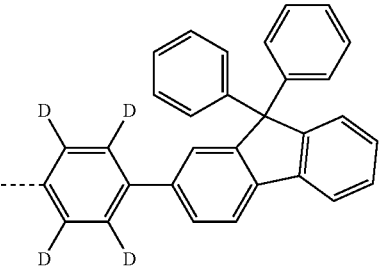 |
| 2-362 | 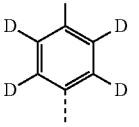 | 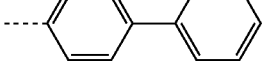 | 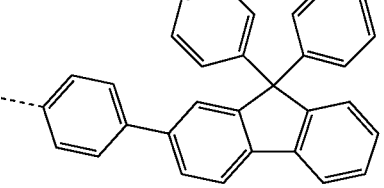 |
| 2-363 | 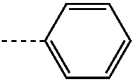 | 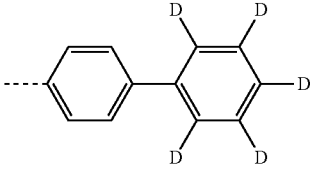 | 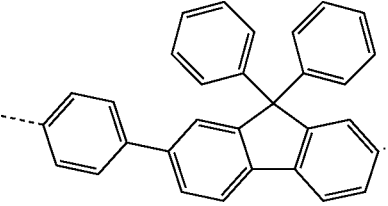 |

9. The organic light emitting diode of claim 1, wherein a dipole moment of the one or two or more of compounds included in the host material comprised in the second electron transporting layer is 1 debye or more.

10. The organic light emitting diode of claim 1, wherein A is any one of the following substituted or unsubstituted structures:

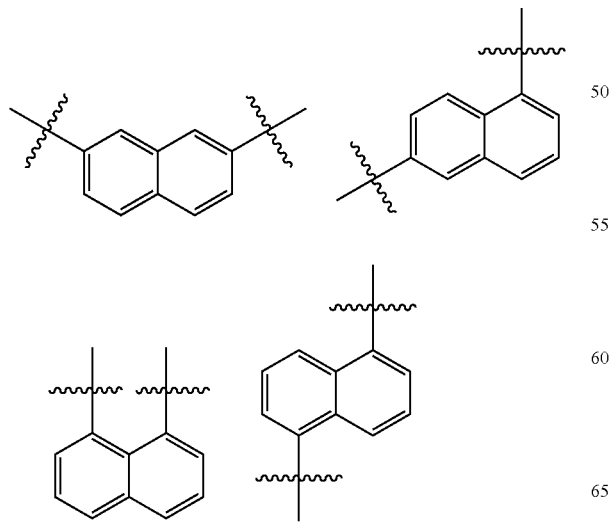

-continued

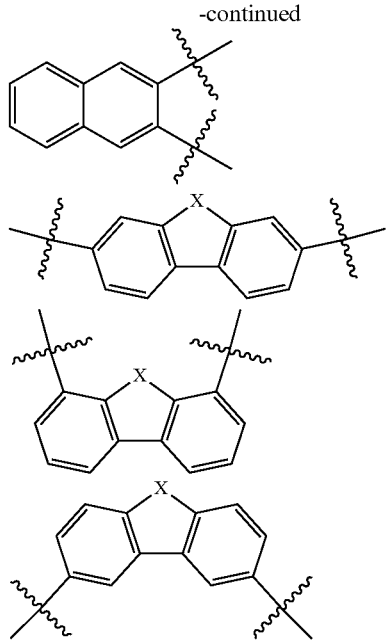

X is the same as that defined in claim 1.

11. The organic light emitting diode of claim 1, wherein the compound represented by Formula 3 is any one of the following compounds:

Formula 3-1
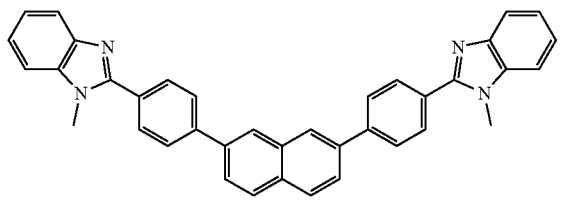
Formula 3-2
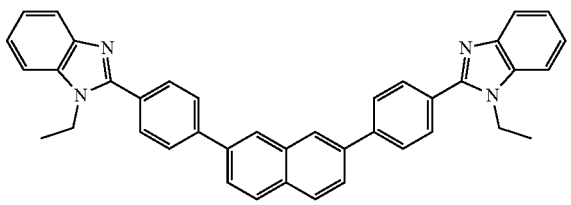
Formula 3-4
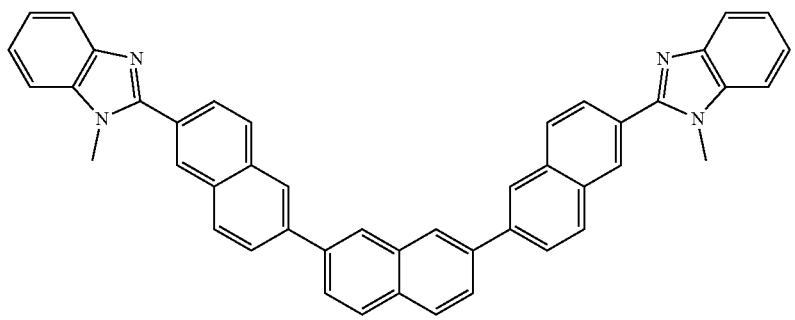
Formula 3-5
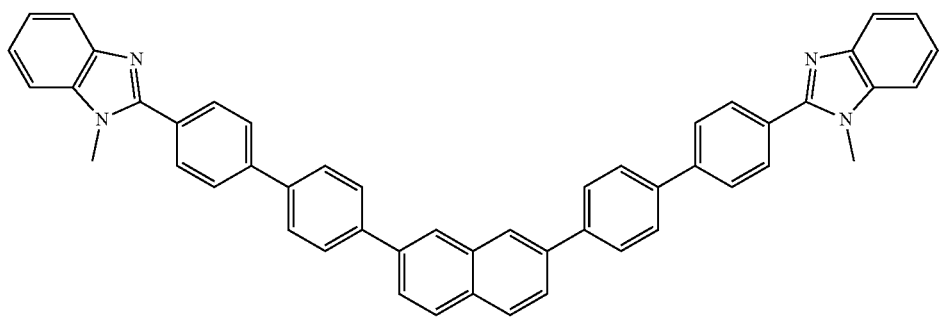
Formula 3-8
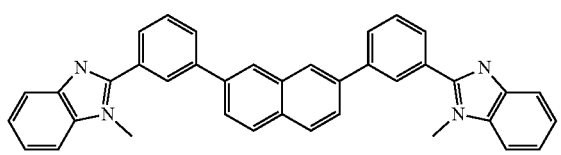
Formula 3-9
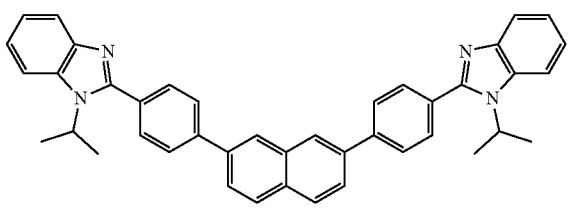
Formula 3-11
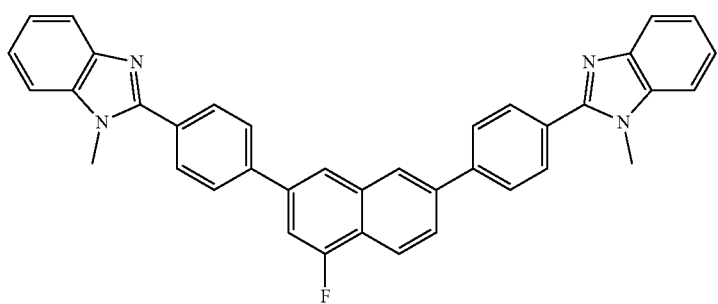

Formula 3-12
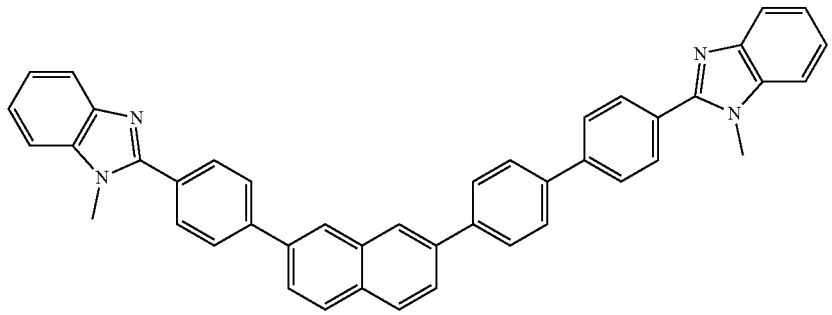
Formula 3-13
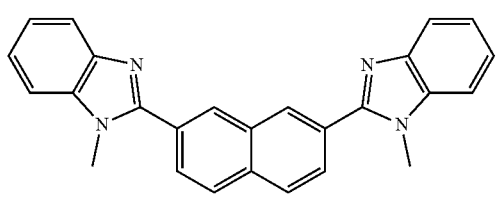
Formula 3-14
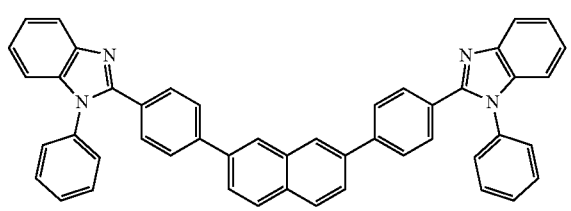
Formula 3-15
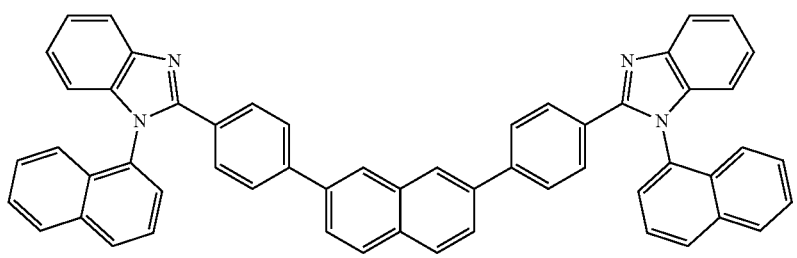
Formula 3-16
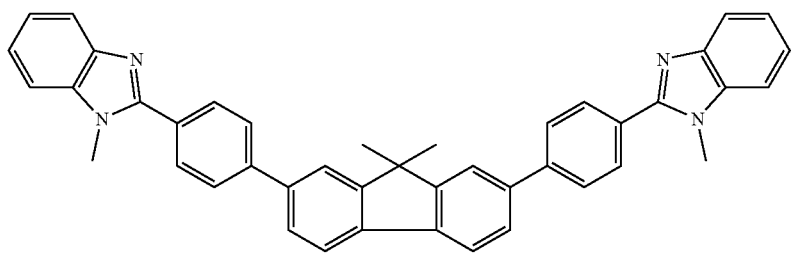
Formula 3-17
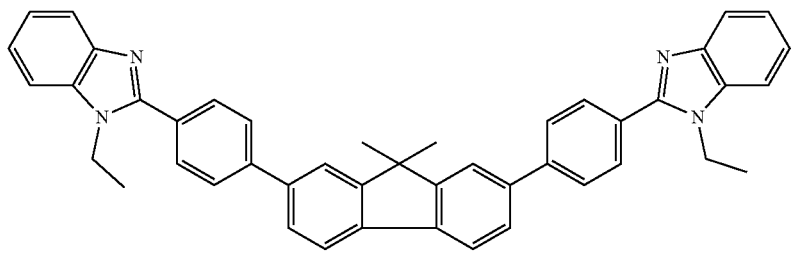
Formula 3-22
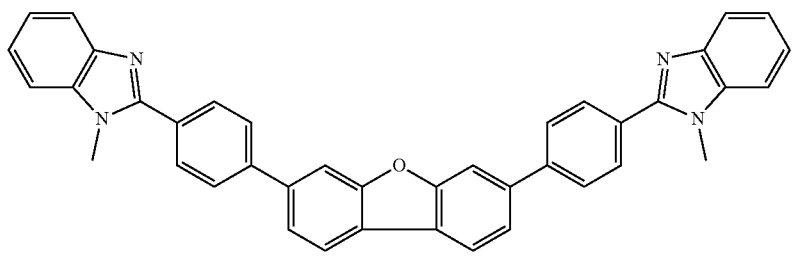

-continued
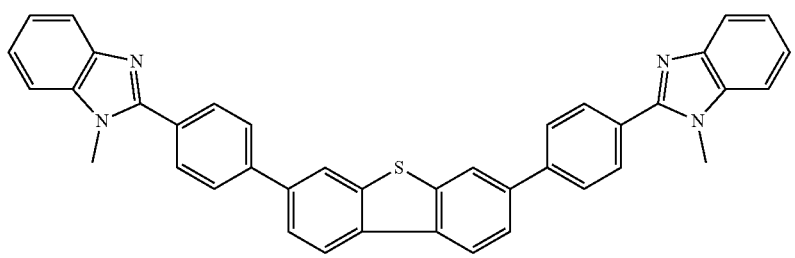
Formula 3-23
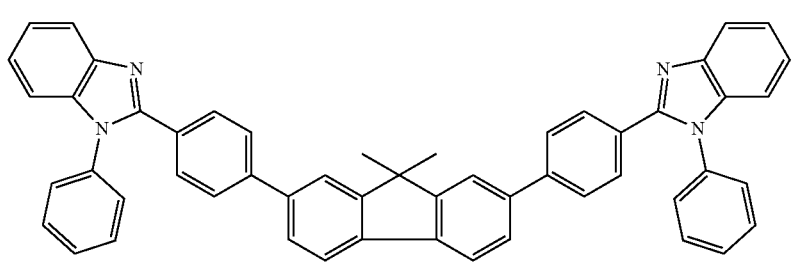
Formula 3-24
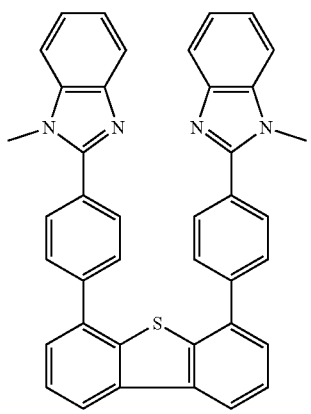
Formula 3-25
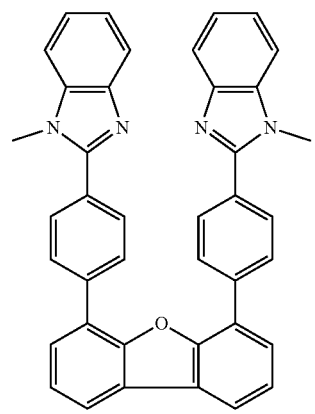
Formula 3-26
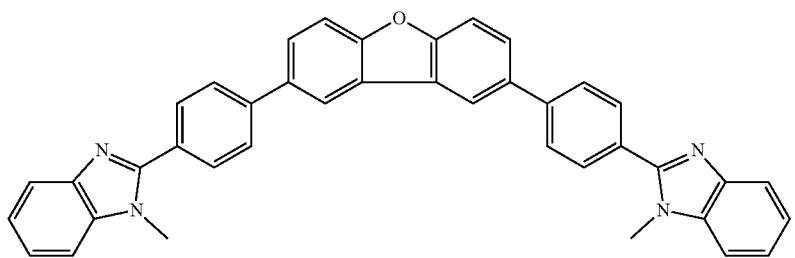
Formula 3-27
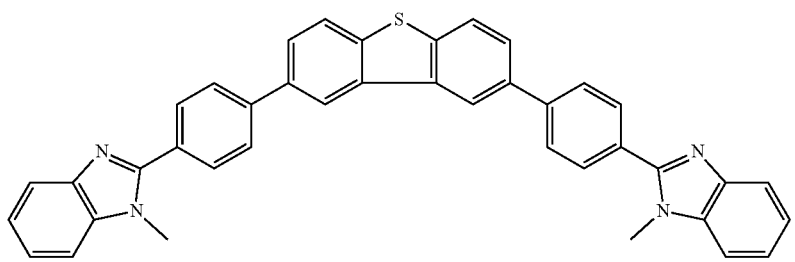
Formula 3-28

-continued
Formula 3-32
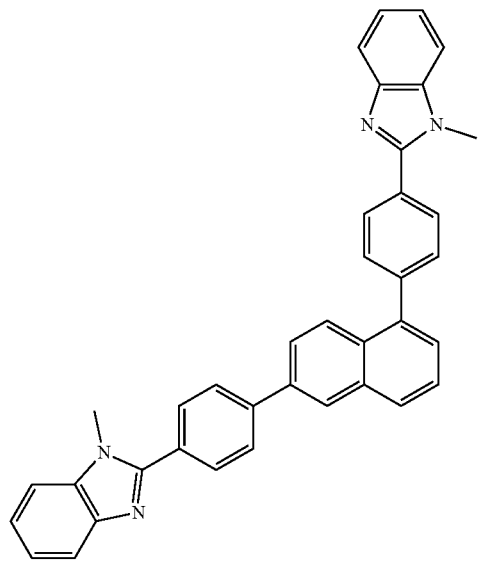
Formula 3-33
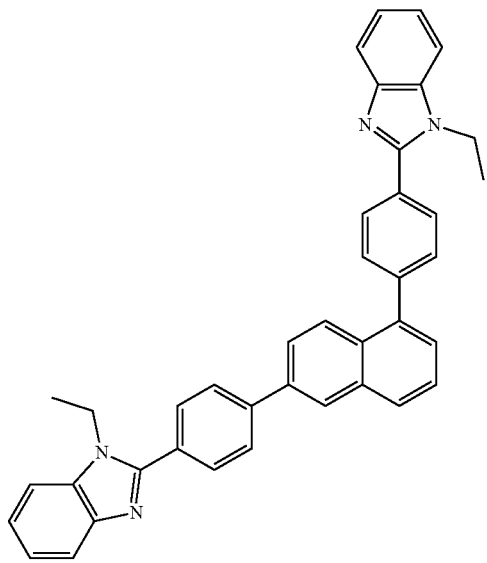
Formula 3-34
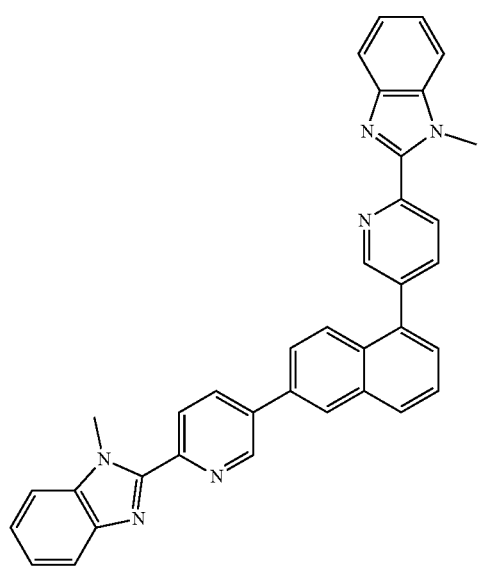
Formula 3-35
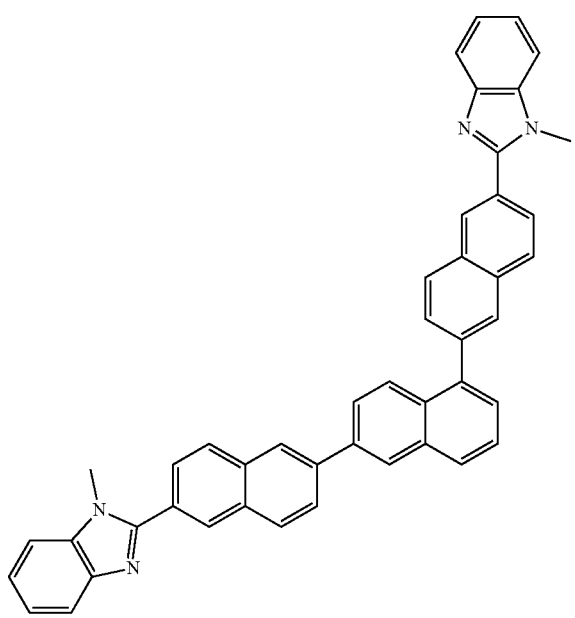

-continued
Formula 3-36
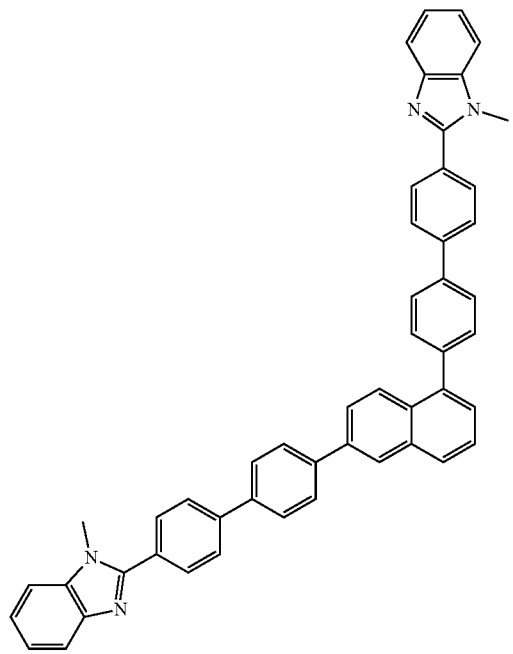
Formula 3-39
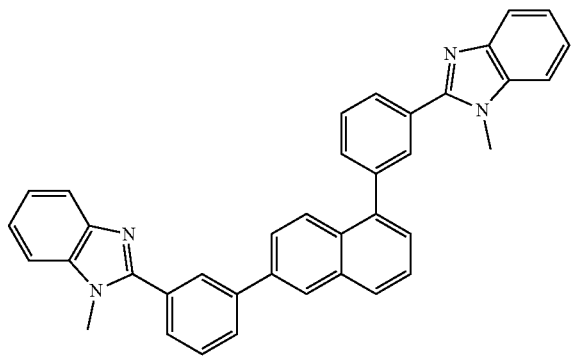
Formula 3-40
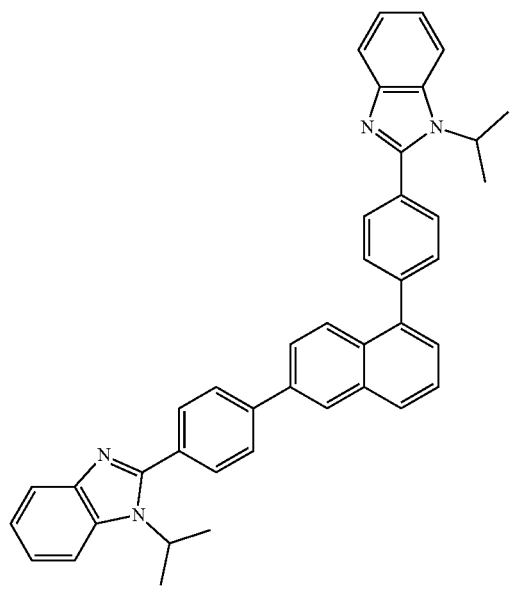
Formula 3-42
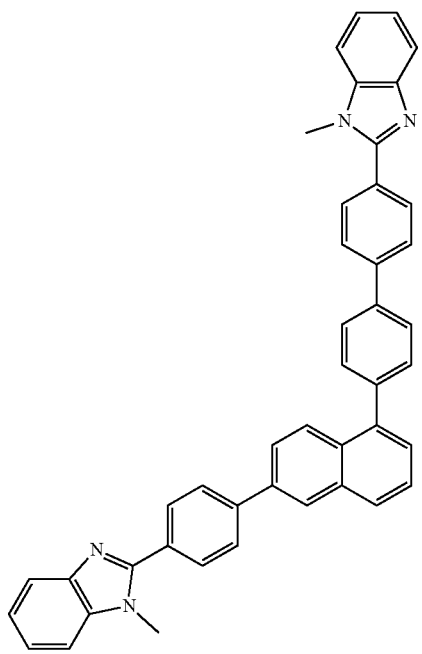

-continued
Formula 3-43
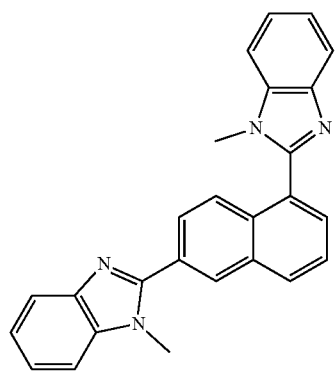
Formula 3-44
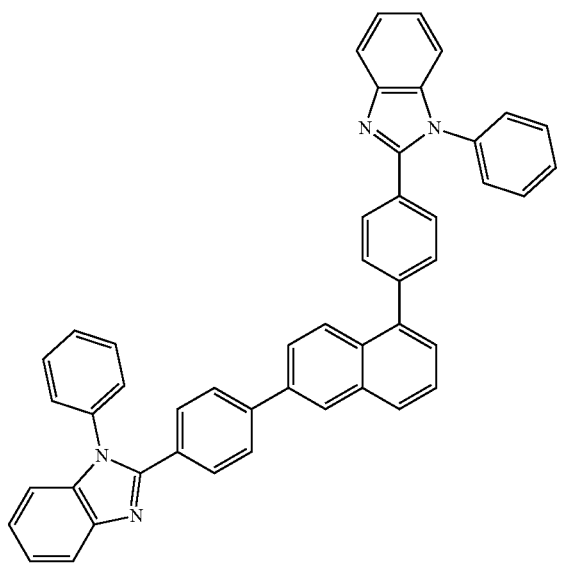
Formula 3-45
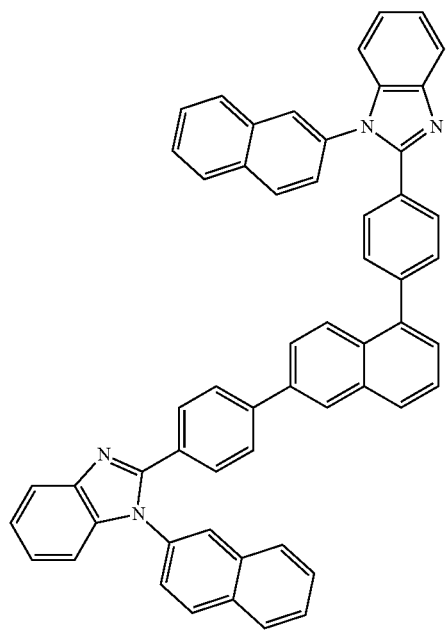
Formula 3-46
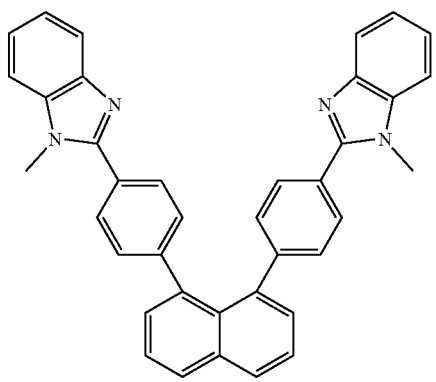
Formula 3-47
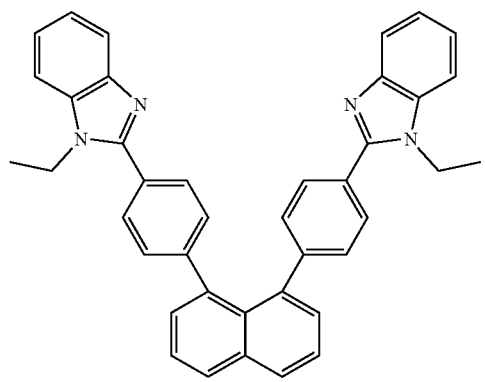
Formula 3-48
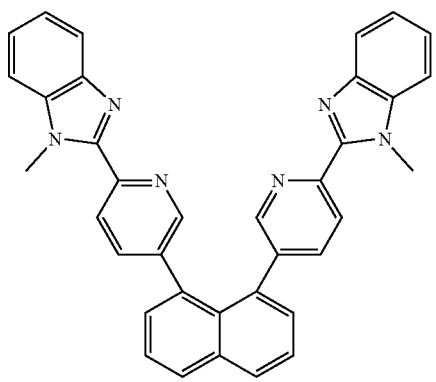

-continued
Formula 3-49
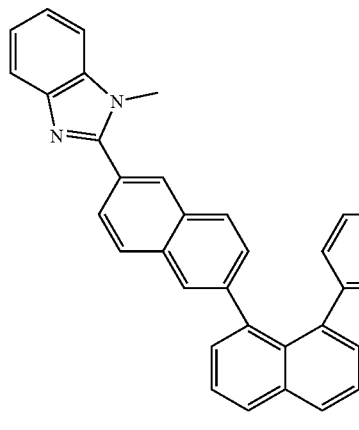
Formula 3-50
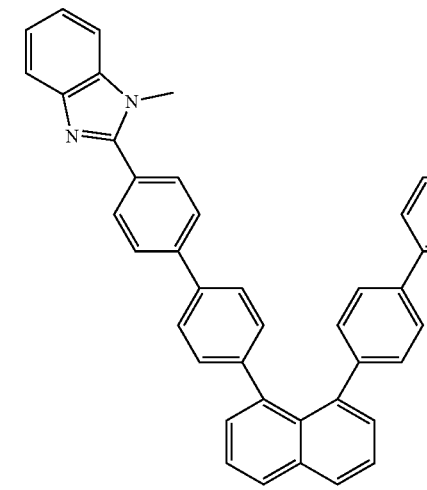
Formula 3-53
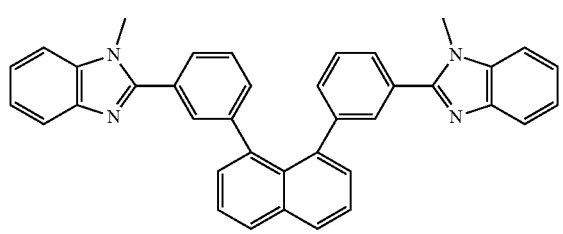
Formula 3-54
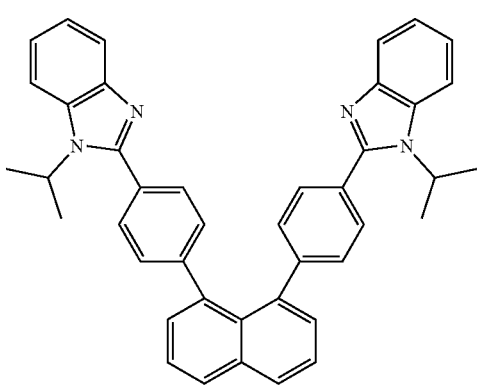
Formula 3-56
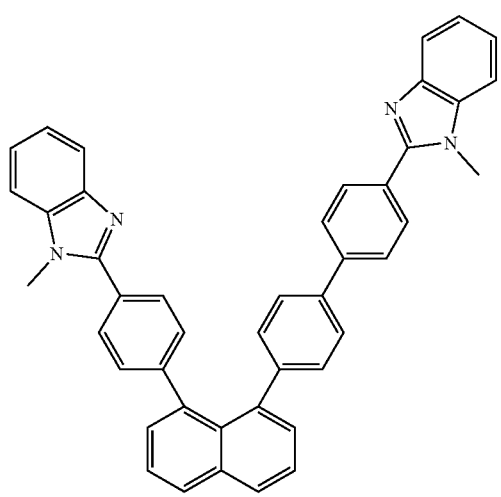
Formula 3-57
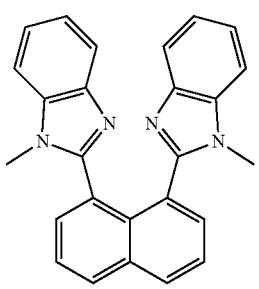

-continued
Formula 3-58
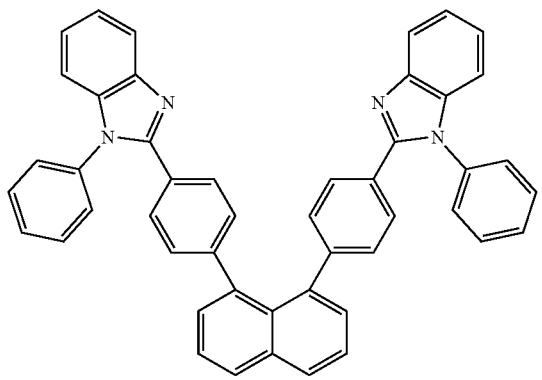
Formula 3-59
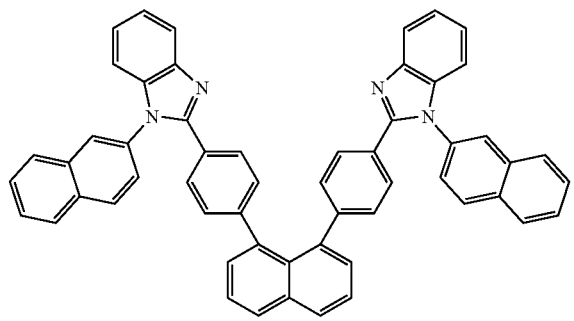
Formula 3-60
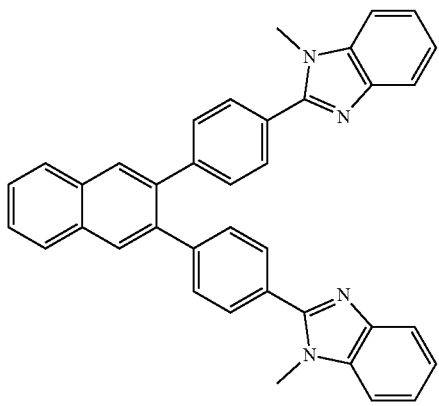
Formula 3-61
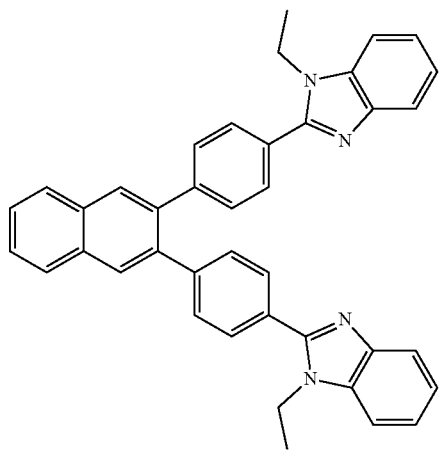
Formula 3-62
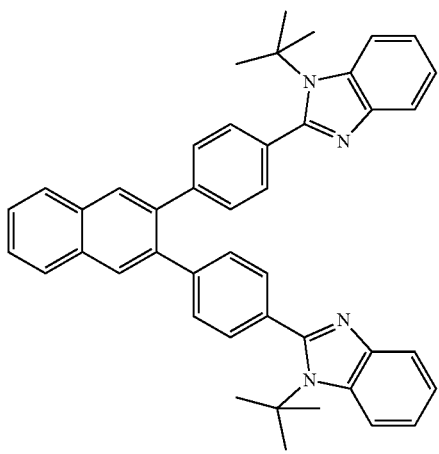
Formula 3-67
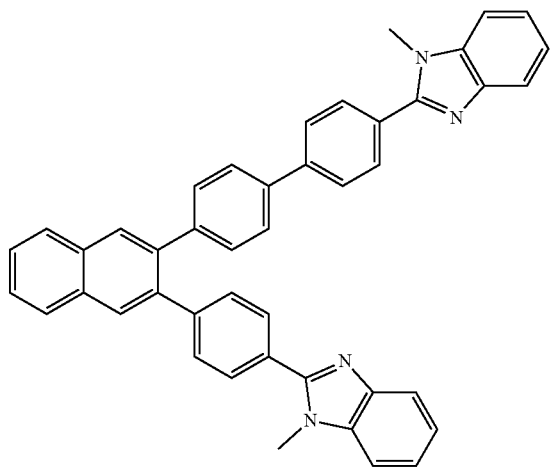

-continued
Formula 3-68
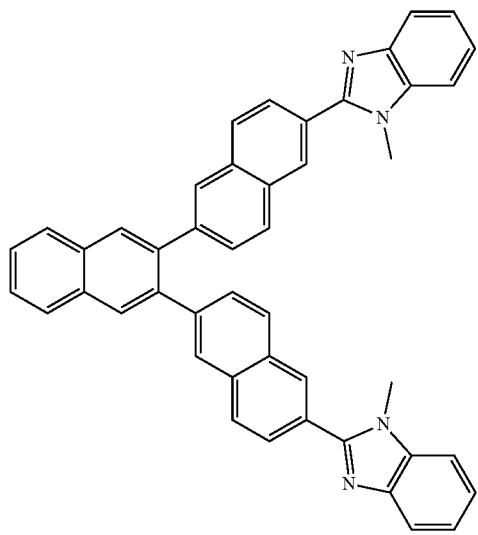
Formula 3-69
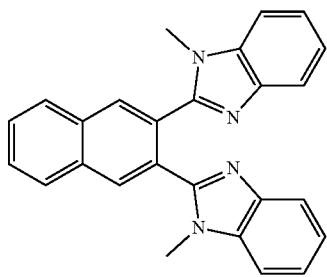
Formula 3-70
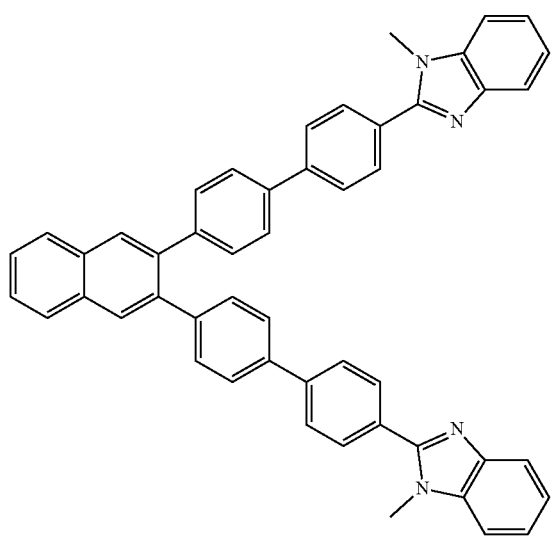
Formula 3-71
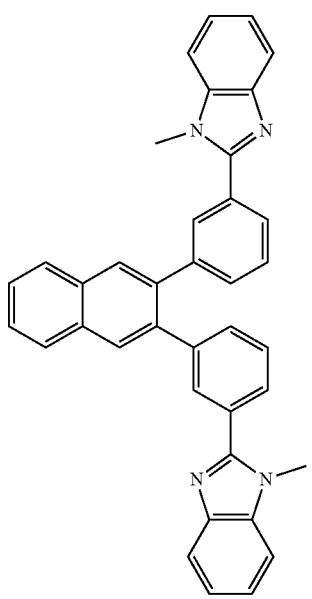

Formula 3-72
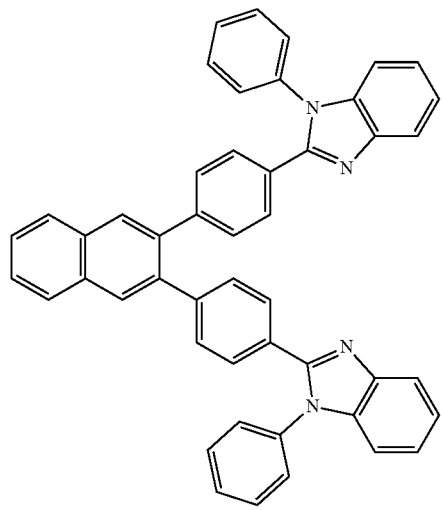
Formula 3-74
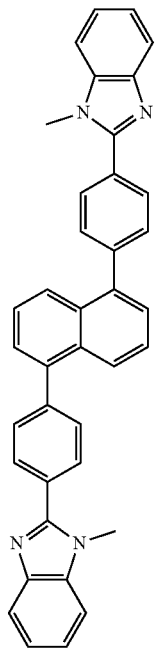
Formula 3-76
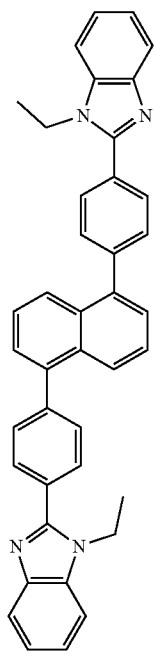
Formula 3-77
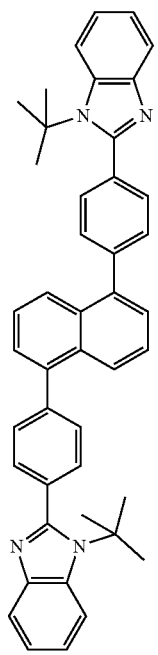

Formula 3-80
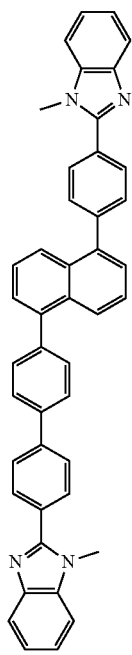
Formula 3-81
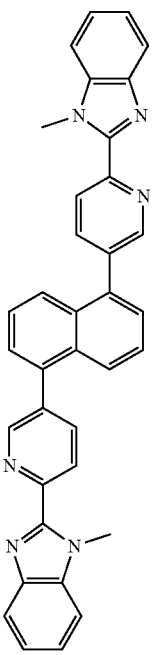
Formula 3-82
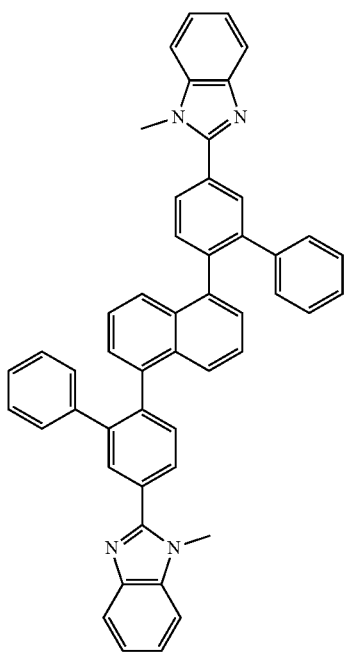
Formula 3-83
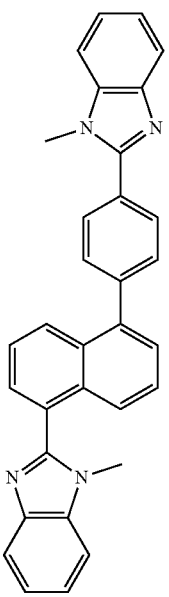

-continued
Formula 3-84
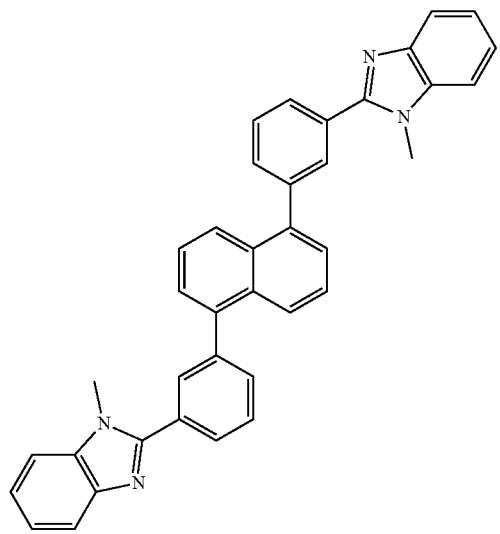
Formula 3-85
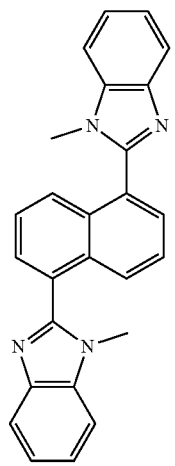
Formula 3-86
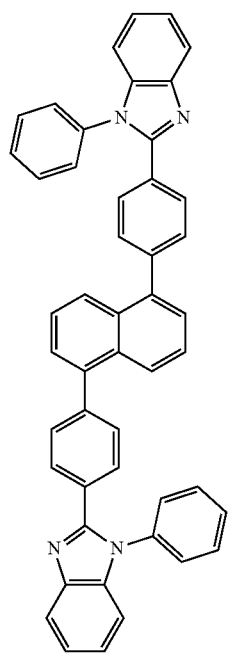
Formula 3-87
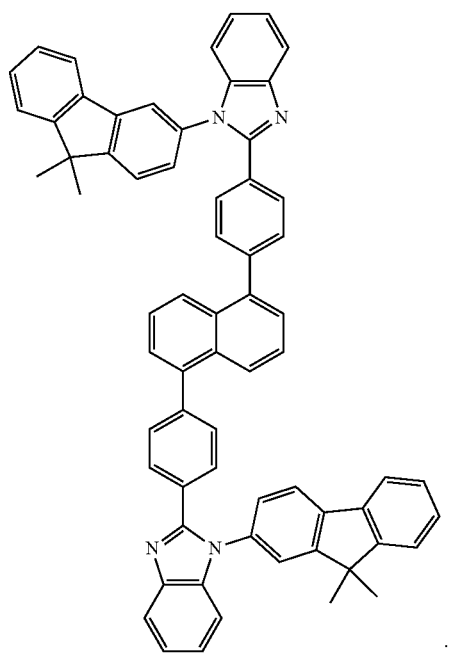

12. The organic light emitting diode of claim 1, wherein the p-type organic material layer comprises one or two or more compounds selected from the group consisting of the following Formulae 7 to 9:

[Formula 7]

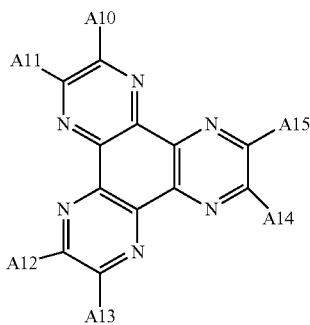

in Formula 7,

A10 to A15 are the same as or different from each other, and each independently hydrogen; a nitrile group; a nitro group; an amide group; a carbonyl group; a substituted or unsubstituted sulfonyl group; a substituted or unsubstituted ester group; a substituted or unsubstituted alkyl group; a substituted or unsubstituted alkenyl group; a substituted or unsubstituted aryl group; or a substituted or unsubstituted heterocyclic group, or combine with an adjacent group to form a substituted or unsubstituted hydrocarbon ring or a substituted or unsubstituted hetero ring,

[Formula 8]

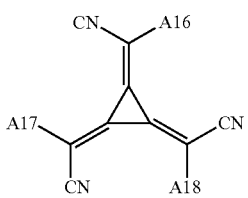

in Formula 8,

A16 to A18 are the same as or different from each other, and each independently an aryl group, which is unsubstituted or substituted with one or two or more substituents selected from the group consisting of a cyano group, a halogen group, and a haloalkyl group; or a heterocyclic group, which is unsubstituted or substituted with one or two or more substituents selected from the group consisting of a cyano group, a halogen group, and a haloalkyl group,

[Formula 9]

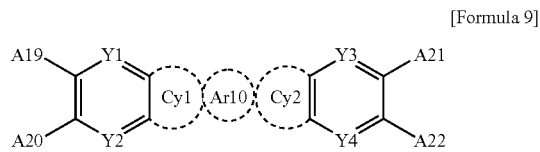

in Formula 9,

Ar10 is a substituted or unsubstituted hydrocarbon ring; or a substituted or unsubstituted hetero ring, Y1 to Y4 are the same as or different from each other, and each independently N; or CA23, A19 to A23 are the same as or different from each other, and each independently hydrogen; a nitrile group; a halogen group; a substituted or unsubstituted alkyl group; a substituted or unsubstituted alkoxy group; a substituted or unsubstituted aryloxy group; a substituted or unsubstituted aryl group; or a substituted or unsubstituted heterocyclic group, or combine with an adjacent group to form a substituted or unsubstituted hydrocarbon ring or a substituted or unsubstituted hetero ring, Cy1 and Cy2 are the same as or different from each other, and each independently any one of the following structures,

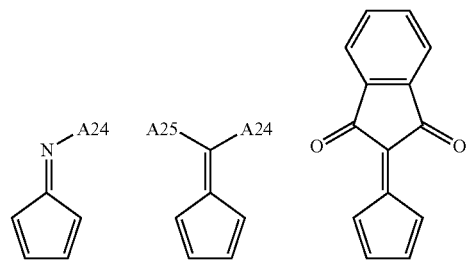

Ar10 combines with both Cy1 and Cy2 at carbons in pentadiene ring to form a fused ring, Cy1 combines with a ring containing Y1 and Y2 at carbons in the pentadiene ring to form a fused ring, Cy2 combines with a ring containing Y3 and Y4 at carbons in the pentadiene ring to form a fused ring, A24 to A26 are the same as or different from each other, and each independently a nitrile group; a substituted or unsubstituted ester group; or an unsubstituted trifluoroalkyl group.

* * * * *